US007875638B2

(12) United States Patent
Danishefsky et al.

(10) Patent No.: US 7,875,638 B2
(45) Date of Patent: *Jan. 25, 2011

(54) SYNTHESIS OF EPOTHILONES, INTERMEDIATES THERETO, ANALOGUES AND USES THEREOF

(75) Inventors: Samuel J. Danishefsky, Englewood, NJ (US); Alexey Rivkin, New York, NY (US); Fumihiko Yoshimura, Kita-Ku Sapporo (JP); Ting-Chao Chou, Paramus, NJ (US); Ana E. Gabarda, Boston, MA (US); Huajin Dong, Beijing (CN); Kaida Wu, New York, NY (US); Malcolm A. S. Moore, New York, NY (US); David Dorn, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/135,823

(22) Filed: Jun. 9, 2008

(65) Prior Publication Data

US 2009/0149516 A1 Jun. 11, 2009

Related U.S. Application Data

(63) Continuation of application No. 10/921,109, filed on Aug. 18, 2004, now Pat. No. 7,384,964, which is a continuation-in-part of application No. 10/435,408, filed on May 9, 2003, which is a continuation-in-part of application No. 10/402,004, filed on Mar. 28, 2003, now Pat. No. 6,921,769.

(60) Provisional application No. 60/405,823, filed on Aug. 23, 2002, provisional application No. 60/408,589, filed on Sep. 6, 2002, provisional application No. 60/423,129, filed on Nov. 1, 2002, provisional application No. 60/456,159, filed on Mar. 20, 2003, provisional application No. 60/496,741, filed on Aug. 21, 2003, provisional application No. 60/548,402, filed on Feb. 27, 2004.

(51) Int. Cl.
*A61K 31/427* (2006.01)
*C07D 417/06* (2006.01)

(52) U.S. Cl. .......................... 514/365; 548/204

(58) Field of Classification Search .................. None
See application file for complete search history.

(56) References Cited

U.S. PATENT DOCUMENTS

| 4,605,661 | A | * | 8/1986 | Hirsch et al. ............... 514/400 |
| 4,916,144 | A | * | 4/1990 | Strehlke et al. ............. 514/326 |
| 5,021,430 | A | | 6/1991 | Ksander |
| 5,917,084 | A | | 6/1999 | Jiang |
| 5,969,145 | A | | 10/1999 | Schinzer et al. |
| 6,043,372 | A | | 3/2000 | Schinzer et al. |
| 6,090,601 | A | | 7/2000 | Gustafsson et al. |
| 6,096,757 | A | | 8/2000 | Bishop et al. |
| 6,117,659 | A | | 9/2000 | Ashley et al. |
| 6,121,029 | A | | 9/2000 | Schupp et al. |
| 6,156,905 | A | | 12/2000 | Schinzer et al. |
| 6,204,388 | B1 | | 3/2001 | Danishefsky et al. |
| 6,211,412 | B1 | | 4/2001 | Georg et al. |
| 6,221,641 | B1 | | 4/2001 | Khosla et al. |
| 6,242,469 | B1 | | 6/2001 | Danishefsky et al. |
| 6,251,636 | B1 | | 6/2001 | Betlach et al. |
| 6,262,094 | B1 | | 7/2001 | Hoefle et al. |
| 6,262,107 | B1 | | 7/2001 | Li et al. |
| 6,280,999 | B1 | | 8/2001 | Gustafsson et al. |
| 6,284,781 | B1 | | 9/2001 | Danishefsky et al. |
| 6,288,237 | B1 | | 9/2001 | Hoefle et al. |
| 6,291,684 | B1 | | 9/2001 | Borzilleri et al. |
| 6,300,355 | B1 | | 10/2001 | Danishefsky et al. |
| 6,302,838 | B1 | | 10/2001 | O'Reilly et al. |
| 6,303,342 | B1 | | 10/2001 | Julien et al. |
| 6,303,767 | B1 | | 10/2001 | Betlach et al. |
| 6,316,630 | B1 | | 11/2001 | Danishefsky et al. |
| 6,320,045 | B1 | | 11/2001 | Kim et al. |
| 6,350,878 | B1 | | 2/2002 | Altmann et al. |
| 6,359,140 | B1 | | 3/2002 | Hofle et al. |
| 6,365,749 | B1 | | 4/2002 | Kim et al. |
| 6,369,234 | B1 | | 4/2002 | Danishefsky et al. |

(Continued)

FOREIGN PATENT DOCUMENTS

DE 4138042 A1 5/1993

(Continued)

OTHER PUBLICATIONS

U.S. Appl. No. 08/923,869, filed Aug. 27, 2002, Nicolaou et al.

(Continued)

*Primary Examiner*—Kamal A Saeed
(74) *Attorney, Agent, or Firm*—Brenda Herschbach Jarrell; Kristen C. Buteau; Choate, Hall & Stewart LLP

(57) ABSTRACT

The present invention provides compounds of formula (I):

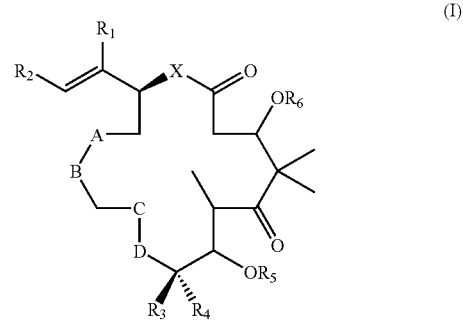

as described generally and in classes and subclasses herein. The present invention additionally provides pharmaceutical compositions comprising compounds of formula (I) and provides methods of treating cancer comprising administering a compound of formula (I).

20 Claims, 153 Drawing Sheets

U.S. PATENT DOCUMENTS

| | | |
|---|---|---|
| 6,380,227 B1 | 4/2002 | Mutz |
| 6,380,394 B1 | 4/2002 | Nicolaou et al. |
| 6,380,395 B1 | 4/2002 | Vite et al. |
| 6,383,787 B1 | 5/2002 | Schupp et al. |
| 6,384,230 B1 | 5/2002 | Mulzer et al. |
| 6,387,927 B1 | 5/2002 | Altmann et al. |
| 6,399,638 B1 | 6/2002 | Vite et al. |
| 6,407,103 B2 | 6/2002 | Nugiel et al. |
| 6,410,301 B1 | 6/2002 | Julien et al. |
| 6,419,692 B1 | 7/2002 | Yang et al. |
| 6,457,303 B1 | 10/2002 | Georg et al. |
| 6,489,314 B1 | 12/2002 | Ashley et al. |
| 6,498,257 B1 | 12/2002 | Vite et al. |
| 6,515,017 B1 | 2/2003 | Li et al. |
| 6,518,421 B1 | 2/2003 | Li et al. |
| 6,525,197 B1 | 2/2003 | Furstner et al. |
| 6,531,497 B1 | 3/2003 | Nicolaou et al. |
| 6,537,988 B2 | 3/2003 | Lee |
| 6,538,038 B1 | 3/2003 | Pero et al. |
| 6,544,544 B2 | 4/2003 | Hunter et al. |
| 6,576,651 B2 | 6/2003 | Bandyopadhyay et al. |
| 6,593,115 B2 | 7/2003 | Vite et al. |
| 6,596,875 B2 | 7/2003 | White et al. |
| 6,603,015 B2 | 8/2003 | Georg et al. |
| 6,603,023 B2 | 8/2003 | Danishefsky et al. |
| 6,605,599 B1 | 8/2003 | Vite et al. |
| 6,605,726 B1 | 8/2003 | Mulzer et al. |
| 6,610,736 B1 | 8/2003 | Klar et al. |
| 6,613,912 B2 | 9/2003 | Hoefle et al. |
| 6,624,310 B1 | 9/2003 | Hoefle et al. |
| 6,625,666 B1 | 9/2003 | Kim |
| 6,670,384 B2 | 12/2003 | Bandyopadhyay et al. |
| 6,683,100 B2 | 1/2004 | van Hoogevest |
| 6,686,380 B2 | 2/2004 | Lee |
| 6,689,802 B2 | 2/2004 | DiMarco et al. |
| 6,719,540 B2 | 4/2004 | Regueiro-Ren et al. |
| 6,723,854 B2 | 4/2004 | Danishefsky et al. |
| 6,727,276 B2 | 4/2004 | Lee |
| 6,730,699 B2 | 5/2004 | Li et al. |
| 6,730,803 B2 | 5/2004 | Iwasaki et al. |
| 6,780,620 B1 | 8/2004 | Li et al. |
| 6,800,653 B2 | 10/2004 | Regueiro-Ren et al. |
| 6,906,188 B2 | 6/2005 | White et al. |
| 6,921,769 B2 * | 7/2005 | Danishefsky et al. ....... 514/365 |
| 6,958,401 B2 | 10/2005 | White et al. |
| 7,145,018 B2 | 12/2006 | White et al. |
| 2001/0031880 A1 | 10/2001 | Borzilleri et al. |
| 2001/0034452 A1 | 10/2001 | Hoefle et al. |
| 2001/0051356 A1 | 12/2001 | Khosla et al. |
| 2002/0002162 A1 | 1/2002 | Lee |
| 2002/0002194 A1 | 1/2002 | Danishefsky et al. |
| 2002/0004229 A1 | 1/2002 | Santi et al. |
| 2002/0010328 A1 | 1/2002 | Reeves et al. |
| 2002/0028839 A1 | 3/2002 | O'Reilly et al. |
| 2002/0042109 A1 | 4/2002 | Vite et al. |
| 2002/0045220 A1 | 4/2002 | Khosla et al. |
| 2002/0045609 A1 | 4/2002 | Ashley et al. |
| 2002/0052028 A1 | 5/2002 | Santi et al. |
| 2002/0058286 A1 | 5/2002 | Danishefsky et al. |
| 2002/0058817 A1 | 5/2002 | Danishefsky et al. |
| 2002/0062030 A1 | 5/2002 | White et al. |
| 2002/0065295 A1 | 5/2002 | Chu et al. |
| 2002/0086812 A1 | 7/2002 | Schweinfest et al. |
| 2002/0091269 A1 | 7/2002 | Avery |
| 2002/0094991 A1 | 7/2002 | Gallaher |
| 2002/0115686 A1 | 8/2002 | Hoogevest |
| 2002/0119202 A1 | 8/2002 | Hunter et al. |
| 2002/0137152 A1 | 9/2002 | Santi et al. |
| 2002/0143026 A1 | 10/2002 | Lombardo et al. |
| 2002/0143038 A1 | 10/2002 | Bandyopadhyay et al. |
| 2002/0147197 A1 | 10/2002 | Newman et al. |
| 2002/0156110 A1 | 10/2002 | Arslanian et al. |
| 2002/0156289 A1 | 10/2002 | Georg et al. |
| 2002/0164377 A1 | 11/2002 | Hunter et al. |
| 2002/0165256 A1 | 11/2002 | Hofmann et al. |
| 2002/0165257 A1 | 11/2002 | Lee |
| 2002/0165258 A1 | 11/2002 | Lee |
| 2002/0165265 A1 | 11/2002 | Hunter et al. |
| 2002/0165415 A1 | 11/2002 | Georg et al. |
| 2002/0169125 A1 | 11/2002 | Leung et al. |
| 2002/0169135 A1 | 11/2002 | Pardee et al. |
| 2002/0169190 A1 | 11/2002 | Bandyopadhyay et al. |
| 2002/0177615 A1 | 11/2002 | Bandyopadhyay et al. |
| 2002/0192778 A1 | 12/2002 | Schupp et al. |
| 2002/0193361 A1 | 12/2002 | Ashley et al. |
| 2002/0197261 A1 | 12/2002 | Li et al. |
| 2002/0198141 A1 | 12/2002 | McChesney et al. |
| 2003/0003094 A1 | 1/2003 | Hunter et al. |
| 2003/0004209 A1 | 1/2003 | Hunter et al. |
| 2003/0004338 A1 | 1/2003 | Li et al. |
| 2003/0023082 A1 | 1/2003 | Ashley et al. |
| 2003/0036177 A1 | 2/2003 | Strohhacker |
| 2003/0036515 A1 | 2/2003 | Pardee et al. |
| 2003/0045711 A1 | 3/2003 | Ashley et al. |
| 2003/0049841 A1 | 3/2003 | Short et al. |
| 2003/0054977 A1 | 3/2003 | Kumar et al. |
| 2003/0060623 A1 | 3/2003 | Vite et al. |
| 2003/0069277 A1 | 4/2003 | Danishefsky et al. |
| 2003/0073205 A1 | 4/2003 | Arslanian et al. |
| 2003/0073615 A1 | 4/2003 | Li et al. |
| 2003/0073617 A1 | 4/2003 | Li et al. |
| 2003/0073677 A1 | 4/2003 | Lee |
| 2003/0087888 A1 | 5/2003 | Regueiro-Ren et al. |
| 2003/0096381 A1 | 5/2003 | Julien et al. |
| 2003/0105330 A1 | 6/2003 | Danishefsky et al. |
| 2003/0109500 A1 | 6/2003 | Pero et al. |
| 2003/0113335 A1 | 6/2003 | Li et al. |
| 2003/0114363 A1 | 6/2003 | Li et al. |
| 2003/0114450 A1 | 6/2003 | Santi et al. |
| 2003/0114504 A1 | 6/2003 | Webster et al. |
| 2003/0114518 A1 | 6/2003 | Li et al. |
| 2003/0124055 A1 | 7/2003 | Li et al. |
| 2003/0125362 A1 | 7/2003 | Danishefsky et al. |
| 2003/0130170 A1 | 7/2003 | Li et al. |
| 2003/0130178 A1 | 7/2003 | Li et al. |
| 2003/0134883 A1 | 7/2003 | Myles et al. |
| 2003/0139460 A1 | 7/2003 | Schwede et al. |
| 2003/0144523 A1 | 7/2003 | Klar et al. |
| 2003/0144533 A1 | 7/2003 | Iwasaki et al. |
| 2003/0147807 A1 | 8/2003 | Li et al. |
| 2003/0149281 A1 | 8/2003 | Westermann et al. |
| 2003/0158412 A1 | 8/2003 | Westermann et al. |
| 2003/0166507 A1 | 9/2003 | Li et al. |
| 2003/0171596 A1 | 9/2003 | Danishefsky et al. |
| 2003/0176320 A1 | 9/2003 | Li et al. |
| 2003/0176368 A1 | 9/2003 | Danishefsky et al. |
| 2003/0176473 A1 | 9/2003 | Taylor et al. |
| 2003/0176710 A1 | 9/2003 | Klar et al. |
| 2003/0180760 A1 | 9/2003 | Basch et al. |
| 2003/0186965 A1 | 10/2003 | Vite et al. |
| 2003/0186983 A1 | 10/2003 | Mastalerz et al. |
| 2003/0187039 A1 | 10/2003 | Favreau et al. |
| 2003/0187273 A1 | 10/2003 | White et al. |
| 2003/0191089 A1 | 10/2003 | Regueiro-Ren et al. |
| 2003/0194787 A1 | 10/2003 | Hofmann et al. |
| 2003/0203876 A1 | 10/2003 | Hoogevest |
| 2003/0203929 A1 | 10/2003 | Ghosh |
| 2003/0203938 A1 | 10/2003 | Nicolaou et al. |
| 2003/0208080 A1 | 11/2003 | Danishefsky et al. |
| 2004/0006087 A1 | 1/2004 | Cutler et al. |
| 2004/0023345 A1 | 2/2004 | Vite et al. |
| 2004/0024032 A1 | 2/2004 | Voi et al. |
| 2004/0024033 A1 | 2/2004 | O'Reilly et al. |
| 2004/0030147 A1 | 2/2004 | White et al. |

| | | | | | | |
|---|---|---|---|---|---|---|
| 2004/0038324 | A1 | 2/2004 | Atadja et al. | DE | 19833750 A1 | 2/1999 |
| 2004/0039026 | A1 | 2/2004 | Nicoloou et al. | DE | 19744135 C1 | 3/1999 |
| 2004/0044203 | A1 | 3/2004 | Wittman et al. | DE | 19749717 A1 | 5/1999 |
| 2004/0044221 | A1 | 3/2004 | Danishefsky et al. | DE | 19751200 A1 | 5/1999 |
| 2004/0049051 | A1 | 3/2004 | Hoefle et al. | DE | 19813821 A1 | 9/1999 |
| 2004/0053910 | A1 | 3/2004 | Danishefsky et al. | DE | 19830060 A1 | 2/2000 |
| 2004/0053978 | A1 | 3/2004 | Lee et al. | DE | 19846493 A1 | 4/2000 |
| 2004/0053995 | A1 | 3/2004 | Danishefsky et al. | DE | 19849464 A1 | 4/2000 |
| 2004/0054186 | A1 | 3/2004 | Das et al. | DE | 19907588 A1 | 8/2000 |
| 2004/0054188 | A1 | 3/2004 | Kusters et al. | DE | 19908760 A1 | 8/2000 |
| 2004/0058899 | A1 | 3/2004 | Klimko | DE | 19908763 A1 | 8/2000 |
| 2004/0058969 | A1 | 3/2004 | Buchmann et al. | DE | 19908765 A1 | 8/2000 |
| 2004/0062810 | A1 | 4/2004 | Hunter et al. | DE | 19908767 A1 | 10/2000 |
| 2004/0063707 | A1 | 4/2004 | Bhide et al. | DE | 19923001 A1 | 11/2000 |
| 2004/0063708 | A1 | 4/2004 | Bhide et al. | DE | 19930111 A1 | 1/2001 |
| 2004/0063712 | A1 | 4/2004 | Salvati et al. | DE | 19954228 A1 | 9/2001 |
| 2004/0063715 | A1 | 4/2004 | Paruch et al. | DE | 10015836 A1 | 10/2001 |
| 2004/0072760 | A1 | 4/2004 | Carboni et al. | DE | 10020517 A1 | 10/2001 |
| 2004/0072832 | A1 | 4/2004 | Bhide et al. | DE | 10020899 A1 | 10/2001 |
| 2004/0072835 | A1 | 4/2004 | Paruch et al. | DE | 19954230 A1 | 11/2001 |
| 2004/0072870 | A1 | 4/2004 | Nicolaou et al. | DE | 10051136 A1 | 4/2002 |
| 2004/0072882 | A1 | 4/2004 | Johnson et al. | EP | 0903348 A1 | 3/1999 |
| 2004/0073026 | A1 | 4/2004 | Das et al. | EP | 0975622 B1 | 2/2000 |
| 2004/0076672 | A1 | 4/2004 | Hunter et al. | EP | 0975638 B1 | 2/2000 |
| 2004/0077696 | A1 | 4/2004 | Borzilleri et al. | EP | 1001951 B1 | 5/2000 |
| 2004/0077875 | A1 | 4/2004 | Das et al. | EP | 1043369 A1 | 10/2000 |
| 2004/0082651 | A1 | 4/2004 | Wessjohann et al. | EP | 1080082 B1 | 3/2001 |
| 2004/0087610 | A1 | 5/2004 | Pardee et al. | EP | 1121364 B1 | 8/2001 |
| 2004/0087634 | A1 | 5/2004 | Hoefle et al. | EP | 1186606 A1 | 3/2002 |
| 2004/0092478 | A1 | 5/2004 | Rothermel et al. | EP | 1201666 A2 | 5/2002 |
| 2004/0092514 | A1 | 5/2004 | Velaparthi et al. | EP | 1275648 A1 | 1/2003 |
| 2004/0092560 | A1 | 5/2004 | Hoefle et al. | EP | 1340498 A1 | 9/2003 |
| 2004/0097516 | A1 | 5/2004 | Dwyer et al. | EP | 1386922 A2 | 2/2004 |
| 2004/0097517 | A1 | 5/2004 | Dwyer et al. | EP | 1407784 A1 | 4/2004 |
| 2004/0102451 | A1 | 5/2004 | Guzi et al. | EP | 1428826 A2 | 6/2004 |
| 2004/0102452 | A1 | 5/2004 | Guzi et al. | EP | 1440973 A2 | 7/2004 |
| 2004/0102495 | A1 | 5/2004 | Danishefsky et al. | WO | WO-9310121 | 5/1993 |
| 2004/0106624 | A1 | 6/2004 | Guzi et al. | WO | WO-9310121 A1 | 5/1993 |
| 2004/0106985 | A1 | 6/2004 | Jang | WO | WO-9503035 | 2/1995 |
| 2004/0116442 | A1 | 6/2004 | Guzi et al. | WO | WO-9719086 A1 | 5/1997 |
| 2004/0126379 | A1 | 7/2004 | Adolf et al. | WO | WO-9808849 A1 | 3/1998 |
| 2004/0127432 | A1 | 7/2004 | Nicolaou et al. | WO | WO-9822461 A1 | 5/1998 |
| 2004/0132146 | A1 | 7/2004 | Benigni et al. | WO | WO-9825929 A1 | 6/1998 |
| 2004/0132692 | A1 | 7/2004 | Sherrill et al. | WO | WO-9838192 A1 | 9/1998 |
| 2004/0132736 | A1 | 7/2004 | Guzi et al. | WO | WO-9847891 | 10/1998 |
| 2004/0132754 | A1 | 7/2004 | Brandt et al. | WO | WO-9854966 | 12/1998 |
| 2004/0133271 | A1 | 7/2004 | Jang | WO | WO-9901124 A1 | 1/1999 |
| 2004/0142931 | A1 | 7/2004 | Vite et al. | WO | WO-9902514 A2 | 1/1999 |
| 2004/0142990 | A1 | 7/2004 | Hofmann et al. | WO | WO-9903848 | 1/1999 |
| 2004/0152708 | A1 | 8/2004 | Li et al. | WO | WO-9903848 A1 | 1/1999 |
| 2004/0157897 | A1 | 8/2004 | DiMarco et al. | WO | WO-9907692 | 2/1999 |
| 2004/0167083 | A1 | 8/2004 | Bosslet et al. | WO | WO-9907692 A2 | 2/1999 |
| 2004/0167097 | A1 | 8/2004 | Zhou et al. | WO | WO-9927890 | 6/1999 |
| 2004/0176429 | A1 | 9/2004 | Li et al. | WO | WO-9928324 | 6/1999 |
| 2004/0192621 | A1 | 9/2004 | Nihei et al. | WO | WO-9939694 | 8/1999 |
| | | | | WO | WO-9942602 | 8/1999 |
| | FOREIGN PATENT DOCUMENTS | | | WO | WO-9943320 | 9/1999 |
| DE | 19542986.9 | | 5/1997 | WO | WO-9943653 | 9/1999 |
| DE | 19607702 | A1 | 9/1997 | WO | WO-9954318 | 10/1999 |
| DE | 19636343 | C1 | 10/1997 | WO | WO-9954319 | 10/1999 |
| DE | 19638870 | A1 | 3/1998 | WO | WO-9954330 | 10/1999 |
| DE | 19639456.2 | | 3/1998 | WO | WO-9958534 | 11/1999 |
| DE | 19645361 | A1 | 4/1998 | WO | WO-9959985 | 11/1999 |
| DE | 19645362 | A1 | 4/1998 | WO | WO-9965913 | 12/1999 |
| DE | 19701758 | A1 | 7/1998 | WO | WO-9966028 | 12/1999 |
| DE | 19713970 | A1 | 10/1998 | WO | WO-9967252 | 12/1999 |
| DE | 19720312 | A1 | 11/1998 | WO | WO-9967253 | 12/1999 |
| DE | 19821954 | A1 | 11/1998 | WO | WO-0000485 A1 | 1/2000 |
| DE | 19726627 | A1 | 12/1998 | WO | WO-0031247 A2 | 6/2000 |
| DE | 19735574 | A1 | 2/1999 | WO | WO-0037473 A1 | 6/2000 |
| DE | 19735575 | A1 | 2/1999 | WO | WO-0039276 A2 | 7/2000 |
| DE | 19735578 | A1 | 2/1999 | WO | WO-0047584 A2 | 8/2000 |
| | | | | WO | WO-0049019 A2 | 8/2000 |

| | | | |
|---|---|---|---|
| WO | WO-0049020 A2 | 8/2000 |
| WO | WO-0049021 A2 | 8/2000 |
| WO | WO-0050423 A1 | 8/2000 |
| WO | WO-0057874 A1 | 10/2000 |
| WO | WO-0058254 A1 | 10/2000 |
| WO | WO-0066589 A1 | 11/2000 |
| WO | WO-0071521 A1 | 11/2000 |
| WO | WO-0107439 A2 | 2/2001 |
| WO | WO-0110412 A1 | 2/2001 |
| WO | WO-0127308 A2 | 4/2001 |
| WO | WO-0164650 A2 | 9/2001 |
| WO | WO-0166154 A2 | 9/2001 |
| WO | WO-0170716 A1 | 9/2001 |
| WO | WO-0173103 A2 | 10/2001 |
| WO | WO-0181341 A2 | 11/2001 |
| WO | WO-0183800 A2 | 11/2001 |
| WO | WO-0192255 A2 | 12/2001 |
| WO | WO-02030356 | 4/2002 |
| WO | WO-02032844 | 4/2002 |
| WO | WO-0242432 | 5/2002 |
| WO | WO-0242432 A2 | 5/2002 |
| WO | WO-0246196 | 6/2002 |
| WO | WO-0246196 A1 | 6/2002 |
| WO | WO-02058699 A1 | 8/2002 |
| WO | WO-02058700 A1 | 8/2002 |
| WO | WO-02058701 A1 | 8/2002 |
| WO | WO-02060904 A2 | 8/2002 |
| WO | WO-02062338 A1 | 8/2002 |
| WO | WO-02066033 A1 | 8/2002 |
| WO | WO-02066038 A1 | 8/2002 |
| WO | WO-02067941 A2 | 9/2002 |
| WO | WO-02072085 A1 | 9/2002 |
| WO | WO-02072858 A2 | 9/2002 |
| WO | WO-02074042 A2 | 9/2002 |
| WO | WO-02080846 A2 | 10/2002 |
| WO | WO-02096281 A1 | 12/2002 |
| WO | WO-02098868 A1 | 12/2002 |
| WO | WO-03007924 A2 | 1/2003 |
| WO | WO-03014063 A2 | 2/2003 |
| WO | WO-03014068 A1 | 2/2003 |
| WO | WO-03018002 A2 | 3/2003 |
| WO | WO-03022844 A2 | 3/2003 |
| WO | WO-03026744 A1 | 4/2003 |
| WO | WO-03029195 A1 | 4/2003 |
| WO | WO-03029260 A1 | 4/2003 |
| WO | WO-03042217 A2 | 5/2003 |
| WO | WO-03045324 A2 | 6/2003 |
| WO | WO-03049734 A1 | 6/2003 |
| WO | WO-03053949 A1 | 7/2003 |
| WO | WO-03057217 A1 | 7/2003 |
| WO | WO-03057830 A2 | 7/2003 |
| WO | WO-03070170 A2 | 8/2003 |
| WO | WO-03074053 A1 | 9/2003 |
| WO | WO-03074521 A1 | 9/2003 |
| WO | WO-03075899 A2 | 9/2003 |
| WO | WO-03076445 A2 | 9/2003 |
| WO | WO-03077903 A1 | 9/2003 |
| WO | WO-03078411 A1 | 9/2003 |
| WO | WO-03084536 A1 | 10/2003 |
| WO | WO-03096975 A2 | 11/2003 |
| WO | WO-03103712 A1 | 12/2003 |
| WO | WO-03105828 A1 | 12/2003 |
| WO | WO-2004007476 A1 | 1/2004 |
| WO | WO-2004012735 A2 | 2/2004 |
| WO | WO-2004014919 A2 | 2/2004 |
| WO | WO-2004016269 A1 | 2/2004 |
| WO | WO-2004017943 A2 | 3/2004 |
| WO | WO-2004018000 A2 | 3/2004 |
| WO | WO-2004018478 A2 | 3/2004 |
| WO | WO-2004018635 A2 | 3/2004 |
| WO | WO-2004022062 A1 | 3/2004 |
| WO | WO-2004022080 A2 | 3/2004 |
| WO | WO-2004022559 A1 | 3/2004 |
| WO | WO-2004022560 A1 | 3/2004 |
| WO | WO-2004024735 A2 | 3/2004 |
| WO | WO-2004025254 A2 | 3/2004 |
| WO | WO-2004026229 A2 | 4/2004 |
| WO | WO-2004026254 A2 | 4/2004 |
| WO | WO-2004026310 A1 | 4/2004 |
| WO | WO-2004026867 A2 | 4/2004 |
| WO | WO-2004026872 A1 | 4/2004 |
| WO | WO-2004026877 A1 | 4/2004 |
| WO | WO-2004028582 A1 | 4/2004 |
| WO | WO-2004028610 A2 | 4/2004 |
| WO | WO-2004030620 A2 | 4/2004 |
| WO | WO-2004030627 A2 | 4/2004 |
| WO | WO-2004032866 A2 | 4/2004 |
| WO | WO-2004032872 A2 | 4/2004 |
| WO | WO-2004032923 A1 | 4/2004 |
| WO | WO-2004035050 A1 | 4/2004 |
| WO | WO-2004043363 A2 | 5/2004 |
| WO | WO-2004043400 A2 | 5/2004 |
| WO | WO-2004043454 A1 | 5/2004 |
| WO | WO-2004043954 A2 | 5/2004 |
| WO | WO-2004048372 A1 | 6/2004 |
| WO | WO-2004050057 A2 | 6/2004 |
| WO | WO-2004050089 A1 | 6/2004 |
| WO | WO-2004052237 A2 | 6/2004 |
| WO | WO-2004052361 A1 | 6/2004 |
| WO | WO-2004052401 A2 | 6/2004 |
| WO | WO-2004054514 A2 | 7/2004 |
| WO | WO-2004054622 A1 | 7/2004 |
| WO | WO-2004054624 A1 | 7/2004 |
| WO | WO-2004056832 A2 | 7/2004 |
| WO | WO-2004061116 A2 | 7/2004 |
| WO | WO-2004063151 A2 | 7/2004 |
| WO | WO-2004078978 A1 | 9/2004 |
| WO | WO-2004080458 A1 | 9/2004 |
| WO | WO-2004085421 A2 | 10/2004 |
| WO | WO-2004087045 A2 | 10/2004 |

OTHER PUBLICATIONS

U.S. Appl. No. 11/123,530, filed Sep. 1, 2005, White et al.
U.S. Appl. No. 60/032,864, filed Dec. 13, 1996, Nicolau et al.
U.S. Appl. No. 08/856,533, filed May 14, 1997, Nicolau et al.
U.S. Appl. No. 10/004,571, filed Dec. 4, 2001, Danishefsky et al.
Abraham, et al., "Phase I Trial and Pharmacokinetic Study of BMS-247550, an Epothilone B Analog, Administered Intravenously on a Daily Schedule for Five Days", *Journal of Clinical Oncology*, 21(9): 1866-1873, 2003.
Agrawal, et al., "Treatment of Recurrent Cervical Adenocarcinoma with BMS-247550, an Epothilone B Analog", *Gynecologic Oncology*, 90: 96-99, 2003.
Ahmed et al., "Total Synthesis of the Microtubule Stabilizing Antitumor Agent Laulimalide and Some Nonnatural Analogues: The Power of Sharpless' Asymmedtric Epoxidation" *J. Org. Chem.* 68:3026-3042, 2003.
Altaha, et al., "Epothilones: A Novel Class of Non-Taxane Microtubule-Stabilizing Agents", *Current Pharmaceutical Design*, 8: 1707-1712, 2002.
Altmann et al., "Epothilone B and Its Analogs -A New Family of Anticancer Agents" *Mini-Rev. Med. Chem.* 3:149-158, 2003.
Altmann et al., "Epothilones and Related Structures—A New Class of Microtubule Inhibitors with Potent in vivo Antitumor Activity" *Biochim. Biophys. Acta*, 1470(3):M79-M91, 2000.
Altmann et al., "Epothilones and Their Analogs—Potential New Weapons in the Fight Against Cancer" *Chimia*, 54:612-621, 2000.
Altmann et al., "Microtubule-Stabilizing Agents: A Growing Class of Important Anticancer Drugs" *Curr. Opin. Chem. Biol.*, 5(4):424-431, Aug. 2001.
Altmann et al., "Synthesis and Biological Evaluation of Highly Potent Analogues of Epothilones B and D" *Bioorg. Med. Chem. Lett.* 10(24):2765-2768, 2000.

Altmann, K., "Microtubule-Stabilizing Agents: A Growing Class of Important Anticancer Drugs", *Current Opinion in Chemical Biology*, 5: 424-431, 2001.

Appendino et al., "The Synthesis of Epothilones: Highlights from a Year's Race" *Chemtracts* 11(9):678-696, 1998.

Arslanian et al., "A New Cytotoxic Epothilone from Modified Polyketide Synthases Heterologously Expresssed in *Myxococcus xanthus*" *J. Nat. Prod.* 65:1061-1064, 2002.

Avila et al., "The Use of Microtubule Poisons on Tumor Cells" *Cancer J.* 10(6):315-318, 1997.

Awada et al., "New Cytotoxic Agents and Molecular-Targeted Therapies in the Treatment of Metastatic" *Breast Cancer Review* 4-15, 2002.

Baggiolini et al., "Stereocontrolled Total Synthesis of 1α, 25-Dihydroxycholecalciferol and 1α, 25-Dihydroxyergocalciferol" *J. Org. Chem.* 51:3098-3108, 1986.

Baik et al., "Diastereoselective Cobalt-Catalyzed Aldol and Michael Cycloreductions" *J. Am. Chem. Soc.* 123:5112-5113, 2001.

Balog et al., "A Novel Aldol Condensation with 2-Methyl-4-Pentenal and Its Application to an Improved Total Synthesis of Epothilone B" *Angew. Chem. Int. Ed.* 37(19):2675-2678, 1998.

Balog et al., "Stereoselective Syntheses and Evaluation of Compounds in the 8-Desmethylepothilone A Series: Some Surprising Observations . . . " *Tetrahedron Letters* 38:26 4529-4532 (1997).

Balog et al., "Total Synthesis of Epothilone A" *Angew. Chem. Int. Ed.* 61:2801-2803, 1996.

Bayes, et al., "Gateways to Clinical Trials", Methods Find Exp Clin. Pharmacol. 25(1): 53-76, 2003.

Bellemin-Laponnaz et al., "The Kinetic Resolution of Allylic Alchols by a Non-Enzymatic Acylation Catalyst: Application to Natural Product Synthesis" *Chem. Commun.* 12:1009-1010, 2000.

Bertinato et al., "Studies Toward a Synthesis of Epothilone A: Stereocontrolled Assembly of the Acyl Region and Models for Macrocyclization" *J. Org. Chem.* 61:8000-8001, 1996.

Beyer et al., "Metabolic Diversity in Myxobacteria" *Biochim. Biophys. Acta* 1445(2):185-195, 1999.

Bijoy, P. et al., "Synthetic Studies Directed Towards Epothilone A: . . . ", *Tetrahedron Letters* 39:209-212 (1998).

Biswas et al., "Highly Concise Routes to Epothilones: The Total Synthesis and Evaluation of Epothilone 490" *J. Am. Chem. Soc.* 124:9825-9832, 2002.

Blum et al., "In vivo Metabolism of Epothilone B in Tumor-Bearing Nude Mice: Identification of Three New Epothilone B Metabolites by Capillary High-Pressure Liquid Chromatography/Mass Spectrometry/Tandem Mass Spectrometry" *Rapid Commun. Mass Spectrom.* 15(1):41-49, 2001.

Bocci et al., "Protracted Low-Dose Effects on Human Endothelial Cell Proliferation and Survival in Vitro Reveal a Selective Antiangiogenic Window for Various Chemotherapeutic Drugs" *Cancer Research* 62:6938-6943, 2002.

Boddy et al., "Epothilone C. Macrolactonization and Hydrolysis Are Catalyzed by the Isolated Thioesterase Domain of Epothilone Polyketide Synthase" *J. Am. Chem. Soc.* 125:3428-3429, 2002.

Bode et al., "Stereoselective Syntheses of Epothilones A and B via Directed Nitrile Oxide Cycloaddition" *J. Am. Chem. Soc.* 123(15):3611-3612, 2001.

Bode et at, "Stereoselective Syntheses of Epothilones A and B via Nitrile Oxide Cycloadditions and Related Studies" *J. Org. Chem.*, 66(19):6410-6424, 2001.

Bollag et al., "Epothilones, a New Class of MT-stabilizing Agents with a Taxol-Like Mechanism of Action" *Cancer Research* 55:2325-2333, 1995.

Bollag et at, "Epothilones: Novel Microtubule Stabilizing Agents" *Expert Opin. Invest. Drugs* 6(7):867-873, 1997.

Bollag, et al., "Epothilones, A New Class of Microtubule-Stabilizing Agents with A Taxol-Like Mechanism of Action", *Chemstracts—Organic Chemistry*, 11: 671-677, 1998.

Bornscheuer, et al., "Directed Evolution of an Esterase for the Stereoselective Resolution of a Key Intermediate in the Synthesis of Epothilones", *Biotechnol Bioeng.* 58: 554-559, 1998.

Borzilleri, et al., "A Novel Application of a Pd(0)-Catalyzed Nucleophilic Substitution Reaction to the Regio and Stereoselective Synthesis of Lactam Analogues of the Epothilone Natural Products" *J. Am. Chem. Soc.* 122(37):8890-8897, 2000.

Borzilleri, et al., "A Novel Application of a Pd(0)-Catalyzed Nucleophilic Substitution Reaction to the Regio—and Stereoselective Synthesis of Lactam Analogues of the Epothilone Natural Products", *Chemtracts—Organic Chemistry*, 14: 401-404, 2001.

Broker, et al., "Late Activation of Apoptotic Pathways Plays a Negligible Role in Mediating the Cytotoxic Effects of Discodermolide and Epothilone B in Non-Small Cell Lung Cancer Cells", *Cancer Research*, 62: 4081-4088, 2002.

Broker, et al., "The Role of New Agents in the Treatment of Non-Small Cell Lung Cancer", *European Journal of Cancer*, 38: 2347-2361, 2002.

Carlomagno et al., "Derivation of Dihedral Angles from Ch-Ch Dipolar-Dipolar Cross-Correlated Relaxation Rates: A C-C Torsion Involving a Quaternary Carbon Atom in Epothilone A Bound to Tubulin" *Angew. Chem. Int. Ed.* 42:2515-2517, 2003.

Carlomagno et al., "The High-Resolution Solution Structure of Epothilone A Bound to Rubulin: An Understanding of the Structure-Activity Relationships for a Powerful Class of Antitumor Agents" *Angew. Chem. Int. Ed.* 42:2511-2515, 2003.

Carreira, "Discovery and Study of New Reaction Chemistry: Applications in Complex Molecule Assembly" *Chimia* 55(10):818-820, 2001.

Casas et al., "BINOLAM, a Recoverable Chiral Ligand for Bifunctional Enantioselective Catalysis: The Asymmetric Synthesis of Cyanohydrins" Organic Letters 4(15):2589-2592, 2002.

Chakraborty,T.K. et al., "Radical-induced Opening of Trisubstituted Epothilones", *Tetrahedron Letters* 39:101-104 (1998).

Chappell, et al., "En Route to a Plant Scale Synthesis of the Promising Antitumor Agent 12,13-Desoxyepothilone B" *Org. Letter.* 2(11): 1633-1636, 2000.

Chen et al., "Epothilone Biosynthesis: Assembly of the Methylthiazolylcarboxy Starter Unit on the EpoB Subunit" *Chem. Biol.* 8(9):899-912, 2001.

Chou et al., "Design and Total Synthesis of a Superior Family of Epothiolone Analogues, which Eliminate Xenograft Tumors to a Nonrelapsable State" Angew. Chem. Int. Ed. Engl. 42:4762-4767, 2003.

Chou et al., "Desoxyepothilone B: An efficacious microtubule-targeted antitumor agent with a promising in vivo profile relative to epothilone B" Proc. Natl. Acad. Sci. USA 95:9642-9647, 1998.

Chou et al., "Quantitative Analysis of Dose-Effect Relationships The Combined Effects of Multiple Drugs or Enzyme Inhibitors" Adv. Enzyme Reg. 22:27-55, 1984.

Chou, et al., "Desoxyepothilone B is curative against human tumor xenografts that are refractory to paclitaxel" Proc. Natl. Acad. Sci. USA 95:15798-15802, 1998.

Claus, E. et al., "Synthesis of the C1-C9 Segment of Epothilones", *Tetrahedron Letters* 38:8:1359-1362 (1997).

Corey, et al., "Chemistry of Diimide. Some New Systems for the Hydrogenation of Multiple Bonds" *Tetrahedron Lett.* 347-352 1961.

Correia et al., "Physiochemical Aspects of Tubulin-Interacting Antimitotic Drugs" *Curr. Pharm. Des.* 7(13):1213-1228, 2001.

Costa, et al., "Neue Aspekte Bei Der Therapie des Ovarialkarzinoms—Was Andert Sich Nach Dem ASCO-Meeting 2001?", *Zentralbl Gynakol*, 124: 96-103, 2002.

Costa, et al., "New Aspects by the Therapy of Ovarian Cancer—What Changes After the ASCO Meeting 2001?", Zentralbl Gynakol, 124: 96-103, 2002.

Cowden et al., "Cancer Drugs-Better than Taxol?" *Nature* 387:238-239, 1997.

Danishefsky et al., "A Novel Aldol Condensation with 2-Methyl-4-Pentenal and the Application to an Improved Total Synthesis of Epothilone B" *Angew. Chem. Int. Ed.* 37:2675, 1998.

Danishefsky et al., "Chemical Synthesis and Biological Studies of the Epothilones-Microtubule Stabilizing Agents with Enhanced Activity Against Multidrug-Resistant Cell Lines and Tumors" *Chem. 21st Century*, Ed. Keinan, Wiley-VCH Verlag, 8-36, 2001.

Danishefsky et al., "Complex Target Oriented Synthesis in the Drug Discovery Process: A Case History in the dEpoB Series" *J. Org. Chem.* 64:8434-8456, 1999.

Danishefsky et al., "Desoxyepothilone B is Curative Against Human Tumor Xenografts that are Refractory to Pacilitaxel" *Proc. Nat. Acad. Sci. USA* 95:15798, 1998.

Danishefsky et al., "En Route to a Plant Scale Synthesis of the Promising Antitumor Agent 12,13- Desocyepothilone B" *Org. Letters* 2:1633-1636, 2000.

Danishefsky et al., "Epothilones: Microtubule Stabilizing Agents with Enhanced Activity Against Multidrug-Resistant Cell Lines and Tumors" Actualites de Chimie Therpaeutique,Vingt-cinqieme serie, Paul Ehrlich Lecture, *Societe de Chimie Therapeutique* , Elsevier, Paris, New York, 25:187-206, 1999.

Danishefsky et al., "Insights into Long-Range Structural Effects on the Stereochemistry of Aldol Condensations: A Practical Total Synthesis of Desoxyepothilone F" *J. Am. Chem. Soc.* 123(22):5249-5259, 2001.

Danishefsky et al., "New Chemical synthesis of the Promising Cancer Chemotherapeutic Agent 12,13-Desoxyepothilone B: Discovery of a Surprising Long-Range Effect on the Diastereoselective of an Aldol Condensation." *J. Am. Chem. Soc.* 121:7050-7062, 1999.

Danishefsky et al., "On the Interactivity of Complex Synthesis and Tumor Pharmacology in the Drug Discovery Process: Total Synthesis and Comparative In Vivo Evaluations of the 15-Aza Epothilones" *J. Org. Chem.* 66(12):4369-4378, 2001.

Danishefsky et al., "On the Total Synthesis and Preliminary Biological Evaluations of 15 (R) and 15 (S) Aza-dEpoB: A Mitsunobu Inversion at C15 in Pre-Epothilone Fragments" *Org. Letters* 2:1637-1639, 2000.

Danishefsky et al., "Remarkable Long Range Effects on the Diastereoface Selectivity in an Aldol Condensation" *Tet. Lett.* 40:2267-2270, 1999.

Danishefsky et al., "Remote Effects in Macrolide Formation Through Ring Forming Olefin Metathesis: An Application to the Synthesis of Fully Active Epothilone Congeners" *J. Am. Chem. Soc.* 119:2733, 1997.

Danishefsky et al., "Structure-Activity Relationships of the Epothilones and the First in Vivo Comparison with Paclitaxel" *Angew. Chem. Int. Ed.* 7:824-826, 1997.

Danishefsky et al., "Subtle Variations in the Long Range Transmission of Stereochemical Information: Matched and Mismatched Aldol Reactions" *Angew. Chem. Int. Ed.* 39:4505-4508, 2000.

Danishefsky et al., "The microtubule-stabilizing agents epothilones A and B and their desoxy-derivatives induce mitotic arrest and apoptosis in human prostate cancer cells" *Prostate Cancer And Prostatic Diseases* 2:41-52, 1999.

Danishefsky et al., "The Synthesis and Evaluation of 12,13-Benzodesoxyepothilone B: a Highly Convergent Route" *Tet. Lett.* 40:6895-6898, 1999.

Danishefsky et al., "The Total Synthesis and Antitumor Activity of 12, 13-Desoxyepothilone F: An Unexpected Solvolysis Problem at C15, Mediated by Remote Substitution at C21" *J. Org. Chem.* 65(20):6525-6533, 2000.

Danishefsky et al., "Total Synthesis of (−)-Epothilone B: An Extension of the Suzuki Coupling Method and Insights into Structure—Activity Relationships of the Epothilones" *Angew. Chem. Int. Ed.* 36:757, 1997.

De Brabander et al., "Towards a Synthesis of Epothilone A" *Synlett.* 3:328, 1998.

De Brabander et al., "Towards a Synthesis of Epothilone A. Rapid Assembly of the C(1)-C(6) and C(7)-C(12) Fragments" *Synlett.* 6:824-826, 1997.

Delbaldo et al., "Nouveaux medicamenets dans le cancer bronchique" La Presse Medicate 31:802-809, 2002.

Denmark et al., "Cyclopropanation with Diazomethane and Bis(Oxazoline) Palladium(II) Complexes" *J. Org. Chem.* 62:3375-3389, 1997.

Duthaler et al., "Enantioselective Aldol Reaction of Tert-Butyl Acetate Using Titanium-Carbohydrate Complexes" *Angew. Chem. Int. Ed. Engl.* 28:495-497, 1989.

End et al., "Synthetic Epothilone Analogs with Modifications in the Northern Hemisphere and the Heterocyclic Side-Chain-Synthesis and Biological Evaluation" Proc. ECSOC-3, Proc. ECSOC-4, 1999, 2000, Meeting Date 1999-2000, 1431-1442, Ed: Pombo-Villar, Esteban. *Molecular Diversity Preservation International*: Basel, Switz. 2000, Doc. No. 134:311010, 2000.

Ermolenko et al., "Synthesis of Epothilones B and D from D-Glucose" *Tet. Lett.* 43:2895-2898, 2002.

Essayan, et al., "Successful Parenteral Desensitization to Paclitaxel", *J. Allergy Clin. Immunol.* 97:42-46, 1996.

Finley et al., "Metathesis vs. Metastasis: The Chemistry and Biology of The Epothilones" *Chem. Ind.* 24:991-996, 1997.

Fletcher et al., "Structure of the Mitogen-Inducible TIS10 Gene and Demonstration That the TIS10-Encoded Protein Is a Functional Prostaglandin G/H Synthase" *J. Biol. Chem.* 267:4338-4344, 1992.

Frykman et al., "Control of Secondary Metabolite Congener Distributions via Modulation of the Dissolved Oxygen Tension" *Biotechnol. Prog.* 18:913-920, 2002.

Furstner et al., "Concise Total Syntheses of Epothilone A and C Based on Alkyne Metathesis" *Chem. Commun.* 12:1057-1059, 2001.

Furstner, "Olefin Metathesis and Beyond", *Angew. Chem. Int. Ed. Engl.* 39:3013-3043, 2000.

Gabriel, "The Chromium-Reformatsky Reaction: Asymmetric Synthesis of the Aldol Fragment of the Cytotoxic Epothilones from 3-(2-Bromoacyl)—2-Oxazolidinones" *Tet. Lett.* 38(8):1363-1366, 1997.

Geng et al., "Design and Synthesis of De Novo Macrocyclic Hybrids as Potential Anticancer Agents" *Abstr. Pap.-Am. Chem. Soc.*, 221st, MEDI-130, 2001.

Georg et al., "Studies Toward the Synthesis of Epothilone Affinity Labels" Book of Abstracts, 219th ACS National Meeting, San Francisco, CA, Mar. 26-30, MEDI-075, 2000.

Gerlach et al., "Synthesis of the C(7)-C(17) Segment of Epothilones by a 10-Membered Ring Closing Metathesis Reaction" *Synlett.* 10:1108-1110, 1998.

Gerth et al., "Studies on the Biosynthesis of Epothilones: The Biosynthetic Origin of the Carbon Skeleton" *J. Antibiot.* 53(12):1373-1377, 2000.

Gerth, K. et al., "Epothilone A and B: Antifungal and Cytotoxic Compounds . . . ", *Liebigs Ann.Chem.* 74 & 75, 49-53 (1996).

Gerth. et al., "Studies on the Biosynthesis of Epothilones: the PKS and Epothilone C/D Monooxygenase" *J. Antibiot.*, 54(2):144-148, 2001.

Giannakakou et al., "Paclitaxel-resistant Human Ovarian Cancer Cells Have Mutant β-Tubulins. That Exhibit Impaired Paclitaxel-Driven Polymerization" *J. Biol. Chem.* 272(27):17118-17125, 1997.

Giannakakou, et al., "A Common Pharmacophore for Epothilone and Taxanes: A Molecular Basis for Drug Resistance Conferred by Tubulin Mutations in Human Cancer Cells" *Proc. Natl. Acad. Sci.*, 97(6): 2904-2909, 2000.

Griffin, et al., "Molecular Determinants of Epothilone B Derivative (BMS 247550) and Apo-2L/TRAIL-induced Apoptosis of Human Ovarian Cancer Cells", Gynecologic Oncology, 89: 37-47, 2003.

Grubbs, et al., "Ring-Closing Metathesis and Related Processes in Organic Synthesis" *Acc. Chem. Res.* 28: 446-452, 1995.

Gupta, et al., Understanding Tubulin-Taxol Interactions: Mutations That Impart Taxol Binding to Yeast Tubulin PNAS, 100: 5394-6397, 2003.

Haar, et al., "Discodermolide, A Cytotoxic Marine Agent That Stabilizes Microtubules More Potently Than Taxol", *Biochemistry*, 35: 243-250, 1996.

Hamashima, et al., "Highly Enantioselective Cyanosilylation of Aldehydes Catalyzed by a Lewis Acid-Lewis Base Bifunctional Catalyst" *Tetrahedron*, 57(5): 805-814, 2001.

Hardt, et al., "New Natural Epothilones from *Sorangium cellulosum*, Strains So ce90/B2 and So ce90/D13: Isolation, Structure Elucidation and SAR Studies" *J. Nat. Prod.*, 64(7): 847-856, 2001.

Harris, et al., "Chemical Synthesis and Biological Studies of the Epothilones—Microtubule Stabilizing Agents with Enhanced Activity Against Multidrug-Resistant Cell Lines and Tumors", *Chemistry for the 21st Century*, 8-36, 2001.

Harris, et al., Complex Target-Oriented Synthesis in the Drug Discovery Process: A Case History in the dEpoB Series *J. Org. Chem.*, 64:8434-8456, 1999.

Hayward, et al. "Total Synthesis of Rapamycin via a Novel Titanium-Mediated Aldol Macrocyclization Reaction", *J. Am. Chem. Soc.*, 115: 9345-9346, 1993.

He, et al., "A Common Pharmacophore for Taxol and the Epothilones Based on the Biological Activity of a Taxane Molecule Lacking a C-13 Side Chain" *Biochemistry*, 39(14): 3972-3978, 2000.

He, et al.. "Novel Molecules that Interact with Microtubules and have Functional Activity Similar to Taxol" *Drug Discovery Today*, 6(22): 1153-1164, 2001.

Hindpur, et al., "Total Synthesis of Epothilone A" *Tetrahedron Letters*, 42(42): 7341-7344, 2001.

Hindupur, et al., "Total Synthesis of Epothilone", *Tetrahedron Lett.* 42: 7341-7344, 2000.

Hofle et al., "Epothilone A and B—Novel 16-Membered Macrolides with Cytotoxic Activity: Isolation, Crystal Structure, and Conformation in Solution" *Angew. Chem. Int. Ed. Engl.* 35:1567-1569, 1996.

Holland, et al., "Design, Synthesis and Biological Evaluation of Epothilone Analogs", Book of Abstracts, 215th ACS National Meeting, Dallas, Mar. 29-Apr. 2, ORGN-015.

Holland, J.M., "The Synthesis of a Cyclopropyl Taxane Analog via Sequential Diels-Alder Reactions: the Design and Synthesis of Novel Epothilone Analogs" University of Pennsylvania Order No. DA9953544 From: Diss. Abstr. Int., B2000, 60(12) 6106, 1999.

Inoue, et al., "Design and Synthesis of Taxoid-Epothilone Hybrids", Book of Abstracts, 216th ACS National Meeting, Boston, Aug. 23-27, ORGN-380.

Ivin, "Some Recent Applications of Olefin Metathesis in Organic Synthesis: A Review", *J. Mol. Catal. A: Chem*, 133(1-2): 1998.

Jaenicke, L., "Epothilone from Amphora" *Chem. Unserer Zeit (German)*, 34(4): 257, 2000.

Jiang, et al., "Advances in Research on Novel Natural Anticancer Compounds: Epothilones" *Tianran Chanwu Yanjiu Yu Kaifa (Chinese)*, 11(3): 77-81, 1999.

Johnson, et al.. "Synthesis, Structure Proof, and Biological Activity of Epothilone Cyclopropanes" *Org. Lett*, 2: 1537-1540, 2000.

Julien, et al., "Isolation and Characterization of the Epothilone Biosynthetic Gene Cluster from *Sorangium cellulosum*" Gene, 249(1-2): 153-160, 2000.

Kalesse, et al., "The Formal Total Synthesis of Epothilone A" *Eur. J. Org. Chem.*, 11: 2817-2823, 1999.

Koch, et al., Diastereoselective Titanium Enolate Aldol Reaction for the Total Synthesis of Epothilones Organic Letters, 2(22): 3811-3814, 2002.

Kowalski, R.J. et al., "Activities of the Microtubule-stabilizing Agents Epothilones A and B . . . ", *J. of Biol.Chem.* 272:4 2534-2541 (1997).

Krische, et al., "Diastereoselective Cobalt-Catalyzed Aldol and Michael Cycloreductions" *J. Am. Chem. Soc.* 123: 5112-5113, 2001.

Lavelle, et al., "Nouveaux Taxanes et Derives d'Epothilone en Cours d'Etudes Cliniques", *Bull Cancer*, 89(4): 343-350, 2002.

Lee, et al., "BMS-247550: A Novel Epothilone Analog with a Mode of Action Similar to Paclitaxel but Possessing Superior Antitumor Efficacy" *Clin. Cancer Res.*, 7(5): 1429-1437, 2001.

Lee, et al., "Insights into Long-Range Structural Effects on the Stereochemistry of Aldol Condensations: A Practical Total Synthesis of Deoxyepothilone F" *J. Am. Chem. Soc.* 123: 5249-5259, 2001.

Lee, et al., "Synthesis of the C11-C21 and C13-C21 Fragments of Epothilones from D-glucose" *Bull. Korean Chem. Soc.*, 21(12): 1177-1178, 2000.

Lee, et al., "Total Synthesis and Antitumor Activity of 12,13-Desoxyepothilone F: An Unexpected Solvolysis Problem at C15, Mediated by Remote Substitution at C21" *J. Org. Chem.*, 65: 6525-6533, 2000.

Levin, et al., "An Alternative Procedure for the Aluminum-Mediated Conversion of Esters to Amides", *Synth. Commun.* 12: 989, 1982.

Li, et al., "Antimitotic Agents" *Annu. Rep. Med. Chem.*, 34: 139-148, 1999.

Li, et al., "Process Development of the Semisynthesis of a Biologically Active Epothilone Analogue" Abstracts of Papers, 222nd ACS National Meeting, Chicago, IL, Aug. 26-30, ORGN-238, 2001.

Li, et al., "Synthesis of a Novel Epothilone B Analog as a Potential Photoaffinity Label" *Abstr. Pap.-Am. Chem. Soc.* 221st, MEDI-137, 2001.

Lichtner, et al., "Subcellular Distribution of Epothilones in Human Tumor Cells" *Proc. Natl. Acad. Sci. U.S.A.*, 98(20): 11743-11748, 2001.

Lin, et al., "Design and Synthesis of Taxoid-Epothilone Hybrids" Book of Abstracts, 216th ACS National Meeting, Boston, Aug. 23-27, ORGN-464.

Lindel, et al., "Eleutherobin, A New Cytotoxin that Mimics Paclitaxel (Taxol) by Stabilizing Microtubules", *J. Am. Chem. Soc.* 119: 8744-8745, 1997.

List, et al., "Proline-Catalyzed Direct Asymmetric Aldol Reactions" *J. Am. Chem. Soc.* 122:2395-2396, 2000.

Liu, et al., "Epoxide Opening with Acetylide for Synthesis of Epothilone A C7-21 Segment", *Tetrahedron Lett.* 39(29): 5261-5264, 1998.

Liu, et al., "Synthesis of the C11-16+C27 Segment of Epothilone A", *Chin. Chem. Lett.* 9(1): 35-38, 1998.

Liu, et al., "Total Synthesis of Epothilone A through Stereospecific Epoxidation of the p-Methoxybenzyl Ether of Epothilone C" *Chem. Eur. J.*, 8(16): 3747-3756, 2002.

Liu, Z.Y. et al., "Chiral Synthesis of the C3-13 Segment of Epothilone A" *Synlett Letters* 1383-84 (1997).

Lythgoe, et al., "Allylic Phosphine Oxides as Precursors of Dienes of Defined Geometry: Synthesis of 3-Deoxyvitamin $D_2$2", *Tetrahedron Lett.* 40:3863-3866, 1975.

Lythgoe, et al., "Synthetic Approaches to Vitamin D and its Relatives", *Chem. Soc. Rev.* 449-475, 1981.

Machajewski, et al., "Chemoenzymic Synthesis of Key Epothilone Fragments" *Synthesis (Spec. Iss.)*, 1469-1472, 1999.

Martello, et al., "Taxol and Discodermolide Represent a Synergistic Drug Combination in Human Carcinoma Cell Lines", Clinical Cancer Research, 6: 1978-1987, 1978.

Martello, et al., "Taxol and Discodermolide Represent a Synergistic Drug Combination in Human Carcinoma Cell Lines", *Clinical Cancer Research*, 6: 1978-1987, 2000.

Martin, "How Stable are Epoxides? A Novel Synthesis of Epothilone B" *Angew. Chem. Int. Ed*, 39(3): 581-583, 2000.

Martin, et al.. "The 12,13-diol Cyclization Approach for a Truly Stereocontrolled Total Synthesis of Epothilone B and the Synthesis of a Conformationally Restrained Analog" *Chem. Eur. J*, 42(47): 8373-8377, 2001.

May, et al., "Total Synthesis of (-) Epothilone B", *Chem. Commun.*, 95: 1369-1374, 1998.

McDaid et al., "Validation of the Pharmacodynamics of BMS-247550, an Analogue of Epothilone B, During a Phase I Clinical Study" Clinical Cancer Research 8:2035-2043, 2002.

Meng et al. "Studies toward a Synthesis of Epothilone A: Use of Hydropyran Templates for the Management of Acyclic Stereochemical Relationships" J. Org. Chem. 61:23 7998-8001 (1996).

Meng et al. "Total Synthesis of Epothilones A and B" *J. Am. Chem. Soc.* 119:42 10073-10092 (1997).

Meng et al., "Chapter I: The First Total Syntheses of Epothilones A, B, C and D. Chapter II: The First Total Syntheses of 12-epi-CP-263,114 and 12-epi-CP-225,917" Columbia University Order No. DA9949022 From: Diss. Abstr. Int., B2000, 60(10), 5096 (1999).

Moasser et al., "Farnesyl transferase inhibitors cause enhanced mitotic sensitivity to taxol . . . "*Proc. Natl. Acad. Sci. USA*, 95:1369-1374 (1998).

Molnar, et al., "The Biosynthetic Gene Cluster for the Microtubule-Stabilizing Agents Epothilones A and B from *Sorangium cellulosum* So ce90" *Chem. Biol.*, 7(2): 97-109, 2000.

Mooberry, et al., "Laulimalide and Isolaulimalide, New Paclitaxel-Like Microtubule-Stabilizing Agents", *Cancer Res.* 59: 653-680, 1999.

Muhlradt et al., "Epothilone B Stabilizes Microtubuli of Macrophages Like Taxol . . . ", *Cancer Res.* 57, 3344-46 (1997).

Mulzer, "Progress in the Synthesis of Chiral Heterocyclic Natural Products: Epothilone B and Tartrolon B" *J. Heterocycl. Chem.*, 36(6): 1421-1436, 1999.

Mulzer, et al., "Total Syntheses of Epothilones B and D" *J. Org. Chem.*, 65(22); 7456-7467, 2000.

Mulzer, et al.,"Epothilone B and its Derivatives as Novel Antitumor Drugs: Total and Partial Synthesis and Biological Evaluation" *Monatsh. Chem.*, 131(3): 205-238, 2000.

Mulzer, et al.. "Easy Access to the Epothilone Family-Synthesis of Epothilone B", *Tetrahedron Letters*, 39(47): 8633-8636, 1998.

Mulzer, J. et al., "Synthesis of the C(1)-C(9) Segment of the Cytotoxic Macrolides Epothilon A and B", *Tetrahedron Letters* 37:51, 9179-9182 (1996).

Nagaoka, et al., "Further Synthetic Studies on Rifamycin S", *Tetrahedron*, 37: 3873-3888, 1981.

Nahm, et al., "N-Methoxy-N-Methylamides as Effective Acylating Agents", *Tetrahedron Lett.* 22: 3815-3818, 1981.

Nakamura, S., "Total Synthesis of Antitumor Antibiotic Epothilone Having Same Mechanism of Action with Taxol", *Kagaku (Kyoto)*, (in Japanese) 52(7): 70-71, 1997.

Newman, et al., "Antitumor Efficacy of 26-Fluoroepothilone B Against Human Prostate Cancer Xenografts" *Cancer Chemother. Pharmacol.*, 48(4): 319-326, 2001.

Nicolaou et al. "Synthesis and Biological Properties of C12,13-Cyclopropyl-Epothilone A and Related Epothilones" *Chem. Biol*, 5(7): 365-372, 1998.

Nicolaou, et al. "Chemical Synthesis and Biological Evaluation of cis- and trans-12,13-cyclopropyl and 12,13-cyclobutyl Epothilones and Related Pyridine Side Chain Analogues" *J. Am. Chem. Soc.*, 123(38): 9313-9323, 2001.

Nicolaou, et al., "Chemical Biology of Epothilones", *Angew. Chem. Int. Ed.*, 37: 2014-2045, 1998.

Nicolaou, et al., "Chemical Synthesis and Biological Properties of Pyridine Epothilones" *Chem. Biol.* 7(8): 593-599, 2000.

Nicolaou, et al., "Chemistry and Biology of Taxol", *Angew. Chem. Int. Ed. Engl.* 33: 15-44, 1994.

Nicolaou, et al., "Chemistry, Biology and Medicine of Selected Tubulin Polymerizing Agents" *Pure Appl. Chem.*, 71(6): 989-997, 1999.

Nicolaou, et al., "Recent Developments in the Chemistry, Biology and Medicine of the Epothilones" *Chem. Commun.*, 17:1523-1535, 2001.

Nicolaou, et al., "Ring-Closing Metathesis in the Synthesis of Epothilones and Polyether Natural Products" *Top. Organomet. Chem. 1 (Alkene Metathesis in Organic Synthesis)*1: 73-104, 1998.

Nicolaou, et al., "Synthesis and Biological Evaluation of 12,13-cyclopropyl and 12,13-cyclobutyl Epothilones" *ChemBioChem (Angew. Chem. Int. Ed. Engl.)*, 2(1): 69-75, 2001.

Nicolaou, et al., "Synthesis of 16-desmethylepothilone B: Improved Methodology for the Rapid, Highly Selective and Convergent Construction of Epothilone B and Analogs" *Chem. Commun.*, 6:519-520, 1999.

Nicolaou, et al., "Synthesis of Epothilones: A and B in Solid and Solution Phase", *Nature*, 390: 100, 1997.

Nicolaou, et al., "Total Synthesis of 16-Desmethylepothilone B, Epothilone B10, Epothilone F, and Related Side Chain Modified Epothilone B Analogues", *Chem. Eur. J.*, 6(15): 2783-2800, 2000.

Nicolaou, et al., "Total Synthesis of Epothilone E and Related Side-Chain Modified Analogues via a Stille Coupling Based Strategy" *Bioorg. Med. Chem.*, 7(5):665-697, 1999.

Nicolaou, et al., Chemie and Biologie der Epothilone, *Agnew. Chem.*, 110: 2120-2153, 1998.

Nicolaou, et al., Intellectual Screening of Natural Products for Drugs, *Farumashia*, 33(12): 1339-1345, 1997.

Nicolaou, K.C. et al. "Total Synthesis of Epothilone A and B via a Macrolactonization-Based Strategy", *J. Am. Chem.Soc.* 119: 7974-7991 (1997).

Nicolaou, K.C. et al. "Total Synthesis of Epothilone E and Analogues with Modified Side Chains through the Stille Coupling Reaction" *Angew. Chem. Int. Ed.*, 37: 84-87 (1998).

Nicolaou, K.C. et al., "An Approach to Epothilones Based on Olefin Metathesis" *Angew,Chem. Int. Ed. EngL* 35:20 2399-2401 (1996).

Nicolaou, K.C. et al., "An Approach to Epothilones Based on Olefin Metathesis" *Angew. Chem. Int. Ed.* 35:20 2399-2401 (1996).

Nicolaou, K.C. et al., "Probing the Riga Size of Epothilone: Total Synthesis of [14]-, [15]-,[17]-, ... " *Angew. Chem. 1st. Ed.* 37:1/2, 81-87 (1998).

Nicolaou, K.C. et al., "Synthesis of Epothilones A and B in solid and solution phase", *Nature* 387:15 268-272, 238-239 (1997).

Nicolaou, K.C. et al., "The Olefin Metathesis Approach to Epothilone A and Its Analogues" *J. Am. Chem. Soc.* 119: 7960-7973 (1997).

Nicolaou, K.C. et al., "Total Synthesis of 26-Hydroxy-Epothilone B and Related Analogs via a Macrolactonization Based Strategy" *Tetrahedron* 54: 7127-7166 (1998).

Nicolaou, K.C. et al., "Total Synthesis of 26 -hydroxyepothilone B and related analogues", *Chem. Commun.* 2343-2344 (1997).

Nicolaou, K.C. et al., "Total Synthesis of Epothilone A: The Macrolactonization Approach", *Angew Chem. Int. Ed. EngL*, (1997).

Nicolaou, K.C. et al., "Total Synthesis of Oxazole-and Cyclopropane-Containing Epothilone A Analogues ... ", *Chem. Eur. J.* 3:12 1957-1970 (1997).

Nicolaou, K.C. et al., "Total Synthesis of Oxazole-and Cyclopropane-Containing Epothilone B Analogues ... ", *Chem. Eur. J.* 3:12 1971-1986 (1997).

Nicolaou, K.C. et al., "Variation der RinggrOPe von Epothilonen-Totalsyntheses von [14]-,[15]-,[17]-, . . . " *Angew. Chem.* 110:1/2 85-92 (1998).

Nicolaou, K.C. et al., Designed Epothilones: Combinatorial Synthesis, Tubulin Assembly . . . *Agnew Chem. Inst. Ed. EngL* 36:19 2097-2103 (1997).

Njardarson, et al., "Discovery of Potent Cell Migration Inhibitors Through Total Synthesis: Lessons from Structure—Activity Studies of (+)-Migrastatin", *J. Am. Chem. Soc.* 126:1038-1040, 2004.

Njardarson, et al., Application of hitherto unexplored macrocyclization strategies in the epothilone series: novel epothilone analogs by total synthesis, *Chem. Commun.*, 2759-2761, 2002.

Noyori, et al., "Asymmetric Hydrogenation of β-Keto Carboxylic Esters. A Practical, Purely Chemical Access to β-Hydroxy Esters in High Enantiomeric Purity" *J. Am. Chem. Soc.* 109: 5856-5859, 1987.

Ojima, et al., A Common Pharamcophore for Cytotoxic Natural Products that Stabilize Microtubules *Proc. Natl. Acad. Sci. U.S.A.*, 96: 4256-4261, 1999.

Ojima, et al., "Enantiopure Fluorine-Containing Taxoids: Potent Anticancer Agents and Versatile Probes for Biomedical Problems", *J. Fluorine Chem.* 97:3-10, 1999.

Ojima, et al., "New-Generation Taxoids and Hybrids of Microtubule-Stabilizing Anticancer Agents" *Book of Abstracts, 219th ACS National Meeting*, San Francisco, CA, Mar. 26-30, ORGN-245, 2000.

Panicker et al., "An unusual Reversal of Stereoselectivity in a Boron Mediated Aldol Reaction: Enantioselective Synthesis of the C1-C6 Segment of the Epothilones" *Tetrahedron*, 56(40): 7859-7868, 2000.

Paterson et al., "Stereocontrolled Aldol Additions to α-Methylene-β-Alkoxy Aldehydes: Application to the Synthesis of a $C_{13}$-$C_{25}$ Segment of Bafilomycin $A_1$" *Tetrahedron Lett.* 36:175-178, 1995.

Petrache et al., "The Role of the Microtubules in Tumor Necrosis Factor-a-Induced Endothelial Cell Permeability" *Am. J. Respir. Cell Mol. Biol.* 28:574-581, 2003.

Pettet et al., "Isolation and Structure of the Cancer Cell Growth Inhibitor Dictyostatin 1", *J. Chem. Soc. Chem. Commun.* 1111-1112, 1994.

Pradella et al., "Characterisation, Genome Size and Genetic Manipulation of the Myxobacterium *Sorangium cellulosum* So ce56" Archives of Microbiology 1-17, 2002.

Pryor et al., "The Microtubule Stabilizing Agent Laulimalide Does Not Bind in the Taxoid Site, Kills Cells Resistant to Paclitaxel and Epothilones, and May Not Require Its Epoxide Moiety for Activity" Biochemistry 41:9109-9115, 2002.

Quitschalle et al., "Improved Synthesis of the Northern Hemisphere of Epothilone A by a Sharpless Asymmetric Dihydroxylation" *Tetrahedron Letters.* 40(44):7765-7768, 1999.

Regentin et al., "Development of a Cost Effective Epothilone D Process in *Myxococcus xanthus*" *Abstr. Pap-Am. Chem. Soc. 221st*, BIOT-061, 2001.

Regentin et al., "Nutrient Regulation of Epothilone Biosynthesis in Heterologous and Native Production Strains" *Appl. Microbiol. Biotechnol.* 61:451-455, 2003.

Regueiro-Ren et al., "Synthesis and Biological Activity of Novel Epothilone Aziridines" *Org. Lett.* 3(17): 2693-2696, 2001.

Regueiro-Ren et al., SAR and pH Stability of Cyano-Substituted Epothilones, Organic Letters, 4(22): 3815-3818, 2002.

Rivkin et al., "On the Introduction of a Trifluoromethyl Substituent in the Epothilone Setting: Chemical Issues Related to Ring Forming Olefin Metathesis and Earliest Biological Findings" *Organic Letters*, 4(23):4081-4084, 2002.

Rivkin et al., "Total Syntheses of [17]- and [18] Dehydrodesoxyepothilones B via a Consise Ring-Closing Metathesis-Based Strategy: Correlation of Ring Size with Biological Activity in the Epothilone Series" *J. Org. Chem.*, 67:7737-7740, 2002.

Rivkin, et al., "Complex Target-Oriented Total Synthesis in the Drug Discovery Process: The Discovery of a Highly Promising Family of Second Generation Epothilones", *J. Am. Chem. Soc.*, 125:2899-2901, 2003.

Rothermel, et al., "EPO906 (Epothilone B): A Promising Novel Microtubule Stabilizer", *Seminars in Oncology*, 30(3): 51-55, 2003.

Roush et al., "Acyclic Diastereoslective Synthesis Using Tartrate Ester Modified Crotylboronates. Double Asymmetric Reactions with α-Methyl Chiral Aldehydes and Synthesis of the C(19)-C(29) Segment of Rifamycin S" *J. Am. Chem. Soc.* 112:6348-6359, 1990.

Santi et al., "An Approach for Obtaining Perfect Hybridization Probes for Unknown Polyketide Synthase Genes: A Search for the Epothilone Gene Cluster" *Gene*, 247(1-2): 97-102, 2000.

Sawada M., "Enantioselective Total Synthesis of Epothilone A Using Multifunctional Asymmetric Catalysis" *Angew. Chem. Int. Ed.* 39(1):209-213, 2000.

Sawada et al., "Enantioselective Total Synthesis of Epothilones A and B Using Multifunctional Asymmetric Catalysis" *J. Am. Chem. Soc.* 122(43):10521-10532, 2000.

Schiff et al., "Promotion of Microtubule Assembly in vitro by Taxol" *Nature*, 277:665-667, 1979.

Schinzer et al., "New and Convenient Synthesis of (R) and (S) of 2-methyl-3-oxa-5-(tert-butyldiphenylsilyloxy)methylpentanoate and 2-methyl-3-oxa-5-(tert-butyldimethylsiloxy)methylpentanoate" *Phosphorus, Sulfur Silicon Relat. Elem.*, 158:187-199, 2000.

Schinzer et al., "Synthesis and Biological Evaluation of Aza-Epothilones" *Angew. Chem. Int. Ed. ChemBiochem*, 1(1): 67-70, 2000.

Schinzer et al., "Synthesis of Epothilones. Stereoselective Routes to Epothilone B" *Synlett*, 8:861-864, 1998.

Schinzer et al., "Total Synthesis of (-)-epothilone A" *Chem.-Eur. J.*, 5(9):2483-2491, 1999.

Schinzer et al., "Total Synthesis of (-)-epothilone B" *Chem.-Eur. J.*, 5(9):2492-2500, 1999.

Schinzer, D. et al., "Studies Toward the Total Synthesis of Epothilones: . . . ", *Chem. Eur. J.*2:11 1477-1488 (1996).

Schinzer, D. et al., "Total Synthesis of 0-Epothilone A", *Angew. Chem. Int. Ed. Engl.* 36:5 523-524 (199'1).

Schneider et al., "Utilization of Alternate Substrates by the First Three Modules of the Epothilone Synthetase Assembly Line" *J. Am. Chem. Soc.* 124:11272-11273, 2002.

Schnizer, et al., "Synthesis and Biological Evaluation of Aza-Epothilones", Chembiochem, 1(1): 67-70, 2000.

Scholl et al., "Increased Ring Closing Metathesis Activity of Ruthenium-Based Olefin Metathesis Catalysts Coordinated with Imidazolin-2-Ylidene Ligands", *Tetrahedron Lett.* 40:2247-2250, 1999.

Scholl, et al., "Increased Ring Closing Metathesis Activity of Ruthenium-Based Olefin Metathesis Catalysts Coordinated with bnidazolin-2-Ylidene Ligands" *Tetrahedron Lett.* 40:2247, 1999.

Schrock, "Olefin Metathesis by Well-Defined Complexes of Molybdenum and Tungsten" *Top. Organomet. Chem.* 1: 1-36 , 1998.

Scudiero et al., "Evaluation of a Soluble Tetrazolium/Formazan Assay for Cell Growth and Drug Sensitivity in Culture Using Human and Other Tumor Cell Lines", *Cancer Res.* 48:4827-4833, 1988.

Sefkow et al., "Derivatization of the C12-C13 Functional Groups of Epothilones A, B, and C" *Bioorg. Med. Chem.* 8:3031-3036, 1998.

Sefkow et al., "Oxidative and Reductive Transformations of Epothilone A" *Bioorg. Med. Chem.* 8(21):3025-3030, 1998.

Sefkow et al., "Substitutions at the Thiazole Moiety of Epothilone" *Heterocycles*, 48(12):2485-2488, 1998.

Seiden, M., "Ovarian Cancer", *The Oncologist*, 6: 327-332, 2001.

Shibasaki et al., "Multifunctional Asymmetric Catalysis" *Chem. Pharm. Bull.*, 49(5):511-524, 2001.

Shioji et al., "Synthesis of C1-C6 Fragment for Epothilone A via Lipase-Catalyzed Optical Resolution" *Synth. Commun.*, 31(23):3569-3575, 2001.

Sinha et al., "Regioselective Synthesis of Fluoro Aldols. Studies Toward Fluro Epothilones Syntheses via Antibody Catalysis" *Tetrahedron Letters*, 41 (43):8243-8246, 2000.

Sinha et al., "Sets of Aldolase Antibodies with Antipodal Reactivities. Formal Synthesis of Epothilone E by Large Scale Antibody-Catalyzed Resolution of Thiazole Aldol" *Org. Lett.*, 1(10):1623-1626, 1999.

Sinha et al., "Synthesis of Epothilone Analogues by Antibody-Catalyzed Resolution of Thiazole Aldol Synthons on a Multigram Scale. Biological Consequences of C-13 Alkylation of Epothilones" *Chem. Bio. Chem.* , 2(9):656-665, 2001.

Sinha, et al., "Catalytic Antibody Route to the Naturally Occurring Epothilones: Total Synthesis of Epothilones A-F" *Chem. Eur. J.* 7(8):1691-1702, 2001.

Sinha, et al., "The Antibody Catalysis Route to the Total Synthesis of Epothilones" *Proc. Natl. Acad. Sci.* 95(25):14603-14608, 1998.

Skehan et al., "New Colorimetric Cytotoxicity Assay for Anticancer-Drug Screening" Journal of the National Cancer Institute, 82:1107-1112, 1990.

Smart, "Fluorine Substituent Effects (on bioactivity)" Journal of Fluorine Chemistry, 109:3-11, 2001.

Stachel et al., "Chemo- and Stereoselective Epoxidation of 12,13-Desoxyepothilone B using 2,2'-dimethyldioxirane" *Tetrahedron Lett.*, 42(39):6785-6787, 2001.

Stachel et al., "On the Interactivity of Complex Synthesis and Tumor Pharmacology in the Drug Discovery Process: Total Synthesis and Comparative in Vivo Evaluations of the 15-Aza Epothilones" *J. Org. Chem.* 66:4369-4378, 2001.

Stachel et al., "The Epothilones, Eleutherobins, and Related Types of Molecules" *Curr. Pharm. Des.* 7(13):1277-1290, 2001.

Still, et al., "Stereoselective Synthesis of 1,3-Diol Derivatives and Application to the Ansa Bridge of Rifamycin S" *J. Am. Chem. Soc.* 105: 2487-2489, 1983.

Su et al., "Structure-Activity Relationships of the Epothilones and the First In Vivo Comparison with Paclitaxel" *Angew. Chem. Int. Ed. Engl.* 36:2093-2096, 1997.

Su et at, "Total Synthesis of (-) Epothilone B: An Extension of the Suzuki Coupling Method and Insights into Structure-Activity Relationships of the Epothilones", *Angew. Chem. Int. Ed. Engl.* 36:757-759, 1997.

Sun et al. "Stereoselective Total Synthesis of Epthilones by the Metathesis Approach involving C9-C10 Bond Formation" *Angew. Chem. Int. Ed.* 8:1381-1383.

Tamao, et al., "Selective Carbon-Carbon Bond Formation by Cross-Coupling of Grignard Reagents with Organic Halides. Catalysis by Nickel-Phospine Complexes" *J. Am. Chem Soc.* 94: 4374-4379, 1972.

Tang et al., "Cloning and Expression of the Epothilone Gene Cluster" *Science*, 287:640-642, 2000.

Tang et al., "Generation of Novel Epothilone Analogs with Cytotoxic Activity by Biotransformation" The Journal of Antibiotics, 56:16-23, 2003.

Tanimori et al., "Easy Access to Both Enantiomers of C7-C12 Segment of Epothilones" *Synth. Commun.* 29(24): 4353-4360, 1999.

Tanimori et al., "Simple Synthesis of Both Enantiomers of the C7-C12 Segment of Epothilones" *Biosci. Biotechnol. Biochem*, 62(12):2428-2430, 1998.

Taylor et al., "Catalytic Diastereoselective Reductive Aldol Reaction: Optimization of Interdependent Reaction Variables by Arrayed Catalyst Evaluation" *J. Am. Chem. Soc.* 121:12202-12203, 1999.

Taylor et al., "Conformational Properties of Epothilone" *J. Org. Chem.* 64(19):7224-7228, 1999.

Taylor et al., "The Conformational Properties of Epothilone"-Erratum *J. Org. Chem.*, 65(17):5449, 2000.

Taylor et al., "Total Synthesis of Epothilones B and D" *Org. Lett.* 3(14):2221-2224, 2001.

Taylor, "A Formal Total Synthesis of Epothilone A: Enantioselective Preparation of the C1-C6 and C7-C12 Fragments" *J. Org. Chem.* 63(25):9580-9583, 1998.

Taylor, R.E., et al., "Towards the Synthesis of Epothilone A: Enantioselective Preparation . . . " *Tetrahedron Letters* 38:12 2061 2064 (1997).

Toh et al., "Studies on a Convergent Route to Side-Chain Analogues of Vitamin D: 25-Hydroxy-23-Oxavitamin $D_3$" *J. Org. Chem.* 48:1414-1417, 1983.

Trnka, et al., "The Development of $L_2X_2Ru=CHR$ Olefin Methathesis Catalysts: An Organometallic Success Story," *Acc. Chem. Res.* 34:18-31, 2001.

Tsuji et al., "Alterations in Cellular Adhesion and Apoptosis in Epithelial Cells Overexpressing Prostaglandin Endoperoxide Synthase 2", *Cell*, 3:493, 1995.

Valluri et al., "Total Synthesis of Epothilone B" *Org. Lett.*, 3(23):3607-3609, 2001.

Victory et al., "Relative Stereochemistry and Solution Conformation of the Novel Paclitaxel-Like Antimitotic Agent Epothilone A" *Bioorganic & Medicinal Chemistry Letters* 6(7):893-898, 1996.

Vite, et al., "Epothilones A and B: Springboards for Semisynthesis of Promising Antimitotic Agents" *Book of Abstracts, 219th ACS National Meeting*, San Francisco, CA, Mar. 26-30, ORGN-286, 2000.

Von Angerer, "Tubulin as a Target for Anticancer Drugs" *Curr. Opin. Drug Discovery Dev.* 3(5):575-584, 2000.

Walsh, "Enzymatic Assembly of Hybrid Polyketide/Nonribosomal Peptide Natural Products" *Abstracts of Papers, 222nd ACS National Meeting*, Chicago, IL, Aug. 26-30, BIOL-126, 2001.

Wartmann et al., "The Biology and Medicinal Chemistry of Epothilones" *Curr. Med. Chem.* 2:123-148, 2002.

Wessjohann et al., "Synthesis of Natural-Product-Based Compound Libraries" *Curr. Opin. Chem. Biol.* 4:303-309, 2000.

Wessjohann et al., "Synthetic Access to Epothilones-Natural Products with Extraordinary Anticancer Activity" *Org. Synth. Highlights IV* Ed: Schmalz, H., Wiley-VCH Verlab GmbH: Weinheim Germany, 251-267, 2000.

Wessjohann, "Epothilones: Promising Natural products with Taxol-Like Activity" *Angew. Chem. Int. Ed. Engl.* 36(7):715-718, 1997.

White et al. "Synthesis, Conformational Analysis, and Bioassay of 9,10-didehydroepothilone D" *Organic Letters* 4:995-997, 2002.

White et al., "Total Synthesis of Epothilone B, Epothilone D, and cis- and trans-9,10-Dehydroepothilone D" *J. Am. Chem. Soc.*, 123(23):5407-5413, 2001.

White et al., Total Synthesis of Epothilone B, Epothilone D, and cis-and trans-9, 10-Dehydroepothilone D, *J. Am. Chem. Soc.*, 125:3190, 2003, Additions and Corrections.

White, et al., "A Highly Stereoselective Synthesis of Epothilone B" *J. Org. Chem.*, 64(3):684-685, 1998.

White, et al., "Improved Synthesis of Epothilone B Employing Alkylation of an Alkyne for Assembly of Subunits" *Org. Lett.*, 1(9):1431-1434, 1999.

White, et al., "Synthetic Approach Towards the Total Synthesis of Epothilone B" *Book of Abstracts, 216th ACS National Meeting*, Boston, Aug. 23-27, ORGN-041.

White, et al., "Two Coupling Strategies for a Stereoselective Synthesis of Epothilone B" *Book of Abstracts, 219th ACS National Meeting*, San Francisco, CA, Mar. 26-30, ORGN-813, 2000.

Winkler, et al., "A Model for the Taxol (Paclitaxel) Epothilone Pharmacophore", *Bioorg., Med. Chem. Letter*, 6: 2963-2966, 1996.

Winkler, et al., "Design and Synthesis of Constrained Epothilone Analogs: The Efficient Synthesis of Eleven-Membered Rings by Olefin Metathesis" *Tetrahedron*, 55(27): 8199-8214, 1999.

Winssinger, et al., "Epothilones and Sarcodictyins: From Combinatorial Libraries to Designed Analogs" *Book of Abstracts, 219th ACS National Meeting*, San Francisco, CA, March 26-30, ORGN-289, 2000.

Wittmann, et al., Flavopiridol Down-Regulates Antiapoptotic Proteins and Sensitizes Human Breast Cancer Cells to Epothilone B-induced Apoptosis, Cancer Research, 63: 93-99, 2003.

Wolff, A., "Epothilone A Induces Apoptosis in Neuroblastoma Cells with Multiple Mechanisms of Drug Resistance", *Int. J. Oncol.*, 11(1):123-126, 1997.

Woltering, et al., Development of a Novel In Vitro Human Tissue-Based Angiogenesis Assay to Evaluate the Effect of Antiangiogenic Drugs, Annals of Surgery, 237: 790-800, 2003.

Wu et al. "Subtle Variations in the Long-Range Transmission of Stereochemical Information: Matched and Mismatched Aldol Reactions" Angew. Chem. Int. Ed. 39(24):4505-4508 (2000).

Yamaguchi, et al., "Epothilone B Analogue (BMS-247550)—Mediated Cytotoxicity Through Induction of Bax Conformational Change in Human Breast Cancer Cells", *Cancer Research*, 62: 466-471, 2002.

Yang, et al., Total Synthesis of Epothilone A: The Olefin Metathesis Approach: *Angew. Chem. Int. Ed.*, 36: 166-168, 1997.

Yoshimura et al., "Synthesis ad Conformational Analysis of (E)-9, 10-Dehydroepothilone B: A Suggestive Link between the Chemistry and Biology of Epothilones", *Angew. Chem. Int. Ed.* 42:2518-2521, 2003.

Zhou, et al., Brominated Derivatives of Noscapine Are Potent Microtubule-Interfering Agents That Perturb Mitosis and Inhibit Cell Proliferation, Molecular Pharmacology, 63:799-807, 2003.

Zhu, et al., "Methodology Based on Chiral Silanes in the Synthesis of Polypropionate-Derived Natural Products-Total Synthesis of Epothilone A" *Eur. J. Org. Chem.*, 9: 1701-1714, 2001.

Zhu, et al., "Studies Toward the Total Synthesis of Epothilone A" Book of Abstracts, 216th ACS National Meeting, Boston, Aug. 23-27, ORGN-660.

Zhu, et al., "Total Synthesis of Epothilone A" *Org. Lett.*, 2(17): 2575-2578, 2000.

Zhu, et al., "Enzymatic Resolution of Thiazole-Containing Vinyl Carbinols. Synthesis of the C12-C21 Fragment of the Epothilones" *Tetrahedron Lett.*, 41(12):1863-1866, 2000.

\* cited by examiner

IC$_{50}$ values for the new Epothilones against CCRF-CEM cell growth

| Compound | IC$_{50}$(μM) for | | |
|---|---|---|---|
| | CCRF-CEM | CCRF-CEM/VBL | CCRF-CEM/Taxol |
| dEpoB (EpoD) | 0.0036±0.0002 | 0.016±0.003$_{[4.6x]}$ | 0.0046±0.0002$_{[1.3x]}$ |
| dEpoF | 0.0015±0.0001 | 0.0456$_{[30.4x]}$ | 0.0035$_{[2.3x]}$ |
| EpoB | 0.00062±0.00013 | 0.0037±0.0011$_{[3.9x]}$ | 0.0011±0.0001$_{[1.3x]}$ |
| 10,11-didehydro-dEpoB (Epo-490) | 0.0160 | 0.078$_{[4.3x]}$ | 0.032$_{[2x]}$ |
| 26-methyl-dEpoB | 0.040 | 0.123$_{[3.1x]}$ | 0.077$_{[1.9x]}$ |
| 4-des-me-EpoB | 0.00081 | 0.0078$_{[9.6x]}$ | 0.017$_{[21x]}$ |
| 11-OH (cis)EpoD | 0.0029 | 0.077$_{[25.6x]}$ | 0.0091$_{[3.1x]}$ |
| 11-a-F-dEpoB | 0.0285 | 0.147$_{[1.9x]}$ | 0.0550$_{[1.9x]}$ |
| 11-β-F-dEpoB | 0.0980 | 0.230$_{[2.3x]}$ | 0.138$_{[1.4x]}$ |
| 19-oxazole EpoD | 0.0054 | 0.045$_{[8.3x]}$ | 0.0017$_{[1.2x]}$ |
| 19-oxazole EpoB | 0.00034 | 0.0057$_{[16.3x]}$ | 0.0057$_{[1.6x]}$ |
| 19-oxazole-Epo490 | 0.0077 | 0.0227$_{[2.9x]}$ | 0.0130$_{[1.7x]}$ |
| 9.10-deH-[16]dEpoB. (Iso-490) | 0.0009±0.0004 | 0.0042±0.0022$_{[4.7x]}$ | 0.0012±0.0006$_{[1.3x]}$ |
| Iso-490-dEpoF | 0.00051±0.00009 | 0.0106$_{[30.3]}$ | 0.00073$_{[1.4x]}$ |
| Iso-490-EpoB | 0.00023±0.00002 | 0.00032$_{[1.4x]}$ | 0.00042$_{[1.8x]}$ |
| 12,13-epi-Iso-490-EpoB | 0.0134±0.0032 | 0.0959$_{[2.1x]}$ | 0.0802$_{[2.6x]}$ |
| 12,13-epi-EpoB | 0.0830±0.0001 | 0.4519$_{[5.6x]}$ | 0.1507$_{[1.8x]}$ |
| Iso-490-dEpo-Me-Ketone | 5.02 | — | — |
| 26-F$_1$-9,10-deH-[16]dEpoB | 0.0035 | 0.0210$_{[5.7x]}$ | 0.0057$_{[1.6x]}$ |
| 26-F$_1$-dEpoB | 0.0041 | 0.080$_{[19.1x]}$ | 0.018$_{[4.6x]}$ |
| Taxol | 0.0016±0.0005 | 2.30$_{[1438x]}$ | 0.058±0.001$_{[36x]}$ |
| Vinblastine | 0.00045 | 0.418±0.076$_{[474x]}$ | 0.026±0.008$_{[38x]}$ |

FIG. 1

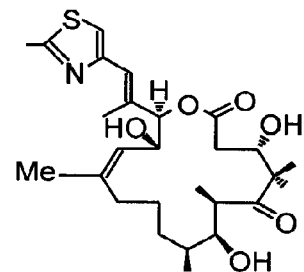
14-hydroxy-EpoD
82
(0.011)
[0.258]
{0.029}
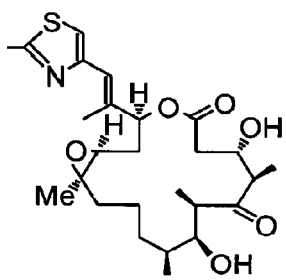
4-desmethyl-EpoB
83
(0.00081)
[0.0078]
{0.0017}
13-oxe spothlions 490
84
(0.0077)
[0.0237]
{0.0130}
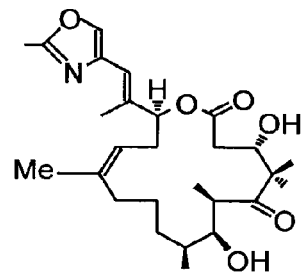
19-oxazole-EpoD
85
(0.0054)
[0.045]
{0.0087}
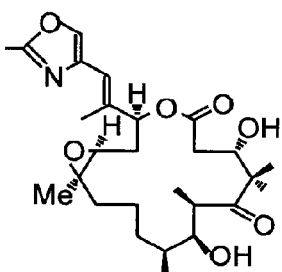
19-oxazole-EpoB
86
(0.00034)
[0.0057]
{0.0005}
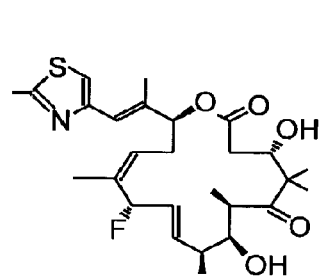
11-α-F-dEpoB
87
(0.0285)
[0.147]
{0.0550}
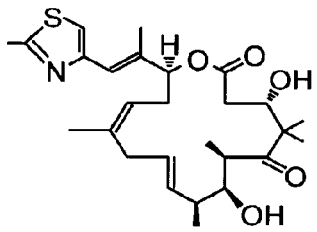
9,10-debydro-[16]dEpoB
88
(0.0014)
[0.0065]
{0.0017}
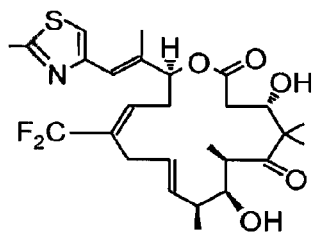
26-tri-F-9,10-debydro-[16]dEpoB
89
(0.0035)
[0.0201]
{0.0057}
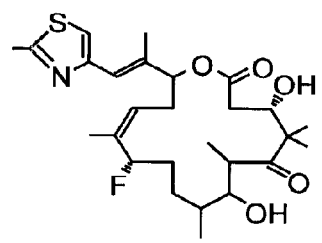
11-β-F-dEpoB
90
(0.0980)
[0.230]
{0.138}
FIG. 5B 1. Macro-Stille Strategy
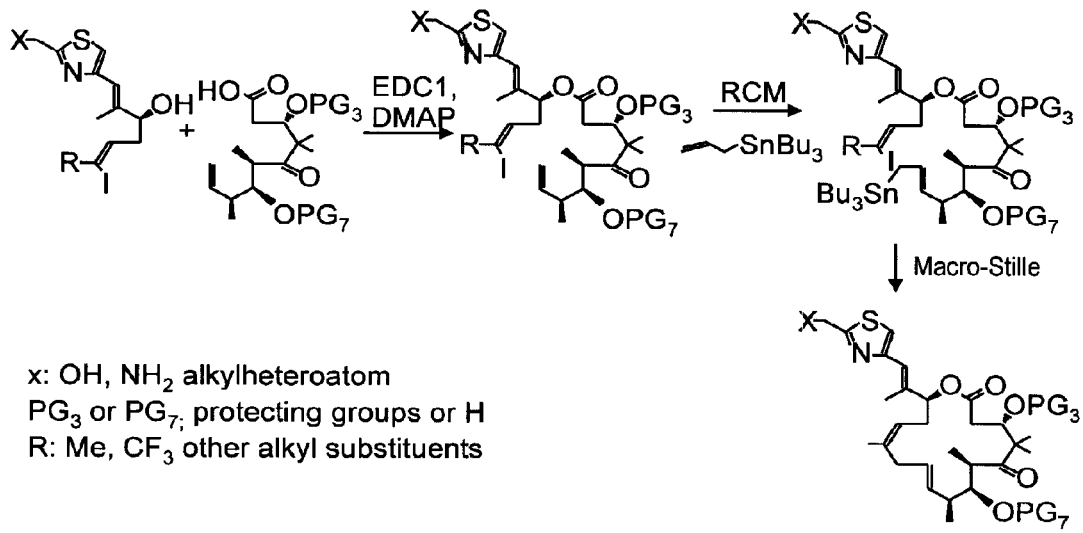
x: OH, NH₂ alkylheteroatom
PG₃ or PG₇: protecting groups or H
R: Me, CF₃ other alkyl substituents
2. sp³-sp³ coupling strategy
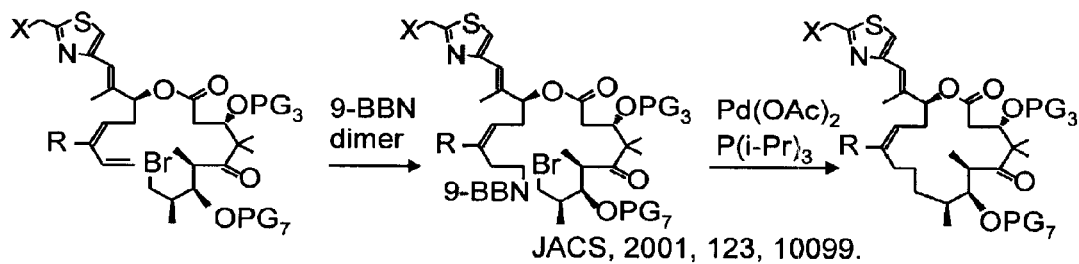
JACS, 2001, 123, 10099.
3. β-Suzuki Coupling
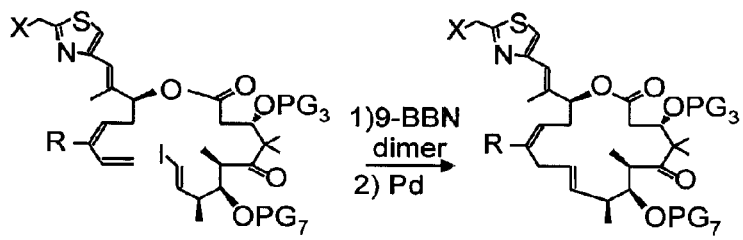
FIG. 6A

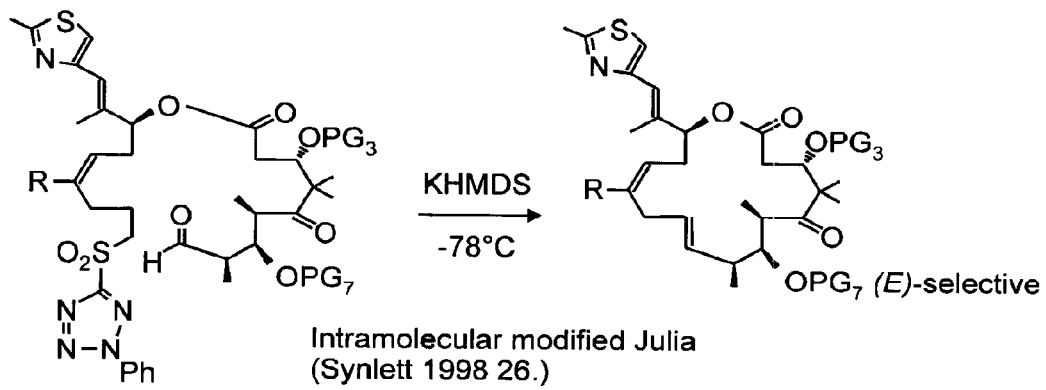
Intramolecular modified Julia
(Synlett 1998 26.)
5. Wadsworth-Emmons Strategy
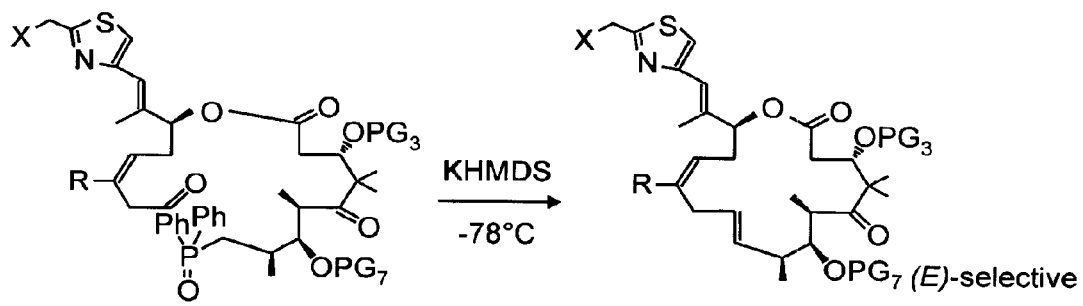
6. Macro-Reformatosky Strategy
FIG. 6B 7. McMurry Coupling Strategy
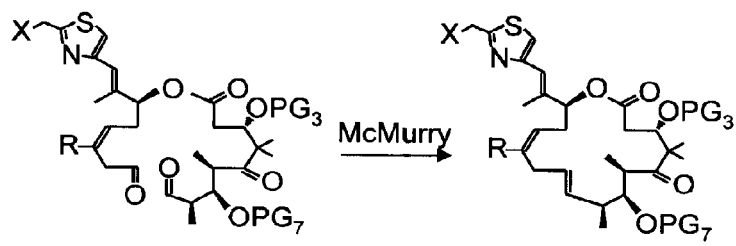
8. Lactam analog synthesis
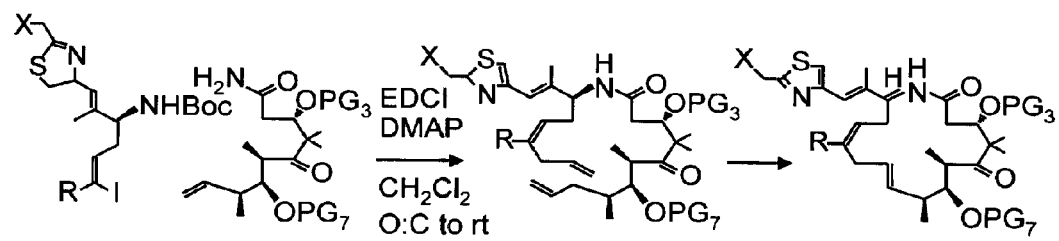
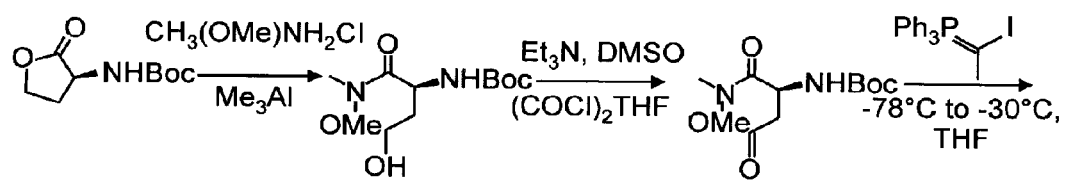
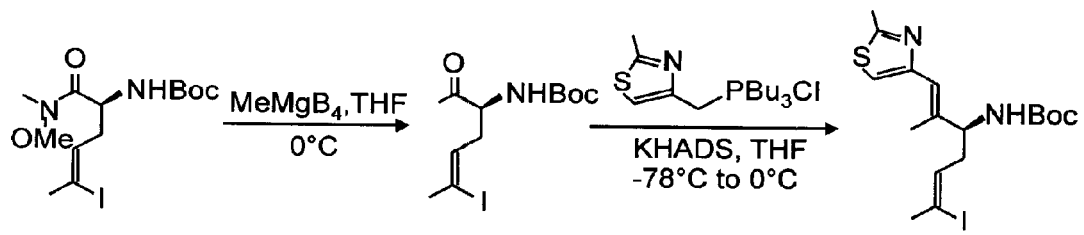
FIG. 6C R: Methyl, CF₃, other alkyl substituents
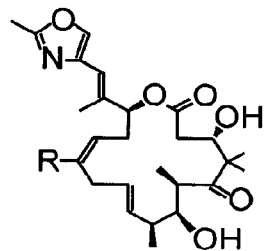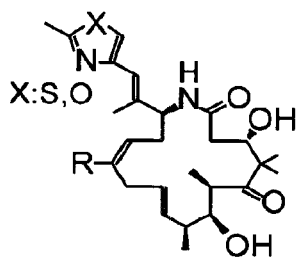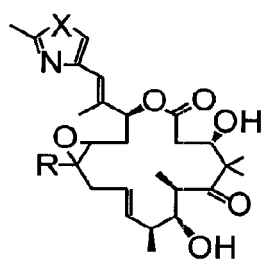
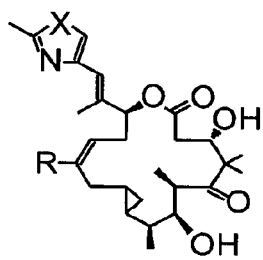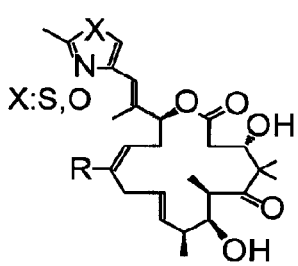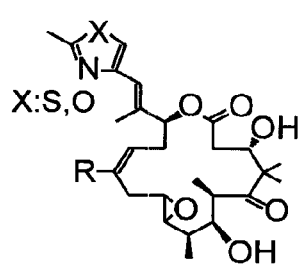
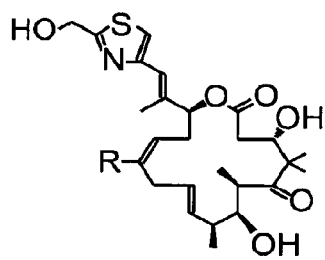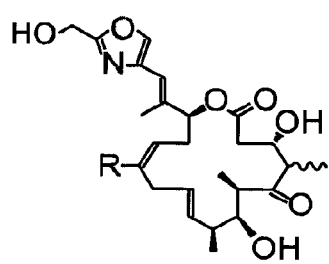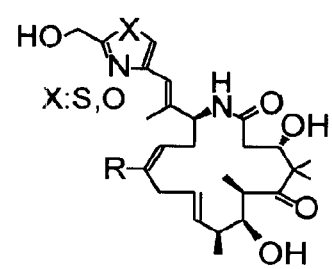
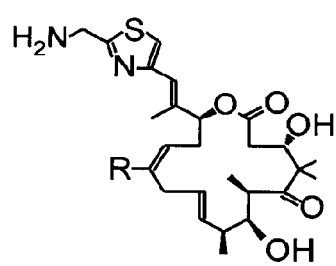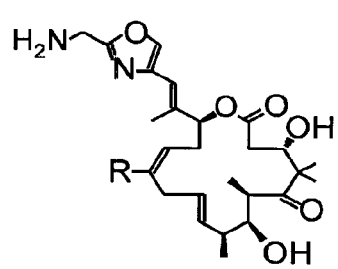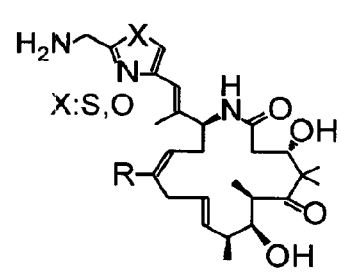
FIG. 7

Potency of epothilone: against tumor cell growth in vitro and relative therapeutic index

| Compound | IC$_{50}$ (µM) for | | | | | Relative Therapeutic Index against Mice Xenograft at MTD |
|---|---|---|---|---|---|---|
| | Human T-cell Lymphoblastic Leukemia Sublines | | | Human Lung Carcinoma A549 | Human Colon Carcinoma HCT-116 | |
| | CCRF-CEM | CCRF-CEM/VBL | CCRF-CEM/Taxol | | | |
| dEpoB | 0.0056 ±0.0028 | 0.016 ±0.003 [2.9x] | 0.0085 ±0.0055 [1.5x] | 0.0039 ±0.0004 | 0.0068 ±0.0032 | ++++ |
| dEpoF | 0.0015 ±0.0001 | 0.055 ±0.09 [16x] | 0.0066 ±0.0031 [4.4x] | 0.012 ±0.004 | 0.0034 ±0.0006 | ++++ |
| EpoB | 0.00053 ±0.00017 | 0.0032 ±0.0012 [6.05x] | 0.0011 ±0.00008 [2.1x] | 0.0008 ±0.0005 | 0.00038 ±0.00001 | +++ |
| 15-Aza-EpoB | 0.0024 ±0.0003 | 2.08 ±0.92 [857x] [1423x] | 0.103 ±0.068 [43x] | 0.0040 ±0.0035 | 0.0014 ±0.00009 | ++ |
| 9,10-deH-dEpoB | 0.0009 ±0.0004 | 0.0042 ±0.0022 [4.7x] | 0.0012 ±0.0006 [1.3x] | 0.00089 ±0.00064 | 0.00094 ±0.00055 | ++++ |
| 9,10-deH-dEpoF | 0.00051 ±0.00009 | 0.021 ±0.010 [41x] | 0.0017 ±0.0010 [3.3x] | 0.00091 ±0.00006 | 0.00056 ±0.00006 | +++ |
| 9,10-deH-EpoB | 0.00023 ±0.00002 | 0.00096 ±0.00064 [4.2x] | 0.00041 ±0.00001 [1.8x] | 0.00026 ±0.00004 | 0.00014 ±0.00001 | ++++ |
| 26-F$_3$-deH-dEpoB | 0.0032 ±0.0003 | 0.023 ±0.002 [7.2x] | 0.0047 ±0.0010 [1.5x] | 0.0037 ±0.0024 | 0.0056 ±0.0010 | ++++ |
| 26-F$_3$-dEpoB | 0.0093 ±0.0052 | 0.085 ±0.005 [9.1x] | 0.018 ±0.001 [1.9x] | 0.015 ±0.004 | 0.012 ±0.001 | ND |
| Paclitaxel | 0.0018 ±0.0005 | 3.22 ±0.92 [1789x] | 0.079 ±0.029 [43.9x] | 0.0029 ±0.0003 | 0.0026 ±0.0009 | ++++ |
| Vinblastine | 0.00054 ±0.00009 | 0.389 ±0.074 [720x] | 0.0196 ±0.0111 [36.3x] | 0.0099 ±0.0018 | 0.0087 ±0.0007 | ++++ |

FIG. 11

Table 2. Therapeutic effect of dEopB, Paclitaxel and F₃-deh-dEpoB against MX-1 xenograft in nude mice in terms of doses body weight loss and regains and tumor disappearance and relapses

| Drug | Dosage (mg/kg) | Changes of body weight (%) | | Tumor free after Q2Dx6 6hr-iv, Infusion | Tumor reappeared on day 10 after stopping administration |
|---|---|---|---|---|---|
| | | On day 4 after stopping administration | On day 8 after stopping administration | | |
| dEpoB | 30 | -25.3 ± 2.1 | -9.1 ± 4.1 | 10/10 | 5/10 |
| Paclitaxel | 20 | -23.9 ± 3.7 | -8.7 ± 0.7 | 7/7 | 3/7 |
| F₃-deH-dEpoB | 20 | -22.4 ± 0.6 | -7.3 ± 0.7 | 4/4 | 0/4 |
| | 30 | -27.1 ± 2.7 | -17.4 ± 5.5 | 4/4 | 0/4 |

FIG. 12

IC$_{50}$ values for the new Epothilones against CCRF-CEM cell growth

| Compound | IC$_{50}$(μM) for | | |
|---|---|---|---|
| | CCRF-CEM | CCRF-CEM/VBL | CCRF-CEM/Taxol |
| dEpoB(EpoD) | 0.0036±0.0002 | 0.016±0.003$_{[4.4x]}$ | 0.0046±0.0002$_{[1.3x]}$ |
| dEpoF | 0.0015±0.0001 | 0.0456$_{[30.4x]}$ | 0.0035$_{[2.3x]}$ |
| EpoB | 0.00062±0.00013 | 0.0037±0.0011$_{[5.9x]}$ | 0.0011±0.0001$_{[1.8x]}$ |
| 26-methyl-dEpoB | 0.040 | 0.123$_{[3.1x]}$ | 0.077$_{[1.9x]}$ |
| 11-α-F-dEpoB | 0.0285 | 0.147$_{[5.2x]}$ | 0.0550$_{[1.9x]}$ |
| 11-β-F-dEpoB | 0.0980 | 0.230$_{[2.3x]}$ | 0.138$_{[1.4x]}$ |
| 19-oxazole-10,11-dehydro-dEpoB | 0.0077 | 0.0227$_{[2.0x]}$ | 0.0130$_{[1.7x]}$ |
| 9,10-deH-[16]dEpoB | 0.0009±0.0004 | 0.0042±0.0022$_{[4.7x]}$ | 0.0012±0.0006$_{[1.3x]}$ |
| 9,10-deH-[16]dEpoF | 0.00051±0.00009 | 0.0106$_{[20.8x]}$ | 0.00073$_{[1.4x]}$ |
| 9,10-deH-[16]dEpoB | 0.00023±0.00002 | 0.00032$_{[1.4x]}$ | 0.00042$_{[1.8x]}$ |
| 12,13-epi-9,10-deH-EpoB | 0.0134±0.0032 | 0.0959$_{[3.1x]}$ | 0.0802$_{[2.6x]}$ |
| 12,13-epi-EpoB | 0.0830±0.0001 | 0.4519$_{[5.4x]}$ | 0.1507$_{[1.1x]}$ |
| 9,10-deH-dEpo-Me-ketone | 5.02 | — | — |
| 26-F-9,10-deH-[16]dEpoB | 0.0035 | 0.0210$_{[5.7x]}$ | 0.0057$_{[1.6x]}$ |
| 26-F$_3$-dEpoB | 0.0041 | 0.080$_{[19.5x]}$ | 0.018$_{[4.4x]}$ |
| Taxol | 0.0016±0.0005 | 2.30$_{[1438x]}$ | 0.058±0.001$_{[36x]}$ |
| Vinblastine | 0.00045 | 0.418±0.076$_{[929x]}$ | 0.026±0.008$_{[58x]}$ |

FIG. 31

Metabolic Stability of Epothilones

| Compound | In vitro t1/2 in | | | |
|---|---|---|---|---|
| | Mouse plasma | Dog plasma | Human plasma | Human liver prep |
| dEpoB(EpoD) | 31 min | >8 hr | >8 hr | 60 min |
| 26-F$_3$-9,10-deH-dEpoB | 150 min | --- | --- | 180 min |
| 16-F3-dEpoB(MDR) | 68 min | --- | --- | 105 min |
| 26-methyl-dEpoB | 50 min | >8 hr | --- | --- |
| 9,10-deH-dEpoB | 90 min | --- | --- | 150 min |

Therapeutic effect of epothilone compounds against human tumor xenografts in mice with 6 hr-iv infusion

| Compound | Dose & Schedule | Xenograft model | Therapeutic effect | | Toxicity | |
|---|---|---|---|---|---|---|
| | | | % tumor volume reduction | Proportion of tumor disappearance | % body weight change | Proportion of mice dead |
| dEpoB(#10) | 30 mg/kg, Q2Dx5 d10-18 | MX-1 | 99.4%(d26) | 4/5 (d26) | (control -0.3%) +3.9%(d26) | 0/5 (d26) |
| Epo-490(#12) | 40 mg/kg, Q2Dx5 d10-18 50 mg/kg, Q2Dx5 d10-18 | MX-1 | 11.9%(d26) 30.5%(d20) | 0/3(d26) 0/4(d26) | -8.9%(d26) -4.0%(d26) | 0/3(d26) 0/4(d26) |
| 14-OH-dEpoB (#82) | 40 mg/kg, Q2Dx5 d8-16 | MX-1 | 65.8%(d24) | 0/4(d24) | (control +1.6%, d24) +7.9%(d24) | 0/4(d24) |
| dEpoB(#10) | 30 mg/kg, Q2Dx5x2 d8-16 then d20-22 | MX-1 | 99.9%(d24) 100%(d28) | 2/4(d24) 4/4(d28) | -14.6%(d24) -0.3%(d28) | 0/4(d28) |
| 4-Des-me-EpoB (#83) | 1.5 mg/kg, Q2Dx3,x6,x3 d8-16,d21-31,d35-39 | MX-1 | 67%(d17) >97.5%(d45) | 0/4(d17) 1/4(d45) | (control -3%,d17) -13%(d45) | 1/4(d19) |
| | 3 mg/kg, Q2Dx3 d11-15 | MX-1 | 77%(d17) | 0/4(d17) | -28%(d17) | 4/4(d17) |
| 19-oxa-EpoB (#86) | 1.5 mg/kg, Q2Dx3,x4 d15-19,d27-33 | HCT-116 | 72.7%(d27) | 0/3(d39) | (control -11%,d27) -18%(d17) -30%(d33) | 3/3 (d24, 34, 34) |
| | 3 mg/kg, Q2Dx3x2 d15-19 | | 79.3%(d27) | 0/4(d39) | -29%(d27) | 4/4 (d20,21,21,22) |
| | 5 mg/kg, Q2Dx3 d15-19 | | 65.4%(d19) | 0/3(d19) | -27%(d19) | 3/3 (d19, 20, 20) |

| | | | | |
|---|---|---|---|---|
| 19-oxa-EpoB (#85) | 30 mg/kg, Q2Dx3 d15-19 | | 71.9% (d27) | 0/4 (d39) | -16% (d27) -28% (d35) |
| | 40 mg/kg, Q2Dx3 d15-19 | HCT-116 | 75.1% (d27) | 0/3 (d39) | -20% (d27) -30% (d35) |
| Epo[17]-490 (#70) (Epo[17]-10,11-deH-dEpoB) | 50 mg/kg, Q2Dx3 then 80 mg/kg, Q2Dx1 then 100 mg/kg, Q2Dx1 d10-14, d16-d18 | MX-1 | 11.3% (d22) | 0/3 (d22) | (control +2%, d22) +2.1% (d22) |
| Epo[18]-490 (#76) (Epo[18]-10,11-deH-dEpoB) | 80 mg/kg, Q2Dx5 d10-18 | MX-1 | 13.2% (d24) | 0/3 (d24) | (control +4.7%, d24) -4.4% (d24) |
| 27-F3-EpoD[17] (#78) | 60 mg/kg, Q2Dx3 then 80 mg/kg, Q2Dx2 d10-14, d16-d18 | MX-1 | 4.8% (d20) | 0/4 (d20) | (control -6.6%, d20) -7.4% (d20) |
| 26-Me-EpoD (#25) | 50 mg/kg, Q2Dx5, x1 d12-20, d24 | MX-1 | 65.7% (d26) | 0/2 (d26) | (control +3.8%, d26) +1.7% (d26) |
| 14-Me-EpoD (#31) | 30 mg/kg, Q2Dx5, x1 d12-20, d24 | MX-1 | 48.9% (d26) | 0/3 (d28) | -1.2% (d26) |
| 19-Oxazole-Epo-490 (#84) (19-Oxazole-10,11-deH-dEpoB) | 30 mg/kg, Q2Dx7 d22-34 | HCT-116 | 43.2% (d44) | 0/3 (d44) | (control -14%, d44) -18% (d44) |
| | 40 mg/kg, Q2Dx7 d22-34 | | 70.3% (d44) | 0/3 (d44) | -18% (d44) |

FIG. 33B

In vitro microtubule assembly

| | MIT assembly (37°C, %) |
|---|---|
| Control | 0 |
| EpoB | 100 |
| dEpoB | 117 |
| 9,10-dehydro-[16]dEpoB | 108 |
| 26-tri-F-9,10-dehydro-[16]dEpoB | 106 |
| 26-tri-F-[16]dEpoB | 84 |
| 21-hydroxy-9,10-dehydro-[16]dEpoB | 88 |

FIG. 41A

Cytotoxicity assay

| | A549 (IC50, nM) | A549EpoB40 (IC50, nM) |
|---|---|---|
| EpoB | 1.94 | 55.44 |
| dEpoB | 11.6 | >500 |
| 9,10-dehydro-[16]dEpoB | 1.88 | 122.78 |
| 26-tri-F-9,10-dehydro-[16]dEpoB | 5.98 | 431.50 |
| 26-tri-F-[16]dEpoB | 44.2 | >500 |
| 21-hydroxy-9,10-dehydro-[16]dEpoB | 3.59 | 244.02 |

| FIG. 52A |
|----------|
| FIG. 52B |

FIG. 52A

Table 1: Potency of epomilanes against tumor cell growth in vitro and the relative therapeutic index

| Compound | IC$_{SD}$(μM) for | | | | | Relative Therapeutic Index against Mice Xenograft al MTD$^d$ |
|----------|---|---|---|---|---|---|
| | Human T-cell Lymphoblastic Leukemia Sublines | | | Human Lung Carcinoma A549 | Human Colon Carcinoma HCT-116 | |
| | CCRF-CEM | CCRF-CEM/VBL | CCRF-CEM/Taxol | | | |
| dEpoB | 0.0056 ±0.0028 | 0.016 ±0.003 | 0.0085 ±0.055 | 0.0039 ±0.0004 | 0.0068 ±0.0032 | ++++ |
| dEpoB | 0.0015 ±0.001 | 0.055 ±0.09 | 0.0066 ±0.0031 | 0.012 ±0.004 | 0.0034 ±0.0006 | ++++ |
| EpoB | 0.00053 ±0.00017 | 0.0032 ±0.0012 | 0.0011 ±0.00008 | 0.0008 ±0.0005 | 0.00038 ±0.00001 | +++ |
| Aza-EpoB | 0.0024 ±0.0003 | 2.08 ±0.92 | 0.103 ±0.068 | 0.0040 ±0.0035 | 0.0014 ±0.00009 | ++ |

| | | | | | |
|---|---|---|---|---|---|
| deH-dEpoB | 0.0009 ±0.0004 | 0.0042 ±0.0022 | 0.0012 ±0.0006 | 0.00089 ±0.00064 | 0.00004 ±0.00055 | ++++ |
| deH-dEpoF | 0.00051 ±0.00009 | ±0.021 ±0.010 | 0.0017 ±0.0010 | 0.00091 ±0.00005 | 0.00056 ±0.00006 | +++ |
| deH-dEpoB | 0.00023 ±0.00002 | 0.00096 ±0.00064 | 0.00041 ±0.00001 | 0.00026 ±0.00004 | 0.00014 0.00001 | ++++ |
| F$_3$-deH-dEpoB | 0.0032 ±0.0003 | 0.023 ±0.002 | 0.0047 ±0.0010 | 0.0037 ±0.0024 | 0.0056 ±0.0010 | +++++ |
| F$_3$-deH-dEpoF | 0.00089 | 0.038 | 0.0058 | | | |
| F$_3$-deH-dEpoB | 0.0093 ±0.0052 | 0.085 ±0.005 | 0.018 ±0.001 | 0.015 ±0.004 | 0.012 ±0.001 | ND |
| Paclitaxel | 0.0018 ±0.0005 | 3.22 ±0.92 | 0.079 ±0.029 | 0.0029 ±0.0003 | 0.0026 ±0.0009 | ++++ |
| Vinblactine | 0.00054 ±0.00009 | 0.389 ±0.074 | 0.0196 ±0.0111 | 0.0099 ±0.0018 | 0.0087 ±0.0007 | ++++ |

FIG. 52B

*In Vitro* Potency C-21 Modified Epothilones

| Compound | IC$_{50}$(μM) | | |
|---|---|---|---|
| | CCRF-CEM | CCRF-CEM/VBL | CCRF-CEM/Taxol |
| dEpoB | 0.0056 ±0.0028 | 0.016 ±0.003 | 0.0085 ±0.0055 |
| 21-OH-dEpoB (dEpoF) | 0.0015 ±0.0001 | 0.055 ±0.09 | 0.0066 ±0.0031 |
| 21-OH-9,10-deH-dEpoB | 0.00051 ±0.00009 | 0.021 ±0.010 | 0.0017 ±0.0010 |
| 21-OH-9,10-deH-26-F$_3$-dEpoB | 0.0013 ±0.0003 | 0.060 ±0.020 | 0.0065 ±0.0007 |
| 21-NH$_2$-F$_3$-deH-dEpoB | 0.0025 ±0.0002 | 0.163 | 0.039 |
| 21-(CH$_3$)$_2$-N-F$_3$-deH-dEpoB | 0.018 | 1.70 | 0.501 |
| 21-CH$_3$-NH-F$_3$-deH-dEpoB | 0.020 | 3.06 | 0.582 |
| 21-Cl-F$_3$-deH-dEpoB | 0.0057 ±0.0006 | 0.049 | 0.017 |

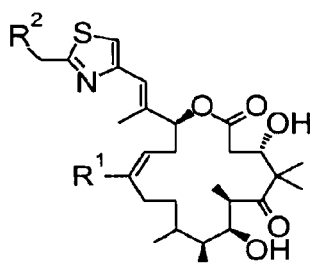
R¹: CF₃, Me
R²: OH, NH₂, H
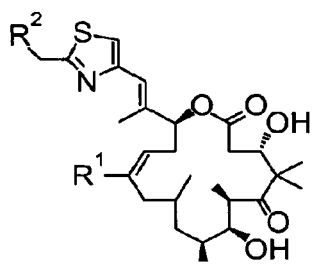
R¹: CF₃, Me
R²: OH, NH₂, H
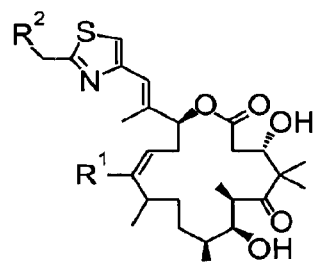
R¹: CF₃, Me
R²: OH, NH₂, H
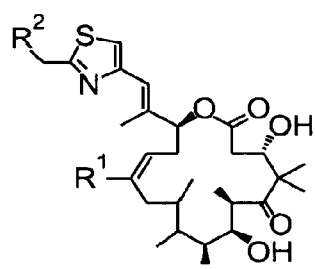
R¹: CF₃, Me
R²: OH, NH₂, H
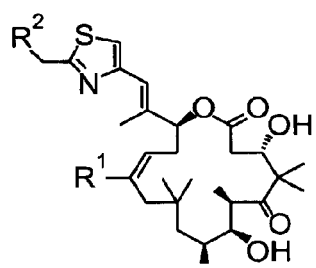
R¹: CF₃, Me
R²: OH, NH₂, H
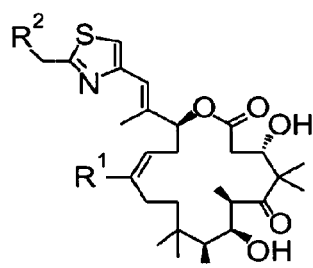
R¹: CF₃, Me
R²: OH, NH₂, H
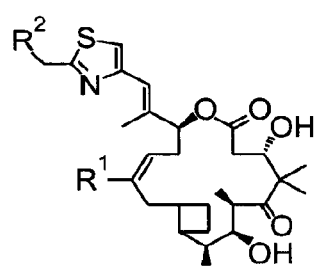
R¹: CF₃, Me
R²: OH, NH₂, H
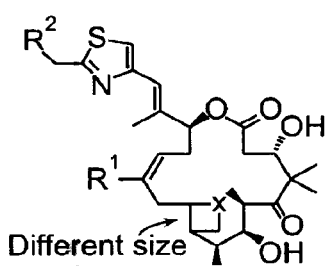
Different size rings
R¹: CF₃, Me
R²: OH, NH₂, H
X=O, NH
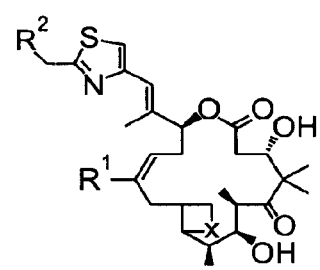
R¹: CF₃, Me
R²: OH, NH₂, H
X=O, NH
FIG. 81B

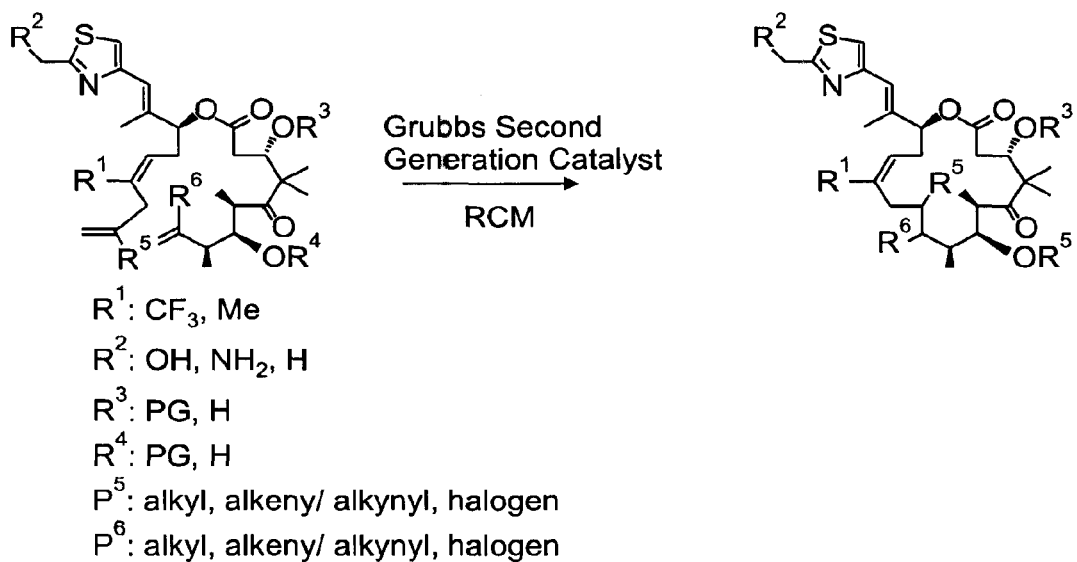
R¹: CF₃, Me
R²: OH, NH₂, H
R³: PG, H
R⁴: PG, H
P⁵: alkyl, alkeny/ alkynyl, halogen
P⁶: alkyl, alkeny/ alkynyl, halogen
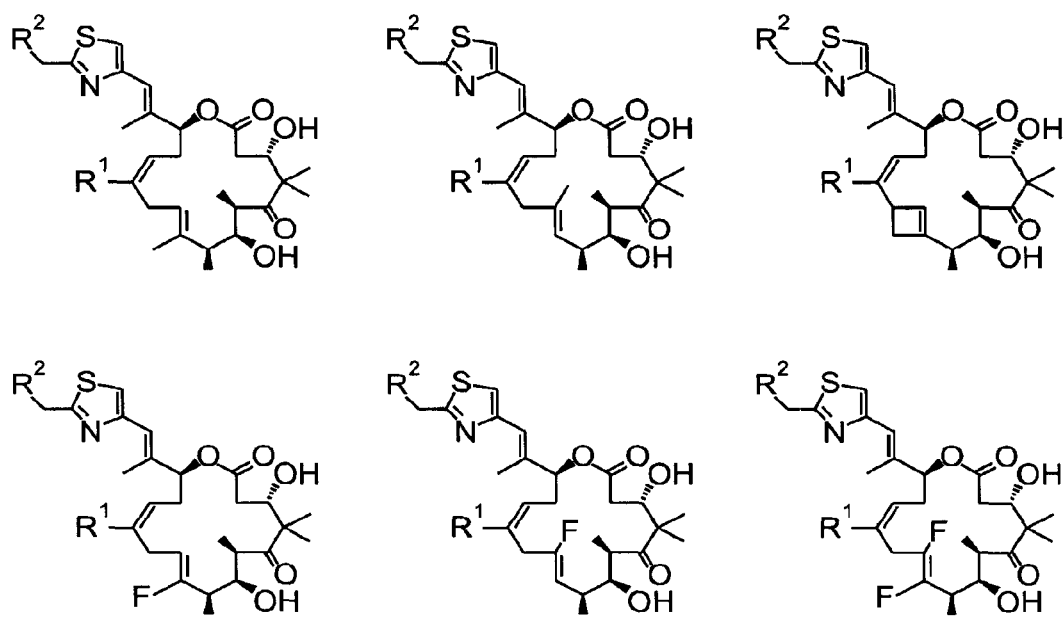
R¹: CF₃, Me
R²: OH, NH₂, H
FIG. 82

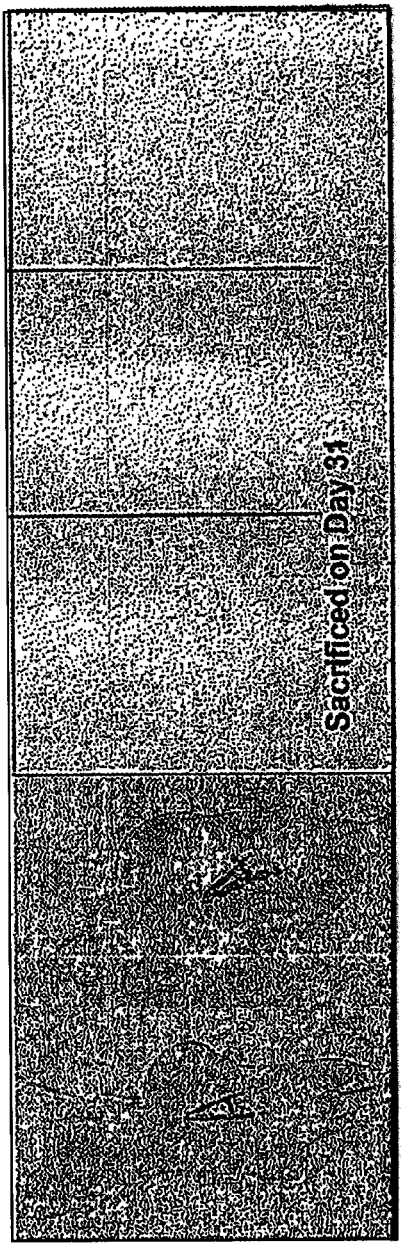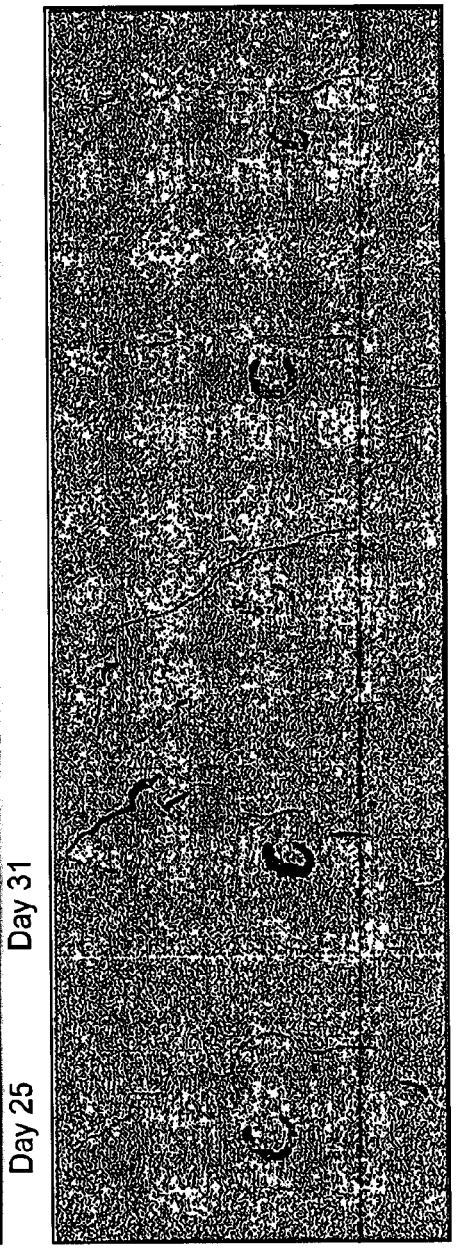
FIG. 83B

Table 2. Physico-Chemical and Metabolic Properties, and Pharmacologic and Therapeutic Profiles of Epothilone Derivatives

| Compound | Potency in Vitro | | Metabolic Stability | | Solubility | Lipophilicity | Pharmacologic Profile in Vivo | | |
|---|---|---|---|---|---|---|---|---|---|
| | Cytotoxic efficacy $IC_{50}$ (nM)[a] | Microtubule stabilization potency (Taxol as 100%) | Stability $t_{1/2}$ in mouse plasma[b] (min) | Stability $t_{1/2}$ in human liver S9 fraction[c] (hr) | Solubility in water (μg/ml) | Octanenol /water partition (POW) | Therapeutic dose (mg/kg), regimen for Q2D, 6hr-iv infusion | Maximal b.w.% drop without death (%) | Relative therapeutic efficacy index at MTD[d] |
| EpoB | 0.53±0.2 | 105 | 57 | 15.8 | ND[e] | ND | 0.6-0.8 | 15 | +++ |
| deH-EpoB | 0.23±0.02 | 95.1 | 38±20 | 12.0 | ND | ND | 0.4-0.5 | 21 | ++++ |
| dEpoB | 5.6±2.8 | 106±6.6 | 46±7 | 1.0±0.1 | 9.4 | 4.4 | 25-30 | 32 | ++++ |
| deH-dEpoB | 0.90±0.40 | 105±0.9 | 84±6 | 4.9±0.7 | 26.5±0.5 | 3.3 | 3-4 | 29 | ++++ |
| F$_3$-dEpoB | 9.3±5.2 | 84.4 | 66±7 | 1.6±0.4 | 8 | 4.1 | 15-20 | 22 | ++ |
| F$_3$-deH-dEpoB | 3.2±0.3 | 121 | 212±88 | 10.5±2.3 | 19±1.0 | 3.3 | 10-30 | 33 | +++++ |
| dEpoF | 1.5±0.1 | 97.3 | 48±3 | 6.9±0.8 | ND | ND | 30 | 25 | +++ |
| deH-dEpoF | 0.51±0.09 | 96±0.9 | 185±15 | 14.5±0.6 | 200 | 1.9 | 2-4 | 23 | +++ |
| F$_3$-deH-dEpoF | 1.3±0.3 | 97.8 | 402±28 | 20.6±3.1 | 110 | 1.9 | 25-30 | 31 | +++ |

[a]$IC_{50}$ values are for CCRF-CEM leukemic cells. Ranges shown are for two experiments. All values are obtained from eight data points based on the median effect plot (21) using a CalcuSyn software (22). [b]Plasma was diluted 2-fold with phosphate buffered saline. [c]Human liver microsomal S9 fraction (400μg) was diluted 15-fold with phosphate buffered saline (see Supporting Online Materials). [d]Graded relative therapeuitic efficacy index at MTD (maximal tolerated dose): +Tumor growth suppressed by 25-50%. ++Tumor growth suppressed by 50-100%. +++Tumor shrinkage but no tumor disappearance. ++++Tumor disappearance in some or all nude mice with slow body-weight recovery and/or with relapse in some mice within two weeks after treatment stopped. +++++Tumor disappearance in all nude mice with rapid body-weight recovery and without relapse for two weeks or longer. The therapeutic effects of epothilones against human xenografts in nude mice, such as MX-1, were studied in references [15] and [16]. [e]ND, not determined.

FIG. 91

Potency of epothilones against tumor cell growth *in vitro* and the relative therapeutic index

| Compound | IC$_{50}$ (μM) | | | | |
|---|---|---|---|---|---|
| | Human T-cell Lymphoblustic Leukemia Sublines | | | Human Lung Carcinoma A549 | Human Colon Carcinoma HCT-116 |
| | CCRF-CEM | CCRF-CEM/VBL | CCRF-CEM/Taxol | | |
| dEpoB | 0.0056 ±0.0028 | 0.016 ±0.003 [2.9x]† | 0.0085 ±0.0055 [1.5x] | 0.0039 ±0.0004 | 0.0068 ±0.0032 |
| dEpoF | 0.0015 ±0.0001 | 0.055 ±0.09[36x] | 0.0066 ±0.0031 [4.4x] | 0.012 ±0.004 | 0.0034 ±0.0006 |
| EpoB | 0.00053 ±0.00017 | 0.0032 ±0.0012 [6.03x] | 0.0011 ±0.00008 [2.1x] | 0.0008 ±0.0005 | 0.00038 ±0.00001 |
| 15-Aza-EpoB | 0.0024 ±0.0003 | 2.08 [1423x] ±0.92 [867x] | 0.103 ±0.068[43x] | 0.0040 ±0.0035 | 0.0014 ±0.00009 |
| deH-dEpoB | 0.0009 ±0.0004 | 0.0042 ±0.0022 [4.7x] | 0.0012 ±0.0006 [1.3x] | 0.00089 ±0.00064 | 0.00094 ±0.00055 |
| deH-dEpoF | 0.00051 ±0.00009 | 0.021 ±0.010 [41x] | 0.0017 ±0.0010 [3.3x] | 0.00091 ±0.00006 | 0.00056 ±0.00006 |
| deH-EpoB | 0.00023 ±0.00002 | 0.00096 ±0.00064 [4.2x] | 0.00041 ±0.00001 [1.8x] | 0.00026 ±0.0004 | 0.00014 ±0.00001 |
| 15-Aza-deH-dEpoB | 1.71 ±0.03 | 82.1 ±40.0 [48x] | 18.6 ±9.3 [10.8x] | 3.41 | 3.38 |
| F$_3$-deH-dEpoB | 0.0032 ±0.0003 | 0.023 ±0.002 [7.2x] | 0.0047 ±0.0010 [1.5x] | 0.0037 ±0.0024 | 0.0056 ±0.0010 |
| 16(z)-F$_3$-deH-dEpoB | 2.04 ±0.20 | 3.78 ±0.98 [1.9x] | 4.85 ±1.56 [2.4x] | 1.93 ±0.21 | 2.37 ±0.41 |
| F$_3$-deH-dEpoF | 0.0013 ±0.0003 | 0.060 0.020[46x] | 0.0065[6.5x] 0.0007[5x] | 0.0009 ±0.00001 | 0.0012 ±0.0002 |
| F$_3$-dEpoB | 0.0093 ±0.0052 | 0.085 ±0.005[9.1x] | 0.018 ±0.001[1.9x] | 0.015 ±0.004 | 0.012 ±0.001 |
| Paclitaxel | 0.0018 ±0.0005 | 3.22 ±0.92 [1789x] | 0.079 ±0.029 [43.9x] | 0.0029 ±0.0003 | 0.0026 ±0.0009 |
| Vinblastine | 0.00054 ±0.00009 | 0.389 ±0.074 [720x] | 0.0196 ±0.0111 [36.3x] | 0.0099 ±0.0018 | 0.0087 ±0.0007 |

*Cell growth inhibition for leukemic cells and solid tumor cells were measured by XTT tetrazonium assay and by sulfortrodemine B (SRB) method, respectively, after 72-hr incubation for cell growth, as described previously (15,16). IC$_{50}$ values were determined from dose-effect relationship at six or seven concentrations of each drug in duplicate, by using a computer program (22) as described earlier (13). Values given are the mean ±SE for 2 to 4 experiments except as otherwise indicated.

† The therapeutic experiments for epothilones against human tumor xenografts in nude mice, such as MX-1, were described *(in Refs 13, 15 and 16)*.

‡ The numbers in brackets are fold of resistance based on the IC$_{50}$ ratilo when compared with the corresponding parent cell lines. CCRF-CEM/VBL and CCRF-CEM/Taxol are the CCRF-CEM leukemic cells resistant to vinblastine and paclitaxel, 720-fold and 44-fold, respectively.

FIG. 94

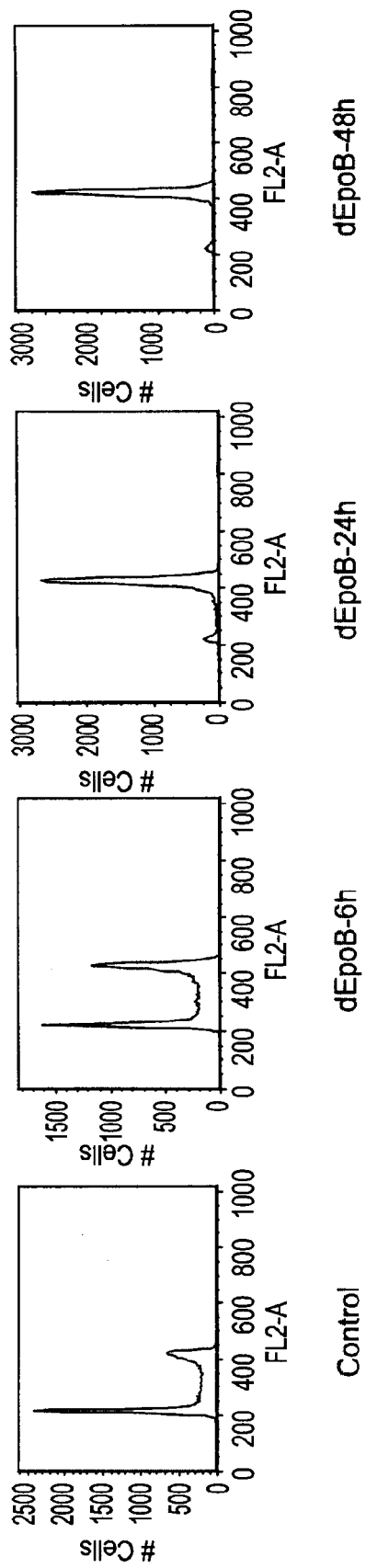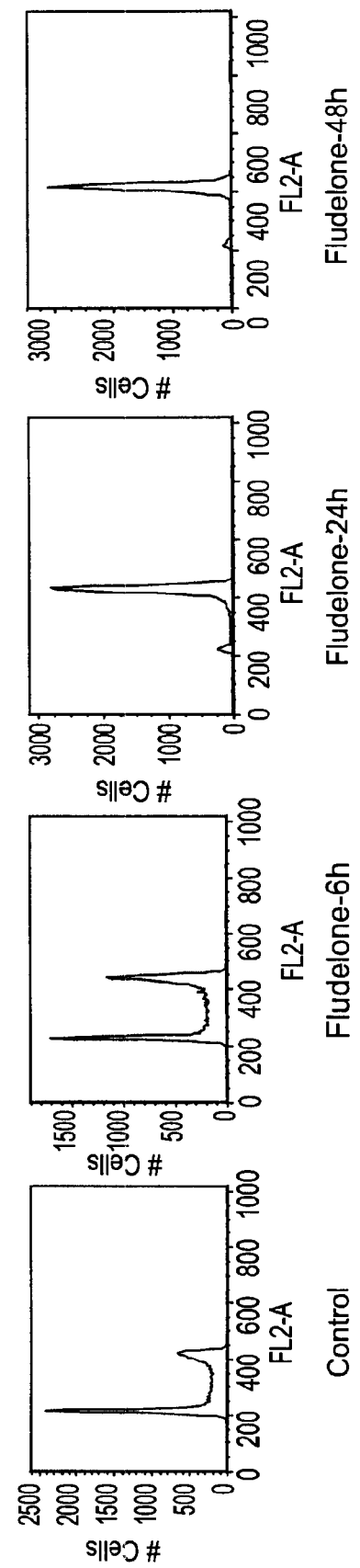
FIG. 95

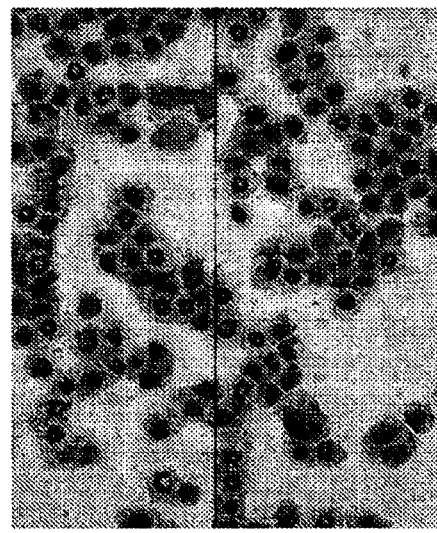
FIG. 97A

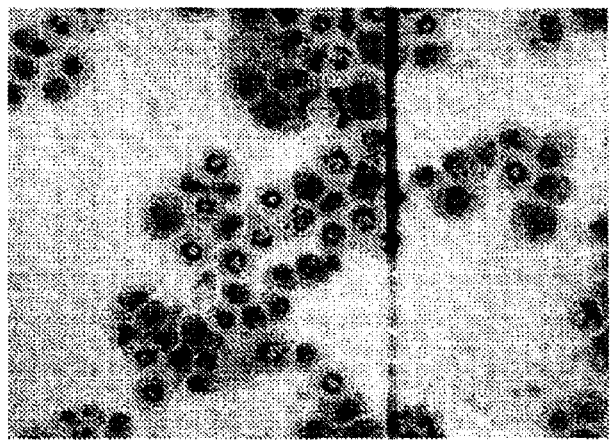
Lymphoma lines
SKI-DLBCL-Fludelone-24hrs
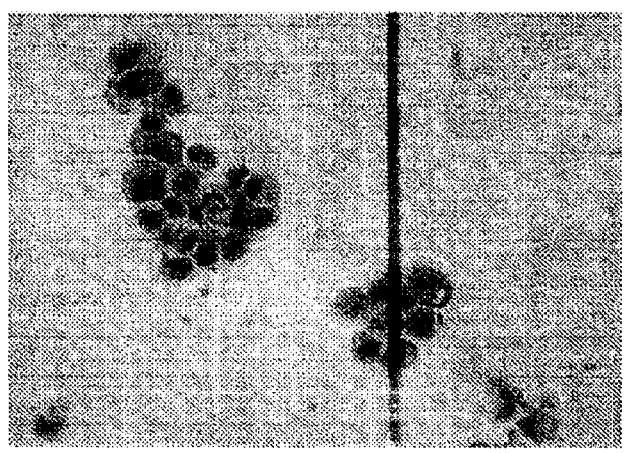
RL-Fludelone-24hrs
FIG. 97B

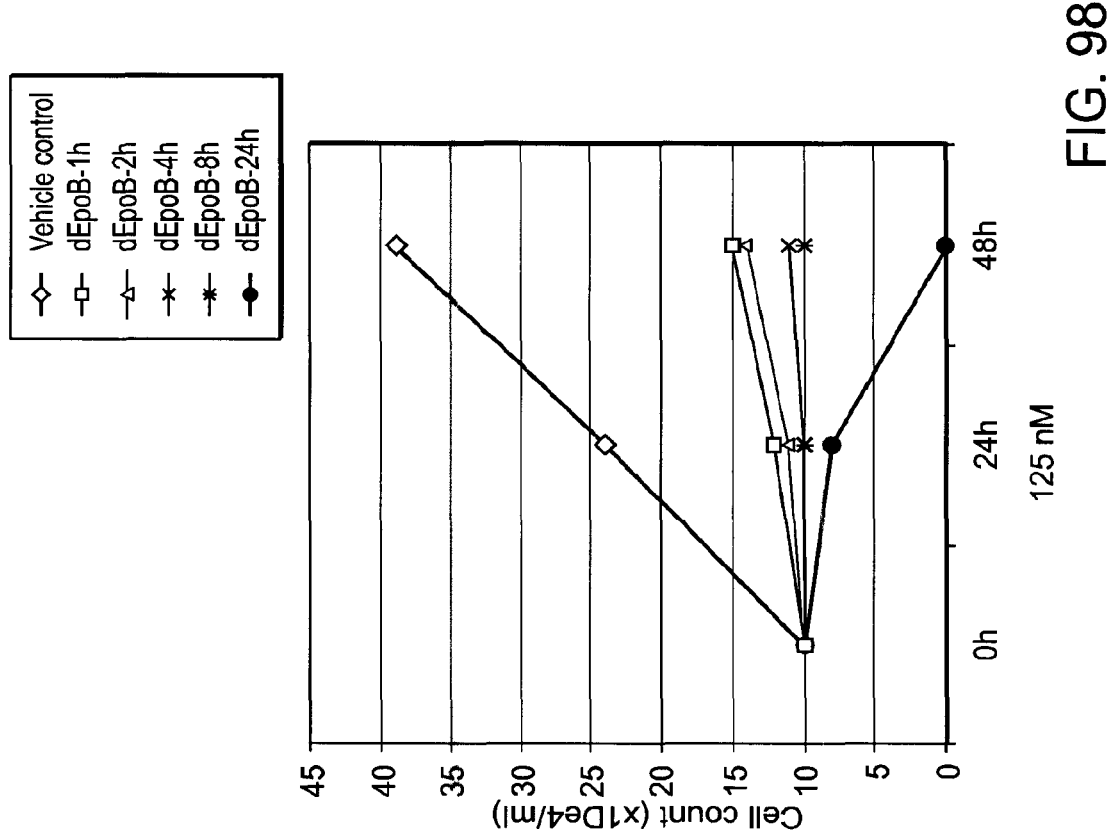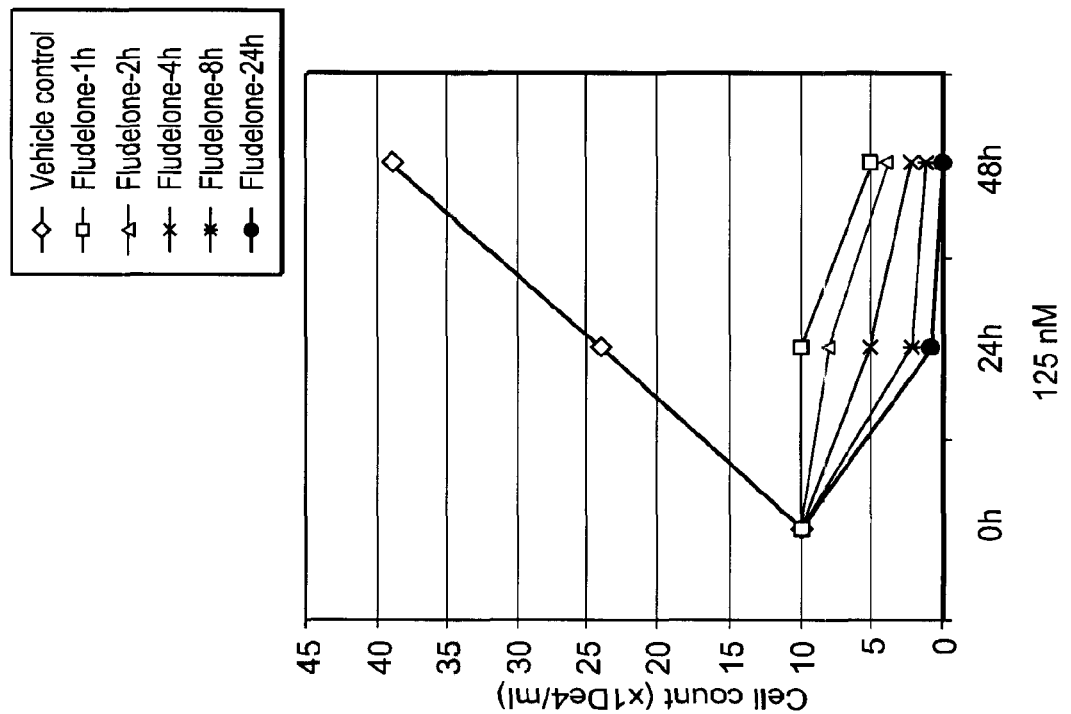
FIG. 98

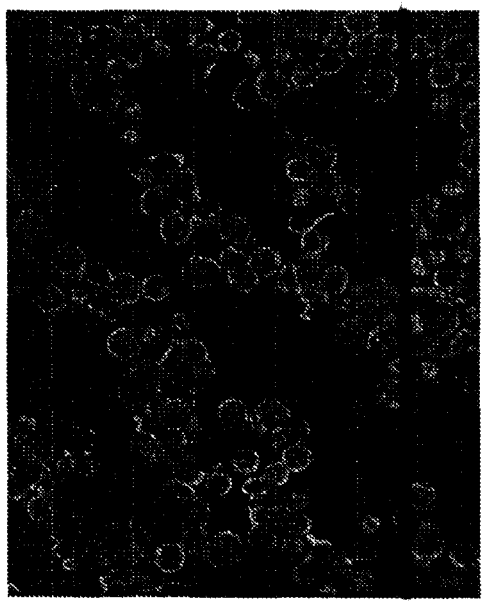
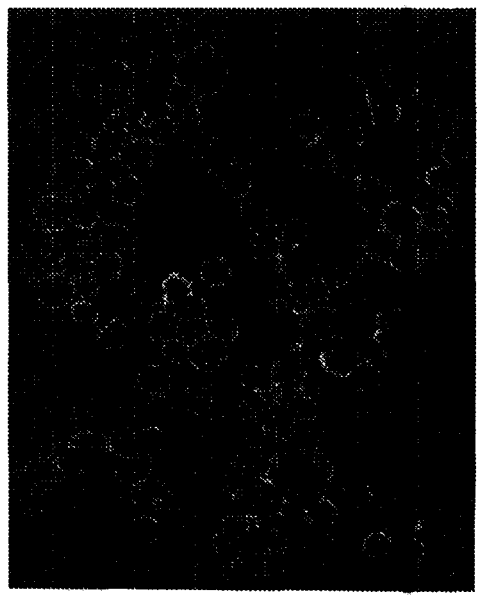
FIG. 99

Treatment of disseminated CAG Xenograft myeloma mice at Day 40
(Tx started on day 10, 20mg/kg Q2d, Images are taken after 12 dosages)

Back

Front

Control    dEpoB    Fludelone

Immunohistochemical staining of CAG myeloma cells using cleaved caspase-3 antibody, showing cytoplasmic and perinuclear localization in apoptotic cells Immunohistochemical staining of CAG myeloma cells using cleaved caspase-3 antibody, showing cytoplasmic and perinuclear localization in apoptotic cells (low and high magnifications)

SYNTHESIS OF EPOTHILONES, INTERMEDIATES THERETO, ANALOGUES AND USES THEREOF

PRIORITY INFORMATION

The present application is continuation of and claims priority under 35 U.S.C. 120 to application U.S. Ser. No. 10/921,109, filed Aug. 18, 2004, now issued as U.S. Pat. No. 7,384,964, which is a continuation-in-part of and claims priority under 35 U.S.C. §120 to application U.S. Ser. No. 10/435,408, filed May 9, 2003, which is a continuation-in-part of and claims priority under 35 U.S.C. §120 to application U.S. Ser. No. 10/402,004, filed Mar. 28, 2003 now U.S. Pat. No. 6,921,769, which claims priority under 35 U.S.C. §119(e) to provisional applications U.S. Ser. No. 60/405,823, filed Aug. 23, 2002, entitled "Synthesis of Epothilones, Intermediates Thereto and Analogues Thereof"; U.S. Ser. No. 60/408,589, filed Sep. 6, 2002, entitled "Synthesis of Epothilones, Intermediates Thereto and Analogues Thereof"; U.S. Ser. No. 60/423,129, filed Nov. 1, 2002, entitled "Synthesis of Epothilones, Intermediates Thereto and Analogues Thereof"; U.S. Ser. No. 60/456,159, filed Mar. 20, 2003, entitled "Synthesis of Epothilones, Intermediates Thereto and Analogues Thereof"; the entire contents of each of which are incorporated herein by reference. The present application also claims priority under 35 U.S.C. §119(e) to provisionals U.S. Ser. No. 60/496,741, filed Aug. 21, 2003, entitled "Synthesis of Epothilones, Intermediates Thereto and Analogues Thereof"; and U.S. Ser. No. 60/548,402, filed Feb. 27, 2004, entitled "Synthesis of Epothilones, Intermediates Thereto and Analogues Thereof"; the entire contents of each of which are incorporated herein by reference.

BACKGROUND OF THE INVENTION

Epothilones A and B (2a and 2b, Scheme 1) are naturally occurring cytotoxic macrolides that were isolated from a cellulose degrading mycobacterium, *Sorangium cellulosum* (Höfle et al. *Angew. Chem., Int. Ed. Engl.* 1996, 35, 1567 and *J. Antibiot.* 1996, 49, 560; each of which is incorporated herein by reference). Despite their vastly different structures, epothilones A and B share the same mechanism of action as paclitaxel (Taxol®) which involves growth inhibition of tumor cells by tubulin polymerization and stabilization of microtubule assemblies (Bollag et al. *Cancer Res.* 1995, 55, 2325; incorporated by reference). In spite of its unquestioned clinical value as a front-line chemotherapeutic agent, Taxol® is far from an ideal drug. Its marginal water solubility necessitates recourse to formulation vehicles such as Cremophores that pose their own risks and management issues (Essayan et al. *J. Allergy Clin. Immunol.* 1996, 97, 42; incorporated herein by reference). Moreover, Taxol® is vulnerable to deactivation through multiple drug resistance (MDR) (Giannakakou et al. *J. Biol. Chem.* 1997, 272, 17118; incorporated herein by reference). However, it has also been demonstrated that epothilones A and B retain remarkable potency against MDR tumor cells (Kowalski et al. *Mol. Biol. Cell* 1995, 6, 2137; incorporated herein by reference). Additionally, the increased water solubility in comparison to paclitaxel may be useful for the formulability of epothilones. While the naturally occurring compound, epothilone B (2b, EpoB, in Scheme 1), is a potent member of the epothilone family of natural products, it unfortunately possesses, at least in xenograft mice, a worrisomely narrow therapeutic index (Su et al. *Angew. Chem. Int. Ed. Engl.* 1997, 36, 1093; Harris et al. *J. Org. Chem.* 1999, 64, 8434; each of which is incorporated herein by reference).

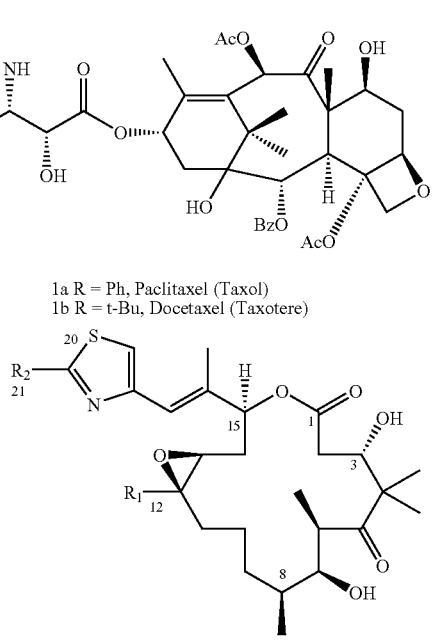

Scheme 1: Taxoids and Epothilones

1a R = Ph, Paclitaxel (Taxol)
1b R = t-Bu, Docetaxel (Taxotere)

2a $R_1$ = H, $R_2$ = $CH_3$, Epothilone A (EpoA)
2b $R_1$ = $CH_3$, $R_2$ = $CH_3$, Epothilone B (EpoB)
2c $R_1$ = H, $R_2$ = $CH_2OH$, Epothilone E (EpoE)
2d $R_1$ = $CH_3$, $R_2$ = $CH_2OH$, Epothilone F (EpoF)

Given the limited therapeutic index of EpoB, other epothilone analogues, in particular the 12,13-desoxyepothilones, were investigated for their ability to provide an improved therapeutic profile (see, U.S. Pat. Nos. 6,242,469, 6,284,781, 6,300,355, 6,369,234, 6,204,388, 6,316,630; each of which is incorporated herein by reference). In vivo experiments conducted on various mouse models demonstrated that 12,13-desoxyepothilone B (3b, dEpoB in Scheme 2) possesses therapeutic potential against various sensitive and resistant human tumors in mice xenografts (Chou et al. *Proc. Natl. Acad. Sci. U.S.A.* 1998, 95, 9642 and 15798; incorporated herein by reference). Recently, the therapeutic superiority of these desoxyepothilones over other anticancer agents has been conclusively demonstrated by thorough comparative studies (Chou et al. *Proc. Natl. Acad. Sci. U.S.A.* 2001, 98, 8113; incorporated herein by reference). Due to its impressive in vivo profile, dEpoB has been advanced through toxicology evaluations in dogs, and is now in human trials as an anticancer drug.

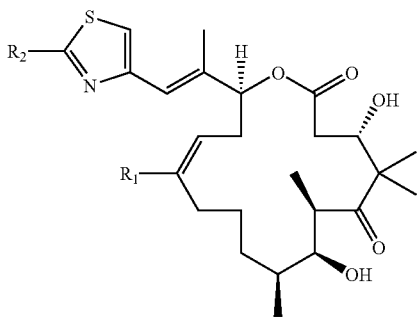

Scheme 2. Various Desoxyepothilone Analogues

3a $R_1$ = H, $R_2$ = $CH_3$, Desoxyepothilone A (dEpoA)
3b $R_1$ = $CH_3$, $R_2$ = $CH_3$, Desoxyepothilone B (dEpoB)
3c $R_1$ = H, $R_2$ = $CH_2OH$, Desoxyepothilone E (dEpoE)
3d $R_1$ = $CH_3$, $R_2$ = $CH_2OH$, Desoxyepothilone F (dEpoF)
3e $R_1$ = H, $R_2$ = $NH_2$, Desmethylamino-dEpoA (dadEpoA)
3f $R_1$ = $CH_3$, $R_2$ = $NH_2$, Desmethylamino-dEpoB (dadEpoB)
3g $R_1$ = $CH_2F$, $R_2$ = $CH_3$, 26-Fluoro-dEpoB
3h $R_1$ = $CF_3$, $R_2$ = $CH_3$, 26-TRifluoro-dEpoB

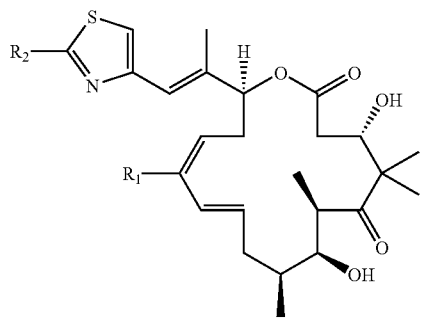

4a $R_1$ = H, $R_2$ = $CH_3$, Dehydro-dEpoA (ddEpoA)
4b $R_1$ = $CH_3$, $R_2$ = $CH_3$, Dehydro-dEpoB (ddEpoB)
4c $R_1$ = H, $R_2$ = $CH_2OH$, Dehydro-dEpoE (ddEpoE)
4d $R_1$ = $CH_3$, $R_2$ = $CH_2OH$, Dehydro-dEpoF (ddEpoF)
4e $R_1$ = H, $R_2$ = $NH_2$, Desmethylamino-ddEpoA
4f $R_1$ = $CH_3$, $R_2$ = $NH_2$, Desmethylamino-ddEpoB
4g $R_1$ = $CH_2F$, $R_2$ = $CH_3$, 26-Fluoro-ddEpoB
4h $R_1$ = $CF_3$, $R_2$ = $CH_3$, 26-TRifluoro-ddEpoB

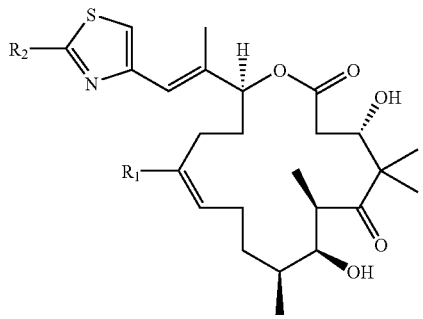

5a $R_1$ = H, $R_2$ = $CH_3$, iso-dEpoA
5b $R_1$ = $CH_3$, $R_2$ = $CH_3$, iso-dEpoB
5c $R_1$ = H, $R_2$ = $CH_2OH$, iso-dEpoE
5d $R_1$ = $CH_3$, $R_2$ = $CH_2OH$, iso-dEpoF (ddEpoF)
5e $R_1$ = H, $R_2$ = $NH_2$, Desmethylamino-iso-dEpoA
5f $R_1$ = $CH_3$, $R_2$ = $NH_2$, Desmethylamino-iso-dEpoB In light of the promising therapeutic utility of the 12,13-desoxyepothilones, it would be desirable to investigate additional analogues as well as additional synthetic methodologies for the synthesis of existing epothilones, desoxyepothilones, and analogues thereof, as well as novel analogues thereof. In particular, given the interest in the therapeutic utility of this class of compounds, it would also be desirable to develop methodologies capable of providing significant quantities of any epothilones or desoxyepothilones previously described, or those described herein, for clinical trials and for large-scale preparation.

DESCRIPTION OF THE DRAWINGS

FIG. 6 depicts alternative synthetic strategies for preparing 9,10-dehydro epothilone analogs. FIG. 6A illustrates a Macro-Stille strategy, a $sp^3$-$sp^3$ coupling strategy, and β-Suzuki strategy. FIG. 6B illustrates a Julia olefination strategy, a Wadsworth-Emmons strategy, and a Macro-Reformatosky strategy. FIG. 6C illustrates a McMurry coupling strategy and a lactam analog synthesis.

FIG. 7 shows various analogs of 9,10-dehydro-12,13-desoxy EpoB.

FIG. 11 shows the potencies of various epothilone analogues against tumor cell growth in vitro and therapeutic index, as compared to paclitaxel and vinblastine.

FIG. 12 is a table summarizing the effect of dEpoB, Taxol, and 26-triF-9,10-deH-dEpoB against MX-1 xenograft in nude mice.

FIG. 31 is a table with $IC_{50}$ values for epothilone analogues against CCRF-CEM cell growth.

FIG. 32 shows the metabolic stability of epothilone analogues in vitro.

FIG. 33 is a table detailing the therapeutic effects of various epothilone analogues against human tumor xenografts in mice with 6 hour iv infusion.

FIG. 41 are tables describing the effect of various epothilone analogues on in vitro microtubule polymerization at 37° C. in the absence of GTP (A) and the cytotoxicity of various epothilone analogs in the human lung cell line A549 (B).

FIG. 52 is a table comparing the potency of various epothilone analogs with respect to inhibition of tumor growth in vitro and relative therapeutic index.

FIG. 60 depicts the synthesis of C-21 modified 9,10-(E)-dehydro-epothilones.

FIG. 61 is table with IC$_{50}$ values for C-21 modified epothilones against tumor cell line CCRF-CEM and its drug-resistant sublines.

FIG. 82 shows the synthesis of various 9,10-dehydro-epothilone analogs using a ring closing metathesis reaction at the 9,10-position.

FIG. 83 shows the results of an experiment in which an extra large MX-1 xenograft was implanted in nude mice. MX-1 tumor tissue (50 mg) was implanted s.c. on day 0. On day 22 (D22) when tumor size reached 960±132 mg (about 3.4% of body weight), Fludelone 25 mg/kg, 6 hr-i.v. infusion, Q3Dx5 was given on D22, D25, D28, D31 and D34 as indicated by arrows. The second cycle of treatment, following 9 day rest, was given on D43, D46, D49 and D52. Tumor size changes in the vehicle treated control (●) and Fludelone treated group (□) (n=5 each). Observation was continued Q3D up to D180 when the experiment was terminated (128 days following cessation of treatment on D52). FIG. 83B shows photographs for the nude mice (one mouse each selected from the control group and the treated group) taken on D25, D31, D37, D43 and D52. No relapse was observed on D180 when the experiment was terminated.

FIG. 84 shows the results of an experiment in which nude mice were implanted with human T-cell lymphoblastic leukemia (CCRF-CEM/Taxol) which is 44-fold resistant to Taxol. Tumor tissue of CCRF-CEM/Taxol (44-fold resistant in vitro), 50 mg/mouse was implanted s.c. into nude mice on Day 0. Treatment of 6 hr-i.v. infusion started on D8 with Fludelone 15 mg/kg (□) (n=3) and 30 mg/kg (Δ) (n=4), or Taxol 20 mg/kg (○) (n=4). Q2Dx7 (D8-D20), skipped D22 dose, and then resumed treatment Q2Dx5 on D24, 26, 28, 30 and 32, as indicated by arrows. The control group (●) (n=4) received vehicle only. For Fludelone at 15 mg/kg, 1/3 mice's tumor disappeared on D37, and at 30 mg/kg, 3/4 mice's tumor disappeared on D22, 22 and 32).

FIG. 85 shows the treatment of nude mice implanted with a human mammary carcinoma MX-1 xenograft using an oral formulation of 26-trifluoro-9,10-dehydro-dEpoB and Taxol (PO, Q2Dx7, x5).

FIG. 86 shows the treatment of nude mice bearing human colon carcinoma HCT-116 xenograft using 26-trifluoro-9,10-dehydro-dEpoB and Taxol ((Q2Dx4)x3, 6 hr. iv infusion). HCT-116 tumor tissue 50 mg/mouse was implanted s.c. into nude mice on Day 0. Treatment of Q2Dx4, 6 hr-i.v. fusion for 3 cycles was carried out on (D9, 11, 13, 15), (D19, 21, 23, 25) and (D31, 34, 35, 37) with Fludelone 20 mg/kg (□), 30 mg/kg (Δ) and Taxol 20 mg/kg (○) (n=4 each). Complete tumor disappearance in all mice occurred on (D33, 35, 41, 45), (D21, 23, 33, 41) and (D33, 33, 41, 45) for Fludelone 20 mg/kg, 30 mg/kg and Taxol 20 mg/kg, respectively. There was no tumor relapse for both of Fludelone treated group on D200 when the experiment was terminated. However, the Taxol treated group (○) suffered relapses on D71, 75, 81, and 81 which represent the relapses on $34^{th}$, $38^{th}$, $41^{st}$ and $41^{st}$ day after stopping treatment.

FIG. 87 shows the treatment of female nude mice bearing large human mammary carcinoma MX-1 xenografts using an oral formulation of 26-trifluoro-9,10-dehydro-dEpoB (PO, Q2Dx7, x9). Female nude mice were used. Fludelone 30 mg/kg (□) (n=3) was given orally Q2Dx7 beginning D16 after tumor implantation and then Q2Dx9 on D32-48, as indicated by arrows. All three mice's tumor disappeared on D40, 45 and 48. For consolidation therapy, the third cycle of treatment was given Q2Dx5 from D58-66 when all mice were tumor free on D48. There was no relapse on D115 (49 days after stopping treatment). Control (●) (n=2) received vehicle only. Parallel comparative experiment was carried out with Taxol 30 mg/kg (Δ) (n=3), orally beginning D16, Q2Dx3 and then the dose was increased to 40 mg/kg, Q2Dx3 (D22-26) and then 60 mg/kg, Q2Dx3 (D28-40).

FIG. 88 shows the treatment of nude mice bearing human lung carcinoma (A549/Taxol) which is 44-fold resistant to Taxol using 26-trifluoro-9,10-dehydro-dEpoB and Taxol (6 hour iv infusion, Q3Dx11).

FIG. 88B shows changes in body weight before and after treatment.

FIG. 90 shows the a comparision of 26-trifluoro-9,10-dehydro-dEpoB, dEpoB, and Taxol in the treatment of nude mice bearing human mammary carcinoma MX-1 xenografts using an oral formulation (PO, Q2Dx7, x5).

FIG. 91 is a table summarizing various therapeutic and pharmacokinetic parameters of epothilone derivatives.

FIG. 92 shows the treatment of nude mice bearing human lung carcinoma (A549) xenograft using 26-trifluoro-9,10-dehydro-dEpoB and dEpoB (6 hour iv infusion, $(Q2Dx6)_{x2}$, x2).

FIG. 94 shows the potency of epothilones against tumor cell growth in vitro and the relative therapeutic index.

FIG. 95 is cell cycle analysis as determined by Propidium iodide DNA staining. Cell cycle was arrested in G2M phase starting from 6 hours and absolutely blocked at 24 hours for OPM-2 myeloma cells after treatment with dEpoB (upper panel) and Fludelone (lower panel). The two drugs induced the same patter of cell cycle arrest.

FIG. 97 show micrographs of myeloma and lymphoma cell lines treated with Fludelone (125 nM) for 24 hours. The characteristic ring-like structures of the cells arrested in G2/M is seen.

FIG. 98 shows the cells count of RPMI8226 myeloma cells treated with Fludelone and dEpoB (125 nM). At different time points (1, 2, 4, 8, 24 hours), the drug was washed out, and the cells were continued to be incubated for up to 48 hours. Note that with as little as 1 hour exposure to Fludelone the tumor cell numbers progressively decrease with the majority of cells undergoing apoptosis at 24 hours whereas with dEpoB cells continue to expand.

FIG. 99 shows α-tubulin staining of RPMI8226 myeloma cells. Fludelone appears to stabilize microtubules and greatly increase the microtubule polymer mass at an early stage of treatment (at 12 hours with RPMI8226 myeloma cells). After 24 hours of drug treatment, microtubules mass was decrease and disrupted while cells underwent apoptosis.

Figure 119:
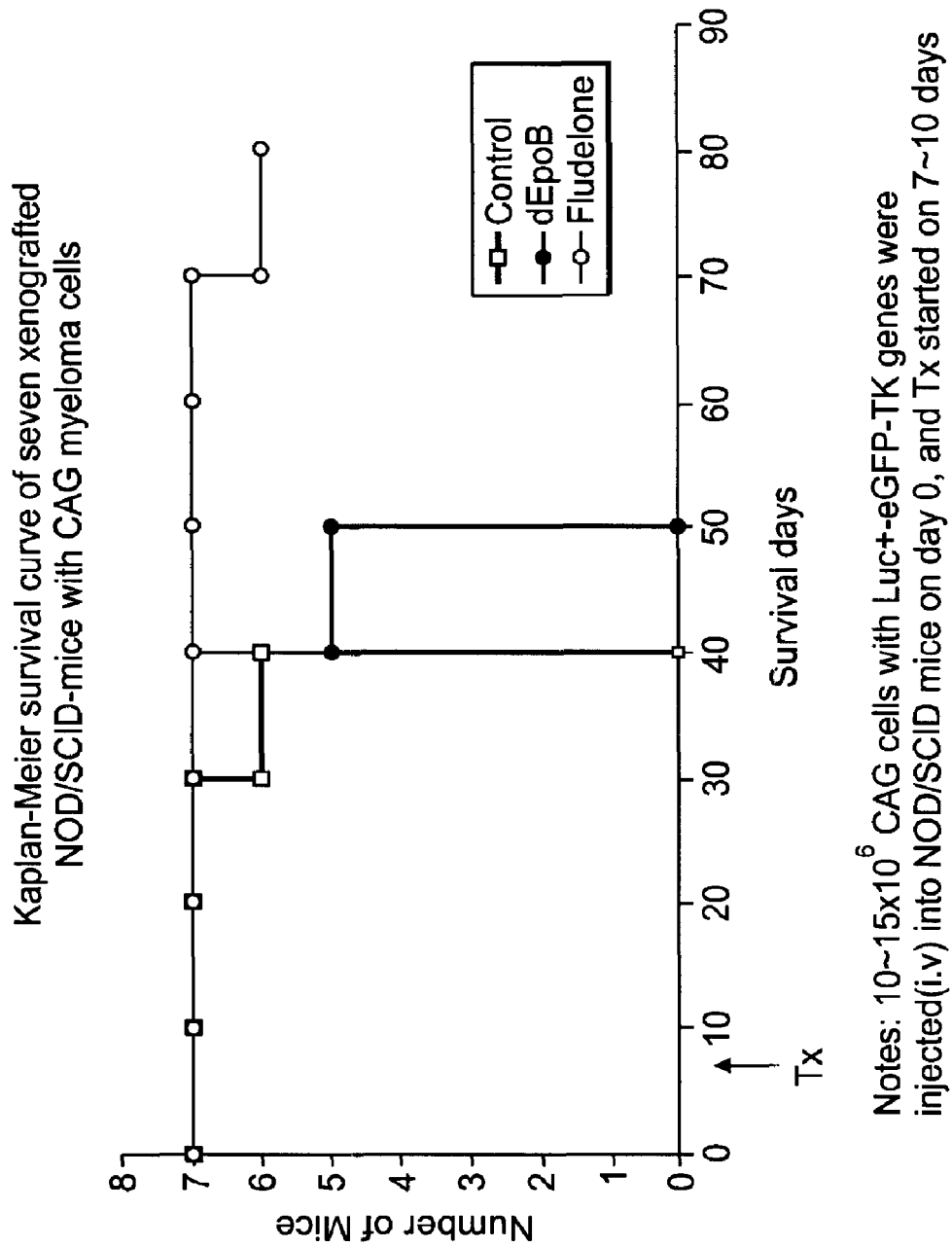

FIG. 119 is a Kaplan-Meier survival curve of seven xenografted NOD/SCID-mice with CAG myeloma cells. Control mice died within 40 days after transplanting CAG cells, and mice treated with dEpoB died within 50 days. Except for one mouse which died in 70 days, all mice treated with Fludelone survived beyond 80 days.

Figure 120:
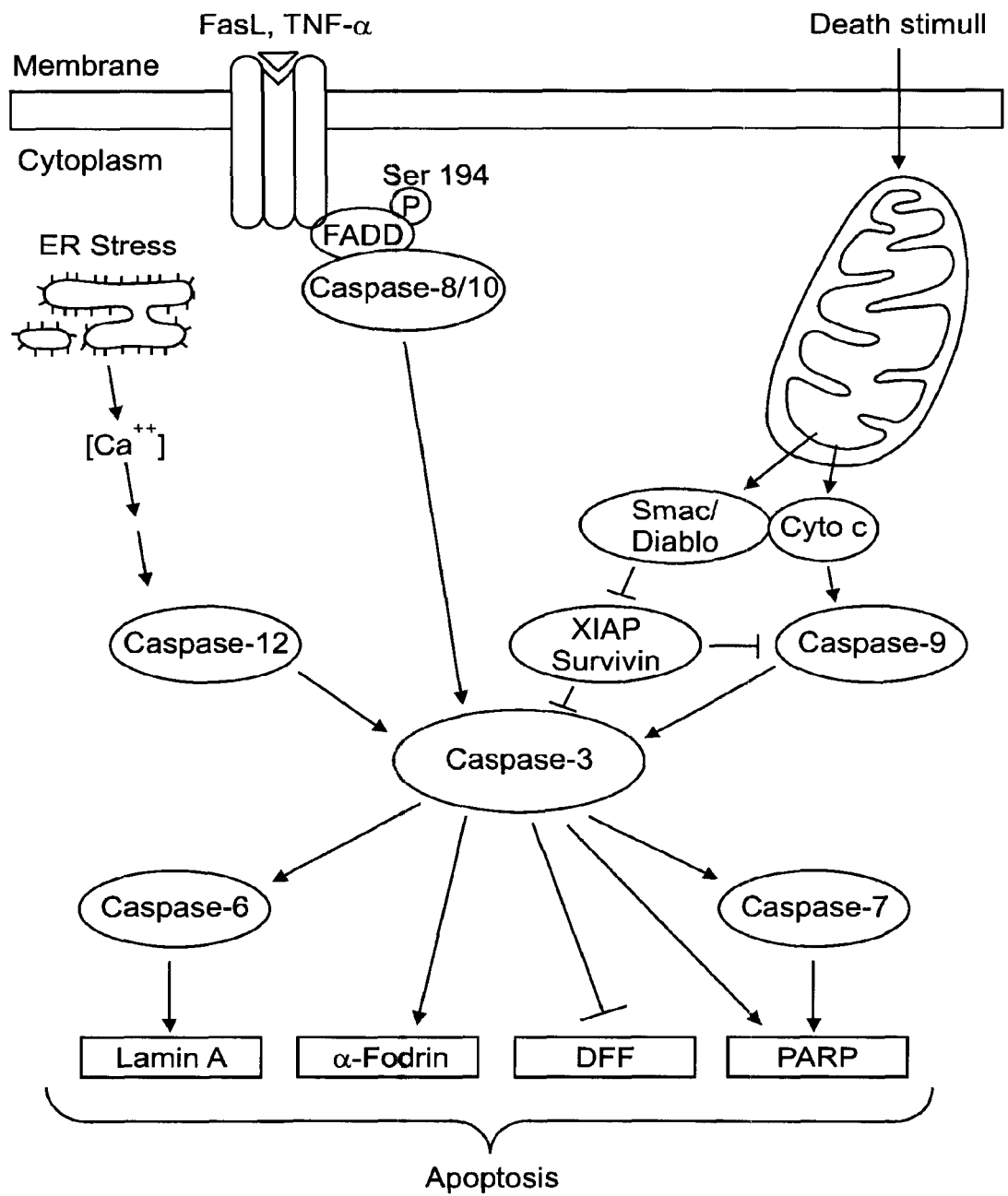

FIG. 120 shows the pathways of cell apoptosis.

Figure 121:
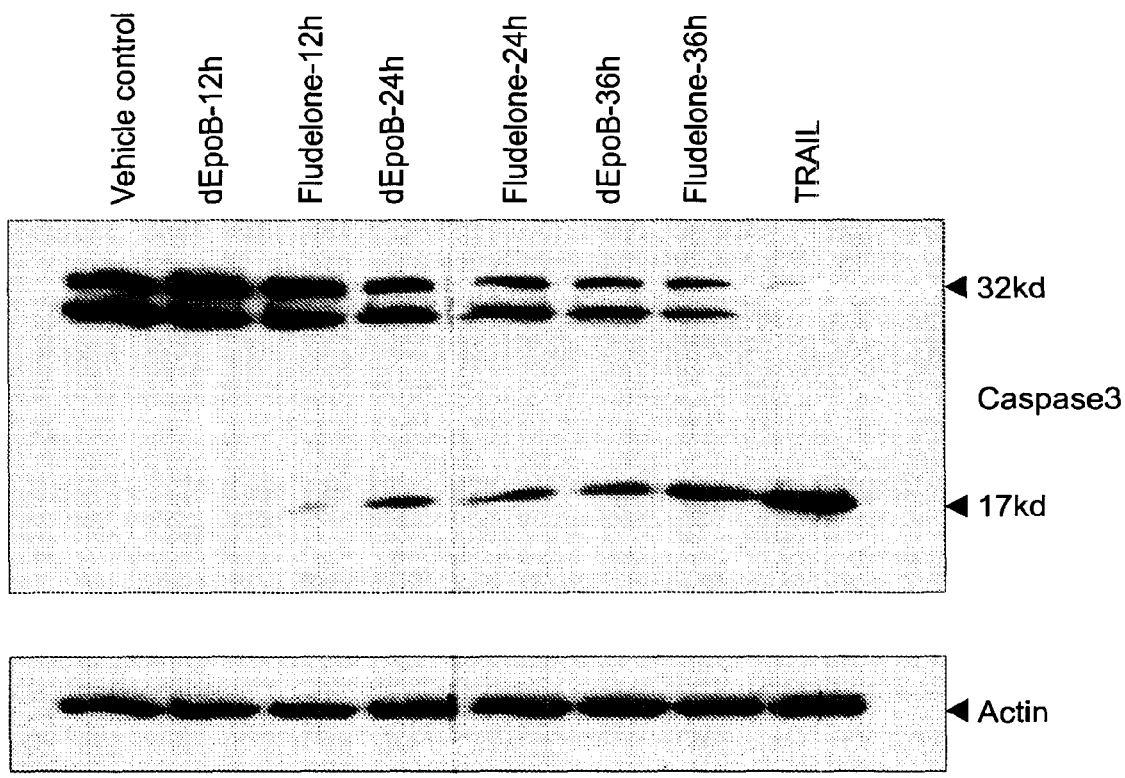

FIG. 121 shows the epothilone-induced time-dependent processing of caspase 3 in CAG myeloma cells, showing an increased 17 kd cleaved form of caspase 3 with drug treatment time.

Figure 122:
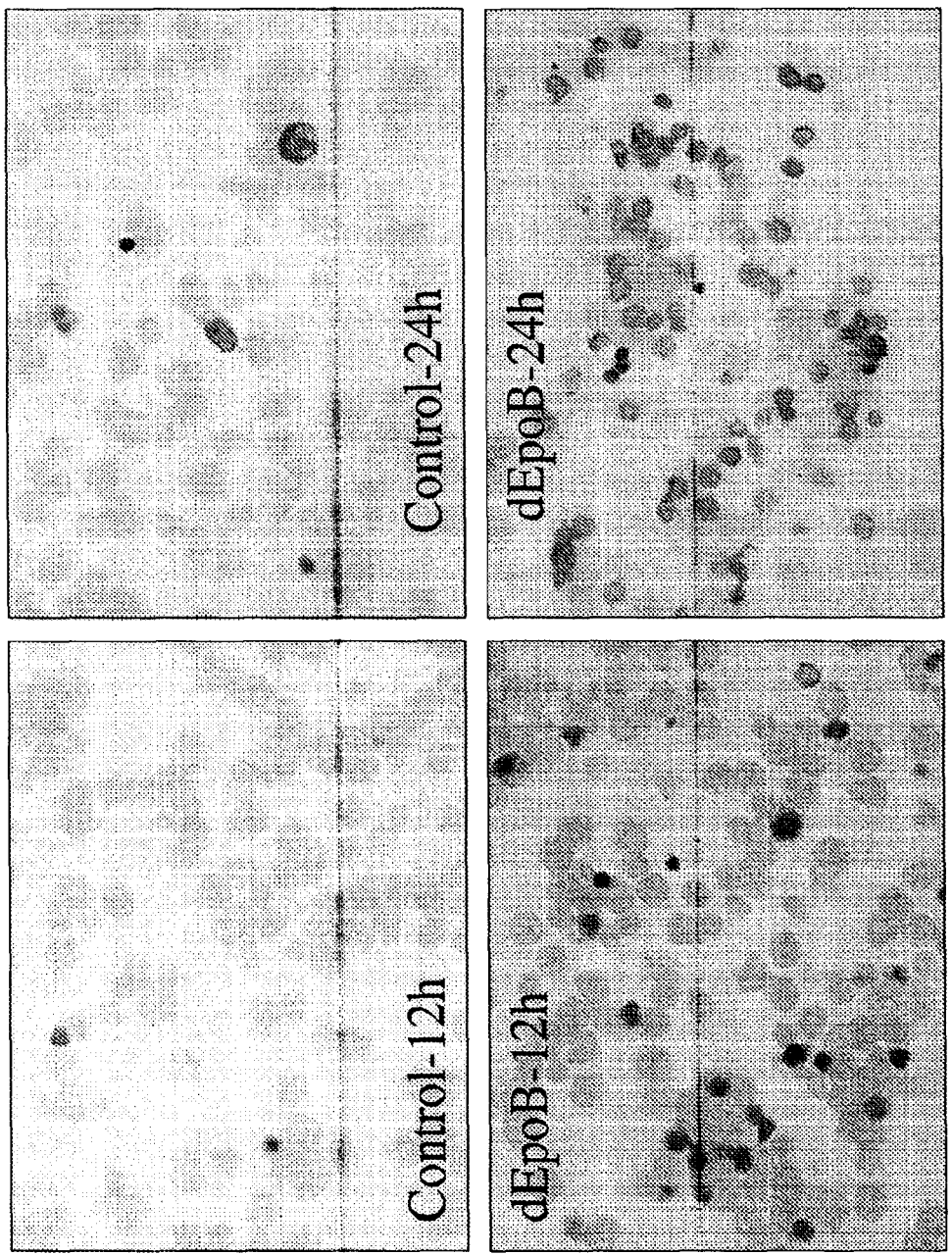

FIG. 122 shows immunohistochemical staining of CAG myeloma cells using cleaved caspase-3 antibody, showing cytoplasmic and perinuclear localization in apoptotic cells (low and high magnifications are shown).

Figure 123:
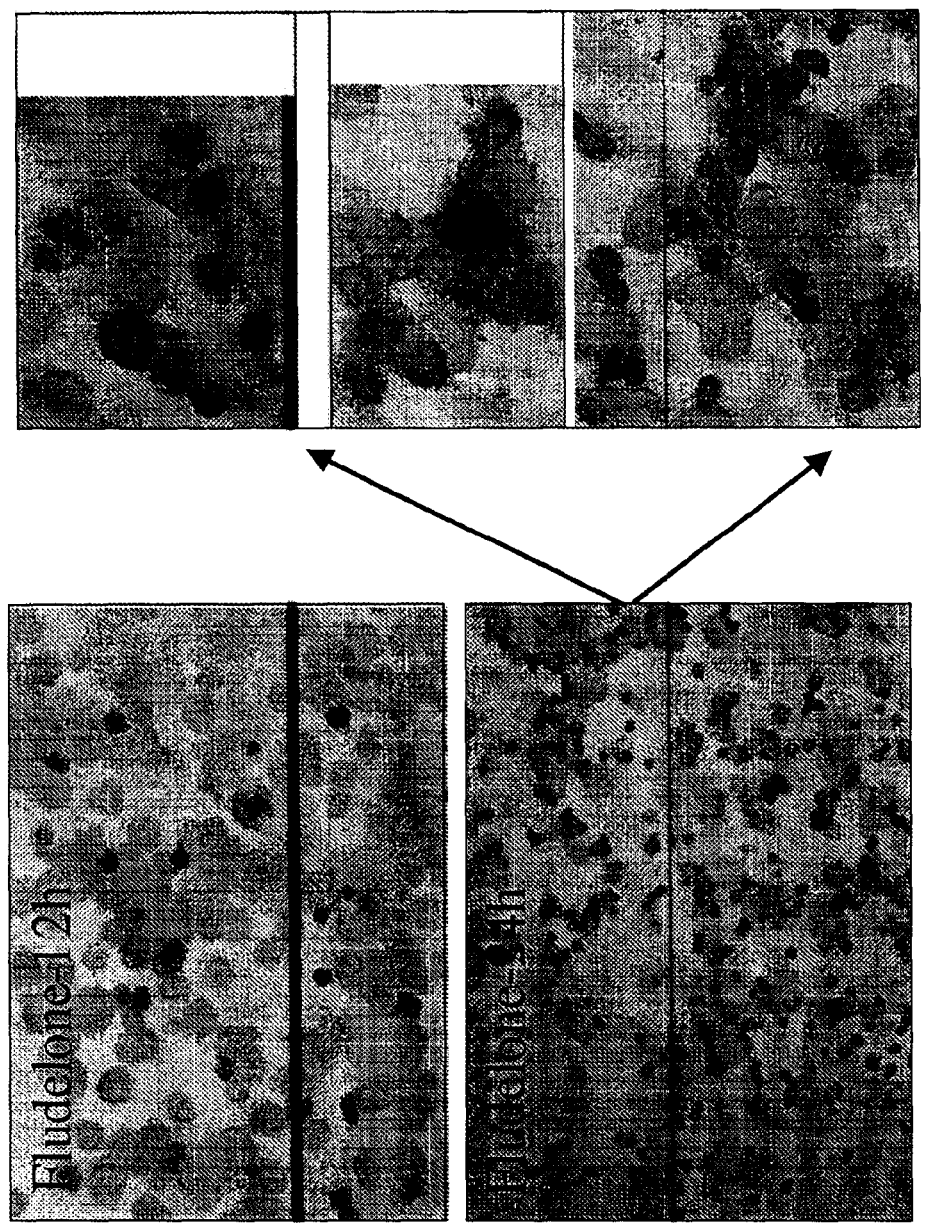

FIG. 123 shows Immunohistochemical staining of CAG myeloma cells using cleaved caspase-3 antibody, showing cytoplasmic and perinuclear localization in apoptotic cells (low and high magnifications are shown).

Figure 124:
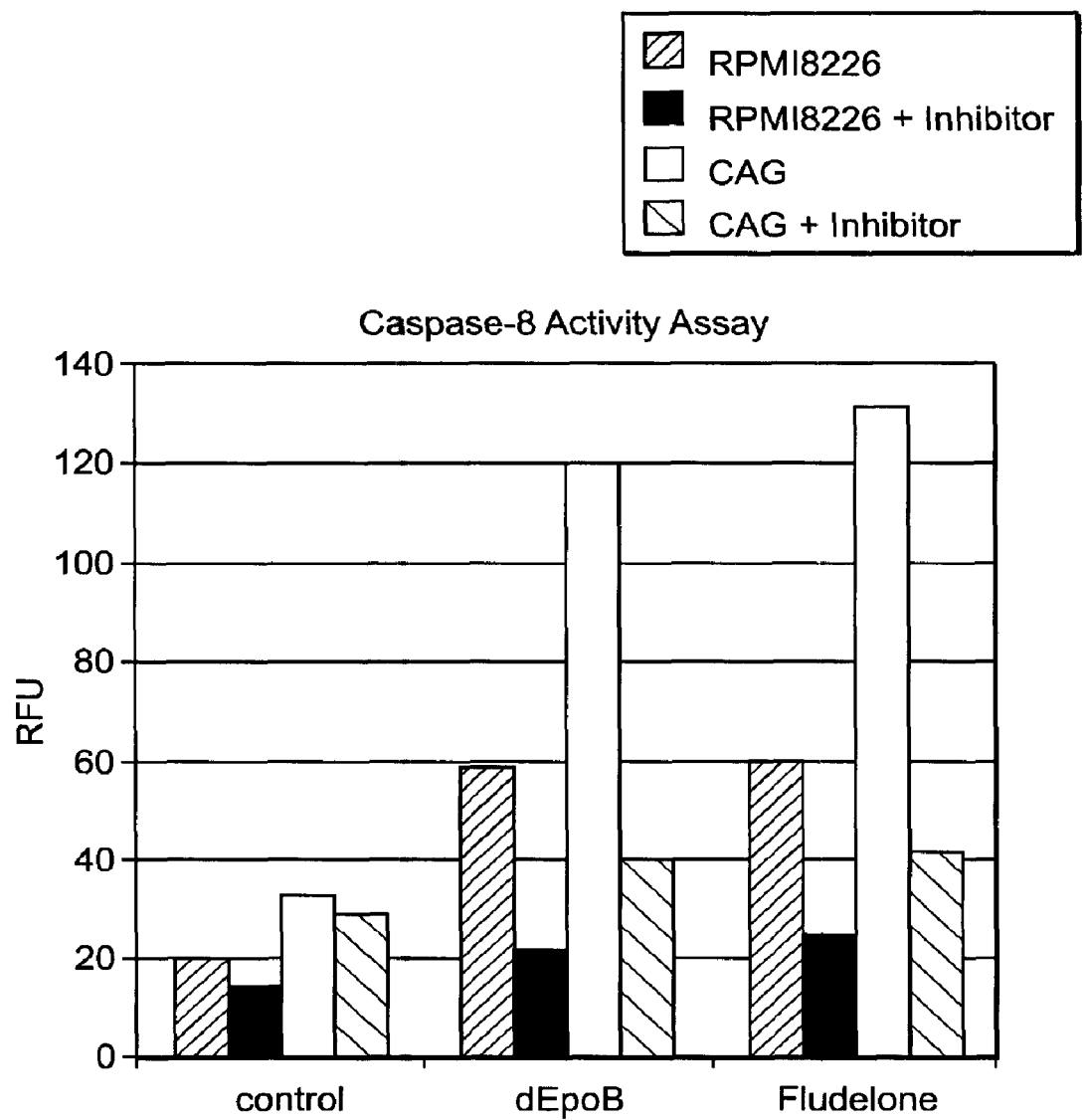

FIG. 124 indicates that caspase 8 activity was increased after epothilone treatment, and that this increase can be inhibited by caspase 8 specific inhibitors.

Figure 125:
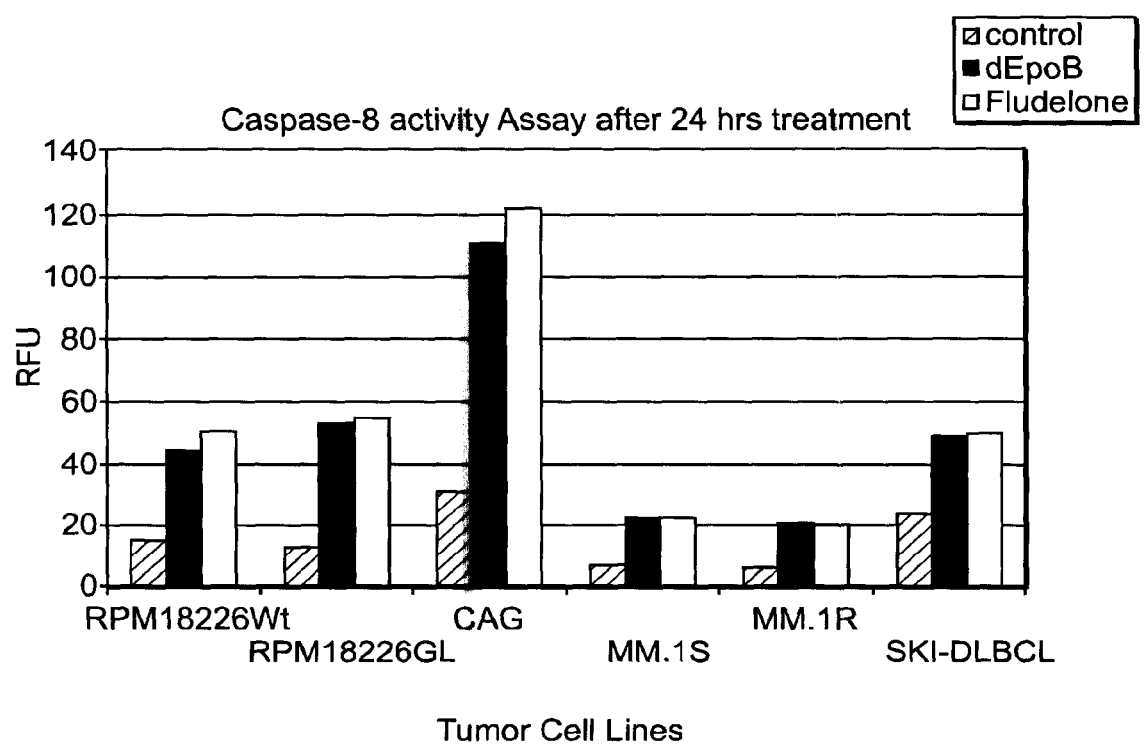

FIG. 125 indicates that caspase 8 activity was increased after epothilone treatment, and that this increase can be inhibited by caspase 8 specific inhibitors.

Figure 126:
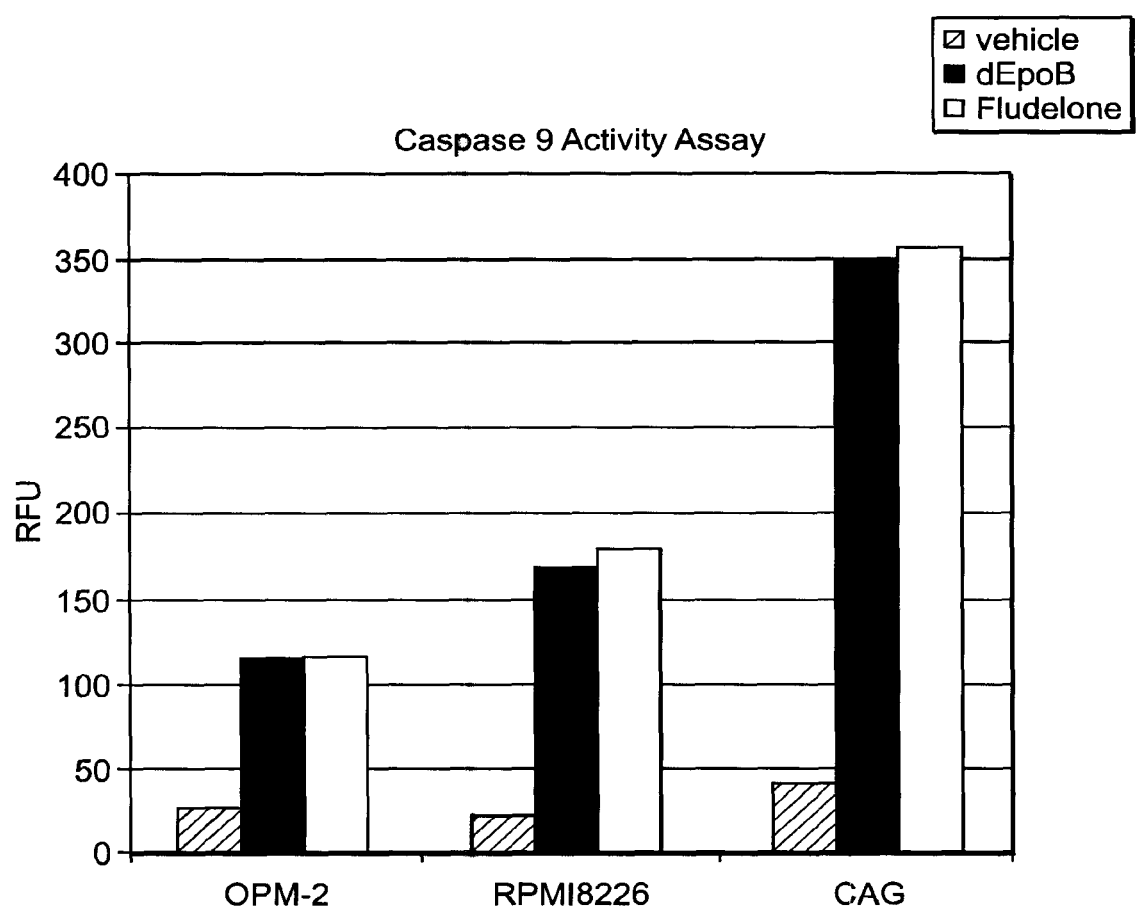

FIG. 126 indicates that caspase 9 activity was increased after epothilone treatment.

Figure 127:
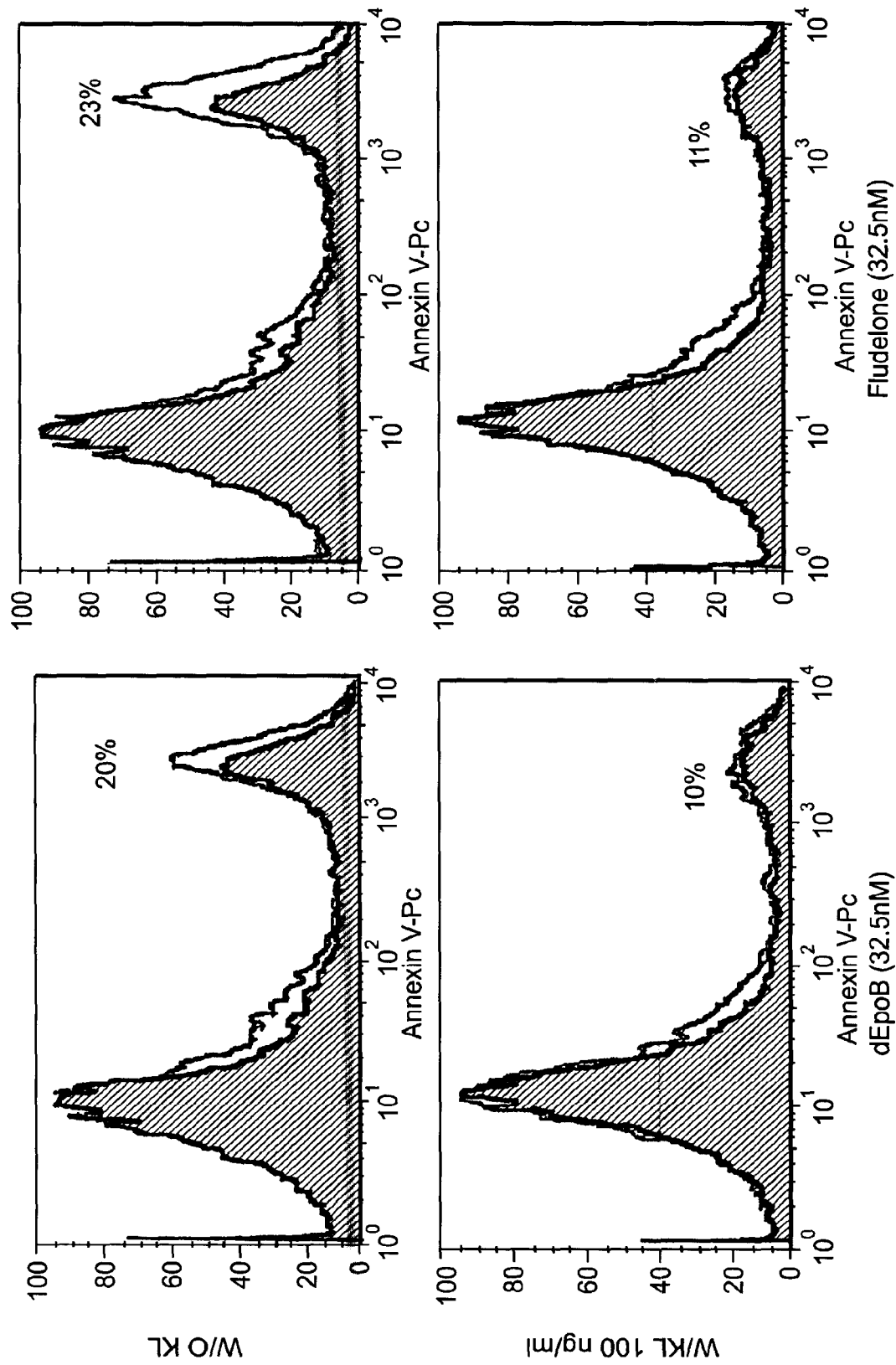

FIG. 127 shows Annexin V staining of CB CD34+ cells incubated with dEpoB or Fludelone in the absence or presence of KL for 24 hours. Then drugs were washed out and annexin V staining was performed. Solid area represents vehicle control and open area represents drug treated group. There is no obvious increased apoptosis of non-cycling human CD34+ cells with short period of exposure to epothilones.

Figure 128:
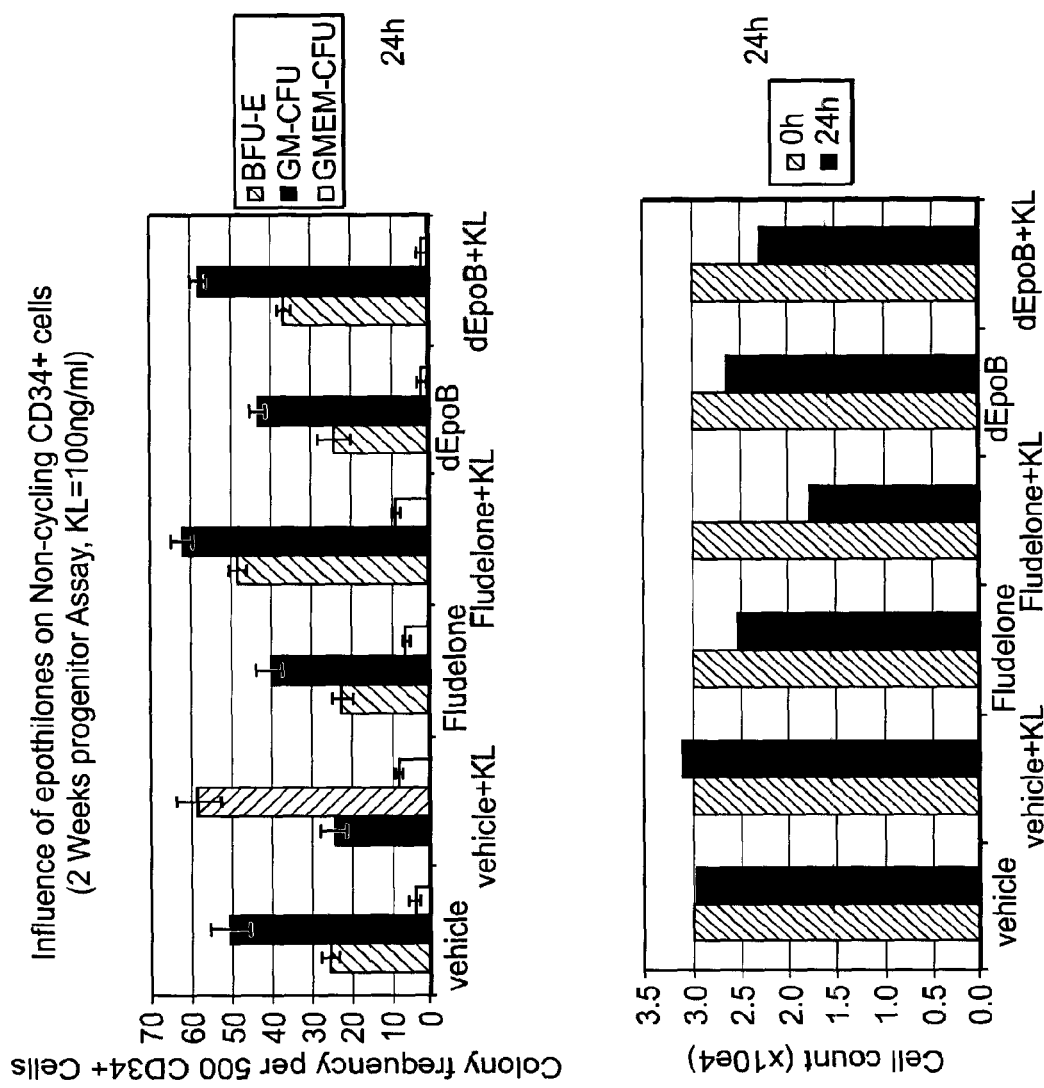

FIG. 128 shows the influence of epothilones on non-cycling human CD34+ cells in colony formation. There is no significant difference of progenitor cells evaluated by 2 weeks colony formation between controls and drug treatment.

Figure 129:
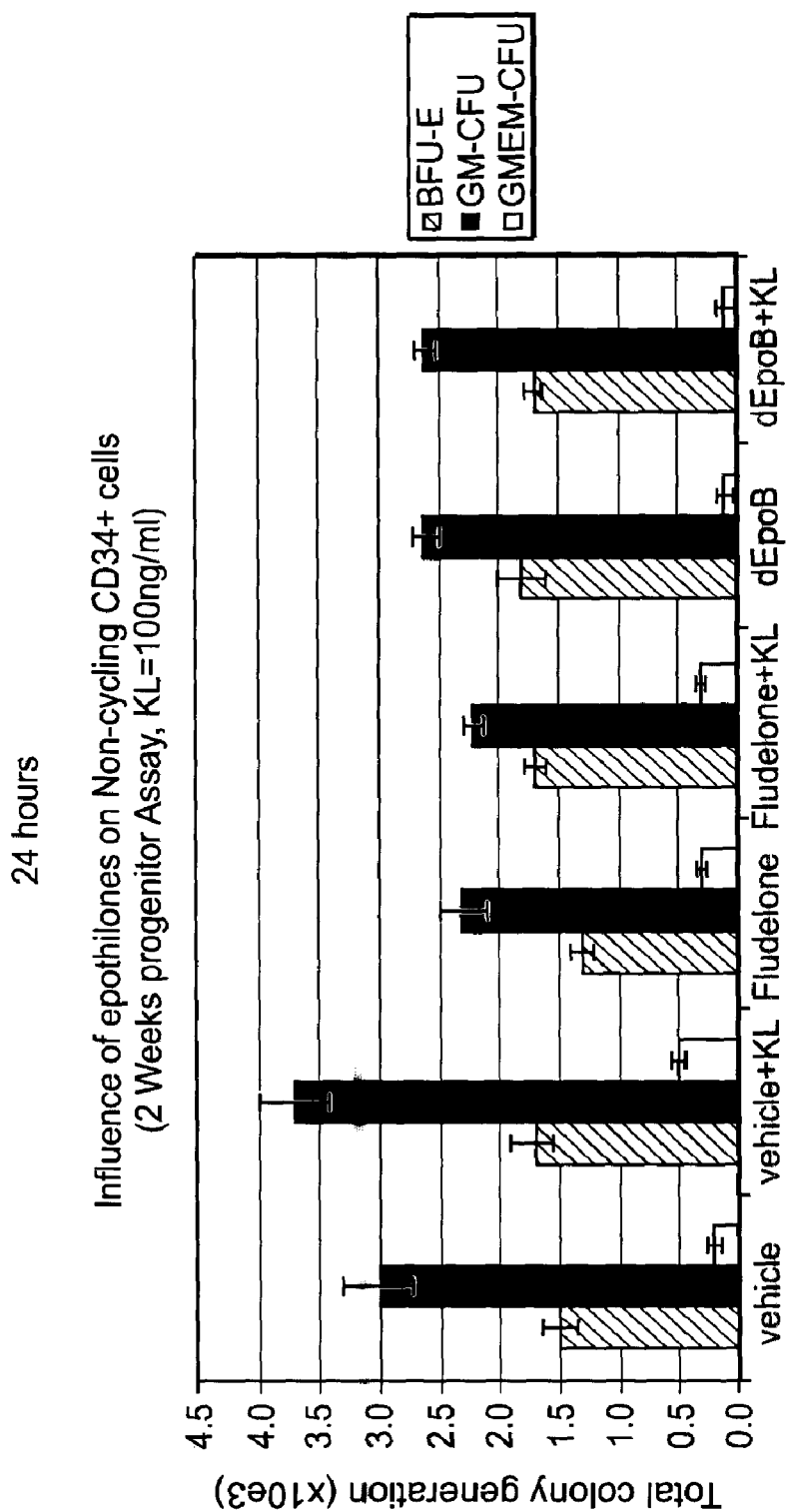

FIG. 129 shows the influence of epothilones on non-cycling human CD34+ cells in colony formation. There is no significant difference of progenitor cells evaluated by 2 weeks colony formation between controls and drugs treatment.

Figure 130:
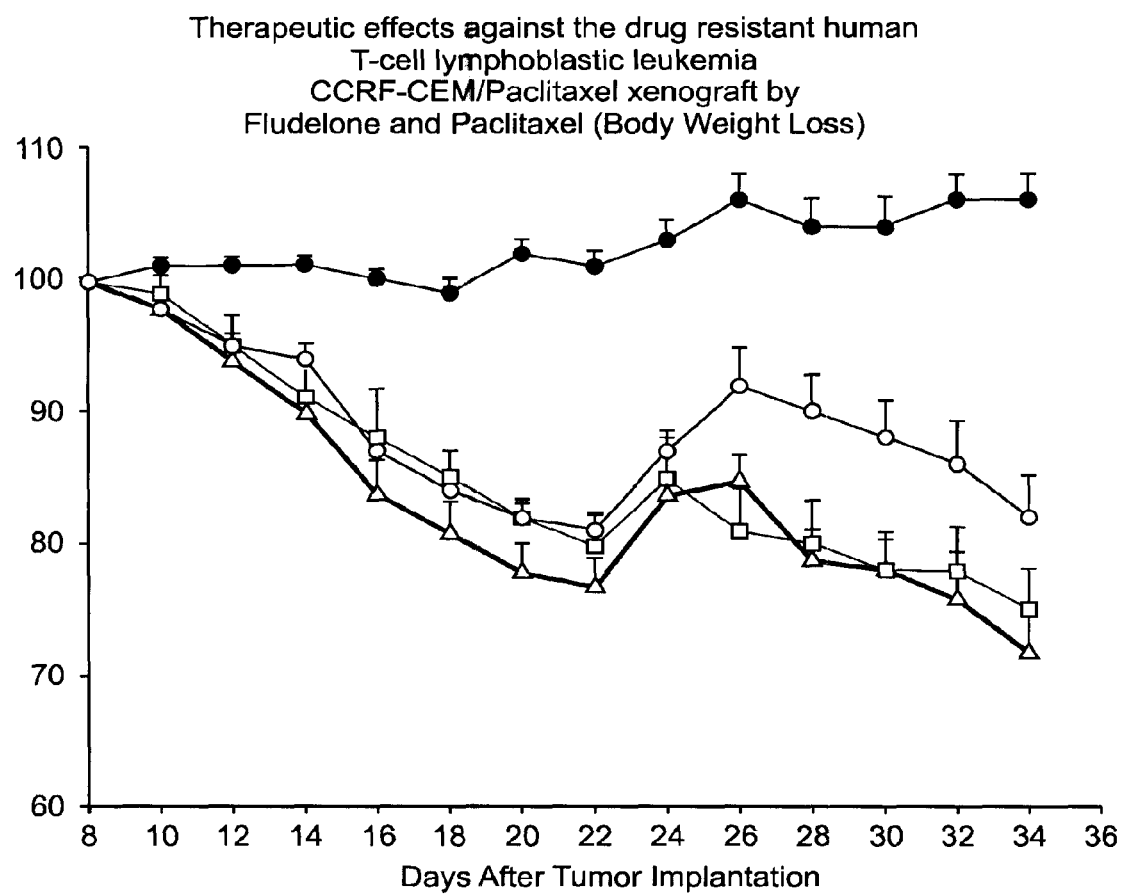

FIG. 130 shows the therapeutic effects against the drug resistant human T-cell lymphoblastic leukemia CCRF-CEM/Paclitaxel xenograft by Fludelone and Paclitaxel (body weight loss). There was no toxicity death for all treatments despite marked body weight decreases.

Figure 131:
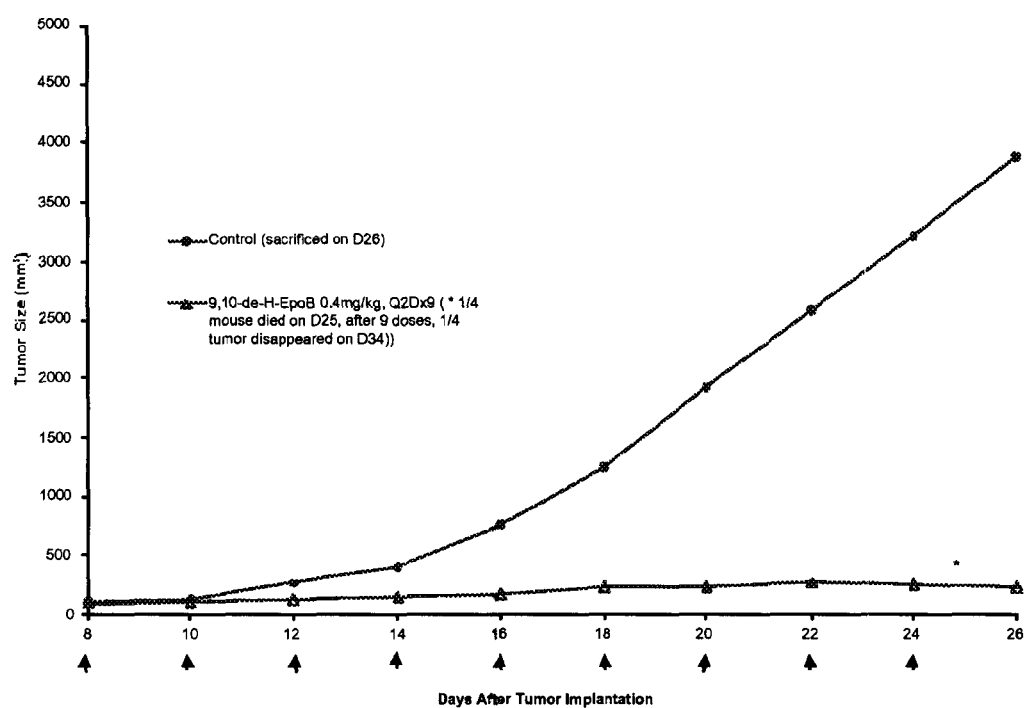

FIG. 131 shows the therapeutic effect of 9,10-de-H-EpoB in nude mice bearing MX-1 xenograft (6 hr-iv infusion, n=4).

DEFINITIONS

Certain compounds of the present invention, and definitions of specific functional groups are also described in more detail below. For purposes of this invention, the chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by readily available, preferably non-toxic reagents that do not attack the other funcational groups; the protecting group forms an easily separable derivative (more preferably without the generation of new stereogenic centers); and the protecting group has a minimum of additional functionality to avoid further sites of reaction. As detailed herein, oxygen, sulfur, nitrogen, and carbon protecting groups may be utilized. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example of proliferative disorders, including, but not limited to cancer. The term "stable", as used herein, preferably refers to compounds which possess stability sufficient to allow manufacture and which maintain the integrity of the compound for a sufficient period of time to be detected and preferably for a sufficient period of time to be useful for the purposes detailed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms. Illustrative aliphatic groups thus include, but are not limited to, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkoxy", or "thioalkyl" as used herein refers to an alkyl group, as previously defined, attached to the parent molecular moiety through an oxygen atom or through a sulfur atom. In certain embodiments, the alkyl group contains 1-20 alipahtic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, tert-butoxy, neopentoxy, and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkylamino include, but are not limited to, methylamino, ethylamino, iso-propylamino and the like.

Some examples of substituents of the above-described aliphatic (and other) moieties of compounds of the invention include, but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substituents are illustrated by the specific embodiments shown in the Examples that are described herein.

In general, the terms "aryl" and "heteroaryl", as used herein, refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In certain embodiments of the present invention, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments of the present invention, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups (including bicyclic aryl groups) can be unsubstituted or substituted, wherein substitution includes replacement of one, two, three, or more of the hydrogen atoms thereon independently with any one or more of the following moieties including, but not limited to: aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$);

—CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "cycloalkyl", as used herein, refers specifically to groups having three to seven, preferably three to ten carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or heterocyclic moieties, may optionally be substituted with substituents including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The term "heteroaliphatic", as used herein, refers to aliphatic moieties that contain one or more oxygen, sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. In certain embodiments, heteroaliphatic moieties are substituted by independent replacement of one or more of the hydrogen atoms thereon with one or more moieties including, but not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples that are described herein.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6-, or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. In certain embodiments, a "substituted heterocycloalkyl or heterocycle" group is utilized and as used herein, refers to a heterocycloalkyl or heterocycle group, as defined above, substituted by the independent replacement of one, two or three of the hydrogen atoms thereon with but are not limited to aliphatic; heteroaliphatic; aryl; heteroaryl; arylalkyl; heteroarylalkyl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described above and herein may be substituted or unsubstituted. Additional examples of generally applicable substitutents are illustrated by the specific embodiments shown in the Examples which are described herein.

"Labeled": As used herein, the term "labeled" is intended to mean that a compound has at least one element, isotope or chemical compound attached to enable the detection of the compound. In general, labels typically fall into three classes: a) isotopic labels, which may be radioactive or heavy isotopes, including, but not limited to, $^2$H, $^3$H, $^{32}$P, $^{35}$S, $^{67}$Ga, $^{99m}$Tc (Tc-99m), $^{111}$In, $^{123}$I, $^{125}$I, $^{169}$Yb, and $^{186}$Re; b) immune labels, which may be antibodies or antigens, which may be bound to enzymes (such as horseradish peroxidase) that produce detectable agents; and c) colored, luminescent, phosphorescent, or fluorescent dyes. It will be appreciated that the labels may be incorporated into the compound at any position that does not interfere with the biological activity or characteristic of the compound that is being detected. In certain embodiments of the invention, photoaffinity labeling is utilized for the direct elucidation of intermolecular interactions in biological systems (e.g., to probe the epothilone binding site in a tubulin dimer). A variety of known photophores can be employed, most relying on photoconversion of diazo compounds, azides, or diazirines to nitrenes or carbenes (See, Bayley, H., Photogenerated Reagents in Biochemistry and Molecular Biology (1983), Elsevier, Amsterdam.), the entire contents of which are hereby incorporated by reference. In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

"Polymer": The term "polymer", as used herein, refers to a composition comprising chains that may be open, closed, linear, branched or cross-linked of repeating units (monomers) that may be the same or different. It will be appreciated that in certain embodiments the term polymer refers to biopolymers, which, as used herein, is intended to refer to polymeric materials found in nature or based upon those materials found in nature, including, but not limited to nucleic acids, peptides, and mimetics thereof. In certain other embodiments, the term polymer refers to synthetic polymers, such as biodegradable polymers or other polymeric materials. It will be appreciated that polymeric solid supports are also encompassed by the polymers of the present invention. Inventive compounds can be attached to polymeric supports and thus certain synthetic modifications can be conducted on the solid phase. As used herein, the term "solid support" is meant to include, but is not limited to, pellets, disks, capillaries, hollow fibers, needles, pins, solid fibers, cellulose beads, pore-glass beads, silica gels, polystyrene beads optionally cross-linked with divinylbenzene, grafted co-poly beads, poly-acrylamide beads, latex beads, dimethylacrylamide beads optionally crosslinked with N-N'-bis-acryloylethylenediamine, and glass particles coated with a hydrophobic polymer. One of ordinary skill in the art will realize that the choice of particular solid support will be limited by the compatability of the support with the reaction chemistry being utilized. An exemplary solid support is a Tentagel amino resin, a composite of 1) a polystyrene bead crosslinked with divinylbenzene and 2) PEG (polyethylene glycol). Tentagel is a particularly useful solid support because it provides a versatile support for use in on-bead or off-bead assays, and it also undergoes excellent swelling in solvents ranging from toluene to water.

DESCRIPTION OF CERTAIN EMBODIMENTS OF THE INVENTION

In recognition of the need to develop novel and effective cancer therapies, the present invention provides novel synthetic methodologies enabling access to macrocycles having a broad range of biological and pharmacological activity, as well as novel compounds with such activity, novel therapeutic compositions, and methods of using these compounds and compositions.

In certain embodiments, the inventive compounds are useful in the treatment of cancer. Certain compounds of the invention exhibit cytotoxic or growth inhibitory effects on cancer cells lines, exhibit an ability to polymerize tubulin and stabilize microtubule assemblies, and/or lead to shrinkage or diappearance of tumors in cancer cell xenograft models. In certain embodiments, the compounds may have reduced or minimal side effects including toxicity to vital organs, nausea, vomiting, diarrhea, allopecia, weight loss, weight gain, liver toxicity, skin disorders, etc. The compounds may also be easier to formulate due to increased water solubility, decreased toxicity, increased therapeutic range, increased efficacy, etc.

General Description of Compounds of the Invention

Compounds of the invention include compounds of the general formula (0) as further defined below:

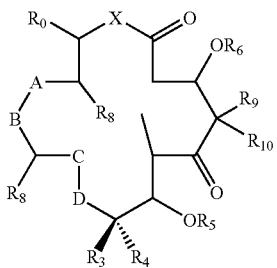

(0)

wherein $R_0$ is a substituted or unsubstituted aryl, heteroaryl, arylalkyl, arylalkenyl, arylalkynyl, heteroarylalkyl, heteroarylalkenyl, or heteroarylalkynyl moiety; in certain embodiments, $R_0$ is a arylalkyl, arylalkenyl, heteroarylalkyl, or heteroarylalkenyl moiety; in other embodiments, $R_0$ is a heteroarylalkenyl moiety; in certain embodiments, $R_0$ is a heteroarylalkyl moiety; in other embodiments, $R_0$ is a 5-7 membered aryl or heteroaryl moiety; in yet other embodiments, $R_0$ is an 8-12 membered bicyclic aryl or heteroaryl moiety; in still other embodiments, $R_0$ is a bicyclic moiety wherein a phenyl ring is fused to a heteroaryl or aryl moiety; in other embodiments, $R_0$ is a bicyclic moiety wherein a phenyl ring is fused to a thiazole, oxazole, or imidazole moiety; in yet other embodiments, $R_0$ is a substituted or unsubstituted phenyl moiety;

$R_3$ and $R_4$ are each independently hydrogen; or substituted or unsubstituted, linear or branched, cyclic or acyclic aliphatic, heteroaliphatic, aryl, heteroaryl, arylalkyl, or heteroarylalkyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroxyimino, or N-alkoxyimino; in certain embodiments, $R_3$ and $R_4$ are each independently hydrogen, fluorine, or lower alkyl; in other embodiments, $R_3$ and $R_4$ are each independently hydrogen or methyl; in still other embodiments, $R_3$ is methyl, and $R_4$ is hydrogen;

$R_5$ and $R_6$ are each independently hydrogen or a protecting group; in certain embodiments, $R_5$ and $R_6$ are both hydrogen;

X is O, S, $C(R_7)_2$, or $NR_7$, wherein each occurrence of $R_7$ is independently hydrogen or lower alkyl; in certain embodiments, X is O; in other embodiments, X is NH;

Y is O, S, NH, $C(R_7)_2$, $CH_2$, $N(R_7)$, or NH, wherein each occurrence of $R_7$ is independently hydrogen or lower alkyl; in certain embodiments, Y is O; in other embodiments, Y is NH; in yet other embodiments, Y is $CH_2$;

each $R_8$ is independently hydrogen; halogen, hydroxy, alkoxy, amino, dialkylamino, alkylamino, fluoro, cyano, or substituted or unsubstituted, linear or branched, cyclic or acyclic aliphatic, heteroaliphatic, aryl, heteroaryl, arylalkyl, arylalkenyl, arylalkynyl, or heteroarylalkyl, heteroarylalkenyl, heteroarylalkynyl moiety, optionally substituted by one or more of hydroxy, protected hydroxy, alkoxy, carboxy, caboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_8$ is hydrogen; in other embodiments, $R_8$ is hydroxy; in yet other embodiments, $R_8$ is fluorine; in still other embodiments, $R_8$ is lower alkyl such as methyl; in other embodiments $R_8$ is —$CF_3$, —$CF_2H$, or —$CFH_2$; in other embodiments, $R_8$ is perfluorinated or fluorinated alkyl group; in yet other embodiments, $R_8$ is halogentated or perhalogenated alkyl group;

$R_9$ and $R_{10}$ are each independently hydrogen; or substituted or unsubstituted, linear or branched, cyclic or acyclic aliphatic, heteroaliphatic, aryl, heteroaryl, aryl, arylalkyl, arylalkenyl, arylalkynyl, heteroarylalkyl, heteroarylalkenyl, or heteroarylalkynyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, one of $R_9$ and $R_{10}$ is methyl; in other embodiments, both $R_9$ and $R_{10}$ are methyl; in yet other embodiments, one of $R_9$ and $R_{10}$ is methyl, and the other is hydrogen; in other embodiments, both $R_9$ and $R_{10}$ are hydrogen;

A-B represents $CR_A$=$CR_B$—, $C(R_A)_2$—$C(R_B)_2$—, or —C≡C—;

C-D represents —$CR_C$=$CR_D$—, —$C(R_C)_2$—$C(R_D)_2$—, or —C≡C—;

wherein each occurrence of $R_A$ is independently hydrogen; halogen; —$OR_{A'}$; —$SR_{A'}$; —$N(R_{A'})_2$; —$C(O)OR_{A'}$; —$C(O)R_{A'}$; —$CONHR_{A'}$; —$O(C$=$O)R_{A'}$; —$O(C$=$O)OR_{A'}$; —$NR_{A'}(C$=$O)R_{A'}$; $N_3$; $N_2R_{A'}$; cyclic acetal; or cyclic or acyclic, linear or branched aliphatic, heteroaliphatic, aryl, or heteroaryl, optionally substituted with one or more of hydrogen; halogen; —$OR_{A'}$; —$SR_{A'}$; —$N(R_{A'})_2$; —$C(O)OR_{A'}$; —$C(O)R_{A'}$; —$CONHR_{A'}$; —$O(C$=$O)R_{A'}$; —$O(C$=$O)OR_{A'}$; —$NR_{A'}(C$=$O)R_{A'}$; $N_3$; $N_2R_{A'}$; cyclic acetal; or cyclic or acyclic, linear or branched substituted or unsubstituted aliphatic, heteroaliphatic, aryl, or heteroaryl moiety;

$R_B$ is, independently for each occurrence, hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C$=$O)R_{B'}$; —$O(C$=$O)OR_{B'}$; —$NR_{B'}(C$=$O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C$=$O)R_{B'}$—$O(C$=$O)OR_{B'}$; —$NR_{B'}(C$=$O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; in certain embodiments, $R_B$ is hydrogen,

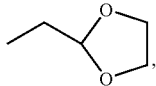

methyl, ethyl, propyl, butyl, pentyl, hexyl, cyclopropyl, cyclobutyl, cyclopentyl, or cyclohexyl, each unsubstituted or optionally substituted with one or more occurrences of halogen, —OH, —$OR_{B'}$, $NH_2$, or $N(R_{B'})_2$, or any combination thereof, wherein each occurrence of $R_{B'}$ is independently hydrogen, alkyl, aryl, or a protecting group, in other embodiments, $R_B$ is hydrogen, methyl, or ethyl, in still other embodiments, $R_a$ is methyl, in other embodiments, —$CY_3$, —$CHY_2$, —$CH_2Y$, where Y is F, Br, Cl, I, $OR_{B'}$, $NHR_{B'}$, $N(R_{B'})_2$, or $SR_{B'}$; in yet other embodiments, $R_B$ is —$CF_3$, —$CH_2F$, or $CHF_2$; in other embodiments, $R_B$ is perfluorinated or fluorinated alkyl group; in yet other embodiments, $R_B$ is halogentated or perhalogenated alkyl group;

$R_C$ is, independently for each occurrence, hydrogen; halogen; —$OR_{C'}$; —$SR_{C'}$; —$N(R_{C'})_2$; —$C(O)OR_{C'}$; —$C(O)R_{C'}$; —$CONHR_{C'}$; —$O(C$=$O)R_{C'}$; —$O(C$=$O)OR_{C'}$; —$NR_{C'}(C$=$O)R_{C'}$; $N_3$; $N_2R_{C'}$; cyclic acetal; or cyclic or acyclic, linear or branched aliphatic, heteroaliphatic, aryl, or heteroaryl, optionally substituted with one or more of hydrogen; halogen; —$OR_{C'}$; —$SR_{C'}$; —$N(R_{C'})_2$; —$C(O)OR_{C'}$; —$C(O)R_{C'}$; —$CONHR_{C'}$; —$O(C$=$O)R_{C'}$; —$O(C$=$O)OR_{C'}$; —$NR_{C'}(C$=$O)R_{C'}$; $N_3$; $N_2R_{C'}$; cyclic acetal; or cyclic or acyclic, linear or branched substituted or unsubstituted aliphatic, heteroaliphatic, aryl, or heteroaryl moiety; in certain embodiments, $R_C$ is halogen, alkyl, hydroxy, or amino; in other embodiments, $R_C$ is fluorine; in yet other embodiments, $R_C$ is hydroxy;

$R_D$ is, independently for each occurrence, hydrogen; halogen; —$OR_{D'}$; —$SR_{D'}$; —$N(R_{D'})_2$; —$C(O)OR_{D'}$; —$C(O)R_{D'}$; —$CONHR_{D'}$; —$O(C$=$O)R_{D'}$; —$O(C$=$O)OR_{D'}$; —$NR_{D'}(C$=$O)R_{D'}$; $N_3$; $N_2R_{D'}$; cyclic acetal; or cyclic or acyclic, linear or branched aliphatic, heteroaliphatic, aryl, or heteroaryl, optionally substituted with one or more of hydrogen; halogen; —$OR_{D'}$; —$SR_{D'}$; —$N(R_{D'})_2$; —$C(O)OR_{D'}$; —$C(O)R_{D'}$; —$CONHR_{D'}$; —$O(C$=$O)R_{D'}$; —$O(C$=$O)OR_{D'}$; —$NR_{D'}(C$=$O)R_{D'}$; $N_3$; $N_2R_{D'}$; cyclic acetal; or cyclic or acyclic, linear or branched substituted or unsubstituted aliphatic, heteroaliphatic, aryl, or heteroaryl moiety; or wherein any two of $R_A$, $R_B$; $R_C$ or $R_D$ taken together may form a cyclic moiety and may be linked through an oxygen, sulfur, carbon or nitrogen atom, or any two adjacent groups $R_A$, $R_B$, $R_C$, or $R_D$, taken together, may form a 3-6-membered substituted or unsubstituted aliphatic, heteroaliphatic, aryl or heteroaryl ring; in certain embodiments, $R_A$ and $R_B$ taken together form a 3-member ring linked through an oxygen, sulfur, carbon, or nitrogen atom; in other embodiments $R_C$ and $R_D$ taken together form a 3-membered ring linked through an oxygen, sulfur, carbon, or nitrogen atom;

wherein each occurrence of $R_{A'}$, $R_{B'}$, $R_{C'}$, and $R_{D'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, arylalkenyl, arylalkynyl, or heteroarylalkyl, heteroarylalkenyl, heteroarylalkynyl moiety; and pharmaceutically acceptable derivatives thereof; and pharmaceutically acceptable derivatives thereof.

Subclasses of the formula (0) includes compounds of the general formula (0') and (0") as further defined below:

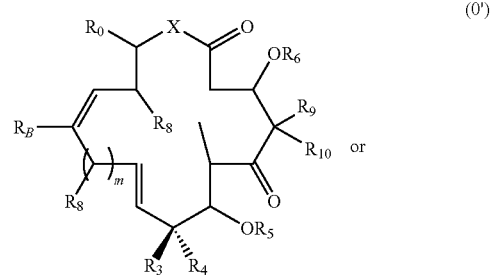

-continued

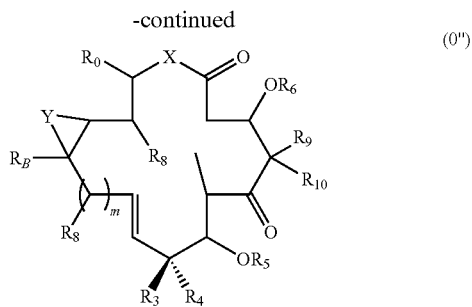

(0''')

wherein $R_0$ is a substituted or unsubstituted aryl, heteroaryl, arylalkyl, arylalkenyl, arylalkynyl, heteroarylalkyl, heteroarylalkenyl, or heteroarylalkynyl moiety; in certain embodiments, $R_0$ is a arylalkyl, arylalkenyl, heteroarylalkyl, or heteroarylalkenyl moiety; in other embodiments, $R_0$ is a heteroarylalkenyl moiety; in certain embodiments, $R_0$ is a heteroarylalkyl moiety; in other embodiments, $R_0$ is a 5-7 membered aryl or heteroaryl moiety; in yet other embodiments, $R_0$ is an 8-12 membered bicyclic aryl or heteroaryl moiety; in still other embodiments, $R_0$ is a bicyclic moiety wherein a phenyl ring is fused to a heteroaryl or aryl moiety; in other embodiments, $R_0$ is a bicyclic moiety wherein a phenyl ring is fused to a thiazole, oxazole, or imidazole moiety; in yet other embodiments, $R_0$ is a substituted or unsubstituted phenyl moiety;

$R_3$ and $R_4$ are each independently hydrogen; or substituted or unsubstituted, linear or branched, cyclic or acyclic aliphatic, heteroaliphatic, aryl, heteroaryl, arylalkyl, or heteroarylalkyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_3$ and $R_4$ are each independently hydrogen, fluorine, or lower alkyl; in other embodiments, $R_3$ and $R_4$ are each independently hydrogen or methyl; in still other embodiments, $R_3$ is methyl, and $R_4$ is hydrogen;

$R_5$ and $R_6$ are each independently hydrogen or a protecting group; in certain embodiments, $R_5$ and $R_6$ are both hydrogen;

X is O, S, $C(R_7)_2$, or $NR_5$, wherein each occurrence of $R_7$ is independently hydrogen or lower alkyl; in certain embodiments, X is O; in other embodiments, X is NH;

Y is O, S, NH, $C(R_7)_2$, $CH_2$, $N(R_7)$, or NH, wherein each occurrence of $R_7$ is independently hydrogen or lower alkyl; in certain embodiments, Y is O; in other embodiments, Y is NH; in yet other embodiments, Y is $CH_2$;

each $R_8$ is independently hydrogen; halogen, hydroxy, alkoxy, amino, dialkylamino, alkylamino, fluoro, cyano, or substituted or unsubstituted, linear or branched, cyclic or acyclic aliphatic, heteroaliphatic, aryl, heteroaryl, arylalkyl, arylalkenyl, arylalkynyl, or heteroarylalkyl, heteroarylalkenyl, heteroarylalkynyl moiety, optionally substituted by one or more of hydroxy, protected hydroxy, alkoxy, carboxy, caboxaldehyde, linear or branched alkyl or cyclic acetal, fluorine, amino, protected amino, amino substituted with one or two alkyl or aryl moieties, N-hydroximino, or N-alkoxyimino; in certain embodiments, $R_8$ is hydrogen; in other embodiments, $R_8$ is hydroxy; in yet other embodiments, $R_8$ is fluorine; in still other embodiments, $R_8$ is lower alkyl such as methyl; in other embodiments $R_8$ is —$CF_3$, —$CF_2H$, or —$CFH_2$; in other embodiments, $R_8$ is perfluorinated or fluorinated alkyl group; in yet other embodiments, $R_8$ is halogentated or perhalogenated alkyl group;

$R_9$ and $R_{10}$ are each independently hydrogen; or substituted or unsubstituted, linear or branched, cyclic or acyclic aliphatic, heteroaliphatic, aryl, heteroaryl, aryl, arylalkyl, arylalkenyl, arylalkynyl, heteroarylalkyl, heteroarylalkenyl, or heteroarylalkynyl moiety, optionally substituted by one or more of hydroxy, protected hydroxy, alkoxy, carboxy, carboxaldehyde, linear or branched alkyl or cyclic acetal, fluorine, amino, protected amino, amino substituted with one or two alkyl or aryl moieties, N-hydroximino, or N-alkoxyimino; in certain embodiments, one of $R_9$ and $R_{10}$ is methyl; in other embodiments, both $R_9$ and $R_{10}$ are methyl; in yet other embodiments, one of $R_9$ and $R_{10}$ is methyl, and the other is hydrogen; in other embodiments, both $R_9$ and $R_{10}$ are hydrogen;

$R_B$ is, independently for each occurrence, hydrogen; halogen; —$OR_{B'}$; —$SR_{B'}$; —$N(R_{B'})_2$; —$C(O)OR_{B'}$; —$C(O)R_{B'}$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$N(R_{B'})_2$; $C(O)OR_{B'}$; —$C(O)R_B$; —$CONHR_{B'}$; —$O(C=O)R_{B'}$; —$O(C=O)OR_{B'}$; —$NR_{B'}(C=O)R_{B'}$; $N_3$; $N_2R_{B'}$; cyclic acetal; or cyclic or acyclic, linear or branched substituted or unsubstituted aliphatic, heteroaliphatic, aryl, or heteroaryl moiety; or is an epothilone, desoxyepothilone, or analogues thereof; or is a polymer; carbohydrate; photoaffinity label; or radiolabel; in certain embodiments, $R_B$ is hydrogen,

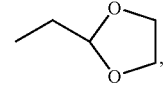, methyl, ethyl, propyl, butyl, pentyl, hexyl, cyclopropyl, cyclobutyl, cyclopentyl, or cyclohexyl, each unsubstituted or optionally substituted with one or more occurrences of halogen, —OH, —$OR_{B'}$, $NH_2$, or $N(R_{B'})_2$, or any combination thereof, wherein each occurrence of $R_{B'}$ is independently hydrogen, alkyl, aryl, or a protecting group, in other embodiments, $R_B$ is hydrogen, methyl, or ethyl, in still other embodiments, $R_B$ is methyl, in other embodiments, —$CY_3$, —$CHY_2$, —$CH_2Y$, where Y is F, Br, Cl, I, $OR_{B'}$, $NHR_{B'}$, $N(R_{B'})_2$, or $SR_{B'}$; in yet other embodiments, $R_B$ is —$CF_3$, —$CH_2F$, or $CHF_2$; in other embodiments, $R_B$ is perfluorinated or fluorinated alkyl group; in yet other embodiments, $R_B$ is halogentated or perhalogenated alkyl group;

each occurrence of $R_{B'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, heteroarylalkyl, heteroarylalkenyl, or heteroarylalkynyl moiety;

m is 1, 2, 3, or 4, m is 1 or 2 in certain embodiments, m is 1 in other embodiments; and pharmaceutically acceptable derivatives thereof.

The compounds of the invention include compounds of the general formula (I) as further defined below:

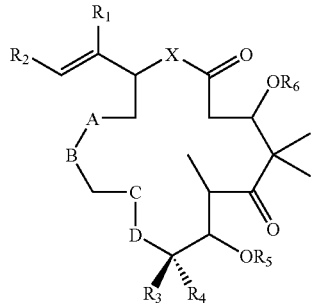
(I)

wherein $R_1$ is hydrogen or lower alkyl; in certain embodiments, $R_1$ is methyl; in certain embodiments, $R_1$ is —$CF_3$, —$CF_2H$, or $CH_2F$; in other embodiments, $R_1$ is perfluorinated or fluorinated alkyl group; in yet other embodiments, $R_1$ is halogentated or perhalogenated alkyl group;

$R_2$ is a substituted or unsubstituted aryl, heteroaryl, arylalkyl, or heteroarylalkyl moiety; in certain embodiments, $R_2$ is substituted or unsubstituted oxazole; in other embodiments, $R_2$ is substituted or unsubstituted thiazole; and A, B, C, D, $R_3$, $R_4$, $R_5$, $R_6$, and X are as defined above.

Subclasses of the formula (I) includes compounds of the general formula (I') and (I") as further defined below:

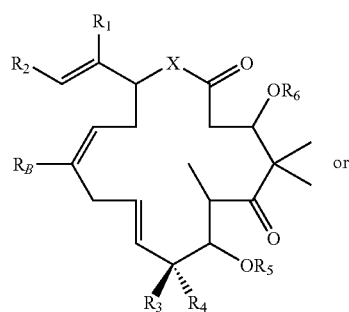
(I') or

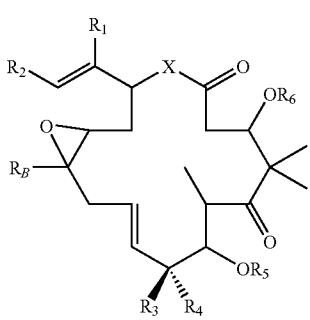
(I")

wherein X, $R_1$, $R_2$, $R_3$, $R_4$, $R_5$, $R_6$, and $R_B$ are as defined above.

In certain embodiments, the compounds of the invention include compounds of the general formula (II) with the stereochemistry defined as shown:

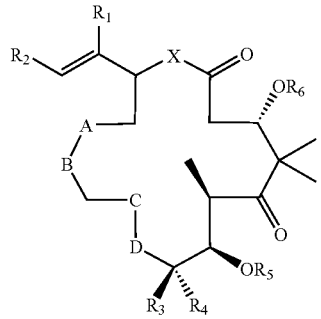
(II)

wherein A, B, C, D, $R_1$, $R_2$, $R_3$, $R_4$, $R_5$, $R_6$, and X are as defined above.

Subclasses of the formula (II) includes compounds of the general formula (II') and (II") as further defined below:

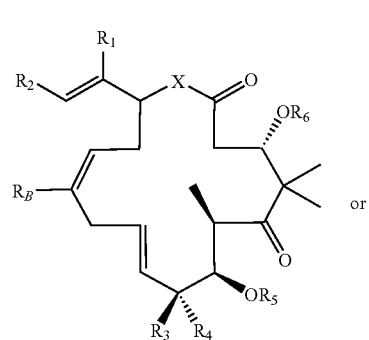
(II') or

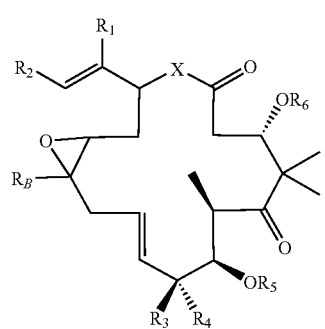
(II")

wherein X, $R_1$, $R_2$, $R_3$, $R_4$, $R_5$, $R_6$, $R_B$, and X are as defined above.

In certain embodiments, the compounds of the invention include compounds of the general formula (III) as shown:

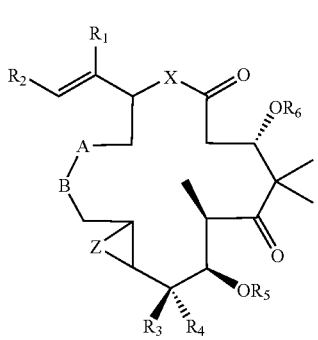
(III)

wherein Z is an oxygen atom, a sulfur atom, —NR$_Z$—, or —C(R$_Z$)$_2$—; and

A, B, R$_1$, R$_2$, R$_3$, R$_4$, R$_5$, R$_6$, and X are as defined above. In certain preferred embodiments, Z is oxygen. In other embodiments, Z is —NH—. In yet other embodiments, Z is —CH$_2$—. In other embodiments, R$_Z$ is hydrogen, alkyl, halogen, or acyl. In certain embodiments, R$_Z$ is fluorine.

In certain embodiments, the compounds of the invention include compounds of the general formula (IV) with the stereochemistry defined as shown:

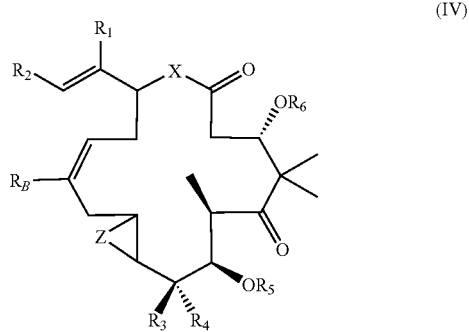

(IV)

wherein A, B, R$_1$, R$_2$, R$_3$, R$_4$, R$_5$, R$_6$, X, and Z are as defined above. In certain embodiments, R$_B$ is methyl. In other embodiments, R$_B$ is —CF$_3$.

In certain embodiments, the compounds of the invention include compounds of the general formula (V) or (VI) as shown:

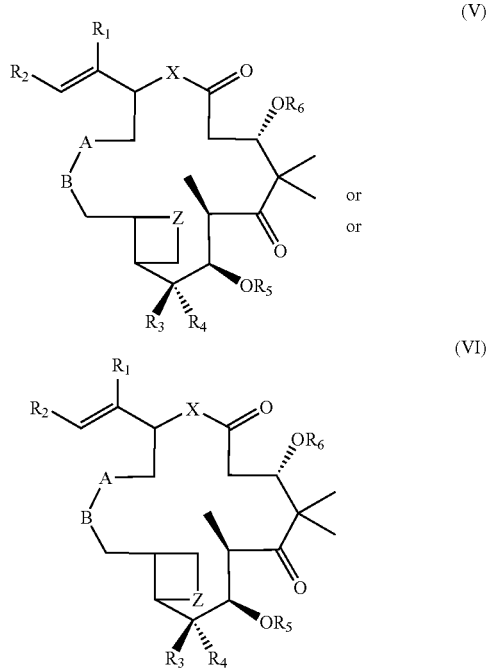

(V)

or (VI)

wherein Z is an oxygen atom, a sulfur atom, —NR$_Z$—, or —C(R$_Z$)$_2$—; and

A, B, R$_1$, R$_2$, R$_3$, R$_4$, R$_5$, R$_6$, and X are as defined above. In certain preferred embodiments, Z is oxygen. In other embodiments, Z is —NH—. In yet other embodiments, Z is —CH$_2$—. In other embodiments, R$_Z$ is hydrogen, alkyl, halogen, or acyl. In certain embodiments, R$_Z$ is fluorine.

In certain embodiments, the compounds of the invention include compounds of the general formula (VII) as shown:

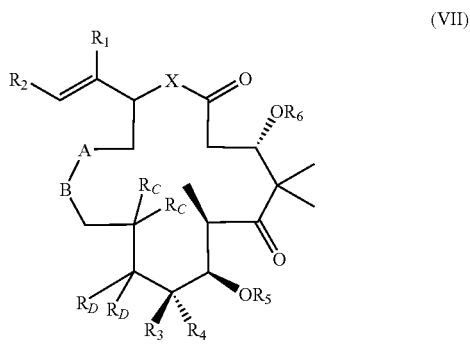

(VII)

wherein A, B, R$_C$, R$_D$, R$_1$, R$_2$, R$_3$, R$_4$, R$_5$, R$_6$, and X are as defined above. In certain preferred embodiments, each R$_C$ is independently hydrogen, halogen, or lower alkyl. In other embodiments, each R$_D$ is independently hydrogen, halogen or lower alkyl.

In certain embodiments, X is O. In other embodiments, X is NH. In other embodiments, X is CH$_2$.

In some embodiments, R$_2$ is a substituted or unsubstituted thiazole. In certain embodiments, R$_2$ is 2-methyl-thiazo-4-yl. In other embodiments, R$_2$ is 2-hydroxylmethyl-thiazo-4-yl. In yet other embodiments, R$_2$ is 2-aminomethyl-thiazo-4-yl. In other embodiments, R$_2$ is 2-thiolmethyl-thiazo-4-yl.

In certain embodiments R$_2$ is a substituted or unsubstituted oxazole. In certain embodiments, R$_2$ is 2-methyl-oxazo-4-yl. In other embodiments, R$_2$ is 2-hydroxylmethyl-oxazo-4-yl. In yet other embodiments, R$_2$ is 2-aminomethyl-oxazo-4-yl. In other embodiments, R$_2$ is 2-thiolmethyl-oxazo-4-yl.

In certain embodiments, R$_B$ is hydrogen, methyl, ethyl, —CF$_3$, —CH$_2$F, —CF$_2$H. In certain embodiments, R$_B$ is methyl. In yet other embodiments, R$_B$ is —CF$_3$. In certain embodiments, R$_B$ is hydrogen. In other embodiments, R$_B$ is ethyl.

Certain preferred compounds include, for example:

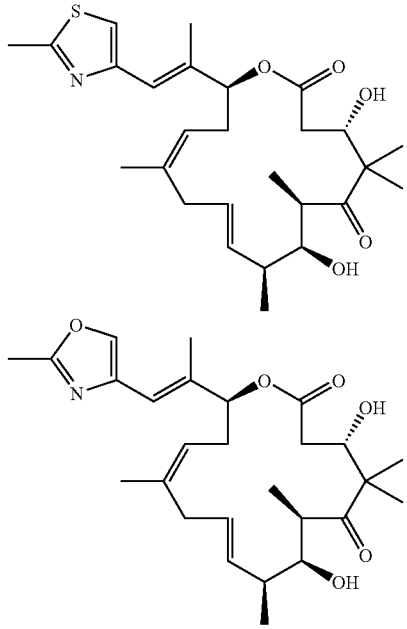

-continued
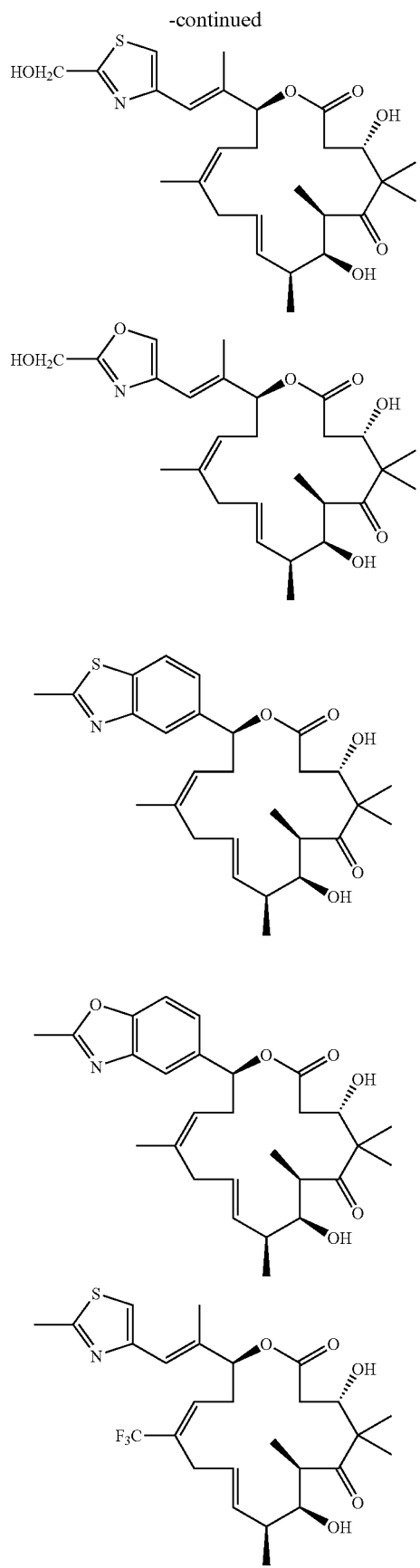
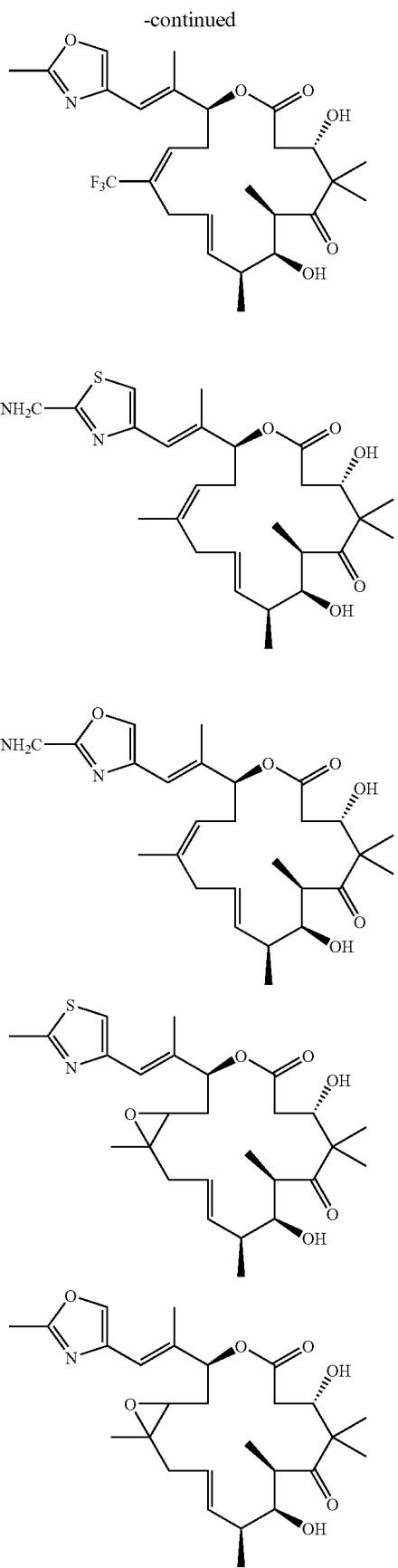

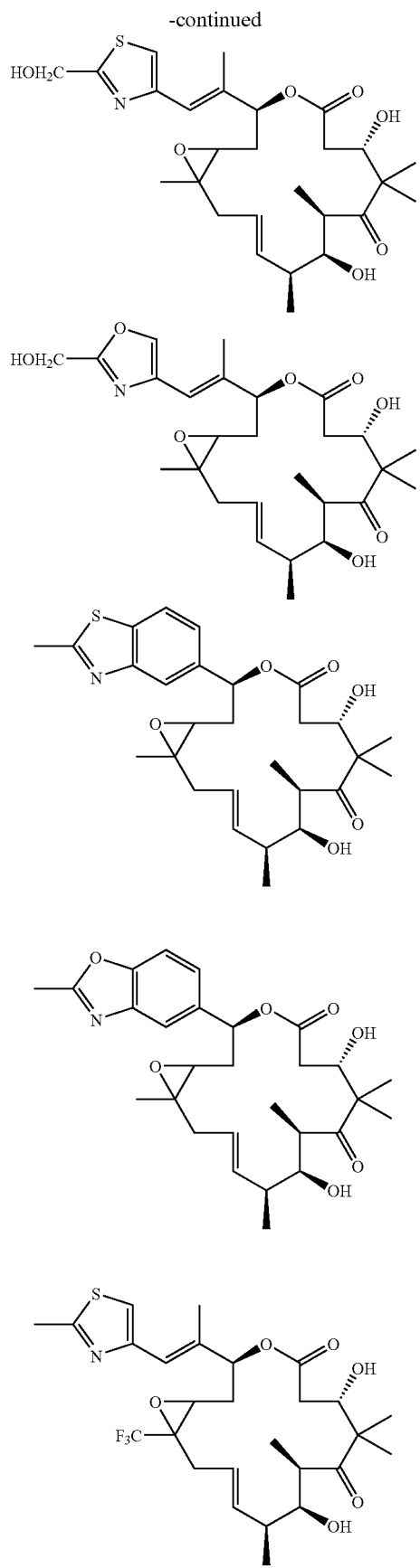
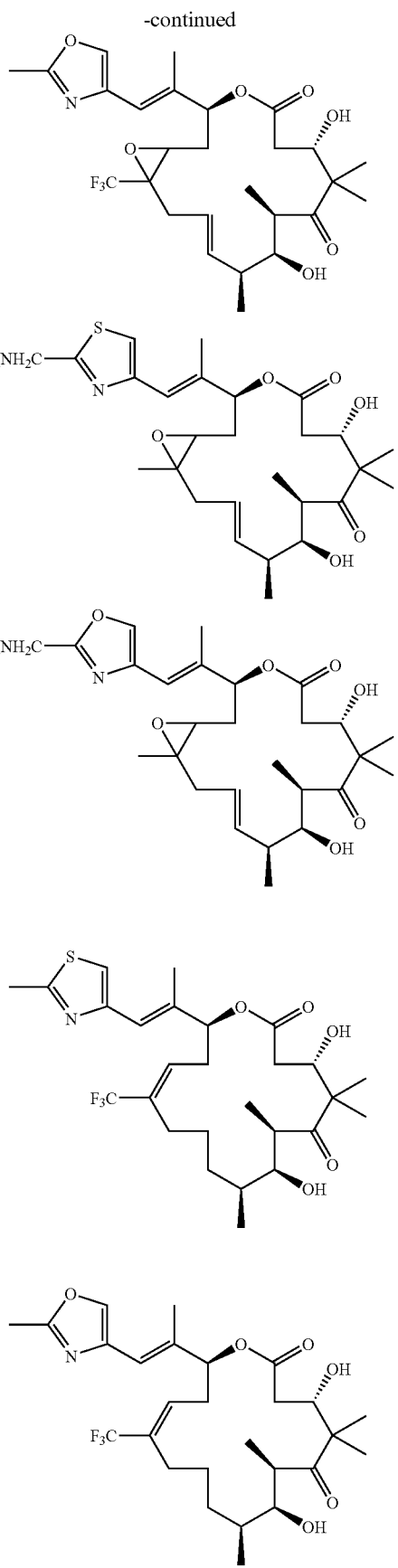

-continued
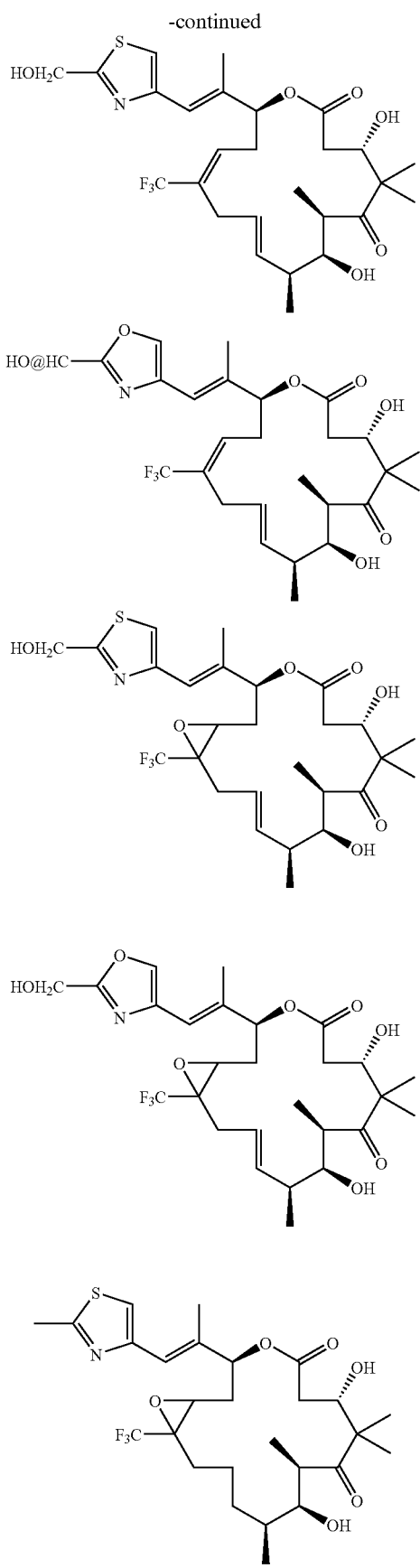
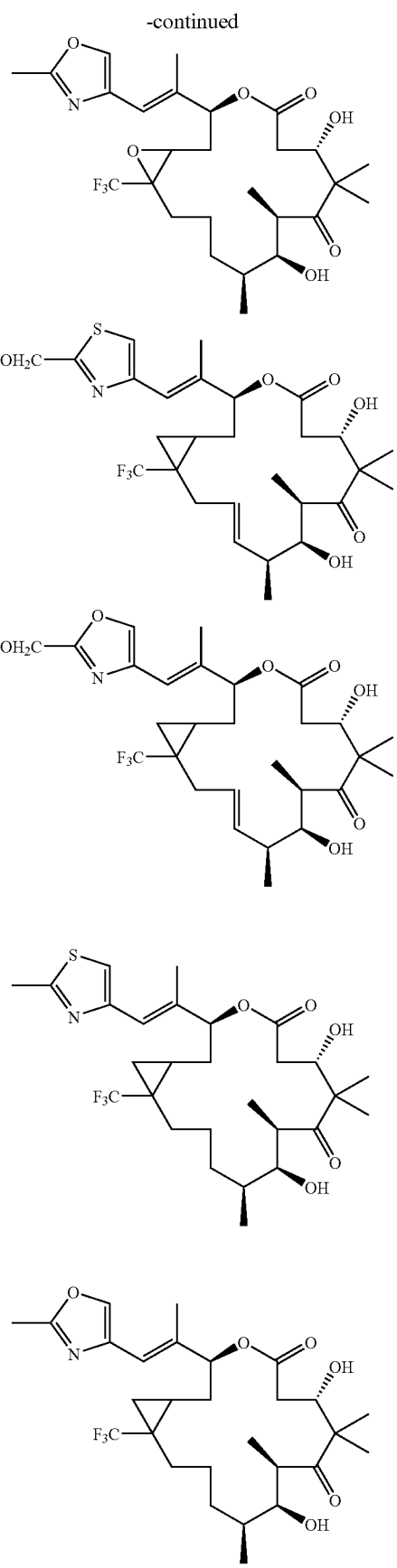

-continued
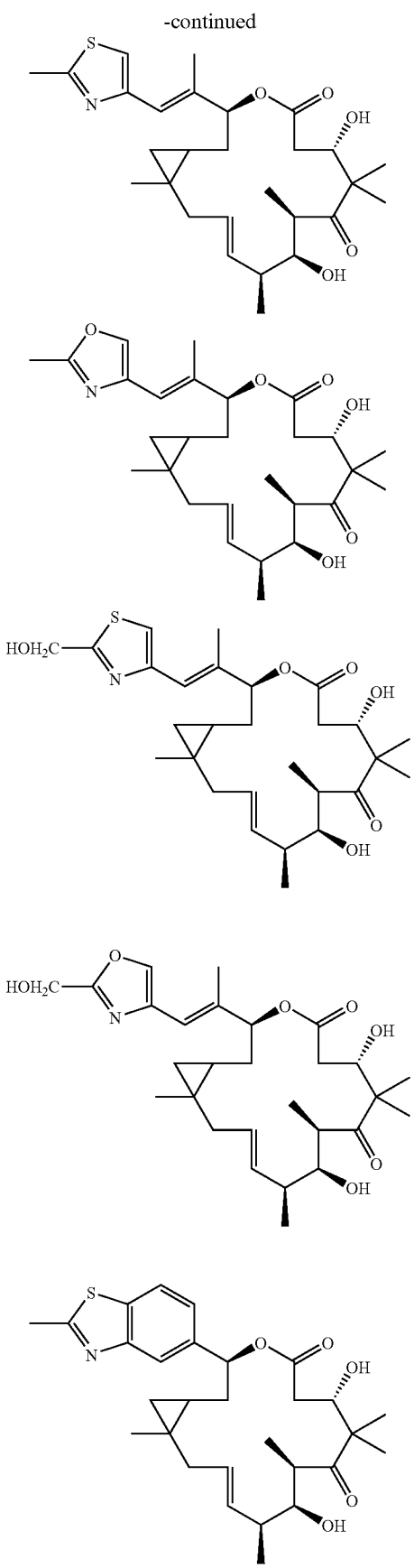
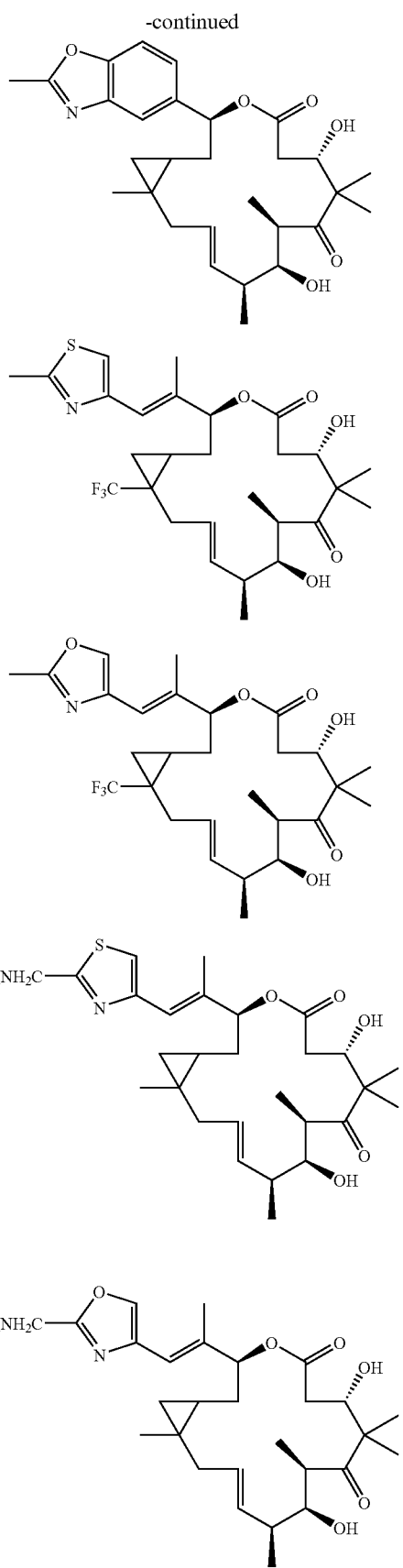

Other preferred compounds include, for example:
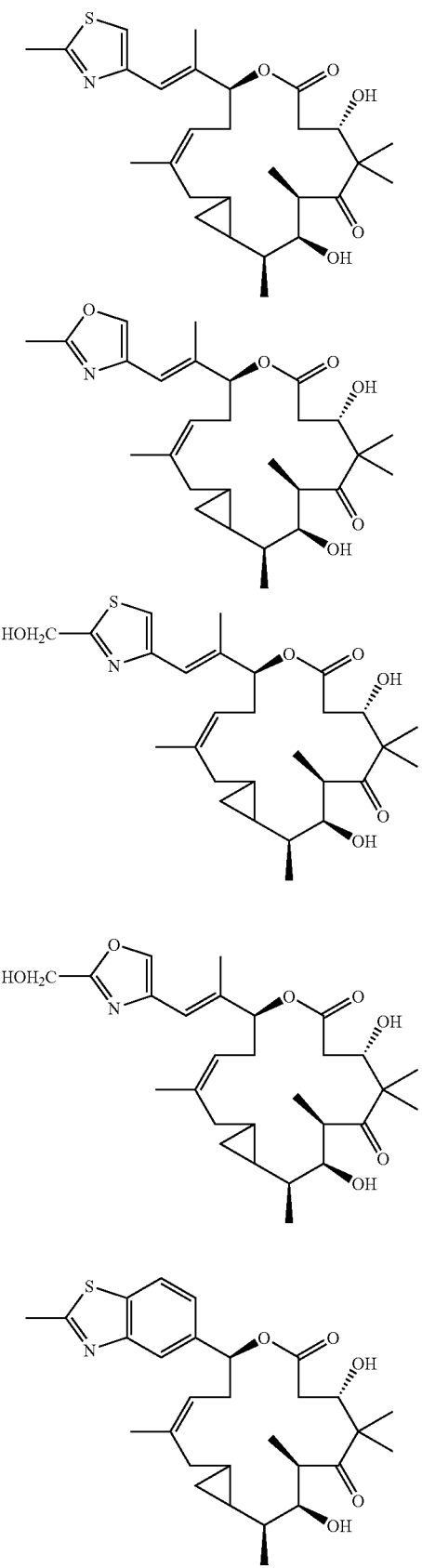
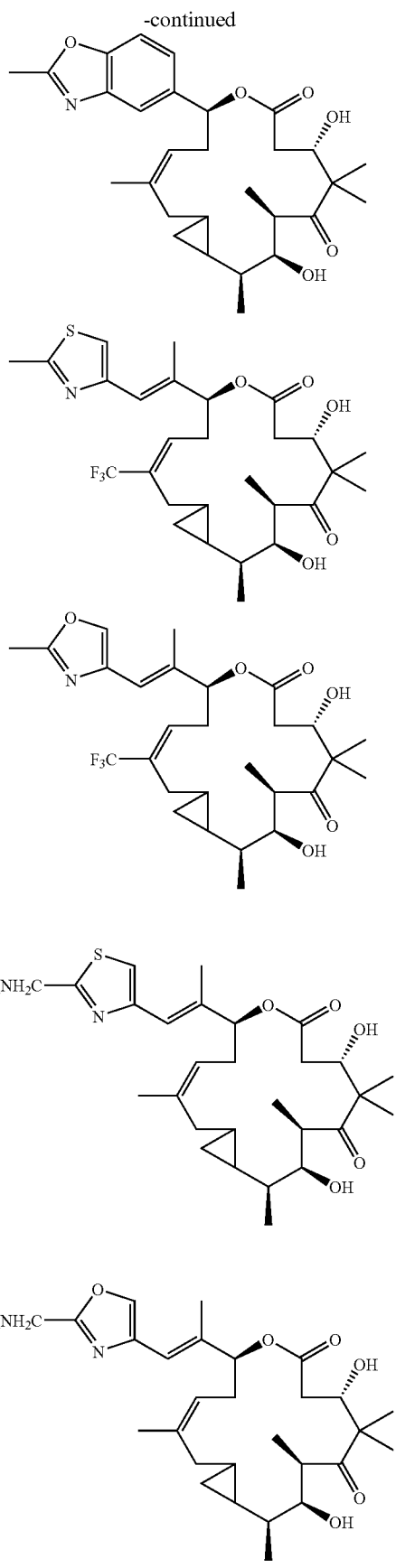

-continued
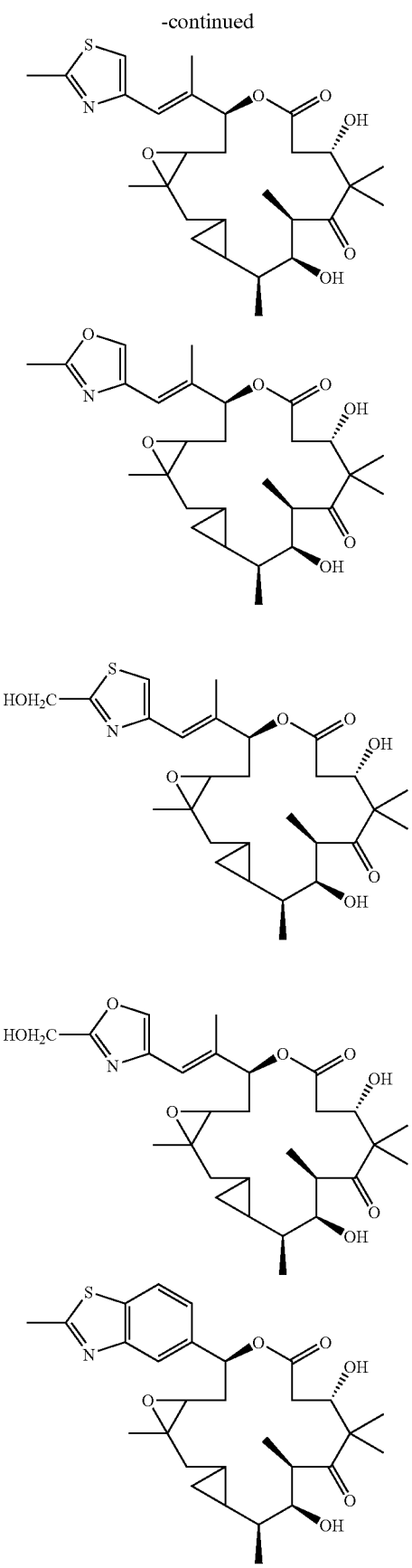
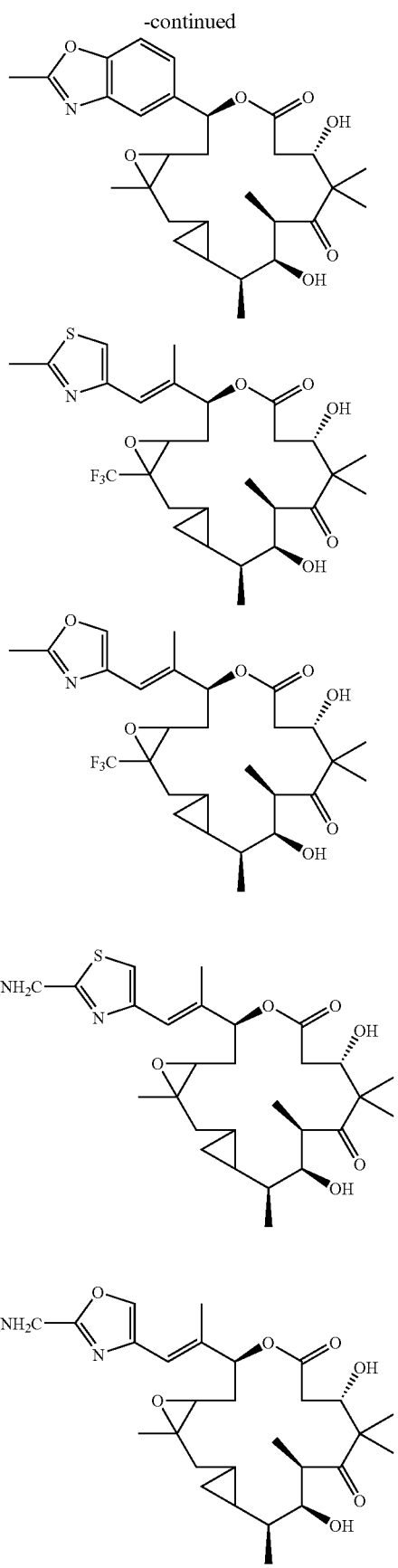

41
-continued
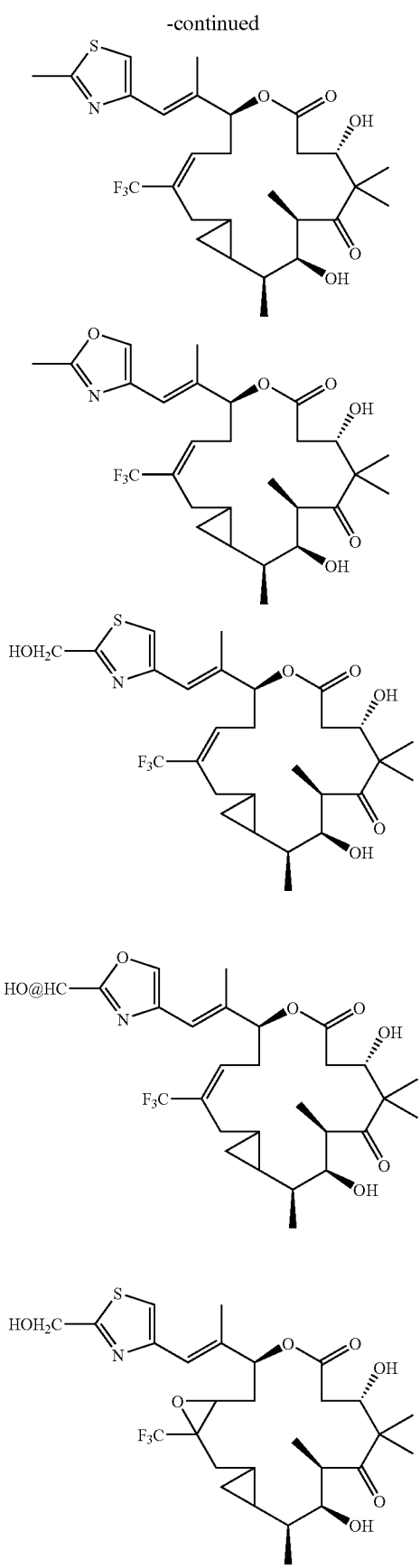
42
-continued
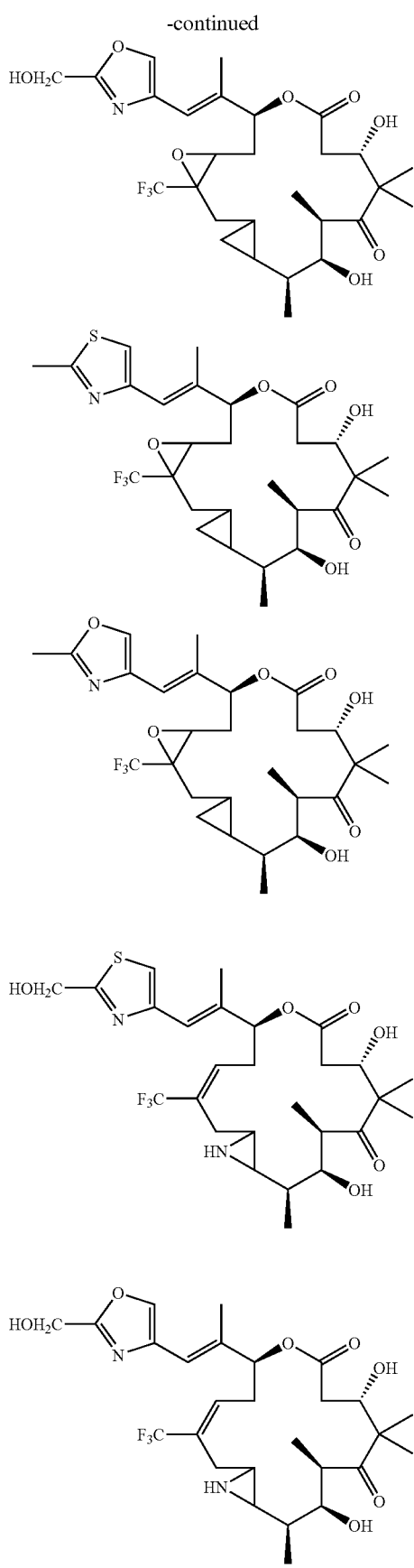

-continued
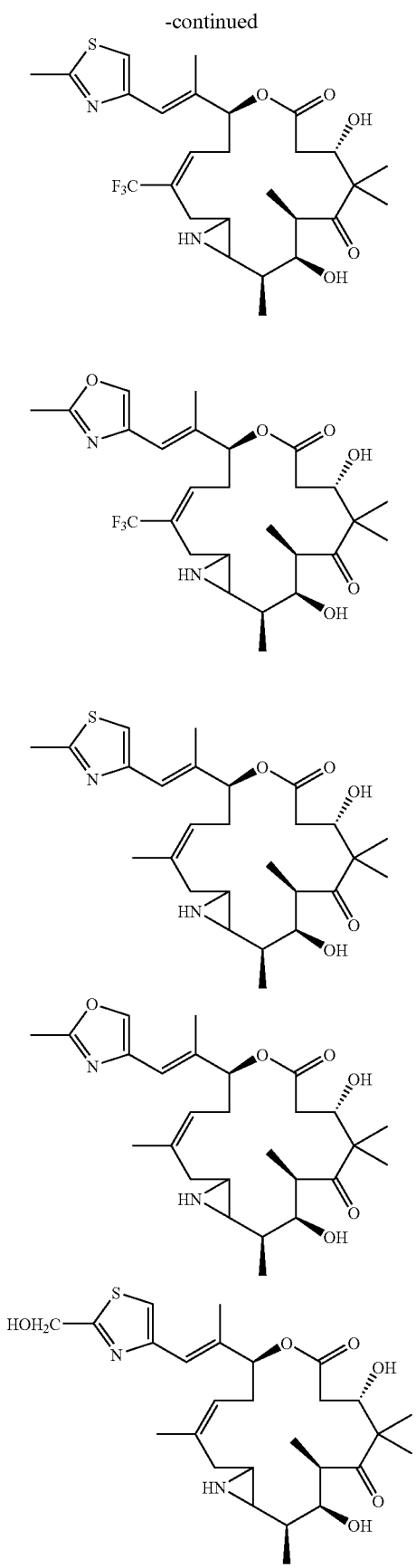
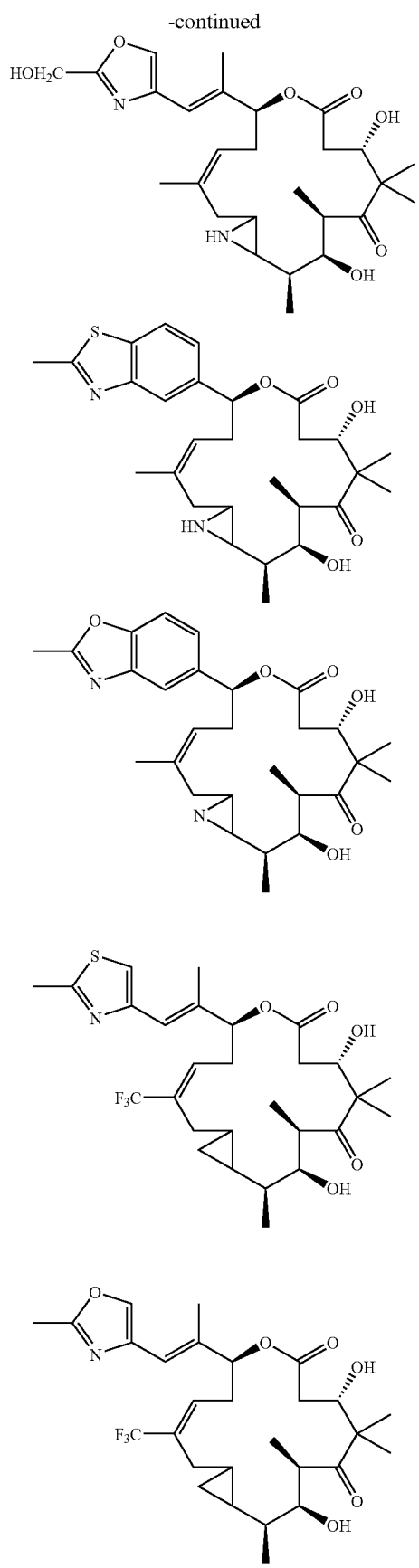

-continued

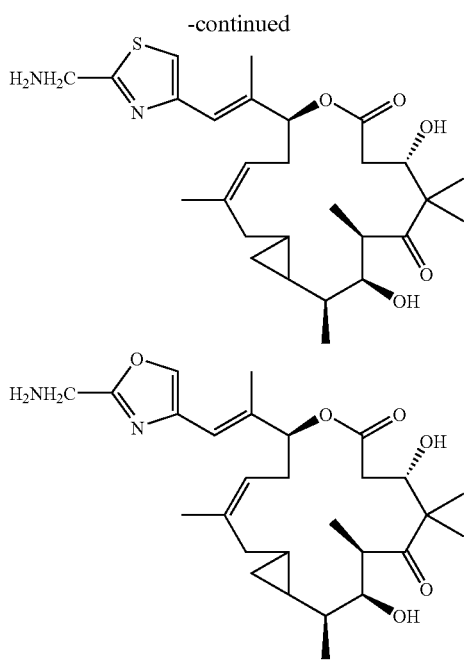

Compounds of this invention include those specifically set forth above and described herein, and are illustrated in part by the various classes, subgenera, and species disclosed elsewhere herein. Without wishing to be bound by any particular theory, certain compounds of the present invention have been modified at C9 and C10 to constrain the conformation of the molecule in much the same manner as a double carbon-carbon bond at the C9-C10 position would. Electronic effects, steric effects, hydrogen bonding, dipole effects, or a combination thereof may be used to create this conformational constraint. For example, cyclic ring systems such as oxiranes, cyclopropyl, and aziridine may be used to constrain the conformation of the molecule. In other embodiments 4, 5, or 6-membered rings are used to accomplish the same effect. The effect may also be accomplished by a conjugated p-orbital system such as that found in an ester, thioester, or amide. The effect may also be accomplished by an extended delocalized pi system such as those found in an aromatic ring system. In other embodiments, the steric effects of substituents around the C9 and C10 positions are used to constrain the conformation of the molecule in the same way the molecule is constrained by a C9-C10 carbon-carbon double bond.

It will be appreciated by one of ordinary skill in the art that asymmetric centers may exist in the compounds of the present invention. Thus, inventive compounds and pharmaceutical compositions thereof may be in the form of an individual enantiomer, diastereomer or geometric isomer, or may be in the form of a mixture of stereoisomers. In certain embodiments, the compounds of the invention are enantiopure compounds. In certain other embodiments, a mixtures of stereoisomers or diastereomers are provided.

It will be appreciated that some of the foregoing classes and subclasses of compounds can exist in various isomeric forms. The invention encompasses the compounds as individual isomers substantially free of other isomers and alternatively, as mixtures of various isomers, e.g., racemic mixtures of stereoisomers. Additionally, the invention encompasses both (Z) and (E) double bond isomers unless otherwise specifically designated. Thus, compounds of the invention generally depicted in structures herein encompass those structures in which double bonds are (Z) or (E). In certain preferred embodiments, the double bond at the C12-C13 position is in the cis or Z configuration. In some embodiments, the double bond at the C9-C10 position is in the trans or E configuration. In still other embodiments, the double bond at the C12-C13 position is in the cis or Z configuration, and the double bond at the C9-C10 position is in the trans or E configuration. The invention also encompasses tautomers of specific compounds as described above.

Additionally, the present invention provides pharmaceutically acceptable derivatives of the inventive compounds, and methods of treating a subject using these compounds, pharmaceutical compositions thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, usually with significantly reduced pharmacological activity, which contains an additional moiety that is susceptible to removal in vivo yielding the parent molecule as the pharmacologically active species. An example of a pro-drug is an ester that is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Compounds of this invention which are of particular interest include those which:

exhibit cytotoxic or growth inhibitory effect on cancer cell lines maintained in vitro or in animal studies using a scientifically acceptable cancer cell xenograft model;

exhibit an ability to polymerize tubulin and stabilize microtubule assemblies;

exhibit minimal levels of toxicity to vital organs;

lead to tumor disappearance in scientifically acceptable cancer cell xenograft models;

lead to tumor shrinkage in scientifically acceptable cancer cell xenograft models;

lead to tumor disappearance in scientifically acceptable cancer cell xenograt models and delayed/or no recurrence of the tumor after stopping treatment;

exhibit transient and reversible body weight decreases and show therapeutic effects in scientifically acceptable cancer cell xenograft models;

exhibit enhanced water solubility over epothilones A, B, C or D, or paclitaxel, or additionally or alternatively exhibit sufficient solubility to be formulated in an aqueous medium using reduced proportion of chremophor; and/or exhibit a therapeutic profile (e.g., optimum safety and curative effect) that is superior to that of epothilone B, epothilone D, or paclitaxel.

A variety of epothilone analogs as described supra have been prepared, characterized, and tested as exemplified herein. 9,10-dehydro-epothilone analogs have been found to be useful in the treatment of cancer, and in particular compounds have been prepared and found to possess one or more of the desired characteristics listed above.

Synthetic Methodology

The synthesis of certain epothilones, desoxyepothilones and analogues thereof have been previously described (see, U.S. Pat. Nos. 6,242,469, 6,284,781, 6,300,355, 6,204,388, 6,316,630, and 6,369,234; U.S. patent application Ser. Nos. 09/797,027, 09/796,959, and 10/236,135; and PCT Publication Nos. WO 99/01124, WO 99/43653, and WO 01/64650, the entire contents of which are hereby incorporated by reference). In recognition of the need for improved or additional synthetic methodologies to efficiently generate epothilones, desoxyepothilones and analogues thereof in large quantities, the present invention provides an efficient and modular route for the synthesis of epothilones, desoxyepothilones and analogues thereof. Although the synthesis of certain exemplary compounds is described in the Exemplification herein, it will be appreciated that this methodology is generally applicable to the generation of analogues and conjugates as discussed above for each of the classes and subclasses described herein.

In particular, the 9,10-dehydroepothilone compounds of the present invention may be prepared in a variety of ways using synthetic methodologies useful in the synthesis of epothilones. In certain embodiments, the compounds are prepared using a convergent synthetic route. For example, the epothilone may be synthesized by preparing two or three intermediates which are brought together to yield the desired compound. In one embodiment, one of the intermediates is an acyl portion containing carbons 1-9, and another intermediate contains carbons 10-15 and may also contain the thiazole side chain. These two roughly equal portions of the epothilone may be brought together first using an esterification reaction between C-1 and an oxygen off C-15. The macrocycle may then be closed using a carbon-carbon coupling reaction such as a Suzuki coupling or ring closing metathesis reaction. In one embodiment, the final ring closing step is accomplished using a ring closing metathesis reaction to form the 9,10-double bond and close the macrocycle. The ring closing metathesis reaction is accomplished using an organometallic catalyst such as the Grubbs catalyst as shown in Scheme 8 below. In certain embodiments, the 9,10-double bond is reduced or oxidized, or the 9,10-double bond may be further functionalized to prepare additional epothilone derivatives. In certain embodiments, the 9,10-double bond is converted into a cyclopropyl moiety by the treatment of the 9,10-double bond with a carbene or carbenoid reagent such as $CH_2N_2$.

In certain embodiments, the 9,10-dehydroepothilone compound is prepared by the isomerization of the double from the 10,11-position (e.g., Epo490) to the 9,10-position. This isomerization may be catalyzed by the presence of a transition metal such as palladium.

In other embodiments, the final ring closing step is accomplished using a ring closing metathesis reaction to form the 12,13-double bond and close the macrocycle. In certain embodiments, the 12,13-double bond is reduced or oxidized. In other embodiments, a macroaldolization or macrolactonization reaction is used to form the macrocycle.

Certain exemplary syntheses of the compounds of the invention are provided in the Figures and in the Examples. As would be appreciated by one of ordinary skill in the art, a variety of analogs and derivatives may be prepared using the synthetic procedures described herein. For example, one could accomplish many of the synthetic steps with different protecting groups or different substituents on the 16-membered ring.

Pharmaceutical Compositions

This invention also provides a pharmaceutical preparation comprising at least one of the compounds as described above and herein, or a pharmaceutically acceptable derivative thereof, which compounds are capable of inhibiting the growth of or killing cancer cells, and, in certain embodiments of special interest are capable of inhibiting the growth of or killing multidrug resistant cancer cells. In certain embodiments, the pharmaceutical preparation also comprises as solubilizing or emulsifying agent such as Cremophor (polyoxyl 35 castor oil) or Solutol (polyethylene glycol 660 12-hydroxystrearate).

As discussed above, the present invention provides novel compounds having antitumor and antiproliferative activity, and thus the inventive compounds are useful for the treatment of cancer. Accordingly, in another aspect of the present invention, pharmaceutical compositions are provided, wherein these compositions comprise any one of the compounds as described herein, and optionally comprise a pharmaceutically acceptable carrier. In certain embodiments, these compositions optionally further comprise one or more additional therapeutic agents. In certain other embodiments, the additional therapeutic agent is an anticancer agent, as discussed in more detail herein.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof, e.g., a prodrug.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1-19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower-alkyl sulfonate and aryl sulfonate.

Additionally, as used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

As described above, the pharmaceutical compositions of the present invention additionally comprise a pharmaceutically acceptable carrier, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the anti-cancer compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; Cremophor; Solutol; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutical Compositions

The invention further provides a method for inhibiting tumor growth and/or tumor metastasis. In certain embodiments of special interest, the invention provides a method of treating cancers by inhibiting tumor growth and/or tumor metastasis for tumors multidrug resistant cancer cells. The method involves the administration of a therapeutically effective amount of the compound or a pharmaceutically acceptable derivative thereof to a subject (including, but not limited to a human or animal) in need of it. In certain embodiments, specifically for treating cancers comprising multidrug resistant cancer cells, the therapeutically effective amount is an amount sufficient to kill or inhibit the growth of multidrug resistant cancer cell lines. In certain embodiments, the inventive compounds are useful for the treatment of solid tumors.

The compounds and pharmaceutical compositions of the present invention may be used in treating or preventing any disease or conditions including proliferative diseases (e.g., cancer), autoimmune diseases (e.g., rheumatoid arthritis), and infections (e.g., bacterial, fungal, etc.). The compounds and pharmaceutical compositions may be administered to animals, preferably mammals (e.g., domesticated animals, cats, dogs, mice, rats), and more preferably humans. Any method of administration may be used to deliver the compound of pharmaceutical compositions to the animal. In certain embodiments, the compound or pharmaceutical composition is administered parenterally.

In yet another aspect, according to the methods of treatment of the present invention, tumor cells are killed, or their growth is inhibited by contacting the tumor cells with an inventive compound or composition, as described herein. Thus, in still another aspect of the invention, a method for the treatment of cancer is provided comprising administering a therapeutically effective amount of an inventive compound, or a pharmaceutical composition comprising an inventive compound to a subject in need thereof, in such amounts and for such time as is necessary to achieve the desired result. In certain embodiments of the present invention a "therapeutically effective amount" of the inventive compound or pharmaceutical composition is that amount effective for killing or inhibiting the growth of tumor cells. The compounds and compositions, according to the method of the present invention, may be administered using any amount and any route of administration effective for killing or inhibiting the growth of tumor cells. Thus, the expression "amount effective to kill or inhibit the growth of tumor cells", as used herein, refers to a sufficient amount of agent to kill or inhibit the growth of tumor cells. The exact amount required will vary from subject to subject, depending on the species, age, and general condition of the subject, the severity of the infection, the particular anticancer agent, its mode of administration, and the like. The anticancer compounds of the invention are preferably formulated in dosage unit form for ease of administration and uniformity of dosage. The expression "dosage unit form" as used herein refers to a physically discrete unit of anticancer agent appropriate for the patient to be treated. It will be understood, however, that the total daily usage of the compounds and compositions of the present invention will be decided by the attending physician within the scope of sound medical judgment. The specific therapeutically effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Furthermore, after formulation with an appropriate pharmaceutically acceptable carrier in a desired dosage, the pharmaceutical compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments of the invention, the inventive compounds as described herein are formulated by conjugating with water soluble chelators, or water soluble polymers such as polyethylene glycol as poly (1-glutamic acid), or poly (1-aspartic acid), as described in U.S. Pat. No. 5,977,163, the entire contents of which are hereby incorporated by reference. In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect. The desired dosage may delivered as delivered every other day, every third day, every week, every two weeks, every three weeks, or every four weeks. In certain embodiments, the desired dosage may be delivered using multiple administrations (e.g., two, three, four, five, six, seven, eight, nine, or ten administrations).

Liquid dosage forms for oral and parenteral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. In certain embodiments for parenteral administration, the compounds of the invention are mixed with solubilizing agents such an Cremophor, alcohols, oils, modified oils, glycols, polysorbates, cyclodextrins, polymers, and combinations thereof. In certain embodiments, the compound is mixed with an alcohol, such as ethanol, and Cremophor (polyethoxylated castor oil).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As discussed above, the compounds of the present invention are useful as anticancer agents, and thus may be useful in the treatment of cancer, by effecting tumor cell death or inhibiting the growth of tumor cells. In general, the inventive anticancer agents are useful in the treatment of cancers and other proliferative disorders, including, but not limited to breast cancer, brain cancer, skin cancer, cervical cancer, colon and rectal cancer, leukemia, lung cancer, melanoma, multiple myeloma, non-Hodgkin's lymphoma, ovarian cancer, pancreatic cancer, prostate cancer, and gastric cancer, to name a few. In certain embodiments, the inventive anticancer agents are active against leukemia cells and melanoma cells, and thus are useful for the treatment of leukemias (e.g., myeloid, lymphocytic, promyelocytic, myelocytic and lymphoblastic leukemias, whether acute or chromic forms) and malignant melanomas. In still other embodiments, the inventive anticancer agents are active against solid tumors and also kill and/or inhibit the growth of multidrug resistant cells (MDR cells). In certain embodiments, the inventive anticancer agents are active against cancers which are resistant to other known anti-neoplastic agents or which have been found not to respond clinically to other known anti-neoplastic agents. In other embodiments, the inventive anticancer agents are active against cancer which are resistant to other anti-neoplastic microtubule-stabilizing agents (e.g., paclitaxel).

It will also be appreciated that the compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another anticancer agent), or they may achieve different effects (e.g., control of any adverse effects).

For example, other therapies or anticancer agents that may be used in combination with the inventive anticancer agents of the present invention include surgery, radiotherapy (in but a few examples, γ-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel, Docetaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), to name a few. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

In still another aspect, the present invention also provides a pharmaceutical pack or kit comprising one or more containers filled with one or more of the ingredients of the pharmaceutical compositions of the invention, and in certain embodiments, includes an additional approved therapeutic agent for use as a combination therapy. Optionally associated with such container(s) can be a notice in the form prescribed by a governmental agency regulating the manufacture, use or sale of pharmaceutical products, which notice reflects approval by the agency of manufacture, use or sale for human administration.

EQUIVALENTS

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification and guidance which can be adapted to the practice of this invention in its various embodiments and equivalents thereof.

EXAMPLES

Example 1

Synthesis of 9,10-dehydro-12,13-desoxy-epothilones

This Example describes the synthesis of trans-9,10-dehydro-12,13-desoxyepothilone B, 26-trifluoro-trans-9,10-dehydro-12,13-desoxyepothilone B, 26-trifluoro-12,13-desoxyepothilone B, and 12,13-desoxyepothilone B and biological testing of these compounds.

Fluorinated derivatives of epothilones were prepared and tested given the enhanced pharmacokinetics and chemotherapeutic indices of other medicinal agents with fluorine substitutions (Ojima, I.; Inoue, T.; Chakravarty, S.; *J. Fluorine Chem.* 1999, 97; Newman, R. A.; Yang, J.; Finlay, M. R. V.; Cabral, F., Vourloumis, D.; Stephens, L. C.; Troncoso, P.; Wu, X.; Logothetis, C. J.; Nicolaou, K. C.; Navone, N. M. *Cancer Chemother. Pharmacol.* 2001, 48, 319-326; each of which is incorporated herein by reference).

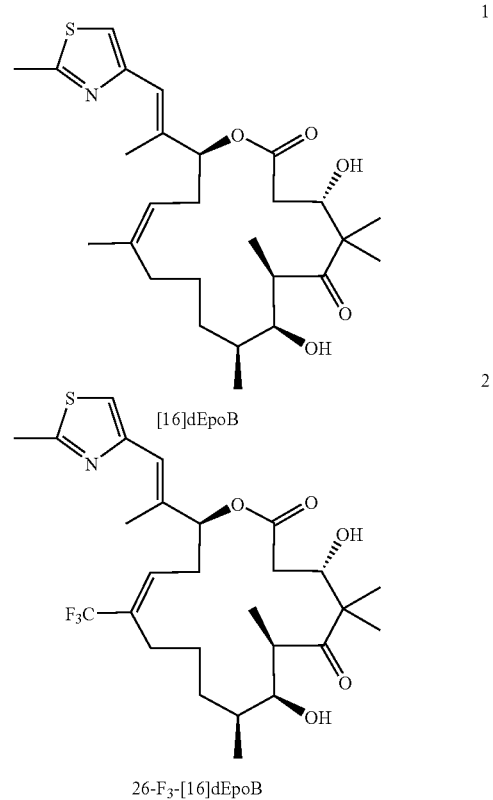

To reach compound 2, we sought to take advantage of a highly convergent route recently reported from our laboratory for the synthesis of epothilone 490 (6, dehydrodeoxy Epo B) en route to dEpoB (1, Scheme 3) (Biswas, K.; Lin, H.; Njardarson, J. T.; Chappell, M. D., Chou, T. C., Guan, Y.; Tong, W. P., He, L.; Horwitz, S. B., Danishefsky, S. J. *J. Am. Chem. Soc.* 2002, 124 (33); 9825-9832; Rivkin, A.; Njardarson, J. T.; Biswas, K; Chou, T. C.; Danishefsky, S. J. *J. Org. Chem.* 2002, 67, 7737-7740; each of which is incorporated herein by reference). In that synthesis, we introduced a flanking vinyl group to compound 4 via a stereospecific Stille coupling of a vinyl iodide precursor 3 with tri-n-butylvinylstannane. Ring closing metathesis followed by deprotection led to 6, which was then transformed to dEpoB (1) via a regioselective diimide reduction.

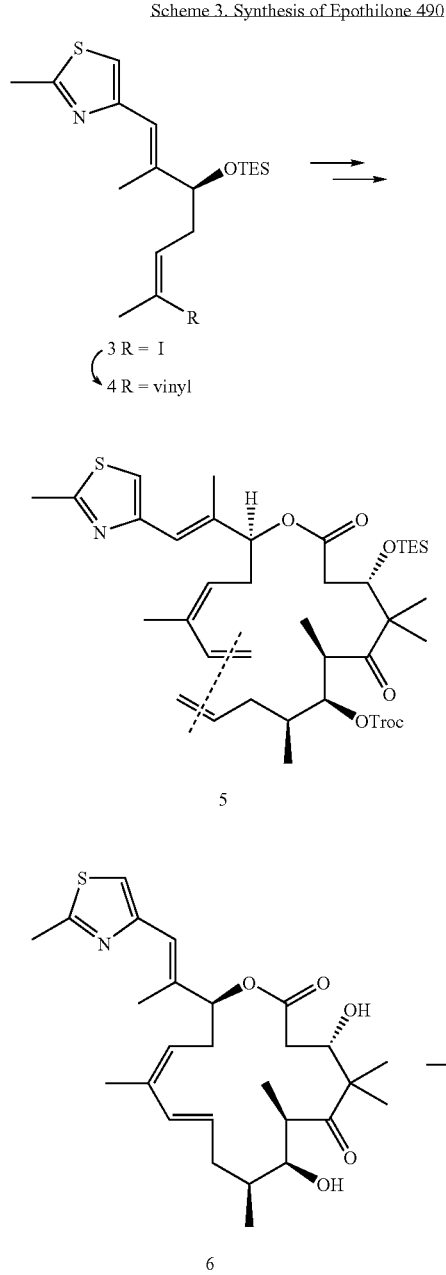

Attention was first directed to the synthesis of 15 (Scheme 4). Alkylation of the previously reported lithium enolate of 7 (Chappell, M. D.; Stachel, S. J.; Lee, C. B.; Danishefsky, S. J. Org. Lett. 2000, 2(11), 1633-1636; incorporated herein by reference) with iodide 8 (synthesized from the known alcohol 16 using TMSI in methylene chloride) afforded 9 in 78% yield and high diastereoselectivity (>25:1 de). Compound 9 was advanced in three steps to 10 as shown. Attempts to accomplish addition of methylmagnesium bromide to the Weinreb amide linkage of 10 failed. The breakdown of this reaction was attributed to the presence of the iodoalkene linkage. However we could accomplish our goal by changing the order of these two C—C bond forming steps. Thus, reaction of 10 with vinyltributyltin under Stille conditions could then be followed by addition of methyl Grignard reagent to give the desired ketone 11. Condensation of ketone 11 with phosphine oxide 12, followed by deprotection of the triethylsilyl ether, afforded fragment 13 in good yield. Esterification of the resulting 13 with C1-C10 acid fragment 14 (Biswas, K.; Lin, H.; Njardarson, J. T.; Chappell, M. D., Chou, T. C., Guan, Y.; Tong, W. P., He, L.; Horwitz, S. B., Danishefsky, S. J. J. Am. Chem. Soc. 2002, 124 (33); 9825-9832; Rivkin, A.; Njardarson, J. T.; Biswas, K; Chou, T. C.; Danishefsky, S. J. J. Org. Chem. 2002, 67, 7737-7740; incorporated herein by reference), provided the desired 15, in 75% yield (Scheme 4).

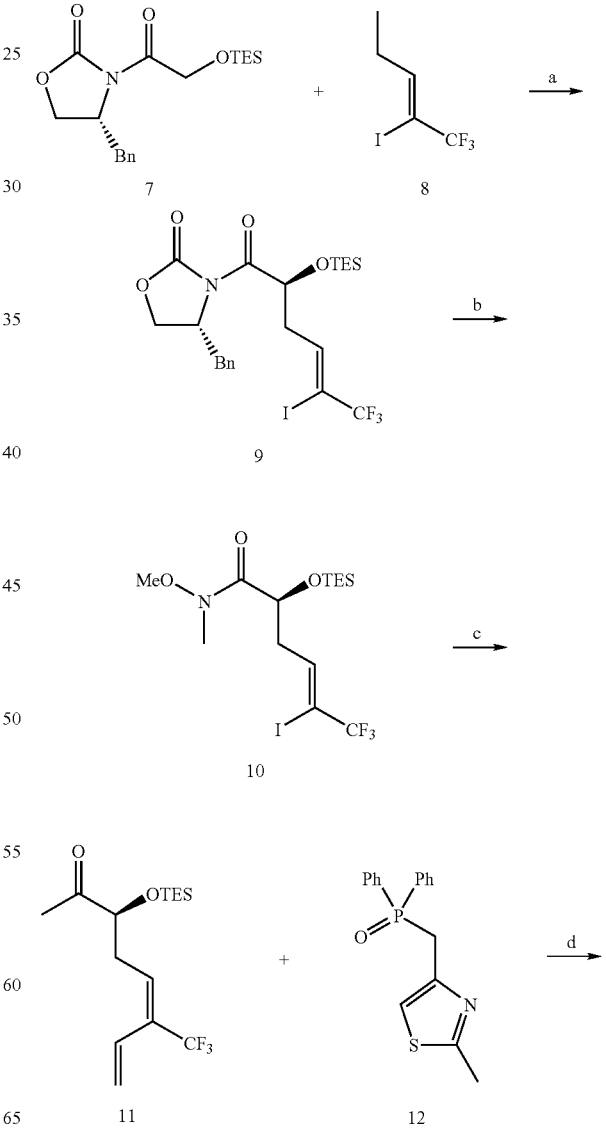

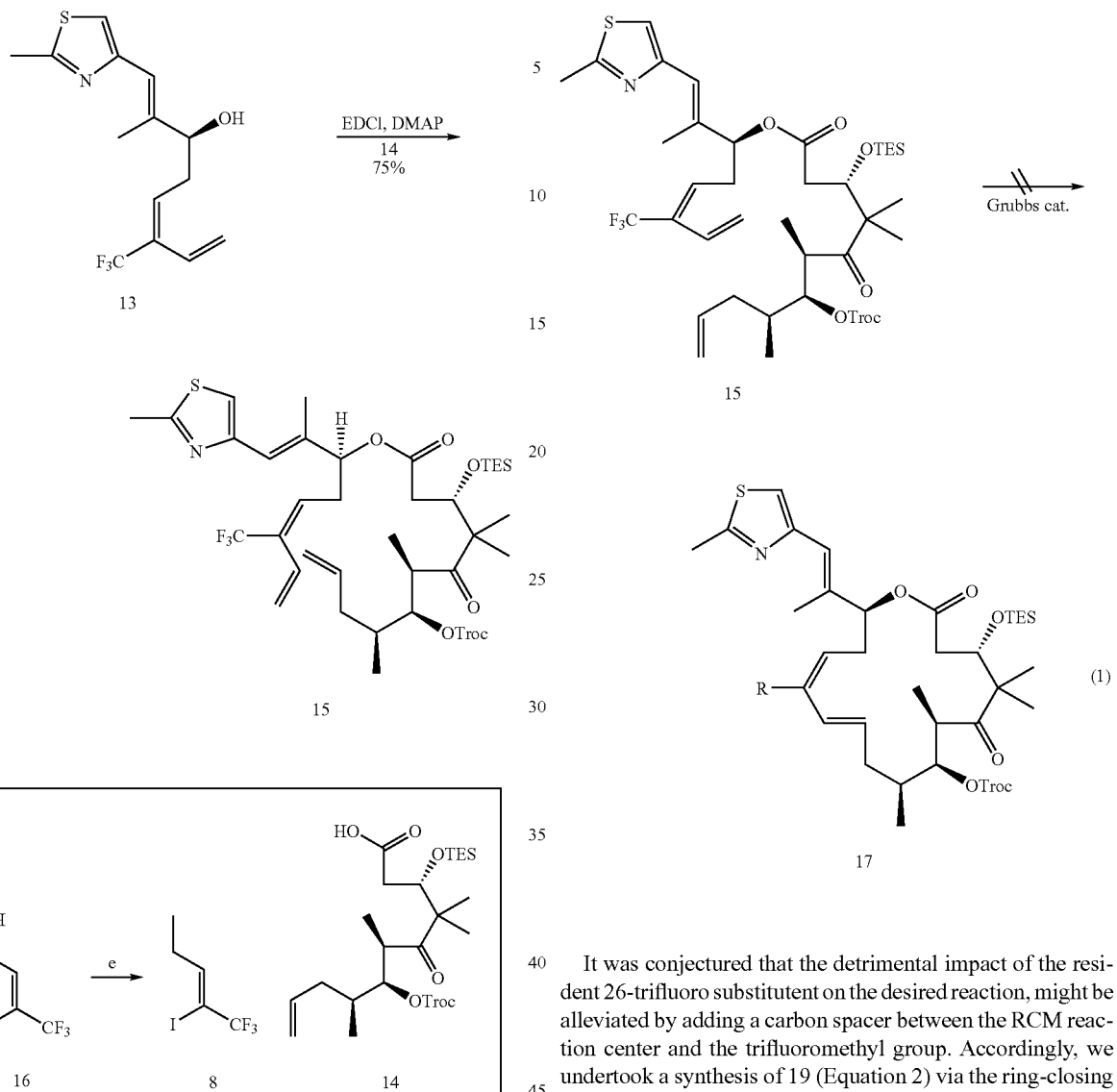

(a) LHMDS, -78° C., 78%; (b) i) HOAc:THF:H₂O (3:1:1); ii) CH₃ONHCH₃, AlMe₃; iii) TESCl, imidazole, DMF, 79% overall; (c) i) Vinyltributyltin, Pd(dba), DMF, 80° C., 3 h 43%; ii) MeMgBr, 0° C., 94%; (d) i) n-BuLi, THF, -78° C., 30 min., ii) 12, -78° C. to rt, 81%; iii) HOAc:THF:H₂O (3:1:1), 94%; (e) TMSI, CH₂Cl₂, 0° C., 92%

Unfortunately, attempts to carry out the ring-closing metathesis reaction of 15 using the second generation Grubbs catalyst (Reviews: Grubbs, R. H.; Miller, S. J.; Fu, G. C. *Acc. Chem. Res.* 1995, 28, 446; Trnka, T. M.; Grubbs, R. H. *Acc. Chem. Res.* 2001, 34, 18; *Alkene Metathesis in Organic Chemistry* Ed.: Fürstner, A.; Springer, Berlin, 1998; Fürstner, A. *Angew. Chem. Int. Ed. Engl.* 2000, 39, 3012; Schrock, R. R. *Top. Organomet. Chem.* 1998, 1, 1; each of which is incorporated herein by reference) in methylene chloride led primarily to apparent dimerization of the starting material (Equation 1). Given the fact that the RCM works quite well in the related setting of 5→6, we naturally attributed the failure in the case of 15 to the presence of the trifluoromethyl group at $C_{12}$.

It was conjectured that the detrimental impact of the resident 26-trifluoro substitutent on the desired reaction, might be alleviated by adding a carbon spacer between the RCM reaction center and the trifluoromethyl group. Accordingly, we undertook a synthesis of 19 (Equation 2) via the ring-closing metathesis of 18, which would present the trifluoromethyl group in the context of a 17-membered ring containing a shipped (1,4)-diene.

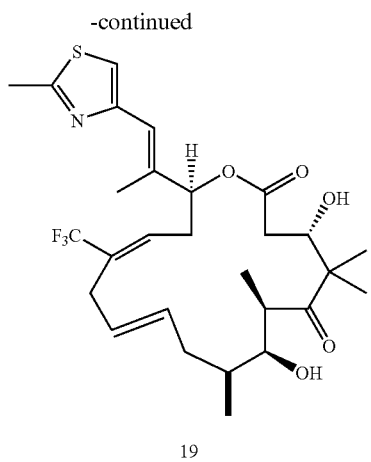

19

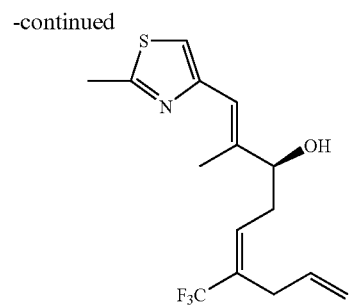

21

The synthesis program directed to 19 commenced with the preparation of compound 21, which corresponds to the O-alkyl sector of our proposed RCM substrate (Scheme 5). We began with allylation of 10, this time under radical reaction conditions as shown (Keck, G. E.; Yates, J. B. *J. Am. Chem. Soc.* 1982, 104, 5829; review: Curran, D. P. *Synthesis* 1988, Part 1, pp 417-439; Part 2, pp. 489; each of which is incorporated herein by reference). This conversion was followed by reaction of the alkylated product with methyl magnesium bromide, thus affording the required ketone 20. Condensation of this compound with phosphine oxide 12, followed by deprotection of the triethylsilyl ether function provided 21 in good yield.

Scheme 5. Synthesis of the alcohol fragment 21

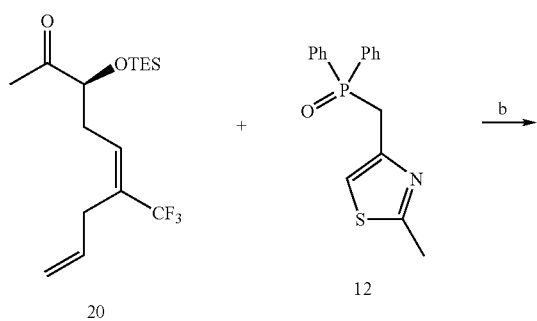

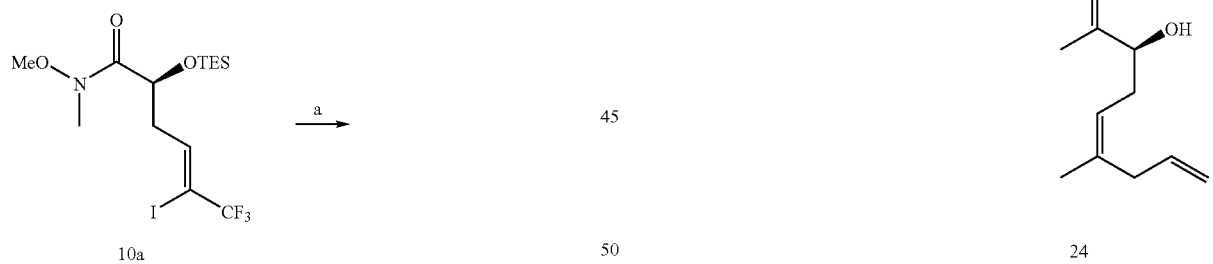

(a) i) Allyltributyltin, AIBN, Benzene, 80° C., 3 h 74%; ii) MeMgBr. 0° C., 93%; (b) i) 12, n-BuLi, THF, -78° C., 30 min., ii) 20, -78° C. to rt, 85%; iii) HOAc:THF:H₂O (3:1:1), 98%; (c) i) Allytributyltin, Pd₂(dba)₃, DMF, 25° C., 3 h, 75%; ii) MeMgBr, 0° þC., 94%; (d) i) 12, n-BuLi, THF, -þ78° C., 30 min., ii) 42, -78° C. to rt, 94%; iii) HOAc:THF:H₂O (3:1:1), 95%.

Esterification of 21 with the C1-C10 acid fragment 14, provided the proposed RCM precursor 18 in 75% yield (Scheme 6). Happily in this case, the ring-closing metathesis reaction of 18 could be accomplished using the second generation Grubbs catalyst in methylene chloride. As in the case of the conversion of 5→6, the reaction provided exclusively the trans isomer 22 in 57% yield.[6] Finally, reductive cleavage of the trichloro ethoxycarbonyl protecting group with zinc and acetic acid, followed by deprotection of the TES ether with HF-pyridine, provided the desired 19 containing a trifluoromethyl function at $C_{12}$, albeit in the context of the 17-membered ring series.

Scheme 6. Synthesis 27-F$_3$-ddEpoB (19)

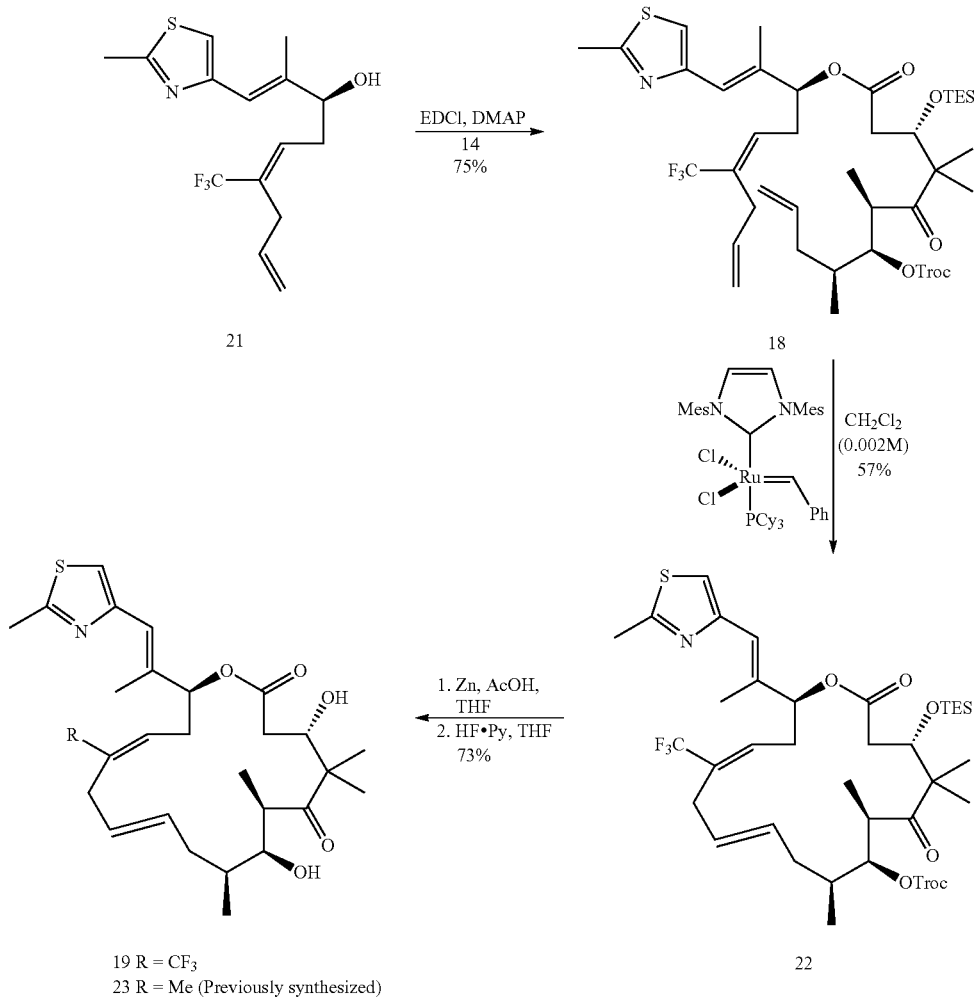

19 R = CF$_3$
23 R = Me (Previously synthesized)

Synthetic 19 was evaluated as to its cytotoxic activity. As shown in Table 1-1 below, direct comparison of the previously reported [17]ddEpoB (23) with 27-F$_3$-[17]ddEpoB (19) indicated that the new perfluorinated compound possessed a comparably high cytotoxic potency.

TABLE 1-1

In vitro Cytotoxicities (IC$_{50}$) with tumor cell lines[a]

| Compound | CCRF-CEM (IC$_{50}$ (μM)[a]) | CCRF-CEM/VBL (IC$_{50}$ (μM)[a]) |
|---|---|---|
| 27-F$_3$-[17]ddEpoB (19) | 0.068 | 0.191 |
| [17]ddEpoB (23) | 0.040 | 0.126 |
| [16]ddEpoB (6) | 0.020 | 0.068 |

[a]XTT assay following 72 h inhibition. CCRF-CEM is a human T-cell acute lymphoblastic leukemia cell line. The CCRF-CEM/$_{VBL100}$, CCRF-CEM/$_{VM1}$ and CCRF-CEM/$_{Taxol}$ cell lines all overexpress P-glycoprotein and display a multidrug resistance phenotype to MDR associated oncolytics (Ojima, I.; Inoue, T.; Chakravarty, S.; J. Fluorine Chem. 1999, 97; Newman, R. A.; Yang, J.; Finlay, M. R. V.; Cabral, F., Vourloumis, D.; Stephens, L. C.; Troncoso, P.; Wu, X.; Logothetis, C. J.; Nicolaou, K. C.; Navone, N. M. Cancer Chemother. Pharmacol. 2001, 48, 319-326; each of which is incorporated herein by reference).

Though the trifluoromethyl isoteric substitution had little effect on the gross cytotoxic activity, preliminary data from metabolic degradation studies in mouse plasma showed 19 to be notably more stable than is the parent 23. Exposure of epothilones 19 and 23 to nude mouse and human plasma led to degradation of 23 within 30 minutes, while epothilone 19 remained mostly intact. Since pharmokinetic issues are likely to be critical in the actual use of any epothilone agent as a drug, we take this finding to be quite encouraging.

The synthesis of 26-F$_3$-dEpoB (2) could be accomplished via a highly convergent strategy, related to that employed in the synthesis of 27-F$_3$-[17]ddEpoB (19). Accordingly, fragments of similar complexity would serve as key building blocks (Scheme 7). We envisioned that the acyl sector 25, could serve as the polypropionate domain and the alkyl sector 21 or 24 would be prepared as previously described in the introduction. The union of the two fragments 21(24) and 25 would be initiated through an esterification and consumated via a subsequent ring-closing metathesis. Finally, cleavage of the protecting groups would provide the desired analogs 28 and 29. Chemoselective reduction of the 9,10-olefin of 28 and 29 would furnish dEpoB (1) and the desired 26-F$_3$-12,13-desoxyEpoB (2).

Scheme 7

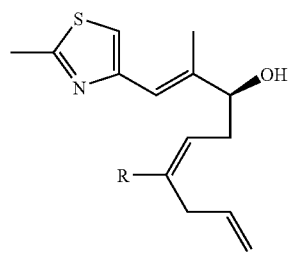

R: CF₃ (21), Me (24)

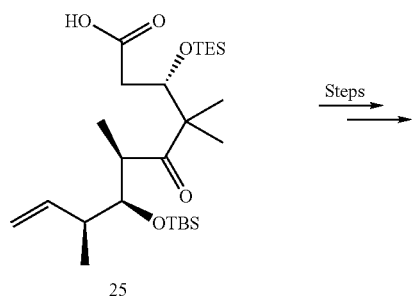

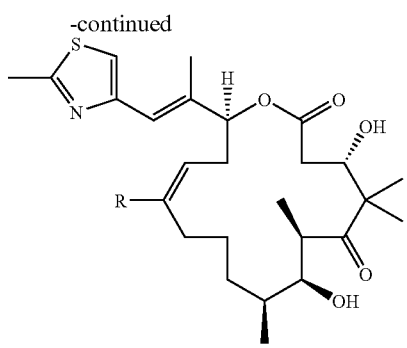

12,13-desoxyEpoB (1)
26-F₃-12,13-desoxyEpoB (2)

The synthesis of 1 and 2 commenced with the preparation of acyl sector 25. Ketone 30, previously reported, was subjected to an aldol reaction with the readily available aldehyde 31. Upon deprotonation and reaction of "lithio" 30 with 31, smooth condensation gave rise to a 5.3:1 mixture of aldol products 32 and 33. The major diastereoisomer 32 was easily separated by flash chromatography and protected as a TBS silyl ether. Hydrolysis of the diisopropyl acetal group under acid catalysis gave keto aldehyde 34, setting the stage for the second aldol reaction. Following the previously practiced "titano" tert-butyl ester method, with the new aldehyde 34 as the coupling partner, the desired aldol product 35 was obtained in high diastereoselectivity (dr>20:1) and yield (86%). Protection of the C3 alcohol of 35 with a TES silyl group was followed by deprotection of the benzyl ether. Oxidation of the resultant primary hydroxy provided the corresponding aldehyde, which was then converted to a terminal olefin via a Wittig reaction to provide 36 in high yield. Finally, hydrolysis of the t-butyl ester of 36 with TESOTf provided the acyl sector 25 (82%) along with side-product 37 (14%), which was converted to acyl sector 38 in high yield. Spectral and chromatographic properties of 38 were identical to previously obtained material from other programs in Dr. Sinha's laboratories (Scripps).

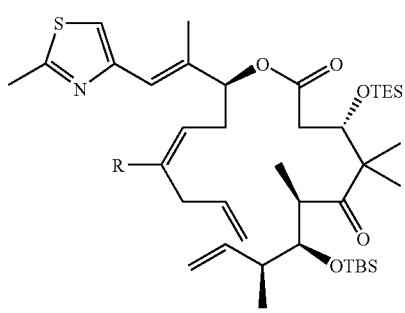

R: CF₃ (26), Me (27)

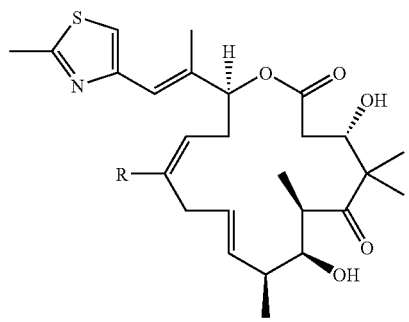

trans-9,10-dehydro-12,13-desoxyEpob (28)
26-F₃-trans-9,10-dehydro-12,13-desoxyEpoB (29)

Scheme 8

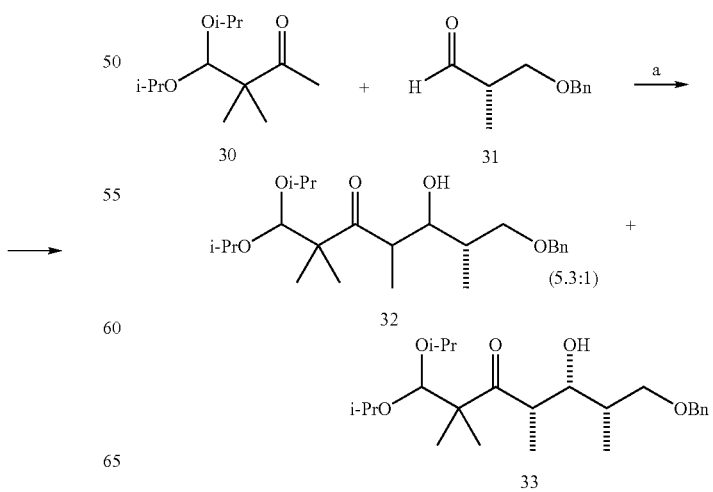

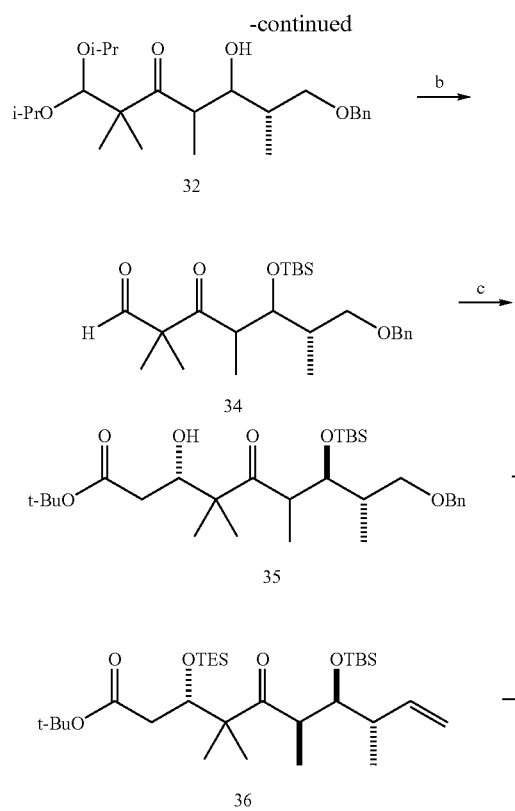
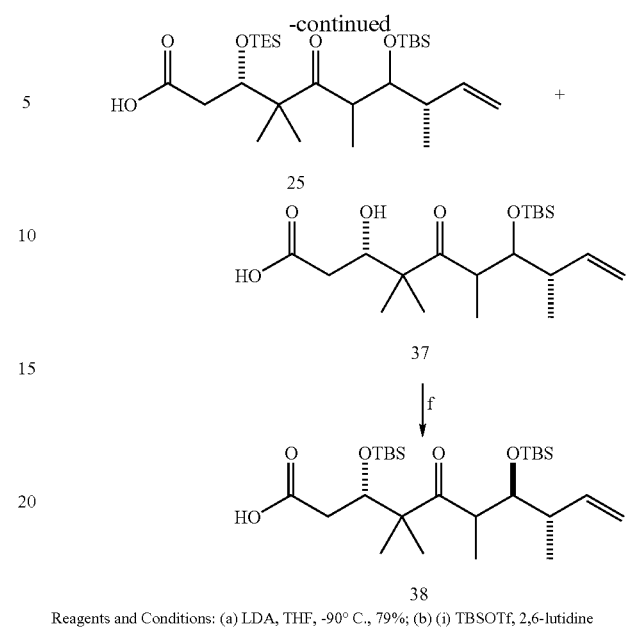

Reagents and Conditions: (a) LDA, THF, -90° C., 79%; (b) (i) TBSOTf, 2,6-lutidine CH$_2$Cl$_2$, -40 to -20° C., 97%, (ii) 2) p-TsOH•H$_2$O (cat.)THF-H$_2$O (4:1), 64° C., 86%; (c) t-butyl acetate, LDA, chiral-Ti complex, Et$_2$O, -78° C., 92%, (dr = >20:1); (d) (i) TESCl, imidazole, DMF, 0° C. to rt, 99%, (ii) H$_2$, Pd/C (10%), EtOH, 83%, (iii) TPAP, NMO, CH$_2$Cl$_2$, 93%, (iv) MePPh$_3$I, n-BuLi, THF, -78 to -5° C., 78%; (e) TESOTf, 2,6-lutidine, CH$_2$Cl$_2$, 0° C. to rt 82%; (f) (i) TBSOTf, 2,6-lutidine, CH$_2$Cl$_2$, 0° C. to rt, (ii) sat. NaHCO$_3$ (aq.), MeOH, THF, rt, 99%.

Esterification of the allylic alcohols 21 and 24 with C$_1$-C$_9$ acid fragment 25 provided the corresponding RCM cyclization precursors 26 and 27, respectively (Scheme 9).

Scheme 9.

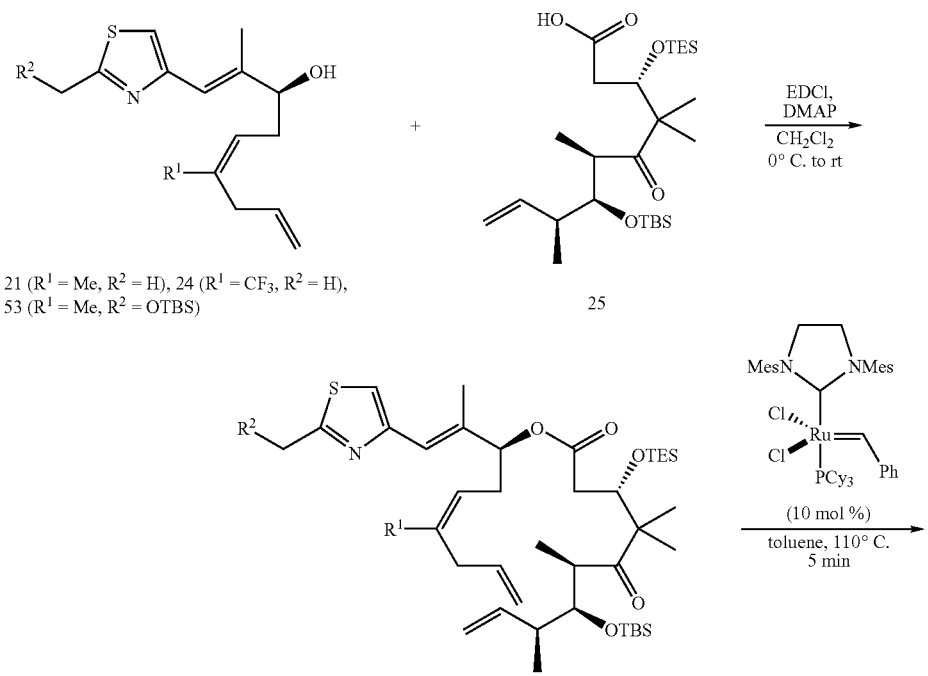

R$^1$ = Me, R$^2$ = H, (26, 79%)
R$^1$ = CF$_3$, R$^2$ = H (27, 70%)
R$^1$ = Me, R$^2$ = OTBS (54, 92% from ester)

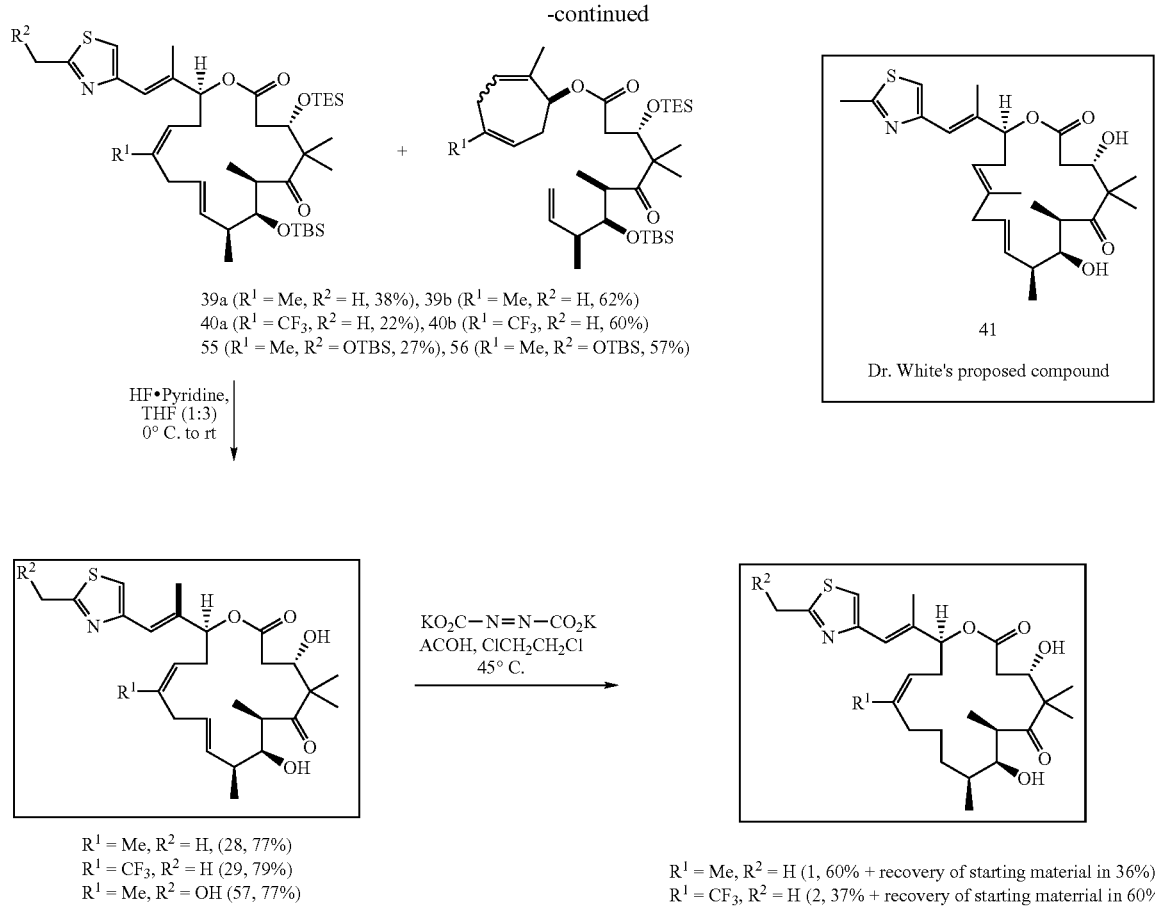

The ring-closing metathesis reactions 26, 27 and 54 were then carried out using the second generation Grubbs catalyst in toluene, which provided, as in our earlier study, exclusively the trans isomer 39a, 40a, and 55 along with the corresponding side products 39b, 40b, and 56. Finally, deprotection of silyl ethers with HF-pyridine led to the desired compounds 28, 29, and 57. Spectral and chromatographic properties of 28 were not identical to previously obtained material from the epothilone program in Dr. James D. White's laboratories (Oregon State University). Dr. James D. White thought he had synthesized 28, however inadvertently he made the 12,13E isomer 41 instead, which would explain the poor biological activity he observed. Consequently, we are the first ones to have synthesized 28 and tested this compound for its antitumor activity.

The fully synthetic 28, 29, and 2 have been evaluated against a variety of cell types to determine their antitumor potential. As shown in Table 1-2, all three compounds exhibited high cytotoxic activity against a variety of sensitive and resistant tumor cell lines. Direct comparison of 28 with the previously reported dEpoB (1) indicates that the new compound possesses nearly three times more potency.

TABLE 1-2

In vitro Cytotoxicities ($IC_{50}$) with tumor cell lines[a].

| Tumor Cell Lines | $IC_{50}$ (µM)[a] | | | |
|---|---|---|---|---|
| | 28 | 29 | dEpoB (1) | 57 |
| CCRF-CEM | 0.0014 | 0.0035 | 0.0036 | 0.00051 |
| CCRF-CEM/$VBL_{100}$ | 0.0065 | 0.0210 | 0.014 | 0.0106 |
| CCRF-CEM/Taxol | 0.0017 | 0.0057 | 0.0057 | 0.00073 |

[a]XTT assay following 72 h inhibition. CCRF-CEM is a human T-cell acute lymphoblastic leukemia cell line. The CCRF-CEM/$VBL100$, CCRF-CEM/$VM1$ and CCRF-CEM/$Taxol$ cell lines all overexpress P-glycoprotein and display a multidrug resistance phenotype to MDR associated oncolytics (Prié, G.; Thibonnet, J.; Abarbri, M.; Duchêne, A.; Parrain, J. Synlett 1998, 839; incorporated herein by reference).

To improve the overall yield of our synthesis of 28, 29, and 2, we decided to carry out the RCM reaction in the absense of the thiazole substituted olefin and in so doing avoid the formation of the undesired side product 39b and 40b. Deprotection of the silyl ether of the previously reported 42 and 20 provided hydroxyketones 43 and 44. Esterification of the resultant hydroxyketones 43 and 44 with $C_1$-$C_9$ acid fragment 25 provided the corresponding RCM cyclization precursors 45 and 46, respectively (Scheme 10). The ring-closing metathesis reaction of 45 and 46 was then carried out using the second generation Grubbs catalyst in toluene, which provided, as in our earlier study, exclusively the trans isomer 47 and 48 in high yields. Installation of the thiazole moiety gave 39a, 40a, and 55 in high yield. Deprotection of the two silyl ethers with HF-pyridine led to 28 and 29. Finally, selective reduction of the C9-C10 olefin afforded the corresponding epothilones 1 and 2. The structure of 28 was rigorously corroborated by its high yielding conversion to 1. The total synthesis of 1 has been very substantially simplified relative to previously practiced routes. Thus the use of the readily available 31, obtained from the chiral pool, is certainly a large improvement relative to reliance on (S)-2-methyl-4-pentenal whose synthesis requires intervening chiral auxilliaries.

Scheme 10

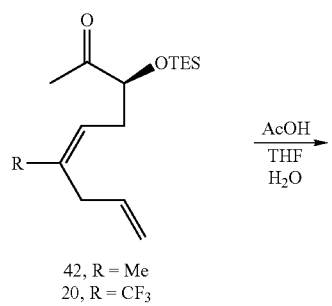

42, R = Me
20, R = CF$_3$

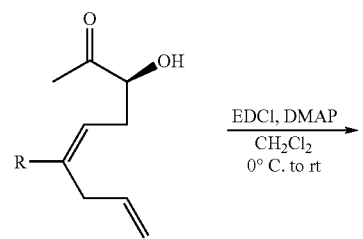

43, R = Me, 83%
44, R = CF$_3$, 76%

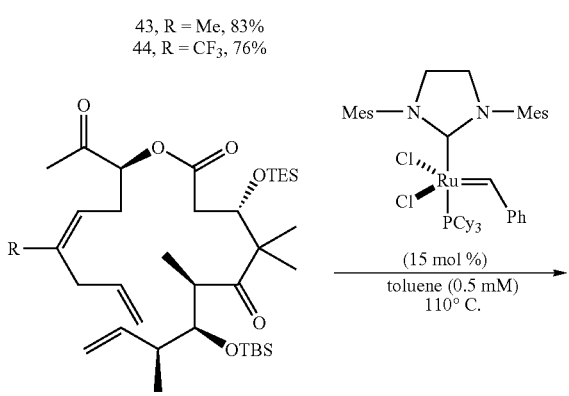

45, R = Me, 81%
46, R = CF$_3$, 86%

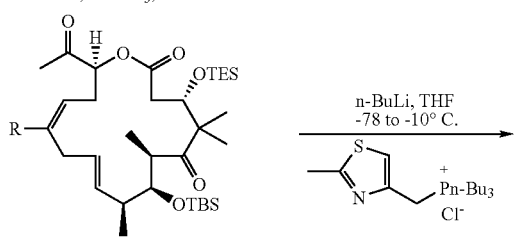

47, R = Me, 78%
48, R = CF$_3$, 71%

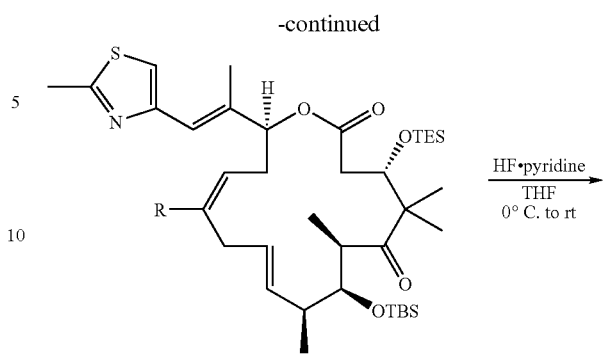

39a, R = Me, 76%
40a, R = CF$_3$, 70%

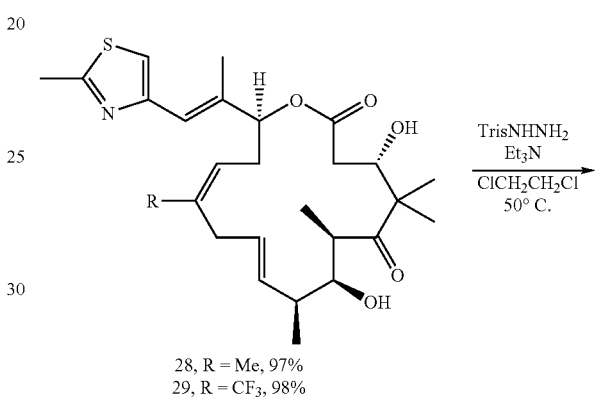

28, R = Me, 97%
29, R = CF$_3$, 98%

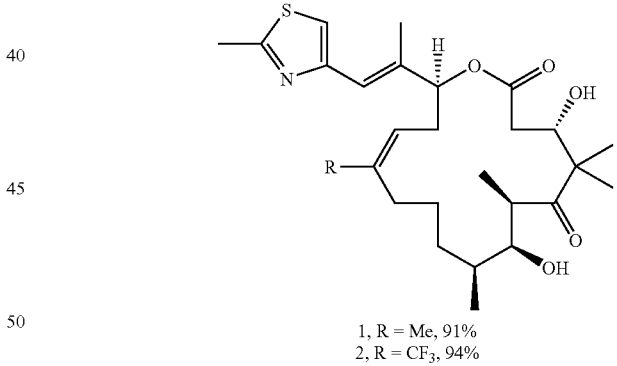

1, R = Me, 91%
2, R = CF$_3$, 94%

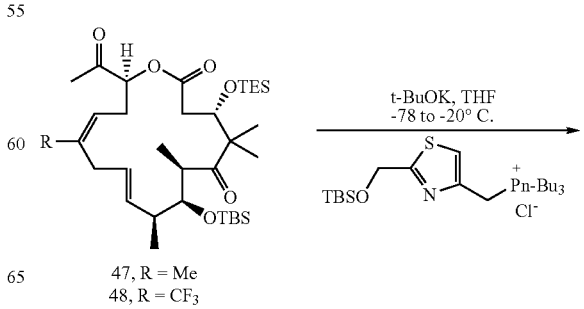

47, R = Me
48, R = CF$_3$

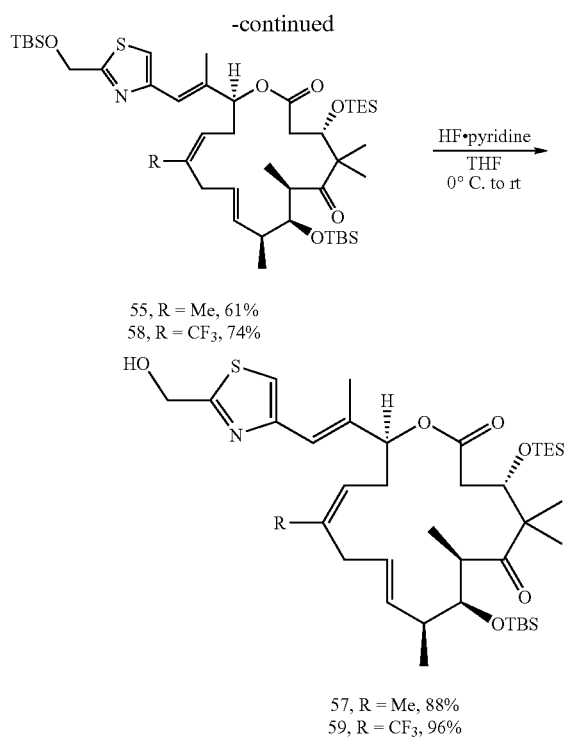

55, R = Me, 61%
58, R = CF₃, 74%

57, R = Me, 88%
59, R = CF₃, 96%

With compound 28 of rigorously proven structure in hand, we were surprised to find that its spectral properties were not congruent with those previously reported for a compound presumed to be the same entity. However it is clear in retrospect that 28 had not been previously prepared and, in fact the whole family of (E)-9,10-dehydroepothilones reported here is a new class of compounds.

Examination of synthetic analogs (2, 28, and 29), in cell culture settings, revealed stronger inhibitory effects on various sensitive and MDR tumor cell lines than are exhibited by our clinical entry dEpoB (1) (Table 1-3). We note that Epo 3 (28) is the first 12,13-desoxyepothilone compound that possessrd substantially improved cytotoxicity relative to that of dEpoB (1).

TABLE 1-3

In vitro Cytotoxicities (IC₅₀) with Tumor Cell Lines[a]

| Compound | CCRF-CEM(C) (μM) | C/VBL₁₀₀ (μM) | C/Taxol (μM) |
|---|---|---|---|
| Epo 1 (1, dEpoB) | 0.0036 | 0.016 | 0.0046 |
| Epo 2 (2) | 0.0041 | 0.080 | 0.018 |
| Epo 3 (28) | 0.0009 | 0.0042 | 0.0012 |
| Epo 4 (29) | 0.0035 | 0.0210 | 0.0057 |

[a]XTT assay following 72 h inhibition. CCRF-CEM is a human T-cell acute lymphoblastic leukemia cell line. The CCRF-CEM/VBL₁₀₀ cell line is resistant to vinblastine and CCRF-CEM/Taxol to taxol.

Figure 9:
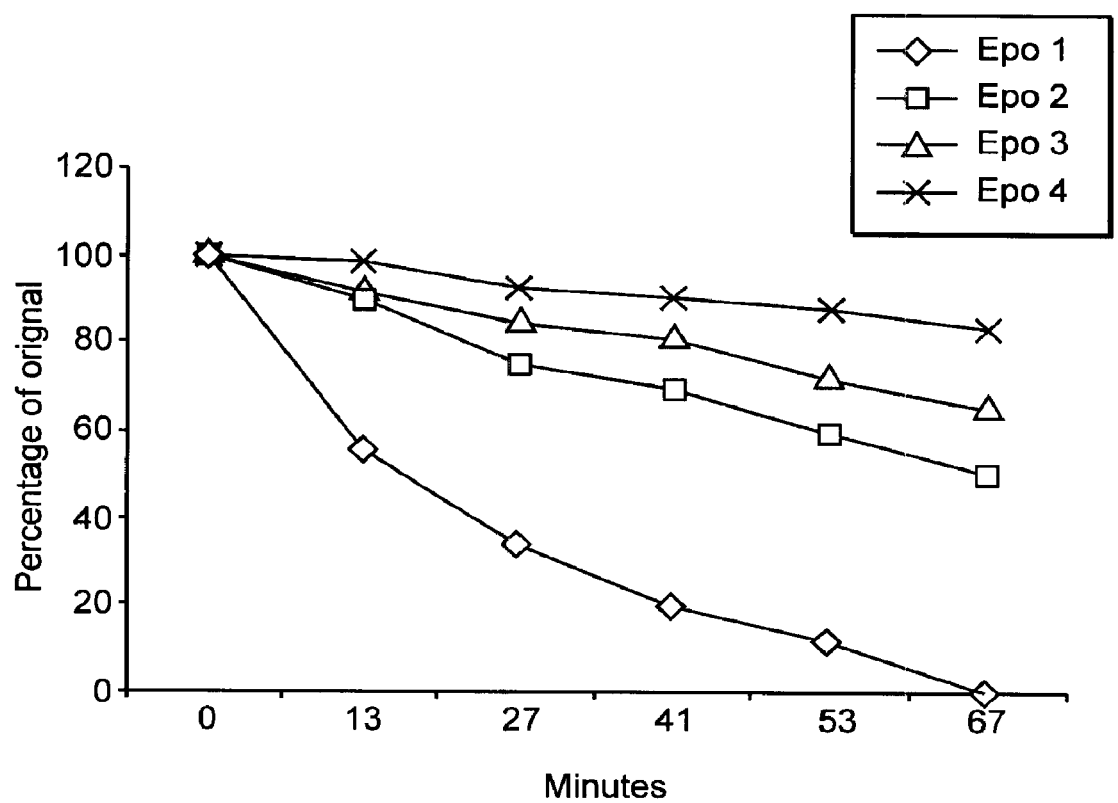
FIG. 9 shows the stability of epothilone analogs in murine plasma. Epo 1 is 12,13-desoxyEpoB, Epo 2 is 26-$F_3$-12,13-desoxyEpoB, Epo 3 is (E)-9,10-dehydro-12,13-desoxyEpoB, and Epo 4 is 26-$F_3$-(E)-9,10-dehydro-12,13-desoxyEpoB.

The impressive cell growth inhibition exhibited by epothilones 2, 28 and 29 (Epo 2-4) across a range of various drug-resistant tumors prompted determination of the blood plasma stability of these new (E)-9,10 congeners. For instance the recently described (E)-10,11-dehydro-dEpoB (of case 1 with a CH₃ group at C-12) exhibits very poor plasma stability with respect to lactone opening. It is this plasma instability which has stifled advancement of (E)-10, 11-dehydro-dEpoB. By contrast, on exposure of 2, 28 and 29 (Epo 2-4) to murine plasma, we observed a much slower drug degradation as compared to dEpoB (1) by a factor of seven. This stability constitutes a substantial advance from a drug availability perspective relative to dEpoB (see FIG. 9).

Figure 10:
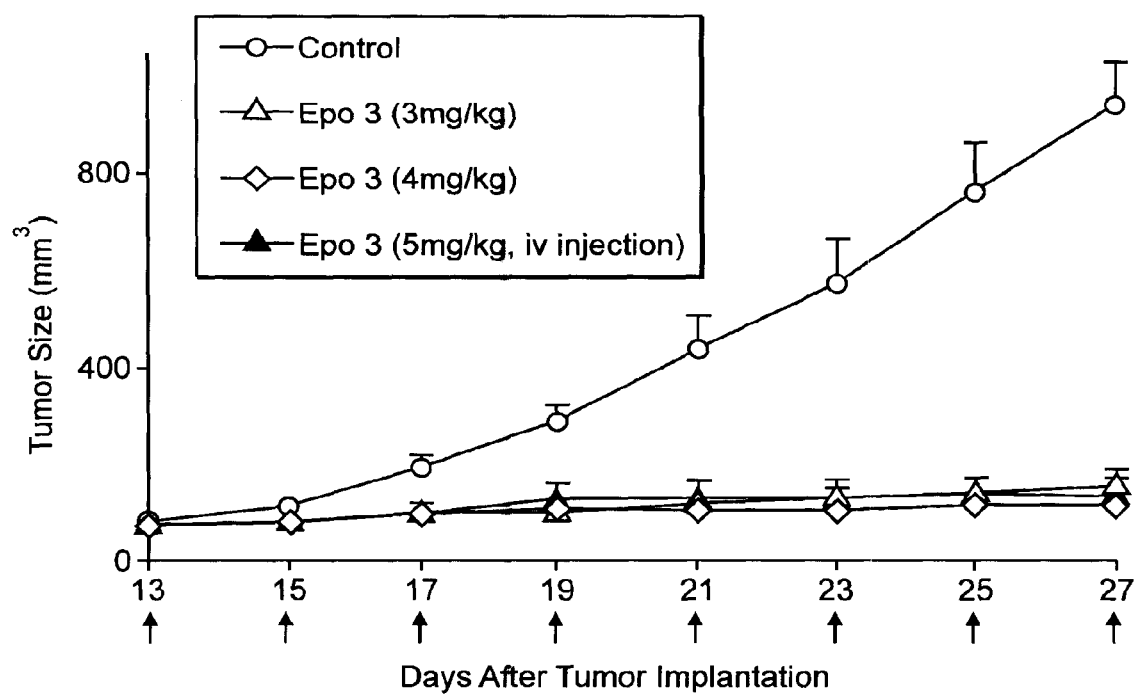
FIG. 10 depicts the therapeutic effect of epothilone analogs in nude mice bearing HCT-116 xenograft (iv infusion, Q2Dx7, n=3). Arrows indicate drug administration. Epo 3 is (E)-9,10-dehydro-12,13-desoxyEpoB.
Figure 13:
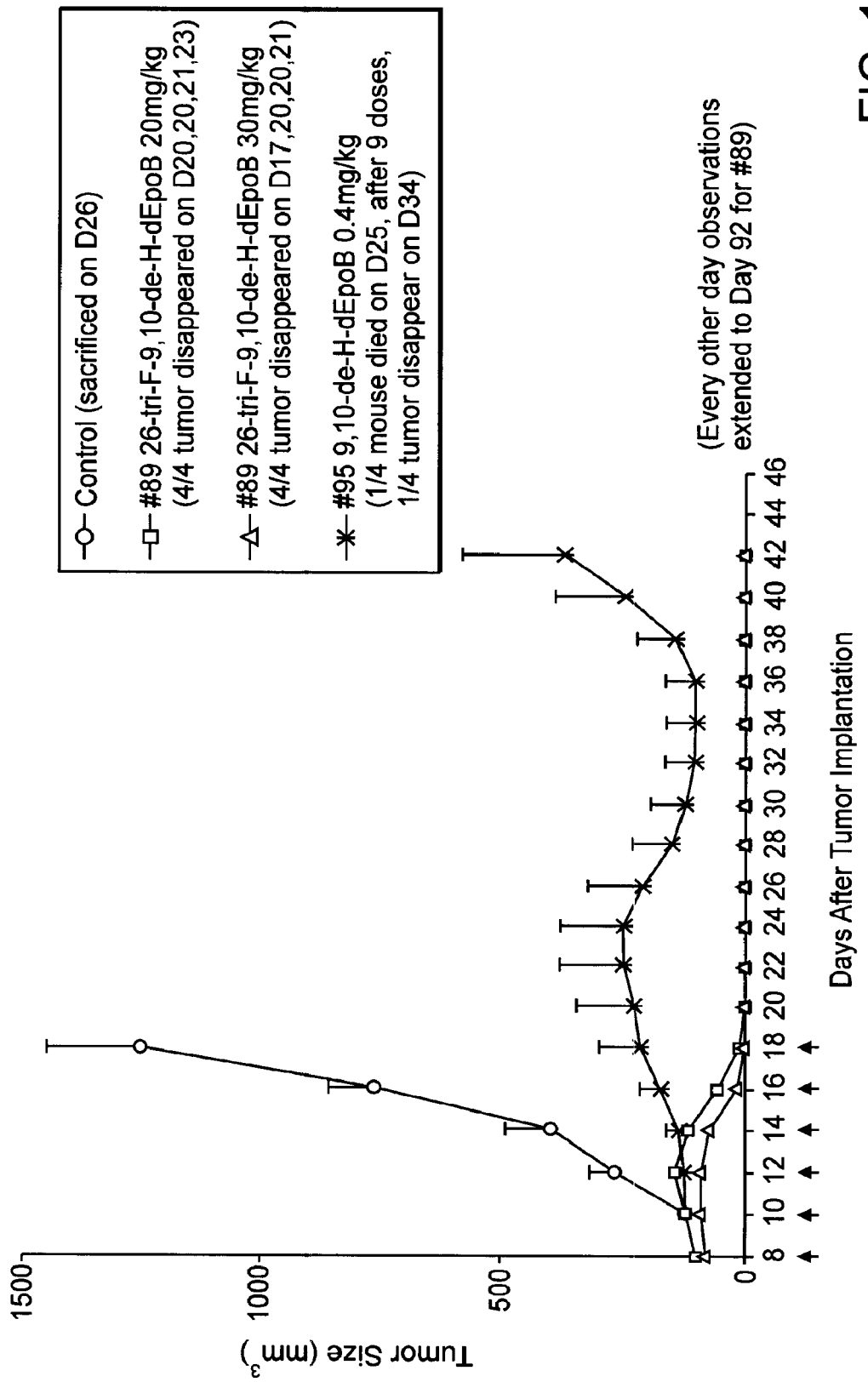
FIG. 13 shows the therapeutic effect of 26-trifluoro-9,10-dehydro-dEpoB and 9,10-dehydro-EpoB on tumor size in nude mice bearing MX-1 xenografts (6 hour iv infusion, Q2Dx6 & Q2Dx9, respectively).
Figure 14:
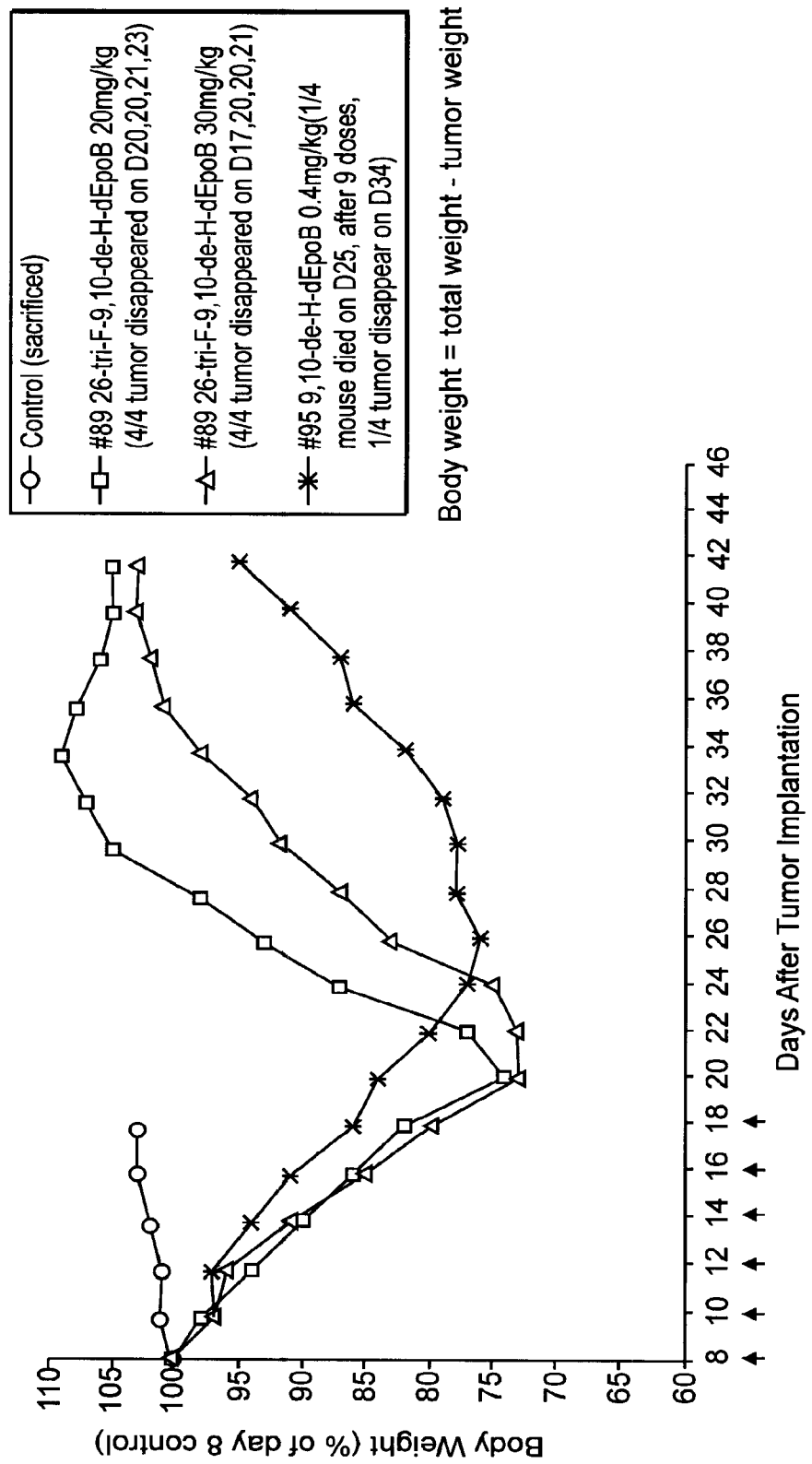
FIG. 14 shows body weight changes of nude mice bearing human mammary carcinoma tumor MX-1 xenograft following treatment with 26-trifluoro-9,10-dehydro-dEpoB and 9,10-dehydro-EpoB (6 hour infusion, Q2Dx6 &, Q2Dx9, respectively).
Figure 15:
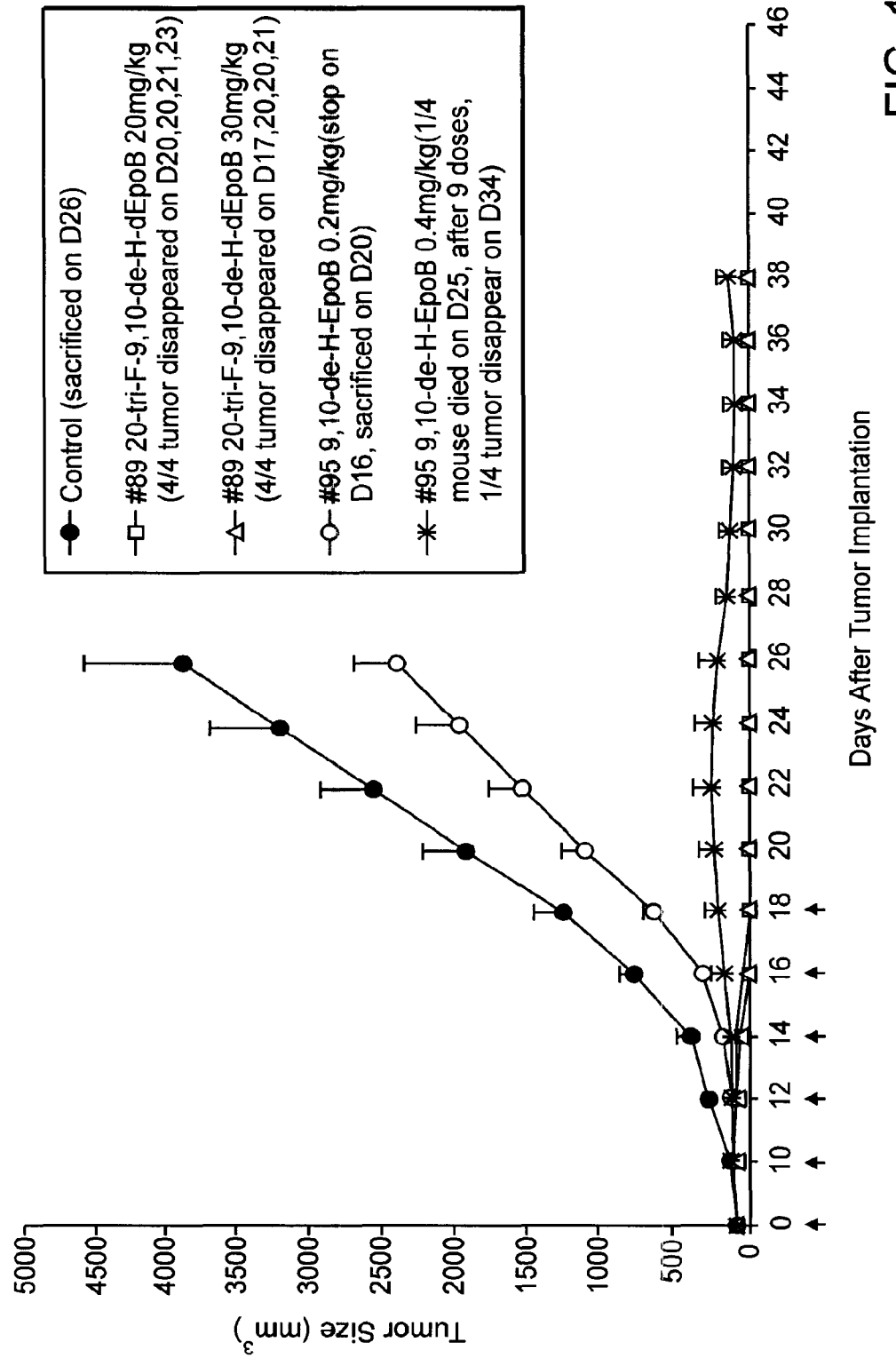
FIG. 15 shows the therapeutic effect of 26-trifluoro-9,10-dehydro-dEpoB and 9,10-dehydroEpoB on tumor size in nude mice bearing MX-1 xenografts (6 hour iv infusion, Q2Dx6 & Q2Dx9, respectively).
Figure 16:
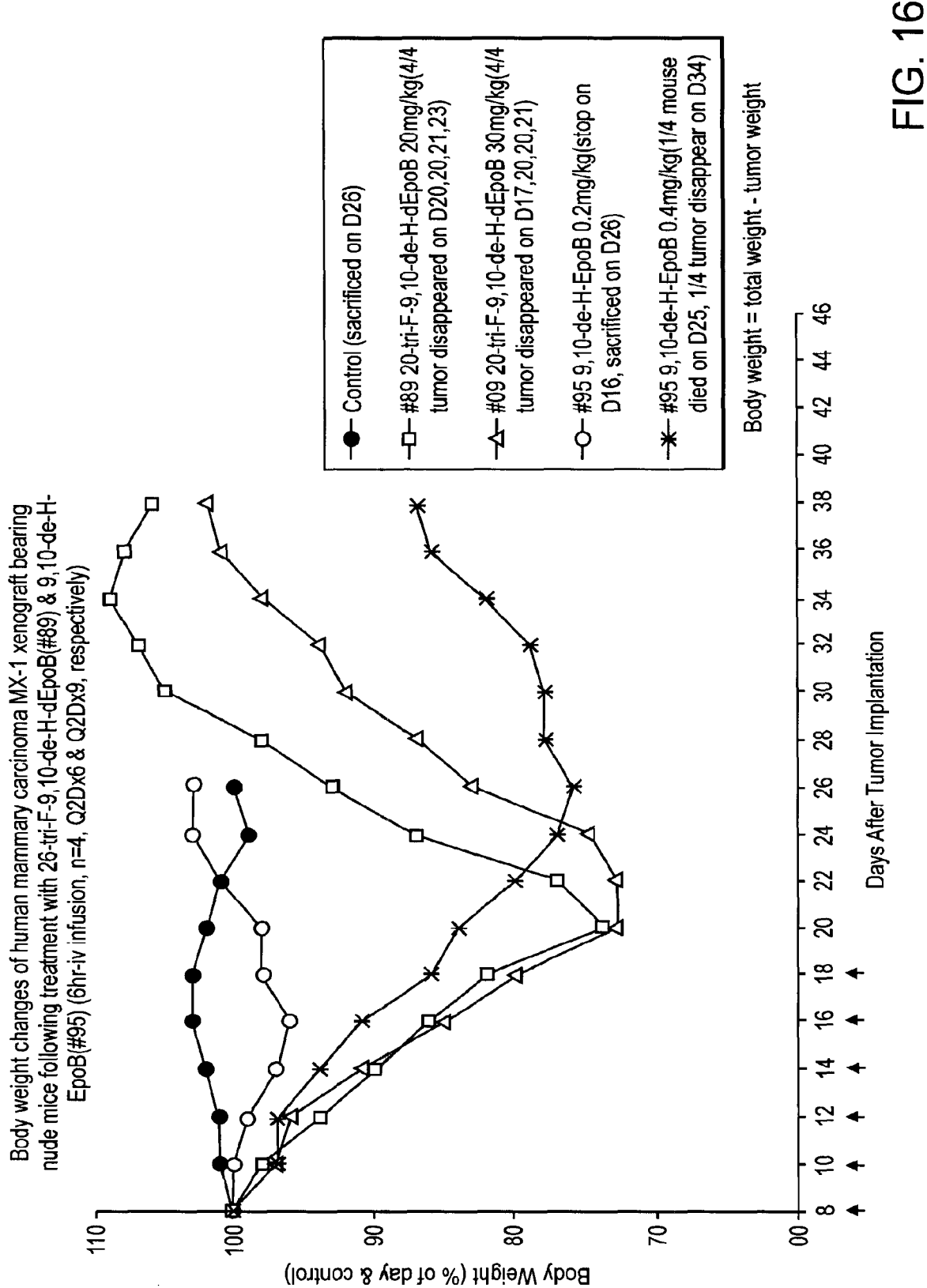
FIG. 16 shows body weight changes of nude mice bearing human mammary carcinoma tumor MX-1 xenograft following treatment with 26-trifluoro-9,10-dehydro-dEpoB and 9,10-dehydro-EpoB (6 hour iv infusion, Q2Dx6 & Q2Dx9, respectively).

The combination of the cytotoxicity and plasma stability data encourged us to synthesize substantial amounts of 28 (Epo 3) in order to determine its in vivo efficacy, in nude mice bearing human tumor xenografts. Epothilone 28 (Epo 3) demonstrated a markedly improved potency in inhibiting on the growth of implanted tumors, relative to dEpoB (see FIG. 10). The improved potency and plasma stability allows very substantial reduction of drug dosing (an order of magnitude) in the context of xenografts of 28 (Epo 3).

In our early studies we had found that epothilone B, by way of the 12,13 epoxide, is significantly more cytotoxic than is its 12,13-desoxy analog (dEpoB). However, from the perspective of theraputic index, the desoxy compound seemed to us to be more much promising. More recently, we reported the total synthesis of (E)-9,10-dehydro-12,13-desoxyepothilone B (28) using a stereoselective ring closing metathesis. We showed that the incorporation of E-9,10 unsaturation in the context of the usual Z-12,13 olefin (see compound 1) results in a great increase in in vitro potency. More to the point, this is translatable to an in vivo setting in xenografts mice. Moreover, compound 28 enjoys major pharmaceutical advantages relative to dEpoB (1). This allowed for the reduction of the dosing levels for 28 relative to 1 in xenograft experiments to be reduced by an order of magnitude.

Accordingly, we wondered if the incorporation of C9-C10 olefin in epothilone B (51, EpoB) would alter its biological profile in the same direction.

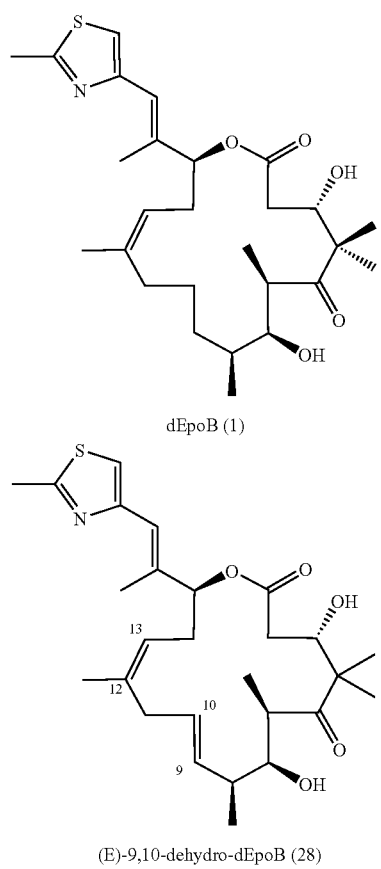

dEpoB (1)

(E)-9,10-dehydro-dEpoB (28)

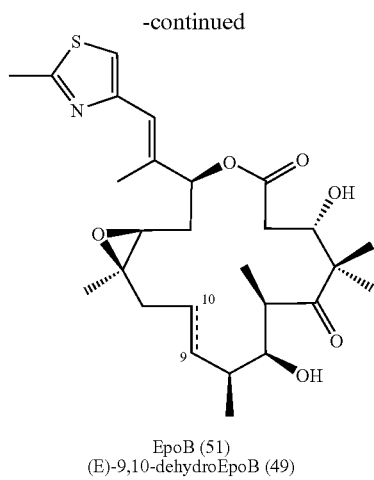

EpoB (51)
(E)-9,10-dehydroEpoB (49)

Epoxidation of 28 with 2,2'-dimethydroxirane (DMDO) proceeded with high chemoselectively at the more substituted C12-C13 olefin to give an 87% yield of a 1:2.6 ratio of the (E)-9,10-dehydroepothilone B (49) and its diastereomer (50). The stereochemistry of the epoxides was determined by selective diimide reduction of the C9-C10 double bonds. Examination of the spectral properties of these products revealed the minor product (49) to be dEpoB. The preference for α-epoxidation in the case of 28 stands in striking contrast to the highly stereoselective epoxidation of dEpoB, which occurs from the β face leading to EpoB (Meng, D.; Bertinato, P.; Balog, A.; Su, D.-S.; Kamenecka, T.; Sorensen, E. J.; Danishefsky, S. J. *J. Am. Chem. Soc.* 1997, 119, 10073; incorporated herein by reference).

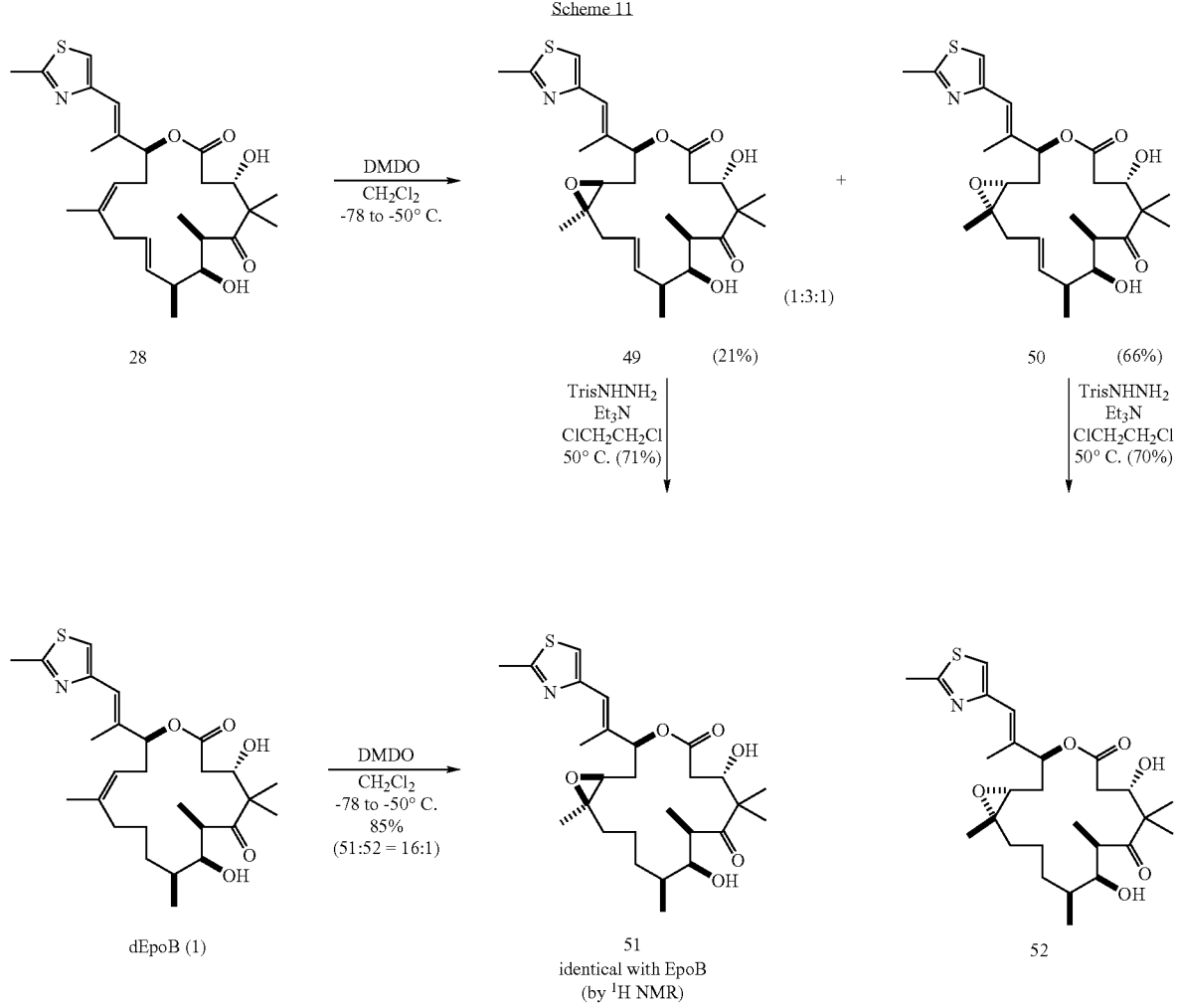

(E)-9,10-dehydroepothilone B (51) was evaluated against a variety of cell types to determine their antitumor potential. As shown in Table 1-4, (E)-9,10-dehydroepothiloneB (49) exhibits high cytotoxic activity against a variety of sensitive and resistant tumor cell lines. Direct comparison of 49 and EpoB (51) indicates this new analog possesses nearly 3-fold more potency than EpoB (51) making it one of the most potent epothilone analogs reported to date. Interestingly, α-epoxide series (50, 52) displayed a much lower activity than EpoB (51). The graph below shows the findings for in vivo studies of compound 49.

TABLE 1-4

In vitro cytotoxicities ($IC_{50}$) with tumor cell lines[a]

| compound | CCRF-CEM | CCRF-CEM/VBL | CCRF-CEM/Taxol |
|---|---|---|---|
| 1 (dEpoB) | 0.0036 | 0.016 | 0.0046 |
| 28 | 0.0009 | 0.0042 | 0.0012 |
| 51 (EpoB) | 0.00062 | 0.0037 | 0.0011 |
| 49 | 0.00023 | 0.00032 | 0.00042 |
| 50 | 0.0134 | 0.0959 | 0.0802 |
| 52 | 0.083 | 0.4519 | 0.1507 |

[a]XTT assay following 72 h inhibition. CCRF-CEM is a human T-cell acute lymphoblastic leukemia cell line. The CCRF-CEM/VBL and CCRF-CEM/Taxol cell lines all overexpress P-glycoprotein and display a multidrug resistance phenotype to MDR-associated oncolytics.

In summary, delineated above is a powerful stereoselective total synthesis of 28 (Epo 3) and, following site-selective diimide reduction, dEpoB (1) itself. The described herein strategy was then straightforwardly applied to the preparation of the corresponding trifluoro analogs 2 and 29 (Epo 4). Furthermore, epoxidation of 28 provided 49 and 50, which upon site-selective diimide reduction gave Epothilone B (51) and 52. The data reported above point to the emergence of a most promising new family of anticancer drugs appropiate for further evaluation en route to then possible advancement to a human clinical setting. Furthermore the new synthesis strategy comprises a significant practical improvement in the total synthesis of dEpoB and Epothilone B.

Experimentals

General Methods: Reagents obtained from commercial suppliers were used without further purification unless otherwise noted. The following solvents were obtained from a dry solvent system (passed through a prepacked column of alumina) and used without further drying: tetrahydrofuran, methylene chloride, diethyl ether, benzene, and toluene. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced to $CDCl_3$ (7.27 ppm for $^1$H and 77.0 ppm for $^{13}$C). Infrared spectra (IR) were obtained on a Perkin-Elmer FT-IR model 1600 spectrometer. Optical rotations were obtained on a JASCO model DIP-370 digital polarimeter at 22±2° C. Analytical thin-layer chromatography was performed on E. Merck silica gel 60 F254 plates. Compounds which were not UV active were visualized by dipping the plates in a eerie ammonium molybdate or para-anisaldehyde solution and heating. Silica gel chromatography was performed using the indicated solvent on Davisil® (grade 1740, type 60A, 170-400 mesh) silica gel.

Acronyms and Abbreviations

TES, triethylsilyl; TBS, Dimethyltertbutylsilyl; EDCI, 1-ethyl-3-(3-dimethylaminopropyl)carbodiimide; HF-PY, hydrogen fluoride in pyridine; DMAP, 4-N,N-dimethylaminopyridine; DCM, dichloromethane; DMF, N,N-dimethylformamide; THF, tetrahydrofuran.

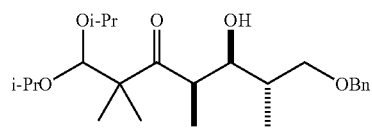

32

Compound 32: To a solution of freshly prepared LDA (11.6 mmol) in THF (25 mmol) was added dropwise a solution of ketone 30 (2.40 g, 10.4 mmol) in THF (6.8 mL) at −78° C. After stirring at −40° C. for 0.5 h, the mixture was cooled to −90° C. A solution of aldehyde 31 (1.38 g, 7.72 mmol) in THF (6.8 mL) was added dropwise. After stirring at −90° C. for 35 min, the reaction was quenched with sat. aq. $NH_4Cl$ (15 mL) and extracted with EtOAc (50 mL×3). The combined organic extracts were dried over $Na_2SO_4$ and concentrated. Purification by flash column chromatography ($SiO_2$, hexane/EtOAc=15:1 to 12:1) gave 32 (2.09 g, 66%) and isomer 33 (0.39 g, 12%) both as yellow oils. 32: $[α]_D^{25}$ 13.1 (c 1.22, $CHCl_3$); IR (film) ν 3494, 2972, 2932, 1708, 1454, 1380, 1329, 1120, 1038, 998, 734 $cm^{-1}$; $^1$H NMR (400 MHz, $CDCl_3$) δ 0.98 (3H, d, J=6.9 Hz), 1.06 (3H, d, J=6.9 Hz), 1.10 (3H, d, J=6.1 Hz), 1.14 (3H, d, J=6.9 Hz), 1.15 (3H, s), 1.17 (3H, d, J=6.2 Hz), 1.18 (3H, s), 1.20 (3H, d, J=6.2 Hz), 1.81-1.92 (1H, m), 3.33 (1H, qd, J=7.0, 2.2. Hz), 3.51 (1H, dd, J=8.9, 6.3 Hz), 3.64 (1H, d, J=1.8 Hz), 3.66-3.71 (2H, m), 3.78-3.86 (2H, m), 4.51 (1H, d, J=12.0 Hz), 4.54 (1H, d, J=12.0 Hz), 4.58 (1H, s), 7.25-7.35 (5H, m); $^{13}$C NMR (100 MHz, $CDCl_3$) δ 10.0, 14.3, 20.5, 21.3, 21.9, 22.5, 23.5, 23.6, 36.4, 42.1, 54.1, 69.8, 71.2, 72.8, 73.3, 73.4, 103.8, 127.6, 127.7 (2C), 128.5 (2C), 138.9, 221.6; LRMS (ESI) calcd for $C_{24}H_{40}O_5Na$ [M+Na$^+$] 431.3, found 431.4; HRMS (ESI) calcd. for $C_{24}H_{40}O_5Na$ [M+Na$^+$] 431.2773, found 431.2761.

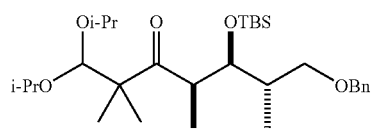

32a

Compound 32a (not shown): To a cooled (−40° C.) solution of alcohol 32 (1.01 g, 2.47 mmol) and 2,6-lutidine (691 μL, 5.93 mmol) was added TBSOTf (681 μL, 3.00 mmol), and the mixture was warmed to −20° C. over 3.5 h. The reaction was quenched with sat. aq. $NaHCO_3$ (10 mL). After extraction with hexane (50 mL×3), the combined organic extracts were dried over $Na_2SO_4$ and concentrated. Purification by flash column chromatography ($SiO_2$, hexane/EtOAc=50:1) gave 32a (1.25 g, 2.39 mmol, 97%) as a colorless oil; $[α]_D^{25}$ −19.7 (c 0.58, $CHCl_3$); IR (film) ν 2966, 2931, 1696, 1455, 1378, 1320, 1255, 1091, 1044, 991, 873, 838, 773 $cm^{-1}$; $^1$H NMR (400 MHz, $CDCl_3$) δ 0.08 (6H, s), 0.89 (9H, s), 0.99 (3H, d, J=7.0 Hz), 1.04 (3H, d, J=7.0 Hz), 1.07 (3H, d, J=7.0 Hz), 1.07 (3H, s), 1.14 (3H, d, J=6.1 Hz), 1.17 (3H, s), 1.17 (3H, d, J=6.0 Hz), 1.20 (3H, d, J=6.2 Hz), 1.76-1.85 (1H, m), 3.21 (1H, dd, J=9.2, 7.3 Hz), 3.32 (1H, quint, J=7.4 Hz), 3.62 (1H, dd, J=9.2, 5.7 Hz), 3.78-3.85 (2H, m), 3.87 (1H, dd, J=7.7, 2.0 Hz), 4.46 (1H, d, J=12.1 Hz), 4.50 (1H, d, J=12.1 Hz), 4.73 (1H, s), 7.24-7.37 (5H, m); $^{13}$C NMR (100 MHz, $CDCl_3$) δ −3.6, −3.3, 15.6, 16.8, 18.7, 18.8, 21.8, 22.1, 22.5, 23.5, 23.7, 26.4 (3C), 39.0, 46.2, 54.0, 69.7, 70.9, 72.1, 73.4, 76.7, 103.1, 127.6, 127.8 (2C), 128.5 (2C), 139.0, 218.9; LRMS (ESI) calcd for $C_{30}H_{54}O_5SiNa$ [M+Na$^+$] 545.4, found 545.4; HRMS (ESI) calcd. for $C_{30}H_{54}O_5SiNa$ [M+Na$^+$] 545.3638, found 545.3643.

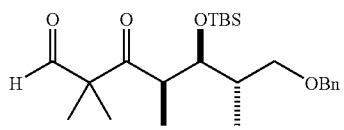

34

Compound 34: The mixture of 32a (3.03 g, 5.79 mmol) and p-TsOH.H$_2$O (286 mg) in aqueous THF (64 mL, THF/H$_2$O=4:1) was heated under reflux for 6.5 h. The reaction mixture was cooled to rt and poured into sat. aq. NaHCO$_3$ (25 mL). After extraction with EtOAc (100 mL+50 mL×2), the combined organic layers were washed with brine, dried over Na$_2$SO$_4$ and concentrated. Purification by flash column chromatography (SiO$_2$, hexane/EtOAc=50:1 to 30:1) gave 34 (2.37 g, 5.64 mmol, 98%) as a colorless oil: $[\alpha]_D^{25}$ −25.8 (c 0.515, CHCl$_3$); IR (film) ν 2955, 2931, 1731, 1696, 1455, 1360, 1255, 1091, 1026, 873, 826, 767 cm$^{-1}$; $^1$H NMR (400 MHz, CDCl$_3$) δ 0.06 (3H, s), 0.07 (3H, s), 0.90 (9H, s), 0.95 (3H, d, J=7.1 Hz), 1.03 (3H, d, J=7.0 Hz), 1.28 (3H, s), 1.33 (3H, s), 1.73-1.82 (1H, m), 3.16 (1H, dd, J=9.2, 6.1 Hz), 3.28 (1H, quint, J=7.3 Hz), 3.55 (1H, dd, J=9.2, 6.7 Hz), 3.91 (1H, dd, J=7.8, 2.1 Hz), 4.46 (2H, s), 7.27-7.36 (5H, m), 9.58 (1H, s); $^{13}$C NMR (100 MHz, CDCl$_3$) δ −3.6, −3.5, 15.7, 16.3, 18.6, 19.8, 20.1, 26.3 (3C), 39.1, 47.0, 61.1, 71.9, 73.4, 75.8, 127.7, 128.0 (2C), 128.5 (2C), 138.6, 201.3, 213.3; LRMS (ESI) calcd for $C_{24}H_{40}O_4SiNa$ [M+Na$^+$] 443.3, found 443.2; HRMS (ESI) calcd. for $C_{24}H_{40}O_4SiNa$ [M+Na$^+$] 443.2594, found 443.2576.

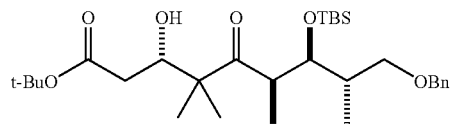

35

Compound 35: To a solution of freshly prepared LDA (18 mL of a 0.5 M solution in Et$_2$O, 9.0 mmol) in Et$_2$O (20 mL) was added t-butyl acetate (1.16 mL, 8.61 mmol) at −78° C. After stirring for 50 min, CpTiCl(OR)$_2$ (100 mL of a 0.1 M solution in Et$_2$O, 10.0 mmol) was added dropwise over 65 min via syringe pump. After stirring for 20 min, the reaction mixture was warmed to −30° C., stirred for 50 min, and re-cooled to −78° C. A solution of 34 (2.42 g, 5.75 mmol) in Et$_2$O (9 mL) was added dropwise over 10 min, and the resulting mixture was stirred at −78° C. After stirring for 2 h, the reaction was quenched with aqueous THF (5 M H$_2$O, 37 mL) and stirred at rt for 2 h. After addition of water (40 mL), the mixture was stirred for further 1 h. The precipitate formed was filtered off by Celite (Et$_2$O rinse), and the filtrate was washed with water (40 mL). The aqueous layer was extracted with Et$_2$O (100 mL×2) and the combined organic layers were washed with brine (40 mL), dried over Na$_2$SO$_4$ and concentrated. Purification by flash column chromatography (SiO$_2$, hexane/EtOAc=10:1) gave 35 (2.65 g, 4.94 mmol, 86%) as a pale yellow oil; $[\alpha]_D^{25}$ −20.3 (c 1.0, CHCl$_3$); IR (film) ν 3523, 2957, 2930, 2856, 1732, 1700, 1472, 1368, 1252, 1152, 1091, 1042, 986, 834, 774 cm$^{-1}$; $^1$H NMR (400 MHz, CDCl$_3$) δ 0.07 (3H, s), 0.07 (3H, s), 0.90 (9H, s), 0.99 (3H, d, J=7.0 Hz), 1.07 (3H, d, J=7.0 Hz), 1.10 (3H, s), 1.14 (3H, s), 1.47 (9H, s), 1.77-1.83 (1H, m), 2.26 (1H, dd, J=16.0, 10.0 Hz), 2.34 (1H, dd, J=15.9, 2.7 Hz), 3.23 (1H, dd, J=9.2, 7.1 Hz), 3.35 (1H, d, J=2.7 Hz, —OH), 3.36 (1H, quint, J=7.0 Hz), 3.61 (1H, dd, J=9.2, 5.9 Hz), 3.88 (1H, dd, J=7.6, 2.0 Hz), 4.17 (1H, dt, J=10.0, 2.7 Hz), 4.48 (2H, s), 7.27-7.36 (5H, m); $^{13}$C NMR (100 MHz, CDCl$_3$) δ −3.5, −3.4, 16.3, 16.7, 18.7, 20.1, 21.6, 26.4 (3C), 28.3 (3C), 38.0, 39.1, 45.8, 51.8, 72.2, 72.9, 73.5, 76.7, 81.4, 127.7, 128.0 (2C), 128.5 (2C), 138.8, 172.7, 219.6; LRMS (ESI) calcd for $C_{30}H_{52}O_6SiNa$ [M+Na$^+$] 559.3, found 559.4; HRMS (ESI) calcd. for $C_{30}H_{52}O_6SiNa$ [M+Na$^+$] 559.3431, found 559.3412.

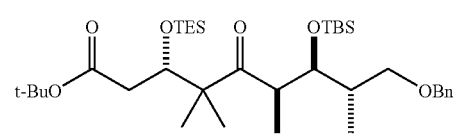

35a

Compound 35a (Not Shown): To a mixture of alcohol 35 (10.2 g, 18.9 mmol) and imidazole (2.70 g, 39.7 mmol) in DMF (25 mL) was added TESCl (3.3 mL, 19.8 mmol) at 0° C., and the mixture was stirred at rt for 2 h. The reaction was quenched with sat. aq. NaHCO$_3$ (50 mL). After extraction with hexane (500 mL+120 mL×2), the combined organic extracts were washed successively water (30 mL×2) and brine (30 mL), dried over Na$_2$SO$_4$ and concentrated. Purification by flash column chromatography (SiO$_2$, hexane/EtOAc=40:1) gave 35a (12.1 g, 18.5 mmol, 98%) as a colorless oil: $[\alpha]_D^{25}$ −38.0 (c 0.46, CHCl$_3$); IR (film) ν 2955, 2877, 1733, 1697, 1456, 1367, 1298, 1251, 1155, 1099, 988, 835, 742 cm$^{-1}$; $^1$H NMR (400 MHz, CDCl$_3$) δ 0.05 (6H, s), 0.57-0.68 (6H, m), 0.89 (9H, s), 0.95 (9H, t, J=7.9 Hz), 0.99 (3H, d, J=7.0 Hz), 1.02 (3H, d, J=6.8 Hz), 1.04 (3H, s), 1.18 (3H, s), 1.45 (9H, s), 1.70-1.79 (1H, m), 2.16 (1H, dd, J=17.0, 7.0 Hz), 2.40 (1H, dd, J=17.0, 3.1 Hz), 3.22 (1H, dd, J=9.1, 7.5 Hz), 3.31 (1H, quint, J=6.9 Hz), 3.61 (1H, dd, J=9.1, 5.4 Hz), 3.83 (1H, dd, J=7.3, 2.3 Hz), 4.30 (1H, dd, J=6.9, 3.1 Hz), 4.48 (2H, s), 7.27-7.36 (5H, m); $^{13}$C NMR (100 MHz, CDCl$_3$) δ −3.5, −3.4, 5.3 (3C), 7.3 (3C), 15.3, 16.9, 18.7, 20.1, 23.4, 26.4 (3C), 28.3 (3C), 39.1, 41.1, 46.2, 53.4, 72.2, 73.4, 74.3, 76.7, 80.6, 127.6, 127.9 (2C), 128.5 (2C), 138.9, 171.5, 218.4; LRMS (ESI) calcd for $C_{36}H_{66}O_6Si_2Na$ [M+Na$^+$] 673.4, found 673.5; HRMS (ESI) calcd. for $C_{36}H_{66}O_6Si_2Na$ [M+Na$^+$] 673.4296, found 673.4306.

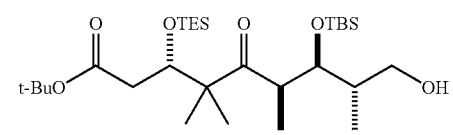

35b

Compound 35b (Not Shown): To a stirred solution of 35a (4.37 g, 6.72 mmol) in THF (67 mL) was added Pd/C (purchased from Acros, 10% wt, 437 mg) and the mixture was stirred under an atmosphere of H$_2$. After stirring for 2.2 h, the mixture was filtered through a pad of Celite, which was rinsed with THF (120 mL). The filtrate was concentrated and purified by flash column chromatography (SiO$_2$, hexane/EtOAc=30:1 to 10:1) to give 35b (3.53 g, 6.28 mmol, 94%) as a colorless oil; $[\alpha]_D^{25}$ −16.1 (c 0.62, CHCl$_3$); IR (film) ν 3543, 2956, 1732, 1696, 1472, 1368, 1299, 1252, 1155, 1100, 988, 837, 775, 742 cm$^{-1}$; $^1$H NMR (400 MHz, CDCl$_3$) δ 0.10

(3H, s), 0.12 (3H, s), 0.60-0.68 (6H, m), 0.93 (9H, s), 0.96 (9H, t, J=8.0 Hz), 0.99 (3H, d, J=7.1 Hz), 1.10 (3H, d, J=6.9 Hz), 1.14 (3H, s), 1.20 (3H, s), 1.45 (9H, s), 1.46-1.55 (1H, m), 2.21 (1H, dd, J=17.2, 7.1 Hz), 2.39 (1H, dd, J=17.2, 2.8 Hz), 2.54 (1H, t, J=5.8 Hz, —OH), 3.30 (1H, quint, J=6.9 Hz), 3.58 (1H, dt, J=11.5, 5.5 Hz), 3.66 (1H, dt, J=11.3, 5.4 Hz), 3.92 (1H, dd, J=8.0, 2.1 Hz), 4.32 (1H, dd, J=7.1, 2.9 Hz); $^{13}$C NMR (100 MHz, CDCl$_3$) δ −3.6, −3.5, 5.3 (3C), 7.2 (3C), 16.0, 16.1, 18.6, 20.0, 23.4, 26.4 (3C), 28.3 (3C), 40.0, 40.9, 46.9, 53.7, 64.8, 73.3, 78.1, 80.9, 171.7, 218.5; LRMS (ESI) calcd for C$_{29}$H$_{60}$O$_6$Si$_2$Na [M+Na$^+$] 583.4, found 583.5; HRMS (ESI) calcd. for C$_{29}$H$_{60}$O$_6$Si$_2$Na [M+Na$^+$] 583.3826, found 583.3851.

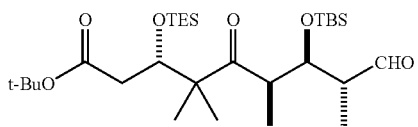

35c

Compound 35c (Not shown): To a stirred mixture of alcohol 35b (3.53 g, 6.28 mmol) and powdered MS4A (freshly activated, 2.50 g) in CH$_2$Cl$_2$ (32 mL) were added NMO (1.17 g, 10.0 mmol) followed by TPAP (132 mg, 0.377 mmol). After stirring at rt for 35 min, the mixture was filtered through a silica gel column (hexane/Et$_2$O=8:1) to give 35c (3.34 g, 5.98 mmol, 95%) as a colorless oil; [α]$_D^{25}$ −69.6 (c 0.25, CHCl$_3$); IR (film) ν 2955, 2878, 1732, 1696, 1472, 1368, 1253, 1155, 1097, 989, 837 cm$^{-1}$; $^1$H NMR (400 MHz, CDCl$_3$) δ 0.09 (3H, s), 0.10 (3H, s), 0.59-0.68 (6H, m), 0.89 (9H, s), 0.95 (9H, t, J=8.0 Hz), 1.08 (3H, s), 1.11 (3H, d, J=6.9 Hz), 1.14 (3H, d, J=7.1 Hz), 1.24 (3H, s), 1.45 (9H, s), 2.19 (1H, dd, J=17.0, 6.7 Hz), 2.33 (1H, qt, J=7.1, 2.2 Hz), 2.41 (1H, dd, J=17.0, 3.3 Hz), 3.28 (1H, quint, J=7.5 Hz), 4.07 (1H, dd, J=7.9, 2.2 Hz), 4.32 (1H, dd, J=6.7, 3.2 Hz), 9.74 (1H, d, J=2.0 Hz); $^{13}$C NMR (100 MHz, CDCl$_3$) δ −3.8, −3.5, 5.3 (3C), 7.2 (3C), 12.6, 15.6, 18.5, 20.5, 23.3, 26.2 (3C), 28.3 (3C), 41.1, 46.9, 51.1, 53.5, 74.0, 76.5, 80.7, 171.1, 204.3, 218.0; LRMS (ESI) calcd for C$_{29}$H$_{58}$O$_6$Si$_2$Na [M+Na$^+$] 581.3, found 581.3; HRMS (ESI) calcd. for C$_{29}$H$_{58}$O$_6$Si$_2$Na [M+Na$^+$] 581.3670, found 581.3691.

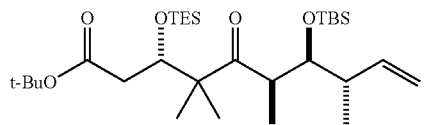

36

Compound 36: MePPh$_3$I (2.56 g, 7.18 mmol) in THF (40.0 mL) was treated with t-BuOK (6.57 mL of a 1.0 M solution in THF, 6.57 mmol) at 0° C. After stirring at 0° C. for 20 min, the resulting suspension was cooled to −78° C. and a solution of aldehyde 35c (3.34 g, 5.98 mmol) in THF (14 mL) was added. After stirring at −78° C. for 15 min, the mixture was stirred at 0° C. for 15 min and at rt for 15 min. The reaction was quenched with sat. aq. NH$_4$Cl (20 mL) and extracted with Et$_2$O (120 mL+50 mL×2). The combined organic extracts were washed with brine (20 mL), dried over Na$_2$SO$_4$, and concentrated. The residue was purified by flash column chromatography (SiO$_2$~80 g, hexane/Et$_2$O=40:1) to give 36 (125.3 mg, 0.225 mmol, 78%) as a colorless oil; [α]$_D^{25}$ −33.6 (c 0.250, CHCl$_3$); IR (film) ν 2956, 2878, 1733, 1696, 1472, 1367, 1299, 1253, 1156, 1100, 988, 837, 774 cm$^{-1}$; $^1$H NMR (400 MHz, CDCl$_3$) δ 0.08 (3H, s), 0.08 (3H, s), 0.60-0.68 (6H, m), 0.93 (9H, s), 0.96 (9H, t, J=8.0 Hz), 1.04 (6H, d, J=7.0 Hz), 1.09 (3H, s), 1.20 (3H, s), 1.45 (9H, s), 2.08-2.15 (1H, m), 2.29 (1H, dd, J=17.0, 7.0 Hz), 2.41 (1H, dd, J=17.0, 3.1 Hz), 3.08 (1H, quint, J=7.0 Hz), 3.84 (1H, dd, J=7.0, 2.1 Hz), 4.32 (1H, dd, J=7.0, 3.1 Hz), 5.02 (1H, dd, J=17.9, 1.0 Hz), 5.06 (1H, dd, J=10.5, 1.0 Hz), 5.93 (1H, ddd, J=17.9, 10.5, 7.7 Hz); $^{13}$C NMR (100 MHz, CDCl$_3$) δ −3.6, −3.3, 5.4 (3C), 7.2 (3C), 15.2, 18.7, 19.0, 20.2, 23.6, 26.4 (3C), 28.3 (3C), 41.1, 43.8, 46.4, 53.5, 73.9, 76.6, 80.6, 115.5, 140.2, 171.5, 218.5; LRMS (ESI) calcd for C$_{30}$H$_{60}$O$_5$Si$_2$Na [M+Na$^+$] 579.4, found 579.4; HRMS (ESI) calcd. for C$_{30}$H$_{60}$O$_5$Si$_2$Na [M+Na$^+$] 579.3877, found 579.3896.

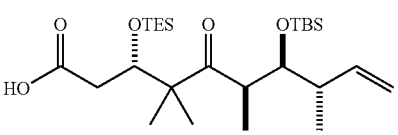

25

Compound 25: To a solution of t-butyl ester 36 (4.87 g, 8.74 mmol) and 2,6-lutidine (freshly distilled, 4.1 mL, 35.0 mmol) in CH$_2$Cl$_2$ (58 mL) was added TESOTf (4.0 mL, 17.5 mmol) at 0° C. After stirring at 0° C. for 25 min, the mixture was stirred at rt for 3.2 h. The mixture was diluted with Et$_2$O (600 mL), washed with successively 5% aqueous KHSO$_4$ (60 mL×2) and brine (60 mL), dried over Na$_2$SO$_4$, and concentrated. The residue was dried under high vacuum for 1.5 h to give crude acid 25 (6.30 g, contaminated with TESOH). The crude product (6.30 g) was dissolved in aqueous THF (87.5 mL, THF/H$_2$O=6:1) and treated with sat. aq. NaHCO$_3$ (12.5 mL). After stirring at rt for 20 min, the resulting suspension was diluted with Et$_2$O (500 mL) and acidified with aqueous 5% KHSO$_4$ (55 mL). After the layers were separated, the aqueous layer was extracted with Et$_2$O (100 mL×2) and the combined organic layers were washed with brine (50 mL×2), dried over Na$_2$SO$_4$ and concentrated. The residue was dried under high vacuum overnight to give crude acid (5.60 g, contaminated with TESOH) as a colorless oil, which was used for next reaction without further purification. Purified for characterization by flash column chromatography over silica gel eluting with hexane/EtOAc=4/1.

[α]$_D^{25}$ −30.7 (c 0.985, CHCl$_3$); IR (film) ν 2956, 2936, 2879, 1712, 1472, 1417, 1303, 1253, 1107, 1046, 1003, 988, 872, 837, 775, 741 cm$^{-1}$; $^1$H NMR (400 MHz, CDCl$_3$) δ 0.08 (3H, s), 0.09 (3H, s), 0.59-0.67 (6H, m), 0.93 (9H, s), 0.96 (9H, t, J=8.1 Hz), 1.05 (3H, d, J=7.0 Hz), 1.05 (3H, d, J=7.0 Hz), 1.20 (3H, s), 1.21 (3H, s), 2.06-2.13 (1H, m), 2.34 (1H, dd, J=16.4, 7.4 Hz), 2.50 (1H, dd, J=16.4, 3.0 Hz), 3.06 (1H, quint, J=7.3 Hz), 3.87 (1H, dd, J=7.5, 1.8 Hz), 4.40 (1H, dd, J=7.3, 2.9 Hz), 5.01 (1H, dd, J=18.0, 0.9 Hz), 5.07 (1H, dd, J=10.4, 1.2 Hz), 5.93 (1H, ddd, J=18.0, 10.4, 7.8 Hz); $^{13}$C NMR (100 MHz, CDCl$_3$) δ −3.6, −3.3, 5.3 (3C), 7.1 (3C), 15.6, 18.7, 19.1, 19.2, 24.1, 26.4 (3C), 39.8, 43.6, 46.4, 53.5, 73.7, 76.6, 115.6, 140.0, 177.9, 218.7; LRMS (ESI) calcd for C$_{26}$H$_{52}$O$_5$Si$_2$Na [M+Na$^+$] 523.3, found 522.9; HRMS (ESI) calcd. for C$_{26}$H$_{52}$O$_5$Si$_2$Na [M+Na$^+$] 523.3241, found 523.3235.

45

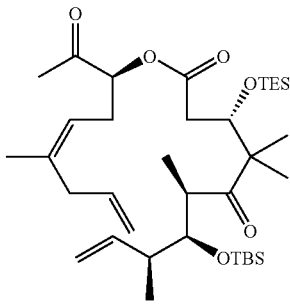

Compound 45: The 3-O-TES-6-O-TBS protected acid 25 was dried through azeotropic distillation from benzene. Freshly dried alcohol 43 (200 mg, 1.19 mmol) is dissolved in DCM (10 mL) and cooled to 0° C., at which point solid DMAP (167 mg, 1.37 mmol) and solid EDCI (261 mg, 1.37 mmol) are added. After stirring the reaction mixture at 0° C. for 15 min, a solution of acid 25 (425 mg, 0.85 mmol) in DCM (2 mL) is added dropwise. The cooling bath is removed and stirring continued for another 2 hours. The crude reaction mixture is diluted with DCM (10 mL) and purified by silica gel chromatography employing 10% EtOAC/Hexanes as the eluent to give ester 45 (380 mg, 81% yield, two steps, starting from 36) as a clear oil: $[\alpha]_D$ −15.1 (c 1.2, CDCl$_3$); IR (neat) 2955, 2932, 2877, 1743, 1732, 1694, 1474, 1461, 1417, 1380, 1360, 1295, 1252, 1169, 1094, 1043, 988.3, 912.9, 871.4, 836.5, 774.8, 741.6 cm$^{-1}$; $^1$H NMR (500 MHz, CDCl$_3$) 0.08 (3H, s), 0.08 (3H, s), 0.60-0.68 (6H, m), 0.93 (9H, s), 0.95 (9H, t, J=8.0 Hz), 1.04 (3H, d, J=6.9 Hz), 1.05 (3H, d, J=6.9 Hz), 1.10 (3H, s), 1.25 (3H, s), 1.69 (3H, s), 2.08-2.15 (2H, m), 2.16 (3H, s), 2.38 (1H, dd, J=17.0, 7.0 Hz), 2.48 (2H, t, J=6.5 Hz), 2.57 (1H, dd, J=17.0, 2.7 Hz), 2.71-2.76 (2H, m), 3.07 (1H, quint, J=7.0 Hz), 3.83 (1H, d, J=7.2 Hz), 4.36 (1H, dd, J=7.0, 2.7 Hz), 4.97-5.07 (4H, m), 5.19 (1H, t, J=7.0 Hz), 5.73 (1H, td, J=15.4, 5.9 Hz), 5.92 (1H, dd, J=15.7, 8.0 Hz); $^{13}$C NMR (500 MHz, CDCl$_3$) δ 218.4, 205.4, 172.1, 140.1, 137.4, 135.4, 119.1, 115.8, 115.6, 78.7, 76.5, 73.9, 53.3, 46.3, 43.7, 39.6, 36.6, 29.2, 26.7, 26.4, 23.8, 23.7, 19.9, 18.9, 18.7, 15.4, 7.06, 5.30, −3.29, −3.62; LRMS (ESI) calcd for C$_{36}$H$_{66}$O$_6$Si$_2$Na [M+Na$^+$] 673.4, found 673.5.

47

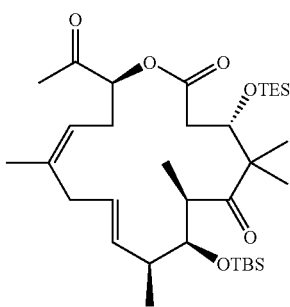

Compound 47: To a solution of compound 45 (20 mg, 0.031 mmol) in dry toluene (60 mL) at reflux was added in one portion a solution of tricyclohexylphosphine[1,3-bis(2,4,6-trimethylphenyl)-4,5-dihydroimidazol-2-ylidene][benzylidene]ruthenium (IV) dichloride (5.2 mg, 0.0061 mmol) in dry toulene (2 mL) and the mixture was heated for 10 minutes. The reaction mixture was cooled immediately in an ice bath and stripped onto silica and purified using silica gel chromatography employing 4-10% EtOAc/pentane gradient as the eluent to furnish compound 47 (15 mg, 78% yield) as an oil: $[\alpha]$ −28.6 (c 1.2, CHCl$_3$); IR (neat) 2955, 2933, 2878, 1745, 1731, 1695, 1471, 1462, 1380, 1361, 1251, 1159, 1104, 1080, 1019, 985.0, 876.1, 835.5, 774.7, 743.1, 670.1 cm$^{-1}$; $^1$H NMR (500 MHz, CDCl$_3$) 0.07 (3H, s), 0.10 (3H, s), 0.59-0.68 (6H, m), 0.91 (9H, t, J=8.0 Hz), 0.93 (9H, s), 1.04 (3H, d, J=7.0 Hz), 1.10 (3H, s), 1.11 (3H, d, J=7.0 Hz), 1.17 (3H, s), 1.71 (3H, s), 2.21 (3H, s), 2.27-2.32 (1H), 2.38 (1H, dd, J=14.6, 6.8 Hz), 2.51-2.61 (2H, m), 2.57 (1H, dd, J=15.5, 3.3 Hz), 2.93-3.1 (3H, m), 3.94 (1H, d, J=8.5 Hz), 4.28 (1H, dd, J=8.6, 3.0 Hz), 5.04 (1H, dd, J=8.7, 2.4), 5.16 (1H, t, J=7.5), 5.73 (1H, 'dd, J=12.8, 9.94, 6.9 Hz), 5.92 (1H, ddd, J=18.0, 10.3, 7.8 Hz); $^{13}$C NMR (125 MHz, CDCl$_3$) δ 215.9, 204.8, 171.3, 140.0, 132.7, 129.2, 118.6, 79.1, 78.2, 75.4, 54.0, 48.2, 41.7, 40.3, 35.0, 29.2, 26.6, 26.5, 23.5, 22.8, 20.6, 18.8, 17.5, 14.3, 7.19, 5.53, −3.36; LRMS (ESI) calcd. for C$_{34}$H$_{62}$O$_6$Si$_2$ 645.4, found 645.4 (M+Na$^+$).

39a

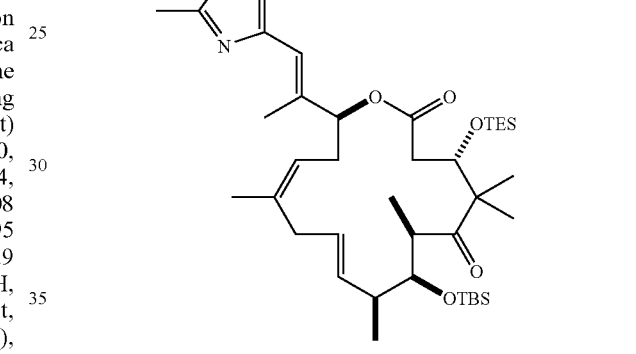

Compound 39a: To a solution of Wittig reagent (19.1 mg, 54.7 μmol) in THF (0.4 mL) was added KHMDS (109 μL of a 0.5 M solution in toluene, 54.7 μmol) at 0° C. The mixture was stirred at 0° C. for 0.5 h and then cooled to −78° C. To the mixture was added dropwise a solution of ketone 47 (5.7 mg, 9.12 μmol) in THF (0.3 mL), and the resulting mixture was allowed to warm to −20° C. over 1.5 h. The reaction was quenched with sat. aq. NH$_4$Cl (2 mL) and extracted with EtOAc (7 mL×3). The combined organic layers were dried over Na$_2$SO$_4$ and concentrated. The residue was purified by flash column chromatography (SiO$_2$, hexane/Et$_2$O=10:1) to give 5.6 mg of an inseparable mixture of E/Z olefins (E/Z=9:1). The mixture was purified by preparative TLC (hexane/Et$_2$O=4:1) to give pure 39a (5.0 mg, 6.96 μmol, 76%) as a colorless oil; $[\alpha]_D^{25}$ −41.5 (c 0.715, CHCl$_3$); IR (film) v 2955, 2884, 1737, 1690, 1467, 1378, 1249, 1179, 1102, 1014, 979, 879, 826, 773 cm$^{-1}$; $^1$H NMR (400 MHz, CDCl$_3$) δ 0.08 (3H, s), 0.12 (3H, s), 0.57 (6H, q, J=7.8 Hz), 0.89 (9H, t, J=8.0 Hz), 0.93 (9H, s), 1.04 (3H, s). 1.06 (3H, d, J=7.1 Hz), 1.12 (3H, s), 1.17 (3H, d, J=7.1 Hz), 1.68 (3H, s), 2.15 (3H, d, J=0.8 Hz), 2.14-2.27 (2H, m), 2.45 (1H, dd, J=14.0, 4.8 Hz), 2.50 (1H, dd, J=14.9, 3.2 Hz), 2.64-2.74 (2H, m), 2.72 (3H, s), 3.02 (1H, quint, J=7.0 Hz), 3.10 (1H, dd, J=14.4, 7.3 Hz), 3.96 (1H, d, J=8.7 Hz), 4.43 (1H, dd, J=8.3, 2.9 Hz), 5.22 (1H, dd, J=9.8, 5.7 Hz), 5.33-5.42 (2H, m), 5.69 (1H, dd, J=15.8, 8.2 Hz), 6.57 (1H, s), 6.96 (1H, s); $^{13}$C NMR (100 MHz, CDCl$_3$) δ −3.3, −3.2, 5.6 (3C), 7.1 (3C), 15.0, 17.2, 18.8, 19.4, 21.4, 21.7, 23.8, 24.3, 26.5 (3C), 33.2, 35.6, 41.3, 41.8, 48.2, 54.0, 74.4, 77.4, 79.3, 116.4, 120.5, 121.0, 129.3, 132.1, 137.8, 138.0, 152.7, 164.8, 170.7, 216.8; LRMS (ESI) calcd for C$_{39}$H$_{68}$NO$_5$SSi$_2$ [M+H$^+$] 718.4, found 718.3; HRMS (ESI) calcd. for C$_{39}$H$_{68}$NO$_5$SSi$_2$ [M+H$^+$] 718.4357, found 718.4355.

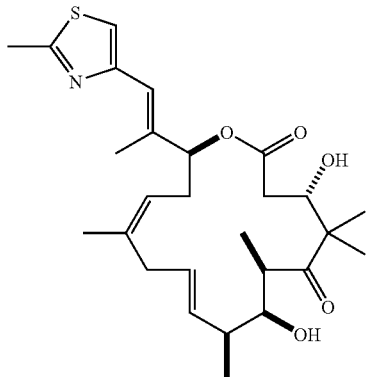

28

Compound 28 (Epo 3): To a solution of 39a (298.8 mg, 0.416 mmol) in THF (6.5 mL) was added HF.pyridine (3.2 mL) at 0° C., and the mixture was stirred at rt for 3 h. The reaction was quenched by dropwise addition of TMSOMe (30 mL) at 0° C. After concentrating and drying under high vacuum, the residue was purified by flash column chromatography (SiO$_2$, hexane/EtOAc=1:1) to give 28 (196.6 mg, 0.402 mmol, 97%) as a white solid; [α]$_D^{25}$ −96.6 (c 0.235, CHCl$_3$); IR (film) ν 3502, 2970, 2927, 1733, 1685, 1506, 1456, 1375, 1251, 1152, 1040, 977 cm$^{-1}$; $^1$H NMR (400 MHz, CDCl$_3$) δ 1.06 (3H, s), 1.11 (3H, d, J=7.0 Hz), 1.22 (3H, d, J=6.8 Hz), 1.28 (3H, s), 1.72 (3H, s), 2.10 (3H, s), 2.31-2.40 (2H, m), 2.43 (1H, dd, J=16.0, 3.7 Hz), 2.49 (1H, dd, J=16.0, 9.2 Hz), 2.55-2.68 (2H, m), 2.71 (3H, s), 2.98 (1H, dd, J=14.4, 6.4 Hz), 3.16 (1H, quint, J=6.2 Hz), 3.76 (1H, dd, J=5.9, 3.2 Hz), 4.30 (1H, dd, J=9.2, 3.7 Hz), 5.18 (1H, brt, J=7.3 Hz), 5.32 (1H, dd, J=8.4, 2.5 Hz), 5.63 (1H, dd, J=15.7, 6.4 Hz), 5.60 (1H, ddd, J=15.7, 6.9, 5.1 Hz), 6.60 (1H, s), 6.98 (1H, s); $^{13}$C NMR (100 MHz, CDCl$_3$) δ 15.1, 16.0, 17.7, 19.2, 19.5, 22.5, 23.6, 32.0, 35.0, 39.6, 40.3, 44.8, 53.3, 71.8, 75.6, 78.3, 116.1, 119.6, 120.5, 129.9, 131.3, 137.5, 138.2, 152.2, 165.0, 170.7, 218.8; LRMS (ESI) calcd for C$_{27}$H$_{40}$NO$_5$S [M+H$^+$] 490.3, found 490.2.

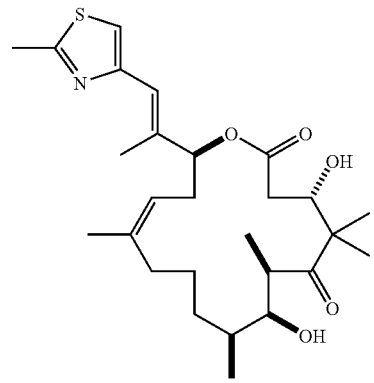

1 dEpoB (1, Epo 1): To a solution of 28 (1.2 mg, 2.5 μmol) and TrisNHNH$_2$ (29.3 mg, 98 μmol) in ClCH$_2$CH$_2$Cl (0.7 mL) at 50° C. was added Et$_3$N (13.7 μL, 98 μmol). The reaction was monitored by HPTLC (hexane/EtOAc/CH$_2$Cl$_2$=1/1/2). After stirring for 7 h, the mixture was cooled to rt, diluted with EtOAc and filtered through a pad of silica gel, which was rinsed with EtOAc. After concentrating, the residue was purified by preparative TLC (hexane/EtOAc/CH$_2$Cl$_2$=1/1/2) to give 1 (1.1 mg, 2.2 μmol, 91%) as a white solid. The spectral data of 1 was identical to those reported of dEpoB.

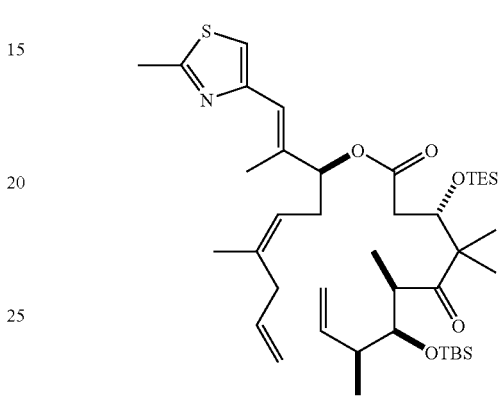

27

Compound 27: Acid 25 and alcohol 24 were azeotroped with dry benzene (5 mL×2) and dried under high vacuum before reaction. To a solution of alcohol 24 (639 mg, 2.63 mmol) in CH$_2$Cl$_2$ (13 mL) were added EDCI (576 mg, 3.09 mmol) and DMAP (366 mg, 3.09 mmol) at 0° C. To the mixture was added a solution of acid 25 (1.11 g, as 1.88 mmol) in CH$_2$Cl$_2$ (5 mL+2 mL rinse) dropwise over 16 min at 0° C. After stirring at 0° C. for 1.5 h, the mixture was stirred at rt for 3.5 h. After concentrating, the residue was purified by flash column chromatography (SiO$_2$, hexane/EtOAc=30:1 to 20:1) to give 27 (1.20 g, 1.61 mmol, 86% from t-butyl ester) as a colorless oil;

[α]$_D^{24}$ −25.1 (c 1.30, CHCl$_3$); IR (film) ν 2955, 2925, 2872, 1732, 1696, 1461, 1378, 1290, 1243, 1173, 1091, 985, 873, 773 cm$^{-1}$; $^1$H NMR (400 MHz, CDCl$_3$) δ 0.06 (3H, s), 0.06 (3H, s), 0.58-0.66 (6H, m), 0.92 (9H, s), 0.95 (9H, t, J=8.0 Hz), 1.02 (3H, d, J=6.5 Hz), 1.03 (3H, d, J=6.5 Hz), 1.07 (3H, s), 1.21 (3H, s), 1.67 (3H, s), 2.07 (3H, s), 2.05-2.12 (1H, m), 2.30 (1H, dd, J=16.9, 7.5 Hz), 2.39 (1H, dt, J=14.8, 6.7 Hz), 2.49 (1H, dd, J=17.0, 3.0 Hz), 2.50 (1H, dt, J=14.8, 6.7 Hz), 2.70 (3H, s), 2.74-2.30 (2H, m), 3.07 (1H, dd, J=7.0 Hz), 3.83 (1H, dd, J=7.1, 2.0 Hz), 4.35 (1H, dd, J=7.4, 2.8 Hz), 4.98-5.07 (4H, m), 5.16 (1H, brt, J=7.0 Hz), 5.23 (1H, t, J=6.9 Hz), 5.74 (1H, ddt, J=16.7, 10.2, 6.5 Hz), 5.91 (1H, ddd, J=17.8, 10.5, 7.8 Hz), 6.50 (1H, s), 6.95 (1H, s); $^{13}$C NMR (100 MHz, CDCl$_3$) δ −3.7, −3.3, 5.3 (3C), 7.2 (3C), 14.8, 15.2, 18.7, 18.9, 19.4, 20.3, 23.6, 23.7, 26.4 (3C), 31.7, 36.7, 40.1, 43.8, 46.4, 53.3, 74.2, 76.5, 79.6, 115.5, 115.6, 116.5, 120.5, 121.3, 135.8, 136.1, 137.4, 140.2, 152.9, 164.7, 171.5, 218.4; LRMS (ESI) calcd for C$_{41}$H$_{71}$NO$_5$SSi$_2$ [M+Na$^+$] 768.5, found 768.5; HRMS (ESI) calcd. for C$_{41}$H$_{72}$NO$_5$SSi$_2$ [M+H$^+$] 746.4670, found 746.4680.

39a

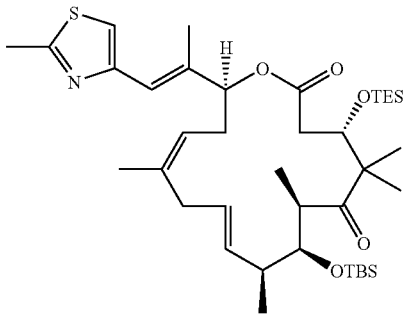

Compound 39a: A solution of 27 (26.9 mg, 36.1 μmol) in toluene (70 mL) was heated to reflux and treated with a solution of Grubbs' catalyst (3.1 mg, 3.61 μmol) in toluene (2 mL). The mixture was stirred for 25 min, cooled to 0° C. and filtered through a pad of silica gel, which was rinsed with hexane/EtOAc=2/1. The combined filtrates were concentrated and purified by flash column chromatography (SiO$_2$, hexane/Et$_2$O=40:1 to 5:1) to give 39a (9.9 mg, 13.8 μmol, 38%) as a colorless oil;

$[\alpha]_D^{25}$ −41.5 (c 0.715, CHCl$_3$); IR (film) ν 2955, 2884, 1737, 1690, 1467, 1378, 1249, 1179, 1102, 1014, 979, 879, 826, 773 cm$^{-1}$; $^1$H NMR (400 MHz, CDCl$_3$) δ 0.08 (3H, s), 0.12 (3H, s), 0.57 (6H, q, J=7.8 Hz), 0.89 (9H, t, J=8.0 Hz), 0.93 (9H, s), 1.04 (3H, s). 1.06 (3H, d, J=7.1 Hz), 1.12 (3H, s), 1.17 (3H, d, J=7.1 Hz), 1.68 (3H, s), 2.15 (3H, d, J=0.8 Hz), 2.14-2.27 (2H, m), 2.45 (1H, dd, J=14.0, 4.8 Hz), 2.50 (1H, dd, J=14.9, 3.2 Hz), 2.64-2.74 (2H, m), 2.72 (3H, s), 3.02 (1H, quint, J=7.0 Hz), 3.10 (1H, dd, J=14.4, 7.3 Hz), 3.96 (1H, d, J=8.7 Hz), 4.43 (1H, dd, J=8.3, 2.9 Hz), 5.22 (1H, dd, J=9.8, 5.7 Hz), 5.33-5.42 (2H, m), 5.69 (1H, dd, J=15.8, 8.2 Hz), 6.57 (1H, s), 6.96 (1H, s); $^{13}$C NMR (100 MHz, CDCl$_3$) δ −3.3, −3.2, 5.6 (3C), 7.1 (3C), 15.0, 17.2, 18.8, 19.4, 21.4, 21.7, 23.8, 24.3, 26.5 (3C), 33.2, 35.6, 41.3, 41.8, 48.2, 54.0, 74.4, 77.4, 79.3, 116.4, 120.5, 121.0, 129.3, 132.1, 137.8, 138.0, 152.7, 164.8, 170.7, 216.8; LRMS (ESI) calcd for C$_{39}$H$_{68}$NO$_5$SSi$_2$ [M+H$^+$] 718.4, found 718.3; HRMS (ESI) calcd. for C$_{39}$H$_{68}$NO$_5$SSi$_2$ [M+H$^+$] 718.4357, found 71.8.4355.

28

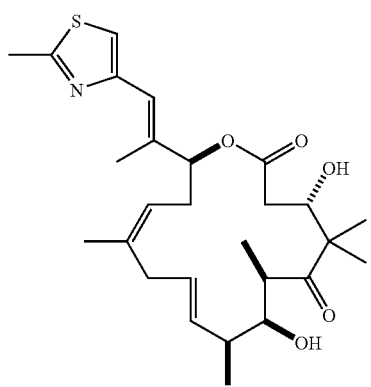

Compound 28: To a solution of 39a (298.8 mg, 0.416 mmol) in THF (6.5 mL) was added HF.pyridine (3.2 mL) at 0° C., and the mixture was stirred at rt for 3 h. The reaction was quenched with dropwise addition of TMSOMe (30 mL) at 0° C. and the mixture was stirred at rt for 3 h. After concentrating and drying under high vacuum, the residue was purified by flash column chromatography (SiO$_2$, hexane/EtOAc=1:1) to give 28 (196.6 mg, 0.402 mmol, 97%) as a white solid;

$[\alpha]_D^{25}$ −96.6 (c 0.235, CHCl$_3$); IR (film) ν 3502, 2970, 2927, 1733, 1685, 1506, 1456, 1375, 1251, 1152, 1040, 977 cm$^{-1}$; $^1$H NMR (400 MHz, CDCl$_3$) δ 1.06 (3H, s), 1.11 (3H, d, J=7.0 Hz), 1.22 (3H, d, J=6.8 Hz), 1.28 (3H, s), 1.72 (3H, s), 2.10 (3H, s), 2.31-2.40 (2H, m), 2.43 (1H, dd, J=16.0, 3.7 Hz), 2.49 (1H, dd, J=16.0, 9.2 Hz), 2.55-2.68 (2H, m), 2.71 (3H, s), 2.98 (1H, dd, J=14.4, 6.4 Hz), 3.16 (1H, quint, J=6.2 Hz), 3.76 (1H, dd, J=5.9, 3.2 Hz), 4.30 (1H, dd, J=9.2, 3.7 Hz), 5.18 (1H, brt, J=7.3 Hz), 5.32 (1H, dd, J=8.4, 2.5 Hz), 5.63 (1H, dd, J=15.7, 6.4 Hz), 5.60 (1H, ddd, J=15.7, 6.9, 5.1 Hz), 6.60 (1H, s), 6.98 (1H, s); $^{13}$C NMR (100 MHz, CDCl$_3$) δ 15.1, 16.0, 17.7, 19.2, 19.5, 22.5, 23.6, 32.0, 35.0, 39.6, 40.3, 44.8, 53.3, 71.8, 75.6, 78.3, 116.1, 119.6, 120.5, 129.9, 131.3, 137.5, 138.2, 152.2, 165.0, 170.7, 218.8; LRMS (ESI) calcd for C$_{27}$H$_{40}$NO$_5$S [M+H$^+$] 490.3, found 490.2; HRMS (ESI) calcd. for C$_{27}$H$_{40}$NO$_5$S [M+H$^+$] 490.2627, found 490.2602.

26

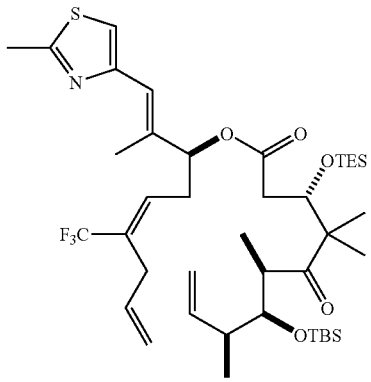

Compound 26: Acid 25 and alcohol 21 were azeotroped with dry benzene (5 mL×2) and dried under high vacuum before reaction. To a solution of alcohol 21 (240 mg, 0.756 mmol) in CH$_2$Cl$_2$ (5 mL) were added EDCI (192.7 mg, 1.01 mmol) and DMAP (122.8 mg, 1.01 mmol) at 0° C. To the mixture was added a solution of acid 25 (314.6 mg, 0.628 mmol) in CH$_2$Cl$_2$ (2 mL+1 mL rinse) dropwise over 15 min at 0° C. After stirring at 0° C. for 2 h, the mixture was stirred at rt for 2 h. After concentrating, the residue was purified by flash column chromatography (SiO$_2$, hexane/EtOAc=20:1 to 15:1) to give 26 (340.1 mg, 0.425 mmol, 68% based on acid) as a colorless oil;

$[\alpha]_D^{24}$ −27.5 (c 0.28, CHCl$_3$); IR (film) ν 2956, 2878, 1740, 1692, 1472, 1378, 1317, 1253, 1174, 1118, 988, 915, 872, 837, 775 cm$^{-1}$; $^1$H NMR (400 MHz, CDCl$_3$) δ 0.06 (6H, s), 0.57-0.65 (6H, m), 0.92 (9H, s), 0.94 (9H, t, J=7.9 Hz), 1.02 (3H, d, J=6.9 Hz), 1.03 (3H, d, J=6.8 Hz), 1.07 (3H, s), 1.22 (3H, s), 2.07-2.10 (1H, m), 2.09 (3H, s), 2.31 (1H, dd, J=16.9, 7.3 Hz), 2.51 (1H, dd, J=16.8, 3.0 Hz), 2.49-2.65 (2H, m), 2.71 (3H, s), 2.96-2.99 (2H, m), 3.06 (1H, quint, J=7.1 Hz), 3.83 (1H, dd, J=7.3, 2.1 Hz), 4.35 (1H, dd, J=7.2, 3.0 Hz), 4.98-5.12 (4H, m), 5.30 (1H, t, J=6.7 Hz), 5.76 (1H, ddt, J=16.7, 10.2, 6.2 Hz), 5.92 (1H, ddd, J=17.8, 9.9, 7.8 Hz), 6.19 (1H, t, J=7.0 Hz), 6.51 (1H, s), 6.97 (1H, s); LRMS (ESI) calcd for C$_{41}$H$_{68}$F$_3$NO$_5$SSi$_2$Na [M+Na$^+$] 822.4, found 822.4; HRMS (ESI) calcd. for C$_{41}$H$_{69}$F$_3$NO$_5$SSi$_2$ [M+H$^+$] 800.4387, found 800.4374.

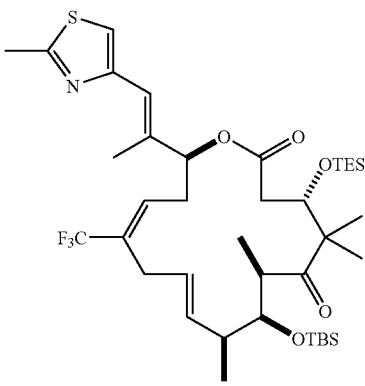

40a

Compound 40a (via RCM of 26): A solution of 26 (57.6 mg, 72.0 mmol) in toluene (142 mL) was heated to reflux and treated with a solution of Grubbs' catalyst (6.1 mg, 7.20 mmol) in toluene (2 mL). The mixture was stirred for 28 min, cooled to 0° C. and filtered through a pad of silica gel, which was rinsed with hexane/EtOAc=2/1 (300 mL). The combined filtrates were concentrated and purified by flash column chromatography (SiO$_2$, hexane/Et$_2$O=40:1 to 15:2) to give 40a (12.0 mg, 15.5 mmol, 22%) as a colorless oil;

$[\alpha]_D^{26}$ −17.1 (c 0.14, CHCl$_3$); IR (film) ν 2955, 2884, 1743, 1690, 1472, 1320, 1173, 1114, 1038, 1008, 873, 832, 773 cm$^{-1}$; $^1$H NMR (400 MHz, CDCl$_3$) δ 0.09 (3H, s), 0.12 (3H, s), 0.55 (6H, q, J=7.7 Hz), 0.88 (9H, t, J=8.0 Hz), 0.96 (9H, s), 1.01 (3H, s), 1.06 (3H, d, J=7.1 Hz), 1.12 (3H, s), 1.20 (3H, d, J=7.1 Hz), 2.07-2.17 (1H, m), 2.19 (3H, s), 2.38 (1H, dd, J=14.3, 3.5 Hz), 2.39-2.49 (1H, m), 2.50 (1H, dd, J=14.3, 7.3 Hz), 2.73 (3H, s), 2.77-2.91 (2H, m), 2.96-3.09 (2H, m), 3.98 (1H, dd, J=8.9 Hz), 4.54 (1H, dd, J=7.3, 3.4 Hz), 5.28-5.38 (1H, m), 5.63 (1H, dd, J=9.6, 2.3 Hz), 5.77 (1H, dd, J=15.9, 8.5 Hz), 6.21-6.28 (1H, m), 6.60 (1H, s), 6.99 (1H, s); LRMS (ESI) calcd for C$_{39}$H$_{65}$F$_3$NO$_5$SSi$_2$ [M+H$^+$] 772.4, found 772.4; HRMS (ESI) calcd. for C$_{39}$H$_{65}$F$_3$NO$_5$SSi$_2$ [M+H$^+$] 772.4074, found 772.4102.

29

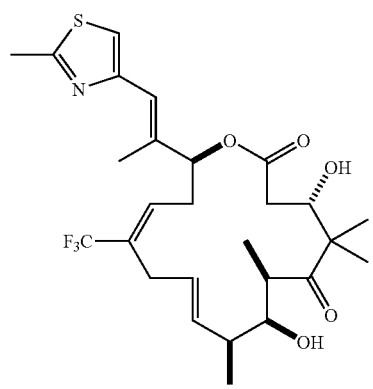

Compound 29: To a solution of 40a (1.78 g, 2.31 mmol) in THF (25 mL) was added slowly HF.pyridine (12.5 mL) at 0° C., and the mixture was stirred at rt for 4 h. The reaction was quenched with dropwise addition of TMSOMe (80 mL) over 10 min at 0° C. The mixture was vigorously stirred at rt for 2.5 h. After concentrating and drying under high vacuum for 2 h, the residue was purified by flash column chromatography (SiO$_2$~50 g, hexane/EtOAc=1:1) to give 29 (1.20 g, 2.21 mmol, 96%) as a colorless powder;

$[\alpha]D^{25}$ −54.6 (c 0.28, CHCl$_3$); IR (film) ν 3478, 2974, 2929, 1736, 1689, 1449, 1381, 1318, 1247, 1169, 1113, 1039, 983, 867, 736 cm$^{-1}$; $^1$H NMR (400 MHz, CDCl$_3$) δ 1.05 (3H, s), 1.12 (3H, d, J=7.0 Hz), 1.23 (3H, d, J=6.8 Hz), 1.37 (3H, s), 2.04 (1H, brd, J=3.8 Hz, —OH), 2.12 (3H, s), 2.25-2.33 (1H, m), 2.38 (1H, dd, J=15.3, 3.0 Hz), 2.48 (1H, dd, J=15.4, 9.8 Hz), 2.54-2.61 (1H, m), 2.66-2.76 (1H, m), 2.71 (3H, s), 2.96 (1H, dd, J=16.5, 4.5 Hz), 3.02 (1H, dd, J=16.3, 6.5 Hz), 3.11 (1H, quint, J=6.7 Hz), 3.19 (1H, brs, =OH), 3.74 (1H, brs), 4.35 (1H, brd, J=9.5 Hz), 5.42 (1H, dd, J=6.2, 4.1 Hz), 5.60 (1H, ddd, J=15.8, 5.6, 4.5 Hz), 5.66 (1H, dd, J=15.8, 5.8 Hz), 6.24 (1H, t, J=7.2 Hz), 6.64 (1H, s), 7.00 (1H, s); $^{13}$C NMR (100 MHz, CDCl$_3$) δ 15.1, 16.1, 17.7, 18.5, 19.3, 22.5, 28.8, 31.1, 39.6, 39.7, 45.0, 53.7, 71.4, 75.3, 76.8, 116.7, 120.2, 124.3 [q, $^1$J (C,F)=273.4 Hz], 127.9, 130.2 [q, $^3$J (C,F)=6.0 Hz], 130.6 [q, $^2$J (C,F)=28.4 Hz], 132.5, 136.7, 152.0, 165.4, 170.2, 218.4; LRMS (ESI) calcd for C$_{27}$H$_{37}$F$_3$NO$_5$S [M+H$^+$] 544.2, found 544.1; HRMS (ESI) calcd. for C$_{27}$H$_{37}$F$_3$NO$_5$S [M+H$^+$] 544.2345, found 544.2346.

2

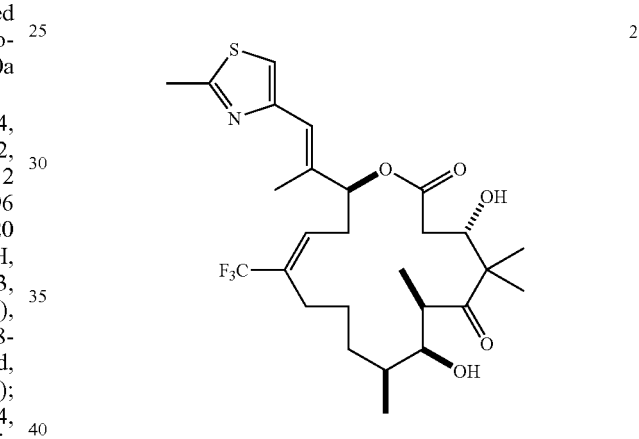

Compound 2: To a solution of 29 (1.22 mg, 2.24 mmol) and TrisNHNH$_2$ (26.7 mg, 89.6 μmol) in ClCH$_2$CH$_2$Cl (1 mL) at 50° C. was added Et$_3$N (12.5 μL, 89.6 μmol). The reaction was monitored by HPTLC (hexane/EtOAc/CH$_2$Cl$_2$=1/1/2). After stirring for 6.5 h, further TrisNHNH$_2$ (26.7 mg, 89.6 mmol) and Et$_3$N (12.5 μL, 89.6 μmol) were added to the mixture. After stirring for 14 h, the mixture was cooled to rt, diluted with EtOAc and filtered through a pad of silica gel, which was rinsed with EtOAc. After concentrating, the residue was purified by preparative TLC (hexane/EtOAc/CH$_2$Cl$_2$=1/1/2) to give 2 (1.16 mg, 2.13 mmol, 94%) as a white solid;

$[\alpha]_D^{24}$ −75.1 (c 0.35, CHCl$_3$); IR (film) ν 3483, 2968, 1337, 1685, 1466, 1381, 1322, 1247, 1168, 1113, 1010, 833, 736 cm$^{-1}$; $^1$H NMR (400 MHz, CDCl$_3$) δ 1.03 (3H, d, J=7.0 Hz), 1.08 (3H, s), 1.19 (3H, d, J=6.8 Hz), 1.25-1.35 (2H, m), 1.37 (3H, s), 1.42-1.55 (2H, m), 1.65-1.82 (2H, m), 2.10 (3H, d, J=0.8 Hz), 2.21-2.47 (2H, m), 2.27 (1H, dd, J=14.2, 2.6 Hz), 2.48 (1H, dd, J=14.3, 10.8 Hz), 2.70 (3H, s), 2.70-2.28 (1H, m), 3.02 (1H, d, J=2.0 Hz, —OH), 3.19 (1H, qd, J=6.9, 2.2 Hz), 3.65 (1H, d, J=6.2 Hz, —OH), 3.69-3.72 (1H, m), 4.34 (1H, ddd, J=10.8, 6.2, 2.6 Hz), 5.28 (1H, dd, J=10.2, 2.2 Hz), 6.12 (1H, dd, J=10.2, 5.2 Hz), 6.61 (1H, s), 6.98 (1H, s); $^{13}$C NMR (100 MHz, CDCl$_3$) δ 13.0, 15.9, 16.0, 17.7, 19.1, 23.0, 25.6, 26.2, 31.3, 32.3, 37.4, 39.8, 41.6, 53.9, 72.3, 73.6, 77.7, 116.2, 119.9, 124.3 [$^1$J (C,F)=274.4 Hz], 129.8 [$^3$J (C,F)=6.1 Hz], 132.6 [$^2$J(C,F)=27.8 Hz], 138.3, 151.7, 165.4, 170.2, 220.7; LRMS (ESI) calcd for $C_{27}H_{39}F_3NO_5S$ [M+H$^+$] 546.3, found 546.2; HRMS (ESI) calcd. for $C_{27}H_{39}F_3NO_5S$ [M+H$^+$] 546.2501, found 546.2496.

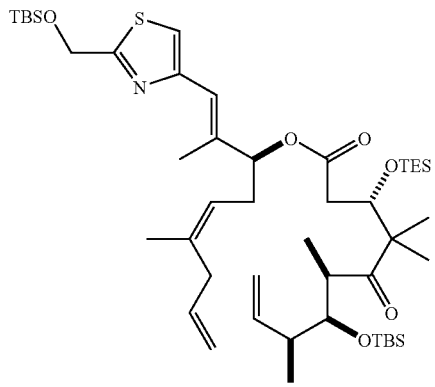

54

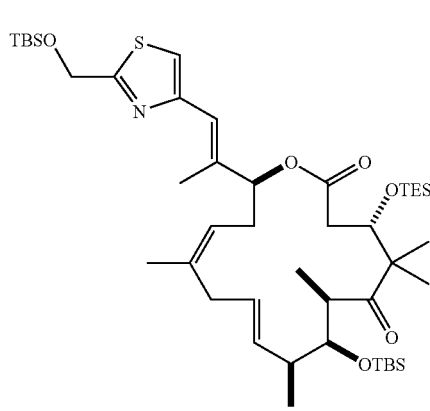

55

Compound 54: Acid 25 and alcohol 53 were azeotroped with dry benzene (3 mL×2) and dried under high vacuum before reaction. To a solution of alcohol 53 (68.0 mg, 0.173 mmol) in CH$_2$Cl$_2$ (1.3 mL) were added EDCI (37.8 mg, 0.197 mmol) and DMAP (24.1 mg, 0.197 mmol) at 0° C. To the mixture was added a solution of acid 25 (72.6 mg, as 0.123 mmol) in CH$_2$Cl$_2$ (0.7 mL) dropwise over 5 min at 0° C. After stirring at 0° C. for 1 h, the mixture was stirred at rt for 2.5 h. After concentrating, the residue was purified by flash column chromatography (SiO$_2$, hexane/EtOAc=30:1) to give 54 (99.5 mg, 0.114 mmol, 92% from t-butyl ester) as a colorless oil;

[α]$_D^{25}$ −23.4 (c 0.56, CHCl$_3$); IR (film) ν 2955, 2931, 2880, 1735, 1696, 1506, 1472, 1386, 1362, 1294, 1254, 1174, 1104, 988, 878, 776, 742 cm$^{-1}$; $^1$H NMR (400 MHz, CDCl$_3$) δ 0.06 (3H, s), 0.06 (3H, s), 0.14 (6H, s), 0.63 (6H, q, J=8.0 Hz), 0.92 (9H, s), 0.94 (9H, t, J=8.0 Hz), 0.97 (9H, s), 1.02 (3H, d, J=6.6 Hz), 1.05 (3H, d, J=6.5 Hz), 1.07 (3H, s), 1.21 (3H, s), 1.67 (3H, s), 2.06 (3H, d, J=0.8 Hz), 2.05-2.14 (1H, m), 2.30 (1H, dd, J=16.9, 7.5 Hz), 2.33-2.53 (2H, m), 2.50 (1H, dd, J=16.9, 2.7 Hz), 2.76-2.80 (2H, m), 3.07 (1H, quint, J=7.0 Hz), 3.83 (1H, dd, J=7.0, 2.2 Hz), 4.35 (1H, dd, J=7.4, 2.8 Hz), 4.97 (2H, s), 4.97-5.07 (4H, m), 5.16 (1H, t, J=7.2 Hz), 5.24 (1H, t, J=6.9 Hz), 5.74 (1H, ddt, J=16.6, 10.0, 6.5 Hz), 5.91 (1H, ddd, J=17.6, 9.9, 7.7 Hz), 6.50 (1H, s), 7.06 (1H, s); $^{13}$C NMR (100 MHz, CDCl$_3$) δ −5.2 (2C), −3.7, −3.3, 5.3 (3C), 7.2 (3C), 14.7, 15.2, 18.5, 18.7, 18.9, 20.3, 23.6, 23.7, 26.0 (3C), 26.4 (3C), 31.7, 36.7, 40.1, 43.8, 46.4, 53.3, 63.4, 74.2, 76.5, 79.6, 115.5, 115.6, 116.6, 120.5, 121.3, 135.8, 136.1, 137.4, 140.1, 153.0, 171.5, 172.2, 218.4; LRMS (ESI) calcd for $C_{47}H_{86}NO_6SSi_3$ [M+H$^+$] 1876.6, found 876.5; HRMS (ESI) calcd. for $C_{47}H_{86}NO_6SSi_3$ [M+H$^+$] 876.5484, found 876.5482.

Compound 55: A solution of 54 (69.7 mg, 79.5 μmol) in toluene (158 mL) was heated to reflux and treated with a solution of Grubbs' catalyst (6.7 mg, 7.95 μmol) in toluene (2 mL). The mixture was stirred for 11 min, cooled to 0° C. and filtered through a pad of silica gel, which was rinsed with hexane/EtOAc=3/1 (280 mL). The combined filtrates were concentrated and purified by flash column chromatography (SiO$_2$, hexane/Et$_2$O=20:1 to 15:1) to give 55 (18.4 mg, 21.7 mmol, 27%) as a colorless oil;

[α]$_D^{24}$ −40.4 (c 0.26, CHCl$_3$); IR (film) ν 2955, 2930, 2879, 1740, 1694, 1472, 1387, 1362, 1253, 1200, 1107, 1007, 838, 776, 742 cm$^{-1}$; $^1$H NMR (400 MHz, CDCl$_3$) δ 0.08 (3H, s), 0.12 (3H, s), 0.15 (6H, s), 0.57 (6H, q, J=7.9 Hz), 0.88 (9H, t, J=8.0 Hz), 0.95 (9H, s), 0.97 (9H, s), 1.04 (3H, s), 1.06 (3H, d, J=7.1 Hz), 1.12 (3H, s), 1.17 (3H, d, J=7.0 Hz), 1.69 (3H, s), 2.06-2.30 (2H, m), 2.14 (3H, s), 2.45 (1H, dd, J=15.6, 3.6 Hz), 2.50 (1H, dd, J=14.9, 3.1 Hz), 2.63-2.75 (2H, m), 2.97-3.06 (1H, m), 3.10 (1H, dd, J=14.6, 7.7 Hz), 3.97 (1H, d, J=8.5 Hz), 4.44 (1H, dd, J=8.4, 2.9 Hz), 4.97 (2H, s), 5.22 (1H, dd, J=8.7, 5.2 Hz), 5.33-5.44 (2H, m), 5.70 (1H, dd, J=15.6, 8.1 Hz), 6.57 (1H, s), 7.07 (1H, s); LRMS (ESI) calcd for $C_{45}H_{82}NO_6SSi_3$ [M+H$^+$] 848.5, found 848.5; HRMS (ESI) calcd. for $C_{45}H_{82}NO_6SSi_3$ [M+H$^+$] 848.5171, found 848.5161.

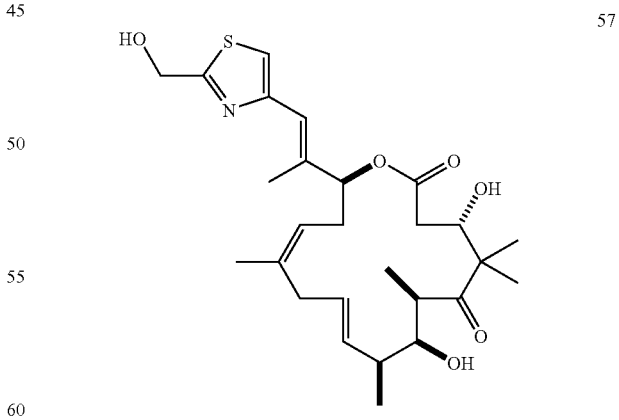

57

Compound 57: To a solution of 55 (61.8 mg, 72.8 μmol) in THF (2 mL) was added HF.pyridine (1 mL) at 0° C., and the mixture was stirred at rt for 3.2 h. The reaction was quenched with dropwise addition of TMSOMe (15 mL) at 0° C. The mixture was stirred at rt for 2 h. After concentrating and drying under high vacuum, the residue was purified by flash column chromatography (SiO$_2$, hexane/EtOAc=1:3) to give 57 (32.4 mg, 64.1 μmol, 88%) as a white solid;

[α]$_D^{25}$ −108.4 (c 0.285, CHCl$_3$); IR (film) ν 3422, 2968, 2919, 2729, 1689, 1449, 1377, 1252, 1152, 1064, 978 cm$^{-1}$; $^1$H NMR (400 MHz, CDCl$_3$) δ 1.05 (3H, s), 1.12 (3H, d, J=6.9 Hz), 1.22 (3H, d, J=6.8 Hz), 1.32 (3H, s), 1.72 (3H, s), 2.08 (3H, s), 2.31-2.40 (3H, m), 2.43 (1H, dd, J=15.5, 3.5 Hz), 2.49 (1H, dd, J=15.5, 9.5 Hz), 2.55-2.67 (2H, m), 2.95 (1H, dd, J=14.6, 6.3 Hz), 3.13 (1H, quint, J=6.6 Hz), 3.34 (1H, brs, —OH), 3.75 (1H, dd, J=6.6, 2.4 Hz), 4.06 (1H, brs, —OH), 4.33 (1H, dd, J=9.4, 3.0 Hz), 4.92 (2H, s), 5.18 (1H, t, J=6.9 Hz), 5.33 (1H, dd, J=8.0, 2.5 Hz), 5.52 (1H, dd, J=15.8, 6.4 Hz), 5.59 (1H, ddd, J=15.8, 6.6, 5.0 Hz), 6.63 (1H, s), 7.13 (1H, s); $^{13}$C NMR (100 MHz, CDCl$_3$) δ 15.3, 16.3, 17.8, 19.2, 22.8, 23.7, 31.9, 35.1, 39.7, 40.2, 45.0, 53.4, 61.8, 71.7, 75.8, 78.1, 116.7, 119.0, 120.5, 130.0, 131.2, 137.6, 138.9, 152.5, 170.0, 170.7, 218.7; LRMS (ESI) calcd for C$_{27}$H$_{39}$NO$_6$SNa [M+Na$^+$] 528.2, found 528.0; HRMS (ESI) calcd. for C$_{27}$H$_{40}$NO$_6$S [M+H$^+$] 506.2576, found 506.2552.

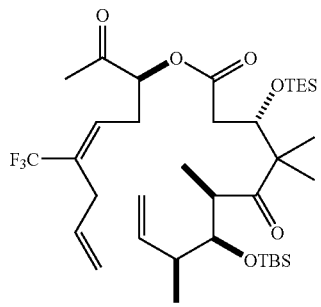

46

Compound 46: Crude acid 25 (4.65 g, as 7.27 mmol) and alcohol 44 (2.18 g, 9.84 mmol) were azeotroped with dry benzene and dried under high vacuum before reaction. To a solution of alcohol 44 (2.18 g, 9.84 mmol) in CH$_2$Cl$_2$ (65 mL) were added EDCI (2.09 g, 10.9 mmol) and DMAP (1.33 g, 10.9 mmol) at 0° C. To the mixture was added a solution of crude acid 25 (4.65 g, as 7.27 mmol) in CH$_2$Cl$_2$ (20 mL+5 mL rinse) dropwise over 20 min at 0° C. After stirring at 0° C. for 40 min, the mixture was stirred at rt for 4 h. After concentrating, the residue was purified by flash column chromatography (SiO$_2$~160 g, hexane/EtOAc=20:1) to give 46 (4.85 g, 6.87 mmol, 94% from t-butyl ester) as a colorless oil;

[α]$_D^{25}$ −22.7 (c 0.26, CHCl$_3$); IR (film) ν 2958, 2936, 2800, 1748, 1732, 1693, 1473, 1416, 1360, 1317, 1296, 1254, 1174, 1119, 989, 916, 872, 838, 776 cm$^{-1}$; $^1$H NMR (400 MHz, CDCl$_3$) δ 0.08 (3H, s), 0.08 (3H, s), 0.60 (6H, q, J=7.8 Hz), 0.93 (9H, s), 0.94 (9H, t, J=8.0 Hz), 1.04 (3H, d, J=7.0 Hz), 1.04 (3H, d, J=7.0 Hz), 1.11 (3H, s), 1.23 (3H, s), 2.05-2.14 (1H, m), 2.17 (3H, s), 2.40 (1H, dd, J=16.9, 7.0 Hz), 2.59 (1H, dd, J=17.0, 3.6 Hz), 2.56-2.64 (2H, m), 2.90-3.01 (2H, m), 3.06 (1H, quintet, J=7.0 Hz), 3.85 (1H, dd, J=7.3, 2.0 Hz), 4.38 (1H, d, J=7.0, 3.4 Hz), 4.97-5.14 (5H, m), 5.75 (1H, ddt, J=16.0, 9.9, 6.2 Hz), 5.92 (1H, ddd, J=17.8, 10.5, 7.8 Hz), 6.21 (1H, td, J=7.2, 1.5 Hz); $^{13}$C NMR (100 MHz, CDCl$_3$) δ −3.7, −3.4, 5.2 (3C), 7.1 (3C), 15.4, 18.7, 18.9, 19.5, 23.9, 26.3 (3C), 26.6, 28.5, 30.0, 39.8, 43.7, 46.3, 53.3, 73.6, 76.5, 77.1, 115.6, 117.8, 124.0 [$^1$J (C,F)=273.5 Hz], 129.2 [$^3$J (C,F)=6.1 Hz], 130.6 [$^2$J (C,F)=28.7 Hz], 133.4, 140.0, 171.8, 204.6, 218.4; LRMS (ESI) calcd for C$_{36}$H$_{63}$F$_3$O$_6$Si$_2$Na [M+Na$^+$] 727.4, found 727.3; HRMS (ESI) calcd. for C$_{36}$H$_{64}$F$_3$O$_6$Si$_2$ [M+H$^+$] 705.4194, found 705.4193.

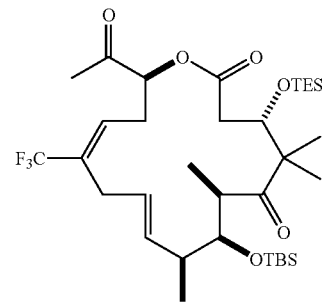

48

Compound 48: A solution of 46 (510.0 mg, 0.723 mmol) in toluene (500 mL) was heated to reflux and treated with a solution of Grubbs' catalyst (92.1 mg, 0.109 mmol) in toluene (10 mL). The mixture was stirred for 17 min under reflux and immediately cooled to 0° C. and kept at 0° C. before filtration through a pad of silica gel. A second batch of diene (510.0 mg, 0.723 mmol) was processed identically and simultaneously. The combined reaction mixtures were filtered through a pad of silica gel (100 g), which was rinsed with hexane/EtOAc=3/1 (1.4 L). The combined filtrates were concentrated and purified by flash column chromatography (SiO$_2$~65 g, hexane/Et$_2$O=10:1 to 5:1) to give 48 (742.4 mg, 1.10 mmol, 76%) as a colorless oil;

[α]$_D^{25}$ −7.5 (c 0.12, CHCl$_3$); IR (film) ν 2956, 2979, 1748, 1732, 1695, 1472, 1415, 1384, 1252, 1170, 1119, 1018, 986, 876, 835 cm$^{-1}$; $^1$H NMR (400 MHz, CDCl$_3$) δ 0.08 (3H, s), 0.10 (3H, s), 0.60 (6H, q, J=7.8 Hz), 0.93 (9H, s), 0.94 (9H, t, J=7.8 Hz), 1.03 (3H, d, J=7.1 Hz), 1.08 (3H, s), 1.13 (3H, d, J=7.0 Hz), 1.17 (3H, s), 2.26 (3H, s), 2.25-2.34 (1H, m), 2.64 (1H, dd, J=15.5, 5.0 Hz), 2.68-2.75 (2H, m), 2.76 (1H, dd, J=15.6, 6.4 Hz), 2.85 (1H, dd, J=15.6, 5.7 Hz), 2.97 (1H, dq, J=8.3, 6.9 Hz), 3.04 (1H, dd, J=15.6, 6.3 Hz), 3.92 (1H, dd, J=8.3, 1.2 Hz), 4.36 (1H, t, J=5.3 Hz), 5.30-5.39 (2H, m), 5.58 (1H, dd, J=15.5, 8.0 Hz), 6.13 (1H, brt, J=7.2 Hz); $^{13}$C NMR (100 MHz, CDCl$_3$) δ −3.6, −3.6, 5.4 (3C), 7.0 (3C), 17.5, 18.5, 19.0, 21.6, 23.5, 26.3 (3C), 26.5, 28.6, 29.1, 41.0, 42.3, 47.3, 54.1, 74.2, 76.8, 77.7, 124.0 [$^1$J (C,F)=273.7 Hz], 126.0, 128.7 [$^3$J (C,F)=5.9 Hz], 132.2 [$^2$J (C,F)=28.1 Hz], 133.8, 170.5, 204.1, 216.1; LRMS (ESI) calcd for C$_{34}$H$_{59}$F$_3$O$_6$Si$_2$Na [M+Na$^+$] 699.4, found 699.4; HRMS (ESI) calcd. for C$_{34}$H$_{60}$F$_3$O$_6$Si$_2$ [M+H$^+$] 677.3881, found 677.3892.

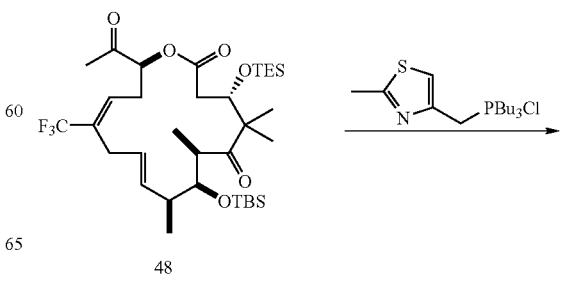

48

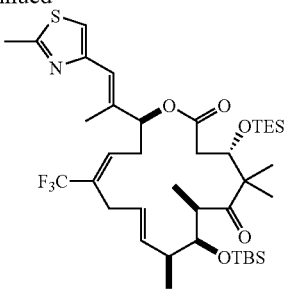

40a

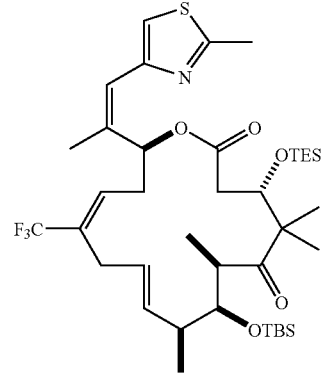

40b

Compound 40a (Via Wittig Reaction of Ketone 48):

Ketone 48 was azeotroped with benzene (5 mL×2) and then dried under high vacuum for 0.5 h. To a solution of Wittig salt (907 mg, 2.59 mmol) in THF (19 mL) was added t-BuOK (2.4 mL of a 1.0 M solution in THF, 2.43 mmol) dropwise over 5 min at 0° C. The mixture was stirred at 0° C. for 0.5 h and then cooled to −78° C. To the mixture was added dropwise a solution of ketone 48 (1.10 g, 1.62 mmol) in THF (13 mL) over 10 min, and the resulting mixture was allowed to warm to −20° C. over 2 h. The reaction was quenched with sat. aqueous NH$_4$Cl (15 mL) and extracted with EtOAc (50 mL×3). The combined organic layers were washed with brine (20 mL), dried over Na$_2$SO$_4$ and concentrated. The residue was purified by flash chromatography (SiO$_2$, hexane/Et$_2$O=20:1 to 10:1) to give the desired 16(E)-isomer 40a (940 mg, 1.22 mmol, 75%) along with the undesired 16(Z)-isomer 40b (140.9 mg, 0.182 mmol, 11%), both as colorless oils;

$[\alpha]_D^{25}$ 62.7 (c 0.33, CHCl$_3$); $^1$H NMR (400 MHz, CDCl$_3$) δ 0.09 (3H, s), 0.13 (3H, s), 0.49 (6H, q, J=7.8 Hz), 0.85 (9H, t, J=7.8 Hz), 0.97 (9H, s), 0.99 (3H, s), 1.06 (3H, d, J=7.1 Hz), 1.11 (3H, s), 1.20 (3H, d, J=7.1 Hz), 2.00 (3H, s), 2.03-2.13 (1H, m), 2.35 (1H, dd, J=14.3, 3.0 Hz), 2.46 (1H, dd, J=14.3, 7.8 Hz), 2.41-2.50 (1H, m), 2.73 (3H, s), 2.71-2.90 (2H, m) 2.98-3.12 (2H, m), 3.99 (1H, d, J=9.2 Hz), 4.56 (1H, dd, J=7.7, 2.8 Hz), 5.33 (1H, ddd, J=15.6, 8.9, 4.1 Hz), 5.82 (1H, dd, J=15.6, 8.4 Hz), 6.29 (1H, s), 6.33-6.40 (1H, m), 6.94 (1H, m), 7.09 (1H, brd, J=8.4 Hz); $^{13}$C NMR (100 MHz, CDCl$_3$) δ −3.2, −3.2, 5.5 (3C), 7.0 (3C), 17.2, 18.7, 19.3, 19.6, 20.0, 22.3, 24.9, 26.4 (3C), 29.7, 32.9, 41.9, 42.0, 48.6, 54.0, 72.2, 73.3, 77.0, 116.7, 120.7, 124.5 [$^1$J (C,F)=273.3 Hz], 127.9, 129.7 [$^2$J (C,F)=28.0 Hz], 131.9 [$^3$J (C,F)=6.1 Hz], 132.9, 136.6, 152.1, 165.4, 170.2, 217.4; LRMS (ESI) calcd for C$_{39}$H$_{65}$F$_3$NO$_5$SSi$_2$ [M+H$^+$] 772.4, found 772.4

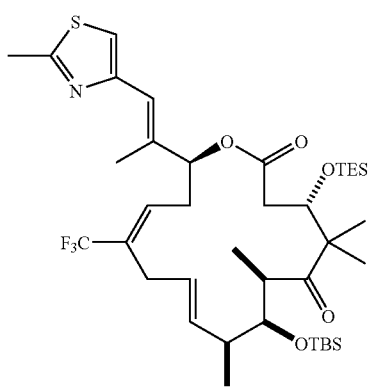

40a

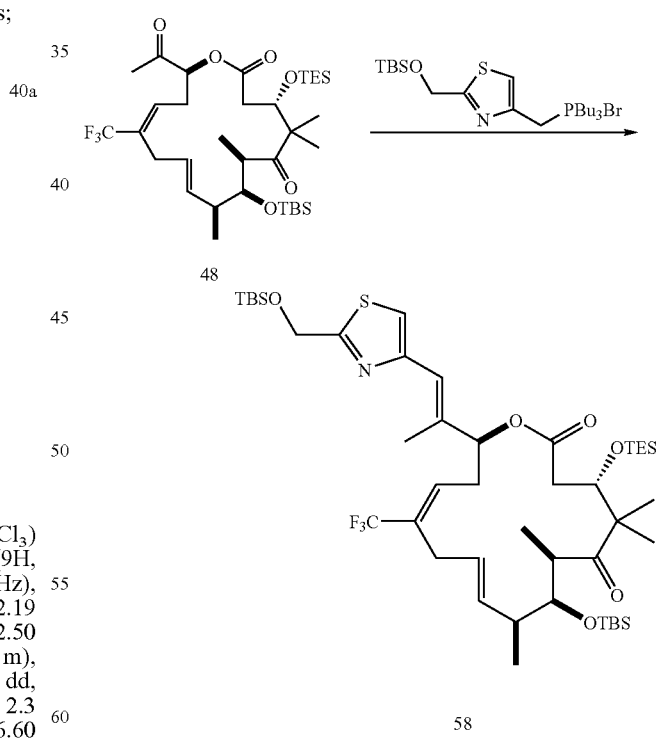

48

58

Compound 58 (Via Wittig Reaction of Ketone 48):

Ketone 48 was azeotroped with benzene (5 mL×2) and then dried under high vacuum for 0.5 h. To a solution of Wittig salt (1.19 g, 2.27 mmol) in THF (18 mL) was added t-BuOK (2.2 mL of a 1.0 M solution in THF, 2.20 mmol) dropwise over 5 min at 0° C. The mixture was stirred at 0° C. for 20 min and $[\alpha]_D^{26}$ −17.1 (c 0.14, CHCl$_3$); $^1$H NMR (400 MHz, CDCl$_3$) δ 0.09 (3H, s), 0.12 (3H, s), 0.55 (6H, q, J=7.7 Hz), 0.88 (9H, t, J=8.0 Hz), 0.96 (9H, s), 1.01 (3H, s), 1.06 (3H, d, J=7.1 Hz), 1.12 (3H, s), 1.20 (3H, d, J=7.1 Hz), 2.07-2.17 (1H, m), 2.19 (3H, s), 2.38 (1H, dd, J=14.3, 3.5 Hz), 2.39-2.49 (1H, m), 2.50 (1H, dd, J=14.3, 7.3 Hz), 2.73 (3H, s), 2.77-2.91 (2H, m), 2.96-3.09 (2H, m), 3.98 (1H, dd, J=8.9 Hz), 4.54 (1H, dd, J=7.3, 3.4 Hz), 5.28-5.38 (1H, m), 5.63 (1H, dd, J=9.6, 2.3 Hz), 5.77 (1H, dd, J=15.9, 8.5 Hz), 6.21-6.28 (1H, m), 6.60 (1H, s), 6.99 (1H, s); $^{13}$C NMR (100 MHz, CDCl$_3$) δ −3.4, −3.3, 5.5 (3C), 7.0 (3C), 14.6, 17.1, 18.7, 19.4, 19.9, 21.3, 24.8, 26.4 (3C), 29.6, 32.8, 42.0, 42.1, 48.2, 54.1, 73.4, 76.9, 77.8, 117.0, 121.6, 124.3 [$^1$J (C,F)=273.5 Hz], 127.2, 130.6 [$^2$J (C,F)=28.2 Hz], 130.8 [$^3$J (C,F)=6.1 Hz], 133.2, 136.5, 152.3, 165.0, 170.1, 217.1; HRMS (ESI) calcd. for C$_{39}$H$_{65}$F$_3$NO$_5$SSi$_2$ [M+H$^+$] 772.4074, found 772.4102.

then cooled to −78° C. To the mixture was added dropwise a solution of ketone (1.06 g, 1.51 mmol) in THF (10 mL+2 mL rinse) over 10 min, and the resulting mixture was allowed to warm to −20° C. over 2 h. The reaction was quenched with sat. aqueous NH$_4$Cl (15 mL) and extracted with EtOAc (50 mL×3). The combined organic layers were washed with brine (20 mL), dried over Na$_2$SO$_4$ and concentrated. The residue was purified by flash column chromatography (SiO$_2$~65 g, hexane/Et$_2$O=30:1 to 20:1) to give the desired 16(E)-isomer 58 (1.01 g, 1.11 mmol, 74%) along with the undesired 16(Z)-isomer 58a (154.5 mg, 0.182 mmol, 11%) both as colorless oils;

58

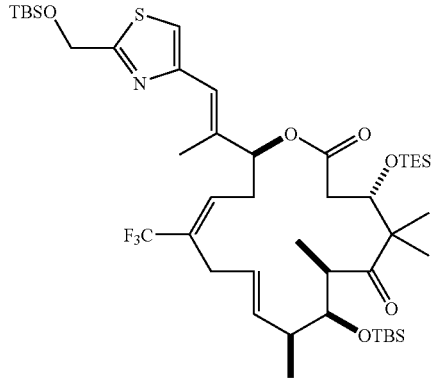

$[\alpha]_D^{24}$ −19.0 (c 0.10, CHCl$_3$); IR (film) ν 2954, 2930, 2880, 1744, 1692, 1472, 1381, 1321, 1252, 1171, 1114, 1038, 1006, 837, 776 cm$^{-1}$; $^1$H NMR (400 MHz, CDCl$_3$) δ 0.09 (3H, s), 0.12 (3H, s), 0.15 (6H, s), 0.55 (6H, q, J=7.8 Hz), 0.87 (9H, t, J=8.0 Hz), 0.96 (9H, s), 0.97 (9H, s), 1.01 (3H, s), 1.06 (3H, d, J=7.1 Hz), 1.12 (3H, s), 1.20 (3H, d, J=7.1 Hz), 2.07-2.16 (1H, m), 2.18 (3H, d, J=1.0 Hz), 2.38 (1H, dd, J=14.4, 3.3 Hz), 2.34-2.46 (1H, m), 2.49 (1H, dd, J=14.4, 7.4 Hz), 2.78-2.90 (2H, m), 2.97-3.09 (2H, m), 3.98 (1H, d, J=8.9 Hz), 4.54 (1H, dd, J=7.3, 3.3 Hz), 4.97 (2H, s), 5.33 (1H, ddd, J=15.8, 8.6, 4.9 Hz), 5.63 (1H, dd, J=9.6, 2.4 Hz), 5.78 (1H, dd, J=15.8, 8.2 Hz), 6.22-6.27 (1H, m), 6.60 (1H, s), 7.09 (1H, s); $^{13}$C NMR (100 MHz, CDCl$_3$) δ −5.3 (2C), −3.4, −3.3, 5.5 (3C), 7.0 (3C), 14.6, 17.1, 18.4, 18.7, 19.8, 21.3, 24.8, 25.9 (3C), 26.4 (3C), 29.6, 32.9, 42.0, 42.1, 48.2, 54.1, 63.4, 73.4, 76.9, 77.8, 117.2, 121.7, 124.3 [$^1$J (C,F)=273.6 Hz], 127.2, 130.7 [$^2$J (C,F)=27.5 Hz], 130.8 [$^3$J (C,F)=6.2 Hz], 133.2, 136.4, 152.6, 170.1, 172.4, 217.1; LRMS (ESI) calcd. for C$_{45}$H$_{78}$F$_3$NO$_6$SSi$_3$Na [M+Na$^+$] 924.5, found 924.5; HRMS (ESI) calcd. for C$_{45}$H$_{79}$F$_3$NO$_6$SSi$_3$ [M+H$^+$] 902.4888, found 902.4887.

58a

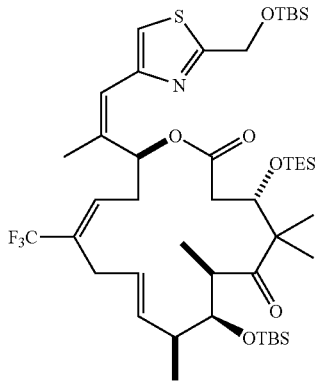

$^1$H NMR (400 MHz, CDCl$_3$) δ 0.07 (3H, s), 0.13 (3H, s), 0.16 (6H, s), 0.48 (6H, q, J=7.8 Hz), 0.84 (9H, t, J=7.9 Hz), 0.97 (18H, s), 0.98 (3H, s), 1.06 (3H, d, J=7.1 Hz), 1.11 (3H, s), 1.20 (3H, d, J=7.2 Hz), 2.00 (3H, s), 2.03-2.11 (1H, m), 2.33 (1H, dd, J=14.1, 2.8 Hz), 2.43 (1H, dd, J=14.0, 7.8 Hz), 2.40-2.48 (1H, m), 2.76-2.89 (2H, m), 2.97-3.10 (2H, m), 3.99 (1H, d, J=9.3 Hz), 4.57 (1H, dd, J=7.8, 2.6 Hz), 4.95 (1H, d, J=14.6 Hz), 5.00 (1H, d, J=14.6 Hz), 5.33 (1H, ddd, J=15.6, 9.1, 3.8 Hz), 5.82 (1H, dd, J=15.6, 8.3 Hz), 6.30 (1H, s), 6.32-6.38 (1H, m), 7.04 (1H, s), 7.11 (1H, dd, J=11.0, 2.3 Hz); LRMS (ESI) calcd for C$_{45}$H$_{78}$F$_3$NO$_6$SNa [M+Na$^+$] 924.5, found 924.5.

59

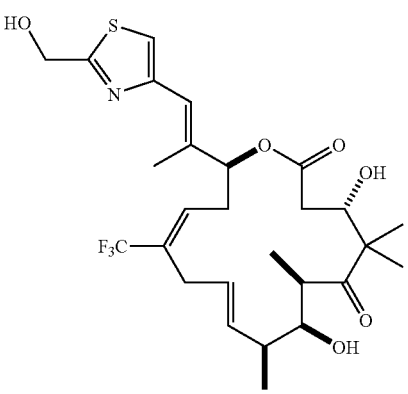

Compound 59:

To a solution of 58 (1.04 g, 2.25 mmol) in THF (22 mL) was added slowly HF.pyridine (11 mL) at 0° C., and the mixture was stirred at rt for 4.3 h. The reaction was quenched with dropwise addition of TMSOMe (75 mL) over 10 min at 0° C. The mixture was vigorously stirred at rt for 4.2 h. After concentrating and drying under high vacuum for 1 h, the residue was purified by flash column chromatography (SiO$_2$~25 g, hexane/EtOAc=3:4 to 1:2) to give 59 (615.7 mg, 1.00 mmol, 96%) as a colorless powder;

$[\alpha]_D^{25}$ −57.7 (c 1.20, CHCl$_3$); IR (film) ν 3441, 2974, 2932, 1734, 1685, 1507, 1456, 1374, 1318, 1248, 1169, 1112, 1054, 982, 888, 737 cm$^{-1}$; $^1$H NMR (400 MHz, CDCl$_3$) δ 1.04 (3H, s), 1.12 (3H, d, J=6.9 Hz), 1.25 (3H, d, J=6.8 Hz), 1.36 (3H, s), 1.90 (1H, d, J=6.6 Hz, OH), 2.08 (3H, s), 2.23-2.32 (1H, m), 2.34 (1H, dd, J=15.7, 2.4 Hz), 2.49 (1H, dd, J=15.7, 10.1 Hz), 2.59-2.69 (2H, m), 2.95-3.01 (2H, m), 3.04 (1H, quintet, J=6.8 Hz), 3.72 (1H, td, J=7.0, 3.0 Hz), 3.78 (1H, d, J=5.7 Hz, OH), 4.38 (1H, ddd, J=10.1, 5.7, 2.4 Hz), 4.90 (2H, d, J=6.1 Hz), 5.10 (1H, t, J=6.1 Hz, OH), 5.44 (1H, t, J=4.7 Hz), 5.60 (1H, dd, J=15.9, 4.4 Hz), 5.66 (1H, dd, J=15.9, 5.0 Hz), 6.28 (1H, t, J=6.7 Hz), 6.73 (1H, s), 7.16 (1H, s); $^{13}$C NMR (100 MHz, CDCl$_3$) δ 16.0, 16.5, 17.4, 17.5, 22.9, 28.5, 30.3, 39.0, 39.6, 45.6, 54.0, 60.9, 70.6, 75.6, 75.7, 116.8, 119.2, 124.2 [$^1$J (C,F)=273.6 Hz], 127.9, 129.8 [$^2$J (C,F)=28.4 Hz], 130.3 [$^3$J (C,F)=5.9 Hz], 131.2, 137.0, 152.2, 169.8, 170.0, 218.3; LRMS (ESI) calcd for C$_{27}$H$_{37}$F$_3$NO$_6$SNa [M+H$^+$] 560.2, found 560.1; HRMS (ESI) calcd. for C$_{27}$H$_{37}$F$_3$NO$_6$S [M+H$^+$] 560.2294, found 560.2299.

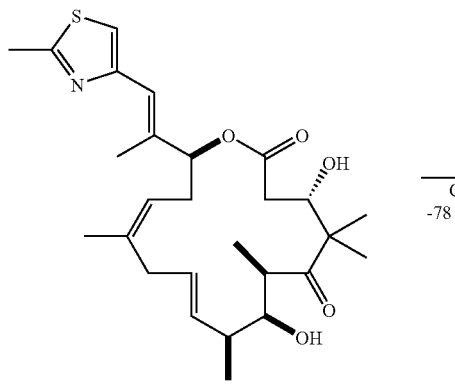

28

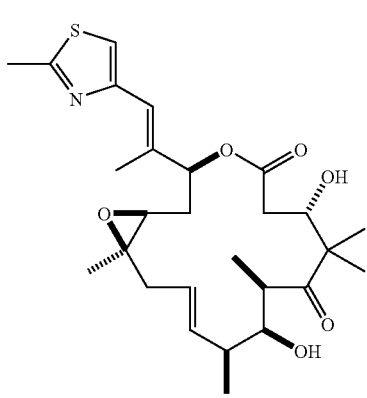

49

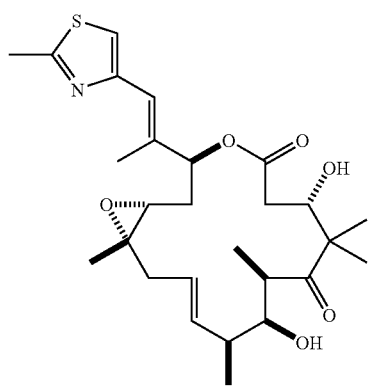

50

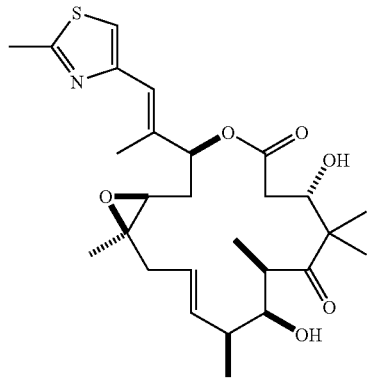

49

Compound 49: $[\alpha]_D^{25}$ −78.5 (c 0.33, CHCl$_3$); IR (film) ν 3454, 2974, 2928, 1734, 1689, 1450, 1379, 1250, 1152, 1061, 978, 735 cm$^{-1}$; $^1$H NMR (400 MHz, CDCl$_3$) δ 1.03 (3H, s), 1.11 (3H, d, J=7.0 Hz), 1.14 (3H, d, J=6.9 Hz), 1.34 (3H, s), 1.36 (3H, s), 2.00 (1H, ddd, J=15.1, 7.3, 4.0 Hz), 2.14 (1H, dt, J=15.1, 5.2 Hz), 2.14 (3H, s), 2.21 (1H, dd, J=14.6, 8.0 Hz), 2.33 (1H, dd, J=14.7, 4.8 Hz), 2.47 (1H, dd, J=13.8, 3.3 Hz), 2.59 (1H, dd, J=13.8, 9.4 Hz), 2.73 (3H, s), 2.77 (1H, brs, OH), 2.93 (1H, dd, J=7.3, 4.8 Hz), 3.34 (1H, qd, J=6.9, 3.8 Hz), 3.75-3.82 (1H, m), 4.12-4.24 (2H, m, including OH), 5.54 (1H, ddd, J=15.7, 7.4, 5.0 Hz), 5.54-5.60 (1H, m), 5.64 (1H, dd, J=15.7, 5.6 Hz), 6.94 (1H, s), 7.01 (1H, s); $^1$H NMR (500 MHz, CD$_2$Cl$_2$) δ 0.91 (3H, s), 1.01 (3H, d, J=6.9 Hz), 1.03 (3H, d, J=6.9 Hz), 1.22 (3H, s), 1.27 (3H, s), 1.96-2.02 (1H, m), 2.04 (3H, d, J=0.7 Hz), 2.16-2.23 (2H, m), 2.33 (1H, dd, J=14.2, 3.1 Hz), 2.30-2.35 (1H, m), 2.44 (1H, dd, J=14.4, 10.3 Hz), 2.69 (3H, s), 2.77 (1H, t, J=5.9 Hz), 3.24 (1H, qd, J=6.9, 4.5 Hz), 3.63 (1H, t, J=4.1 Hz), 4.18-4.26 (1H, m), 5.37 (1H, t, J=4.5 Hz), 5.48 (1H, dtd, J=15.7, 6.7, 0.5 Hz), 5.58 (1H, dd, J=15.7, 6.2 Hz), 6.58 (1H, s), 7.00 (1H, s); $^{13}$C NMR (100 MHz, CDCl$_3$) δ 14.4, 16.3 (2C), 19.3, 19.7, 21.6, 22.6, 31.8, 35.9, 38.7, 39.6, 44.1, 52.8, 60.8, 61.8, 74.0, 75.7, 75.9, 116.5, 119.6, 124.3, 135.8, 136.2, 152.1, 165.2, 170.8, 221.5; LRMS (ESI) calcd for C$_{27}$H$_{40}$NO$_6$S [M+H$^+$] 506.3, found 506.3; HRMS (ESI) calcd. for C$_{27}$H$_{40}$NO$_6$S [M+H$^+$] 506.2576, found 506.2566.

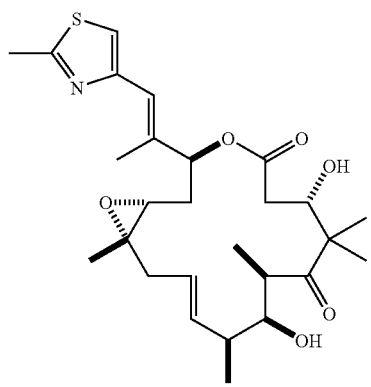

50

Compounds 49 and 50: A solution of 28 (12.2 mg, 24.9 μmol) in CH$_2$Cl$_2$ (1.25 mL) was cooled to −78° C. and treated with a cooled solution of DMDO (−78° C., 0.06 M in acetone, 914 μL, 54.8 mmol). The mixture was allowed to warm to −50° C. and stirred at −50° C. for 2.7 h. The excess DMDO was quenched at −50° C. by the addition of dimethylsulfide (117 μL) and the mixture was stirred at this temperature for 0.5 h. The solvent was removed in vacuo. Purification by preparative thin layer chromatography (hexane/EtOAc=1/2) gave β-epoxide 49 (3.0 mg, 5.93 μmol, 24%) and α-epoxide 50 (7.9 mg, 15.6 μmol, 63%) both as colorless solids.

Compound 50: $[\alpha]_D^{25}$ −53.9 (c 0.700, CHCl$_3$); IR (film) ν 3460, 2976, 2928, 1735, 1688, 1506, 1451, 1378, 1252, 1186, 1151, 1087, 1042, 976, 879, 735 cm$^{-1}$; $^1$H NMR (400 MHz, CDCl$_3$) δ 1.00 (3H, s), 1.04 (3H, d, J=6.9 Hz), 1.12 (3H, d, J=7.0 Hz), 1.35 (3H, s), 1.35 (3H, s), 1.87 (1H, dt, J=15.0, 9.2 Hz), 2.03 (1H, dd, J=13.9, 9.2 Hz), 2.13 (3H, s), 2.13-2.19 (1H, m), 2.36 (1H, dd, J=13.9, 3.4 Hz), 2.39 (1H, dd, J=12.2, 2.1 Hz), 2.42-2.51 (1H, m), 2.49 (1H, dd, J=12.4, 10.9 Hz), 2.69 (1H, d, J=2.7 Hz), 2.72 (3H, s), 3.06 (1H, dd, J=9.7, 3.1 Hz), 3.54 (1H, qd, J=7.0, 1.8 Hz), 3.76-3.80 (1H, m), 4.07-4.14 (1H, m), 4.31 (1H, d, J=4.1 Hz), 5.52 (1H, dd, J=15.5, 8.7 Hz), 5.60 (1H, ddd, J=15.1, 9.4, 3.4 Hz), 5.71 (1H, d, J=8.4 Hz), 6.63 (1H, s), 6.99 (1H, s); $^{13}$C NMR (100 MHz, CDCl$_3$) δ 13.7, 15.3, 15.7, 18.5, 19.4, 21.2, 22.4, 32.5, 35.5, 39.1, 43.4, 43.8, 51.9, 61.3, 64.8, 73.5, 75.9, 76.4, 116.7, 120.1, 124.3, 137.5, 137.7, 152.3, 165.2, 171.0, 222.3; LRMS (ESI) calcd for $C_{27}H_{39}NO_6SNa$ [M+Na$^+$] 528.2, found 528.2; HRMS (ESI) calcd. for $C_{27}H_{40}NO_6S$ [M+H$^+$] 506.2576, found 506.2583.

884, 735 cm$^{-1}$; $^1$H NMR (400 MHz, CDCl$_3$) δ 0.95 (3H, d, J=7.1 Hz), 1.04 (3H, s), 1.11 (3H, d, J=7.0 Hz), 1.28 (3H, s), 1.37 (3H, s), 1.25-1.44 (2H, m), 1.45-1.59 (2H, m), 1.71-1.82 (3H, m), 1.86 (1H, dt, J=15.3, 9.5 Hz), 2.10 (1H, dd, J=15.3, 3.6 Hz), 2.13 (3H, s), 2.40 (1H, dd, J=12.5, 2.5 Hz), 2.49 (1H, dd, J=12.5, 11.0 Hz), 2.74 (3H, s), 2.80 (1H, brs, OH), 3.07 (1H, dd, J=10.3, 3.3 Hz), 3.34 (1H, qd, J=7.0, 0.5 Hz), 3.89 (1H, brs, OH), 4.03-4.09 (1H, m), 4.12-4.17 (1H, m), 5.69 (1H, d, J=9.1 Hz), 6.63 (1H, s), 7.00 (1H, s); $^{13}$C NMR (100 MHz, CDCl$_3$) δ 12.9, 15.4, 16.3, 18.8, 19.3, 21.6, 22.0, 23.0, 31.5, 32.1, 33.6, 38.6, 38.9, 42.6, 51.7, 62.6, 65.5, 71.2, 74.5, 76.3, 116.6, 119.9, 138.0, 152.2, 165.2, 170.6, 222.7; LRMS (ESI) calcd for $C_{27}H_{41}NO_6SNa$ [M+Na$^+$] 530.3, found 530.2; HRMS (ESI) calcd. for $C_{27}H_{42}NO_6S$ [M+H$^+$] 508.2733, found 508.2754.

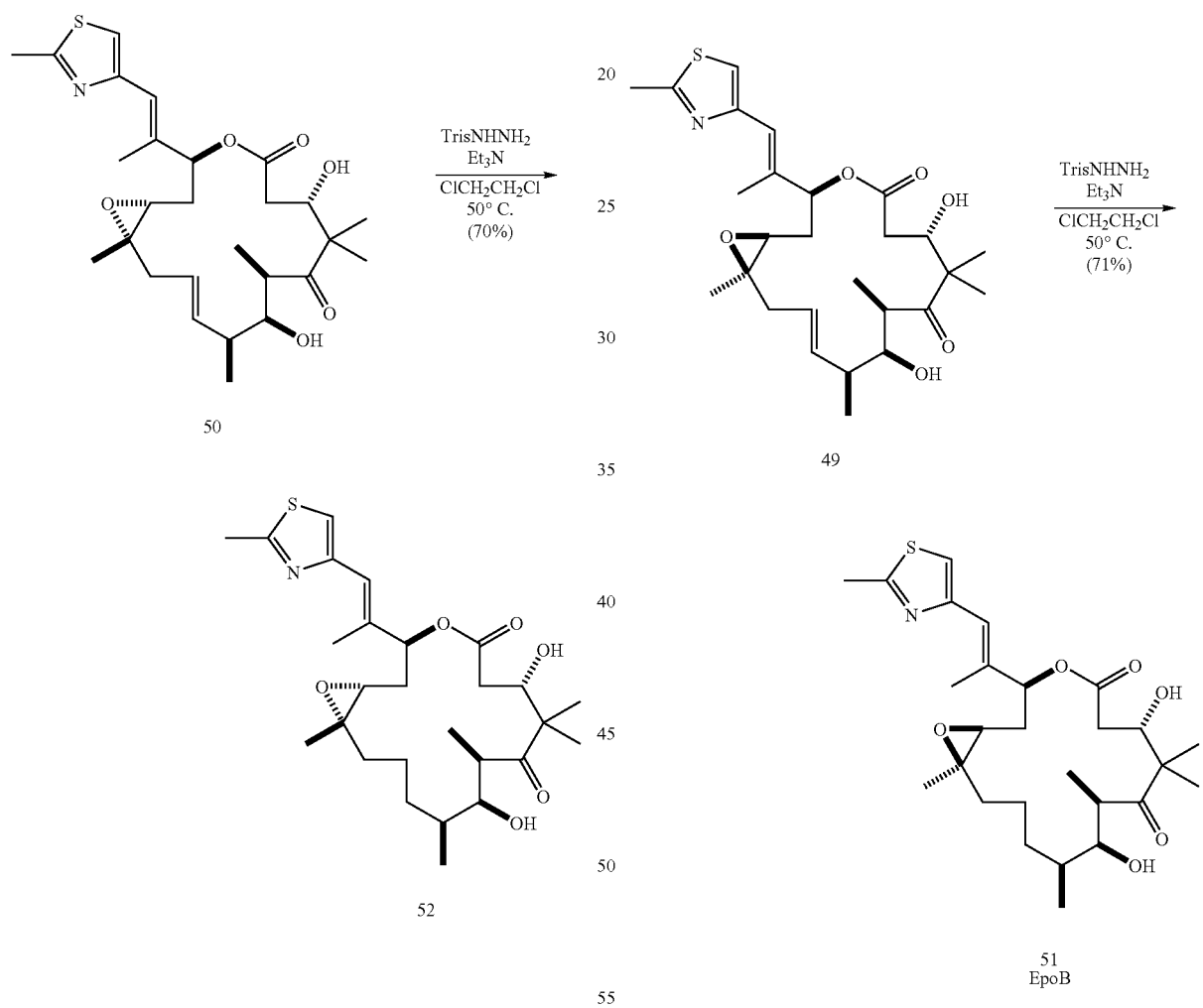

Compound 52: To a solution of 50 (1.7 mg, 3.4 μmol) and TrisNHNH$_2$ (40.1 mg, 0.134 mmol) in ClCH$_2$CH$_2$Cl (0.8 mL) at 50° C. was added Et$_3$N (18.7 μL, 0.134 mmol). The reaction was monitored by HPTLC (hexane/EtOAc=1/2). After stirring for 4 h, the mixture was cooled to rt, diluted with EtOAc and filtered through a pad of silica gel, which was rinsed with EtOAc. After concentrating, the residue was purified by preparative TLC (hexane/EtOAc=1/2) to give 52 (1.2 mg, 2.4 μmol, 70%) as a white solid.

[α]$_D^{24}$ −13.8 (c 0.61, CHCl$_3$); IR (film) ν 3475, 2971, 2875, 1735, 1689, 1456, 1382, 1253, 1181, 1151, 1056, 980, Compound 51: To a solution of 49 (0.7 mg, 1.38 μmol) and TrisNHNH$_2$ (20.6 mg, 69 μmol) in ClCH$_2$CH$_2$Cl (0.4 mL) at 50° C. was added Et$_3$N (9.6 μL, 69 μmol). The reaction was monitored by HPTLC (hexane/EtOAc=1/2). After stirring for 6 h, the mixture was cooled to rt, diluted with EtOAc and filtered through a pad of silica gel, which was rinsed with EtOAc. After concentrating, the residue was purified by preparative TLC (hexane/EtOAc=1/2) gave 51 (0.5 mg, 0.985 μmol, 71%) as a white solid. The spectral data of 51 was identical to those reported of EpoB.

Example 2
Alternative Synthetic Strategies for Synthesizing Intermediates of Epothilones
The following examples offer methods of preparing the various intermediates in the synthesis of epothilone analogs.
Optimization of the Syntheses of 9,10-dehydroEpothilones
Example 1
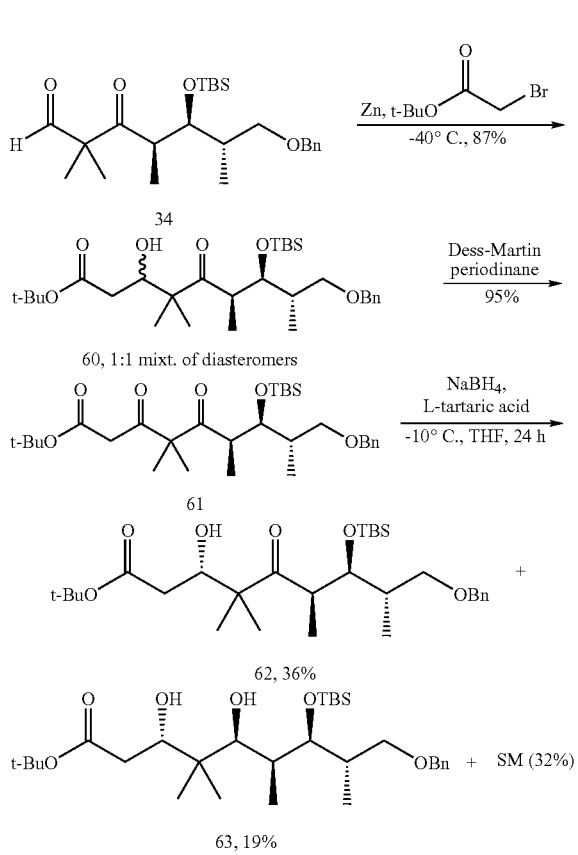
Example 2
Noyori Reductions
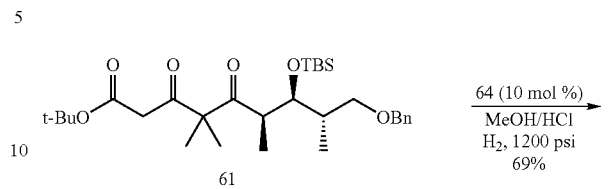
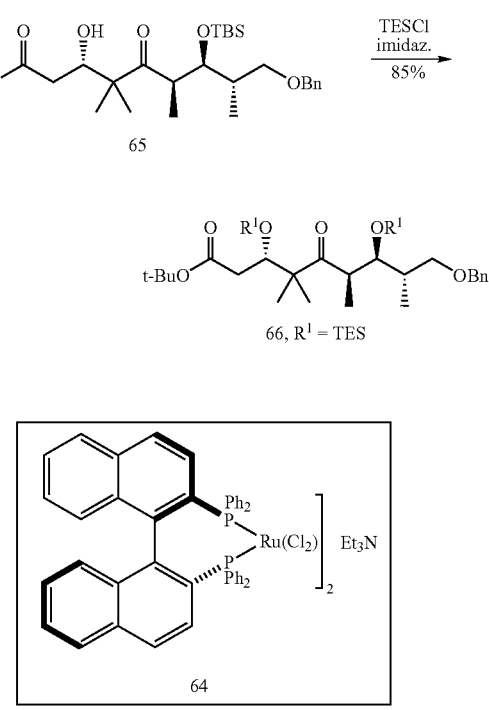
Example 3
Noyori Reductions
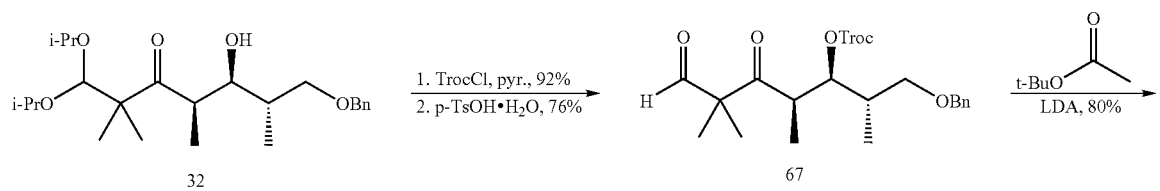
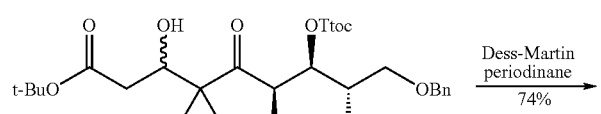
68, 1:1 mixt. of diasteromers

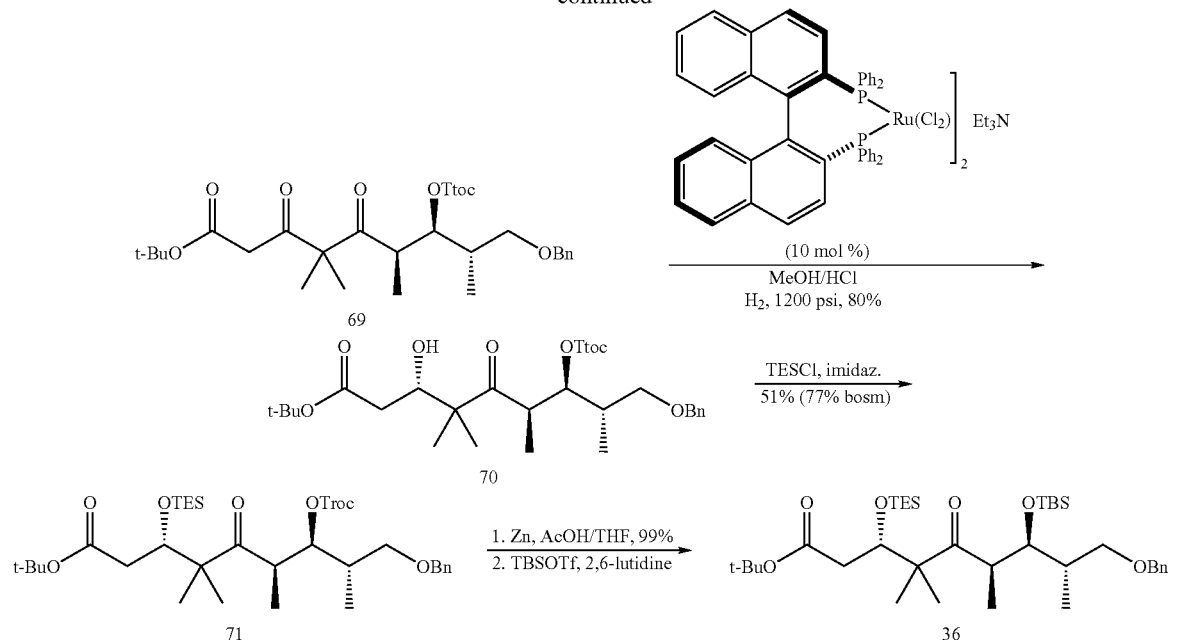
Example 4
Alternative Synthesis of the Key Diketone
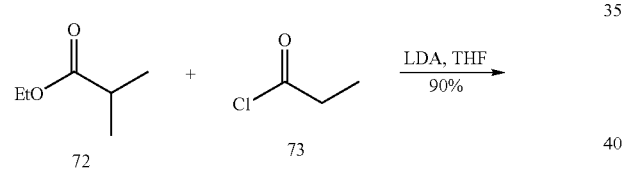
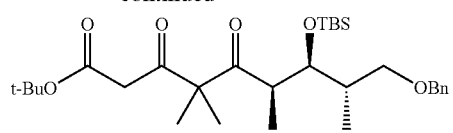
Example 5
Approach 1. Silyl Group Migration - Decarboxylation
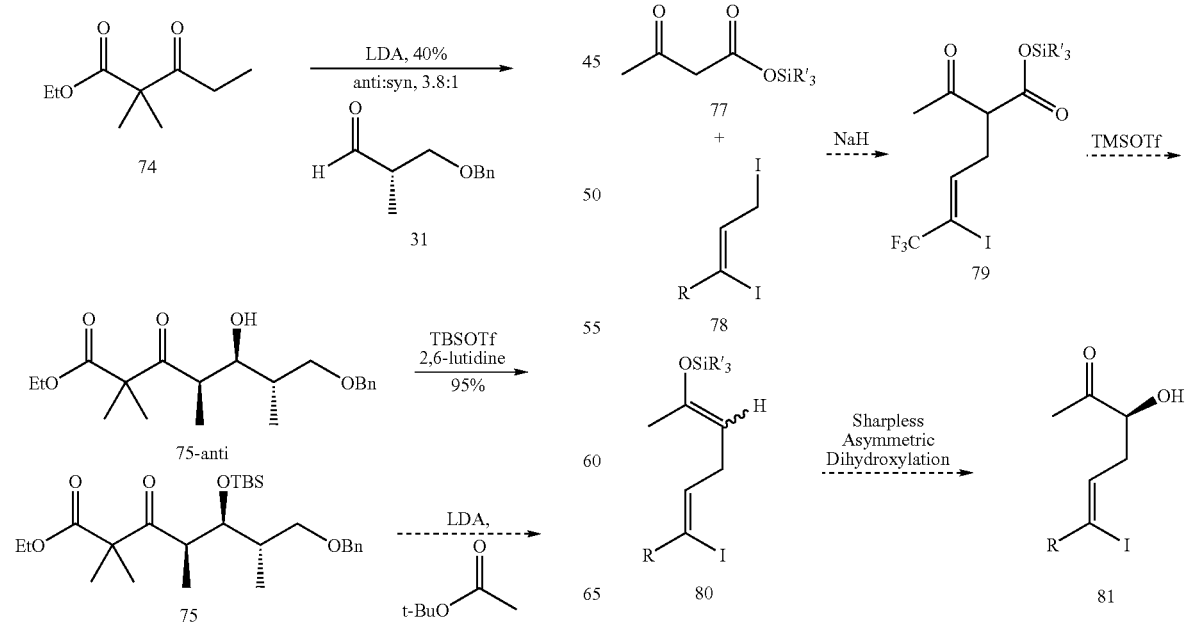

Approach 2. Decarboxylation - Silyl Group Incorporation
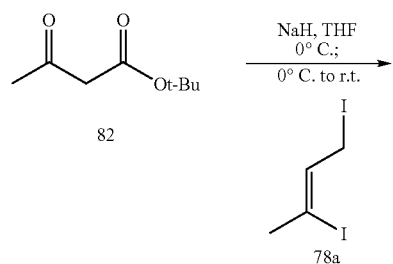
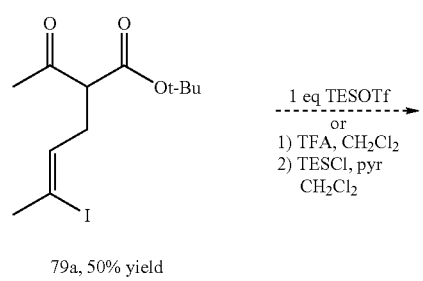
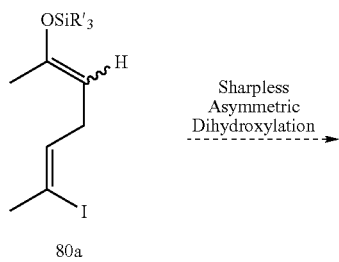
Example 6
Evans Auxiliary Approach to the Synthesis of 2-Hydroxyketone
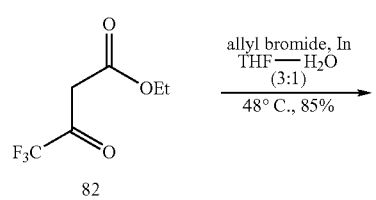
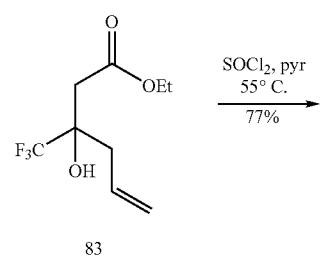
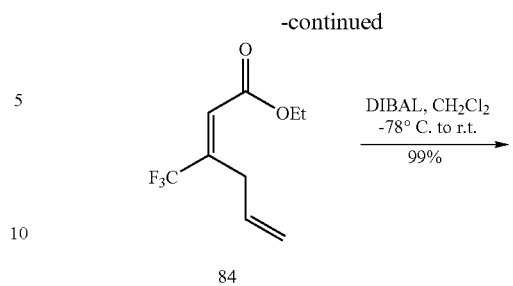
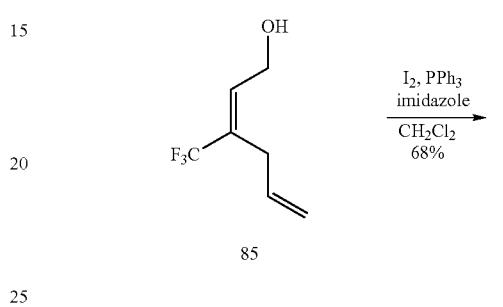
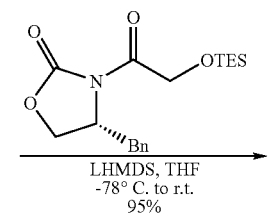
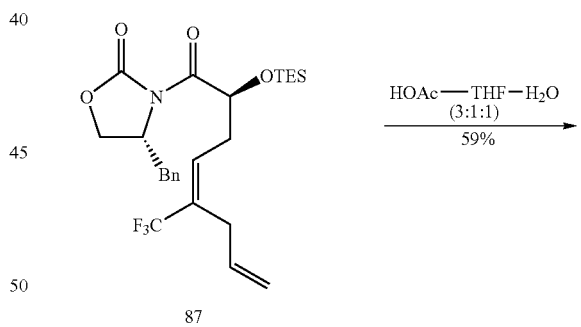

-continued

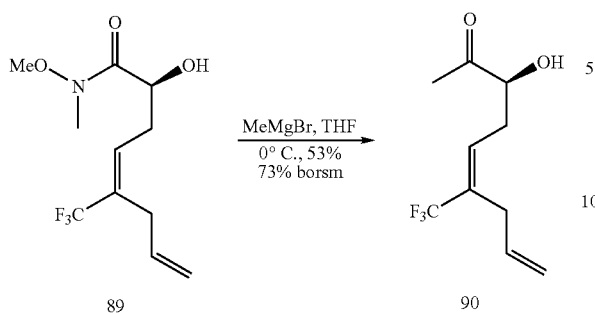

Example 7

Kowalsky—Sharpless Approach to the Synthesis of 2-Hydroxyketone

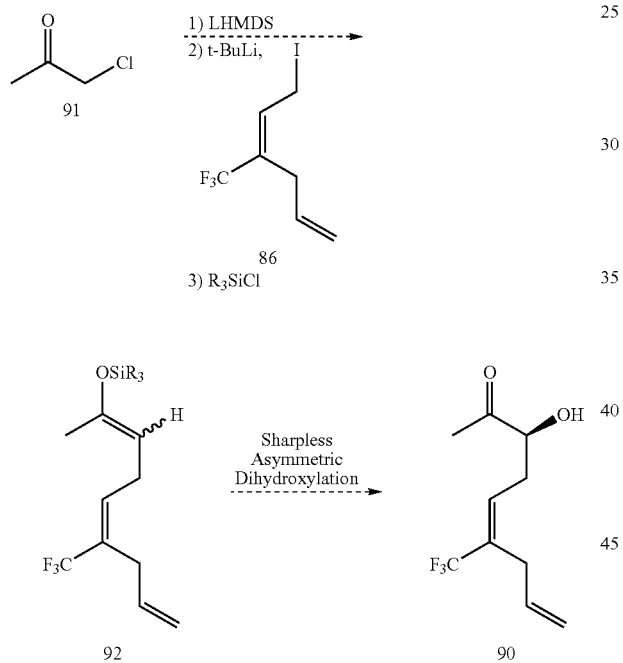

Experimentals

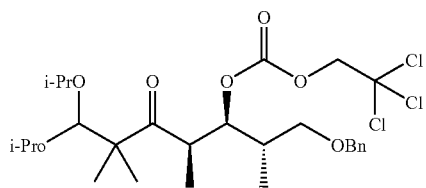

32a

Carbonic acid 1-(2-benzyloxy-1-methylethyl)-5,5-diisopropoxy-2,4,4-trimethyl-3-oxopentyl ester 2,2,2-trichloroethyl ester (32a)

To a solution of 7-Benzyloxy-5-hydroxy-1,1-diisopropoxy-2,2,4,6-tetramethyl-heptan-3-one 32 (1.0 g, 2.4 mmol) and pyridine (0.8 mL, 7.3 mmol) in CH$_2$Cl$_2$ (10.0 mL) at 0° C. was added 2,2,2-trichloroethyl chloroformate (668.0 μL, 4.9 mmol) and the mixture was then allowed to warm to rt. After 1 h, the reaction mixture was quenched with brine and then extracted with CH$_2$Cl$_2$. The combined organic layers were dried over MgSO$_4$ and concentrated under reduced pressure. The crude product was purified by flash chromatography (gradient hexane to hexane/EtOAc 93:7) to give 32a (1.285 g, 92%) as a clear oil: $^1$H NMR (400 MHz, CDCl$_3$) δ 1.03-1.09 (m, 12H), 1.15 (d, J=1.8 Hz, 3H), 1.17 (d, J=1.9 Hz, 3H), 1.19-1.21 (m, 6H), 1.97-2.11 (m, 1H), 3.2 (dd, J=6.2 and 9.0 Hz, 1H), 3.54 (dd, J=4.8 and 9.1 Hz, 1H), 3.57-3.60 (m, 1H), 3.82 (qd, J=3.6 and 5.9 Hz, 2H), 4.47 (s, 2H), 4.57 (s, 1H), 4.72 (d, J=11.9 Hz, 1H), 4.81 (d, J=11.9 Hz, 1H), 5.08 (t, J=6.0 Hz, 1H), 7.29-7.35 (m, 5H); $^{13}$C NMR (100 MHz, CDCl$_3$) δ 11.9, 15.0, 18.8, 21.4, 21.7, 22.3, 23.2, 23.4, 35.7, 42.5, 53.4, 53.9, 69.4, 70.9, 71.4, 73.3, 81.3, 94.7, 103.4, 127.5, 127.6, 128.2, 138.2, 154.0, 215.6; IR (film, NaCl, cm$^{-1}$) 2966, 1760, 1698, 1247; LRMS (ESI) calcd for C$_{27}$H$_{41}$O$_7$Cl$_3$Na [M+Na$^+$] 605.2, found 605.2; [α]$^{23}$$_D$=−20.4 (c=1.0, CHCl$_3$.

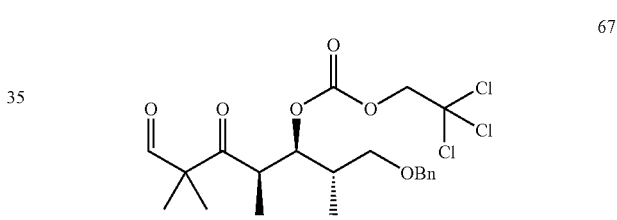

Carbonic acid 1-(2-benzyloxy-1-methylethyl)-2,4,4-trimethyl-3,5-dioxopentyl ester 2,2,2-trichloroethyl ester (67)

To solution of 32a (1.28 g, 2.25 mmol) in 4:1 THF/H$_2$O (25 mL) was added p-TsOH (111.0 mg, 0.6 mmol). After heating at 70° C. 5 h, the reaction mixture was poured into a cold (0° C.) sat. NaHCO$_3$ aq solution (12 mL) and then extracted with EtOAc. The combined organic layers were washed with brine, dried over MgSO$_4$ and concentrated under reduced pressure. The crude product was purified by flash chromatography (gradient hexane to hexane/EtOAc 84:16) to give 67 (793.2 mg, 76%) as a clear oil: $^1$H NMR (400 MHz, CDCl$_3$) 0.90 (d, J=5.8 Hz, 3H), 1.0 (d, J=6.9 Hz, 3H), 1.24 (s, 6H), 1.97-2.04 (m, 1H), 3.24 (dd, J=4.8 and 9.2 Hz, 1H), 3.34 (m, 1H), 3.42 (dd, J=5.8 and 9.2 Hz, 1H), 4.35 (d, J=11.9 Hz, 1H), 4.39 (d, J=11.9 Hz, 1H), 4.64 (d, J=11.9 Hz, 1H), 4.69 (d, J=11.9 Hz, 1H), 4.96 (t, J=6.0 Hz, 1H), 7.19-7.28 (m, 5H), 9.49 (s, 1H); $^{13}$C NMR (100 MHz, CDCl$_3$) −12.0, 14.8, 19.5, 19.6, 35.4, 43.3, 60.9, 71.1, 73.3, 80.37, 94.5, 127.7, 127.8, 128.3, 137.9, 154.1, 201.0, 210.1; IR (film, NaCl., cm$^{-1}$) 2973, 2880, 1758, 1701, 1453, 1380, 1248; LRMS (ESI) calcd for C$_{21}$H$_{27}$O$_6$Cl$_3$Na [M+Na$^+$] 503.0, found 503.0; [α]$^{23}$$_D$=−18.5 (c=0.8, CHCl$_3$).

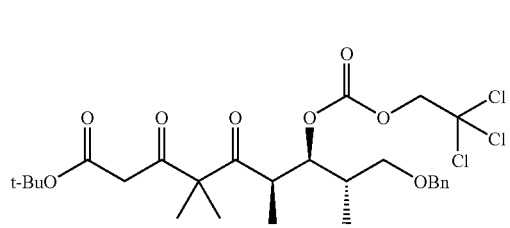

9-Benzyloxy-4,4,6,8-tetramethyl-3,5-dioxo-7-(2,2,2-trichloroethoxycarbonyloxy)-nonanoic acid tert-butyl ester (69)

To a solution of LDA (1.17 mmol, 0.3 M in Et$_2$O) at −78° C. was added t-butyl acetate (1.0 mmol, 135.0 μL). After 30 min, a solution of 67 (464.0 mg, 1 mmol) in Et$_2$O (2 mL) was slowly added over 15 min. After stirring for 1 h, the reaction was quenched with a sat. NH$_4$Cl aq solution and then extracted with EtOAc. The combined organic layers were washed with brine, dried over MgSO$_4$ and concentrated under reduced pressure. The crude product was purified by flash chromatography (gradient hexane to hexane/EtOAc 86:14) to give 68 (1:1 epimeric mixture, 461.4 mg, 80%) as a clear oil: $^1$H NMR (400 MHz, CDCl$_3$) δ 0.87 (d, J=5.3 Hz, 3H), 0.89 (d, J=5.5 Hz, 3H), 1.02-1.10 (m, 18H), 1.38 (s, 18H), 1.97-2.2 (m, 2H), 2.27-2.31 (m, 2H), 3.22-3.27 (m, 3H), 3.39-3.48 (m, 5H), 4.03-4.06 (m, 1H), 4.11-4.14 (m, 1H), 4.38-4.45 (m, 4H), 4.58-4.73 (m, 4H), 4.97 (t, J=5.8 Hz, 1H), 5.02 (t, J=5.8 Hz, 1H), 7.18-7.27 (m, 10H); $^{13}$C NMR (100 MHz, CDCl$_3$) δ 11.9, 12.7, 14.9, 15.2, 18.7, 19.3, 21.4, 21.6, 28.0, 35.6, 37.4, 41.7, 42.0, 51.8, 51.9, 71.3, 71.3, 72.5, 73.0, 73.3, 73.3, 80.6, 81.2, 81.3, 94.6, 127.5, 127.7, 127.8, 128.3, 138.0, 138.1, 154.0, 154.1, 172.3, 172.4, 216.0, 216.3; IR (film, NaCl, cm$^{-1}$) 3509, 2975, 1759, 1707, 1368, 1248, 1152; LRMS (ESI) calcd for C$_{27}$H$_{39}$O$_8$Cl$_3$Na [M+Na$^+$] 619.1, found 619.2.

To a 0° C. solution of 68 (350.0 mg, 0.6 mmol) in CH$_2$Cl$_2$ (10 mL) was added Dess-Martin periodinane (398.0 mg, 0.9 mmol). The mixture was stirred at rt for 1 h and then poured into a well-stirred mixture of 1:1 sat. Na$_2$S$_2$O$_3$/sat. NaHCO$_3$. The layers were separated after 30 min. The aqueous layer was extracted three times with Et$_2$O. The combined organic extracts were washed with sat. NaHCO$_3$, brine, dried over MgSO$_4$ and concentrated under vacuum. The crude product was purified by flash chromatography (gradient hexane to hexane/EtOAc 91:9) to give 69 (258.4 mg, 74%) as a clear oil: $^1$H NMR (400 MHz, CDCl$_3$) δ 0.80 (d, J=6.9 Hz, 3H), 0.87 (d, J=6.9 Hz, 3H), 1.13 (s, 3H), 1.19 (s, 3H), 1.23 (s, 9H), 2.04-2.12 (m, 1H), 3.09-3.28 (m, 5H), 4.23 (s, 2H), 4.48 (d, J=11.9 Hz, 1H), 4.55 (d, J=11.9 Hz, 1H), 4.79 (dd, J=4.6 and 7.3 Hz, 1H), 7.04-7.13 (m, 5H); $^{13}$C NMR (100 MHz, CDCl$_3$) δ 11.7, 14.6, 20.7, 21.5, 27.9, 35.5, 42.2, 43.4, 63.3, 71.3, 73.3, 79.9, 81.5, 90.5, 94.5, 127.6, 127.7, 128.2, 138.0, 154.0, 166.2, 202.9, 210.0; IR (film, NaCl, cm$^{-1}$) 2977, 1758, 1697, 1368, 1248, 1154; LRMS (ESI) calcd for C$_{27}$H$_{37}$O$_8$Cl$_3$Na [M+Na$^+$] 617.1, found 617.1; [α]$^{23}{}_D$=−49.1 (c=0.9, CHCl$_3$.

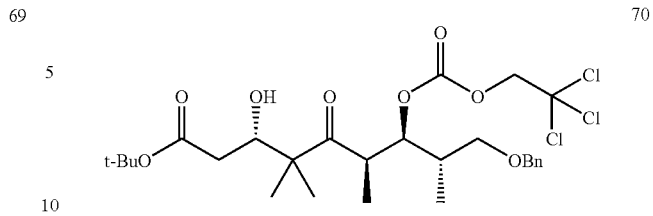

9-Benzyloxy-3-hydroxy-4,4,6,8-tetramethyl-5-oxo-7-(2,2,2-trichloroethoxycarbonyloxy)-nonanoic acid tert-butyl ester (70)

A bomb liner was charged with (R)-RuBINAP catalyst (16.8 mg, 10.0 μmol). HCl (555 μL, 0.2N in MeOH) was added and the mixture was then sonicated for 15 sec. Then a solution of 69 (59.4 mg, 0.1 mmol) in MeOH (555 μL) was added and the mixture transferred to a Parr apparatus. The vessel was purged with H$_2$ for 5 min and then pressurized to 1200 psi. After 17 h, the reaction was returned to atmospheric pressure and poured into a sat NaHCO$_3$ aq solution. The aqueous layer was extracted three times with EtOAc. The combined organic extracts were dried over MgSO$_4$ and concentrated under reduced pressure. The crude product was purified by flash chromatography (gradient hexane to hexane/EtOAc 88:12) to give 70 (dr>20:1 as judged by $^1$H NMR analysis) (47.6 mg, 80%) as a clear oil: $^1$H NMR (400 MHz, CDCl$_3$) δ 1.06 (d, J=6.9 Hz, 3H), 1.11 (d, J=6.8 Hz, 3H), 1.14 (s, 3H), 1.18 (s, 3H), 1.47 (s, 9H), 2.05-2.12 (m, 1H), 2.35-2.40 (m, 1H), 3.31-3.37 (m, 2H), 3.51-3.54 (m, 2H), 4.11-4.14 (m, 1H), 4.46 (s, 2H), 4.72 (d, J=11.9 Hz, 1H), 4.80 (d, J=11.9 Hz, 1H), 5.05 (dd, J=5.0 and 6.7 Hz, 1H), 7.27-7.35 (m, 5H); $^{13}$C NMR (100 MHz, CDCl$_3$) δ 12.0, 15.0, 19.3, 21.7, 28.0, 35.6, 37.5, 41.7, 51.8, 71.3, 73.0, 73.3, 80.6, 81.3, 94.7, 127.5, 127.7, 128.3, 138.2, 154.1, 172.4, 216; IR (film, NaCl, cm$^{-1}$) 3849, 2974, 2879, 1758, 1701, 1454, 1368, 1248, 1152, 926, 734; LRMS (ESI) calcd for C$_{27}$H$_{39}$O$_8$Cl$_3$Na [M+Na$^+$] 619.1, found 619.2; [α]$^{23}{}_D$=−13.0 (c=0.4, CHCl$_3$).

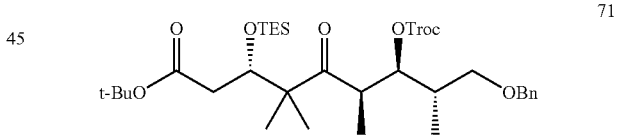

9-Benzyloxy-4,4,6,8-tetramethyl-5-oxo-7-(2,2,2-trichloroethoxycarbonyloxy)-3-(triethylsilanyloxy)-nonanoic acid tert-butyl ester (71)

To a solution of 70 (37.6 mg, 6.3 μmol) and imidazole (9.4 mg, 13.8 μmol) in DMF (0.4 mL) at 0° C. was added TESCl (11.6 μL, 69.3 μmol). After 3 h, the mixture was diluted with sat aq NaHCO$_3$. The aqueous layer was extracted three times with hexanes. The combined organic extracts were washed with brine, dried over MgSO$_4$ and concentrated under reduced pressure. The crude product was purified by flash chromatography (gradient hexane to hexane/EtOAc 93:7) to yield, in order of elution, 71 (22.9 mg, 51%), and recovered 70 (12.9 mg, 34%) as clear oils. 7: $^1$H NMR (400 MHz, CDCl$_3$) δ 0.66 (q, J=7.9 Hz, 6H), 0.96 (t, J=7.9 Hz, 9H), 1.01 (s, 3H), 1.05 (d, J=5.2 Hz, 3H), 1.07 (d, J=5.3 Hz, 3H), 1.35

(s, 3H). 1.44 (s, 9H), 2.05-2.11 (m, 2H), 2.50 (dd, J=3.5 and 17.2 Hz, 1H), 3.35 (dd, J=5.9 and 9.0 Hz, 1H), 3.49 (dd, J=4.0 and 9.0 Hz, 1H), 3.53 (dd, J=3.8 and 6.7 Hz, 1H), 4.18 (dd, J=3.5 and 6.5 Hz, 1H), 4.45 (s, 2H), 4.65 (d, J=11.9 Hz, 1H), 4.79 (d, J=11.9 Hz, 1H), 4.97 (dd, J=3.7 and 8.1 Hz, 1H), 7.29-7.52 (m, 5H); $^{13}$C NMR (125 MHz, CDCl$_3$) δ 5.3, 7.3, 10.9, 14.9, 21.3, 22.6, 28.4, 35.9, 41.1, 42.7, 53.7, 71.9, 73.7, 75.7, 80.1, 80.9, 95.1, 127.9, 128.0, 128.7, 138.6, 154.3, 171.7, 215.7; IR (film, NaCl, cm$^{-1}$) 2956, 2876, 1732, 1694, 1456, 1366, 1257, 1154, 1098, 988, 835, 774, 741; LRMS (ESI) calcd for C$_{33}$H$_{53}$O$_8$SiCl$_3$Na [M+Na$^+$] 733.2, found 733.3. $[α]^{23}_D$=−16.1 (c=0.1, CHCl$_3$).

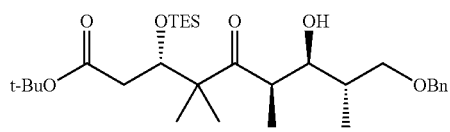

9-Benzyloxy-3-(diethylmethylsilanyloxy)-7-hydroxy-4,4,6,8-tetramethyl-5-oxo-nonanoic acid tert-butyl ester (71a)

To a solution of 71 (22.9 mg, 3.2 μmol) in 1:1 THF/AcOH (1.4 mL) was added Zn (5.0 mg, 7.8 μmol, nanosize). The mixture was sonicated for 15 min. More Zn (5.0 mg, 7.8 μmol, nanosize) was added, followed by sonication for a further 15 min. The suspension was filtered through a celite pad, washing with EtOAc several times. The filtrates were washed with sat. NaHCO$_3$, brine, dried over MgSO$_4$ and concentrated under vacuum. The crude residue was passed through a short plug of silica gel eluting with hexane/EtOAc 4:1 to give 17.1 mg (99% yield) of 71a as colorless oil: $^1$H NMR (400 MHz, CDCl$_3$) δ (m, 6H), 0.96 (t, J=7.9 Hz, 9H), 0.97 (d, J=6.8 Hz, 3H), 1.05 (d, J=6.8 Hz, 3H), 1.11 (s, 3H), 1.26 (s, 3H), 1.44 (s, 9H), 1.84-1.90 (m, 1H), 2.21 (dd, J=6.7 and 17.0 Hz, 1H), 2.36 (dd, J=6.7 and 17.0 Hz, 1H), 3.24-3.29 (m, 1H), 3.44-3.52 (m, 2H), 3.67 (dd, J=3.9 and 8.9 Hz, 1H), 4.36 (dd, J=3.5 and 6.5 Hz, 1H), 4.50 (d, J=12.0 Hz, 1H), 4.54 (d, J=12.0 Hz, 1H), 7.32-7.36 (m, 5H); $^{13}$C NMR (100 MHz, CDCl$_3$) δ 5.0, 6.9, 9.7, 13.9, 20.2, 21.8, 28.0, 36.3, 40.8, 41.5, 53.7, 72.5, 72.9, 73.2, 73.6, 80.7, 127.4, 127.5, 128.2, 138.6, 171.0, 221.4; IR (film, NaCl, cm$^{-1}$) 3502, 2959, 2875, 1731, 1683, 1456, 1366, 1154, 1098, 996, 739; LRMS (ESI) calcd for C$_{30}$H$_{52}$O$_6$SiCl$_3$Na [M+Na$^+$] 559.3, found 559.3; $[α]^{23}_D$=−41.0 (c=0.4, CHCl$_3$).

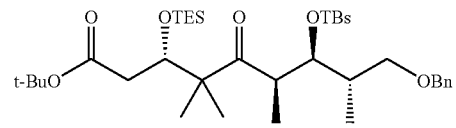

9-Benzyloxy-7-(tert-butyldimethylsilanyloxy)-3-(diethylmethylsilanyloxy)-4,4,6,8-tetramethyl-5-oxo-nonanoic acid tert-butyl ester (36)

To a solution of 71a (4.1 mg, 7.6 μmol) and 2,6-lutidine (10.0 μL, 43.5 mmol) in CH$_2$Cl$_2$ (0.2 mL) at −78° C. was added TBSOTf (10.0 μL, 85.8 mmol). After 2 h, more, 6-lutidine (10.0 μL, 43.5 mmol) and TBSOTf (10.0 μL, 85.8 mmol) were added. After 6 h, the mixture was diluted with sat aq NaHCO$_3$. The aqueous layer was extracted three times with EtOAc. The combined organic extracts were washed with brine, dried over MgSO$_4$ and concentrated under reduced pressure. The crude product was purified by flash chromatography (gradient hexane to hexane/EtOAc 91:9) to give 36 (5.4 mg, 82%) as a clear oil. Spectroscopic data agreed well with the reported values.

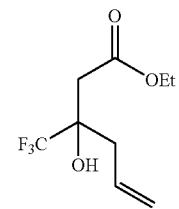

Alcohol 83. To a solution of ethyl 4,4,4-trifluoroacetoacetate (24.0 mL, 0.164 mol) in THF-water (3:1=V:V, 320 mL) at room temperature were added allyl bromide (20.0 mL, 1.4 equiv) and indium (powder, −100 mesh, 25 g, 1.3 equiv) and the resulting mixture was stirred at 48° C. for 15 h. The reaction mixture was cooled to room temperature, quenched with 2 N aq. HCl (400 mL) and extracted with CH$_2$Cl$_2$ (400 mL, 2×200 mL). Combined organics were dried (MgSO$_4$), filtered, and concentrated in vacuo. Flash chromatography (hexanes→hexanes-ether 10:1→8:1→6:1→4:1) gave alcohol 83 as a clear oil (31.64 g, 85% yield): IR (film) 3426 (br m), 2986 (m), 1713 (s), 1377 (m), 1345 (m), 1301 (m), 1232 (m), 1173 (s), 1095 (m), 1023 (m), 927 (m) cm$^{-1}$; $^1$H NMR (400 MHz, CDCl$_3$) δ 5.82 (m, 1H), 5.15 (m, 3H), 4.17 (m, 2H), 2.59 (m, 1H), 2.58 (d, J=3.4 Hz, 2H), 2.29 (dd, J=14.2, 8.6 Hz, 1H), 1.24 (t, J=7.2 Hz, 3H); $^{13}$C NMR (100 MHz, CDCl$_3$) δ 172.08, 130.89, 125.65 (q, J=280 Hz), 120.27, 73.79 (q, J=28 Hz), 61.55, 38.97, 35.65, 13.82; high resolution mass spectrum m/z 227.0895 [(M+H)$^+$; calcd for C$_9$H$_{14}$O$_3$F$_3$: 227.0895].

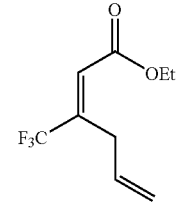

Ester 84. A mixture of alcohol 83 (16.71 g, 0.07386 mol) and pyridine (15.0 mL, 2.5 equiv) was cooled to −10° C. and treated with thionyl chloride (11.3 mL, 2.1 equiv) slowly over 11 min. The resulting mixture was warmed to 55° C. and stirred for 12 h. The reaction mixture was cooled to −5° C., quenched with water (200 mL) and extracted with CH$_2$Cl$_2$ (2×200 mL, 2×150 mL). Combined organics were washed with saturated NaHCO$_3$ (2×200 mL), and brine (200 mL), dried (MgSO$_4$), and concentrated in vacuo. Flash chromatography (pentane:ether 15:1) afforded ester 84 (11.90 g, 77% yield) as yellow oil: IR (film) 2986 (w), 1731 (s), 1308 (s), 1265 (w), 1227 (m), 1197 (s), 1133 (s), 1025 (m), 920 (w), 896 (w) cm$^{-1}$; $^1$H NMR (400 MHz, CDCl$_3$) δ 6.36 (s, 1H), 5.79 (ddt, J=16.9, 10.2, 6.6 Hz, 1H), 5.15 (dd, J=17.1, 1.5 Hz, 1H), 5.08 (dd, J=10.0, 1.4 Hz, 1H), 4.22 (q, J=7.1 Hz, 2H), 3.44 (d, J=6.5 Hz, 2H), 1.29 (t, J=7.1 Hz, 3H); $^{13}$C NMR (100 MHz, CDCl$_3$) δ 164.22, 143.37 (q, J=29 Hz), 132.71, 123.21 (q, J=274 Hz), 122.60 (q, J=6 Hz), 117.32, 60.85, 30.54, 13.85; high resolution mass spectrum m/z 209.0788 [(M+H)$^+$; calcd for C$_9$H$_{12}$O$_2$F$_3$: 209.0789].

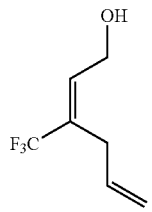

85

Alcohol 85. To a cooled (–75° C.) solution of ester 84 (7.12 g, 0.0342 mol) in CH$_2$Cl$_2$ (120 mL) was added a solution of DIBAL-H (75 mL, 2.2 equiv) in CH$_2$Cl$_2$ (1.0 M) and the resulting mixture was warmed to room temperature over 3 h. The reaction mixture was cooled to 0° C., quenched with saturated NH$_4$Cl (12 mL) and stirred at room temperature for 20 min. The reaction mixture was diluted with ether (200 mL), dried (MgSO$_4$), and concentrated in vacuo. Flash chromatography (pentane:ether 3:1→1:1) provided alcohol 85 (5.68 g, 99%) as clear oil: IR (film) 3331 (br s), 2929 (m), 1642 (m), 1445 (m), 1417 (w), 1348 (s), 1316 (s), 1217 (s), 1175 (s), 1119 (s), 1045 (m), 985 (s), 921 (m), 831 (w) cm$^{-1}$; $^1$H NMR (400 MHz, CDCl$_3$) δ 6.33 (td, J=6.1, 1.6 Hz, 1H), 5.75 (ddt, J=17.2, 10.0, 6.2 Hz, 1H), 5.07 (m, 2H), 4.29 (ddd, J=6.3, 4.3, 2.1 Hz, 2H), 2.95 (d, J=6.2 Hz, 2H); $^{13}$C NMR (100 MHz, CDCl$_3$) δ 134.45 (q, J=6 Hz), 133.38, 127.97 (q, J=29 Hz), 123.76 (q, J=271 Hz), 116.25, 57.87, 29.79

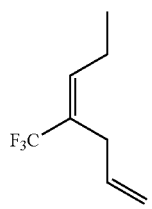

86

Iodide 86. A cooled (0° C.) solution of alcohol 85 (5.97 g, 0.0358 mol) in CH$_2$Cl$_2$ (50 mL) was treated with PPh$_3$ (11.17 g, 1.2 equiv), imidazole (3.55 g, 1.5 equiv) and I$_2$ (9.10 g, 1.1 equiv) and the resulting mixture was stirred at 0° C. for 10 min. The reaction mixture was quenched with satureted Na$_2$S$_2$O$_3$-saturated NaHCO$_3$ (1:1=V:V, 200 mL) and extracted with pentane (3×200 mL). Combined organics were washed with satureted Na$_2$S$_2$O$_3$-saturated NaHCO$_3$ (1:1=V:V, 200 mL), and brine (100 mL), dried (MgSO$_4$), and concentrated in vacuo. Flash chromatography (pentane) gave iodide 86 (6.69 g, 68%) as pale red oil: (IR Ifilm) 3083 (w), 2982 (w), 1636 (w), 1558 (w), 1456 (w), 1367 (w), 1317 (s), 1216 (m), 1181 (s), 1151 (s), 1120 (s), 989 (m), 921 (m), 896 (m) cm$^{-4}$; $^1$H NMR (400 MHz, CDCl$_3$) δ 6.45 (td, J=8.9, 1.5 Hz, 1H), 5.79 (ddt, J=16.8, 10.3, 6.2 Hz, 1H), 5.12 (m, 2H), 3.85 (ddd, J=8.9, 2.9, 1.4 Hz, 2H), 3.00 (dt, J=6.1, 1.4 Hz, 2H); $^{13}$C NMR (100 MHz, CDCl$_3$) δ 132.42, 131.64 (q, J=6 Hz), 129.63 (q, J=29 Hz), 123.64 (q, J=272 Hz), 117.00, 29.32, –4.27; low resolution mass spectrum m/z 298.7 [(M+Na)$^+$; calcd for C$_7$H$_8$F$_3$INa: 299.0].

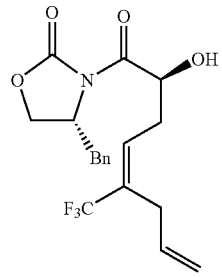

88

α-Hydroxyoxazolidinone 88. To a cooled (–78° C.) of TES protected 4-Benzyl-3-hydroxy acetyl-oxazolidin-2-one 7 (16.28 g, 1.92 equiv) in THF (160 mL) was added a solution of LHMDS (42.0 mL, 1.73 equiv) in THF (1.0 M) dropwise over 51 min and the resulting mixture was stirred at –78° C. for 35 min. The reaction mixture was treated with a solution of iodide 86 (6.69 g, 24.2 mmol) in THF (10 mL) and the resulting mixture was allowed to warm to room temperature slowly overnight. The reaction mixture was quenched with saturated NaHCO$_3$ (200 mL) and extracted with EtOAc (3×200 mL). Combined organics were washed with saturated NH$_4$Cl (150 mL), brine (150 mL), dried (MgSO$_4$), and concentrated in vacuo. Flash chromatography (hexanes-EtOAc 6:1→3:1) provided a mixture of alkylation products (13.6 g) which were used for the next reaction without further purification. A solution of the alkylation products in HOAc-water-THF (3:1:1=V:V:V, 200 mL) was stirred at room temperature for 4 h. The reaction mixture was concentrated in vacuo to remove HOAc, quenched with saturated NaHCO$_3$ (400 mL), and extracted with EtOAc (3×200 mL). Combined organics were dried (MgSO$_4$), and concentrated in vacuo. Flash chromatography (hexanes:EtOAc 3:1->2:1) provided α-hydroxy-oxazolidinone 88 (7.55 g, 81% yield for two steps) as clear oil: [α]$_D^{25}$ –48.2 (c 1.08, CHCl$_3$); IR (film) 3486 (br s), 3030 (m), 2983 (s), 2925 (m), 1790 (s), 1682 (s), 1481 (m), 1393 (m), 1360 (m), 1217 (m), 1171 (m), 1113 (m), 992 (m), 919 (m), 847 (w) cm$^{-1}$; $^1$H NMR (400 MHz, CDCl$_3$) δ 7.32 (m, 3H), 7.17 (m, 2H), 6.33 (td, J=7.2, 1.5 Hz, 1H), 5.77 (ddt, J=16.6, 10.1, 6.2 Hz, 1H), 5.08 (m, 3H), 4.74 (ddt, J=4.8, 3.7, 4.4 Hz, 1H), 4.33 (dd, J=8.6, 8.6 Hz, 1H), 4.26 (dd, J=9.2, 3.4 Hz, 1H), 3.42 (br d, J=6.4 Hz, 1H), 3.24 (dd, J=13.5, 3.4 Hz, 1H), 2.99 (m, 2H), 2.79 (dd, J=13.5, 9.4 Hz, 1H), 2.70 (m, 1H), 2.50 (m, 1H); $^{13}$C NMR (125 MHz, CDCl$_3$) δ 173.93, 153.05, 134.43, 133.64, 129.98 (q, J=6 Hz), 129.82 (q, J=28 Hz), 129.29, 120.01, 127.58, 124.00 (q, J=272 Hz), 116.34, 69.60, 67.31, 54.95, 37.78, 32.29, 29.84; high resolution mass spectrum m/z 384.1421 [(M+H)$^+$; calcd for C$_{19}$H$_{21}$NO$_4$F$_3$: 384.1423].

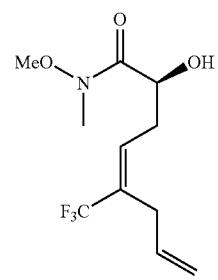

89

α-Hydroxyamide 89. A suspension of (MeO)NHMe.HCl (10.1 g, 5.25 equiv) in THF (100 mL) at 0° C. was treated with a solution of AlMe$_3$ (50 mL, 5.1 equiv) in toluene (2.0 M) dropwise and the resulting clear solution was stirred at room temperature for 34 min, then added to a cooled (0° C.) solution of α-hydroxyoxazolidinone 88 (7.55 g, 19.7 mmol) in THF (70 mL). The resulting mixture was warmed to room temperature and stirred for 12 h. The reaction mixture was cooled to 0° C., quenched by slow addition of 1N aq. Tartaric acid (100 mL), stirred at room temperature for 25 min, and extracted with EtOAc (3×200 mL). Combined organics were dried (MgSO$_4$), and concentrated in vacuo. Flash chromatography (hexanes:EtOAc 2:1→1:1) gave α-hydroxyamide 89 (5.12 g, 97% yield) as clear oil: $[α]_D^{25}$ −57.2 (c 1.03, CHCl$_3$); IR (film) 3432 (br s), 3084 (w), 2980 (m), 2943 (m), 1652 (s), 1464 (m), 1373 (m), 1318 (m), 1214 (m), 1171 (m), 1112 (m), 991 (m), 919 (m), 818 (w) cm$^{-1}$; $^1$H NMR (400 MHz, CDCl$_3$) δ 6.32 (td, J=7.3, 1.5 Hz, 1H), 5.74 (ddt, J=16.9, 10.3, 6.1 Hz, 1H), 5.05 (m, 2H), 4.43 (dd, J=7.6, 3.5 Hz, 1H), 3.70 (s, 3H), 3.35 (br s, 1H), 3.24 (s, 3H), 2.94 (d, J=6.1 Hz, 2H), 2.59 (m, 1H), 2.36 (m, 1H); $^{13}$C NMR (100 MHz, CDCl$_3$) δ 173.43, 133.68, 130 59 (q, J=6 Hz), 129.25 (q, J=28 Hz), 124.05 (q, J=271 Hz), 116.17, 67.57, 61.44, 32.56, 32.38, 29.75; high resolution mass spectrum m/z 268.1161 [(M+H)$^+$; calcd for C$_{11}$H$_{17}$NO$_3$F$_3$: 268.1161].

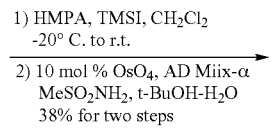

90

α-Hydroxyketone 90. To a cooled (0° C.) solution of α-hydroxyamide 89 (4.87 g, 18.2 mmol) in THF (150 mL) was added a solution of MeMgBr (75 mL, 12 equiv) in ether (3.0 M). After 5 min, the reaction mixture was quenched with saturated NH$_4$Cl (250 mL), and extracted with EtOAc (5×200 mL). Combined organics were dried (MgSO$_4$), and concentrated in vacuo. Flash chromatography (hexanes:EtOAc 4:1→2:1→1:2) provided α-hydroxyketone 90 (2.16 g, 53% yield, 73% yield based on the recovered starting material) as clear oil and the starting material α-hydroxyamide 89 (1.30 g, 27% yield): $[α]_D^{25}$ +58.5 (c 1.30, CHCl$_3$); IR (film) 3460 (br s), 3085 (w), 2984 (m), 2926 (m), 1716 (s), 1679 (m), 1641 (m), 1417 (m), 1361 (m), 1319 (s), 1247 (m), 1216 (s), 1172 (s), 1113 (s), 1020 (m), 994 (m), 968 (w), 919 (m) cm$^{-1}$; $^1$H NMR (500 MHz, CDCl$_3$) δ 6.21 (t, J=7.0 Hz, 1H), 5.75 (ddt, J=16.7, 10.4, 6.2 Hz, 1H), 5.07 (m, 2H), 4.26 (dt, J=7.1, 4.5 Hz, 1H), 3.51 (d, J=4.7 Hz, 1H), 2.96 (d, J=6.1 Hz, 2H), 2.66 (m, 1H), 2.42 (m, 1H), 2.19 (s, 3H); $^{13}$C NMR (100 MHz, CDCl$_3$) δ 208.53, 133.43, 129.80 (q, J=28 Hz), 129.76 (q, J=6 Hz), 123.85 (q, J=271 Hz), 116.32, 75.36, 31.22, 29.81, 25.11; high resolution mass spectrum m/z 223.0945 [(M+H)$^+$; calcd for C$_{10}$H$_{14}$NO$_2$F$_3$: 223.0946].

Example 8

Catalytic Asymmetric Oxidation Approach

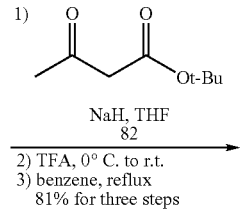

86

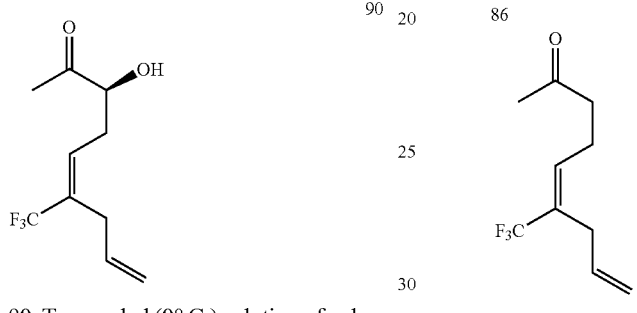

93

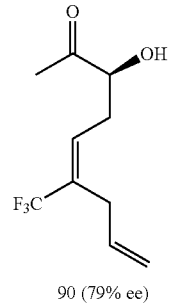

90 (79% ee)

Example 9

Synthesis of 21-amino-26-trifluoro-(E)-9,10-dehydro-dEpoB

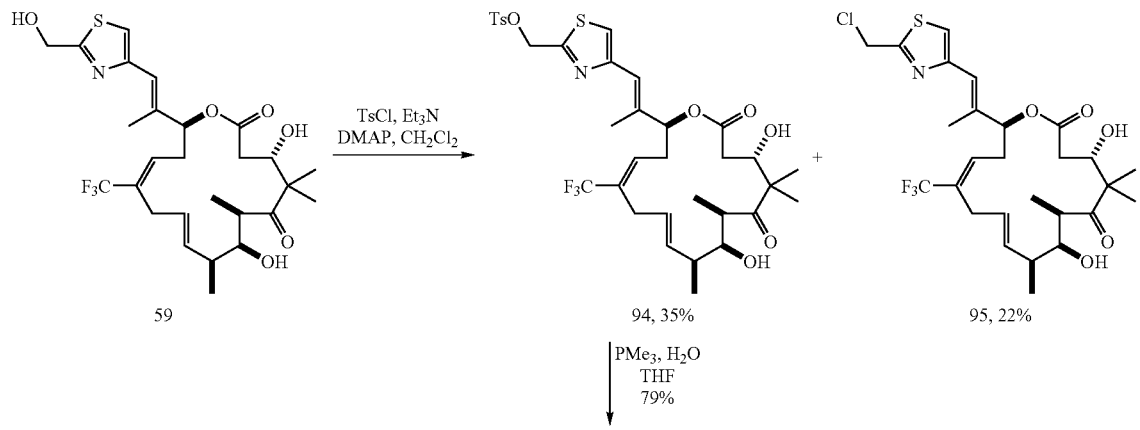

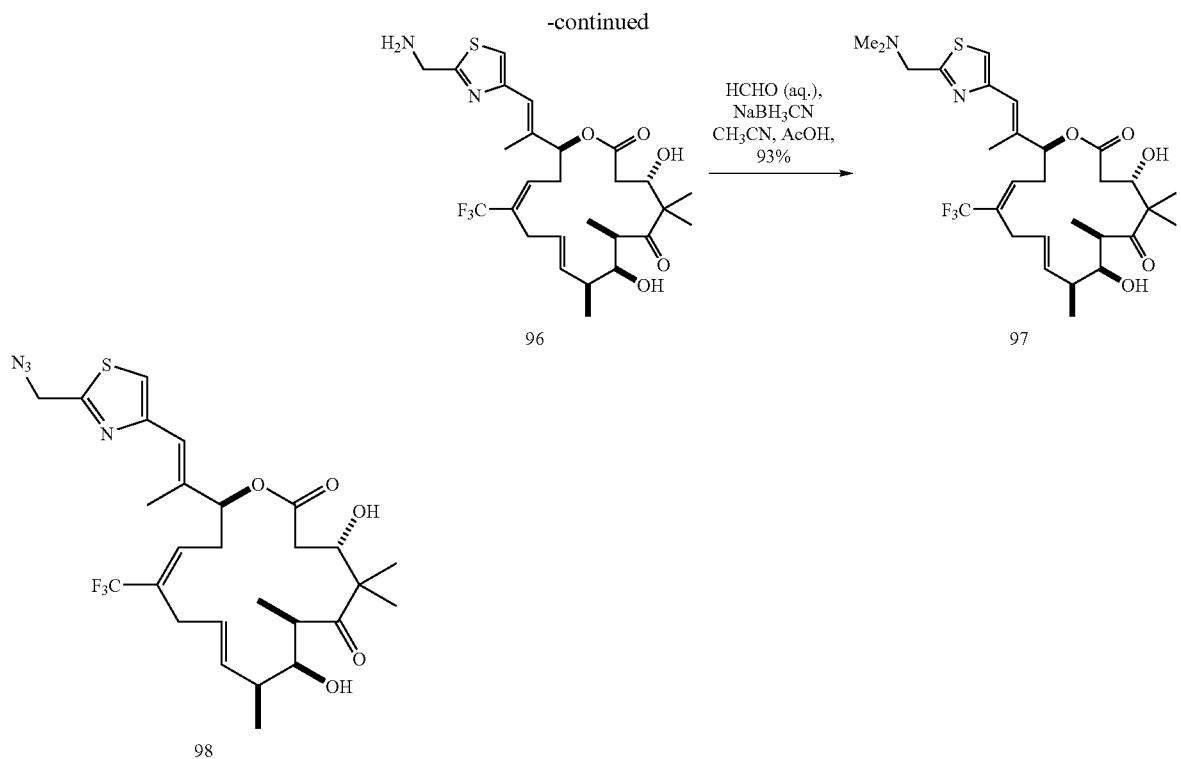

Compound 98:

To a solution of 59 (50.4 mg, 90.1 μmol) in THF (1 mL) was added (PhO)$_2$PON$_3$ (27.2 μL, 126 μmol) at 0° C. After stirring at 0° C. for 5 min, DBU (16.2 μL, 108 μmol) was added. After stirring at 0° C. for 2 h, the mixture was stirred at rt for 20.5 h. The reaction mixture was diluted with EtOAc and quenched by addition of water (2 mL). After the layers were separated, the aqueous layer was extracted with EtOAc (three times), and the combined organic layers were dried over Na$_2$SO$_4$. After concentrating, the residue was dried under high vacuum for 10 min to remove DBU. Purification by flash column chromatography (SiO$_2$, hexane/EtOAc=3:2) gave azide 98 (45.6 mg, 78.0 μmol, 87%) as a colorless solid;

$[\alpha]_D^{24}$ −60.3 (c 0.345, CHCl$_3$); IR (film) ν 3492, 2975, 2931, 2105, 1732, 1688, 1319, 1248, 1169, 1113, 982, 733 cm$^{-1}$; $^1$H NMR (400 MHz, CDCl$_3$) δ 1.05 (3H, s), 1.12 (3H, d, J=7.0 Hz), 1.23 (3H, d, J=6.8 Hz), 1.33 (3H, s), 2.01 (1H, d, J=5.5 Hz, OH), 2.17 (3H, s), 2.25-2.35 (1H, m), 2.41 (1H, dd, J=15.5, 3.2 Hz), 2.49 (1H, dd, J=15.5, 9.5 Hz), 2.54-2.60 (1H, m), 2.66 (1H, d, J=6.0 Hz), 2.65-2.76 (1H, m), 2.96 (1H, dd, J=16.0, 4.2 Hz), 3.03 (1H, dd, J=16.1, 6.7 Hz), 3.11 (1H, quintet, J=6.8 Hz), 3.71-3.76 (1H, m), 4.31 (1H, ddd, J=9.2, 5.9, 3.2 Hz), 4.65 (2H, s), 5.43 (1H, dd, J=6.0, 4.3 Hz), 5.58 (1H, ddd, J=15.8, 6.4, 4.6 Hz), 5.66 (1H, dd, J=15.8, 6.1 Hz), 6.23 (1H, t, J=7.3 Hz), 6.63 (1H, s), 7.18 (1H, s); $^{13}$C NMR (100 MHz, CDCl$_3$) δ 15.4, 15.9, 17.8, 18.6, 22.8, 28.7, 30.9, 39.5, 39.7, 45.1, 51.3, 53.5, 71.5, 75.4, 76.8, 118.2, 119.6, 122.7 [$^1$J (C,F)=273.6 Hz], 127.9, 130.0 [$^3$J (C,F)=6.1 Hz], 130.6 [$^2$J (C,F)=27.9 Hz], 132.3, 137.2, 153.1, 163.9, 170.0, 218.3; LRMS (ESI) calcd for C$_{27}$H$_{35}$F$_3$N$_4$O$_5$SNa [M+Na$^+$] 607.2, found 607.2.

Compound 96:

To a solution of azide 98 (21.0 mg, 35.9 μmol) in THF (0.6 mL) was added PMe$_3$ (1.0 M in THF, 43.1 μL, 43.1 μmol). After stirring at rt for 2 min, water (0.1 mL) was added and the mixture was stirred at rt for 3 h. PMe$_3$ (1.0 M in THF, 7.2 μL, 7.2 μmol) was added and the mixture was stirred at rt for 1.5 h. To the mixture was added 28% NH$_4$OH (aq.) (54.5 μL). After stirring for 1 h, the mixture was directly purified by preparative TLC (CH$_2$Cl$_2$/MeOH=100:7.5) to give amine 96 (15.9 mg, 28.5 μmol, 79%) as a colorless solid;

$[\alpha]_D^{26}$ −64.2 (c 0.815, CHCl$_3$); IR (film) ν 3504, 3363, 2975, 2931, 1733, 1688, 1450, 1383, 1318, 1248, 1169, 1113, 1054, 984, 736 cm$^{-1}$; $^1$H NMR (400 MHz, CDCl$_3$) δ 1.05 (3H, s), 1.12 (3H, d, J=7.0 Hz), 1.23 (3H, d, J=6.8 Hz), 1.34 (3H, s), 2.12 (3H, d, J=0.7 Hz), 2.24-2.35 (1H, m), 2.39 (1H, dd, J=15.4, 3.0 Hz), 2.49 (1H, dd, J=15.4, 9.8 Hz), 2.54-2.63

(1H, m), 2.66-2.76 (1H, m), 2.97 (1H, dd, J=16.2, 4.2 Hz), 3.03 (1H, dd, J=16.3, 6.5 Hz), 3.10 (1H, quintet, J=6.8 Hz), 3.74 (1H, dd, J=6.7, 3.5 Hz), 4.18 (2H, s), 4.34 (1H, dd, J=9.8, 2.9 Hz), 5.43 (1H, dd, J=6.0, 4.3 Hz), 5.55-5.64 (1H, m), 5.67 (1H, dd, J=15.9, 5.8 Hz), 6.24 (1H, brt, J=7.3 Hz), 6.66 (1H, s), 7.10 (1H, s); $^{13}$C NMR (100 MHz, CDCl$_3$) δ 15.3, 16.1, 17.7, 18.2, 22.6, 28.7, 30.9, 39.4, 39.7, 43.9, 45.1, 53.8, 71.2, 75.3, 76.6, 116.8, 120.1, 124.2 [$^1$J (C,F)=273.5 Hz], 127.8, 130.2 [$^3$J (C,F)=6.1 Hz], 130.4 [$^2$J (C,F)=28.6 Hz], 132.2, 136.6, 152.3, 170.1, 172.7, 218.4; LRMS (ESI) calcd for $C_{27}H_{38}F_3N_2O_5S$ [M+H$^+$] 559.2, found 559.2.

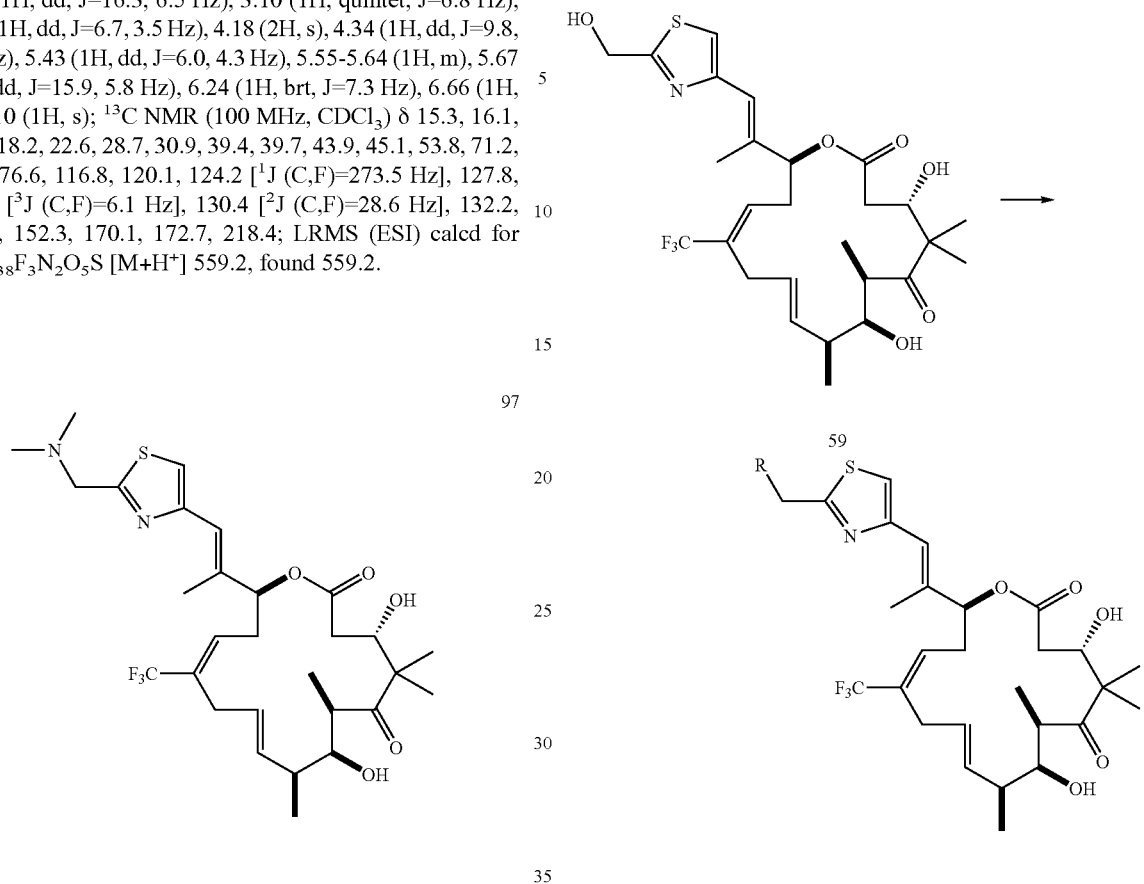

97

Compound 97:

To a solution of amine 96 (15.9 mg, 28.5 µmol) in CH$_3$CN (0.78 mL) was added 37% HCHO (aq.) (31.4 µL, 0.143 mmol) followed by NaBH$_3$CN (1.0 M in THF, 85.5 µL, 85.5 µmol), and the mixture was stirred at rt for 20 min. AcOH (1 drop) was added, and the mixture was stirred at rt for 40 min. The mixture was purified directly by preparative TLC (CH$_2$Cl$_2$/MeOH=100:8) to give the product 97 (15.6 mg, 26.6 µmol, 93%) as a colorless solid;

[α]$_D^{24}$ −49.9 (c 0.74, CHCl$_3$); IR (film) ν 3424, 2974, 1729, 1689, 1468, 1318, 1247, 1169, 1112, 754 cm$^{-1}$; $^1$H NMR (400 MHz, CDCl$_3$) δ 1.05 (3H, s), 1.12 (3H, d, J=6.9 Hz), 1.23 (3H, d, J=6.8 Hz), 1.33 (3H, s), 2.17 (3H, s), 2.24-2.35 (1H, m), 2.43 (1H, dd, J=15.7, 3.6 Hz), 2.49 (1H, dd, J=15.6, 9.1 Hz), 2.55-2.64 (2H, m, including OH), 2.68-2.77 (1H, m), 2.80 (3H, s), 2.81 (3H, s), 2.92-3.06 (2H, m), 3.10 (1H, quintet, J=6.8 Hz), 3.69-3.76 (1H, m), 4.25-4.34 (1H, m), 4.33 (2H, s), 5.42 (1H, t, J=5.5 Hz), 5.57 (1H, dt, J=15.8, 6.3 Hz), 5.66 (1H, dd, J=15.7, 6.4 Hz), 6.22 (1H, brt, J=7.2 Hz), 6.64 (1H, s), 7.30 (1H, s); $^{13}$C NMR (100 MHz, CDCl$_3$) δ 15.3, 15.8, 17.8, 18.8, 22.3, 28.8, 30.9, 39.6, 39.6, 45.2, 49.7, 49.7, 53.4, 61.5, 71.7, 75.4, 77.4, 119.2, 120.2, 124.2 [$^1$J (C,F)=273.5 Hz], 127.8, 129.9 [$^3$J (C,F)=6.2 Hz], 130.7 [$^2$J (C,F)=28.4 Hz], 132.4, 137.6, 154.2, 157.2, 170.0, 218.7; LRMS (ESI) calcd for $C_{29}H_{42}F_3N_2O_5S$ [M+H$^+$] 580.3, found 580.2.

Compounds 94 and 95:

To a mixture of 59 (18.9 mg, 33.8 µmol) and Et$_3$N (18.8 µL, 0.135 mmol) in CH$_2$Cl$_2$ (1 mL) was added TsCl (12.9 mg, 67.5 µmol) and DMAP (2.1 mg, 16.9 µmol) at 0° C. After stirring at rt for 1.5 h, the mixture was diluted with EtOAc and filtered through a pad of silica gel (EtOAc rinse). After concentrating, the residue was purified by preparative TLC (hexane/EtOAc=1:1) to give tosylate 94 (8.5 mg, 11.9 µmol, 35%) and chloride 95 (4.3 mg, 7.44 µmol, 22%); both as colorless solids;

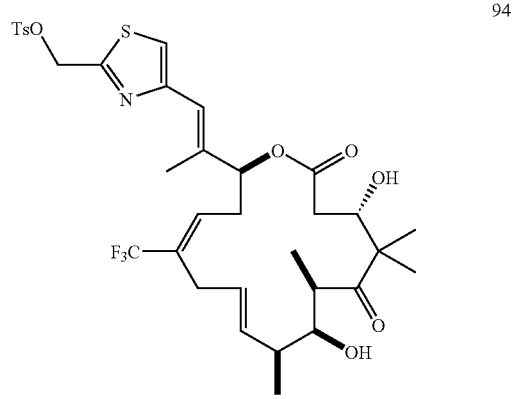

$^1$H NMR (400 MHz, CDCl$_3$) δ 1.06 (3H, s), 1.12 (3H, d, J=7.0 Hz), 1.23 (3H, d, J=6.7 Hz), 1.33 (3H, s), 1.99 (1H, d, J=5.5 Hz), 2.10 (3H, s), 2.25-2.34 (1H, m) 2.41 (1H, dd, J=15.5, 3.3 Hz), 2.47 (3H, s), 2.48 (1H, dd, J=15.7, 9.4 Hz), 2.51-2.63 (1H, m), 2.63 (1H, d, J=6.1 Hz, OH), 2.64-2.75 (1H, m), 2.91-3.05 (2H, m), 3.10 (1H, quintet, J=6.8 Hz), 3.70-3.75 (1H, m), 4.30 (1H, ddd, J=9.3, 6.1, 3.2 Hz), 5.32 (2H, s), 5.41 (1H, dd, J=5.8, 4.5 Hz), 5.57 (1H, ddd, J=15.8, 6.4, 4.6 Hz), 5.65 (1H, dd, J=15.8, 6.0 Hz), 6.21 (1H, t, J=7.1 Hz), 6.59 (1H, s), 7.18 (1H, s), 7.37 (2H, d, J=8.1 Hz), 7.84 (2H, d, J=8.3 Hz); LRMS (ESI) calcd for C$_{34}$H$_{42}$F$_3$NO$_8$S$_2$Na [M+Na$^+$] 736.2, found 736.3.

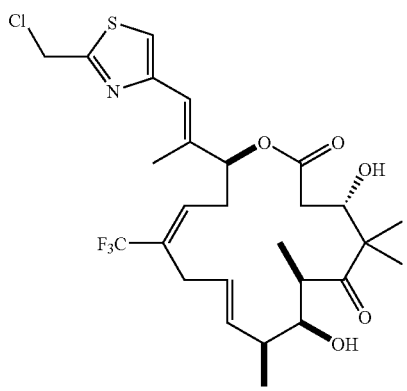

95

IR (film) ν 3494, 2975, 2935, 1734, 1689, 1319, 1248, 1170, 1113, 1040, 979, 738 cm$^{-1}$; $^1$H NMR (400 MHz, CDCl$_3$) δ 1.06 (3H, s), 1.12 (3H, d, J=6.9 Hz), 1.23 (3H, d, J=6.7 Hz), 1.34 (3H, s), 2.00 (1H, d, J=5.6 Hz, OH), 2.15 (3H, s), 2.25-2.35 (1H, m), 2.41 (1H, dd, J=15.5, 3.2 Hz), 2.49 (1H, dd, J=15.5, 9.4 Hz), 2.53-2.62 (1H, m), 2.69 (1H, d, J=6.1 Hz, OH), 2.66-2.76 (1H, m), 2.92-3.05 (2H, m), 3.11 (1H, quintet, J=6.4 Hz), 3.70-3.76 (1H, m), 4.32 (1H, ddd, J=9.2, 5.9, 3.1 Hz), 4.85 (2H, s), 5.43 (1H, dd, J=6.0, 4.4 Hz), 5.59 (1H, ddd, J=15.9, 6.4, 4.5 Hz), 5.66 (1H, dd, J=15.9, 6.1 Hz), 6.23 (1H, t, J=6.8 Hz), 6.63 (1H, s), 7.20 (1H, s); LRMS (ESI) calcd for C$_{27}$H$_{35}$ClF$_3$NO$_5$SNa [M+Na$^+$] 600.2, found 600.2.

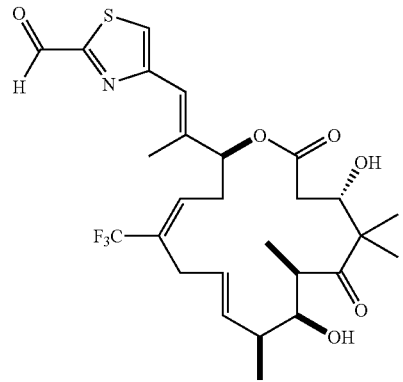

99

Compound 99 (not Shown):

To a solution of 59 (6.9 mg, 12.3 μmol) in CH$_2$Cl$_2$ (0.4 mL) was added activated MnO$_2$ (purchased from Acros, 26.8 mg, 0.308 mmol). After vigorously stirring at rt for 4 h, the mixture was filtered through a pad of Celite, which was rinsed with EtOAc. After concentrating, the residue was purified by preparative TLC (hexane/EtOAc=1:1) to give aldehyde 99 (2.7 mg, 4.84 μmol, 39%) as a colorless solid;

$^1$H NMR (400 MHz, CDCl$_3$) δ 1.06 (3H, s), 1.13 (3H, d, J=7.2 Hz), 1.24 (3H, d, J=6.9 Hz), 1.35 (3H, s), 1.96 (1H, d, J=5.6 Hz, OH), 2.22 (3H, d, J=0.7 Hz), 2.25-2.35 (1H, m), 2.44 (1H, dd, J=15.4, 3.5 Hz), 2.46 (1H, d, J=5.9 Hz, OH), 2.51 (1H, dd, J=15.7, 9.3 Hz), 2.57-28 (1H, m), 2.68-2.79 (1H, m), 2.96-3.03 (2H, m), 3.10 (1H, quintet, J=6.8 Hz), 3.71-3.76 (1H, m), 4.31 (1H, ddd, J=9.4, 6.3, 3.5 Hz), 5.45 (1H, t, J=5.0 Hz), 5.53-5.63 (1H, m), 5.67 (1H, dd, J=15.7, 6.2 Hz), 6.24 (1H, t, J=6.6 Hz), 6.72 (1H, s), 7.57 (1H, d, J=0.9 Hz), 10.01 (1H, d, J=1.2 Hz); LRMS (ESI) calcd for C$_{27}$H$_{34}$F$_3$NO$_6$SNa [M+Na$^+$] 580.2, found 580.2.

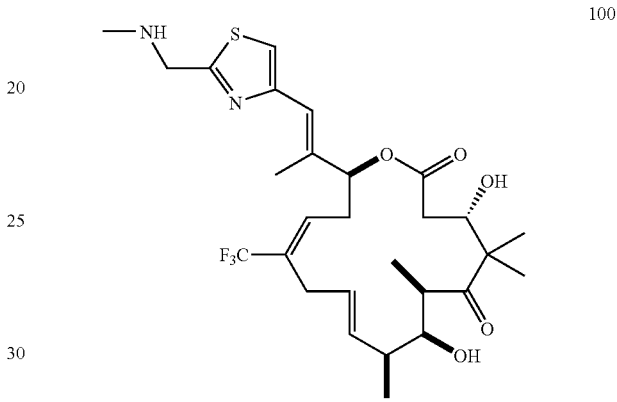

100

Compound 100:

To a solution of aldehyde 99 (4.6 mg, 8.25 μmol) in CH$_3$CN (0.5 mL) at 0° C. was added MeNH$_2$ (2.0 M in THF, 41.3 μL, 41.3 μmol). After stirring at 0° C. for 15 min, NaBH$_3$CN (1.0 M in THF, 25 μL, 25 μmol) was added. After stirring at 0° C. for 0.5 h, AcOH (3 drops) was added. After stirring at 0° C. for 2 h, 28% NH$_4$OH (aq.) (40 μL) was added, and the mixture was stirred at rt for 10 min. The mixture was directly purified twice by preparative TLC (CH$_2$Cl$_2$/MeOH=100:9) to give 100 (2.4 mg, 4.19 μmol, 51%) as a colorless solid;

$^1$H NMR (400 MHz, CDCl$_3$) δ 1.05 (3H, s), 1.12 (3H, d, J=7.0 Hz), 1.23 (3H, d, J=6.8 Hz), 1.34 (3H, s), 2.13 (3H, s), 2.25-2.34 (1H, m), 2.39 (1H, dd, J=15.3, 3.0 Hz), 2.49 (1H, dd, J=15.3, 9.7 Hz), 2.56 (3H, s), 2.54-2.64 (1H, m), 2.66-2.75 (1H, m), 2.89 (1H, d, J=5.1 Hz), 2.94-3.05 (2H, m), 3.11 (1H, quintet, J=6.8 Hz), 3.74 (1H, dd, J=6.6, 3.5 Hz), 4.08 (2H, s), 4.34 (1H, dd, J=9.6, 2.9 Hz), 5.43 (1H, dd, J=6.2, 4.1 Hz), 5.56-5.63 (1H, m), 5.66 (1H, dd, J=15.9, 5.7 Hz), 6.24 (1H, t, J=7.3 Hz), 6.66 (1H, s), 7.11 (1H, s); LRMS (ESI) calcd for C$_{28}$H$_{40}$F$_3$N$_2$O$_5$S [M+H$^+$] 573.3, found 573.3.

Example 10

Epothilone Analogs that Ablate Xenograft Tumors to a Non-Relapsable State

By a combination of chemical synthesis, molecular modeling, and spectroscopic analysis, we discovered that introduction of an E-9,10-double bond (see compound 28 below)

accomplishes ca. 10 fold enhancement of drug potency in xenograft experiments with drug resistive MX-1 tumors (A. Rivkin et al. *J. Am. Chem. Soc.* 2003, 125, 2899; incorporated herein by reference). Following correlation of in vitro and in vivo experiments directed to MX-1 tumor types, it was apparent that 28 is inherently more cytotoxic than 2b. However, another contributing factor is that the lactone moiety in the 9,10-dehydro series is significantly more stable in mouse and human plasma than is the case for 9,10-dehydro congeners. The sum of these two complementary effects was to render 28 capable of accomplishing complete suppression of tumor in a variety of xenografts at 3 mg/kg as opposed to 30 mg/kg regiment for 1.

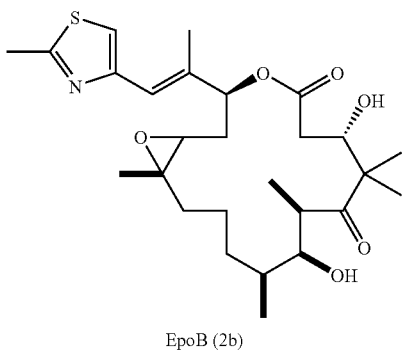

EpoB (2b)

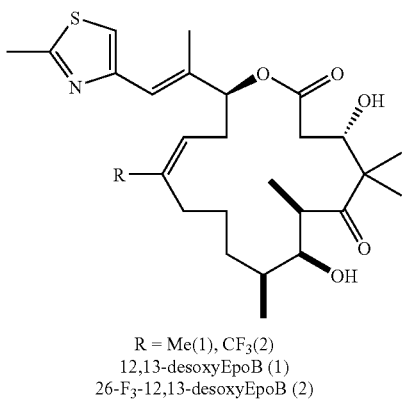

R = Me(1), CF$_3$(2)
12,13-desoxyEpoB (1)
26-F$_3$-12,13-desoxyEpoB (2)

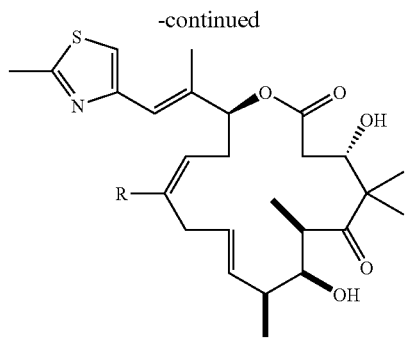

-continued

R = Me(28), CF$_3$(29)
(E)-9,10-dehydro-12,13-desoxyEpoB (28)
26-F$_3$-(E)-9,10-dehydro-12,13-desoxyEpoB (29)

Upon suspension of treatment, palpable tumors re-appear in some fraction of the animals. Accordingly, at least at present, fully synthetic 28 has not fully met the stringent standards of highly favorable effective therapeutic index and elimination of tumors to a non-relapsing state.

These findings directed our attention to the consequences of substituting the three hydrogens of the 26-methyl group of 28 with three fluorine atoms. Incorporation of the fluorine atoms at this site led to improved stability of the 12,13-double bond toward oxidation (Smart, B. E. *J. Fluorine Chem.* 2001, 109, 3; incorporated herein by reference). Previous experience had pointed toward some attenuation of cytotoxicity, by placement of polar groups in the area of the C12-C13 double bond (A. Rivkin et al. *J. Am. Chem. Soc.* 2003, 125, 2899; incorporated herein by reference). In this disclosure, we report the discovery, through total chemical synthesis, of the 9,10-dehydro-26-trifluoroepothilones, focusing particularly on the unique biological performance of parent structure 29.

The therapeutic efficacy of dEpoB (30 mg/kg), paclitaxel (20 mg/kg) and F$_3$-deH-dEpoB (29, 20 and 30 mg/kg) against human mammary carcinoma MX-1 xenografts in terms of tumor disappearance and relapse were closely studied, and the results are shown in Table 10-1. Each dose group consisted of four or more nude mice. Body weight refers to total body weight minus tumor weight. All three compounds achieved tumor disappearance. On day 10 after suspension of treatment, 5/10 (dEpoB), 2/7 (Paclitaxel), and 0/4 (compound 29) mice relapsed. Extended observation following suspension of treatment with 20 mg/kg dosages of 29 showed a long term absence of tumors until day 27 at which point 2 out of 4 mice's tumors relapsed. Remarkably, treatment with 30 mg/kg dosages of 29, resulted in complete tumor disappearance and the absence of any relapse for over two months after suspension of treatment.

TABLE 10-1

Therapeutic effect of dEpoB, Paclitaxel and F$_3$-deH-dEpoB against MX-1 xenograft in nude mice[a]

| | | Changes of body weight (%) | | | |
| --- | --- | --- | --- | --- | --- |
| Drug | Dosage (mg/kg) | On day 4 after stopping administration | On day 8 after stopping administration | Tumor free after Q2Dx6 6 hr-iv. Infusion | Tumor reappeared on day 10 after administration |
| dEpoB (1) | 30 | −25.3 ± 2.1 | −9.1 ± 4.1 | 10/10 | 5/10 |
| Paclitaxel | 20 | −23.9 ± 3.7 | −8.7 ± 0.7 | 7/7 | 2/7 |

TABLE 10-1-continued

Therapeutic effect of dEpoB, Paclitaxel and $F_3$-deH-dEpoB against MX-1 xenograft in nude mice[a]

| | | Changes of body weight (%) | | | |
|---|---|---|---|---|---|
| Drug | Dosage (mg/kg) | On day 4 after stopping administration | On day 8 after stopping administration | Tumor free after Q2Dx6 6 hr-iv. Infusion | Tumor reappeared on day 10 after administration |
| $F_3$-deH-dEpoB (29) | 20 | | | 4/4 | 0/4[b] |
| | 30 | −22.4 ± 0.6 | −7.3 ± 0.7 | 4/4 | 0/4[b] |
| | | −27.1 ± 2.7 | −17.4 ± 5.5 | | |

[a]Human mammary carcinoma MX-1 xenograft tissue 50 mg was implanted S.C. on Day 0. The treatment, Q2Dx6 6 hr-iv infusion was started on Day 8 and stopped on Day 18.
[b]Detectable tumor reappearance in 2/4 on 27th day after stopping treatment. No further tumor reappearance during the 28th-64th days after stopping treatment.
[c]No tumor reappearance during 64 days after stopping treatment when experiment terminated.

Figure 57:
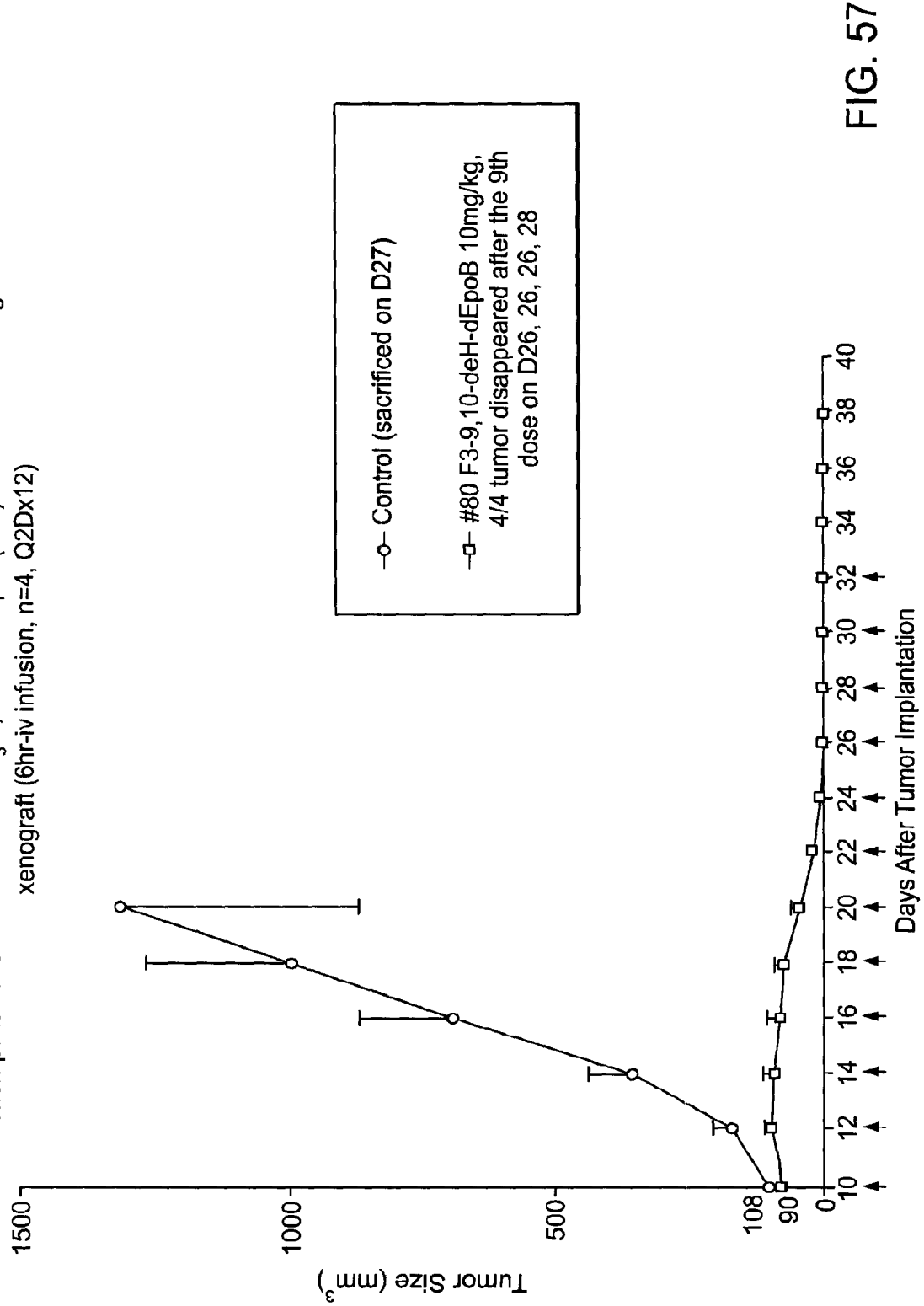
FIG. 57 shows the therapeutic effect at low doses of 26-trifluoro-9,10-dehydro-dEpoB in nude mice bearing MX-1 xenograft (6 hr.-i.v. infusion, Q2Dx12).
Figure 58:
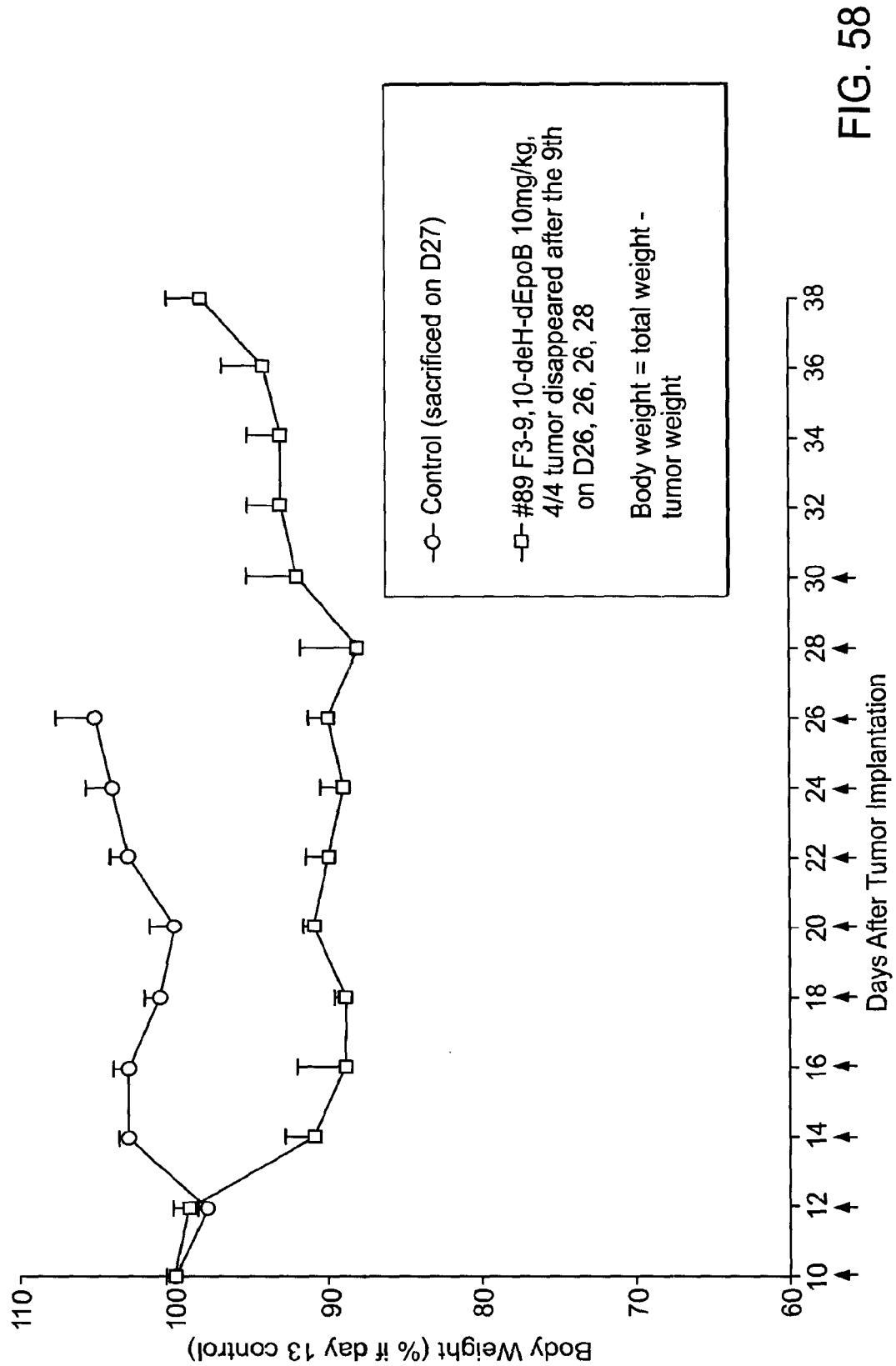
FIG. 58 shows changes in body weight of nude mice bearing a MX-1 xenograft following treatment with low doses of 26-trifluoro-9,10-dehydro-dEpoB (6 hr.-i.v. infusion, Q2Dx12).
Figures 59A, 59B:
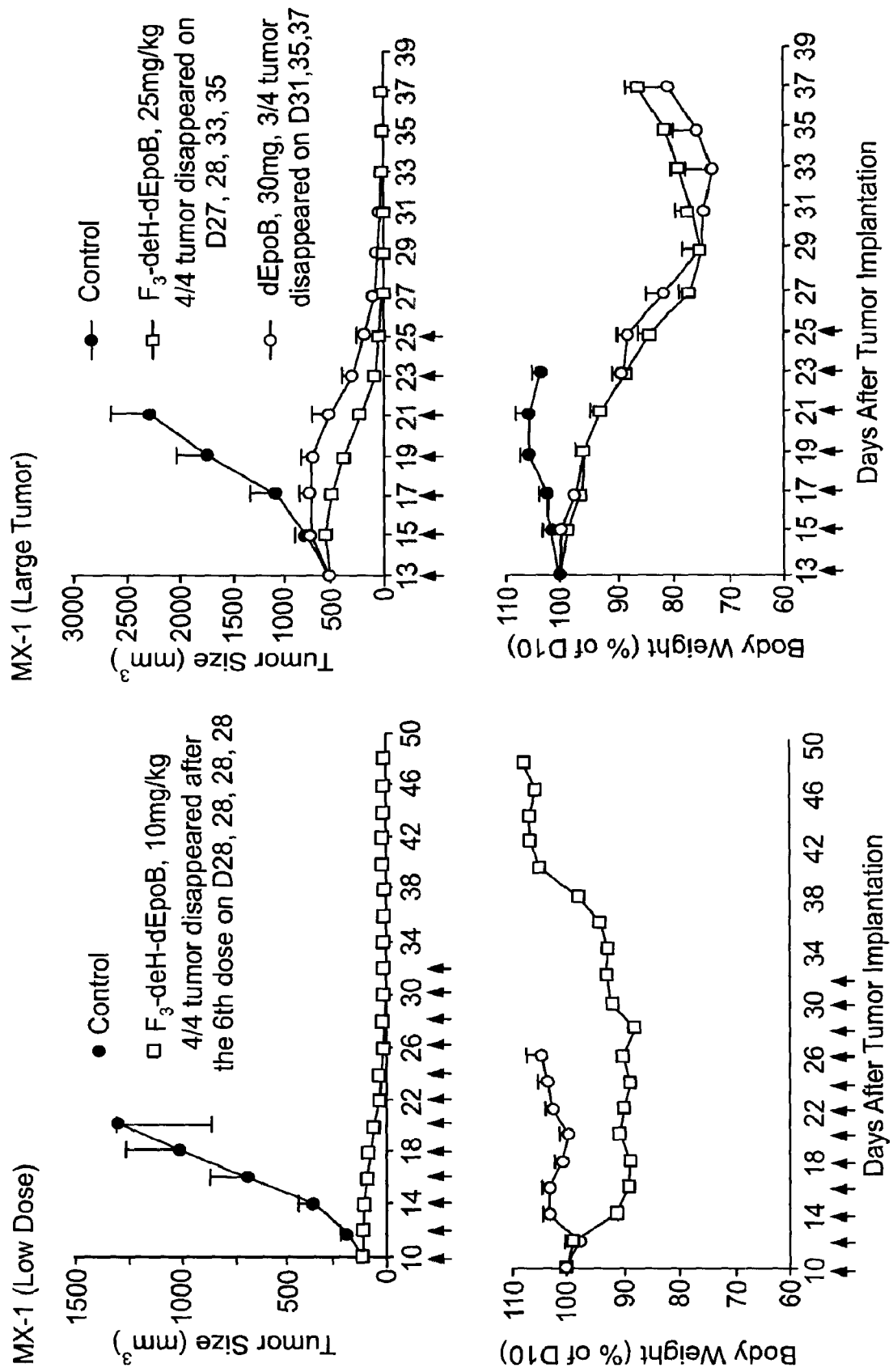
FIG. 59 shows the chemotherapeutic effect of epothilone analogs against human tumor xenografts in nude mice. Tumor tissue (40-50 mg) was implanted s.c. on Day 0. Treatment was started when tumor size reached about 100 mm$^3$ or greater as indicated. All treatments as indicated by arrows were carried out with 6-hr-i.v. infusion via tail vein using a mini-catheter and programmable pump as described earlier (Su, D.-S. et al, *Angew. Chem. Int. Ed.* 1997, 36, 2093; Chou, T. C. et al. *Proc. Natl. Acad. Sci. USA.* 1998, 95, 15798; each of which is incorporated herein by reference). Each dose group consisted of four or more mice. Body weight was referred to as the total body weight minus tumor weight assuming 1 mm$^3$ of tumor equals 1 mg of tumor tissue. A. Mammary carcinoma MX-1 xenograft treated with a low dose of 25-trifluoro-(E)-9,10-dehydro-12,13-desoxyEpoB (10 mg/kg) when compared with those in Table 1 (20 mg/kg and 30 mg/kg). B. MX-1 large xenografts (500 mm$^3$) were treated with 25-trifluoro-(E)-9,10-dehydro-12,13-desoxyEpoB (25 mg/kg) and dEpoB (30 mg/kg). C. Slow growing A549 lung carcinoma xenograft treated with 25-trifluoro-(E)-9,10-dehydro-12,13-desoxyEpoB (25 mg/kg) and dEpoB (30 mg/kg). D. A549/Taxol (44-fold resistance to paclitaxel in vitro) xenograft treated with 25-trifluoro-(E)-9,10-dehydro-12,13-desoxyEpoB (20 mg/kg) and (E)-9,10-dehydro-12,13-desoxyEpoB (4 mg/kg). The treatment for deH-dEpoB on day 28 was skipped due to marked and rapid body weight decreases.

Lowering the dose of agent 29 to 10 mg/kg (Q2D) also led to MX-1 tumor disappearance, but nine doses were required to achieve this result (FIGS. 57, 58 and 59A). As an added challenge, chemotherapeutic treatment was delayed until the tumor size reached 0.5 g (~2.3% of body weight). Treatment with 25 mg/kg (Q2Dx7) dosages of 29, caused 4/4 of the mouse tumors to disappear. By contrast for dEpoB, 30 mg/kg dosages (Q2Dx8) were required to induce the disappearance of tumors in 3 of 4 mice. However, unlike the case with 29, the apparent disappearances that occurred following treatment with dEpoB were subject to relapses with time. (FIG. 59B).

The fact that agent 29 completely suppressed the growth of the human mammary carcinoma MX-1 xenografts, shrank the tumors and made them disappear for as long as 64 days is impressive. Moreover, following the cures accomplished by 29, (20 mg/kg or 30 mg/kg Q2Dx6, i.v.-6 hr infusion, Table 1, above) the body weight of the xenografts returned to pretreatment control level within 12-18 days after suspension of treatment. This finding suggests the lack of vital organ damage. At a curative low dosage of 10 mg/kg, Q2DX12 (FIG. 59B), the maximal body weight decrease was only 12%, with a body weight gain of 6% during the last three doses. The body weight recovered to the pretreatment control level only three days after cessation of treatment. Table 1 above shows that the animals could survive body weight losses of as much as 27%. The therapeutic safety margin realized herein is remarkably broad for a curative cancer therapeutic agent.

Figures 59C, 59D:
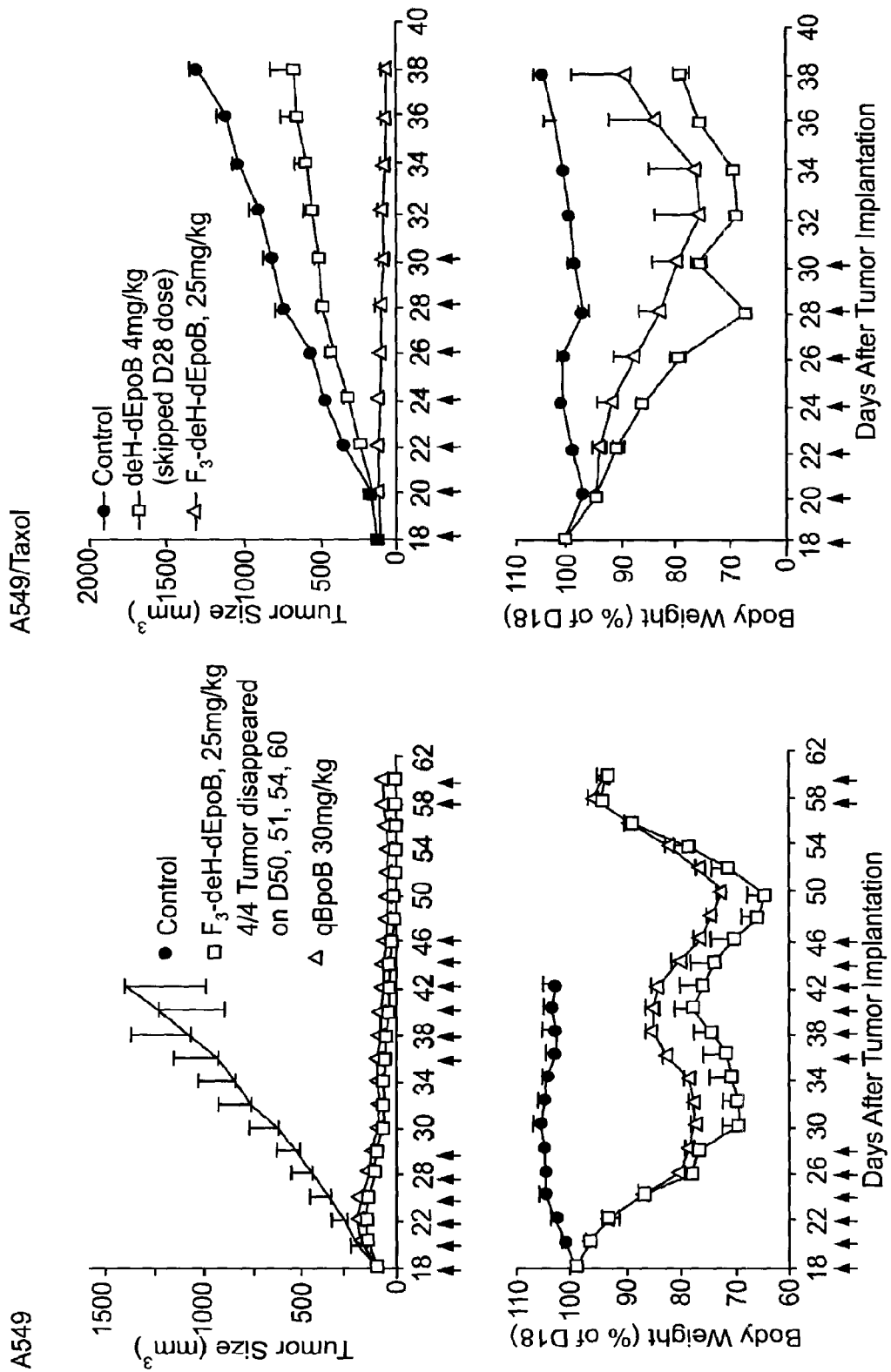
Figure 60A:
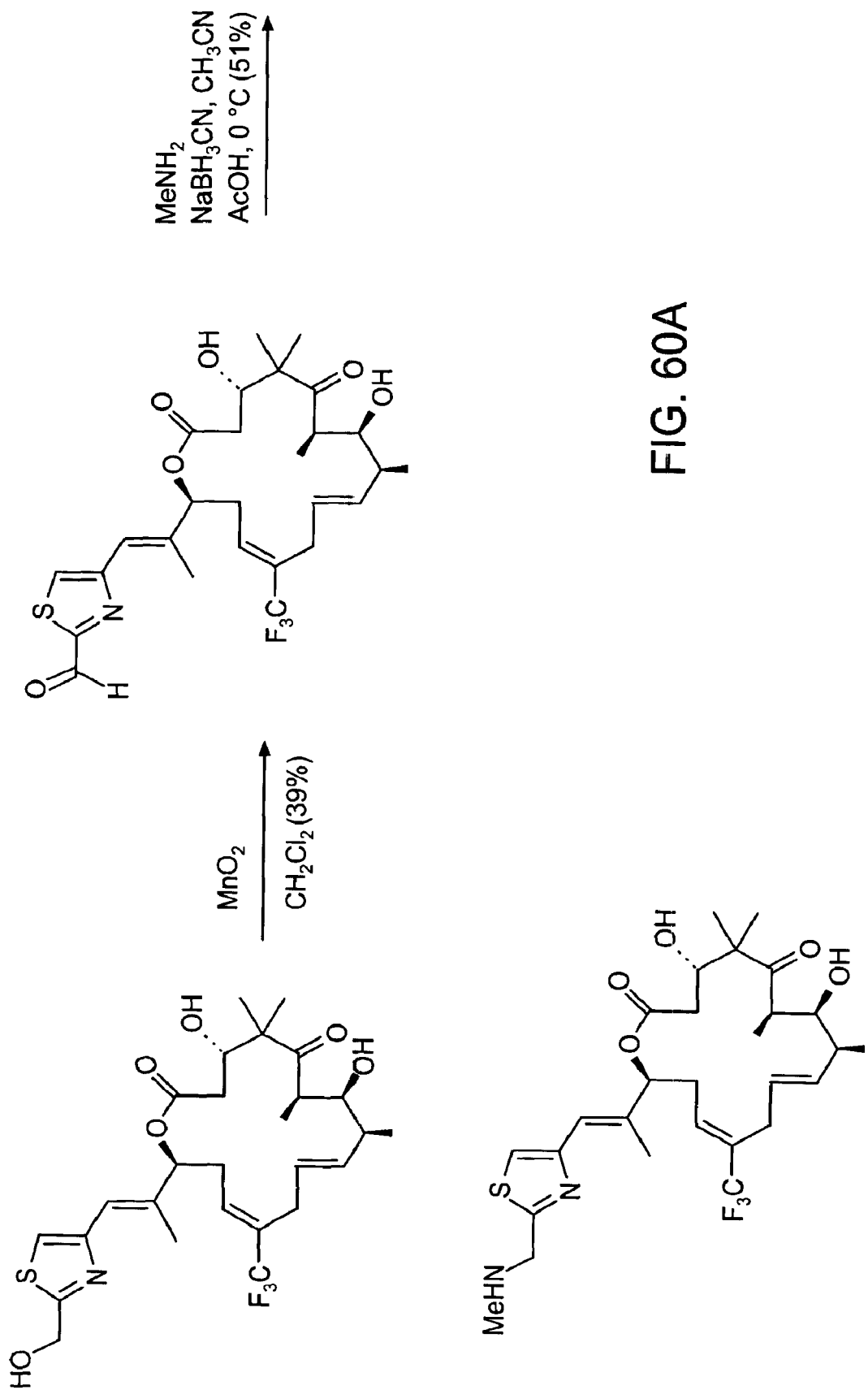
FIG. 60A shows the synthesis of 26-trifluoro-2'-methylamino-9,10-(E)-dehydro-12,13-desoxyepothilone B.
Figures 1, 60B:
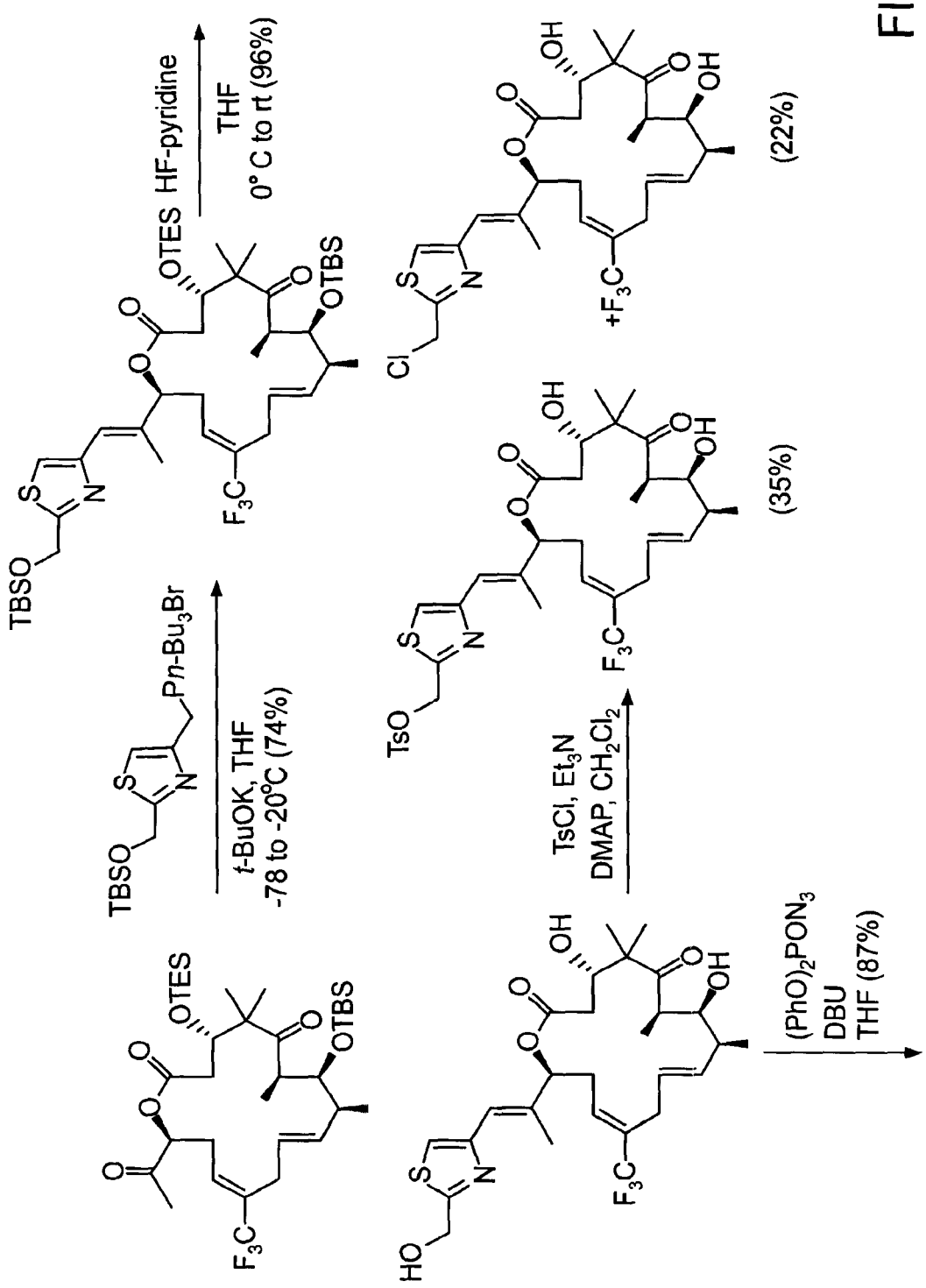
FIG. 1 is a table of $IC_{50}$ values of epothilones against CCRF-CEM, CCRF-CEM/VBL, and CCRF-CEM/Taxol cell growth. Cell growth inhibition was measured by XTT tetrazonium assay after 72-hour incubation for cell growth, as described previously (Scudiero et al. Cancer Res. 46:4827-4833, 1988; incorporated herein by reference). $IC_{50}$ values were determined from dose-effect relationship at six or seven concentrations of each drug, by using a computer program (Chou et al. Adv. Enzyme Regul. 22:27-55, 1984; Chou et al. CalcuSyn for Windows (Biosoft, Cambridge, UK), 1997; each of which is incorporated herein by reference) as described earlier (Chou et al. Proc. Natl. Acad. Sci. USA 95:15798-15802, 1998; incorporated herein by reference).
FIG. 60B is a synthetic scheme for the preparation to 26-trifluoro-21-amino-9,10-(E)-dehydro-12,13-desoxyepothilone B as an intermediate in the synthesis of 26-trifluoro-21-dimethylamino-9,10-(E)-dehydro-12,13-desoxyepothilone B.
Figures 2, 60B:
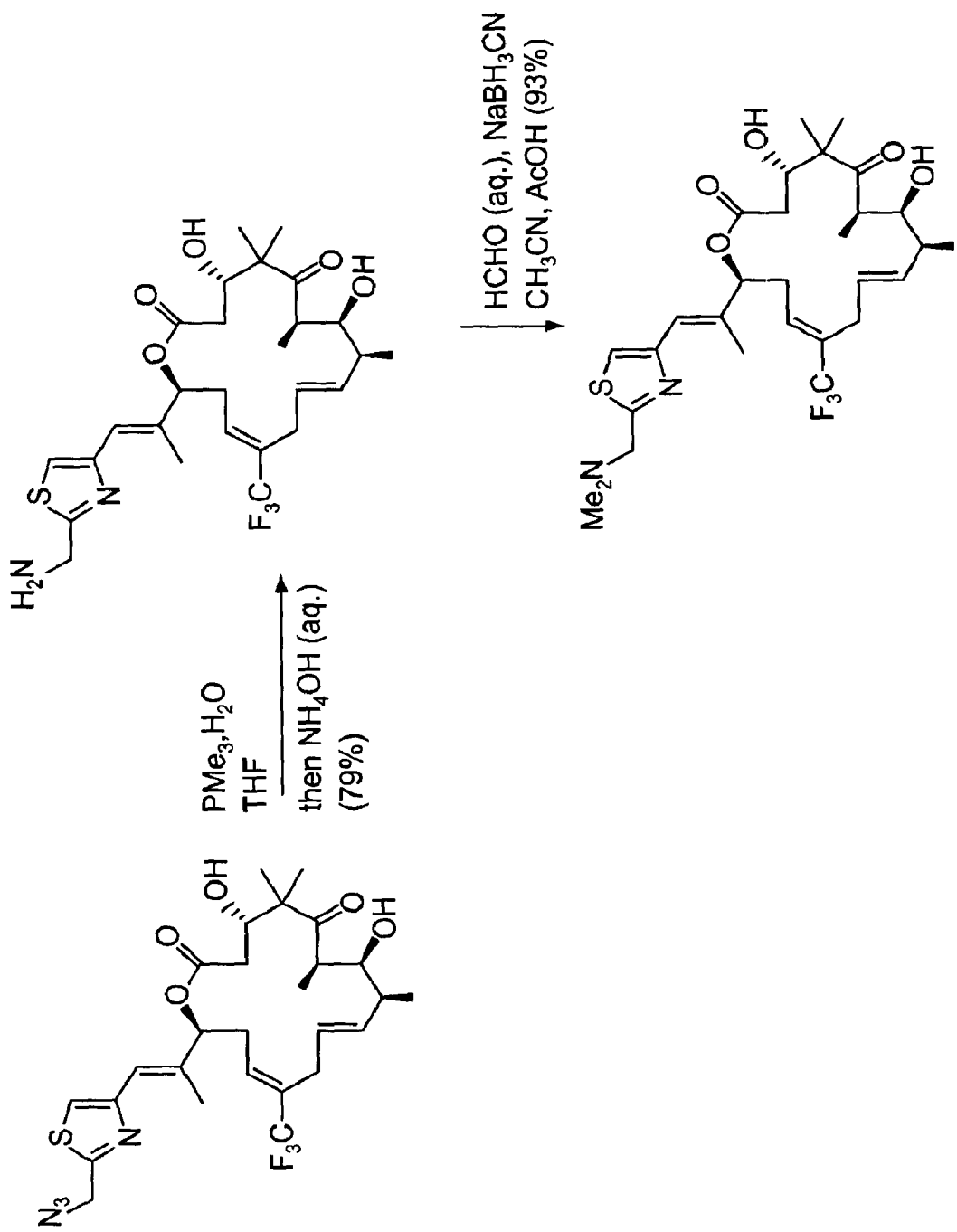

The therapeutic efficacy of 29 against human lung carcinoma xenograft (A549) and the paclitaxel resistant human lung carcinoma A549/Taxol xenografts were also evaluated (FIGS. 59C and 59D). The slow growing lung carcinoma xenografts A549 were treated with 29 (25 mg/kg, Q2DX6, twice, eight days apart), which resulted in 99.5% tumor suppression with the eventual complete eradication of 4 of the 4 tumors after two more doses (FIG. 59C). Interestingly, the body weight of the mice decreased as much as 35% without any lethality and suspension of the treatment led to rapid body weight recovery to near the pretreatment control level (FIG. 59C). In contrast, a parallel study with dEpoB (30 mg/kg, Q2Dx6) resulted in 97.6% tumor suppression but led to no tumor eradication. In an additional study of 29 (20 mg/kg dosage) against A549/Taxol resistant xenograft (FIG. 59D), tumor growth was totally suppressed and the tumor eventually reduced by 24.4% of the pretreatment control. During this study, the maximal body weight decreased by 24%, however upon suspension of drug treatment the body weight recovered to 90% of the pretreatment control. In a comparison study of (E)-9,10-dehydro-dEpoB (28, 4 mg/kg group), tumor growth was suppressed by 41.6%.

The pertinent data for analyzing what factors endow compound 29 with its remarkable therapeutic index in conjunction with comparable data pertinent to closely related congeners are provided in Table 10-2. One notes that in terms of inherent cytotoxicity in moving from EpoB(2b) to dEpoB (1) a whole order of magnitude is lost. About 60% of this loss is restored in the case of 9,10-dehydro-dEpoB (28). Some of this inherent cytotoxicity is forfeited in going to 29, which at least in the cell is ~1.8 fold as cytotoxic as the benchmark compound dEpoB.

We note that among the 12,13-dehydroepothilones, 29 exhibits by far the best stability in mouse plasma and is also the most stable in human liver S9 plasma. We also note that, in the 2-sets of 12,13-dehydro isomers, the 26-trifluoro pattern carries with it decreased lypophilicity and somewhat increased water solubility (Table 10-2, below). For the moment it would appear that the great advantage of 29 arises from improvements in serum stability and bioavailability.

TABLE 10-2

Profile of dEpoB derivatives.

| | | Maximal | Stability half-life | | | Therapeutic | | |
|---|---|---|---|---|---|---|---|---|
| Compounds | Cytotoxic Efficacy $IC_{50}$ (nM)[a] | b.w. % drop without death | Mouse plasma (min) | Human Liver S9 Fraction (hr) | Solubility in water (μg/mL) | Lipophilicity octanol/water partition (POW) | dose regimen for Q2D 6 hr-iv infusion (mg/kg) | Relative therapuetic index at MTD[b] |
| EpoB (2b) | 0.53 ± 0.2 | 15 | 57 | 15.8 | ND | ND | 0.6-0.8 | +++ |
| dEpoB (1) | 5.6 ± 2.8 | 32 | 46 ± 7 | 1.0 ± 0.1 | 9.4 | 4.4 | 25-30 | ++++ |

TABLE 10-2-continued

Profile of dEpoB derivatives.

| Compounds | Cytotoxic Efficacy IC$_{50}$ (nM)[a] | Maximal b.w. % drop without death | Stability half-life | | Solubility in water (μg/mL) | Therapeutic | | |
|---|---|---|---|---|---|---|---|---|
| | | | Mouse plasma (min) | Human Liver S9 Fraction (hr) | | Lipophilicity octanol/water partition (POW) | dose regimen for Q2D 6 hr- iv infusion (mg/kg) | Relative theraputic index at MTD[b] |
| deH-dEpoB (28) | 0.90 ± 0.40 | 29 | 84 ± 6 | 4.9 ± 0.7 | 27 | 3.3 | 3-4 | ++++ |
| F$_3$-dEpoB (2) | 9.3 ± 5.2 | 22 | 66 ± 7 | 1.6 ± 0.4 | 8 | 4.1 | 15-20 | ++ |
| F$_3$-deH-dEpoB (29) | 3.2 ± 0.3 | 33 | 212 ± 88 | 10.5 ± 2.3 | 20 | 3.3 | 10-30 | +++++ |

[a]IC$_{50}$ values are for CCRF-CEM leukemic cells. Values are the range of two experiments; all values are obtained from seven concentration points; ND = Not Determined.
[b]Graded relative therapeutic index (TI) at MTD (maximal tolerated dose):
+ Tumor growth suppressed 25-50%.
++ Tumor growth suppressed 50-100%.
+++ Tumor shrinkage but no tumor disappearance.
++++ Tumor disappearance in some or all nude mice with slow body weight recovery and/or with relapse in some mice within one week after stopping treatment.
+++++ Tumor disappeared in all nude mice, body weight rapidly recovered and/or without relapse. The therapeutic experiment for epothilones against human xenografts in nude mice, such as MX-1, were studied in Chou, T. C. et al. Proc. Natl. Acad. Sci. USA. 1998, 95, 15798 and in 2001, 98, 8113.

All of the agents, 1-2 and 28-29, were initially discovered through total synthesis. A practical synthesis of 1 has been previously described (Rivkin et al. *J. Am. Chem. Soc.* 2003, 125, 2899; White et al. *J. Am. Chem. Soc.* 2001, 123, 5407; Yoshimura et al. *Angew. Chem.* 2003, 42, 2518; Rivkin et al. *J. Org. Chem.* 2002, 124, 7737; each of which is incorporated herein by reference). First generation discovery level routes to 28 and 29 have also been described. Selective reduction of the 9,10-double bond of 29 afforded 2. The remarkable results obtained from xenograft studies described above, for what is currently the most promising compound 29, clearly called for its advancement for detailed toxicology and pharmacokinetic studies in higher animals and, from there if appropiate, advancement to human clinical trials. Such prospects totally altered the nature of the synthesis challenge from the preparation of probe samples, to that of producing multigram quantities of these new epothilone agents. A major revamping of our previous routes, initially conceived and demonstrated in a discovery setting, has been accomplished. In particular our new protocols accomplished major simplifications in the stereospecific elaborations of carbons 3 and 26. Alcohol 32 is prepared as described earlier (Rivkin et al. *J. Am. Chem. Soc.* 2003, 125, 2899; incorporated herein by reference). It will be noted that in the new synthesis, stereocenters 6, 7, and 8 are derived from the trivially available ketone 30 and aldehyde 31. Upon alcohol protection and acetal hydrolysis, the corresponding aldehyde was condensed with t-butyl acetate to afforded an aldol like product. Since this condensation is not diastereomerically-controlled, a remedial measure was necessary and achieved. Oxidation of this 1:1 mixture of C3 epimers, afforded ketone 69. Following a highly successful Noyori reduction (Noyori et al. *J. Am. Chem. Soc.* 1987, 109, 5856; incorporated herein by reference) under the conditions shown, alcohol 70 was in hand. Preparation of acid 25 was then accomplished in a few additional simple steps as shown.

Scheme 12. Synthesis of the acyl sector 25.

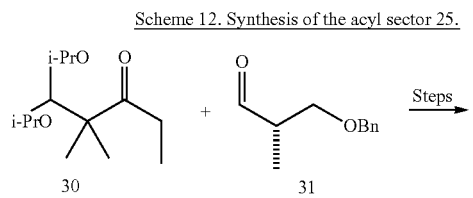

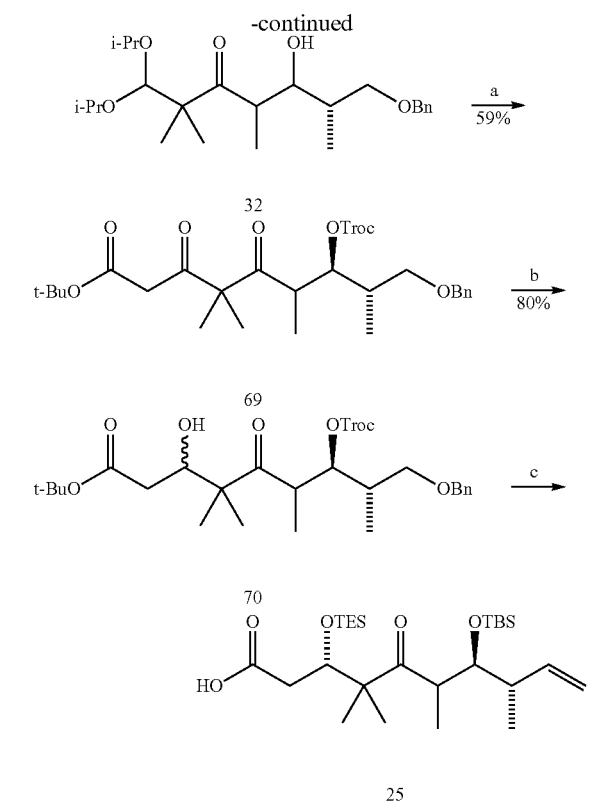

Reagents and conditions: (a) (i) TrocCl, pyr., 92%; (ii) p-TsOH•H$_2$O, 76%;
(iii) LDA, t-butyl acetate, THF, 80%; (iv) Dess-Martin periodinane, 74%;
(b) Noyori catalyst (10 mol %), MeOH/HCl, H$_2$, 1200 psi, 80%.
(c) (i) TESCl, imidazole, 77%; (ii) Zn, AcOH, THF, 99%; (iii) TBSOTf, 2,6-lutidine, 82%; for remaining steps see Rivkin et al. J. Am. Chem. Soc. 2003, 125, 2899.

A new, straightforward and readily scalable synthesis has also been developed for 90 (Scheme 13). The synthesis starts with reaction of commerically available trifluoro ketoester 82 with allyl indium bromide. The key step in the synthesis is the positionally specific and stereospecific dehydration of the resulting tertiary alcohol to produce 84 (in 65% overall yield for two steps). The stereocontrol of this reaction arises from a "dipolar effect" wherein the strongly electron-withdrawing $CF_3$ and $CO_2Et$ groups are best presented trans with respect to the emerging double bond. The required iodide 86 was obtained in two steps from 84. Alkylation of the previously reported lithium enolate of 7 with iodide 86 in THF afforded 88 in 81% yield and high diastereoselectivity (>25:1 de). Following deprotection of the secondary alcohol, compound 88 was advanced in three steps to 90 as shown.

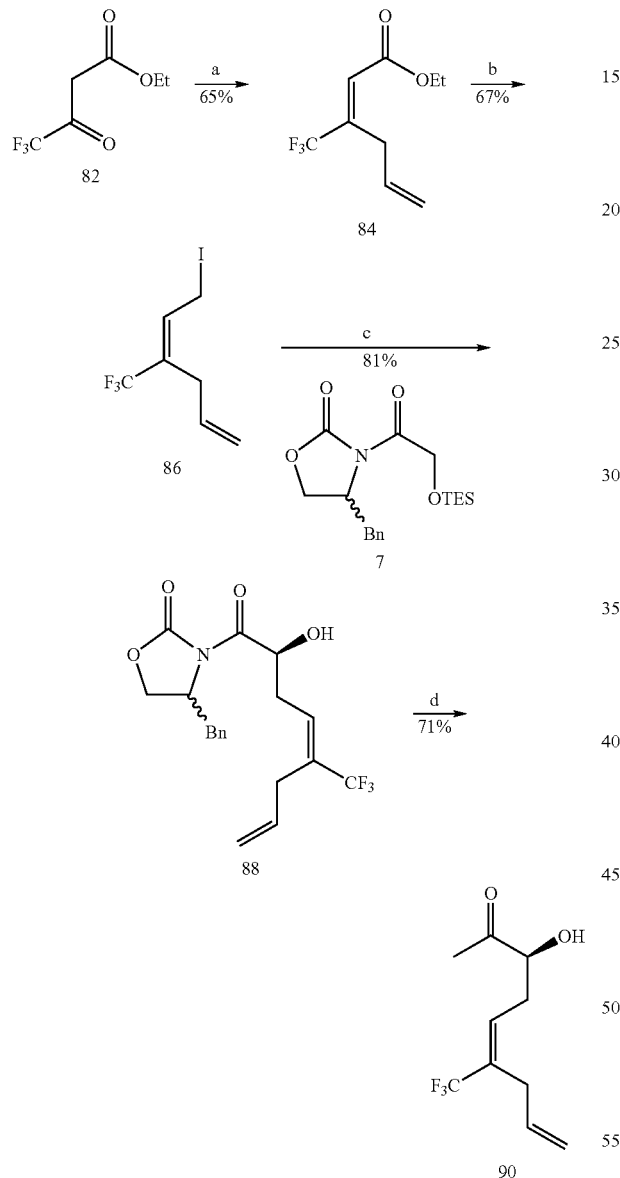

Reagents and conditions: (a) (i) Allyl bromide, In, THF-water (3:1) 48° C., 85%; $SOCl_2$, pyr 55° C., 77%; (b) (i) DIBAL-H, $CH_2Cl_2$, -78° C. to r.t. 99%; (ii) $I_2$, $PPh_3$, imidazole, $CH_2Cl_2$, 74%; (c) (i) LHMDS, THF, -78° C. to r.t.; (ii) HOAc-THF-$H_2O$ (3:1:1), 81% for two steps; (d) (i) $AlMe_3$, MeONHMe, THF, 0° C. to r.t., 97%; (ii) MeMgBr, THF, 0° C., 53% (73% borsm)

With 25 and 90 in hand by easily processable chemistry, the route to 29 was clear following protocols first developed in our discovery phase (A. Rivkin et al. *J. Am. Chem. Soc.* 2003, 125, 2899; incorporated herein by reference). The key ring-closing metathesis reaction of 25 was carried out in toluene using the second generation Grubbs catalyst (Grubbs, R. H.; Miller, S. J.; Fu, G. C. *Acc. Chem. Res.* 1995, 28, 446; Trnka, T. M.; Grubbs, R. H. *Acc. Chem. Res.* 2001, 34, 18; *Alkene Metathesis in Organic Chemistry* Ed.: Fürstner, A.; Springer, Berlin, (1998); Fürstner, A. *Angew. Chem. Int. Ed. Engl.* 2000, 39, 3012; Schrock, R. R. *Top. Organomet. Chem.* 1998, 1, 1; each of which is incorporated herein by reference). The reaction afforded, exclusively the trans isomer 48 in 71% yield. Installation of the thiazole moiety via the protocol shown in Scheme 14 was followed by removal of the two silyl protecting groups with HF-pyridine thereby leading to 29, which was then converted via reduction of the 9,10-olefin to 2 in high yield. Gram quantities of structurally novel epothilones have been prepared by total syntheses in the setting of an academic scale laboratory.

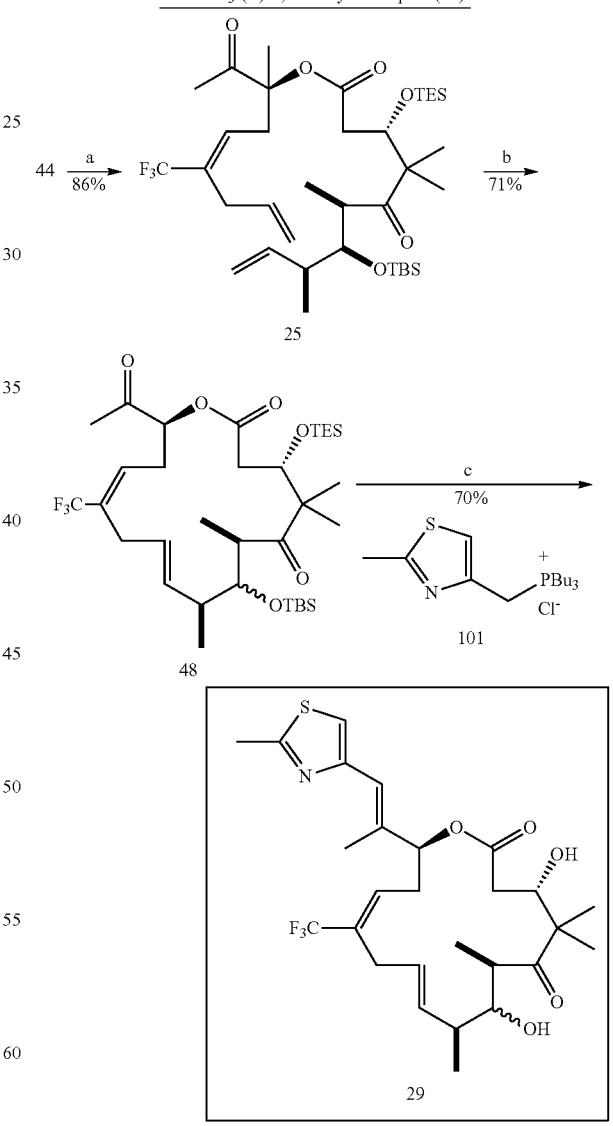

Reagents and conditions: (a) EDCI, DMAP, $CH_2Cl_2$, 25, 0° C. to rt, 86% from t-butyl ester; (b) Grubb's catalyst, toluene, 110° C., 20 min, 71%; (c) (i) KHMDS, 101, THF, -78° C. to -20° C., 70%; (ii) HF-pyridine, THF, 98%.

Experimentals

General Methods: Reagents obtained from commercial suppliers were used without further purification unless otherwise noted. Methylene chloride was obtained from a dry solvent system (passed through a prepacked column of alumina) and used without further drying. All air and water sensitive reactions were performed in flame-dried glassware under a positive pressure of prepurified argon gas. NMR ($^1$H and $^{13}$C) spectra were recorded on Bruker AMX-400 MHz or Bruker Advance DRX-500 MHz as noted individually, referenced to CDCl$_3$ (7.27 ppm for $^1$H and 77.0 ppm for $^{13}$C) or CD$_2$Cl$_2$ (5.32 ppm for $^1$H and 53.5 ppm for $^{13}$C). Infrared spectra (IR) were obtained on a Perkin-Elmer FT-IR model 1600 spectrometer. Optical rotations were obtained on a JASCO model DIP-370 digital polarimeter. Analytical thin-layer chromatography was performed on E. Merck silica gel 60 F254 plates. Compounds which were not UV active were visualized by dipping the plates in para-anisaldehyde solution and heating. Preparative thin layer chromatography was performed using the indicated solvent on Whatman® (LK6F Silica gel 60A) TLC plate.

Chemicals. All epothilones were synthesized in-house (C. R. Harris, S. J. Danishefsky, *J. Org. Chem.* 1999, 64, 8434; D.-S. Su et al. *Angew. Chem. Int. Ed. Engl.* 1997, 36, 2093; Smart, B. E. *J. Fluorine Chem.* 2001, 109, 3; F. Yoshimura, et al. Angew. *Chem.* 2003, 42, 2518; Rivkin et al. *J. Org. Chem.* 2002, 124, 7737; each of which is incorporated herein by reference). Paclitaxel (Taxol®) and vinblastine sulfate (VBL) were purchased from Sigma. All these compounds were dissolved in dimethylsulfoxide for the in vitro assays, (except VBL in saline). For in vivo studies, all epothilones and paclitaxel were dissolved in Cremophor/ethanol (1:1) vehicle and then diluted with saline for iv infusion for 6 hrs via tail vein using a custom-designed mini-catheter (T.-C. Chou et al. *Proc. Natl. Acad. Sci. USA.* 2001, 98, 8113-8118; T.-C. Chou et al. *Proc. Natl. Acad. Sci. U.S.A.* 1998, 95, 15798-15802; each of which is incorporated herein by reference).

Tumor and Cell Lines. The CCRF-CEM human lymphoblastic leukemia cells were obtained from Dr. William Beck of the University of Illinois, Chicago. Human mammary carcinoma (MX-1) and human lung carcinoma cells (A549) were obtained from American Type Culture Collection (ATCC, Rockville, Md.). The paclitaxel-resistant A549/taxol cells (44-fold resistance) were developed with the method as described above (T.-C. Chou et al. *Proc. Natl. Acad. Sci. USA.* 2001, 98, 8113-8118; incorporated herein by reference).

Animals. Athymic nude mice bearing the nu/nu gene were obtained from NCI, Frederick, Md. and used for all human tumor xenografts. Male nude mice 6 weeks or older weighing 20-22 g or more were used. Drugs were administered via the tail vein for 6 hours by i.v. infusion using a home-made infusion mini-catheter and containment tube (T.-C. Chou et al. *Proc. Natl. Acad. Sci. USA.* 2001, 98, 8113-8118; incorporated herein by reference). A programmable Harvard PHD2000 syringe pump with multitrack was used for i.v. infusion. A typical 6 hrs infusion volume for each drug in Cremophor/ethanol (1:1) was 100 ml in 2.0 ml of saline. Tumor volume was assessed by measuring length×width×height (or width) by using a caliper. For tumor-bearing nude mice during the course of experiment, the body weight refers to total weight minus the weight of the tumor. All animal studies conducted in accordance with the guidelines for the National Institute of Health Guide for the Care and Use of Animals and the protocol approved by the Memorial Sloan-Kettering Cancer Center's Institutional Animal Care and Use Committee.

Cytotoxicity Assays. In preparation for in vitro cytotoxicity assays, cells were cultured at an initial density 2-5×10$^4$ cells per milliliter. They were maintained in a 5% CO$_2$-humidified atmosphere at 37° C. in RPMI medium 1640 (GIBCO/BRL) containing penicillin (100 units/mL), streptomycin (100 µg/mL, GIBCO/BRL), and 5% heat-inactivated FBS. For solid tumor cells growing in a monolayer (such as A549), cytotoxicity of the drug was determined in 96-well microtiter plates by using the sulforhodamine B method (P. Skehan et al. *J. Natl. Cancer. Inst.* 1990, 82, 1107-1112; incorporated herein by reference). For cells grown in suspension (such as CCRF-CEM and its sublines), cytotoxicity was measured, in duplicate, by using the 2,3-bis-(2-methoxy-4-nitro-5-sulfophenyl)-5-carboxanilide)-2H-terazodium hydroxide (XTT) microculture method (D. A. Scudiero et al. *Cancer Res.* 1988, 48, 4827-4833; incorporated herein by reference) in 96-well microtiter plates. For both methods, the absorbance of each well was measured with a microplate reader (Power Wave XS, Bio-Tek, Winooski, Vt.). Dose-effect relationship data from 6 to 7 concentrations of each drug, in duplicate, were analyzed with the median-effect plot by using a computer program (T.-C. Chou, M. Hayball. *CalcuSyn for Windows*, Multiple-drug dose effect analyzer and manual. Biosoft, Cambridge Place, Cambridge, UK (1997); incorporated herein by reference).

Stability of epothilones in mouse and in human liver S9 fraction. The stability study was carried out with a fully automated HPLC system which consisted of a Prospekt-2 (Spark Holland, Netherlands) sample preparation system and an Agilent 1100 HPLC system. Briefly, the Prospekt 2 picked up a C8 extraction cartridge and washed it with acetonitrile and water. The Agilent autosampler, set at 37° C., picked up 20 µl of the sample, loaded it onto the cartridge, washed it with water, then the Prospekt-2 diverted the mobile phase stream through the extraction cartridge onto the analytical column, Reliance Stable Bond C8 4×80 mm with guard column (MacMod, Chadds Ford, Pa.) and the eluent was monitored at 250 nm. The mobile phase consisted of 53 or 65% acetonitrile/0.1% formic acid at 0.4 ml/min, so that the retention time of the compound of interest was about 6 minutes. Sample preparation involved the addition of equal volumes of plasma to PBS for a total volume of 300-400 µl, filtered, and the addition of 0.5-2 µl of the substrate (20 mM) to achieve about 30-50 mAU at 250 nm in the HPLC analysis. For pooled human liver microsome S9 fraction (Xeno Tech, Lenex, Kans.), 20 µl (400 µg) or S9 fraction was mixed with 280 µl of PBS then proceeded as above. The sampling period was controlled by the autosampler and peak area data were collected to compare the rate of disappearance of the parent compound.

Determination of partition of octanol-water (POW) number. An HPLC method is used to estimate octanol-water partition. An Agilent 1100 HPLC system is used with an eclipse XDB C18 column 4.6×250 mm with a mobile phase of 60% acetonitrile/40% 25 mM potassium phosphate buffer at pH 7.4 with a flow rate of 0.8 ml per min. and the eluent is monitored at 250 nm. The standards used are benzyl alcohol, acetophenone, benzophenone, naphthalene, diphenyl ether and dibenzyl with known POW of 1.1, 1.7, 3.2, 4.2, and 4.8 respectively. Sodium dichromate is used to evaluate time zero which is 2.5 min and the retention times for the standards are 3.9, 5.4, 10.6, 14, 18.7 and 19.8 min, respectively. The k value is calculated by the formula of $k=(t_{rt}-t_0)/t_0$. Linear regression of log k vs. log POW gives a straight line with $r^2=0.966$. This graph is used to evaluate the POW value of the epothilone analogs.

Spectroscopic Data for 29 (26-trifluoro-(E)-9,10-dehydro-dEpoB)

$[\alpha]_D^{25}$ −54.6 (c 0.28, CHCl$_3$); IR (film) v 3478, 2974, 2929, 1736, 1689, 1449, 1381, 1318, 1247, 1169, 1113, 1039, 983, 867, 736 cm$^{-1}$; $^1$H NMR (400 MHz, CDCl$_3$) δ 1.05 (3H, s), 1.12 (3H, d, J=7.0 Hz), 1.23 (3H, d, J=6.8 Hz), 1.37 (3H, s), 2.04 (1H, brd, J=3.8 Hz, —OH), 2.12 (3H, s), 2.25-2.33 (1H, m), 2.38 (1H, dd, J=15.3 and 3.0 Hz), 2.48 (1H, dd, J=15.4 and 9.8 Hz), 2.54-2.61 (1H, m), 2.66-2.76 (1H, m), 2.71 (3H, s), 2.96 (1H, dd, J=16.5 and 4.5 Hz), 3.02 (1H, dd, J=16.3 and 6.5 Hz), 3.11 (1H, quintet, J=6.7 Hz), 3.19 (1H, brs, =OH), 3.74 (1H, brs), 4.35 (1H, brd, J=9.5 Hz), 5.42 (1H, dd, J=6.2 and 4.1 Hz), 5.60 (1H, ddd, J=5.8, 5.6, and 4.5 Hz), 5.66 (1H, dd, J=15.8 and 5.8 Hz), 6.24 (1H, t, J=7.2 Hz), 6.64 (1H, s), 7.00 (1H, s); $^{13}$C NMR (100 MHz, CDCl$_3$) δ 15.1, 16.1, 17.7, 18.5, 19.3, 22.5, 28.8, 31.1, 39.6, 39.7, 45.0, 53.7, 71.4, 75.3, 76.8, 116.7, 120.2, 124.3 [q, $^1$J (C,F)=273.4 Hz], 127.9, 130.2 [q, $^3$J (C,F)=6.0 Hz], 130.6 [q, $^2$J (C,F)=28.4 Hz], 132.5, 136.7, 152.0, 165.4, 170.2, 218.4; LRMS (ESI) calcd for C$_{27}$H$_{37}$F$_3$NO$_5$S [M+H$^+$] 544.2, found 544.1.

Example 11

In Vitro Studies

A typical experiment involves culturing cells (e.g., CCRF-CEM) at an initial density of 2-5×10$^4$ cells per ml. They are maintained in a 5% CO$_2$-humidified atmosphere at 37° C. in RPMI medium 1640 (GIBCO/BRL) containing penicillin (100 units/ml), streptomycin (100 µg/ml) (GIBCO/BRL), and 5% heat-inactivated fetal bovine serum. For cells that were grown in suspension (such as CCRF-CEM and its sublines), cytotoxicitiy is measured by using the 2,-3-bis(2-methoxy-4-nitro-5-sulfophenyl)-5 carboxanilide)-2H terazodium hydroxide (XTT)-microculture tetrazonium method in duplicate in 96-well microtiter plates. For both methods, the absorbance of each well is measured with a microplate reader (EL-340, Bio-Tek, Burlington, Vt.). Each run entails six or seven concentrations of the tested drugs. Dose-effect relationship data are analyzed with the median-effect plot.

The CCRF-CEM human T cells, acute lymphoblastic leukemic cells, its teniposide-resistant subline (CCRF-CEM/VM$_1$) and vinblastine-resistant subline (CCRF-CEM/VBL$_{100}$) are obtained from W. T. Beck (University of Illinois, Chicago, Ill.).

In a typical experiment, as outlined generally above, certain of the inventive compounds (e.g., 9,10-dehydro-EpoD) demonstrated activity in CCRF-CEM cell lines and CCRF-CEM cell lines resistant to Taxol. Certain of these compounds exhibit IC$_{50}$s in the range of 0.0015 to about 0.120 for CCRF-CEM cell lines. Certain other compounds exhibit IC$_{50}$s in the range of 0.0015 to about 10.5. Certain of these compounds also exhibit IC$_{50}$s in the range of 0.011 to about 0.80 for CCRF-CEM/Taxol resistant cell lines and certain other compounds exhibit IC$_{50}$s in the range of about 0.011 to about 13.0 µM. In certain embodiments, 26F-EpoD exhibits activities in the range of 0.0015 µM for CCRF-CEM cell lines and in the range of 0.011 µM for CCRF-CEM/Taxol resistant cell lines (FIG. 11).

Example 12

In Vivo Studies

Athymic nude mice bearing the nu/nu gene are typically used for tumor xenografts. Outbred, Swiss-background mice were obtained from Charles River Laboratories. Male mice 8 weeks or older weighing 22 g and up were used for most experiments. The drug was administered via the tail vein for 6 hr.-i.v. infusion. Each individual mouse was confined in a perforated Falcon polypropylene tube restrainer for drug administration. Tumor volume was assessed by measuring length×width×height (or width) using a caliper. The programmable Harvard PHD2000 syringe pump (Harvard Apparatus) with multi-track was used for i.v. infusion. All animal studies were conducted in accordance with the guidelines of the National Institutes of Health "Guide for the Care and Use of Animals" and the protocol approved by the Memorial Sloan-Kettering Cancer Center's Institutional Animal Care and Use Committee. In keeping with the policy of this committee for the humane treatment of tumor-bearing animals, mice were euthanized when tumors reached ≧10% of their total body weight.

Figure 2A:
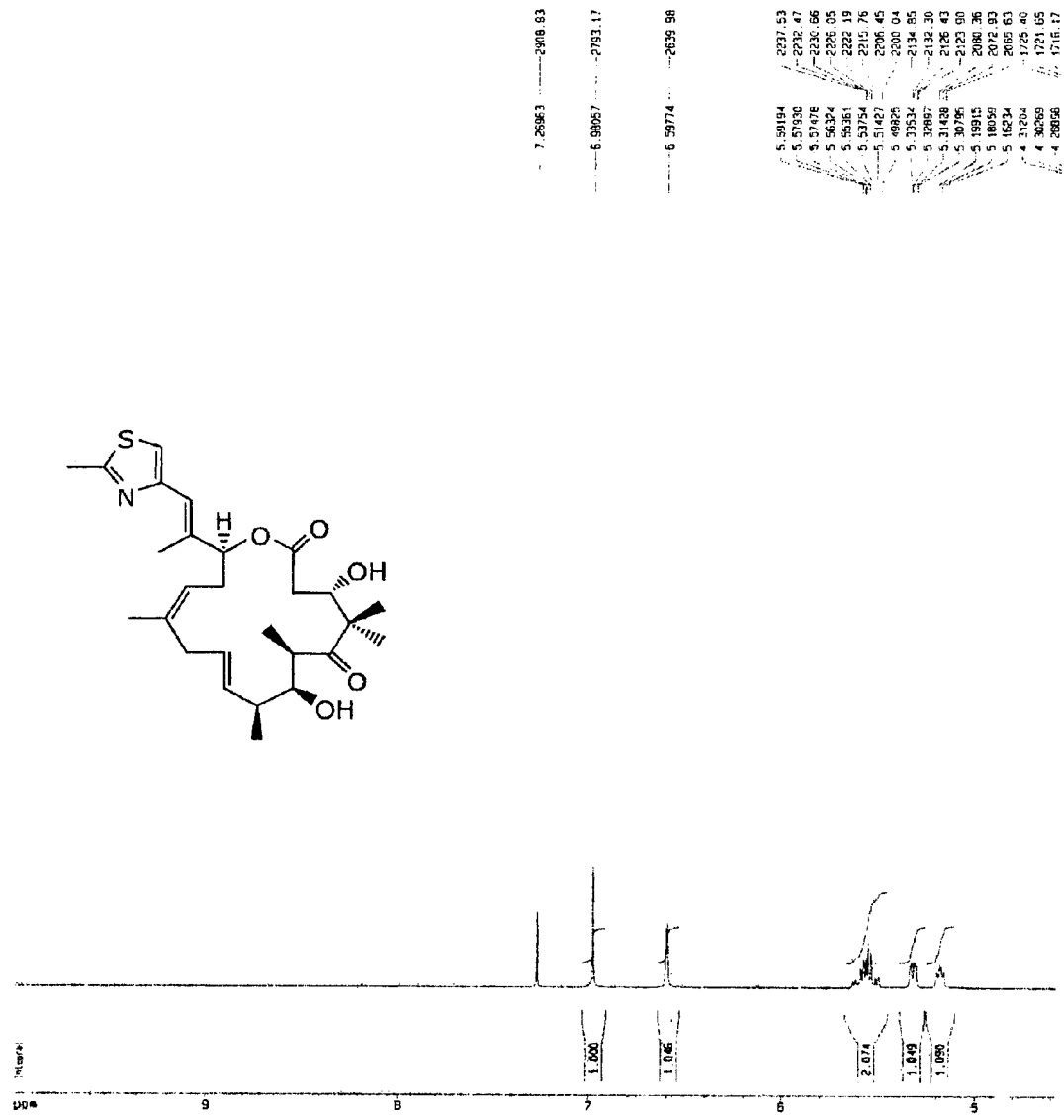
FIG. 2 is a $^1H$ NMR spectrum of trans-9,10-dehydro-12,13-desoxyEpoB.
Figure 2B:
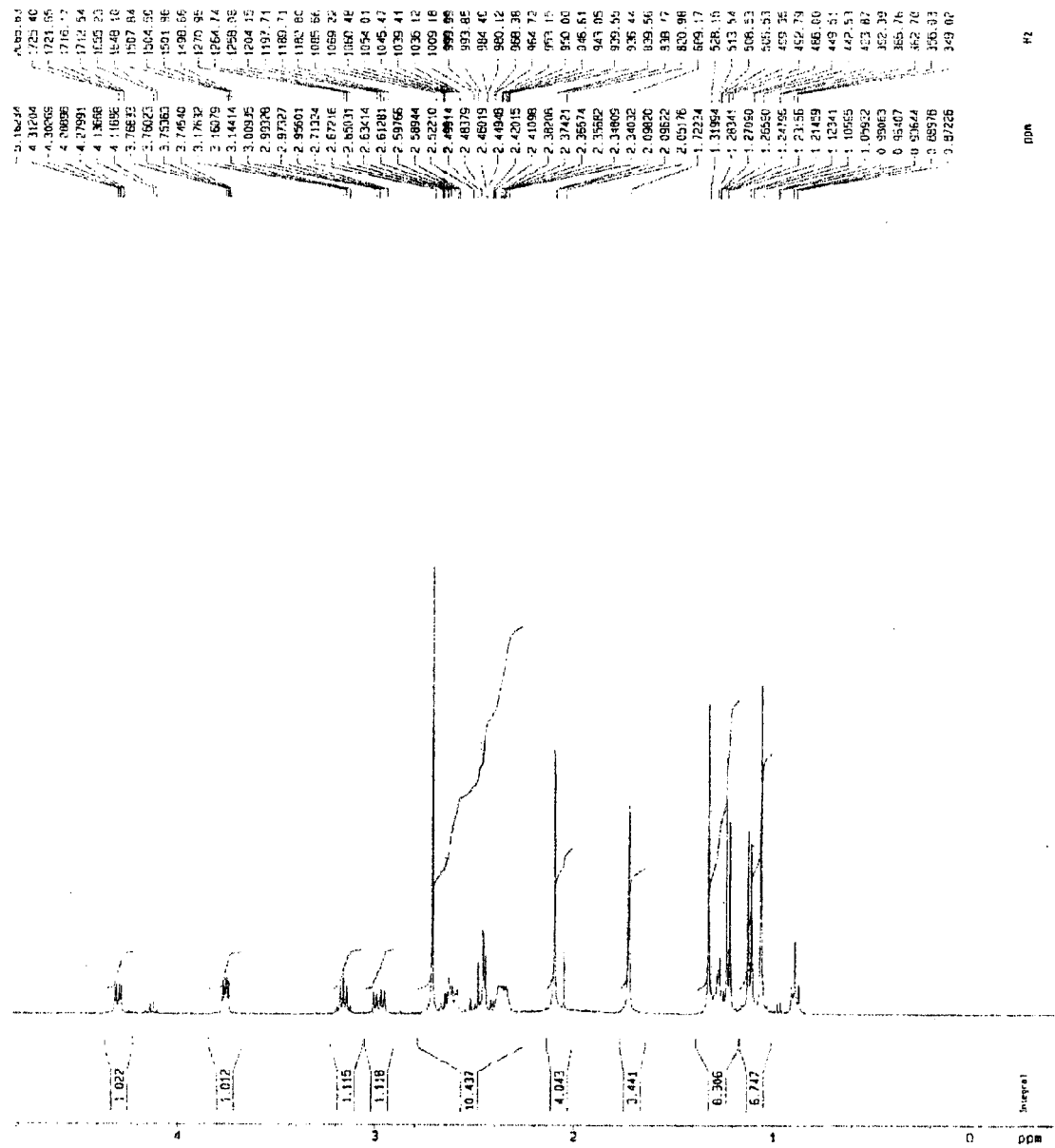
Figure 3A:
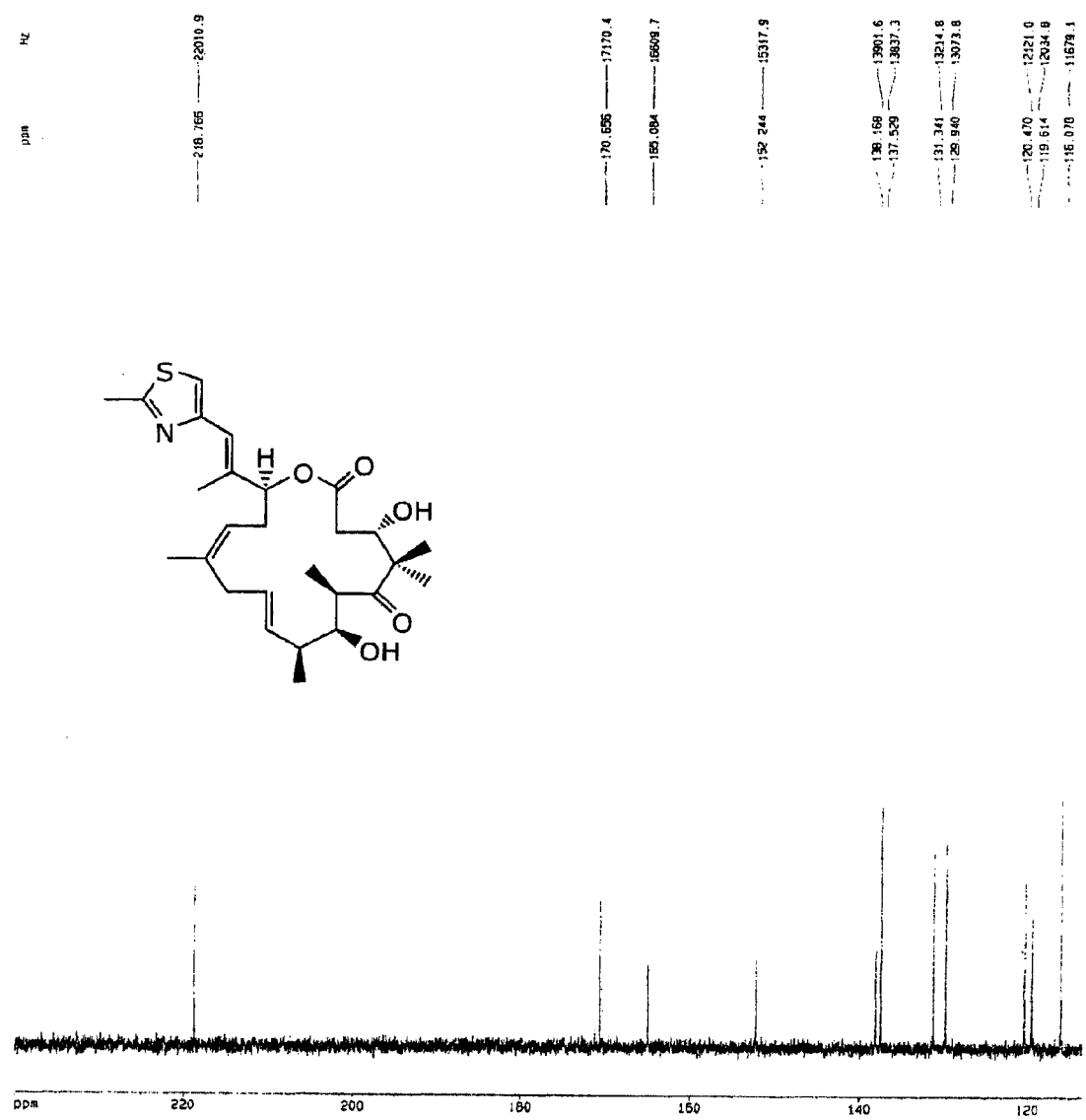
FIG. 3 is a $^{13}C$ NMR spectrum of trans-9,10-dehydro-12,13-desoxyEpoB.
Figure 3B:
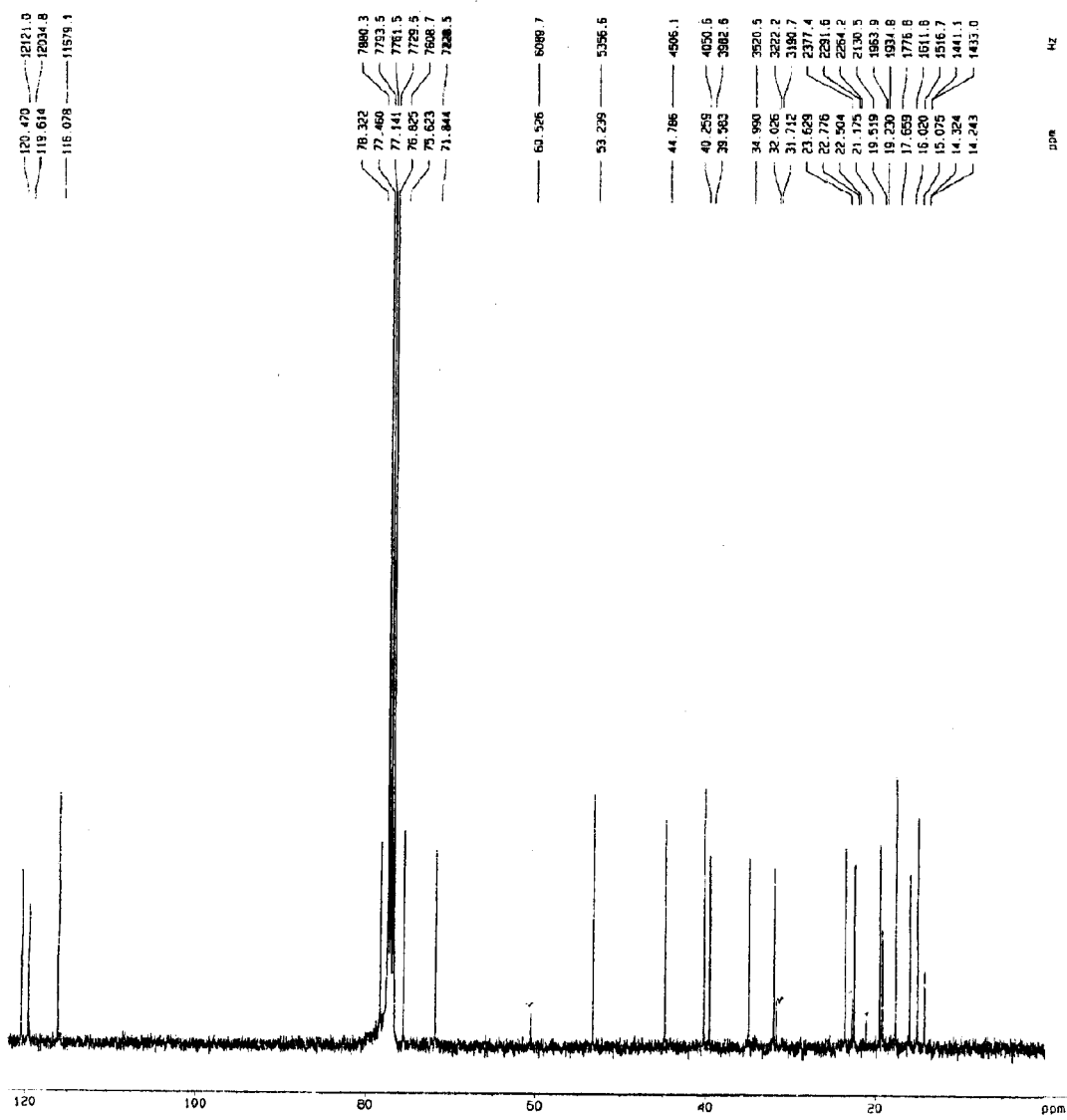
Figure 4:
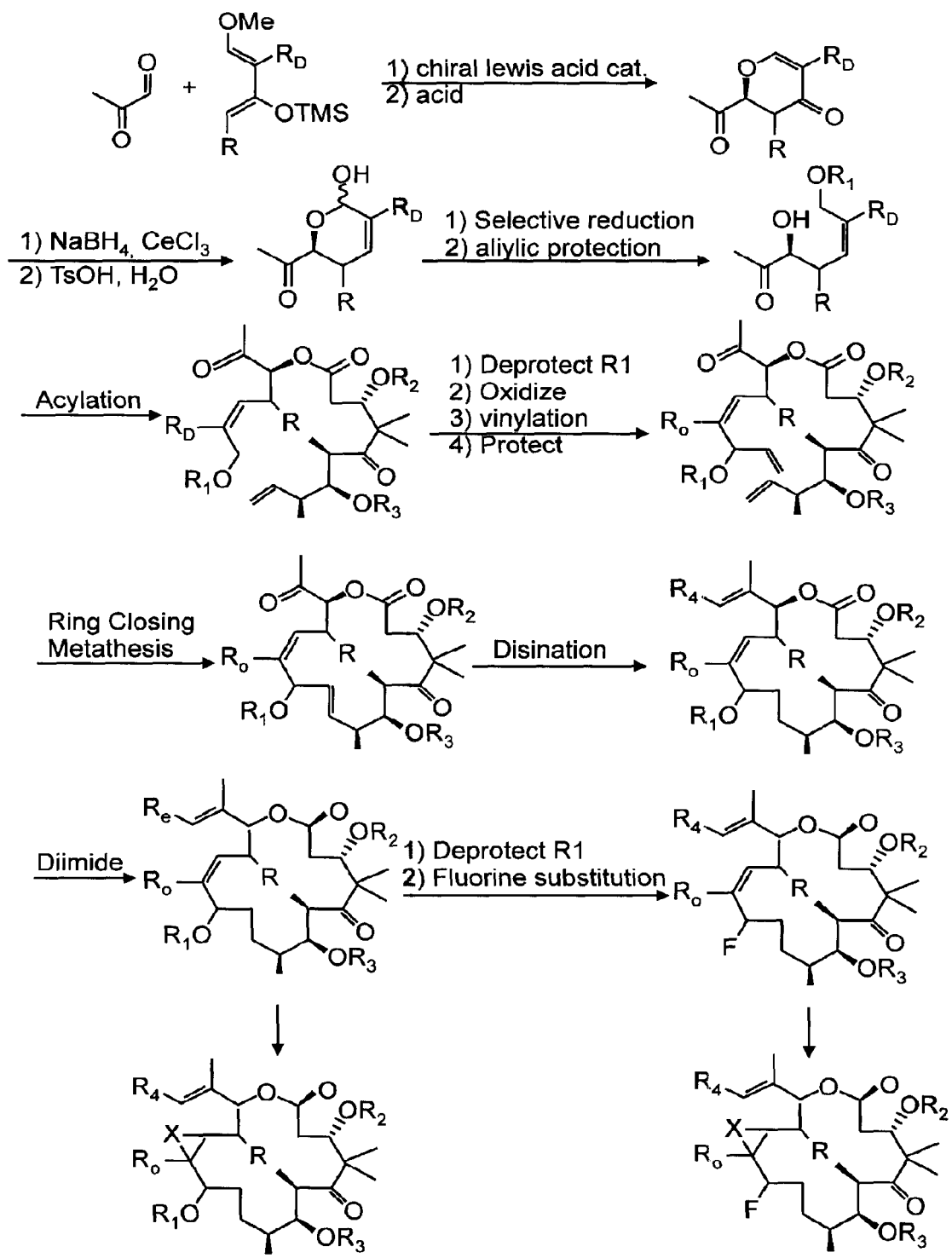
FIG. 4 shows a scheme for synthesis of 11-R and 14-R epothilones using LACDAC-ring closing olefin methathesis, and illustrates certain substitutions available with synthetic strategies that pass through a 9,10-dehydro epothilone.
Figure 5A:
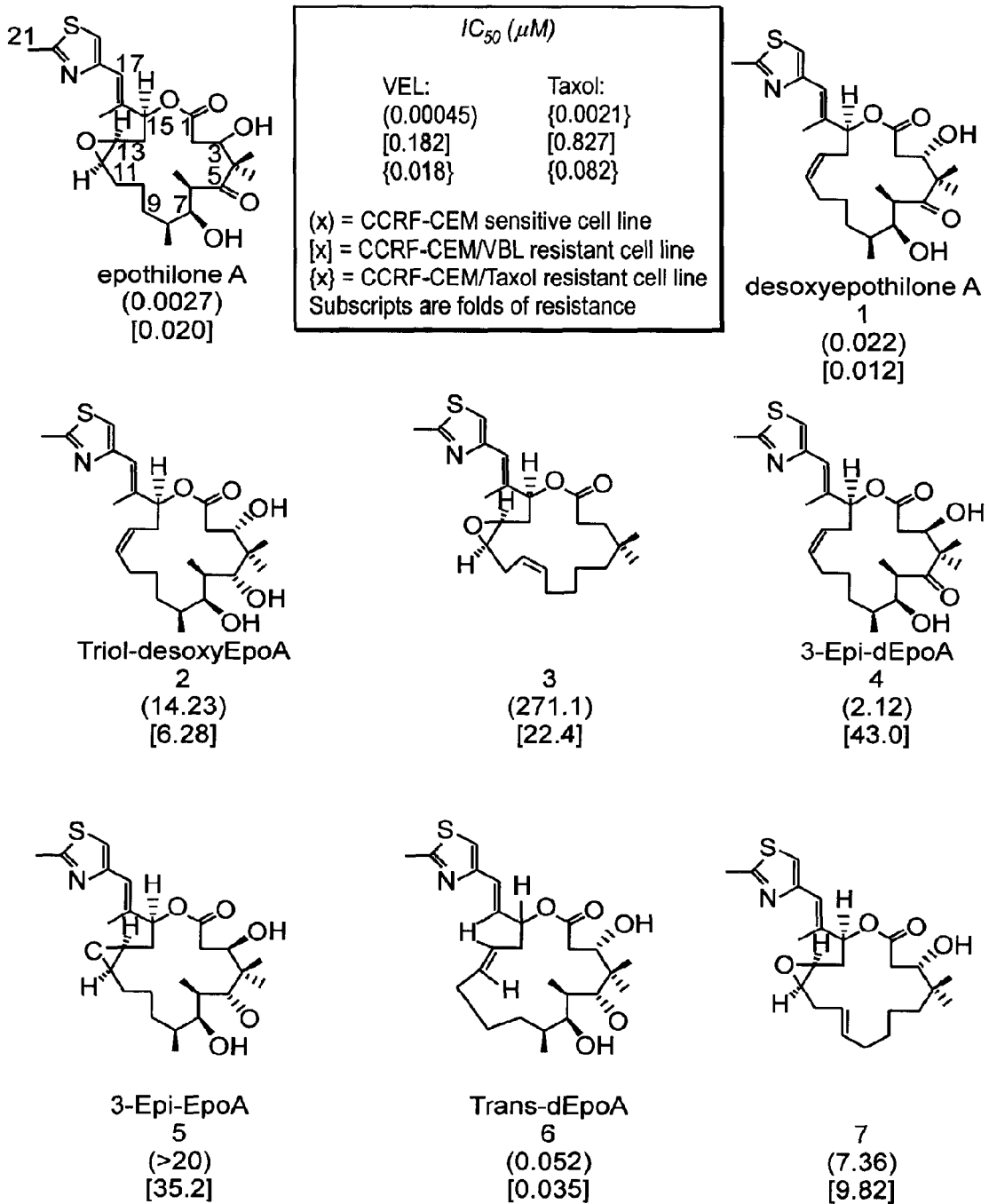
FIG. 5 presents relative cytotoxicity data against human leukemic cells in vitro for a variety of epothilone compounds and derivatives including certain 9,10-dehydro compounds (e.g., compound 7 in FIG. 5A and compound 88 and 89 in FIG. 5B).
Figure 8:
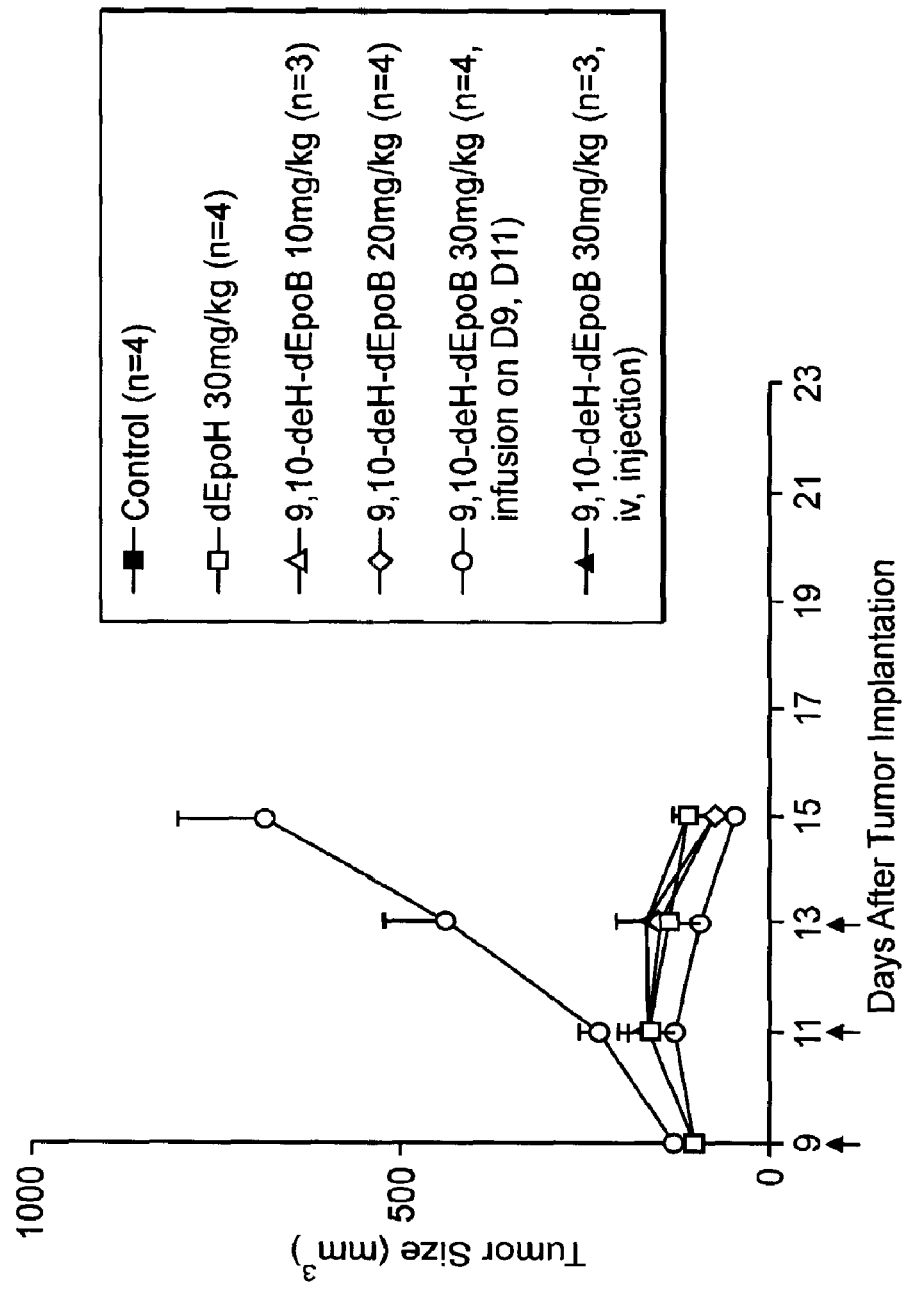
FIG. 8 shows the therapeutic effect of 9,10-dehydro-dEpoB and dEpoB in nude mice bearing human mammary carcinoma MX-1 xenograft (iv infusion, Q2Dx3).
Figure 23:
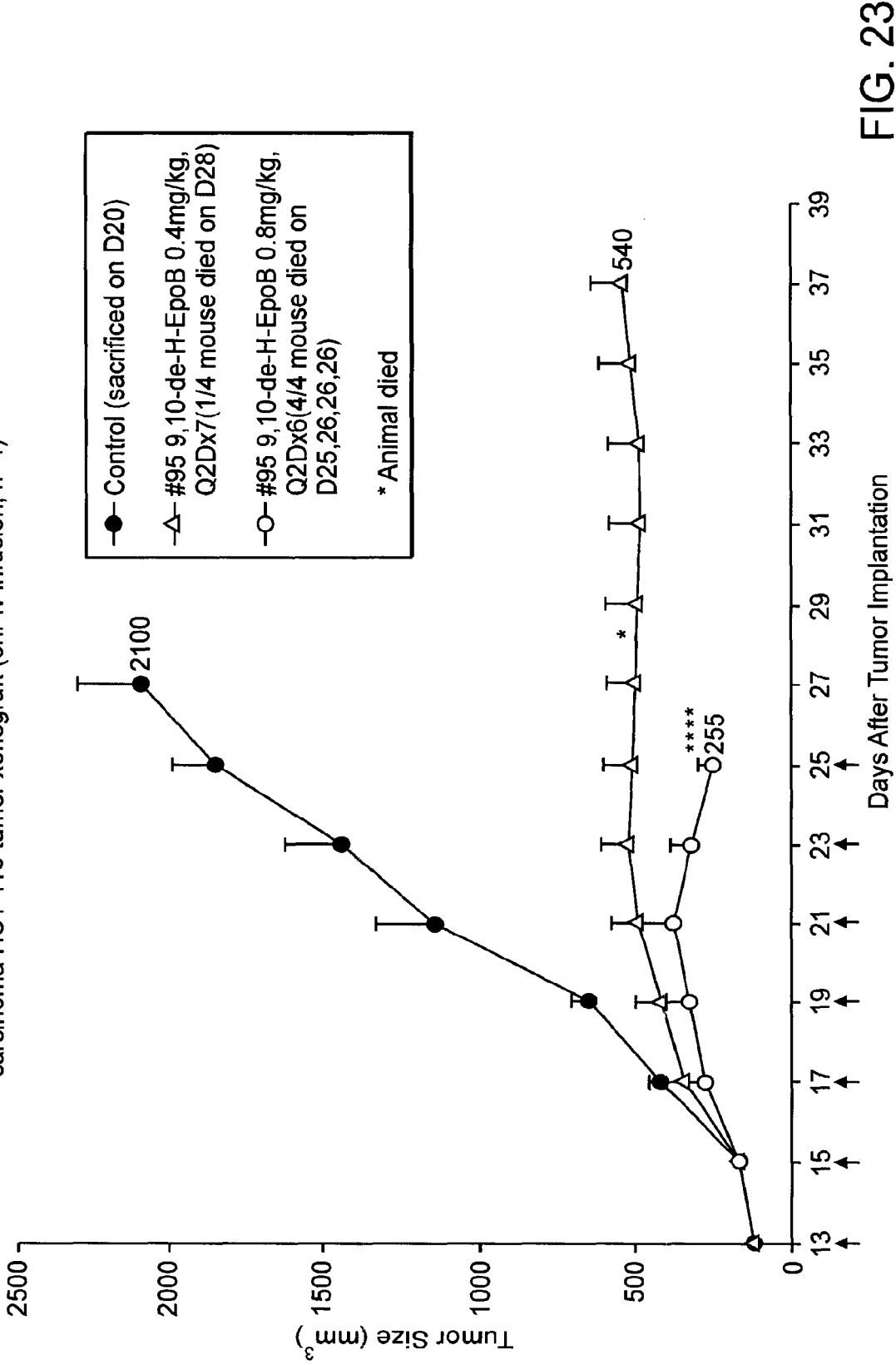
FIG. 23 shows the effect of 9,10-dehydro-EpoB on tumor size in nude mice bearing human colon carcinoma HCT-116 tumor xenografts (6 hour iv infusion).
Figure 24:
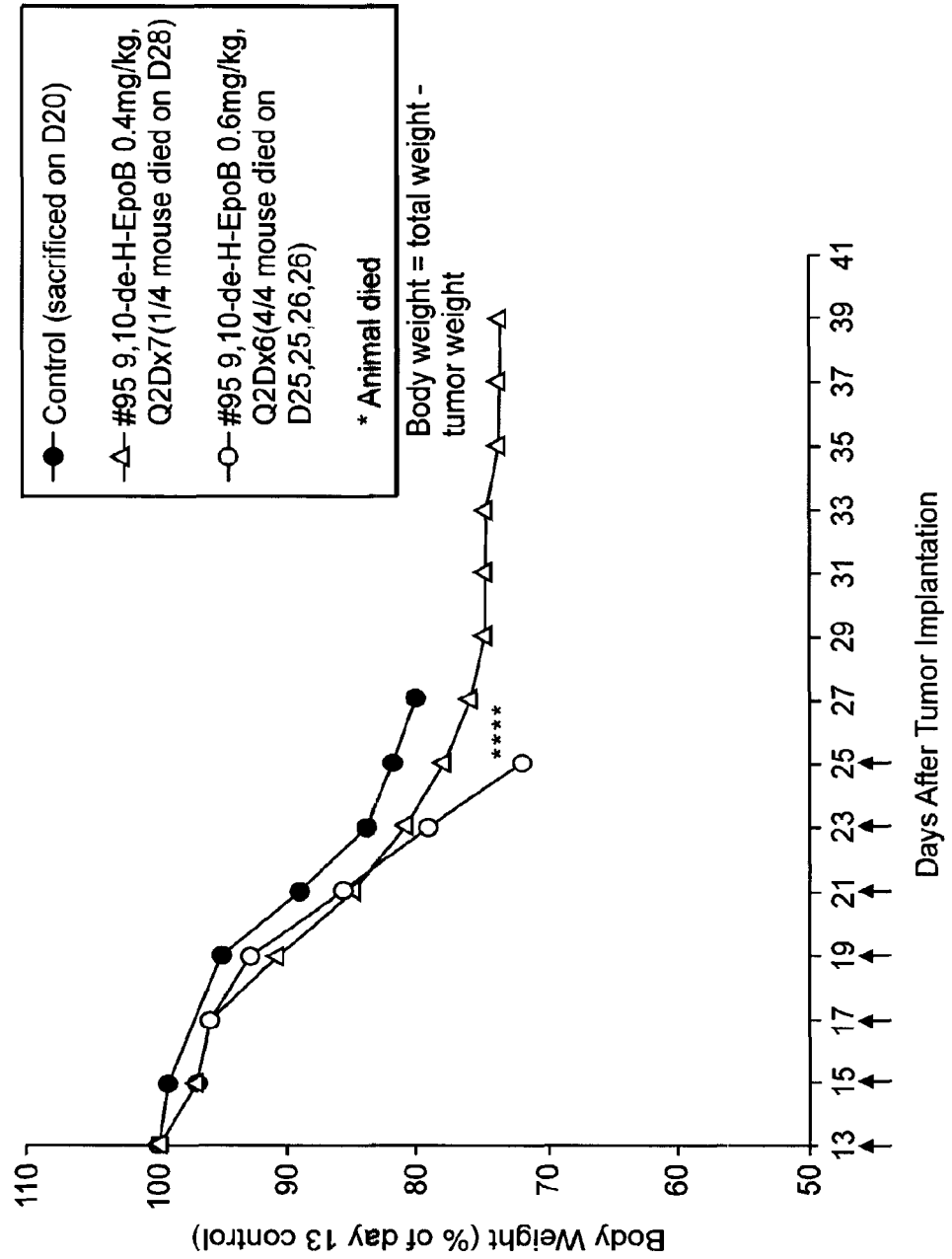
FIG. 24 shows changes in body weight of nude mice bearing human colon carcinoma HCT-116 tumor xenograft following treatment with 9,10-dehydro-EpoB (6 hour iv infusion).
Figure 25:
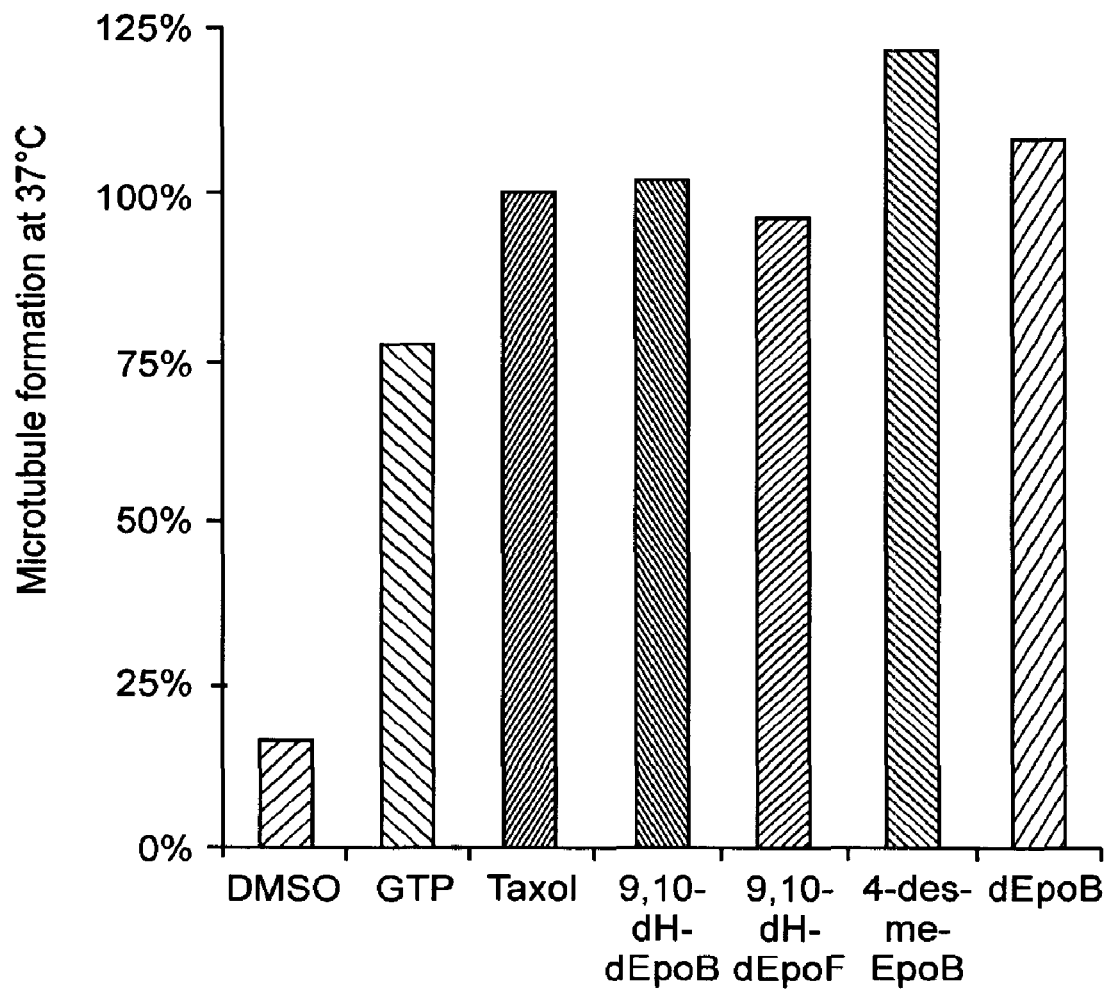
FIG. 25 shows microtubule formation from tubulin in the presence of various epothilone analogues at 37° C.
Figure 26:
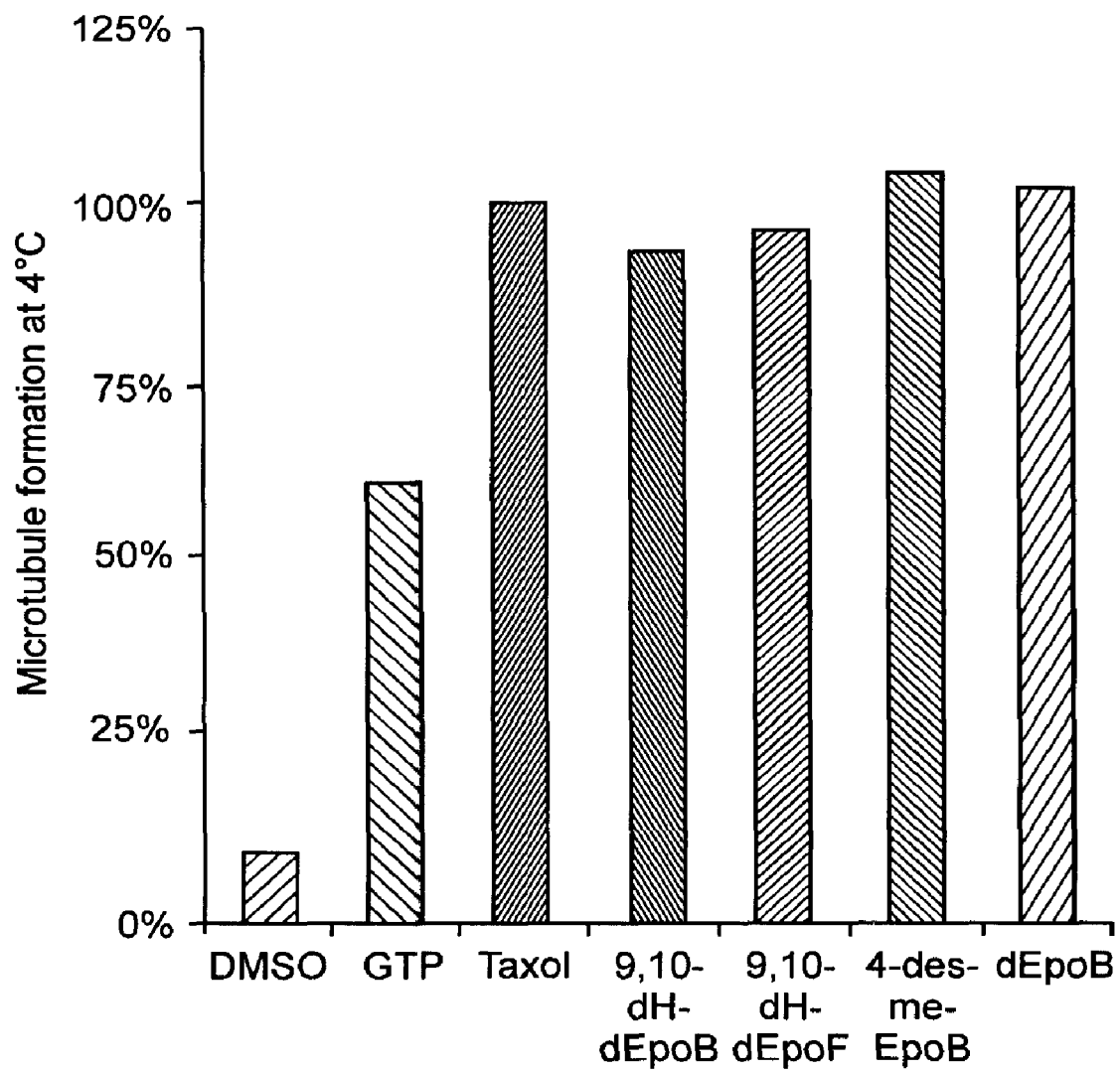
FIG. 26 shows microtubule formation from tubulin in the presence of various epothilone analogues at 4° C.
Figure 27:
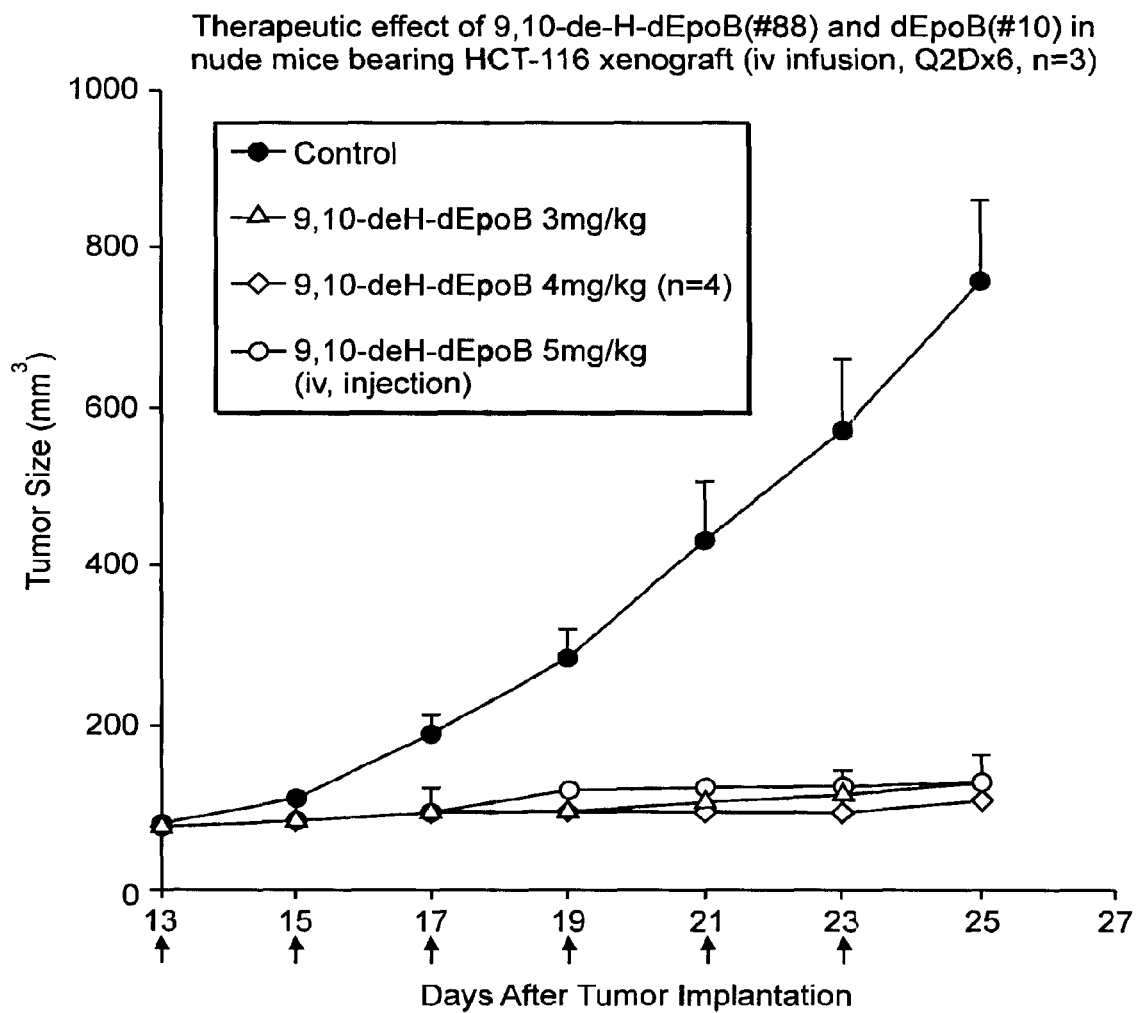
FIG. 27 shows the effect of 9,10-dehydro-dEpoB and dEpoB on tumor size in nude mice bearing HCT-116 xenografts (iv infusion, Q2Dx6).
Figure 28:
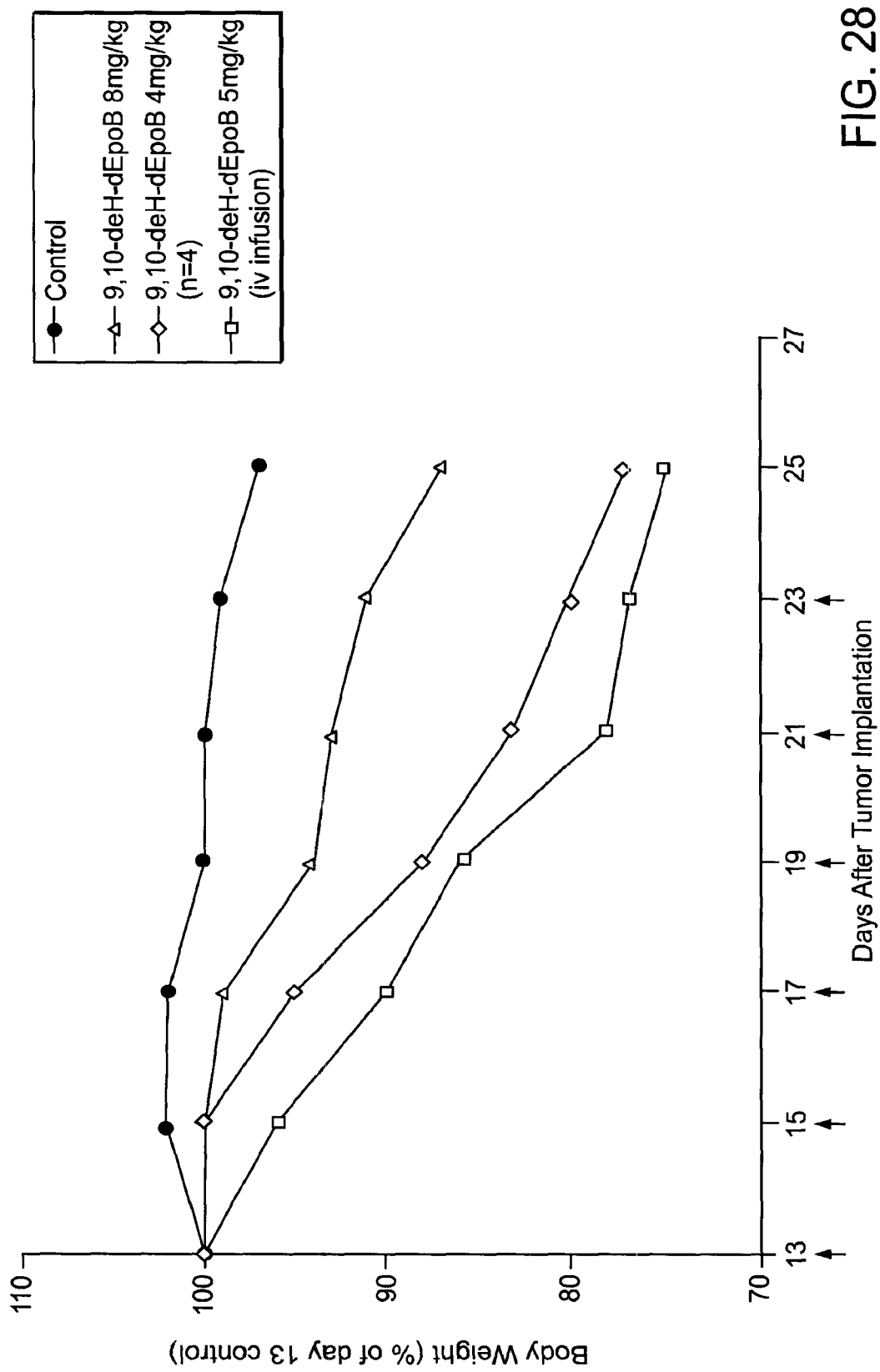
FIG. 28 shows changes in body weight of nude mice bearing HCT-116 xenografts after treatment with 9,10-dehydro-dEpoB and dEpoB (iv infusion, Q2Dx6).
Figure 29:
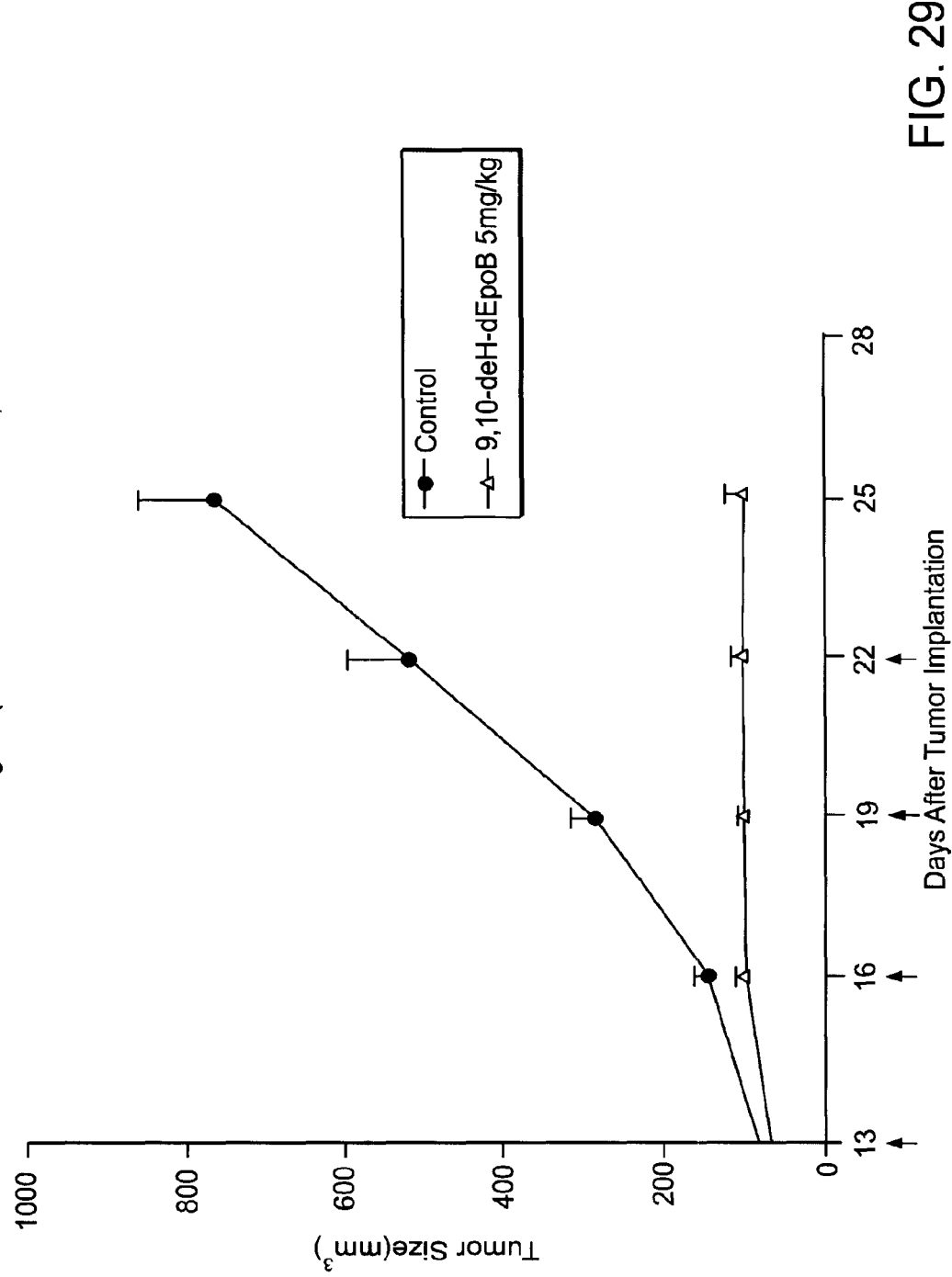
FIG. 29 shows the effect of 9,10-dehydro-dEpoB on tumor size in nude mice bearing human colon carcinoma HCT-116 xenografts (iv infusion, Q3Dx4).
Figure 30:
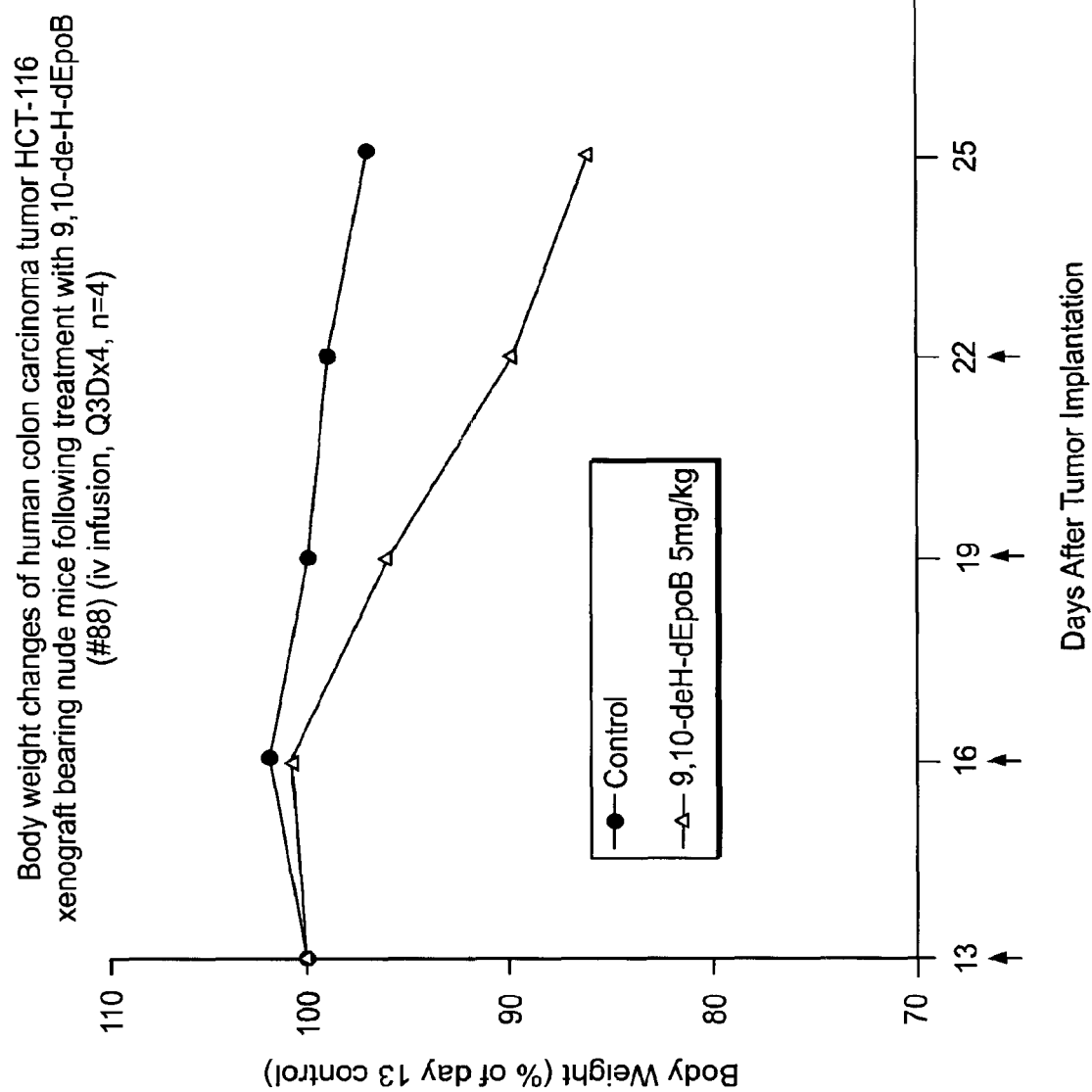
FIG. 30 shows changes in body weight of nude mice bearing human colon carcinoma tumor HCT-116 xenografts following treatment with 9,10-dehydro-dEpoB (5 mg/kg, iv infusion, X3Dx4).
Figure 34:
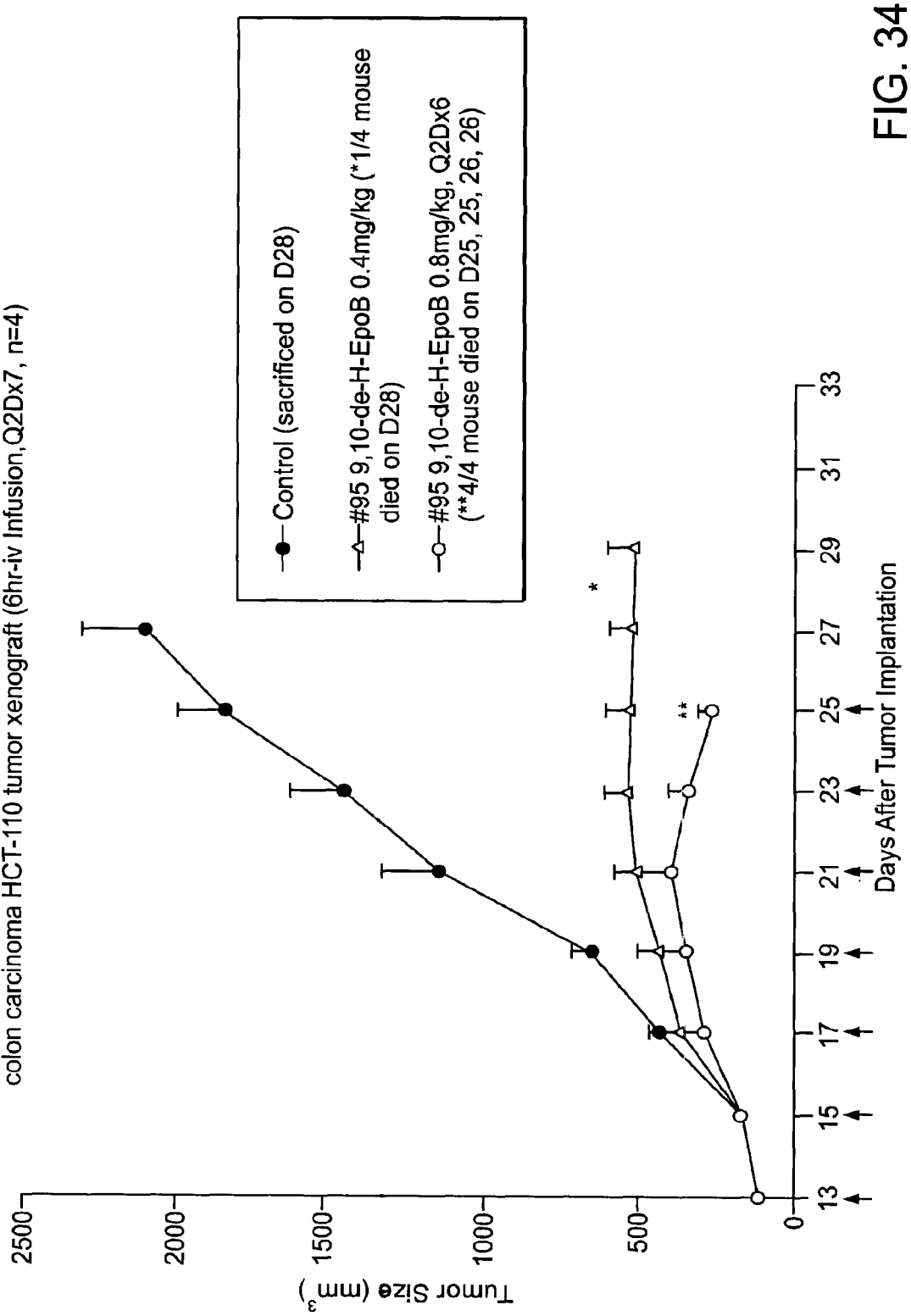
FIG. 34 shows the effect of 9,10-dehydro-EpoB on tumor size in nude mice bearing human colon carcinoma HCT-116 tumor xenograft (6 hour iv infusion, Q2Dx7).
Figure 35:
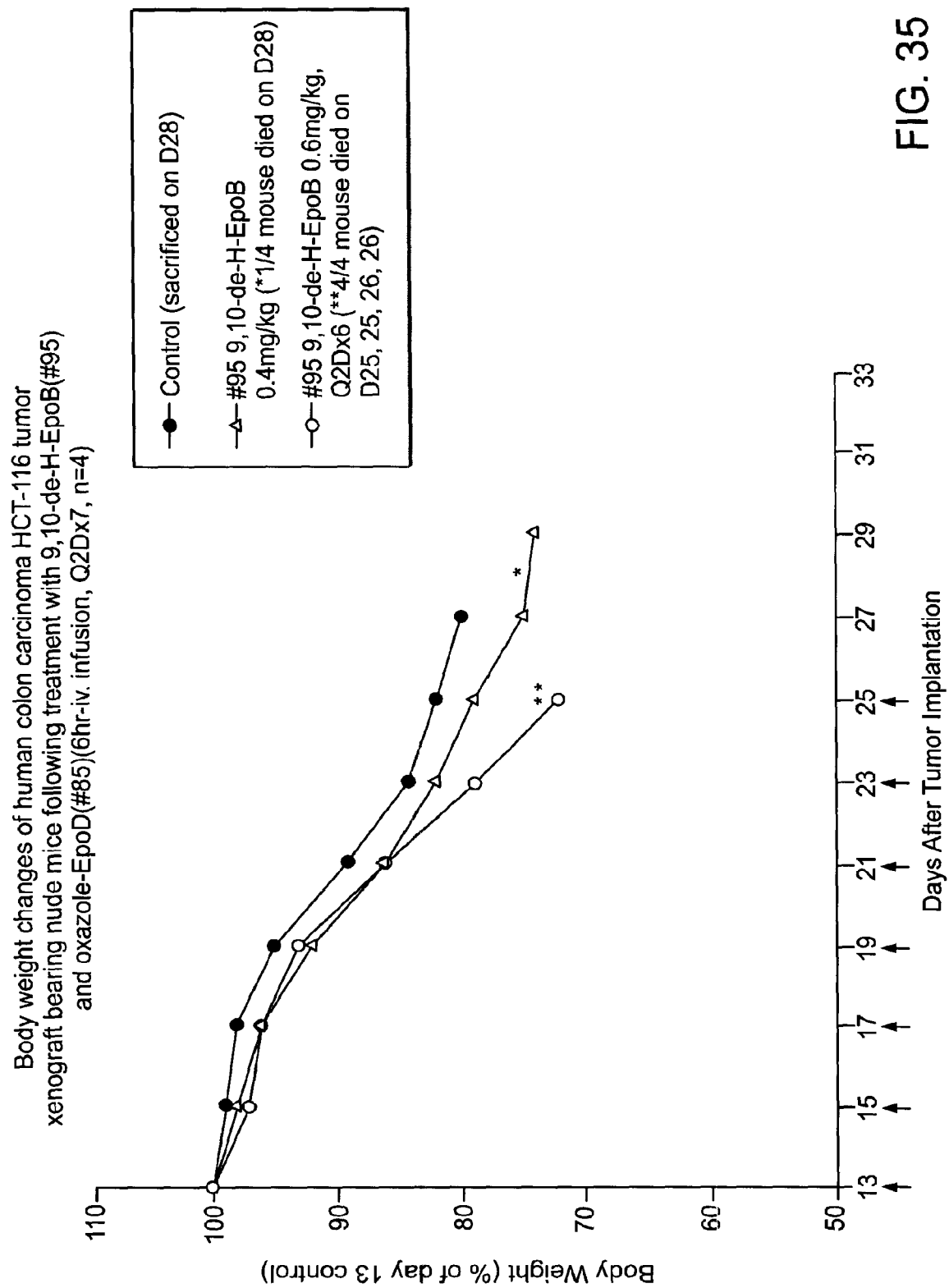
FIG. 35 shows changes in body weight of nude mice bearing human colon carcinoma HCT-116 tumor xenografts following treatment with 9,10-dehydro-EpoB and oxazole-EpoD (6 hour infusion, Q2Dx7).
Figure 36:
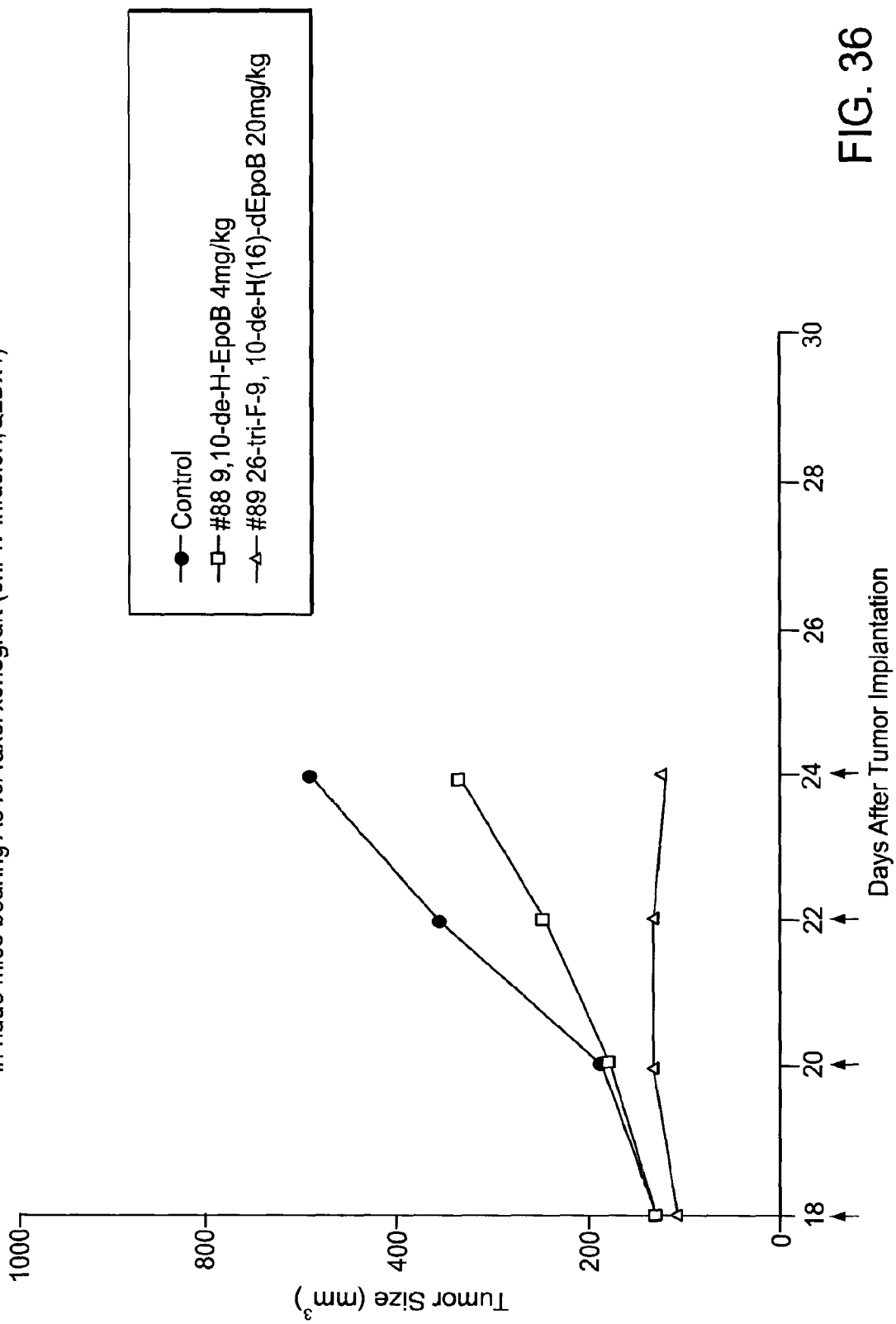
FIG. 36 shows the effect of 26-trifluoro-9,10-dehydro-dEpoB and 9,10-dehydro-dEpoB on tumor size in nude mice bearing A549/Taxol xenografts (6 hour iv infusion, Q2Dx4).
Figure 37:
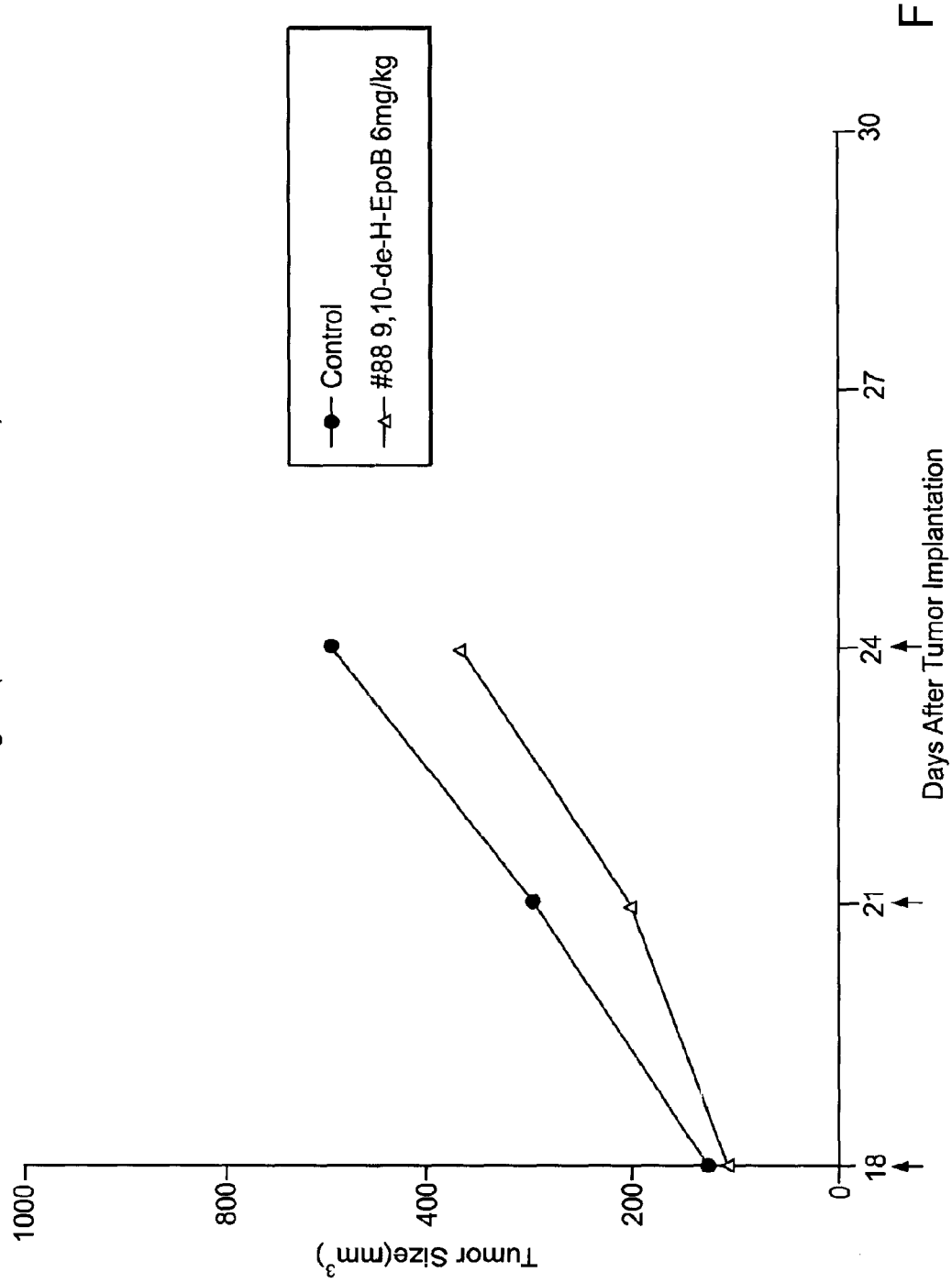
FIG. 37 shows the effect of 9,10-dehydro-dEpoB on tumor size in nude mice bearing A549/Taxol xenografts (6 hour iv infusion, Q3Dx3).
Figure 38:
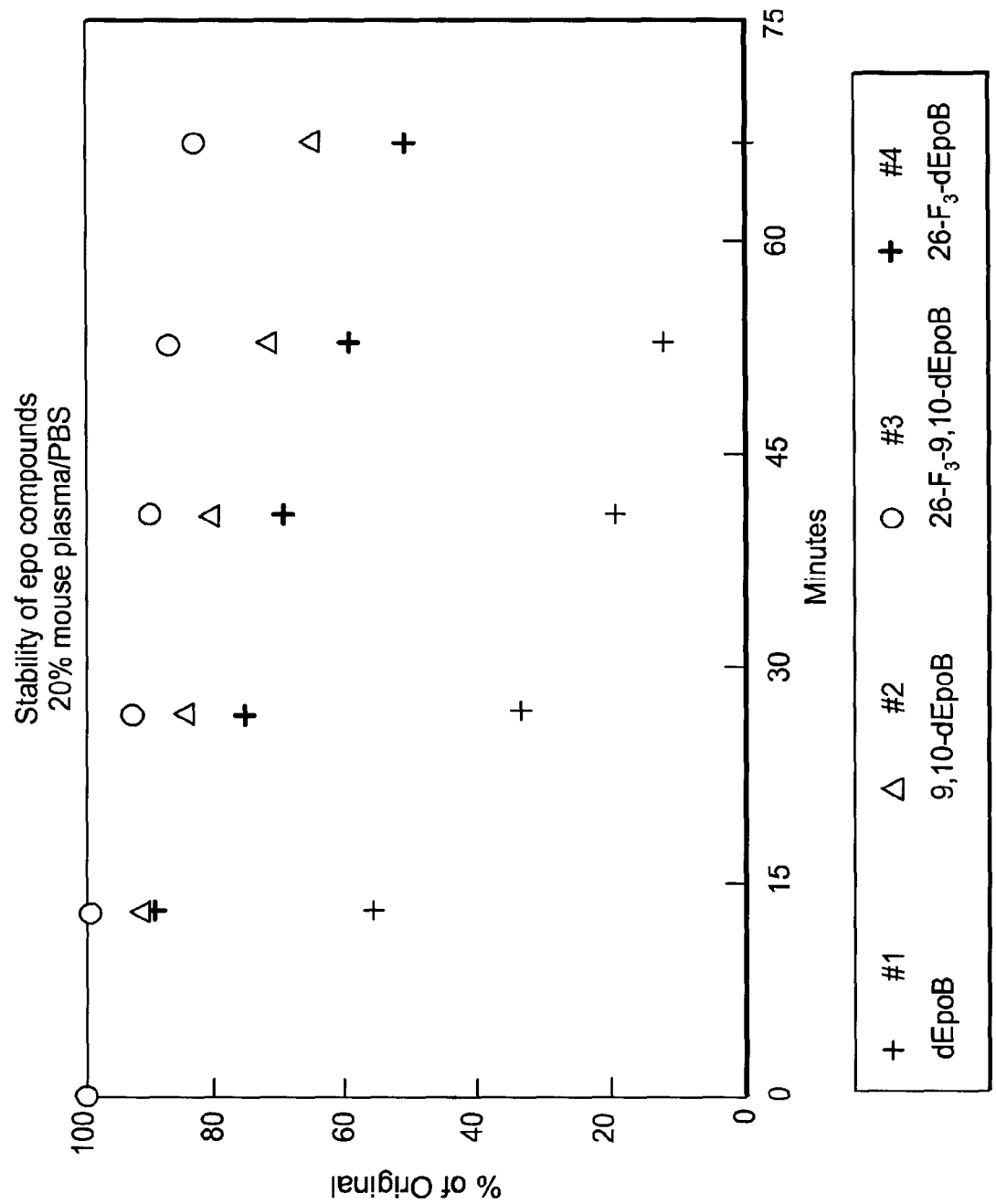
FIG. 38 shows the stability of epothilone analogues in 20% mouse plasma/PBS.
Figure 39:
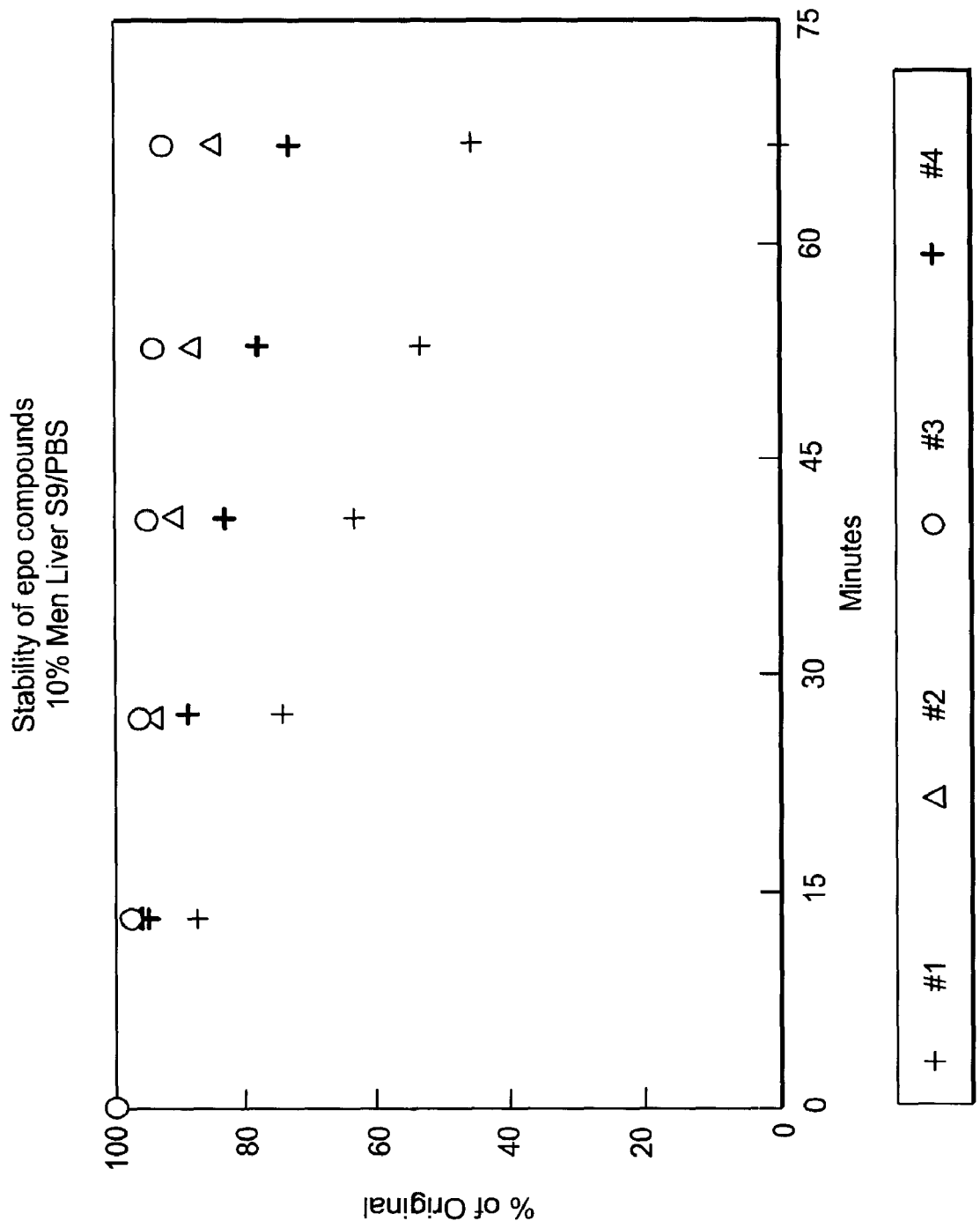
FIG. 39 shows the stability of epothilone analogues in 10% Men Liver S9/PBS.
Figure 40:
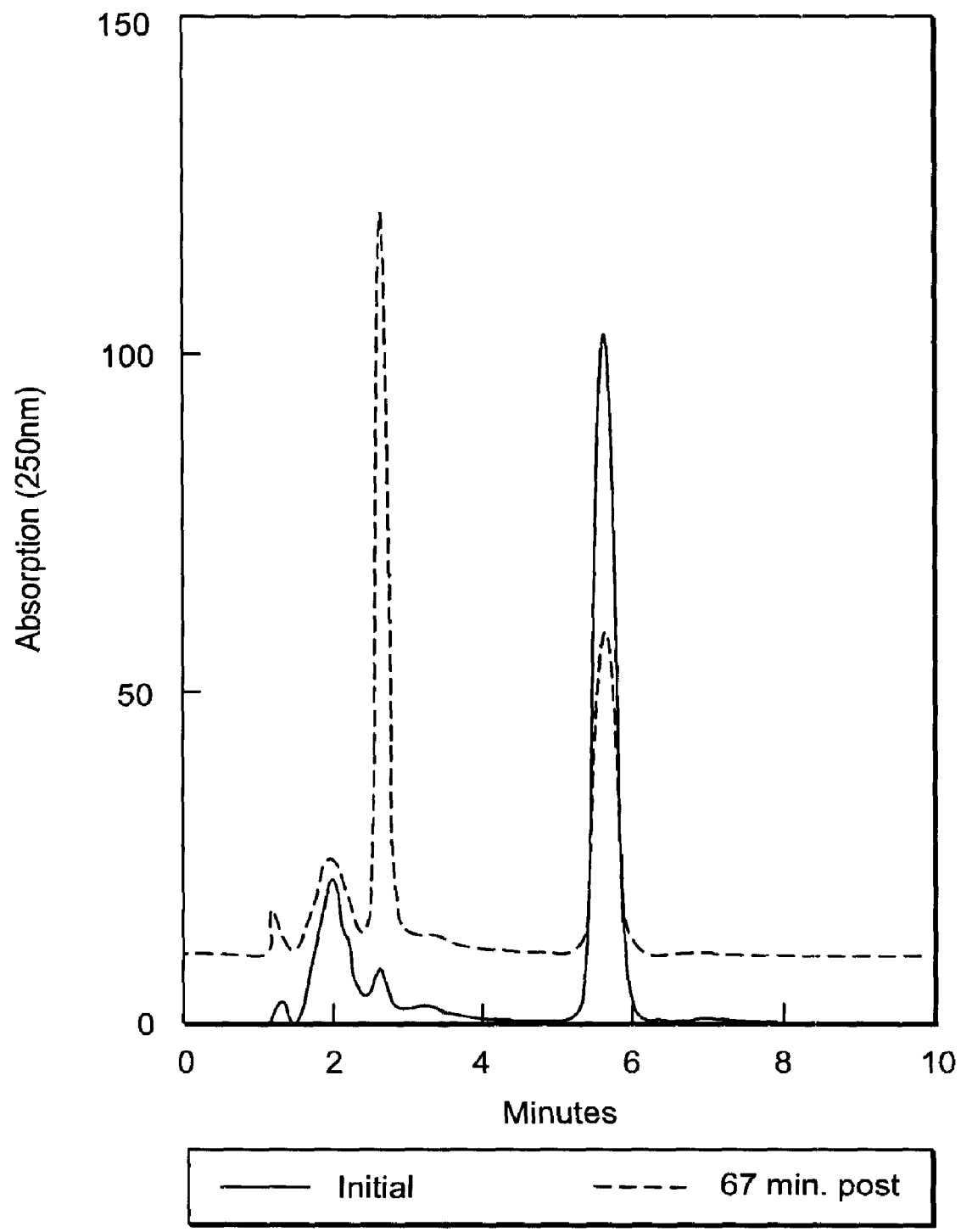
FIG. 40 shows EpoD stability chromatogram in 10% Men Liver S9/PBS.
Figure 42:
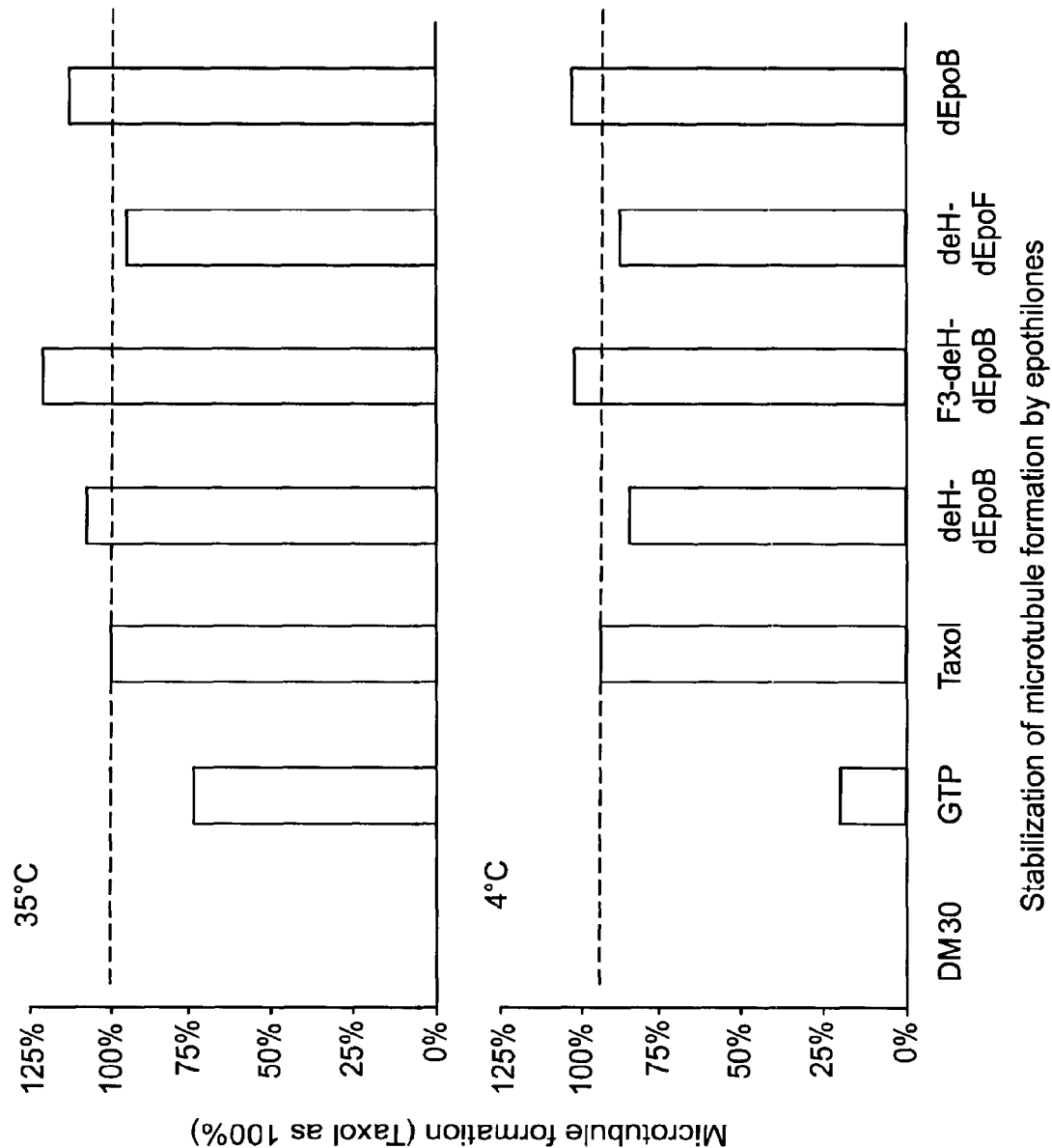
FIG. 42 shows the stabilization of microtubule formation by epothilones at 35° C. and 4° C.
Figure 43:
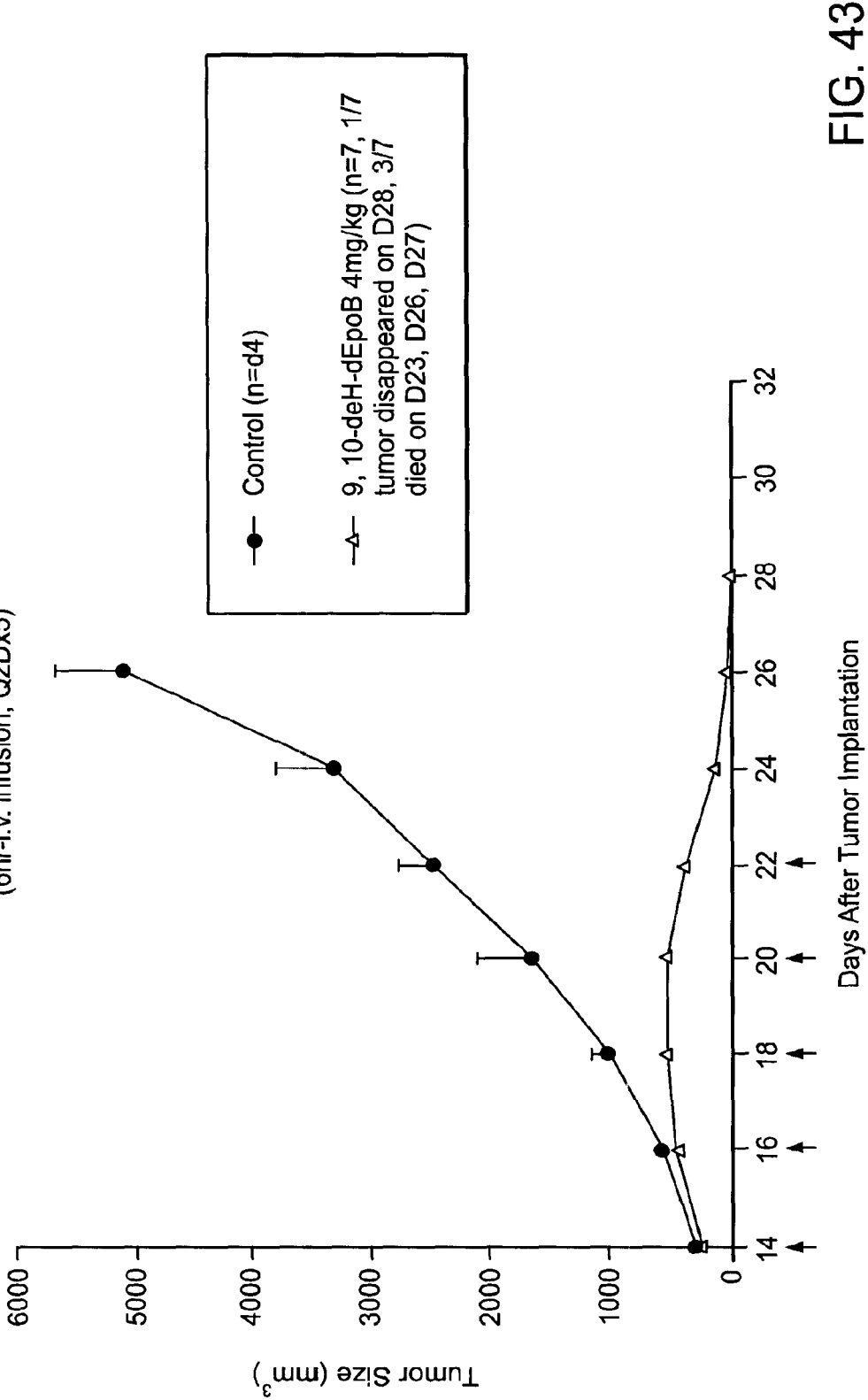
FIG. 43 shows the therapeutic effect of 9,10-dehydro-dEpoB in nude mice bearing T human mammary carcinoma (MX-1) xenograft (6 hour infusion, Q2Dx5).
Figure 44:
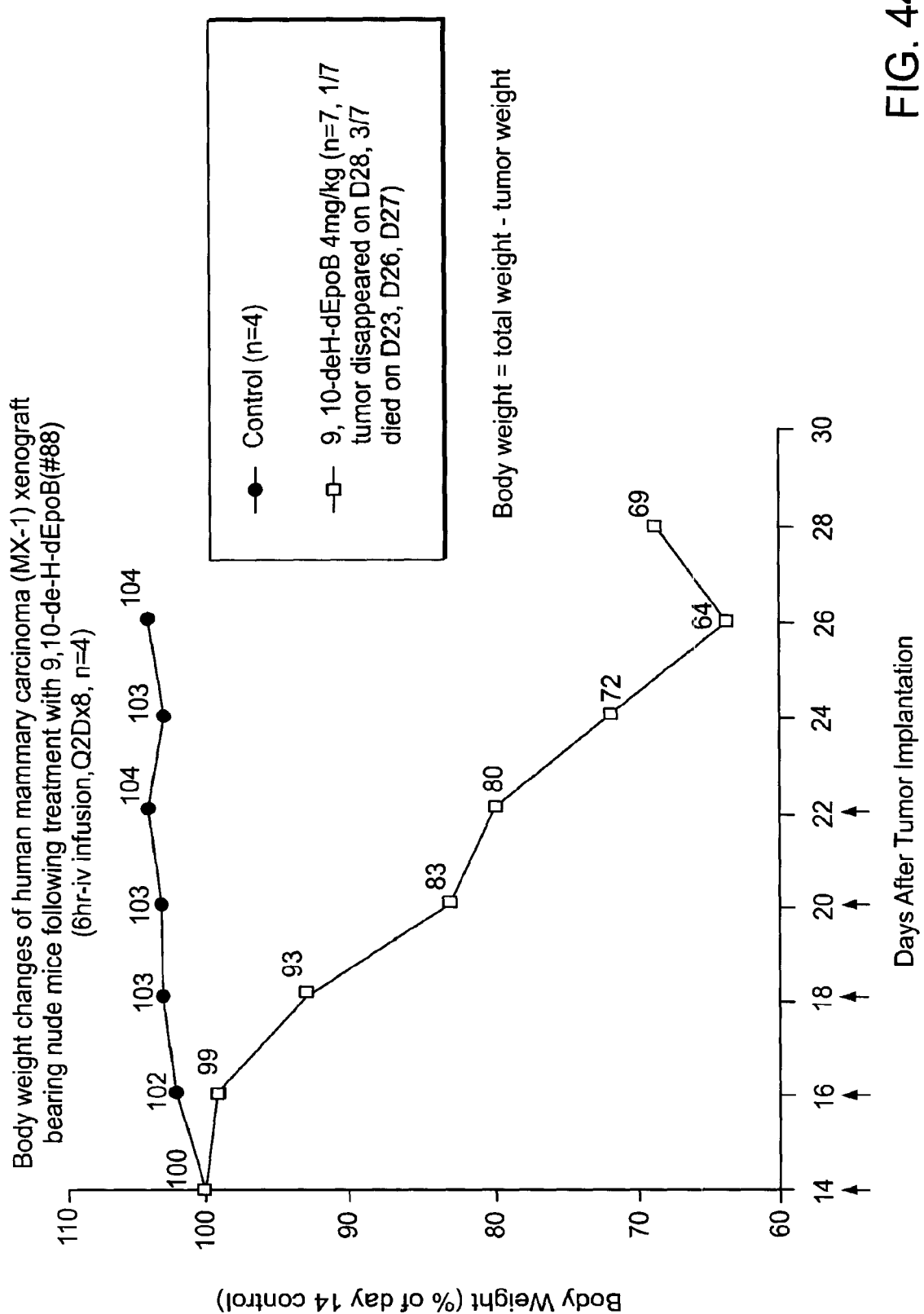
FIG. 44 shows the change in body weight of nude mice bearing human mammary carcinoma (MX-1) xenograft following treatment with 9,10-dehydro-dEpoB (6 hour infusion, Q2Dx8).
Figure 45:
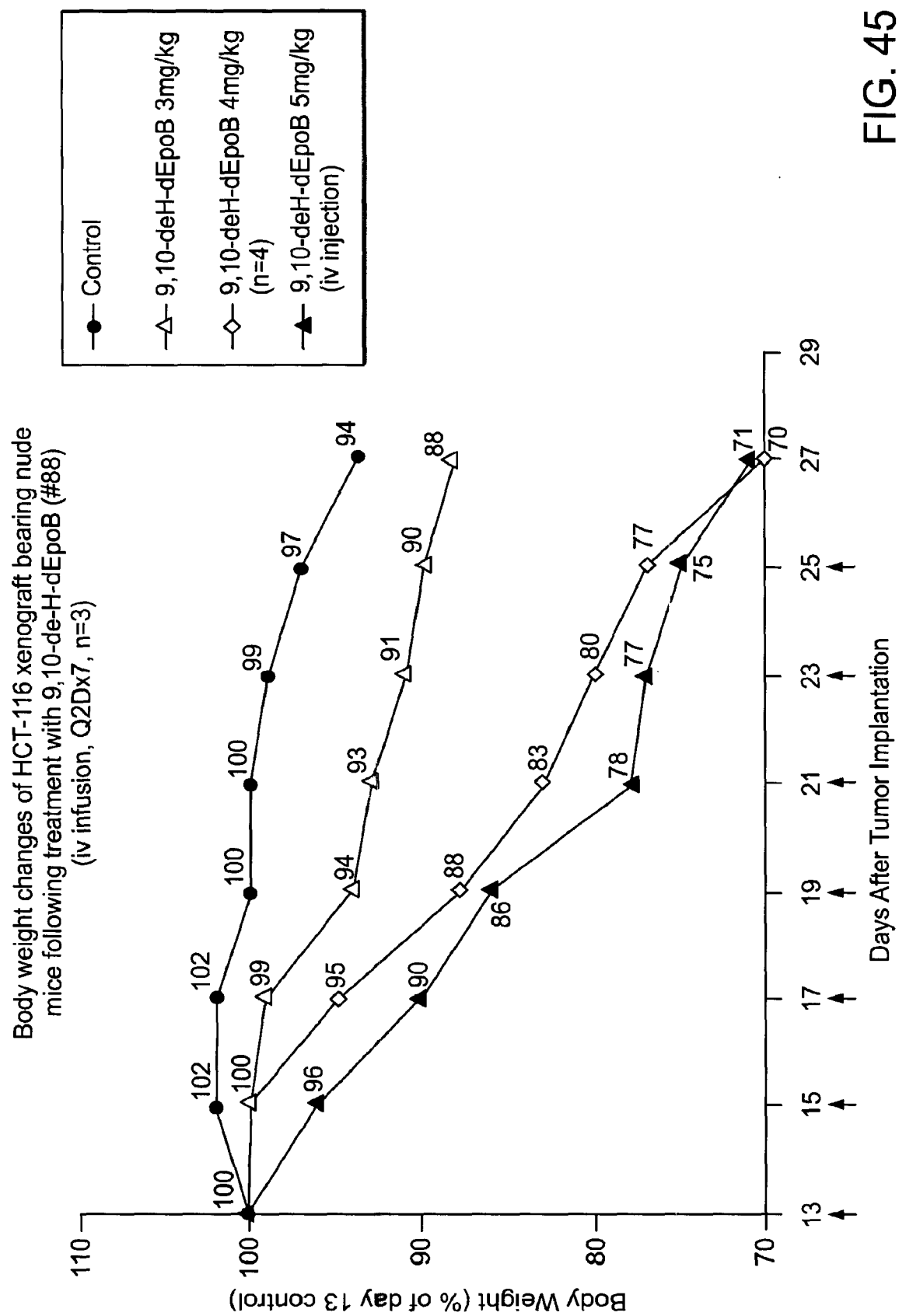
FIG. 45 shows the change in body weight of nude mice bearing HCT-116 xenograft following treatment with 9,10-dehydro-dEpoB (iv infusion, Q2Dx7).
Figure 46:
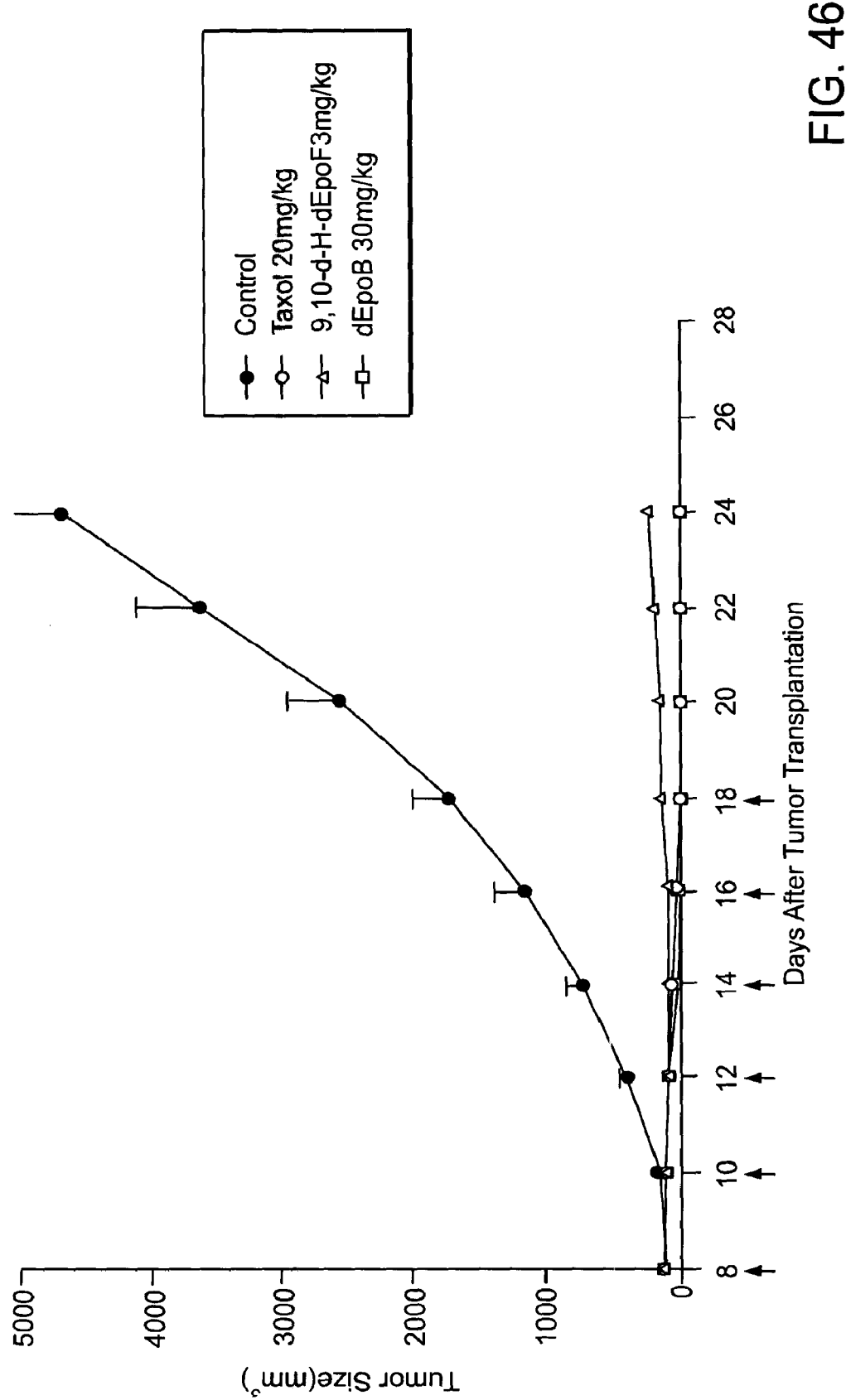
FIG. 46 shows the therapeutic effect of 9,10-dehydro-dEpoF, dEpoB, and Taxol on tumor size in nude mice bearing human mammary carcinoma (MX-1) tumor xenograft (6 hour iv infusion, Q2Dx6).
Figure 47:
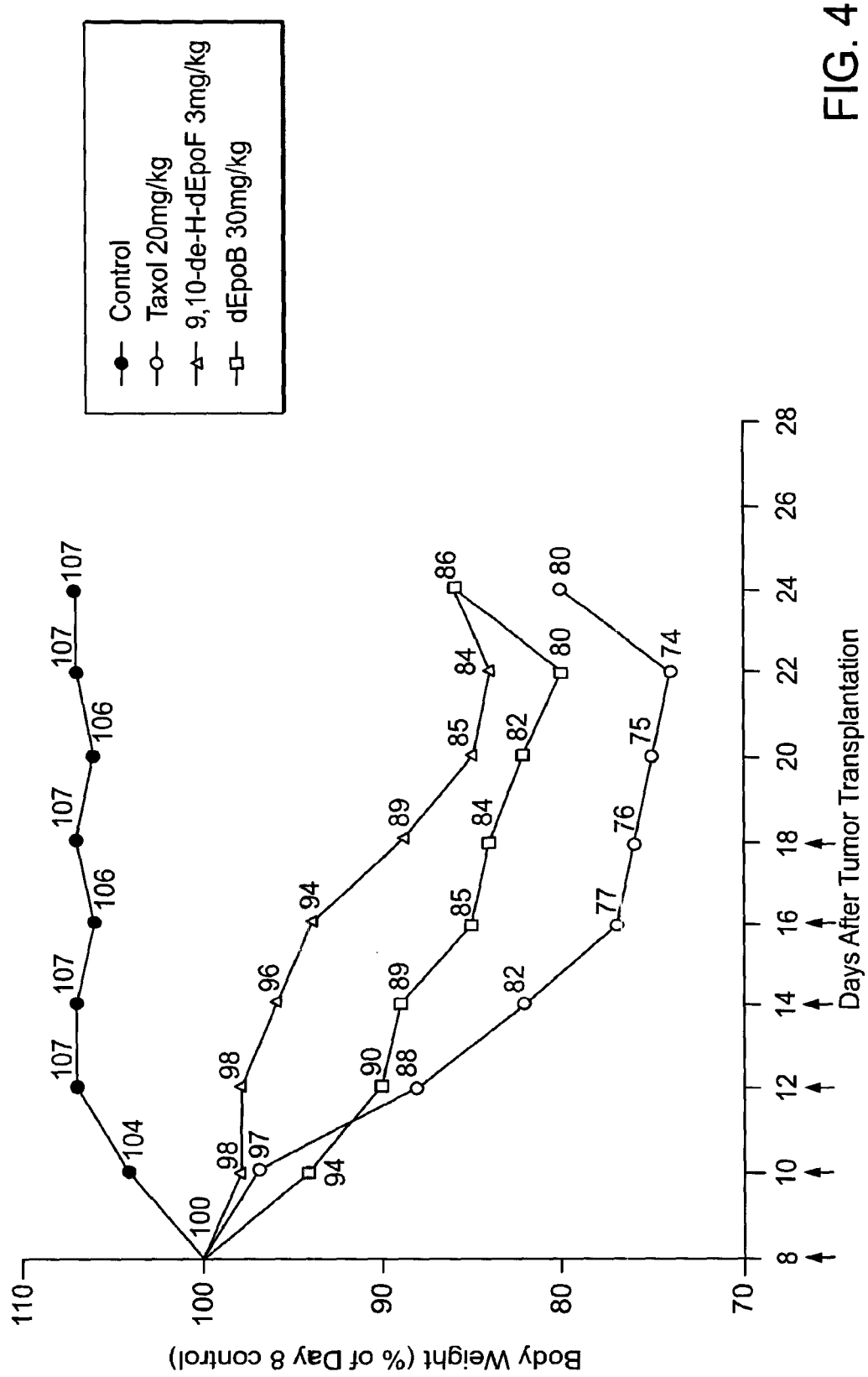
FIG. 47 shows the changes in body weight of nude mice bearing human mammary carcinoma (MX-1) tumor xenograft following treatment with 9,10-dehydro-dEpoF, dEpoB, and Taxol (6 hour infusion, Q2Dx6).
Figure 48:
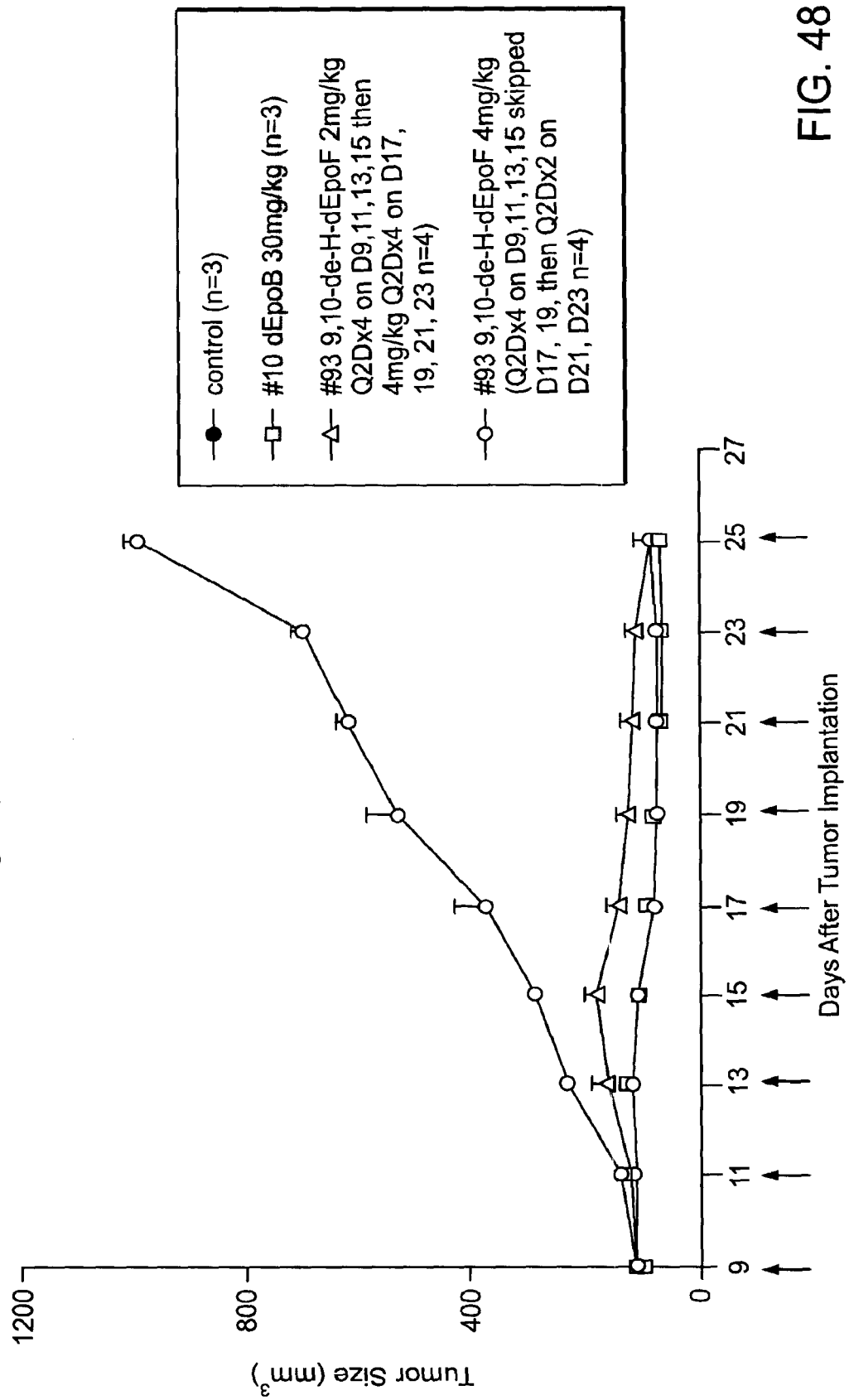
FIG. 48 shows the therapeutic effect of 9,10-dehydro-dEpoF and dEpoB in nude mice bearing human colon carcinoma HCT-116 xenograft (6 hour infusion, Q2Dx8).
Figure 49:
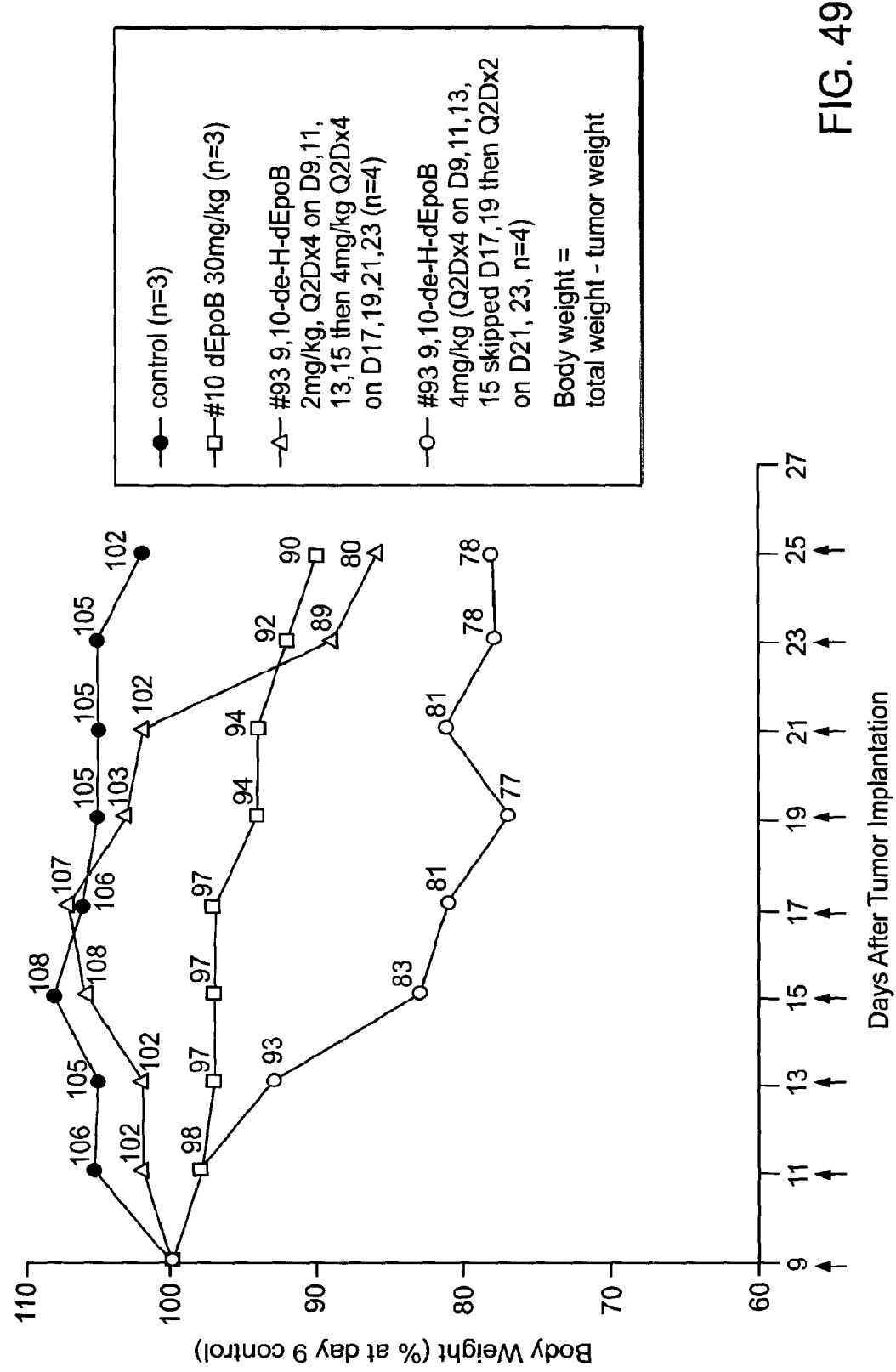
FIG. 49 shows the changes in body weight of nude mice bearing HCT-116 xenograft following treatment with 9,10-dehydro-dEpoF and dEpoB (6 hour infusion, Q2Dx8).
Figure 50:
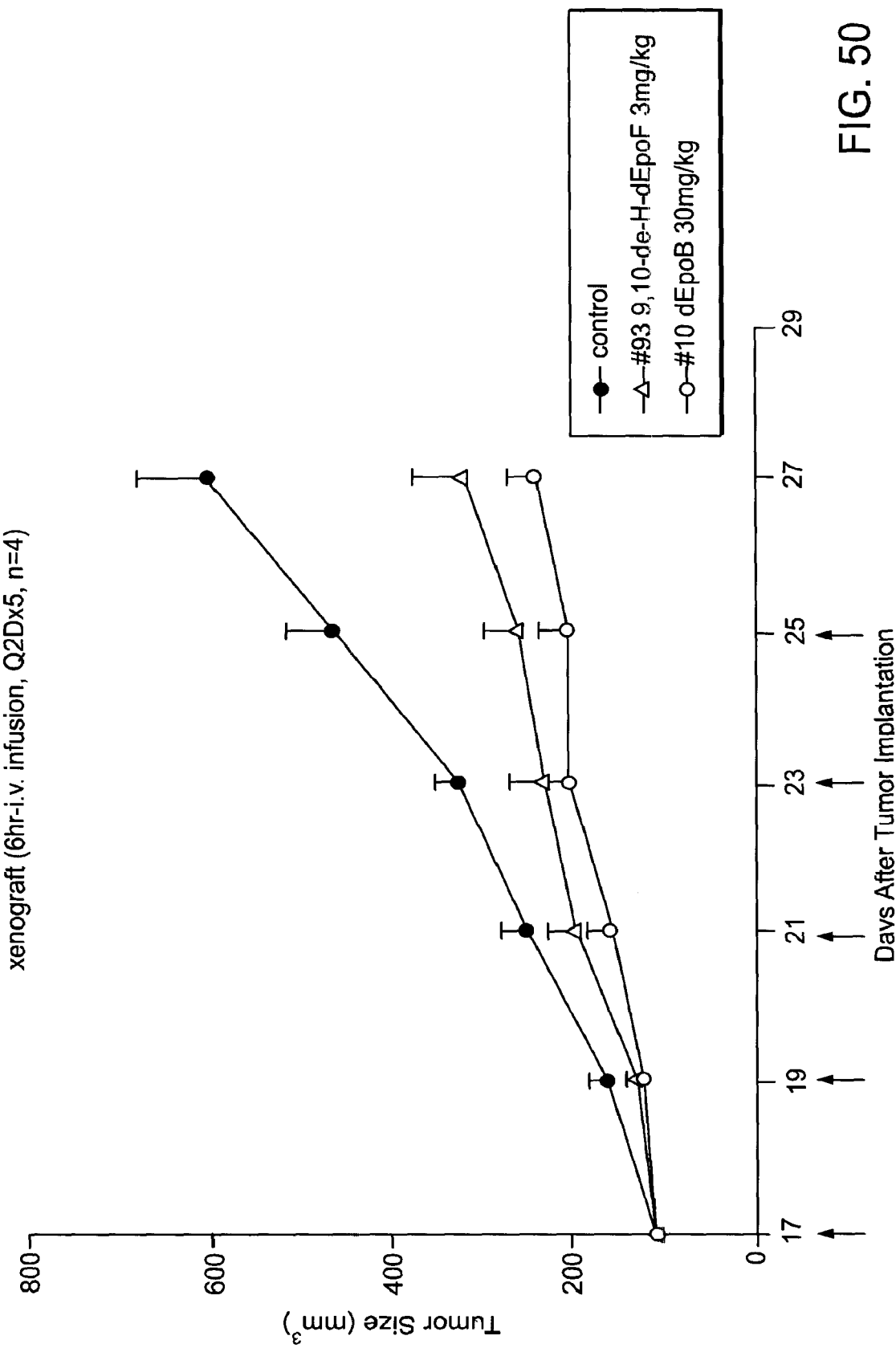
FIG. 50 shows the therapeutic effect of 9,10-dehydro-dEpoF and dEpoB in nude mice bearing Taxol-resistant human lung carcinoma (A549/Taxol) xenograft (6 hour infusion, Q2Dx5).
Figure 51:
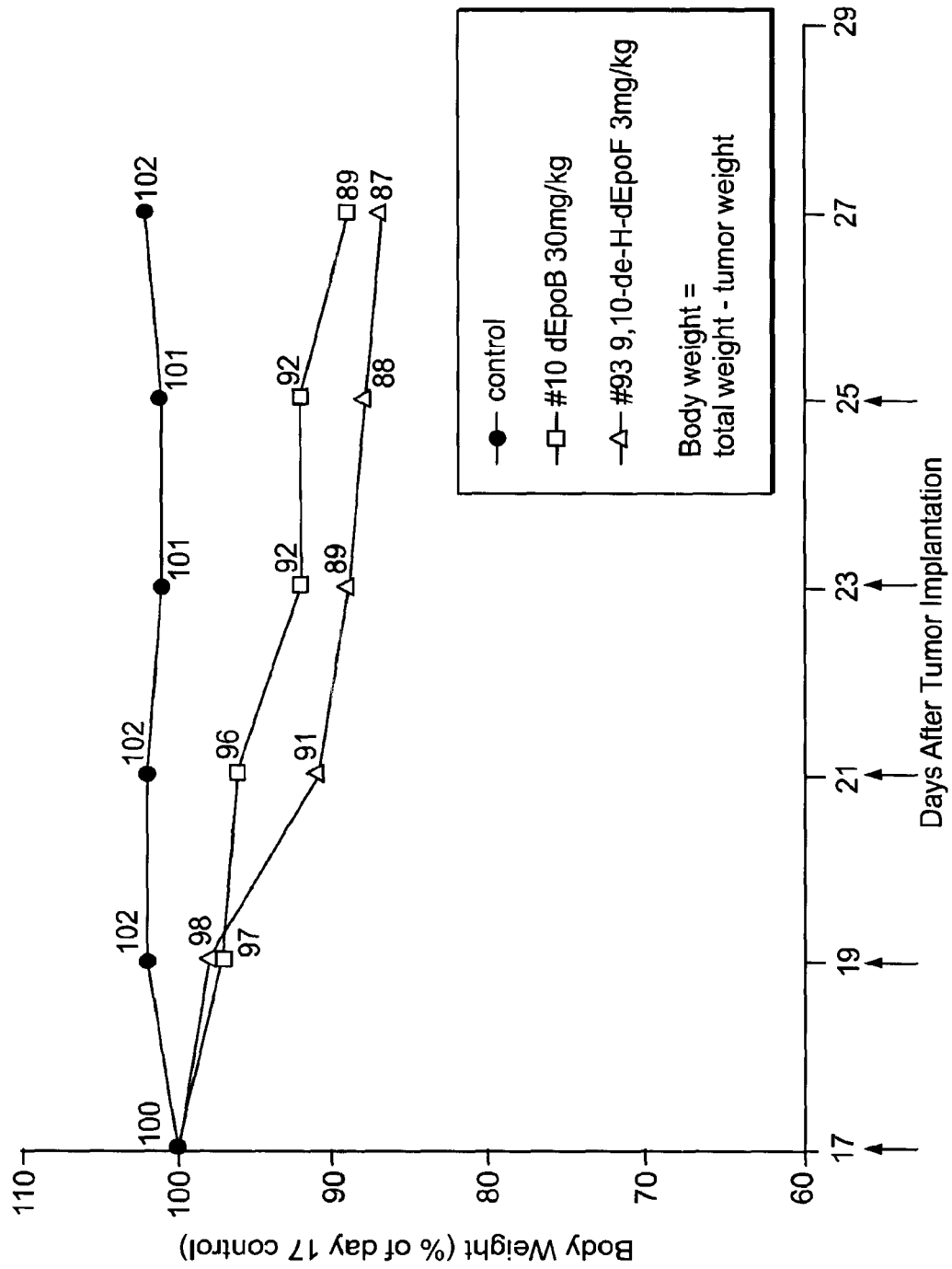
FIG. 51 shows changes in body weight of nude mice bearing Taxol-resistant human lung carcinoma (A549/Taxol) xenograft following treatment with 9,10-dehydro-dEpoF and dEpoB (6 hour infusion, Q2Dx5).
Figure 70:
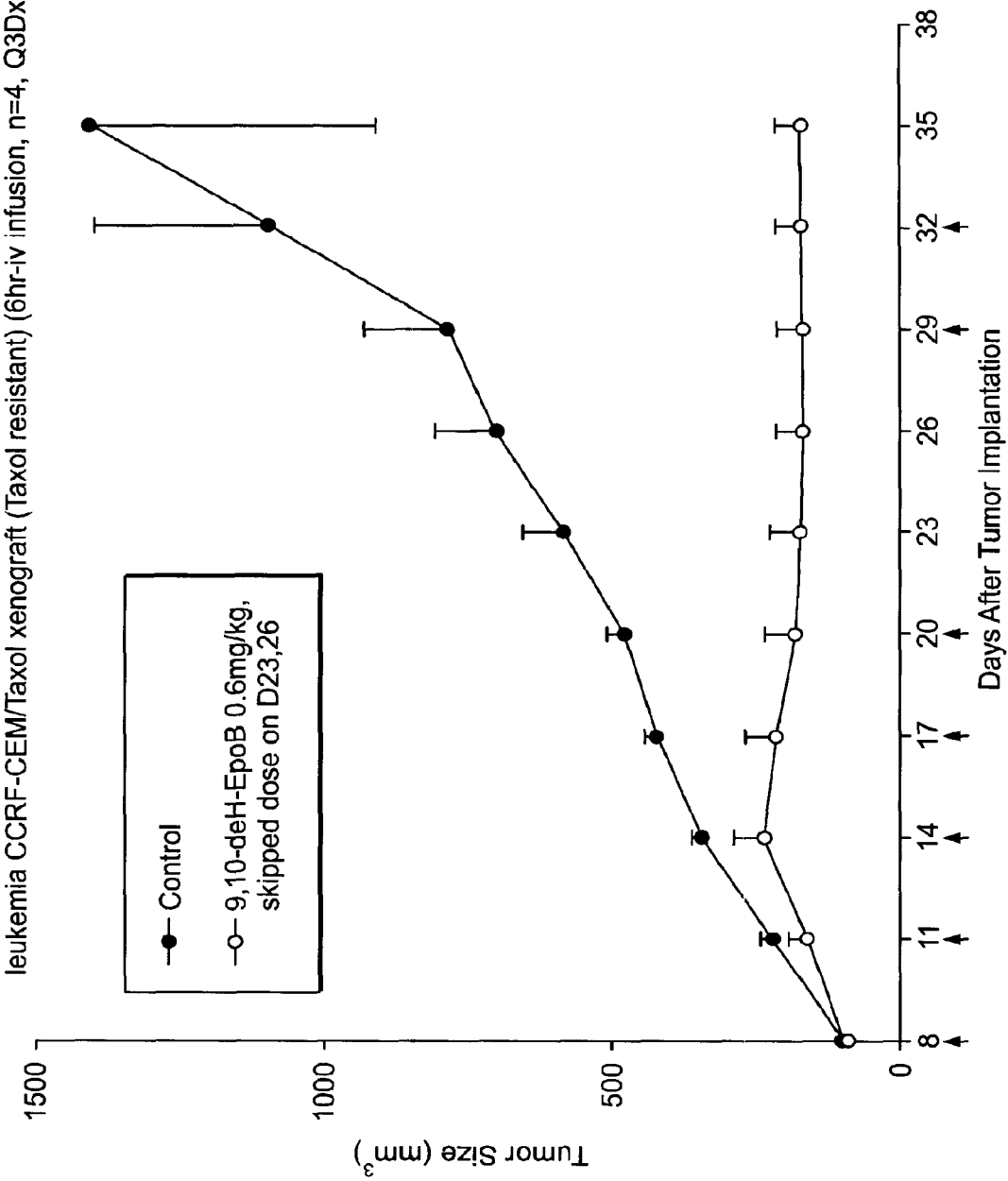
FIG. 70 shows the therapeutic effect of 9,10-dehydro-EpoB in nude mice bearing human T-cell lymphoblastic leukemia CCRF-CEM/Taxol xenograft (Taxol resistant) (6 hour iv infusion, Q3Dx5, x2).
Figure 71:
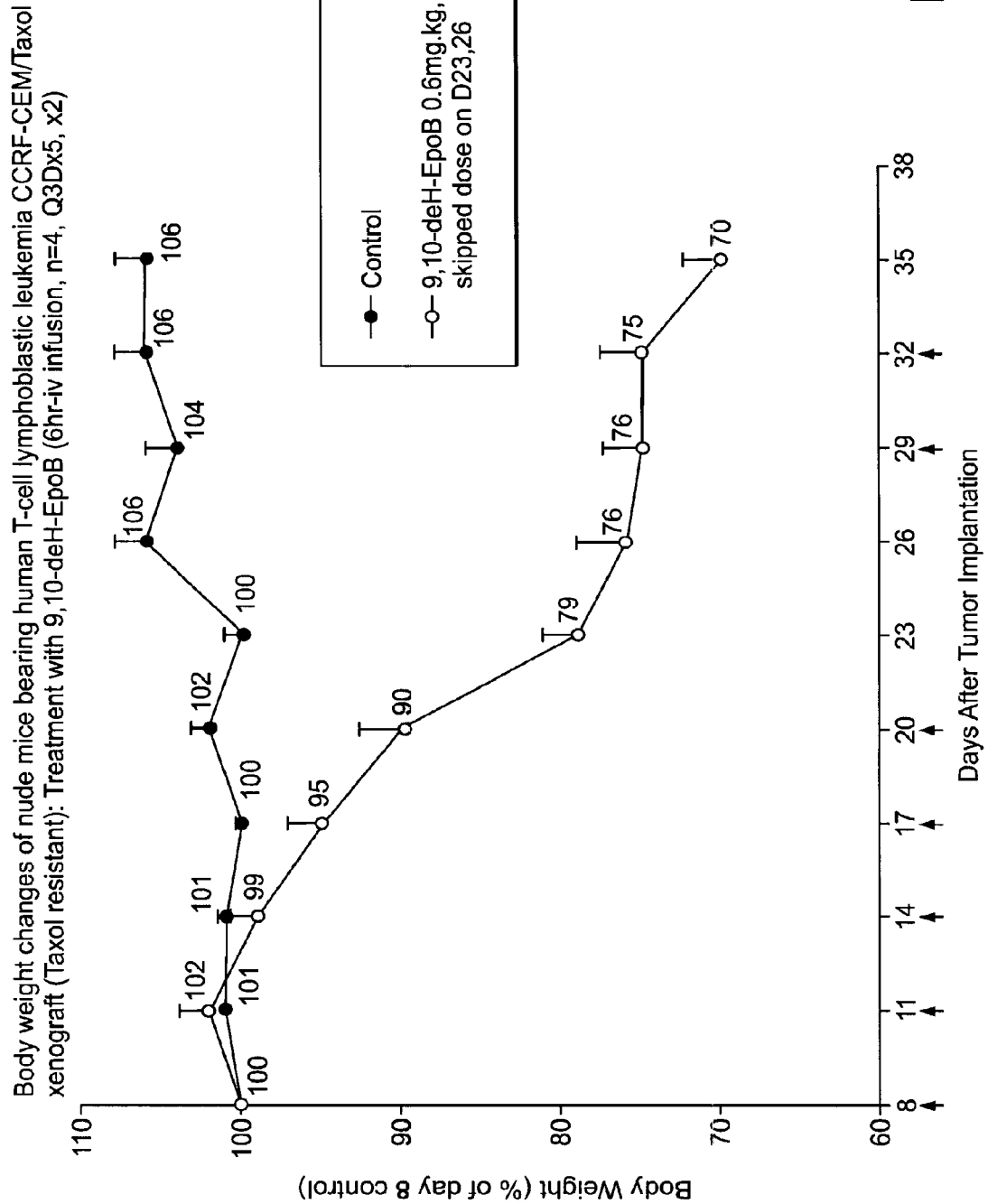
FIG. 71 shows the changes in body weight of nude mice bearing human T-cell lymphoblastic leukemia CCRF-CEM/Taxol xenograft (Taxol resistant) following treatment with 9,10-dehydro-EpoB (6 hour iv infusion, Q3Dx5, x2).
Figure 72:
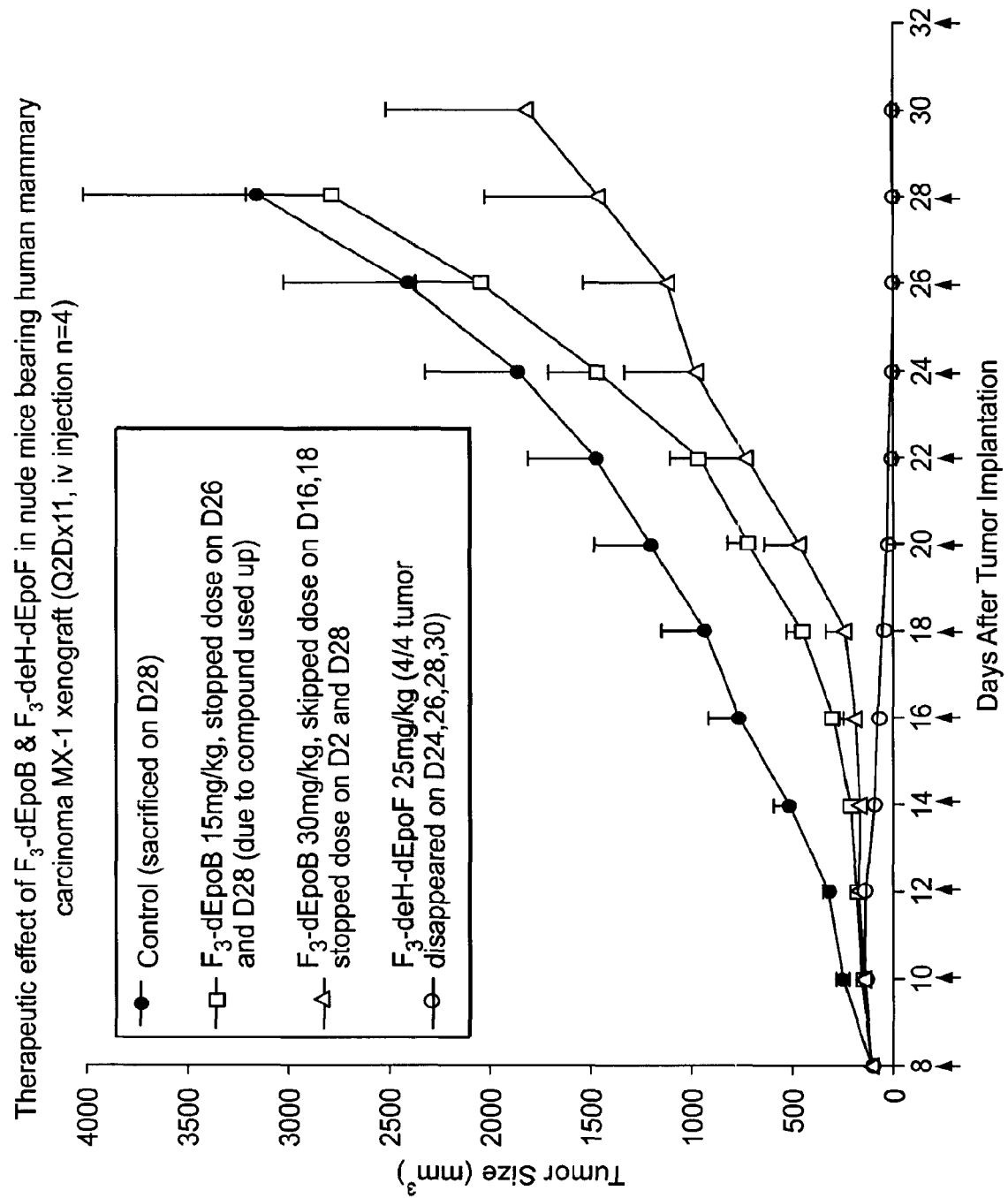
FIG. 72 shows the therapeutic effect of 26-trifluoro-dEpoB and 26-trifluoro-9,10-dehydro-dEpoF in nude mice bearing human mammary carcinoma MX-1 xenograft (Q2Dx11, iv injection).
Figure 73:
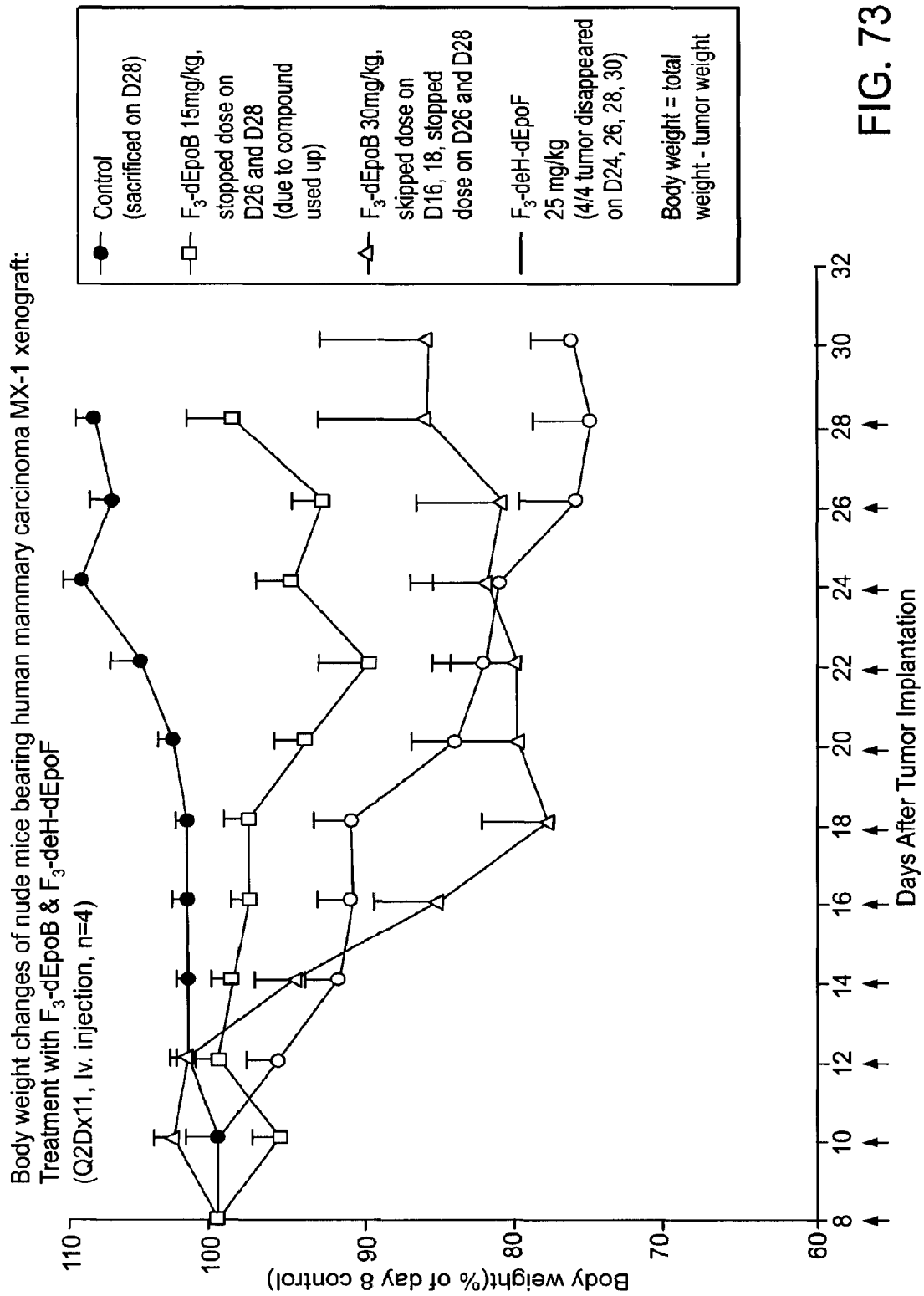
FIG. 73 shows the changes in body weight of nude mice bearing human mammary carcinoma MX-1 xenograft following treatment with 26-trifluoro-dEpoB and 26-trifluoro-9,10-dehydro-dEpoF (Q2Dx11, iv injection).

As depicted in FIG. 8, 9,10-dehydro-EpoB was tested in nude mice bearing human mammary carcinoma MX-1. In general, 9,10-dehydro-EpoB was formulated as follows: 9,10-dehydro-EpoB was dissolved in ethanol and Cremophor was added (1:1) at a concentration of 20 mg/ml. This solution was diluted with saline for i.v. infusion. The diluted solution was used for i.v. infusion within one hour. Tumor size and body weight were then measured using dosages of 10 mg/kg, 20 mg/kg, and 30 mg/kg over 15 days. Tumor size and body weight were also measured using a dosage regimen of 0.4 mg/kg Q3Dx2, 0.5 mg/kg Q3Dx2, and 0.6 mg/kg Q3Dx5 (see FIGS. 33, 34, 55 and 56). The every third day dosing regimen was used to reduce toxicity. Other therapeutic studies on 9,10-dehydro-Epo B are shown in FIGS. 70 and 71 (CCRF-CEM/Taxol Q3Dx5) and in FIGS. 23 and 24 (HCT-116, Q2Dx7).

Figure 17:
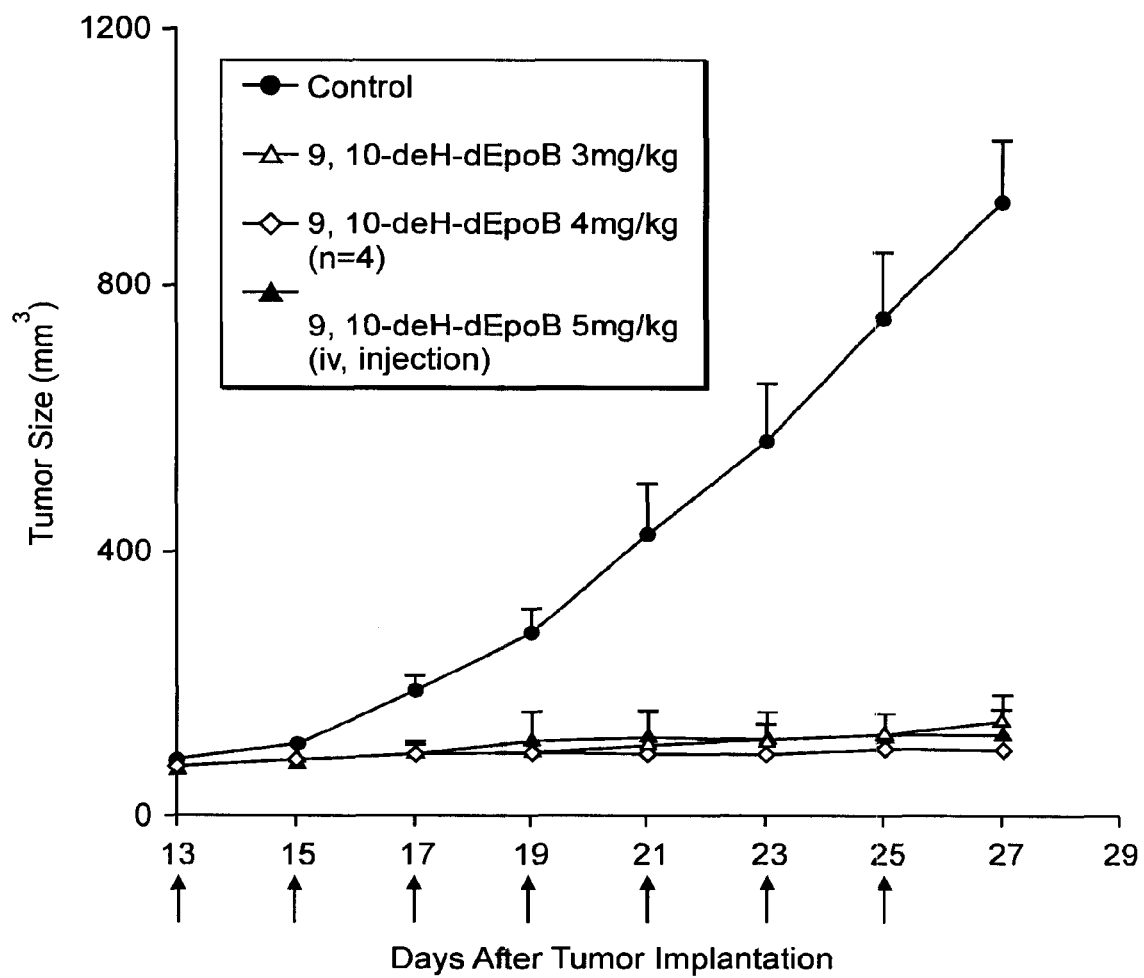
FIG. 17 shows the therapeutic effect of 9,10-dehydro-dEpoB on tumor size in nude mice bearing HCT-116 xenografts (iv infusion, Q2Dx7).
Figure 18:
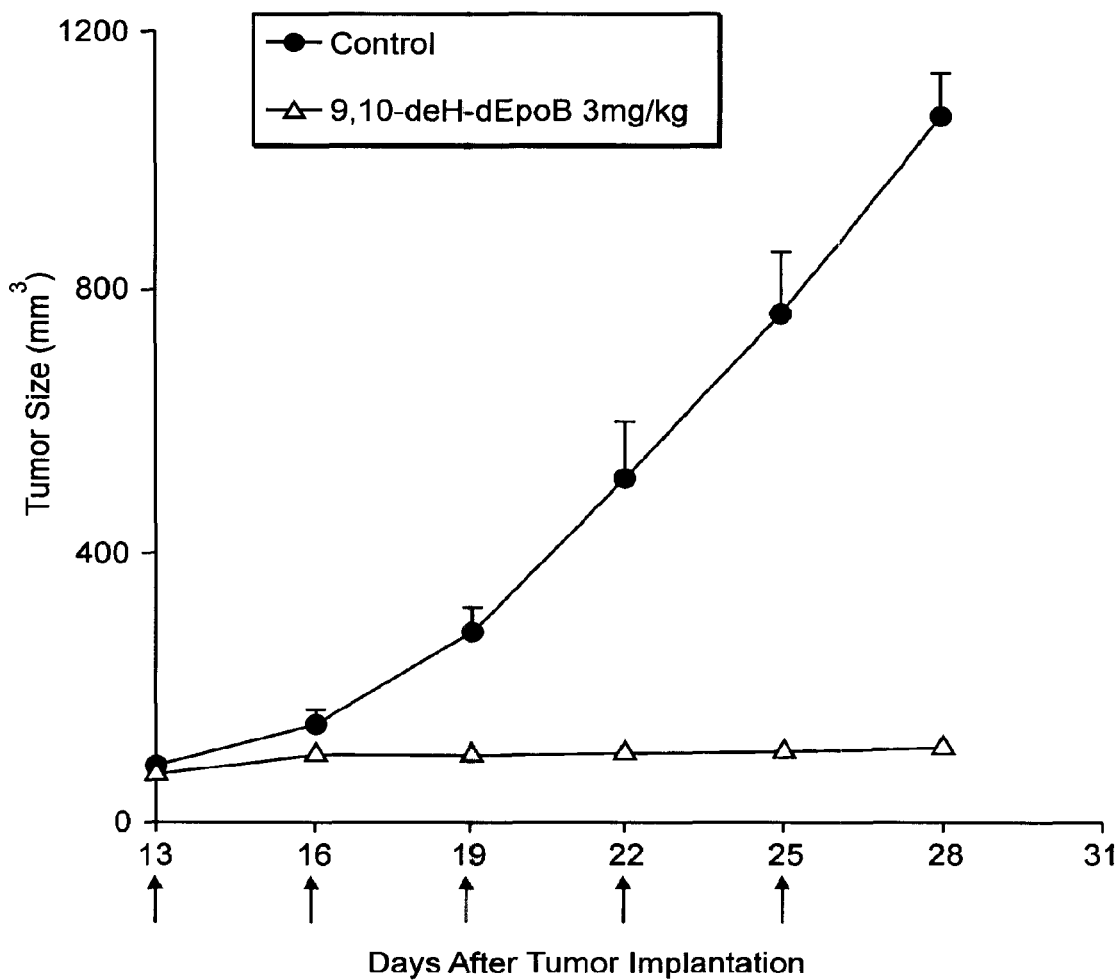
FIG. 18 shows the effect of 9,10-dehydro-dEpoB on tumor size in nude mice bearing human colon carcinoma HCT-116 xenografts (iv infusion, Q3Dx5).
Figure 19:
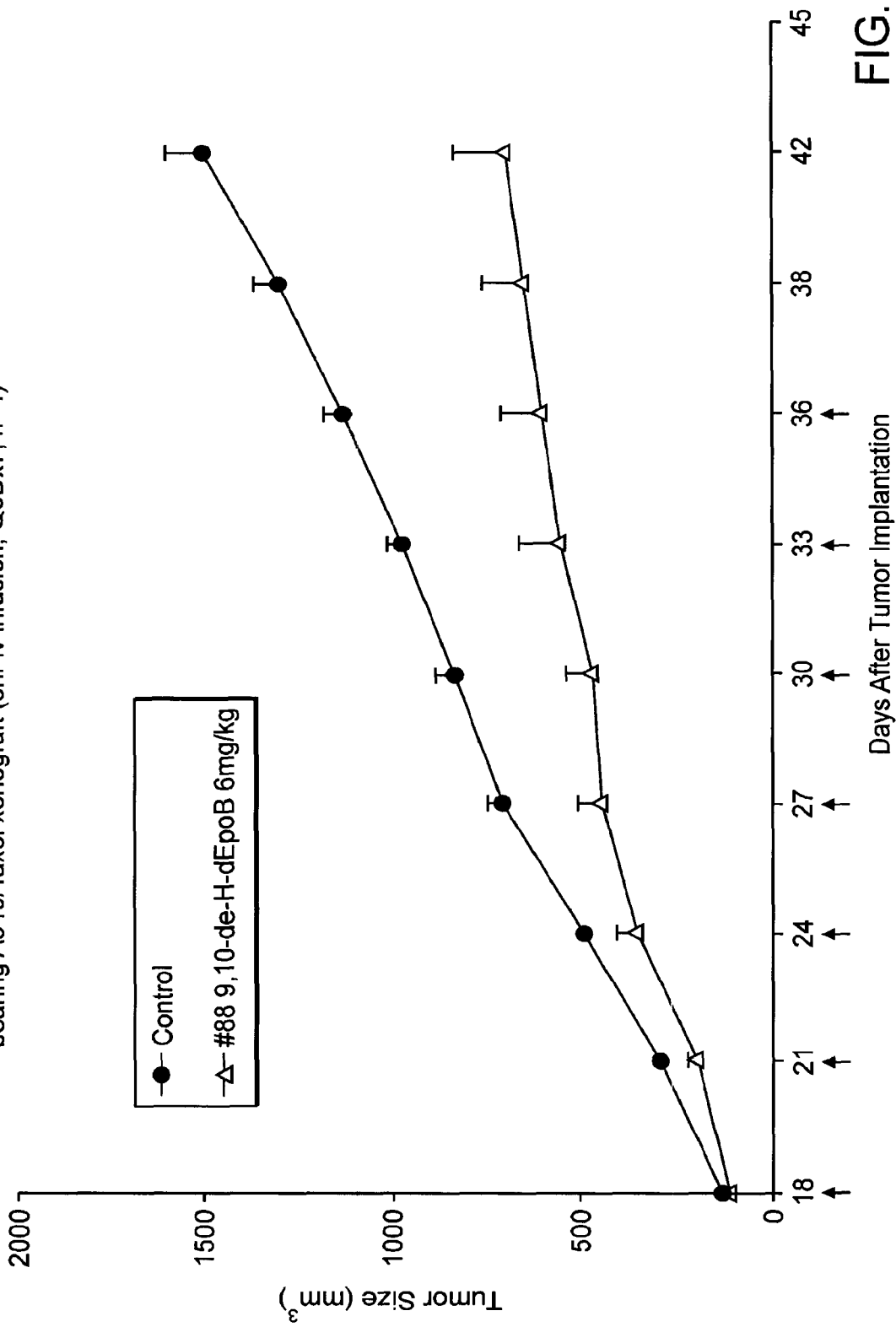
FIG. 19 shows the effect of 9,10-dehydro-dEpoB on tumor size in nude mice bearing A549/Taxol xenografts (6 hour iv infusion, Q3Dx7).
Figure 20:
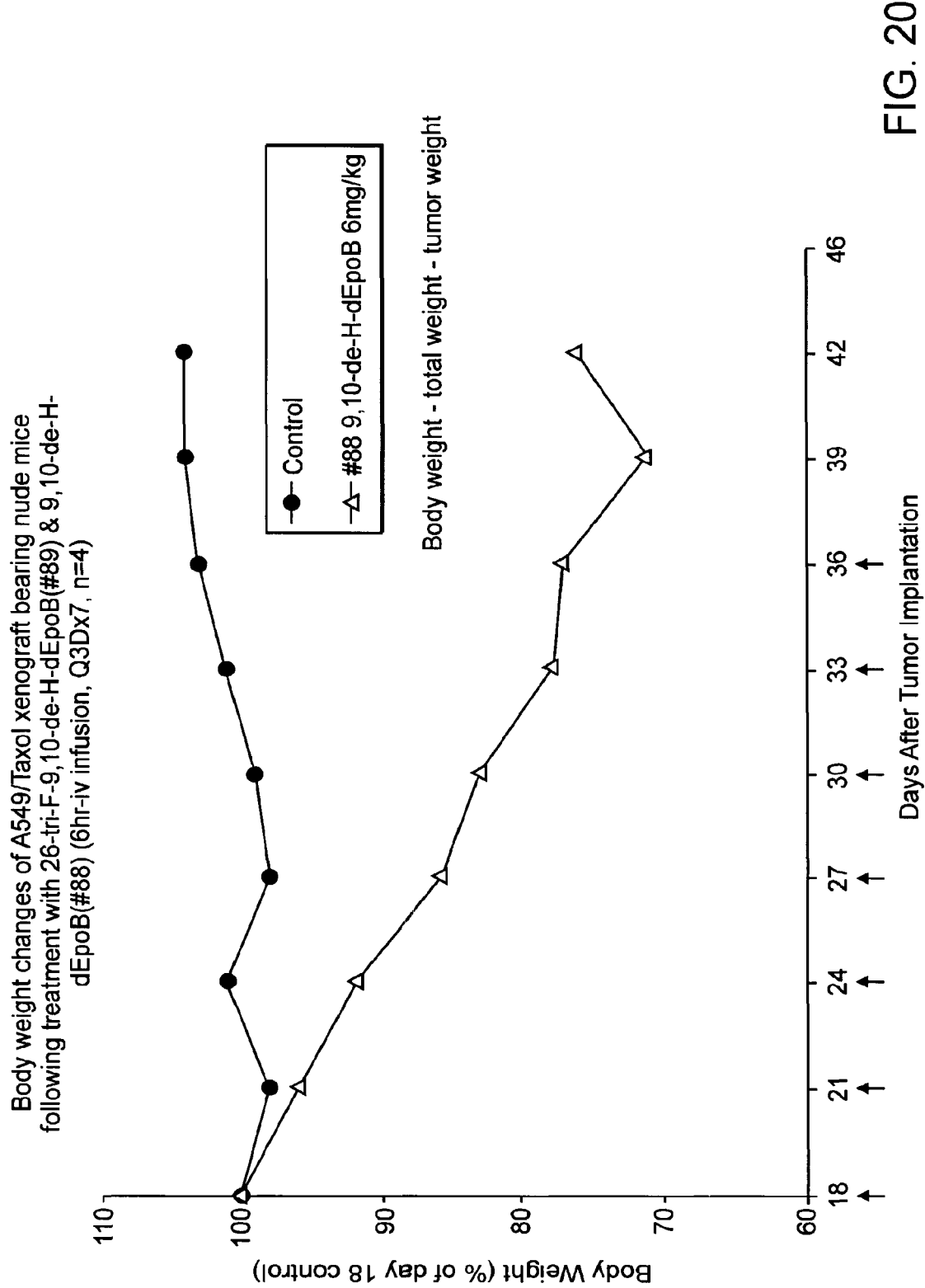
FIG. 20 shows changes in body weight of nude mice bearing A549/Taxol xenograft treated with 26-trifluoro-9,10-dehydro-dEpoB and 9,10-dehydro-dEpoB (6 hour iv infusion, Q3Dx7).
Figure 21:
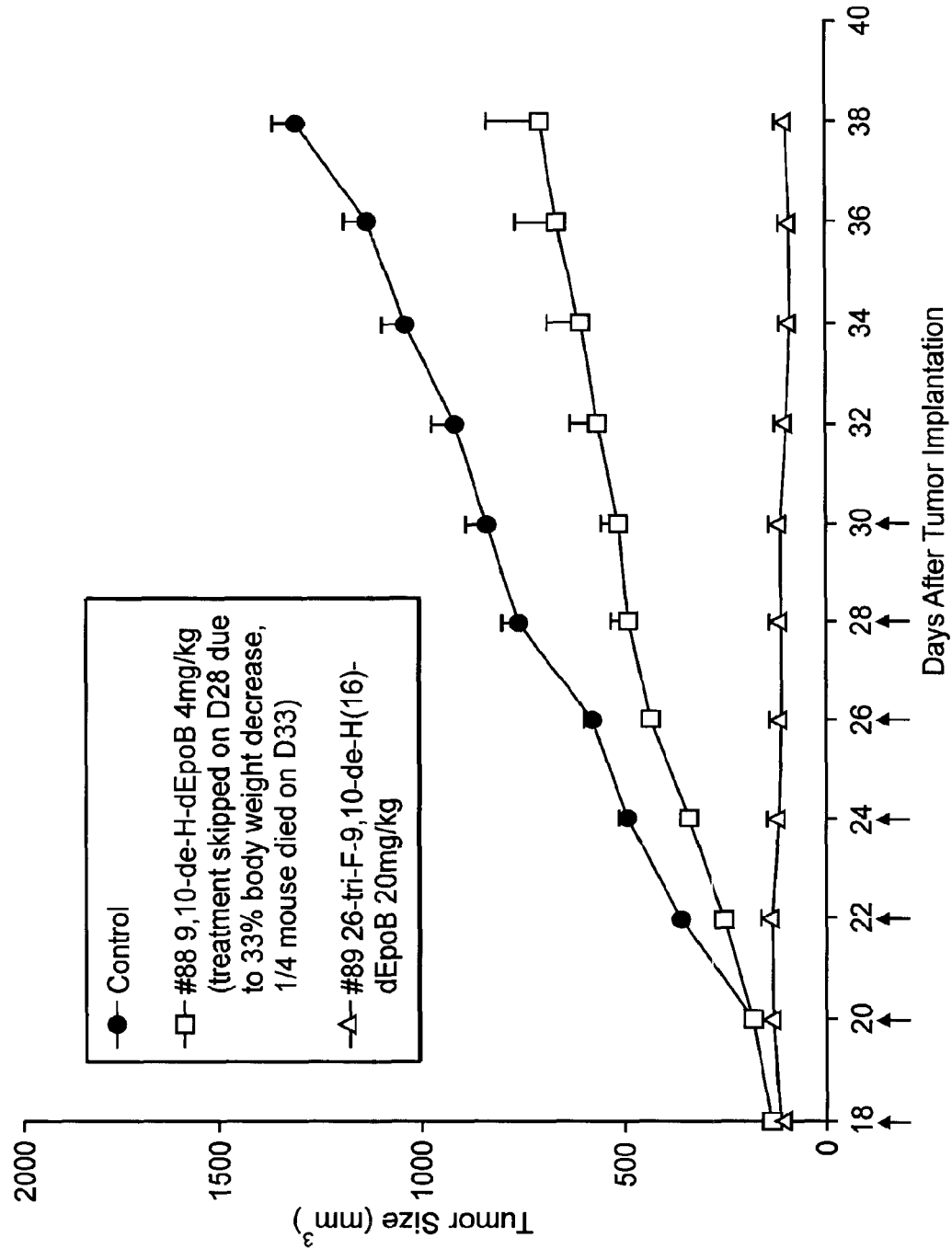
FIG. 21 shows the effect of 26-trifluoro-9,10-dehydro-dEpoB and 9,10-dehydro-dEpoB on tumor size in nude mice bearing A549/Taxol xenografts (6 hour iv infusion, Q2Dx7).
Figure 22:
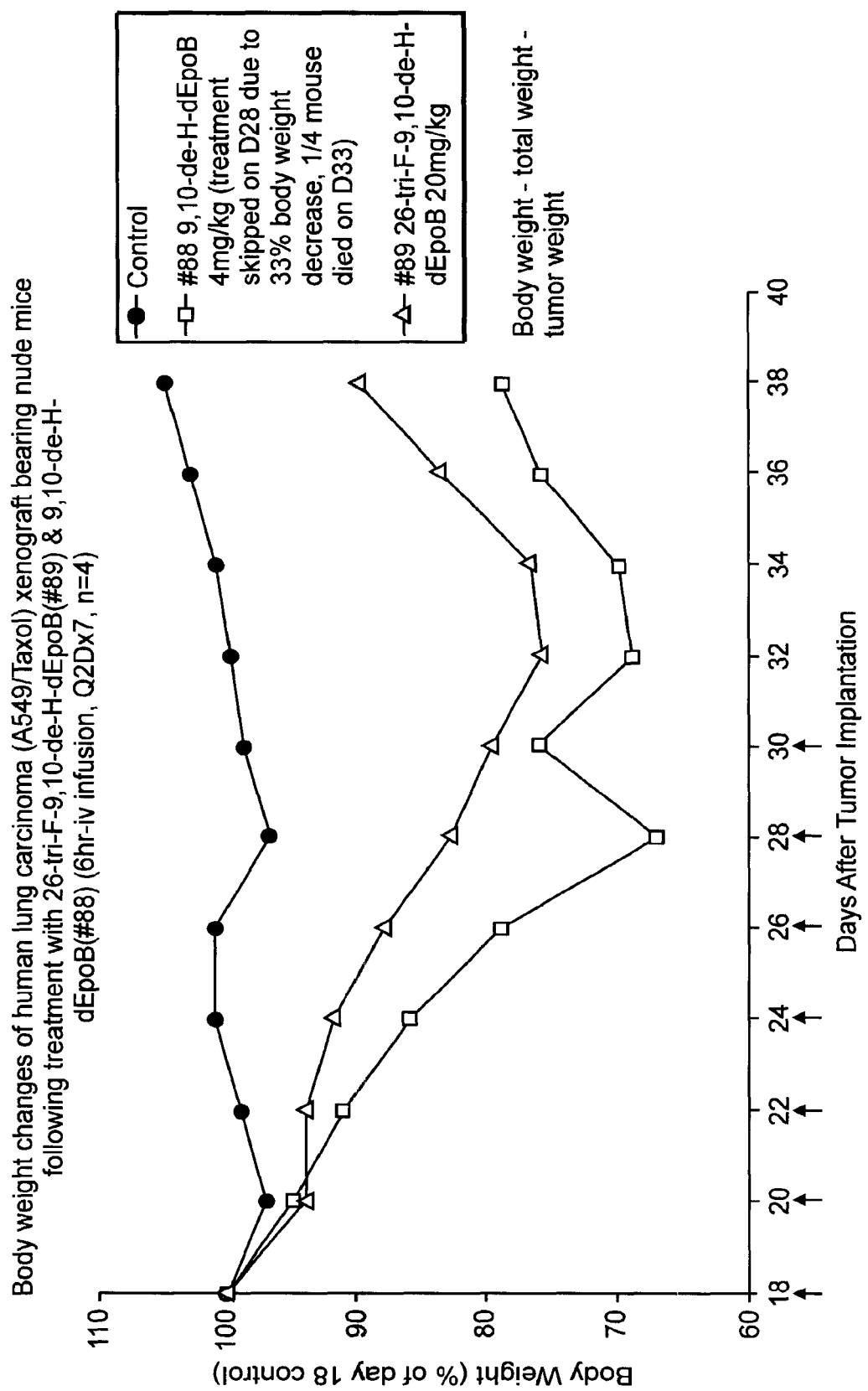
FIG. 22 shows changes in body weight of nude mice bearing A549/Taxol xenografts treated with 26-trifluoro-9,10-dehydro-dEpoB and 9,10-dehydro-dEpoB (6 hour iv infusion, Q2Dx7).
Figure 53:
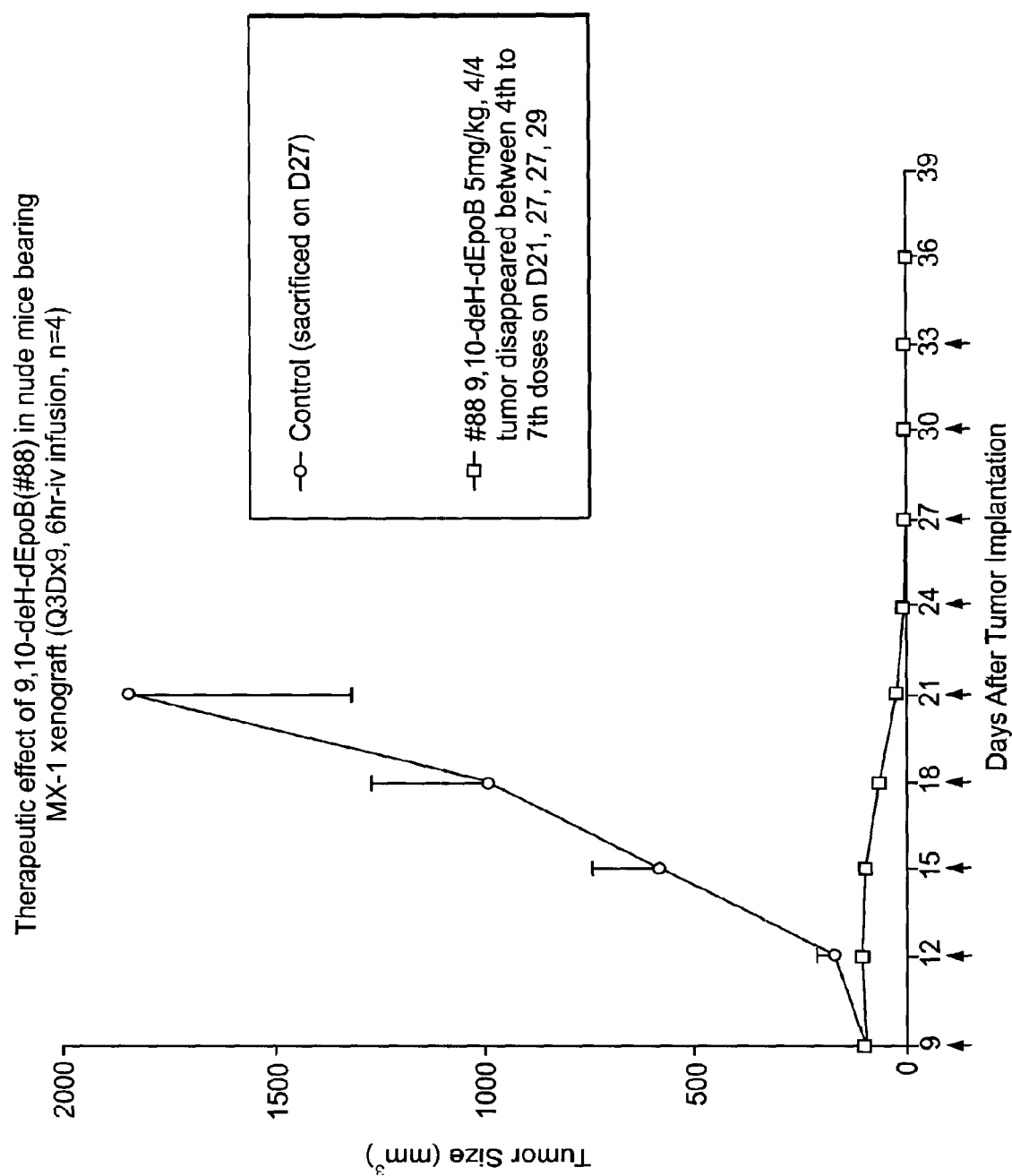
FIG. 53 shows the therapeutic effect of 9,10-dehydro-dEpoB in nude mice bearing MX-1 xenograft (Q3Dx9, 6 hr.-iv infusion).
Figure 54:
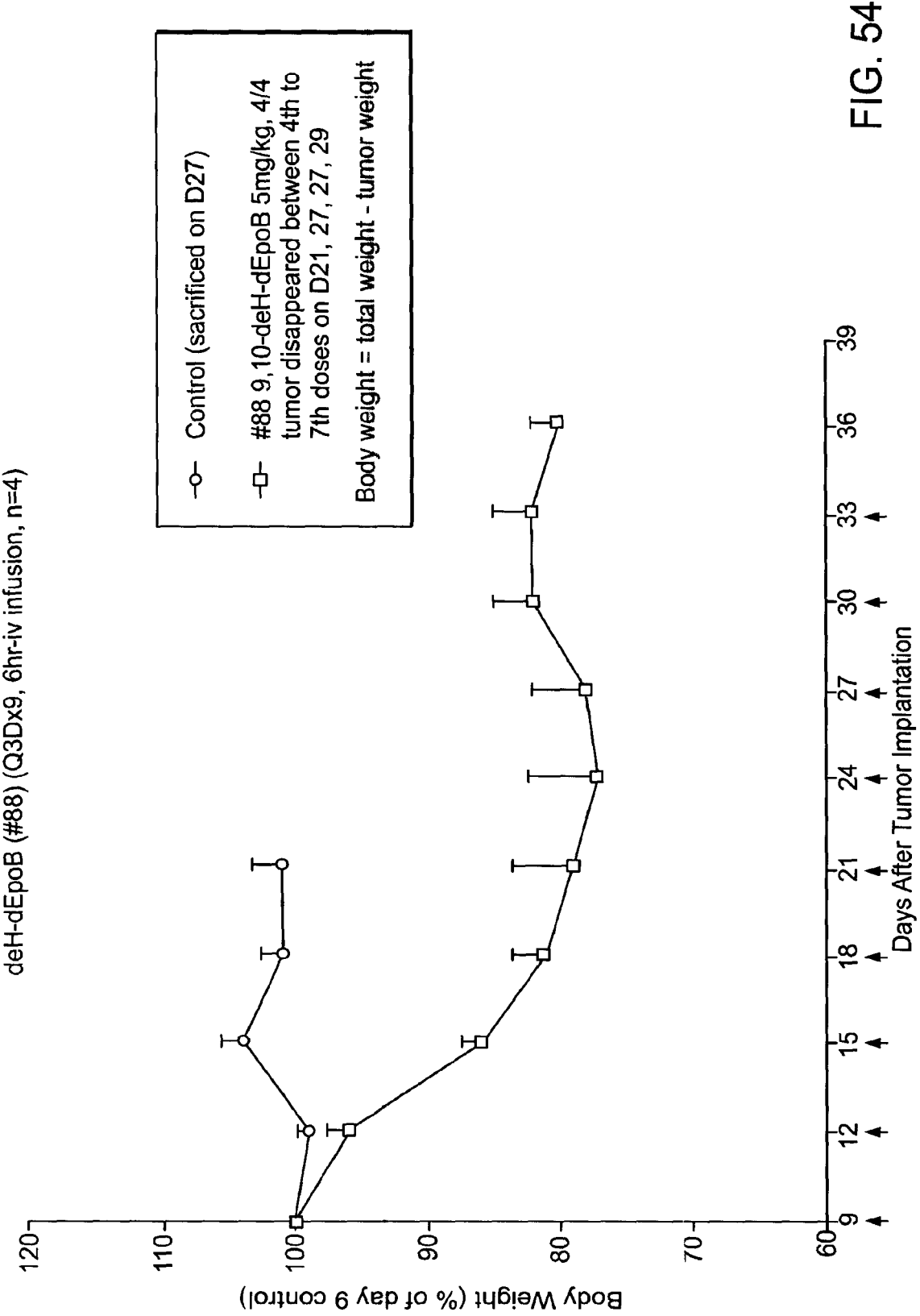
FIG. 54 shows changes in body weight of nude mice bearing an MX-1 xenograft following treatment with 9,10-dehydro-dEpoB (Q3Dx5, 6 hr.-iv infusion).
Figure 55:
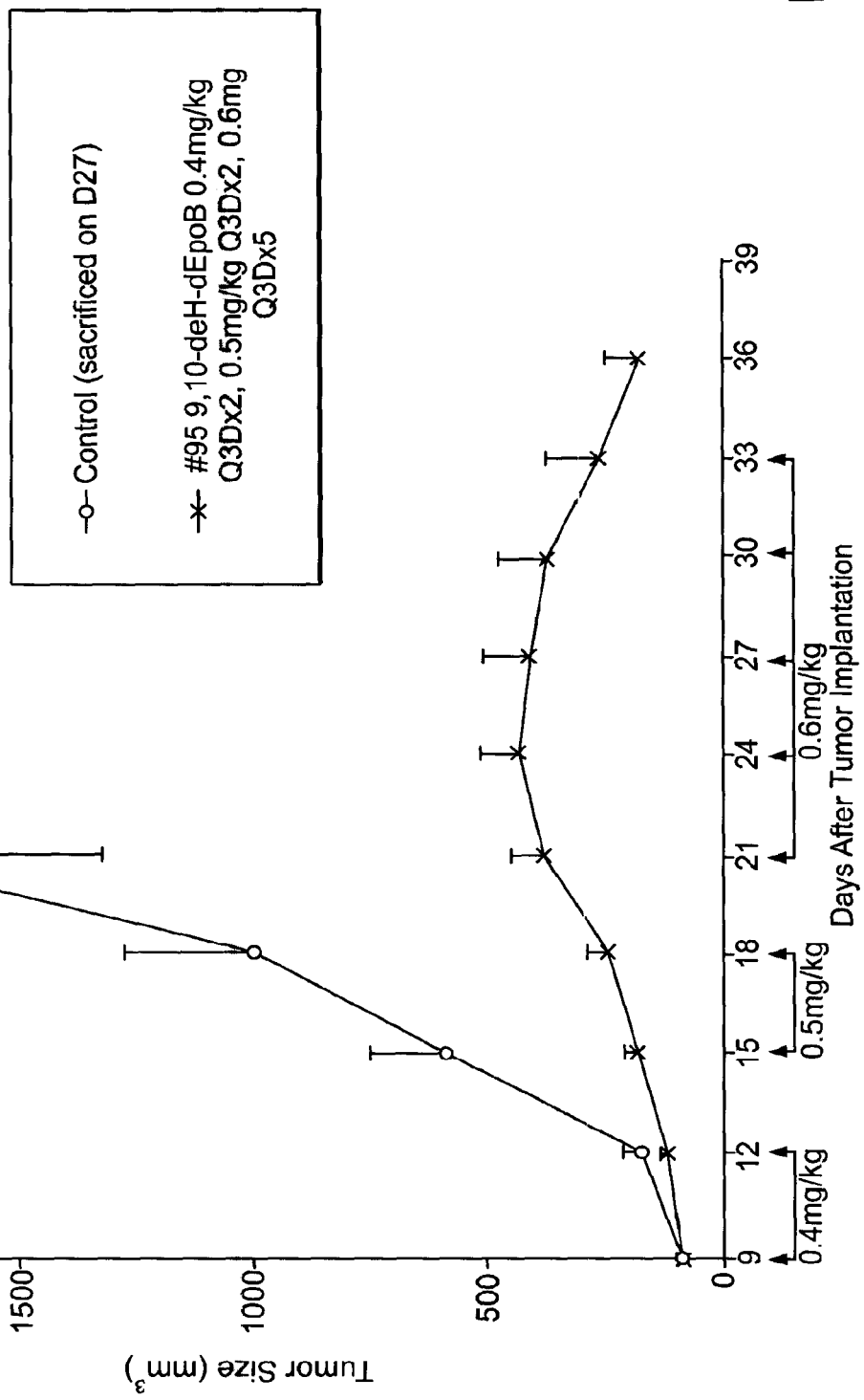
FIG. 55 shows the therapeutic effect of 9,10-dehydro-epothilone B in nude mice bearing MX-1 xenograft (Q3Dx9, 6 hour infusion).
Figure 56:
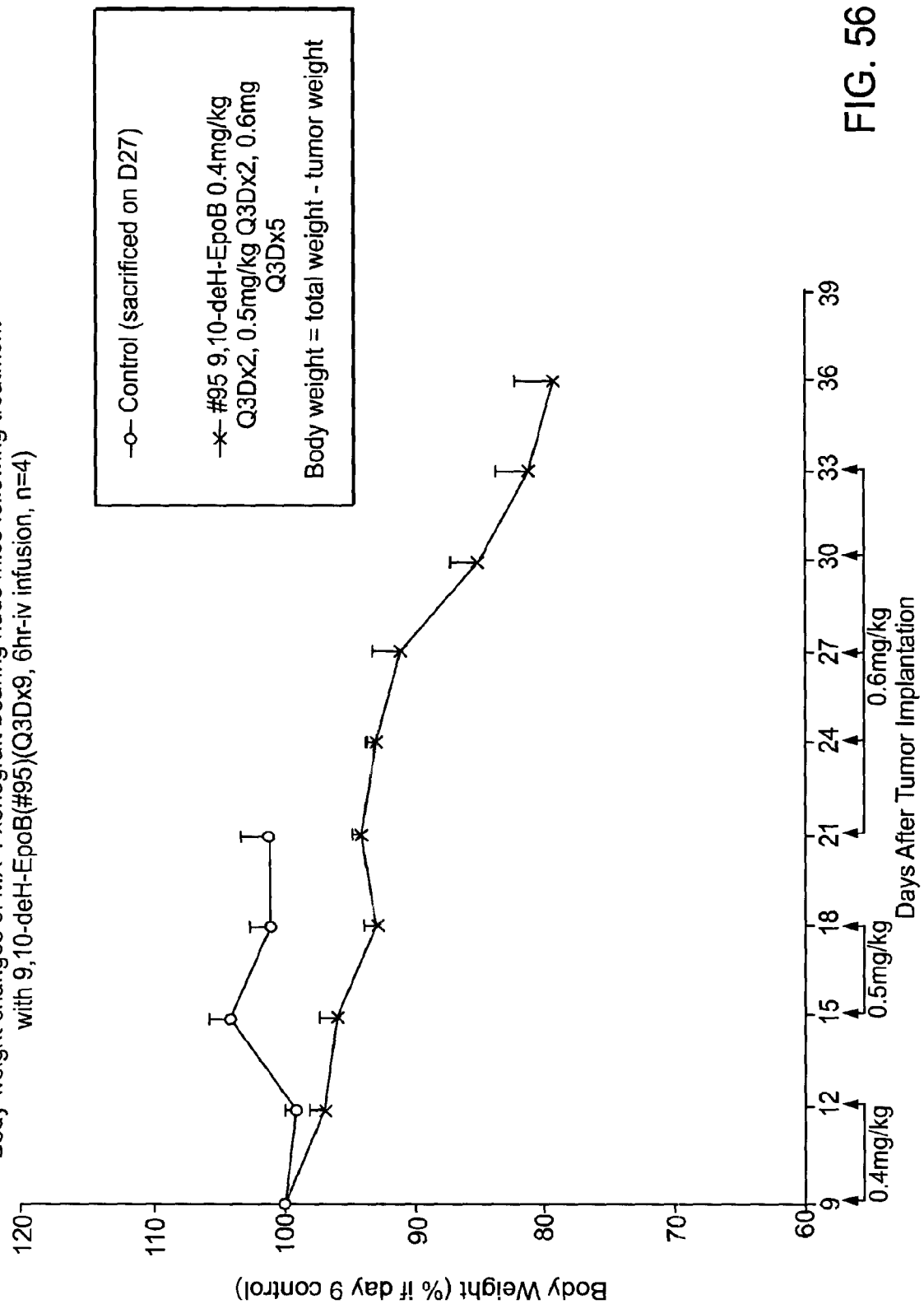
FIG. 56 shows changes in body weight of nude mice bearing MX-1 xenograft following treatment with 9,10-dehydro-epothilone B (Q3Dx9, 6 hr.-iv infusion).
Figure 74:
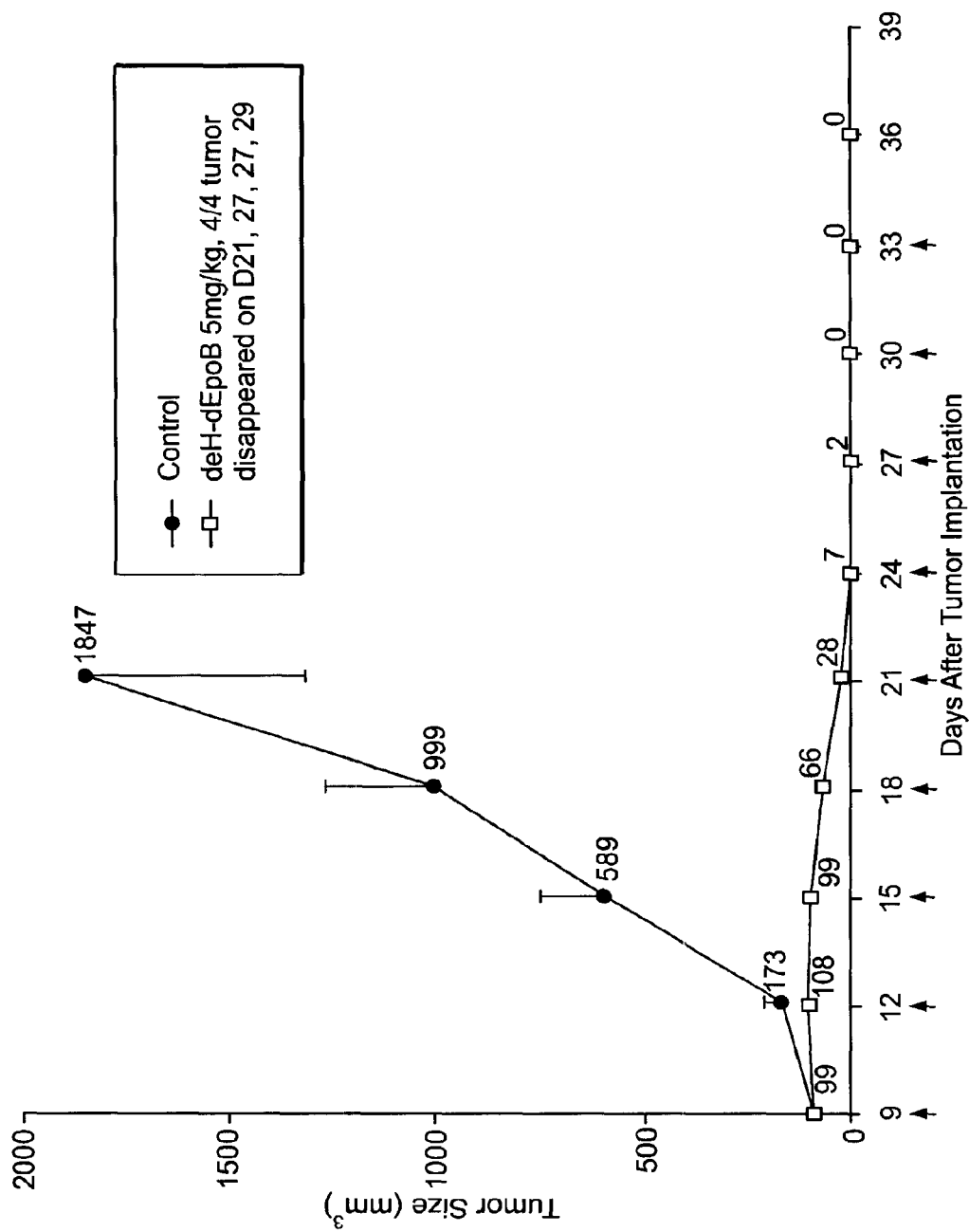
FIG. 74 shows the therapeutic effect of 9,10-dehydro-dEpoB in nude mice bearing human mammary carcinoma MX-1 xenograft (Q3Dx9, 6 hour iv infusion).
Figure 75:
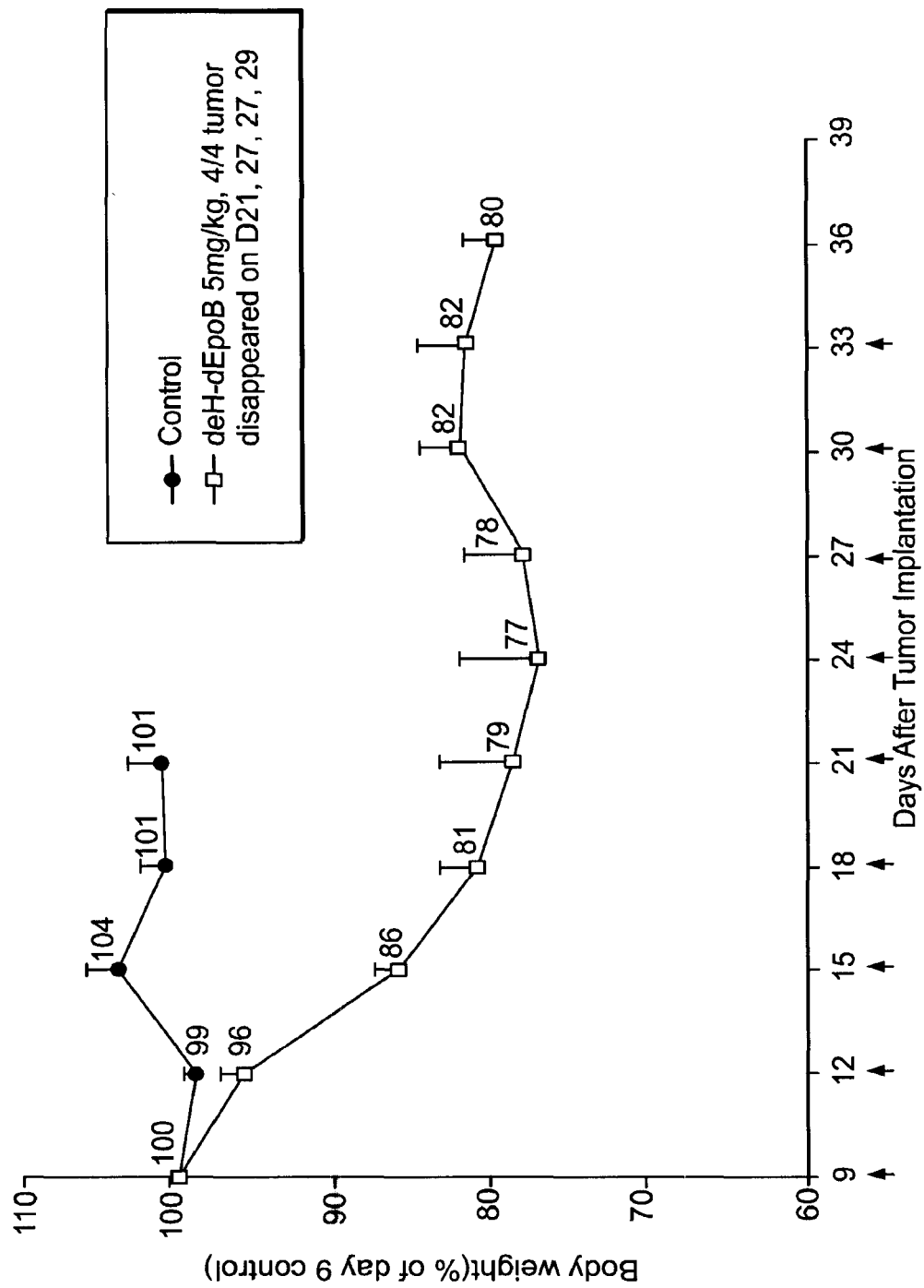
FIG. 75 shows the changes in body weight of nude mice bearing human mammary carcinoma MX-1 xenograft following treatment with 9,10-dehydro-dEpoB (Q3Dx9, 6 hour iv infusion).

The compound, 9,10-dehydro-12,13-desoxyepothilone B (iso-490 epothilone), is three times more efficacious than dEpoB. 9,10-dehydro-12,13-desoxyepothilone D has been shown to arrest tumor growth after two to three infusions of 10 mg/kg or 20 mg/kg, each of which was administered every other day. Better results in mice were obtained using a dose of 30 mg/kg of 9,10-dehydro-12,13-desoxyepothilone B using two 6 hour infusion iv every other day. 9,10-dehydro-dEpoB at 5 mg/kg, Q3Dx9, 6 hr.-iv infusion, was also shown to achieve tumor disappearance in nude mice bearing MX-1 xenograft without mouse death and with only a moderate loss of body weight (FIGS. 74 and 75). This seems to have been accomplished by administering the epothilone analogs every third day to reduce toxicity (see FIGS. 53 and 54). In summary, 9,10-dehydro-12,13-desoxyepothilone B shows decreased toxicity as compared to other epothilones, greater potency in arresting tumor growth, and greater serum stability. Other therapeutic studies are shown in FIGS. 17 and 18 (HCT-116, Q2Dx5 and Q3Dx5); in FIGS. 19 and 20 (A549/Taxol, Q3Dx7); and in FIGS. 21 and 22 (A549/Taxol, Q2Dx7).

Figure 68:
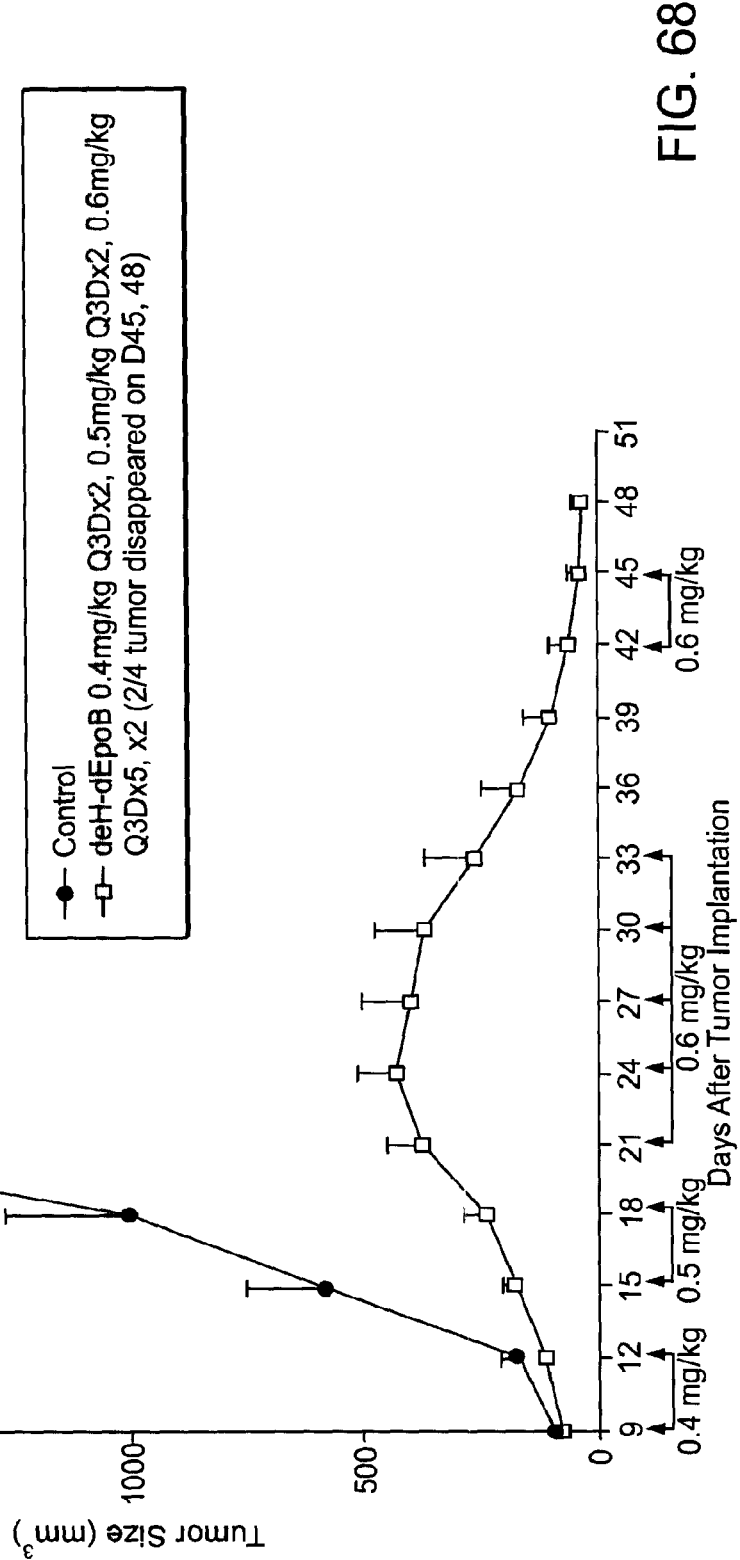
FIG. 68 shows the therapeutic effect of 9,10-dehydro-EpoB in nude mice bearing MX-1 xenograft (6 hour iv infusion).
Figure 69:
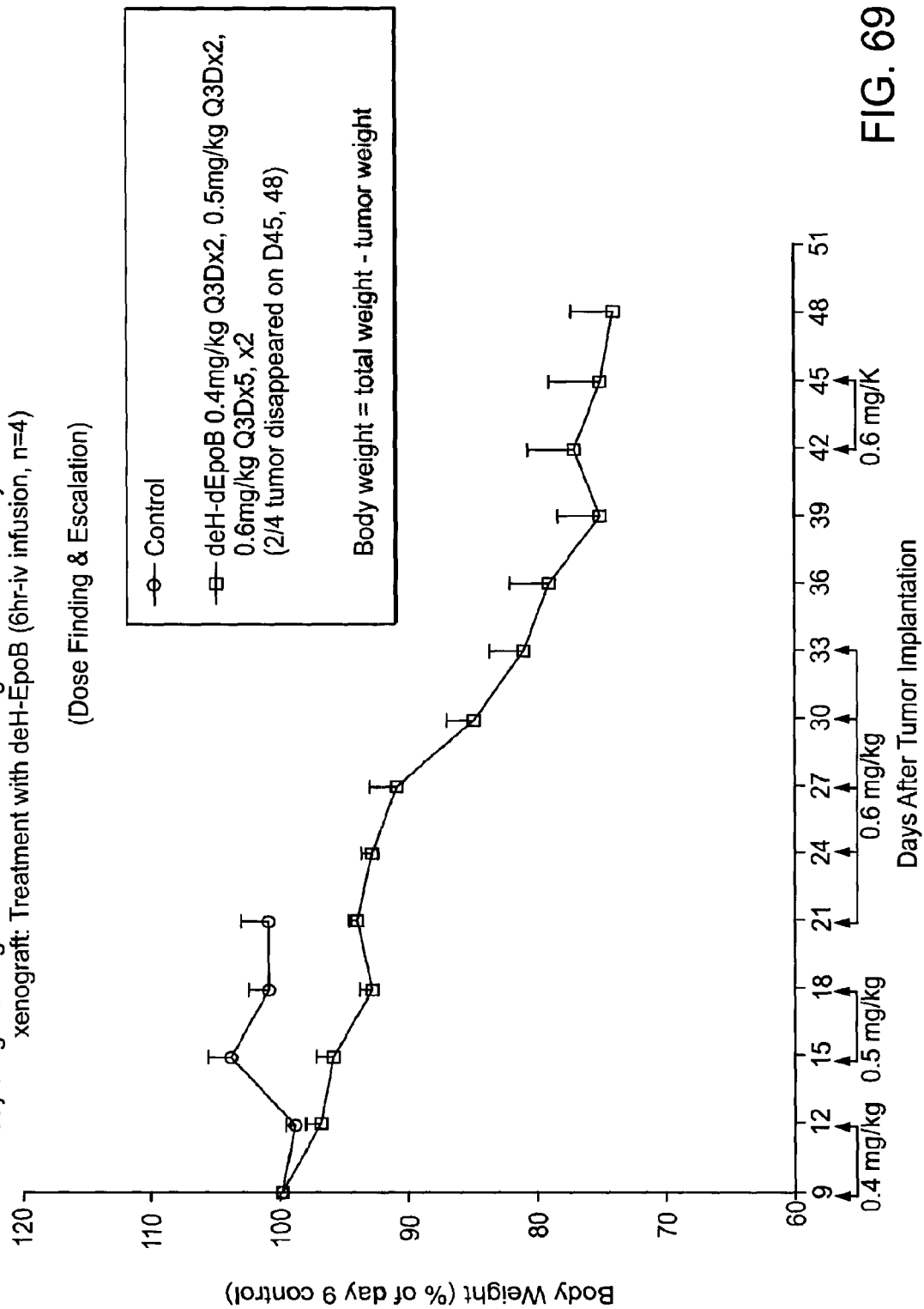
FIG. 69 shows the changes in body weight of nude mice bearing human mammary carcinoma MX-1 xenograft following treatment with 9,10-dehydro-EpoB (6 hour iv infusion).

9,10-dehydro-Epo B when administered every three days 9-11 times, 6 hour iv infusion, at 0.4-0.6 mg/kg, led to shrinkage and disappearance of the tumor in nude mice with implanted human mammary carcinoma MX-1 xenografts (FIGS. 68 and 69). Administration every other day for 8 doses led to tumor growth suppression but no shrinkage of the tumor. When 9,10-dehydro-Epo B was administered every other day for 9 doses, the implanted tumor continued to shrink moderately from the second to the eighth day, but body weight recovered very slowly from 76% to 82% of the control during the same period. On the tenth day, one-fourth of tumor was gone. When a dosage of 0.6 mg/kg of 9,10-dehydro-EpoB was administered Q2Wx6, 6 hour infusion, to nude mice with HCT-116 xenografts, four out of four mice died of toxicity within three days after the sixth dosage. 9,10-dehydro-EpoB abolished tumor growth against CCRF-CEM/Taxol using 0.6 mg/kg, Q3Dx5,x2 schedule (FIGS. 70 and 71).

26-trifluoro-9,10-dehydro-12,13-desoxy-epothilone B ($F_3$-deH-dEpoB) as shown in the Figures is curative at 20 mg/kg and 30 mg/kg, Q2Dx6, 6 hour infusions, in a nude mouse model implanted with human mammary carcinoma MX-1 xenografts. The data also suggests that 30 mg/kg Q2Dx6 is approximately the maximal tolerated dose. At 20 mg/kg, Q2Dx6, 6 hour infusion, 26-trifluoro-9,10-dehydro-12,13-dexoxy-epothilone B led to tumor shrinkage and disappearance in four out of four nude mice with human mammary carcinoma MX-1 xenografts. There was no reappearance of the tumor on the $20^{th}$ day after stopping treatment. On the $27^{th}$ day after stoping treatment 2/4 reappeared. No further tumor reappearance during $28^{th}$-$64^{th}$ days after stopping treatment. By comparison, dEpoB at 30 mg/kg achieved tumor disappearance in the same mouse model in seven out of seven mice; however, the tumor reappeared in 2 out of five mice on the $8^{th}$ day after stopping treatment. Administration of 26-trifluoro-9,10-dehydro-12,13-desoxy-epothilone B at 20 mg/kg, Q2Dx6, 6 hr. iv infusion led to a transient drop in body weight of the mice up to 26%. This drop in body weight did not lead to death suggesting no severe toxicity toward vital organs. Two days after the last treatment, body weight began to recover. On the $16^{th}$ day after treatment, body weight returned to 109% of the pretreatment control suggesting that toxicity, if any, is completely reversible. In comparison, dEpoB administered at 30 mg/kg led to a 31% decrease in body weight without lethality.

When 26-trifluoro-9,10-dehydro-12,13-desoxy-epothilone B was administered at 30 mg/kg, Q2Dx6, 6 hour iv infusion, tumor disappearance was 2-3 days earlier than the 20 mg/kg dosage. Body weight dropped 27% at this higher dose and persisted 4 days without leading to lethality confirming no severe toxicity to vital organs. Four days after the last treatment at 30 mg/kg, body weight began to recover. On the $16^{th}$ day after treatment, body weight returned to 98% of the pretreatment control again confirming the reversibility of toxicity. Treatment with 26-trifluoro-9,10-dehydro-dEpoB at 20 mg/kg and 30 mg/kg led to total tumor disappearance, and no relapse after 62 days was seen at the 30 mg/kg dose. Tumor disappearance was also achieved at 10 mg/kg by administering 9 doses with three additional doses given (FIG. 57). Only minor loss of body weight was observed at 10 mg/kg 26-trifluoro-9,10-dehydro-dEpoB (FIG. 58). No further loss of body weight was seen with continued treatment.

FIG. 59 summarizes the effect of 26-$F_3$-9,10-deH-dEpo B (and other epothilones) against MX-1 xenograft, A. at low dose; B. against large tumor; against A549 lung carcinoma xenograft, C; and against Taxol resistant lung carcinoma A549/Taxol xenograft, D.

FIG. 61 lists in vitro potency of C-21 modified epothilones against CCRF-CEM, CCRF-CEM/VBL and CCRF-CEM/Taxol.

Figure 62:
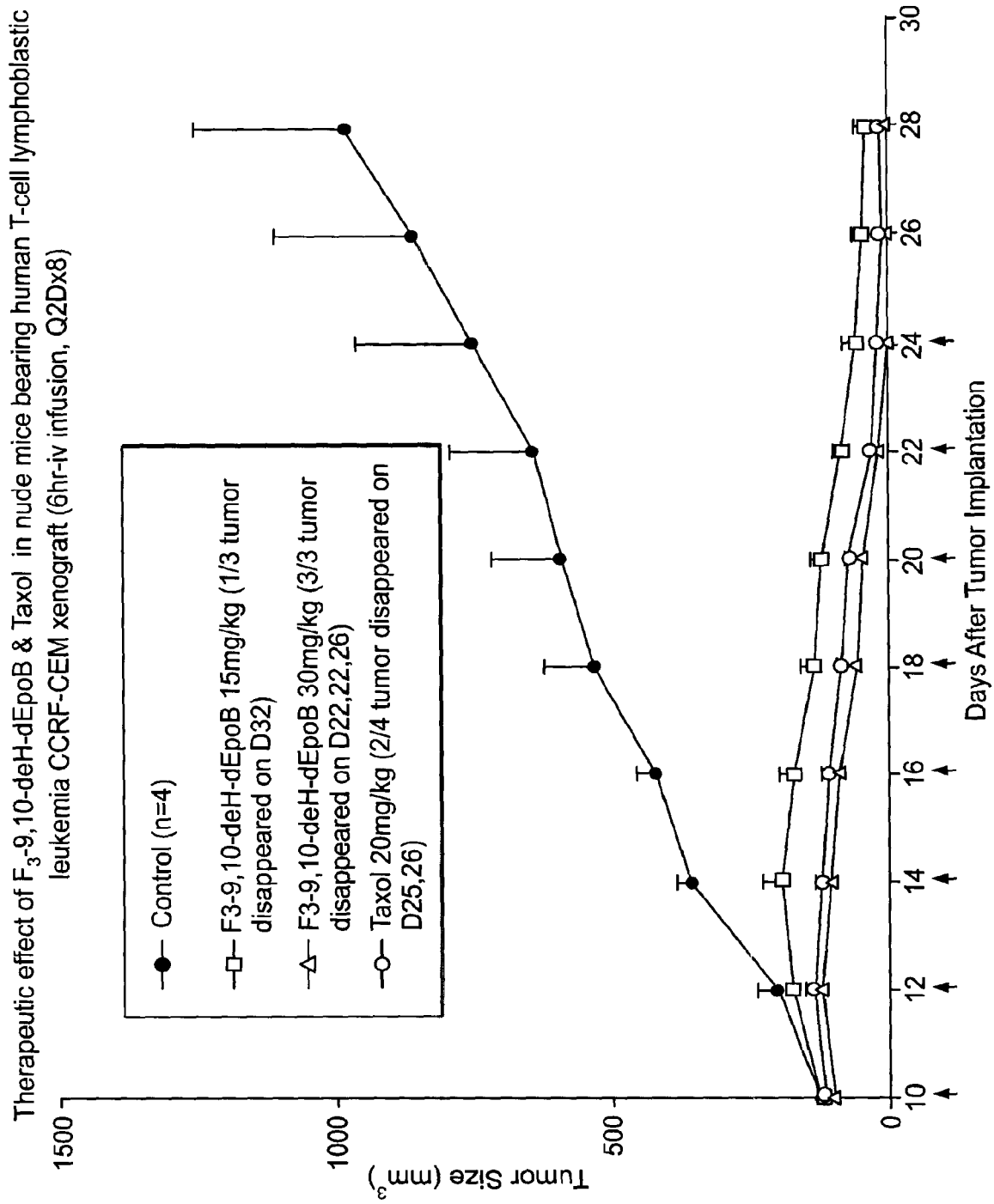
FIG. 62 shows the therapeutic effect of 26-trifluoro-9,10-dehydro-dEpoB and Taxol in nude mice bearing human T-cell lymphoblastic leukemia CCRF-CEM xenograft (6 hour iv infusion, Q2Dx8).
Figure 63:
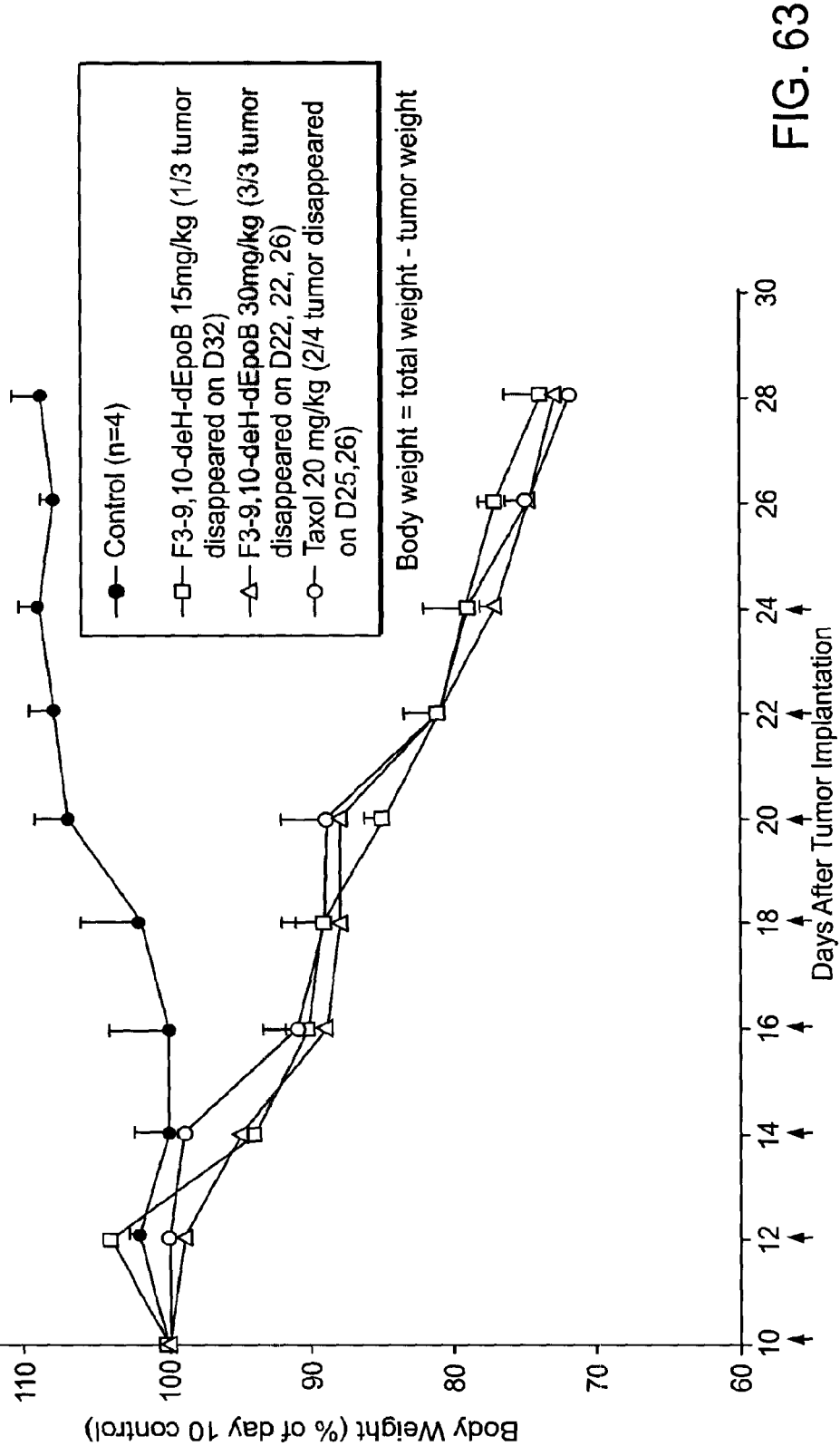
FIG. 63 shows the changes in body weight changes of nude mice bearing human T-cell lymphoblastic leukemia CCRF-CEM xenograft following treatment with 25-trifluoro-9,10-dehydro-dEpoB and Taxol (6 hour iv infusion, Q2Dx8).

FIG. 62 shows therapeutic effect of 26-$F_3$-9,10-deH-dEpoB (15 mg/kg and 30 mg/kg) and Taxol (20 mg/kg) Q2Dx8, 6 hour i.v. infusion against human T-cell lymphoblastic leukemia CCRF-CEM xenograft. Similar body weight decreases were observed in all three groups of treatment (FIG. 63).

Figure 64:
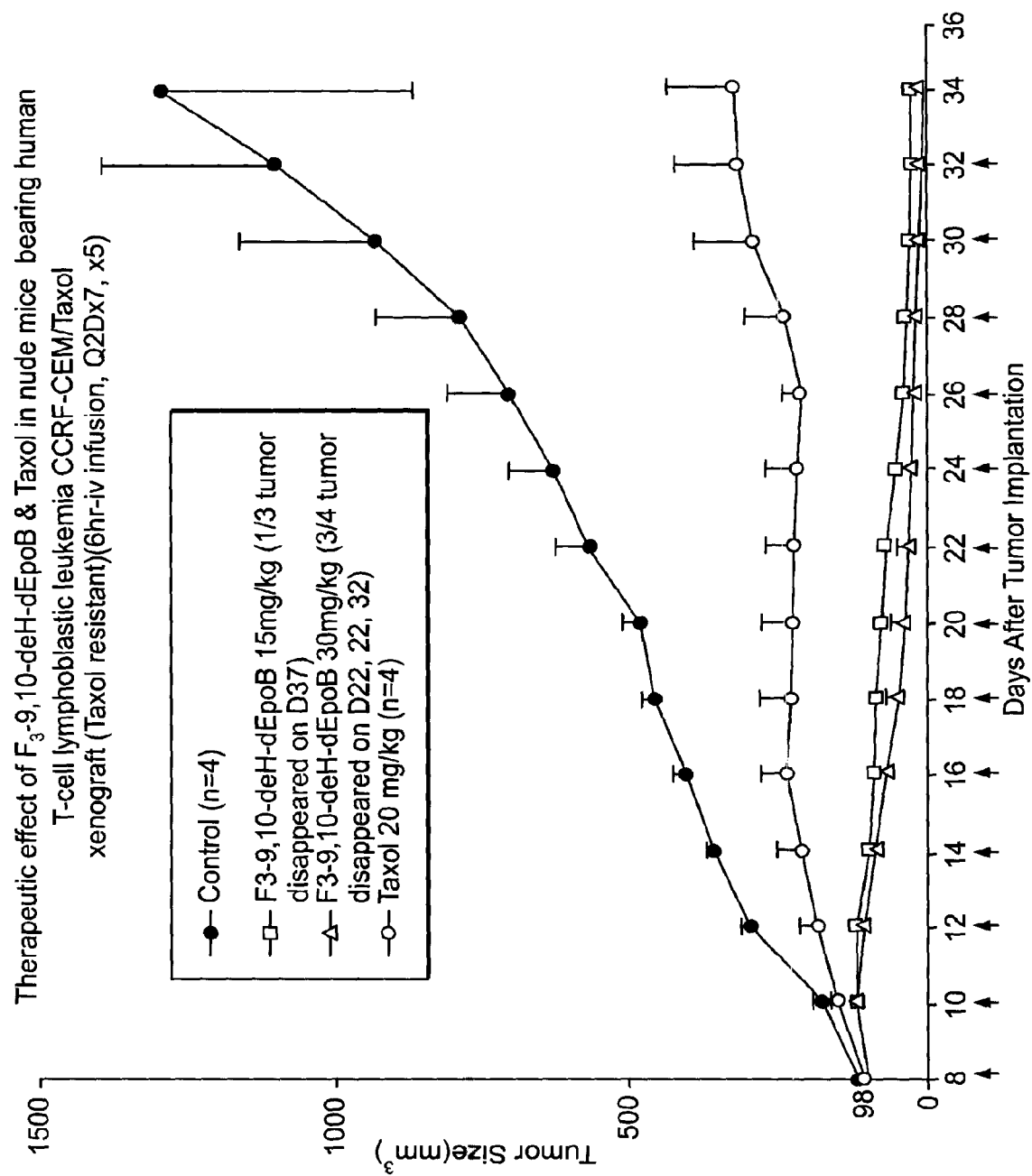
FIG. 64 shows the therapeutic effect of 26-trifluoro-9,10-dehydro-dEpoB and Taxol in nude mice bearing human T-cell lymphoblastic leukemia CCRF-CEM/Taxol xenograft (Taxol resistant) (6 hour iv infusion, Q2Dx7, x5).
Figure 65:
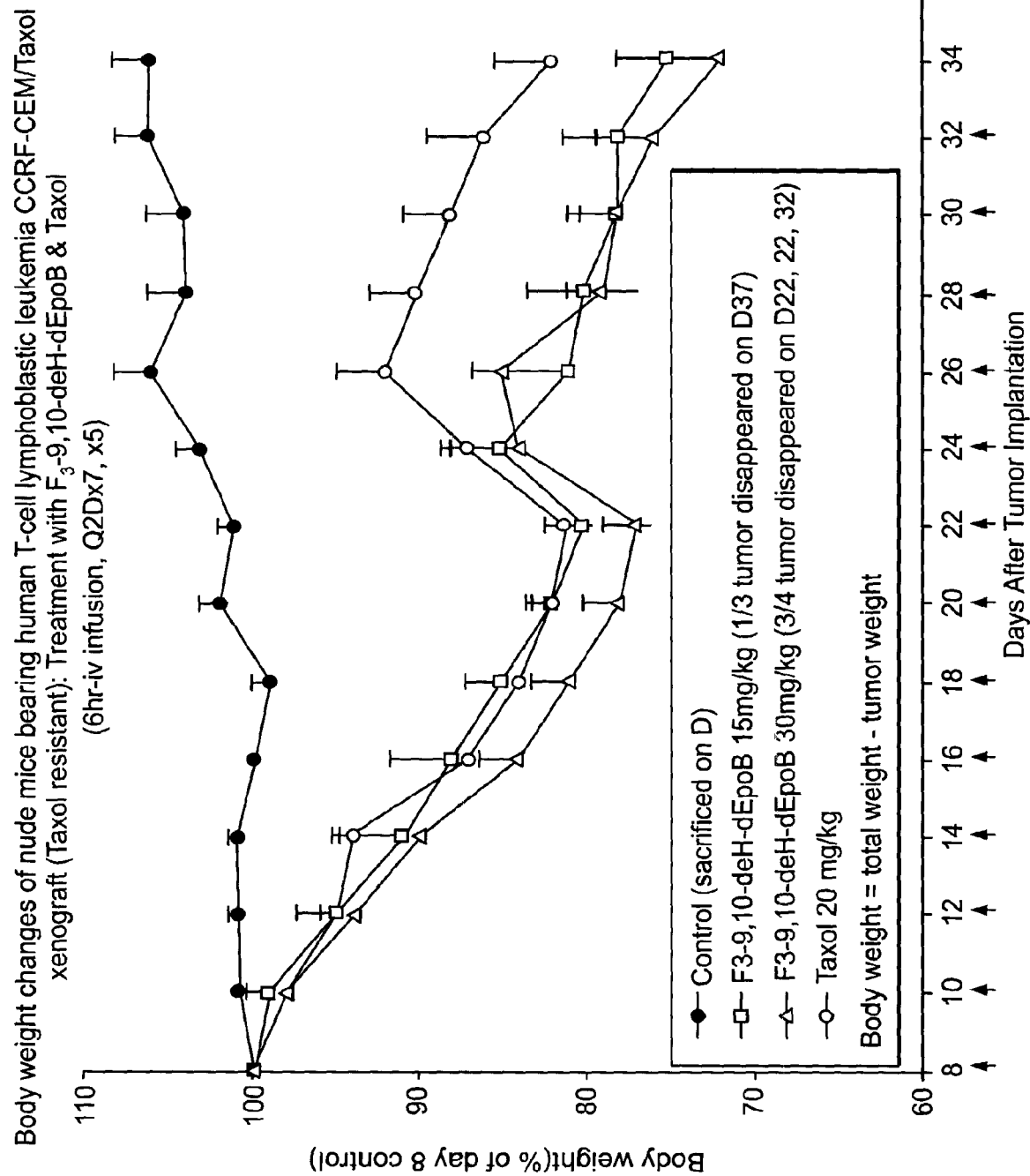
FIG. 65 shows the changes in body weight changes of nude mice bearing human T-cell lymphoblastic leukemia CCRF-CEM/Taxol xenograft (Taxol resistant) following treatment with 26-trifluoro-9,10-dehydro-dEpoB and Taxol (6 hour iv infusion, Q2Dx7, x5).

Treatment of CCRF-CEM/Taxol xenograft (Taxol resistant) with 26-$F_3$-9,10-deH-dEpo B, 15 mg/kg achieved 1/3 tumor disappearance, and 30 mg/kg achieved ¾ tumor disappearance. The same treatment with Taxol, 20 mg/kg yielded only partial suppression of tumor growth and failed to achieve tumor shrinkage (FIG. 64). The body weight changes during this experiment were shown in FIG. 65.

Figure 66:
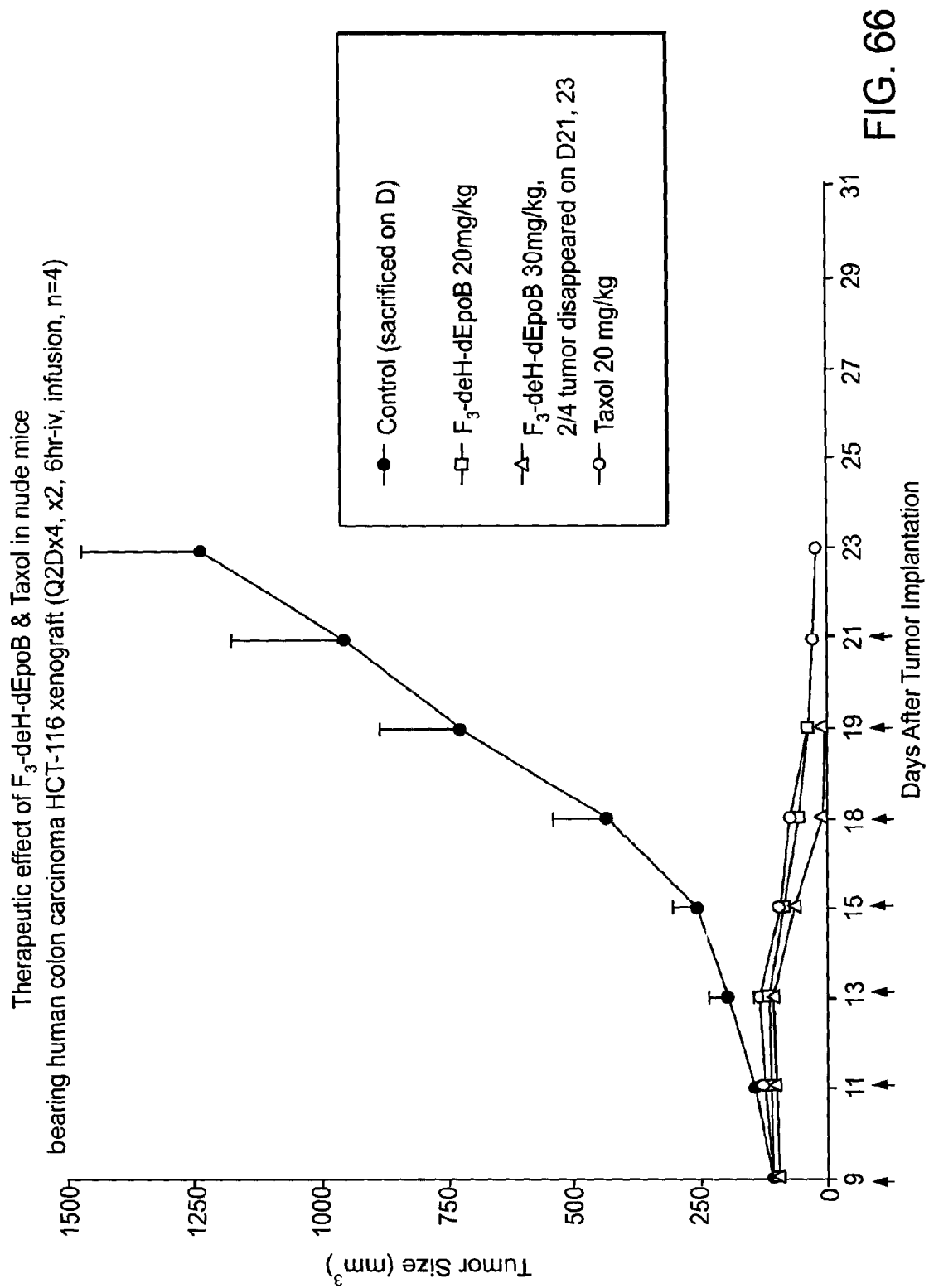
FIG. 66 shows the therapeutic effect of 26-trifluoro-9,10-dehydro-dEpoB and Taxol in nude mice bearing human colon carcinoma HCT-116 xenograft (Q2Dx4, x2, 6 hour iv infusion).
Figure 67:
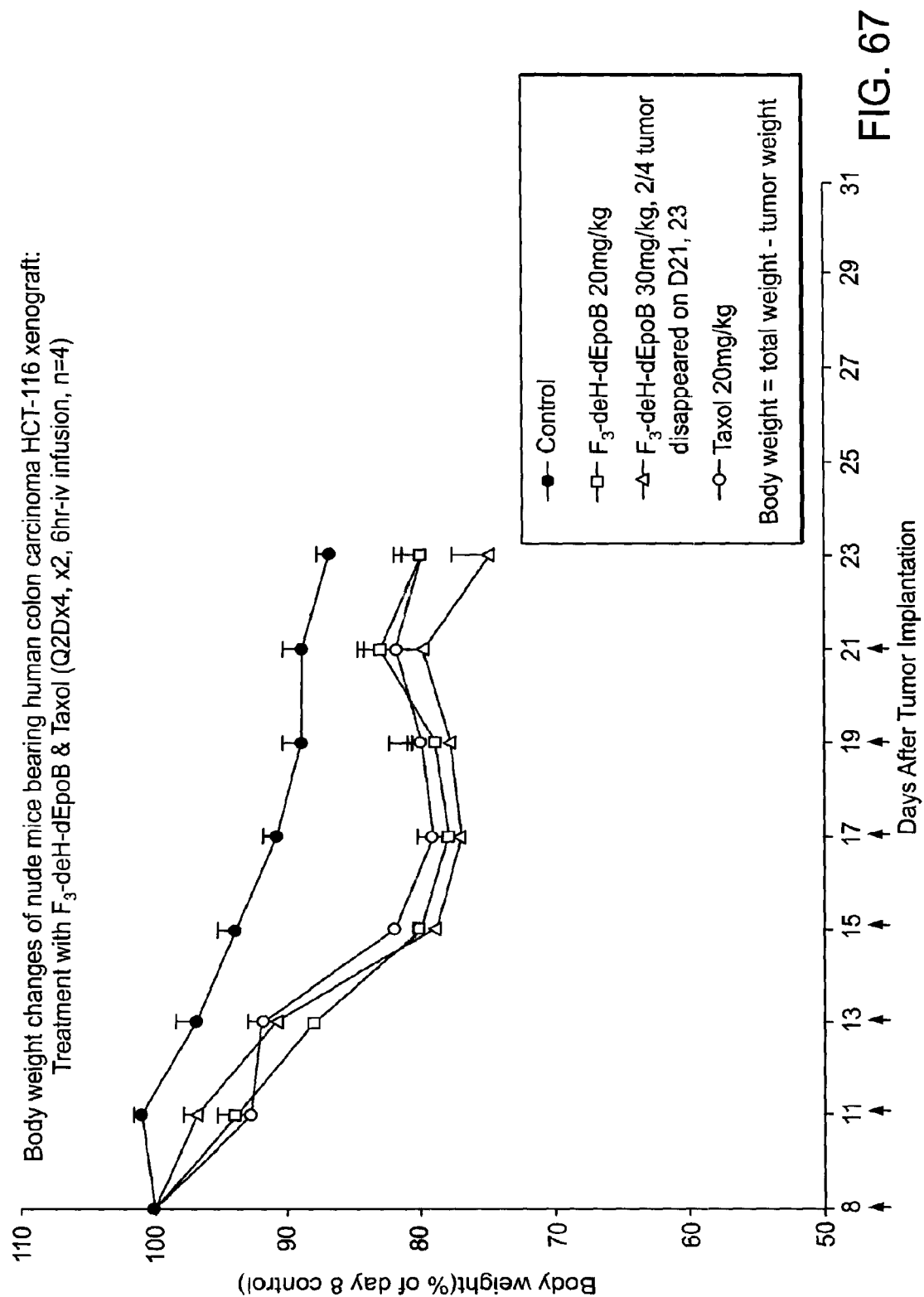
FIG. 67 shows the changes in body weight of nude mice bearing human colon carcinoma HCT-116 xenograft following treatment with 26-trifluoro-9,10-dehydro-dEpoB and Taxol (Q2Dx4, x2, 6 hour iv infusion).

Treatment of human colon carcinoma HCT-116 xenograft with 26-$F_3$-9,10-deH-dEpo B (20 mg/kg) achieved similar efficacy as Taxol (20 mg/kg). However, $F_3$-deH-dEpo B at 30 mg/kg yield better therapeutic effect with 2/4 tumor disappearance following 5 doses (FIG. 66). The body weight changes during this experiment were shown in FIG. 67.

Figure 76:
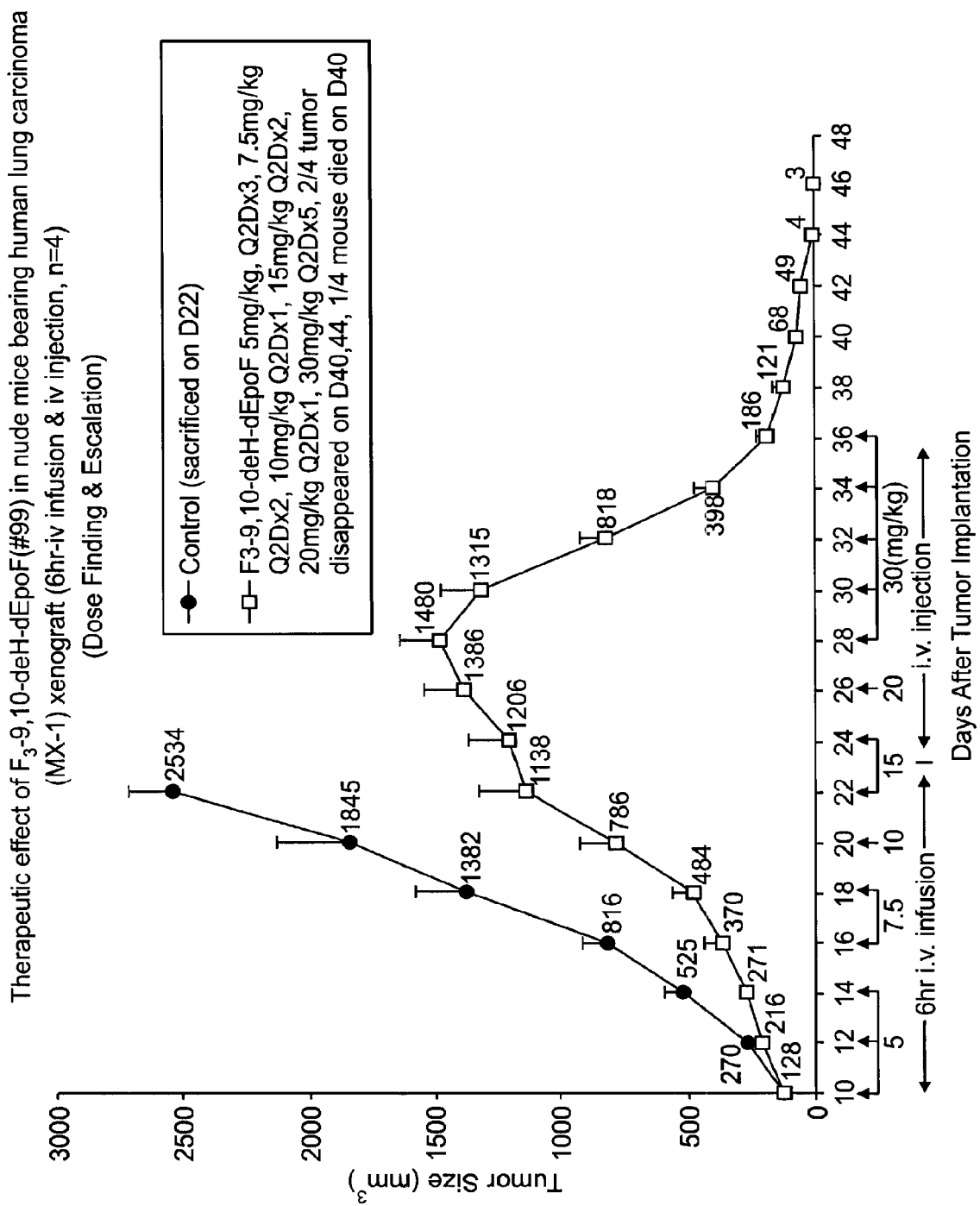
FIG. 76 shows the therapeutic effect of 26-trifluoro-9,10-dehydro-dEpoF in nude mice bearing human lung carcinoma (MX-1) xenograft (6 hour iv infusion and iv injection).
Figure 77:
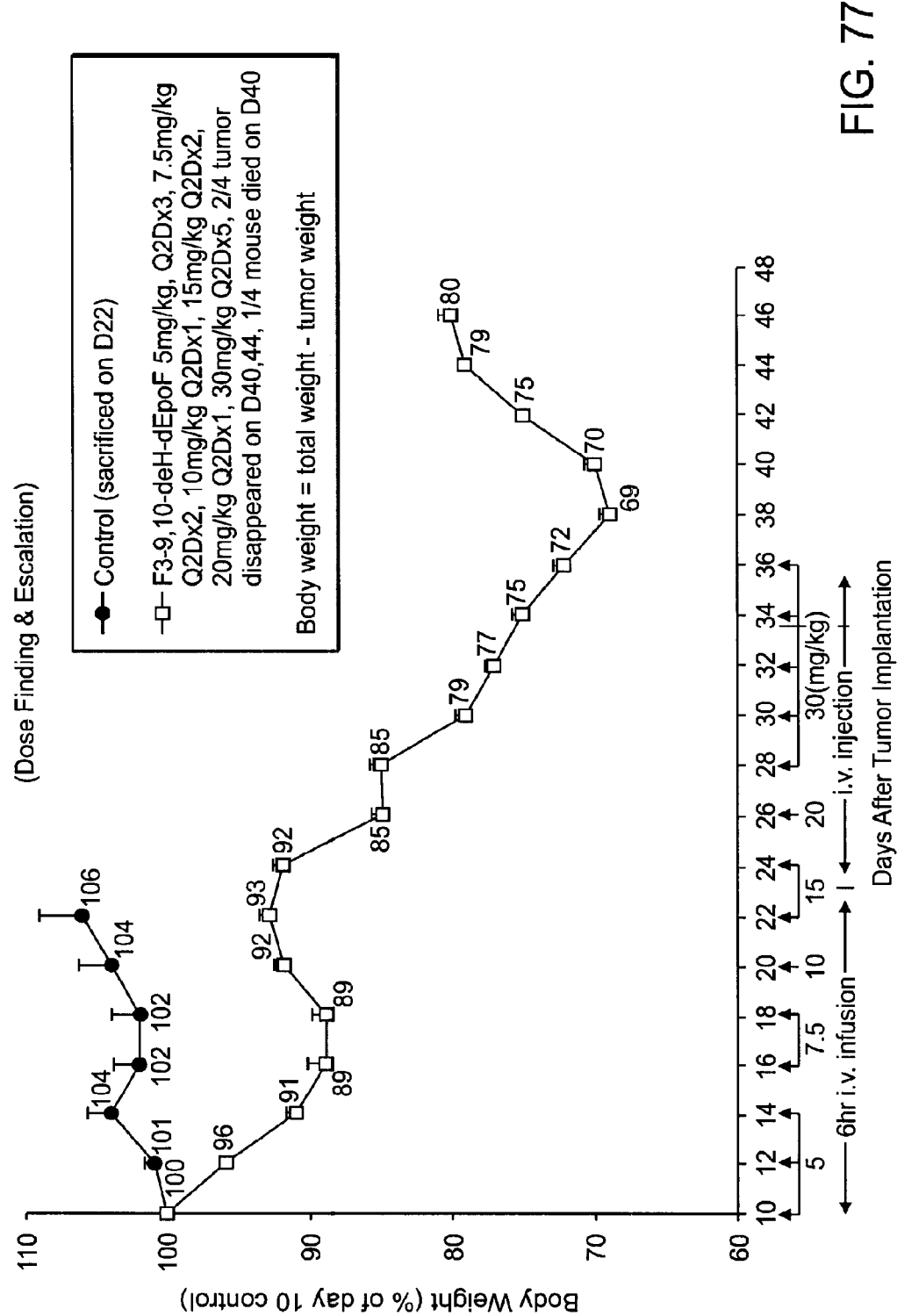
FIG. 77 shows the changes in body weight of nude mice bearing MX-1 xenograft following treatment with 26-trifluoro-9,10-dehydro-dEpoF (6 hour iv infusion and iv injection).
Figure 78:
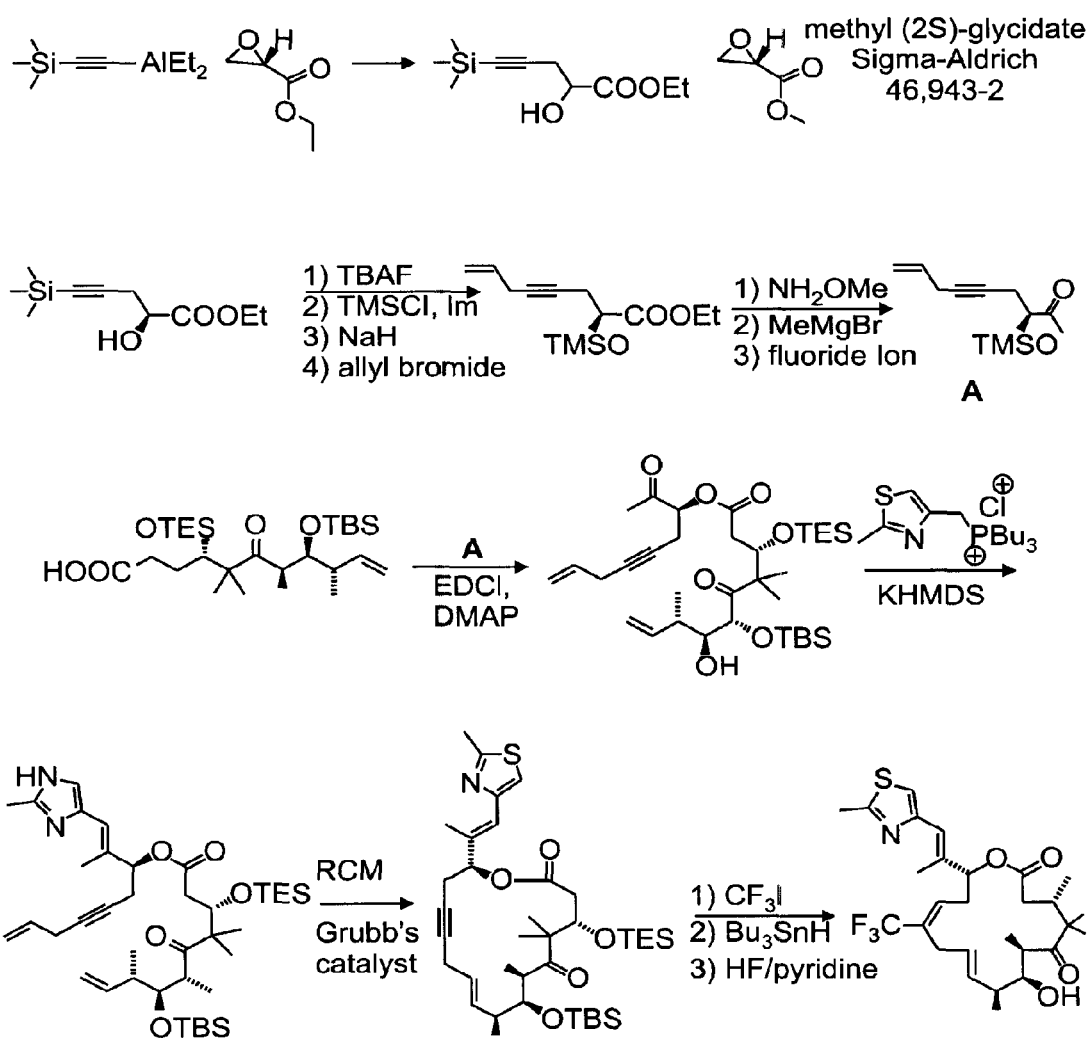
FIG. 78 shows a synthesis of 12-trifluoromethyl-9,10-dehydro-desoxyepothilone D.
Figure 79A:
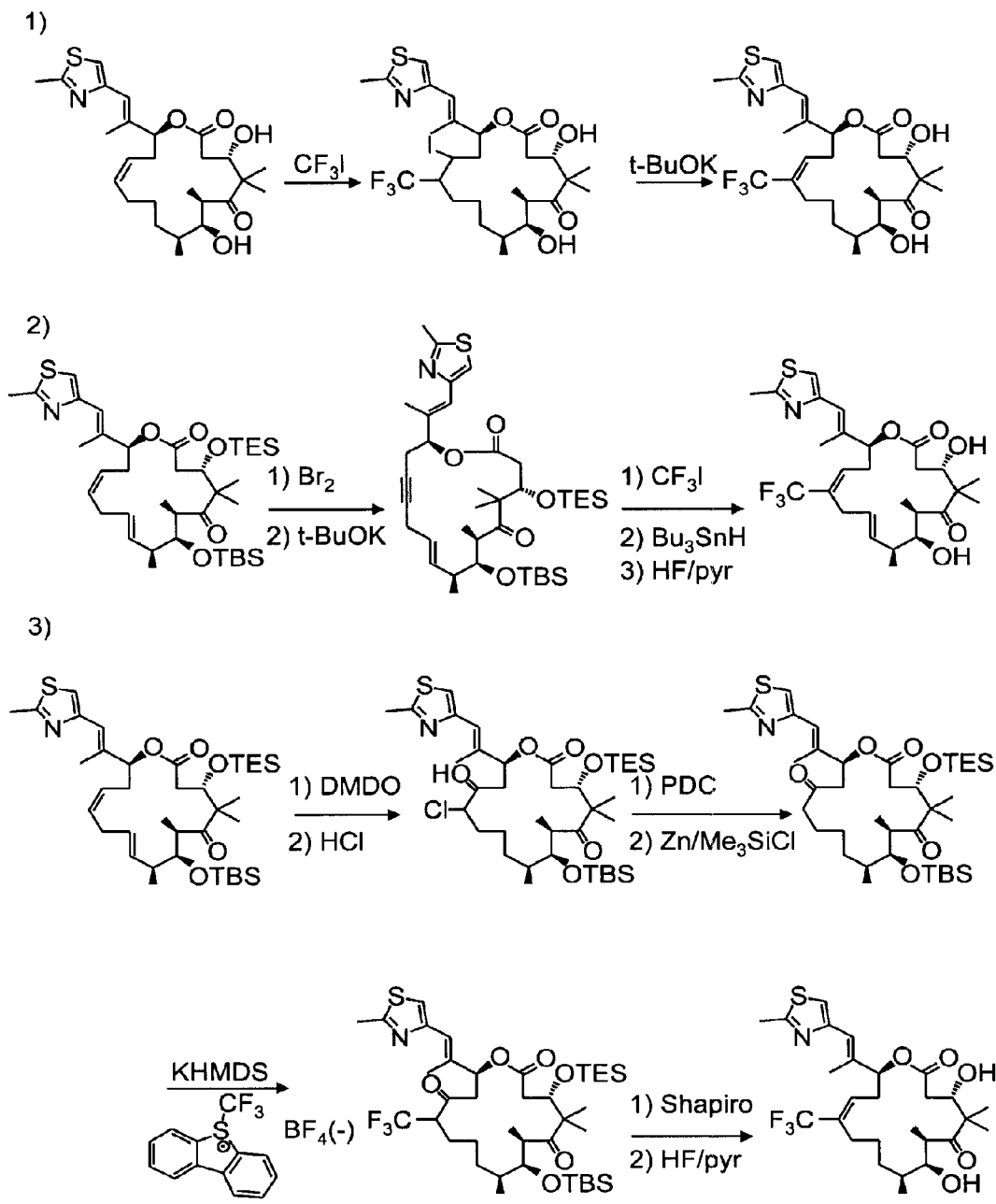
FIG. 79 shows several methods of preparing 12-trifluoromethyl-9,10-dehydro-desoxyepothilone D from Epo A.
Figure 79B:
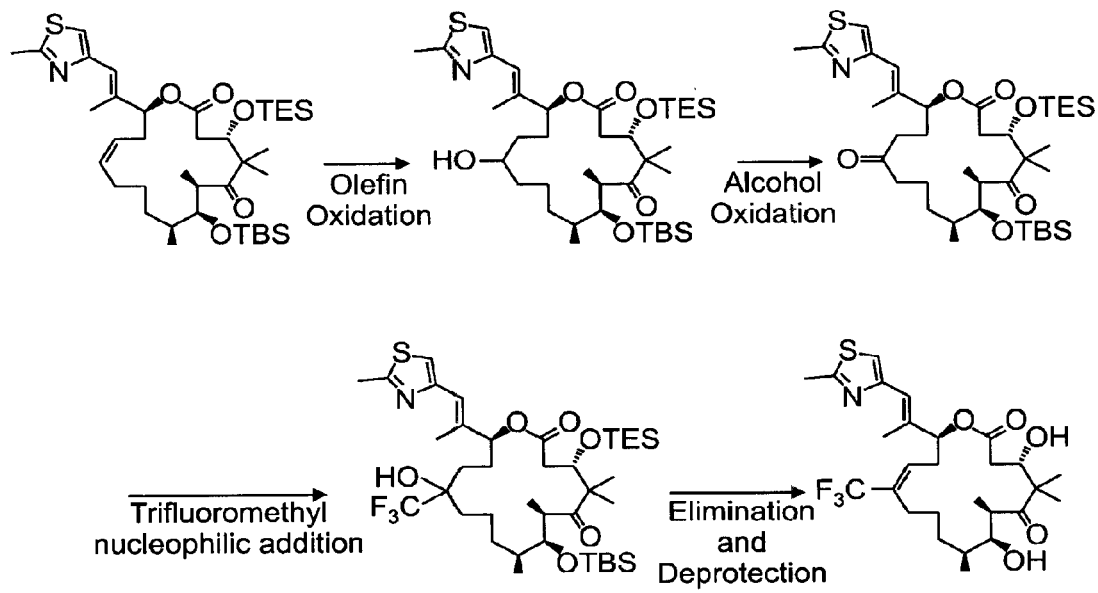
Figure 80:
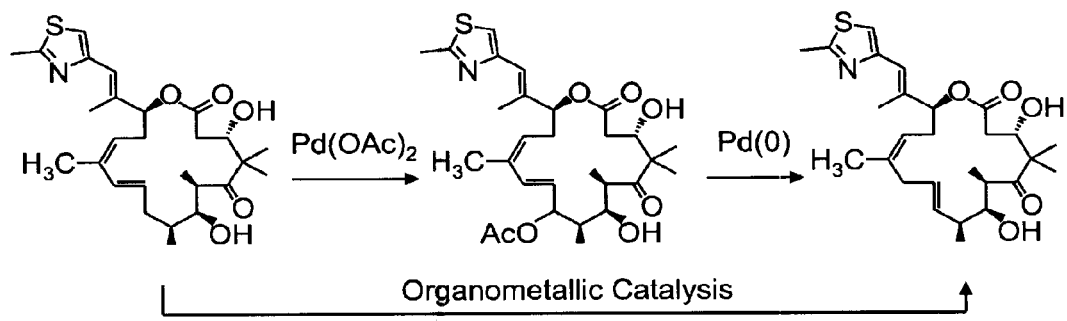
FIG. 80 shows the preparation of 9,10-dehydro-epoD from Epo 490 by isomerizing the C10-C11 double bond to the C9-C10 position.
Figure 81A:
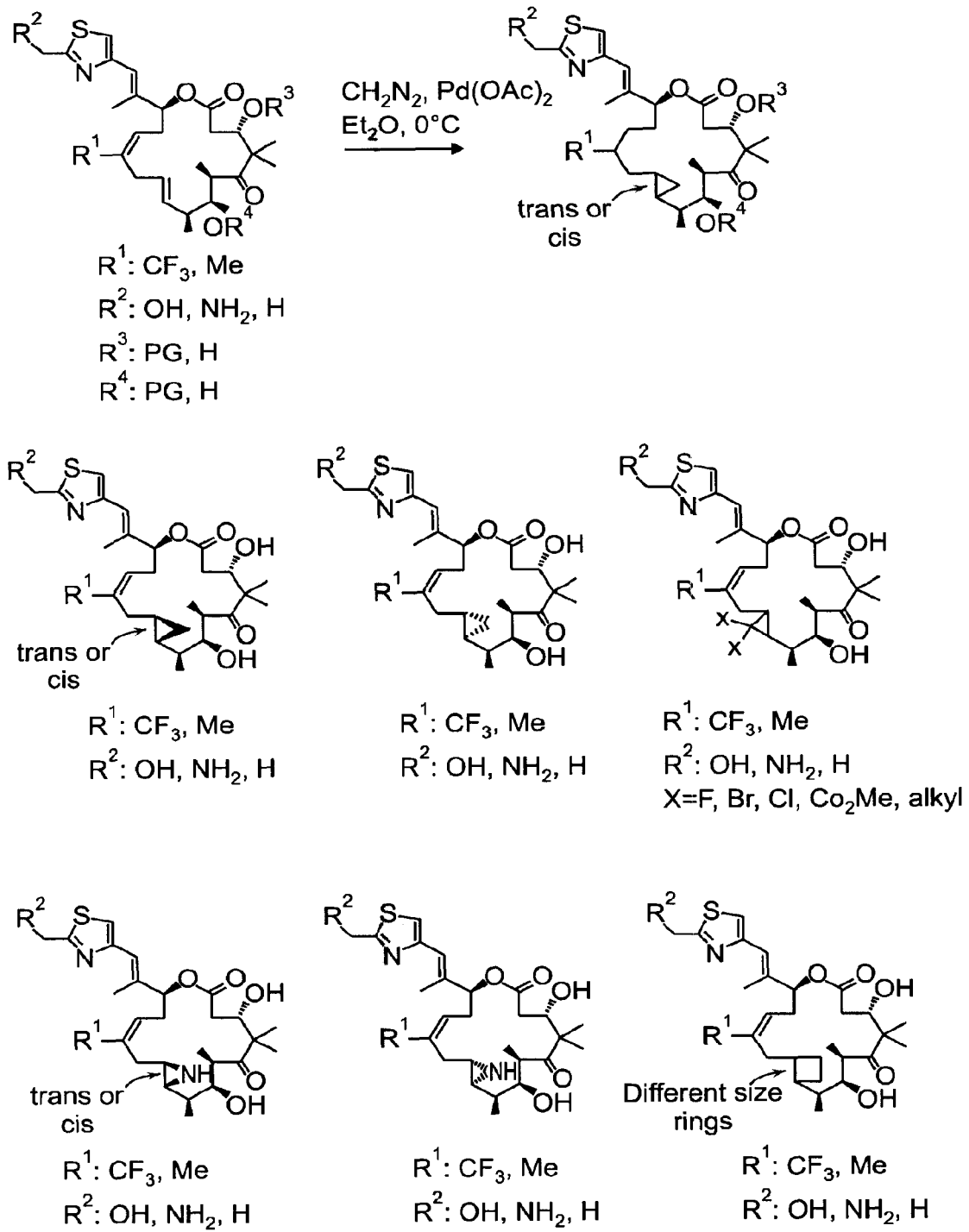
FIG. 81 depicts various epothilone analogs with modifications at the 9,10-position.

The therapeutic effects of $F_3$-9,10-dehydro-dEpoF against MX-1 xenografts at different doses (5-30 mg/kg) with 6 hour i.v. infusion and i.v. injection are shown in FIGS. 76 and 77.

Conclusion. The 9,10-dehydro, 26-trifluoro, or both modifications to dEpoB result in a 1.5- to 5-fold increase in cytotoxicity in vitro and a 2- to 5-fold increase in half-life in mouse plasma in vitro. By using human solid tumor xenograft models in nude mice and using the Q2Dx5-9, 6 hr-i.v. infusion technique via tail vein at maximal tolerated doses, the antitumor efficacy and toxicity of 9,10-dehydro-epothilones were evaluated. The ability to achieve complete tumor growth suppression, tumor shrinkage, and disappearance allowed for further investigation to determine the relapse rate and cure rate after stopping treatment. 9,10-dehydro-EpoB, the most potent epothilone known in vitro, although highly efficacious, showed a narrow therapeutic safety margin in vivo. 9,10-dehydro-dEpoB at 4 mg/kg, 9,10-dehydro-EpoB at 0.4 mg/kg, and 21-hydroxy-9,10-dehydro-dEpoB at 3 mg/kg all strongly suppressed tumor growth for a sustained period of time and achieved some tumor shrinkage, and some achieved tumor disappearance. dEpoB at 30 mg/kg, 26-trifluoro-9,10-dehydro-dEpoB at 20 mg/kg, and paclitaxel at 20 mg/kg all showed strong suppression of tumor growth and achieved tumor shrinkage and disappearance of human mammary carcinoma MX-1 xenografts in all mice tested. 26-trifluoro-9,10-dehydro-dEpoB, when compared with dEpoB or paclitaxel, achieved a long term cure without a tumor relapse and showed an equally rapid recovery of body weight to the pretreatment control level.

Example 13
Synthesis of Cyclopropyl-Epothilone Analogs
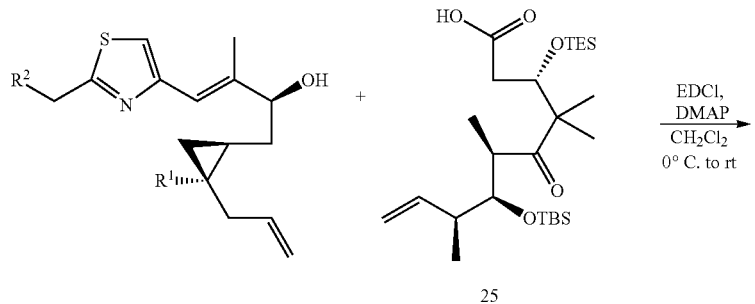
102 ($R^1$ = Me, $R^2$ = H), 103 ($R^1$ = CF$_3$, $R^2$ = H),
104 ($R^1$ = Me, $R^2$ = OTBS), 105 ($R^1$ = CF$_3$, $R^2$ = OTBS)
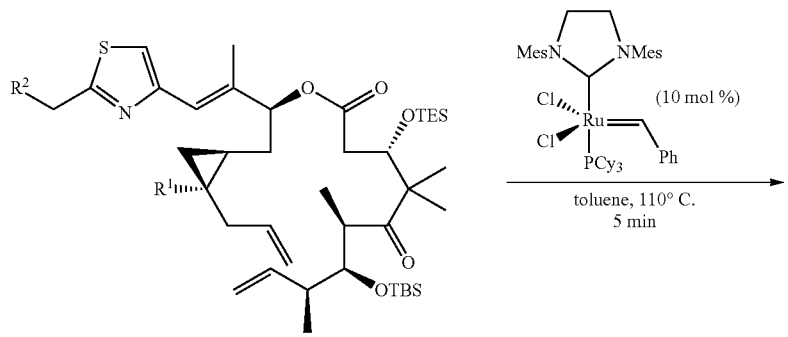
$R^1$ = Me, $R^2$ = H, (106)
$R^1$ = CF$_3$, $R^2$ = H (107)
$R^1$ = Me, $R^2$ = OTBS (108)
$R^1$ = CF$_3$, $R^2$ = OTBS (109)
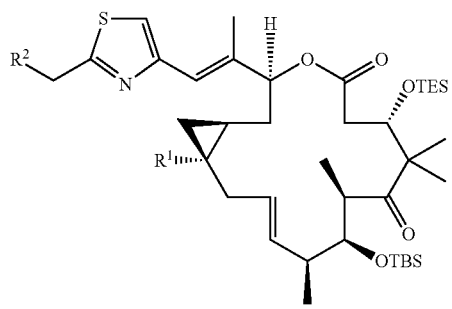
110 ($R^1$ = Me, $R^2$ = H)
111 ($R^1$ = CF$_3$, $R^2$ = H)
112 ($R^1$ = Me, $R^2$ = OTBS)
113 ($R^1$ = CF$_3$, $R^2$ = OTBS)
HF·Pyridine,
THF (1:3)
0° C. to rt

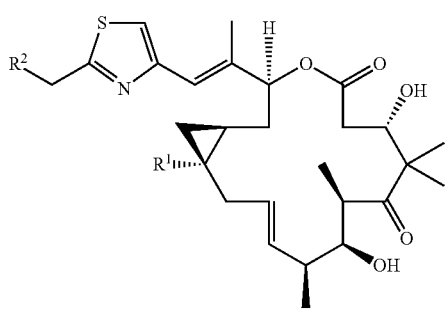
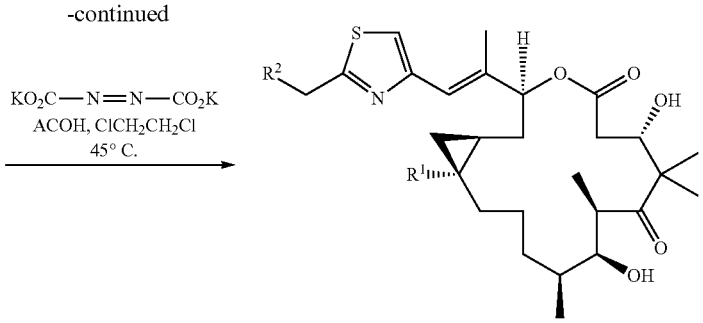

$R^1$ = Me, $R^2$ = H, (114)
$R^1$ = $CF_3$, $R^2$ = H (115)
$R^1$ = Me, $R^2$ = OH (116)
$R^1$ = $CF_3$, $R^2$ = OH (117)

$R^1$ = Me, $R^2$ = H, (118)
$R^1$ = $CF_3$, $R^2$ = H (119)
$R^1$ = Me, $R^2$ = OH (120)
$R^1$ = $CF_3$, $R^2$ = OH (121)

Example 14

Figure 83A:
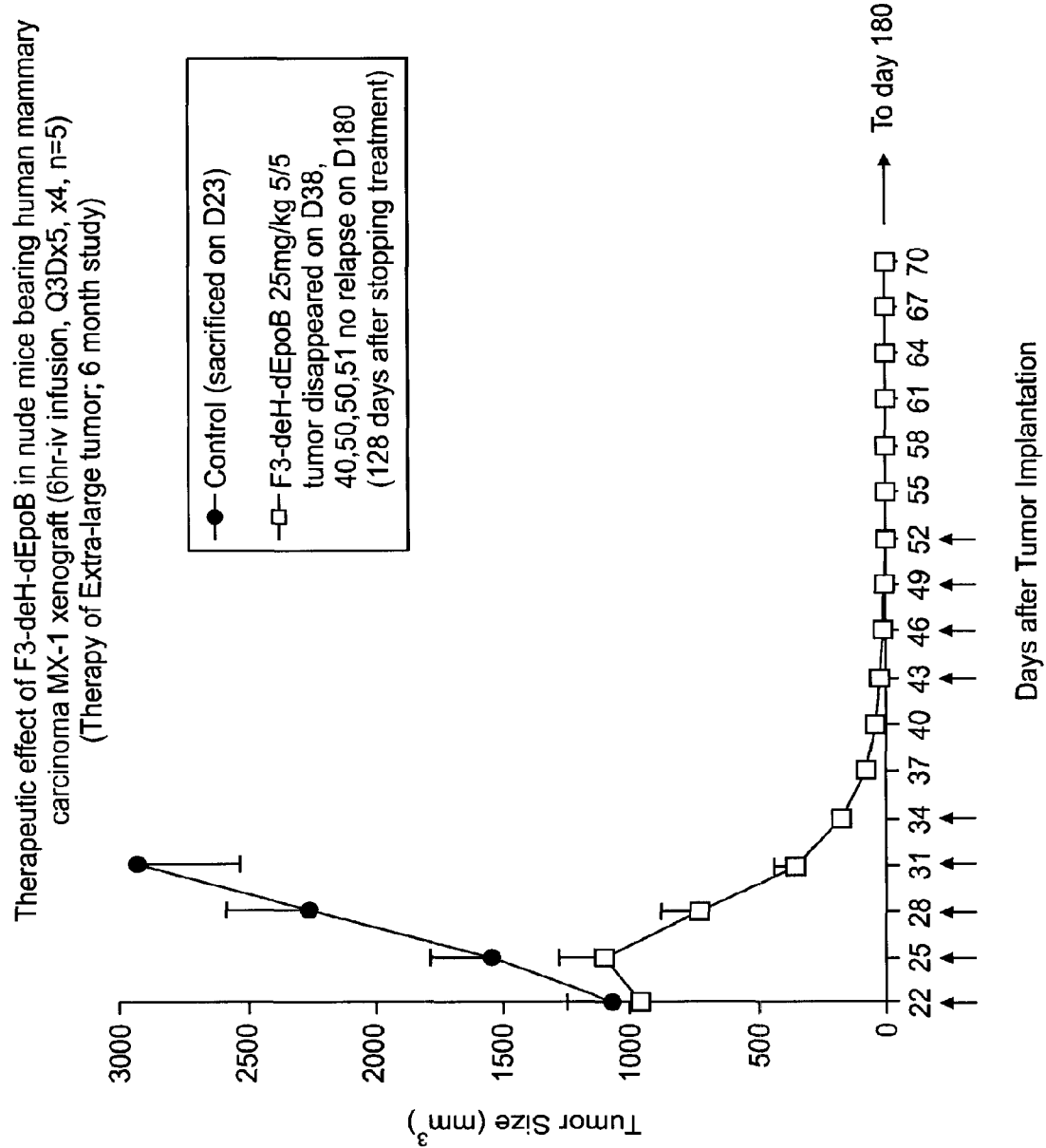
FIG. 83A shows the therapeutic effect as demonstrated by a reduction in tumor size.
Figure 83C:
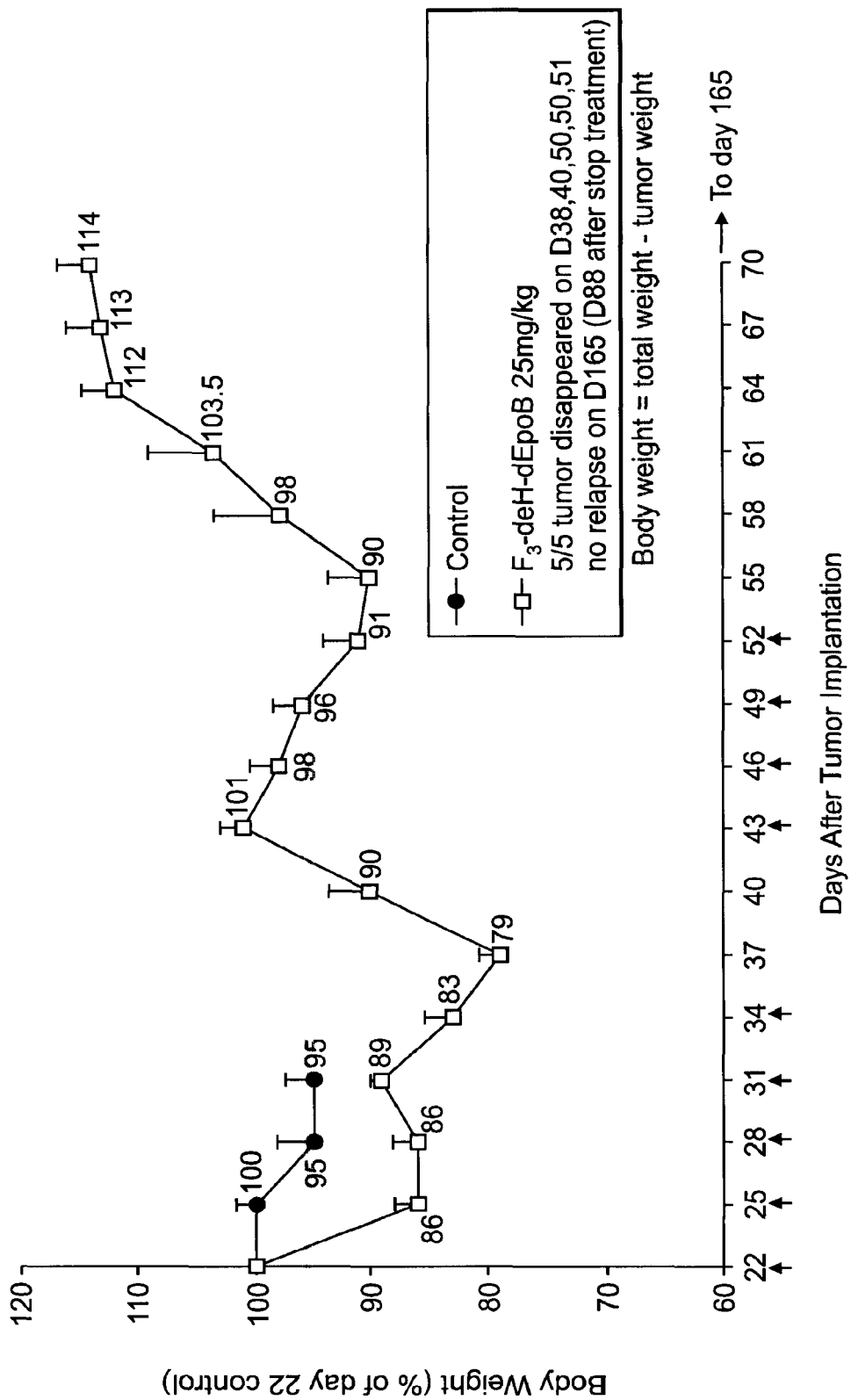
FIG. 83C shows changes in body weight.

Oral and Parenteral Administration of 26-trifluoro-9,10-trans-dehdyro-epothilone D in the Treatment of Human Tumors implanted in Nude Mice In this Example, it is demonstrated that structurally designed 16-membered macrolide microtubule-stabilization agent, 26-trifluoro-9,10-trans-dehdyro-epothilone D, shrinks tumors, renders tumor disappearance, and achieves long term non-relapse when given by 6 hr.-i.v. infusion or orally. Mice bearing large size tumor (FIG. 83) or Taxol-resistant tumor xenografts (FIG. 84) are shown to be curable with 26-trifluoro-9,10-trans-dehdyro-epothilone D as a single agent monotherapy. The curative therapeutic spectrum encompasses leukemia as well as breast, colon, and lung carcinomas (FIGS. 83, 86, and 90). All chemotherapeutic experiments in vivo reported here were carried out using human tumor xenografts in immunodeficient nude mice. This animal model is commonly used in evaluating anti-tumor compounds prior to clinical trials in cancer patients.

The MX-1 and HCT-116 experiments lasted 5.5 and 6.5 months, respectively (FIGS. 83 and 86). There was no tumor relapse in both experiments with 3.8 and 5.2 months tumor free, respectively, following the cessation of treatment. For the HCT-116 experiment (FIG. 86), both paclitaxel and 26-trifluoro-9,10-trans-dehdyro-epothilone D at 20 mg/kg were used and both achieved tumor disappearance. However, the paclitaxel treated group relapsed at 1.1 months after stopping treatment, whereas 26-trifluoro-9,10-trans-dehdyro-epothilone D treated animals were tumor free for over 5.2 months. Assuming a tumor doubling time of 4 days (based on the vehicle treated control), the paclitaxel treatment of HCT-116 tumor resulted in 99.7% tumor suppression or 2.56-log cell kill, whereas the cell kill by 26-trifluoro-9,10-trans-dehdyro-epothilone D in MX-1 and HCT-116 experiments would be >8.5-log and >11.6 log, respectively, when the experiments were terminated. Based on the healthy, active conditions of the treated mice with body weight returned to pre-treatment levels, it is expected that "cure" can be ensured throughout the 2 year life span of the mice if prolonged treatment or additional cycles of treatment were enforced. This result should be achievable despite the fact that "cure" would be more difficult to attain in immunodeficient mice than in the immuno-competent mice. To our knowledge, this is the longest xenograft therapeutic studies carried out in nude mice in biomedical literature, and the longest complete remission that has been reported either with parenteral or oral administration for a single antitumor agent. It is pertinent to state that it is relatively easy to find a compound that suppresses tumor growth. But it is relatively rare to find a compound that achieves tumor shrinkage. The finding with our compound, 26-trifluoro-9,10-trans-dehdyro-epothilone D, that achieves complete tumor disappearance in all mice with no relapse for as long as 5.2 months to our knowledge has never been reported previously, indicating the great potential of 26-trifluoro-9,10-trans-dehdyro-epothilone D for therapeutic development.

Additional significant benefit of oral therapy is that the use of Cremophor formulation that can cause severe allergic reactions can be avoided. It is well known that the use of Cremophor in the formulation in Taxol, desoxy-EpoB, and 15-aza-Epo13 induced troublesome allergic reactions which make pretreatment with antihistamine and/or steroid necessary.

Oral effectiveness of 26-trifluoro-9,10-trans-dehdyro-epothilone D is consistent with its remarkable metabolic stability in mouse plasma and in human liver microsomal S9 fraction in vitro. This metabolic stability is attributable to the trifluorination at C-26 position of the epothilone molecule (FIG. 91). Introducing the double bond at C9-C10 also increased metabolic stability (FIG. 91). The closeness of the optimal dose of 26-trifluoro-9,10-trans-dehdyro-epothilone D for i.v. infusion (20-30 mg/kg, Q2D) and for the oral administration (20 mg/kg, QD or 30 mg/kg Q2D) suggests that the compound is well absorbed and has excellent bioavailability in vivo.

It is worthy of noting that many of our in vivo therapeutic studies on Fludelone (FIGS. 90, 84, 86, 87, 88, and 93) against xenografts were carried out in parallel with Taxol, which is one of the most important cancer therapeutic agents currently in use in clinics. The profound findings with Fludelone, in comparison with Taxol, indicate the promising potential of this compound for the treatment of cancer.

Materials and Methods

Chemicals: All epothilones were synthesized as indicated herein. Paclitaxel (Taxol®) and vinblastine sulfate (VBL) were purchased from Sigma. All these compounds were dissolved in dimethylsulfoxide for the in vitro assays, (except VBL in saline). For in vivo studies, all epothilones and paclitaxel were dissolved in Cremophor/ethanol (1:1) vehicle and then diluted with saline for iv infusion for 6 hrs via tail vein using a custom-designed mini-catheter and a programmable pump (Chou, T.-C., Zhang, X.-G., Harris, C. R., Kuduk, S. D., Balog, A., Savin, K. & Danishefsky, S. J. (1998) *Proc. Natl. Acad. Sci. USA* 95, 15798-15802; Chou, T.-C., O'Connor, O. A., Tong, W. P., Guan, Y., Zhang, X.-G., Stachel, S. J., Lee, C & Danishefsky, S. J. (2001) *Proc. Natl. Acad. Sci. USA* 98, 8113-8118; each of which is incorporated herein by reference). Oral administration of the drugs were prepared by dissolving the compound in ethanol and suspended with equal volume of Tween-80 and the suspension was diluted with 5 volumes of saline prior to administration to nude mice. The gavage was carried out using a 1 ml syringe and a gauge #22 ball-tipped animal feeding needle. (Popper & Sons, Inc. New Hyde Park, N.Y.).

Tumor and Cell Lines: The CCRF-CEM human lymphoblastic leukemia cells and their vinblastine resistant subline (CCRF-CEM/VBL$_{100}$, 720-fold resistance) were obtained from Dr. William Beck of the University of Illinois, Chicago, and CCRF-CEM/Taxol (44-fold resistance) by exposing CCRF-CEM cells to increasing sublethal concentration (IC$_{50}$-IC$_{90}$) of paclitaxel for six months. The degree of resistance are shown in FIG. 91. Human mammary carcinoma (MX-1), human lung carcinoma cells (A549), and human colon carcinoma (HCT-116) were obtained from American Type Culture Collection (ATCC, Rockville, Md.).

Animals: Athymic nude mice bearing the nu/nu gene were obtained from NCI, Frederick, Md. and used for all human tumor xenografts. Male nude mice 6 weeks or older weighing 20-22 g or more were used. Drugs were administered via the tail vein for 6 hours by iv infusion using a homemade infusion mini-catheter and containment tube. A programmable Harvard PHD2000 syringe pump with multitrack was used for iv infusion. A typical 6 hr infusion volume for each drug in Cremophor/ethanol (1:1) was 100 µl in 2.0 ml of saline. For oral administration, both Fludelone and Taxol were dissolved in ethanol and the diluted 5-fold with Tween-80. The Taxol solution should be used within 5 min to avoid precipitation. Tumor volume was assessed by measuring length×width×height (or width) by using a caliper. For tumor-bearing nude mice during the course of experiment, the body weight refers to total weight minus the weight of the tumor. All animal studies conducted in accordance with the guidelines for the National Institute of Health Guide for the Care and Use of Animals and the protocol approved by the Memorial Sloan-Kettering Cancer Center's Institutional Animal Care and Use Committee.

Cytotoxicity Assays: In preparation for in vitro cytotoxicity assays, cells were cultured at an initial density 2-5×10$^4$ cells per milliliter. They were maintained in a 5% CO$_2$-humidified atmosphere at 37° C. in RPMI medium 1640 (GIBCO/BRL) containing penicillin (100 units/mL), streptomycin (100 µg/mL, GIBCO/BRL), and 5% heat-inactivated FBS. For solid tumor cells growing in a monolayer (such as HCT-116 and A549), cytotoxicity of the drug was determined in 96-well microtiter plates by using the sulforhodamine B method (Skehan, P., Storeng, R., Scudiero, D., Monks, A., McMahon, J., Vistica, D., Warren, J. T., Bokesch, H., Kenny, S. & Boyd, M. R. (1990) *J. Natl. Cancer Inst.* 82, 1107-1112; incorporated herein by reference). For cells grown in suspension (such as CCRF-CEM and its sublines), cytotoxicity was measured, in duplicate, by using the 2,3-bis-(2-methoxy-4-nitro-5-sulfophenyl)-5-carboxanilide)-2H-terazodium hydroxide (XTT) microculture method (Scudiero, D. A., Shoemaker, R. H., Paull, K. D., Monks, A., Tierney, S., Nofziger, T. H., Currens, M. J., Seniff, D. & Boyd, M. R. (1988) *Cancer Res.* 48, 4827-4833; incorporated herein by reference) in 96-well microtiter plates. For both methods, the absorbance of each well was measured with a microplate reader (Power Wave XS, Bio-Tek, Winooski, Vt.). Dose-effect relationship data from 6 to 7 concentrations of each drug, in duplicate, were analyzed with the median-effect plot by using a computer program (Chou, T.-C. & Talalay, P. T. (1984) *Adv. Enzyme Reg.* 22, 27-55; Chou, T.-C. & Hayball, M. (1997) *CalcuSyn for Windows* (Biosoft, Cambridge, U.K.); each of which is incorporated herein by reference).

Stability of epothilones in mouse and in human liver S9 fraction: The stability study was carried out with a fully automated HPLC system which consisted of a Prospekt-2 (Spark Holland, Netherlands) sample preparation system and an Agilent 1100 HPLC system. Briefly, the Prospekt 2 picked up a C8 extraction cartridge and washed it with acetonitrile and water. The Agilent autosampler, set at 37° C., picked up 20 µl of the sample, loaded it onto the cartridge, washed it with water, then the Prospekt-2 diverted the mobile phase stream through the extraction cartridge onto the analytical column, Reliance Stable Bond C8 4×80 mm with guard column (MacMod, Chadds Ford, Pa.) and the eluent was monitored at 250 nm. The mobile phase consists of 53 or 65% acetonitrile/0.1% formic acid at 0.4 ml/min, so that the retention time of the compound of interest is about 6 minutes. Sample preparation involves the addition of equal volumes of plasma to PBS for a total volume of 400 µl, filtered, and the addition of 0.5-2 µl of the substrate (20 mM) to achieve about 30-50 mAU at 250 nm in the HPLC analysis. For pooled human liver microsome S9 fraction (Xeno Tech, Lenex, Kans.), 20 µl (400 µg) or S9 fraction was mixed with 280 µl of PBS then proceeds as above. The sampling period was controlled by the autosampler and peak area data were collected to compare the rate of disappearance of the parent compound.

Results

Structure-Activity Relationships In Vitro against Human Leukemic, Taxol-and Vinblastin-resistant Leukemic Cells and Solid Tumor Cells. The potency in terms of IC$_{50}$ (in µM) for twelve representative epothilones against the growth of human leukemic CCRF-CEM cells and their sublimes resistant to vinblastine CCRF-CEM/VBL and resistant to paclitaxel, CCRF-CEM/Taxol were listed in the table in FIG. 94. Also listed are the IC$_{50}$ values for two human solid tumor cell lines: lung carcinoma A549 and colon carcinoma HCT-116. It is shown that deH-EpoB replaces EpoB as the most potent epothilone known. It is also shown that i) 9,10-dehydromodification on dEpoB, dEpoF, or F$_3$-dEpoF always resulted in marked increase in potency, whereas trifluorination on the C-26 position somewhat reduced the potency, however metabolic stability is greatly increased by the trifluorination (FIG. 91); and ii) Most epothilones are not cross-resistant with vinblastine, typical substrate for the P-glycoprotein of multidrug resistance (MDR) nor cross-resistant with Taxol. Taxol is a good substrate for MDR phenotype but Taxol resistance may also be generated by mutation in tubulin gene. The exceptions are 15-aza-EpoB, 15-aza-deH-dEpoB which shows considerable cross-resistance to both vinblastine and paclitaxel. dEpoF and its derivative showed some cross-resistance with vinblastine but not paclitaxel. iii) Leukemic CCRF-CEM cells and solid-tumor cells A549 and HCT-116 are almost equally susceptible to epothilones. iv) F$_3$-deH-dEpoB, deH-dEpoB, and deH-EpoB, which are our new lead compounds for further pharmacologic evaluations, are not appreciably cross-resistant to vinblastine nor to paclitaxel.

In earlier studies (Schiff, P. B., Fant, J. & Horwitz, S. B. (1979) *Nature* (London) 277, 665-667; Meng, D., Su, D.-S., Balog, A., Bertinato, P., Sorsensen, E. J., Danishefsky, S. J., Zheng, Y.-H., Chou, T.-C., He, L. & Horwitz, S. B. (1997) *J.*

*Am. Chem. Soc.* 119, 2733-2734; each of which is incorporated herein by reference) it was concluded that epothilone molecules can be dissected into three zones. Thus, in the C-1-8 acyl sector, structural changes are not tolerated in terms of in vitro cytotoxicity and microtubule stabilizing ability. This is in contrast to the C-9~15 O-alkyl sector and the C-15 pendant aryl sectors wherein considerable modification of structures is tolerated (Haar, E. T., Kowalski, R. J., Hamel, E., Lin, C. M., Longley, R. E., Gunasekera, S. P., Rosenkranz, H. S. & Day, B. W. (1996) *Biochemistry* 35, 243-250; Kowalski, R. J., Giannakakou, P. & Hamel, E. (1997) *J. Biol. Chem.* 272, 2534-2541; each of which is incorporated herein by reference). The design and editing of chemical structures for the present paper follows these rules, guided by pharmacological activities, pharmacokinetic properties and therapeutic selectivity.

Epothilones with 12,13-epoxyl moiety, such as EpoB, and deH-EpoB, although the most potent agents in the epothilone series but they possessed rather poor therapeutic index at their maximal tolerated doses. This hypothesis is illustrated with the therapeutic data given in the table in FIG. 91.

Physico-chemical, Metabolic, Pharmacological Properties and Therapeutic Results of Epothilone Derivatives. Interrelating different properties of a series of epothilones facilitates the understanding of factors that contribute to the therapeutic end-results for the lead compounds. Table 91 summarizes the profiles of nine epothilone derivatives. The structure-cytotoxic activity relationship in vitro (FIG. 94) provides potency-based initial evaluation. For example, new class of 9,10-dehydro modification greatly increased potency in vitro and in vivo. In these preselected compounds, it is more difficult to correlate the structure-microtubule stabilization potency because the potency are all quite high (i.e., similar to the paclitaxel potency). Water solubility and lipophilicity play varied role in the therapeutic effect and may be important for the design of formulation. DeH-dEpoF, $F_3$-deH-dEpoF and deH-dEpoB greatly increased water solubility relative to other epothilones. The finding that $F_3$-deH-dEpoB is orally efficacious (see data below in FIG. 84) reduces the concern of water-insolubility in the drug formulation and the usage of allergy causing Cremophor can be avoided.

In vitro, deH-EpoB, deH-dEpoF, EpoB and deH-dEpoB, in this order have sub-nanomolar $IC_{50}$'s whereas $F_3$-deH-dEpoF, dEpoF, $F_3$-deH-dEpoB, dEpoB and $F_3$-dEpoB, in this order, have $IC_{50}$'s range of 1.3 to 9.3 nM (FIG. 94). DeH-EpoB and EpoB are the most potent epothilones known in vitro and in vivo but they do not yield the best therapeutic index. Apparently, epoxyl moiety on C-12-13 of EpoB and deH-EpoB contribute greatly to the toxicity toward the host as evident by lower value in the maximal-body weight percent drop without a death (FIG. 91). By contrast, $F_3$-deH-dEpoB and dEpoB tolerated the highest values of body weight dropped and they showed excellent therapeutic results such as complete tumor remission in all animals. In general, in vitro potency and the optimal therapeutic dose revealed good correlations with 6 hr-i.v. infusion of treatment. Of special interest is that $F_3$-deH-dEpoB (Fludelone) possesses the widest curative therapeutic dose range (10-30 mg/kg) (Chou, T.-C., Dong, H., Rivkin, A., Yoshimura, F., Gabarda, A. E., Cho, Y. S., Tong, W. F. & Danishefsky, S. J. (2003) *Angew Chem. Int. Ed. Engl.* 42, 4762-4767; incorporated herein by reference) the excellent metabolic stability and the best overall therapeutic results among the epothilones listed (FIG. 91). Furthermore, $F_3$-deH-dEpoB provides curative therapeutic effect via oral route of administration. It is concluded that the most potent epothilones does not necessarily perform better as antitumor agents and that $F_3$-deH-dEpoB is the lead candidate for the therapeutic development.

Therapy on Extra Large MX-1 Tumor Xenografts. As shown in FIG. 83A, treatment of MX-1 xenografts as large as 3.4% of body weight with $F_3$-deH-dEpoB, 25 mg/kg, 6 hr-i.v. infusion Q3Dx5 beginning D22 after tumor implantation, led to marked tumor shrinkage (>97.4%). During the resting period of 9 days without treatment (D34-D43), the tumor size continued to shrink (>99.3%) and tumor disappeared in 2 out of 5 mice studied, whereas body weight of the treated group recovered to the pretreatment level during the same resting period (FIG. 83B). Resumption of treatment on D43, Q3Dx4, led to tumor disappearance on the remaining 3 mice on D50, D50 and D51. After D52 (i.e., date of the last dose), animals were observed every three days until D165 when the experiment was terminated. There was no tumor relapse in all 5 animals on D165 (i.e., over 3.7 months after cessation of treatment).

The photographs of the nude mice of this experiment taken on D25, D31, D37, D43 and D52 from one mouse each for the control and treated groups are shown in FIG. 83B.

Figure 90A:
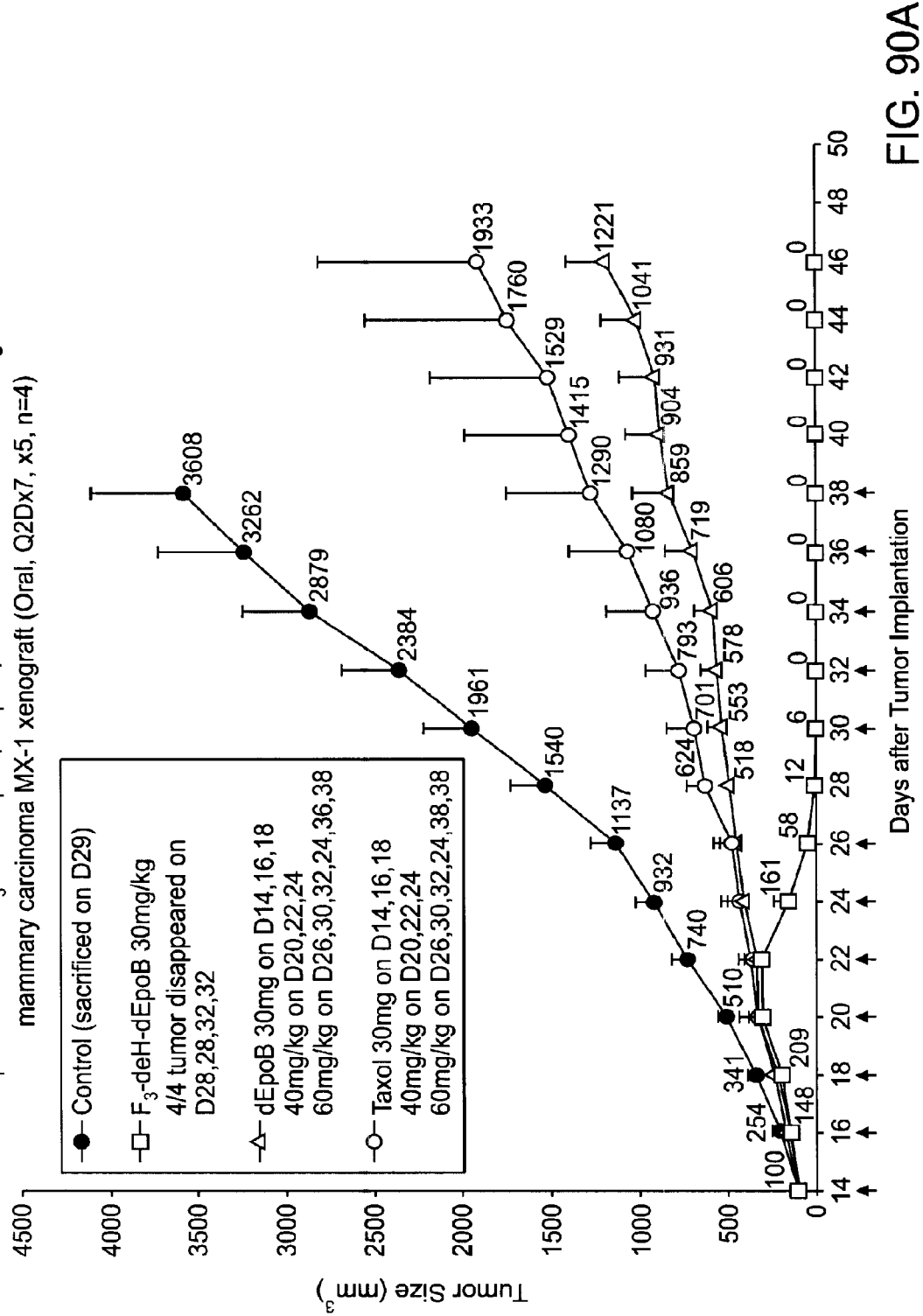
FIG. 90A shows the therapeutic effect as demonstrated by a reduction in tumor size.
Figure 90B:
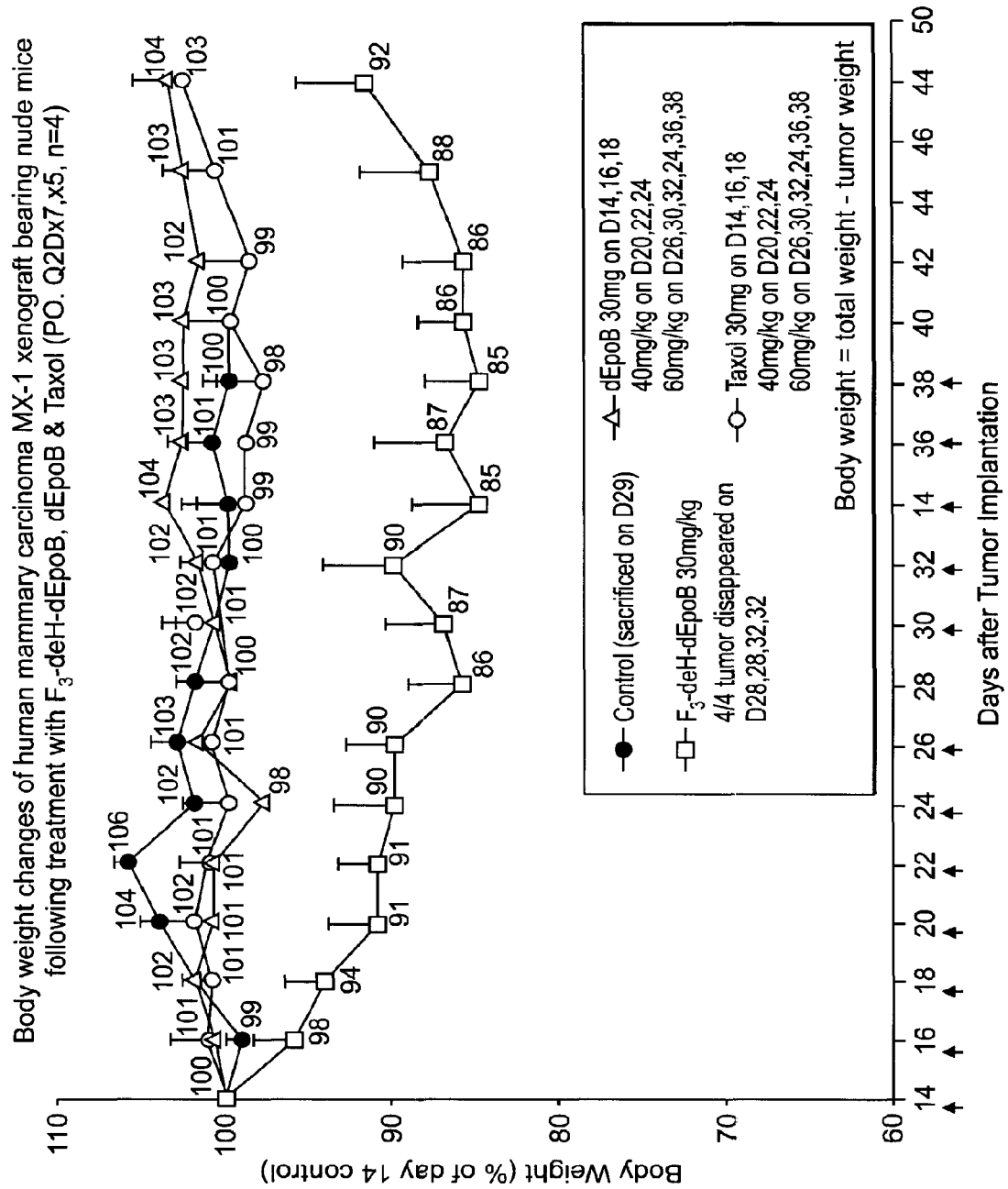
FIG. 90B shows changes in body weight.
Figure 92A:
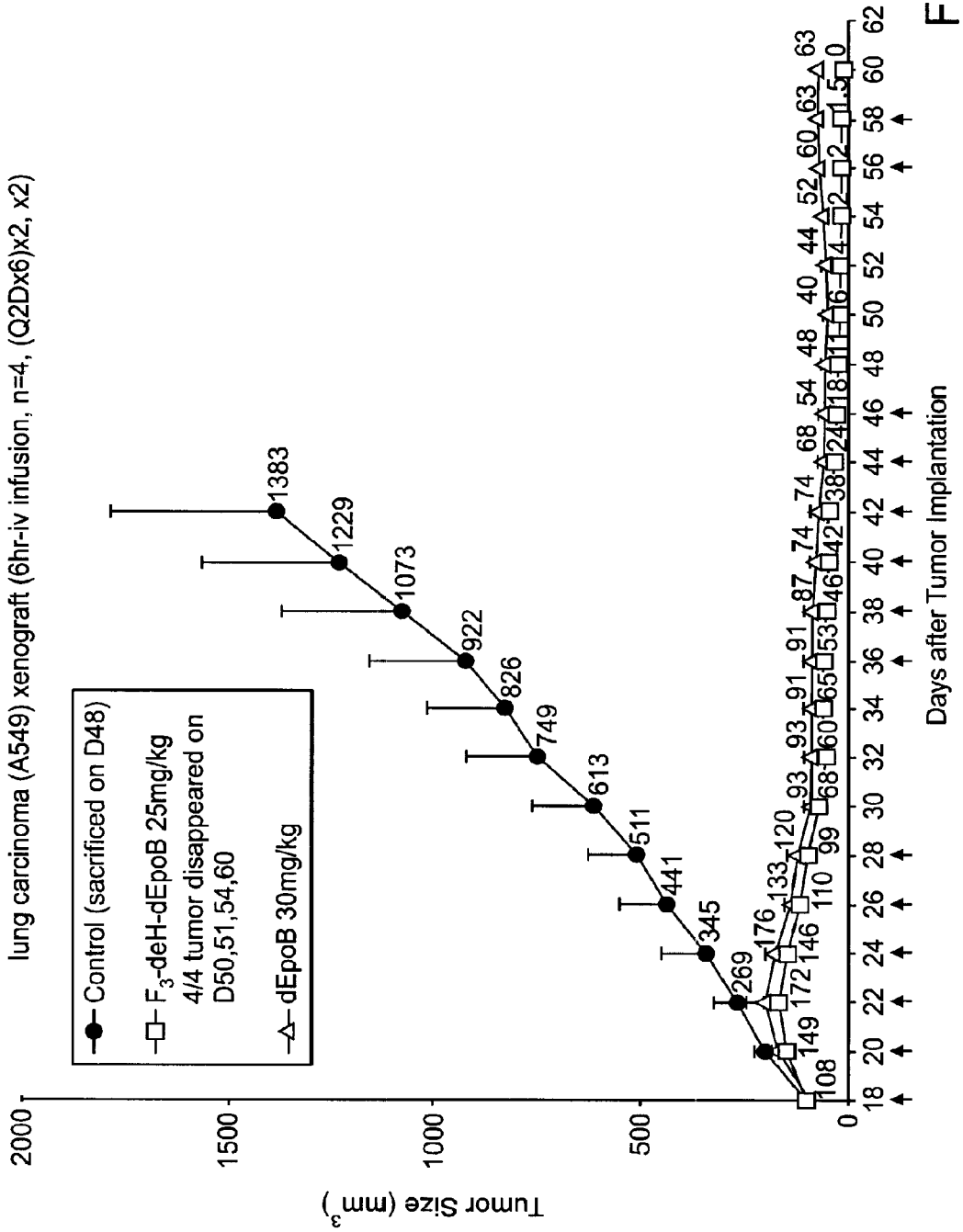
FIG. 92A shows the therapeutic effect as demonstrated by reduction in tumor volume.
Figure 92B:
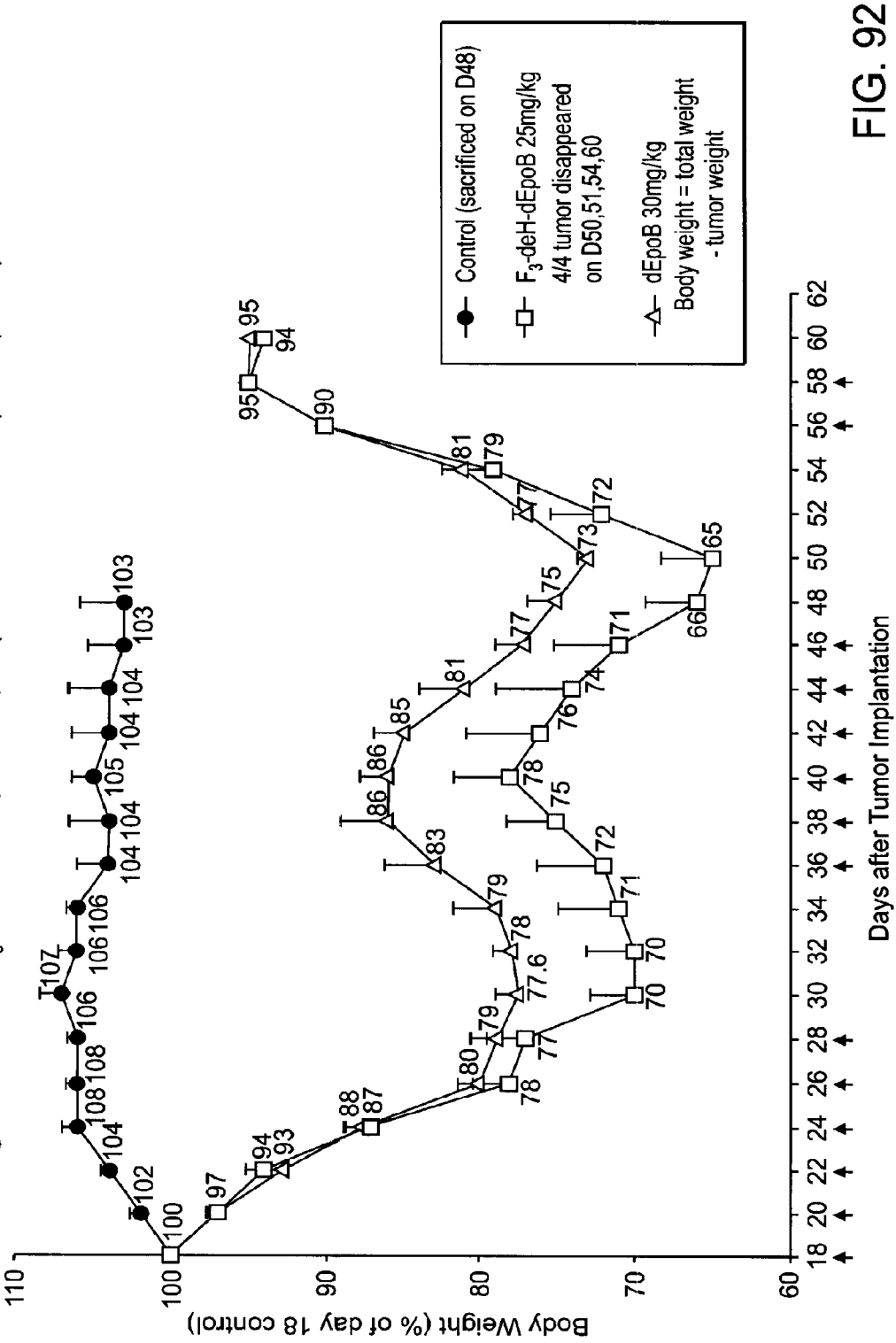
FIG. 92B shows changes in body weight during and after treatment.
Figure 93:
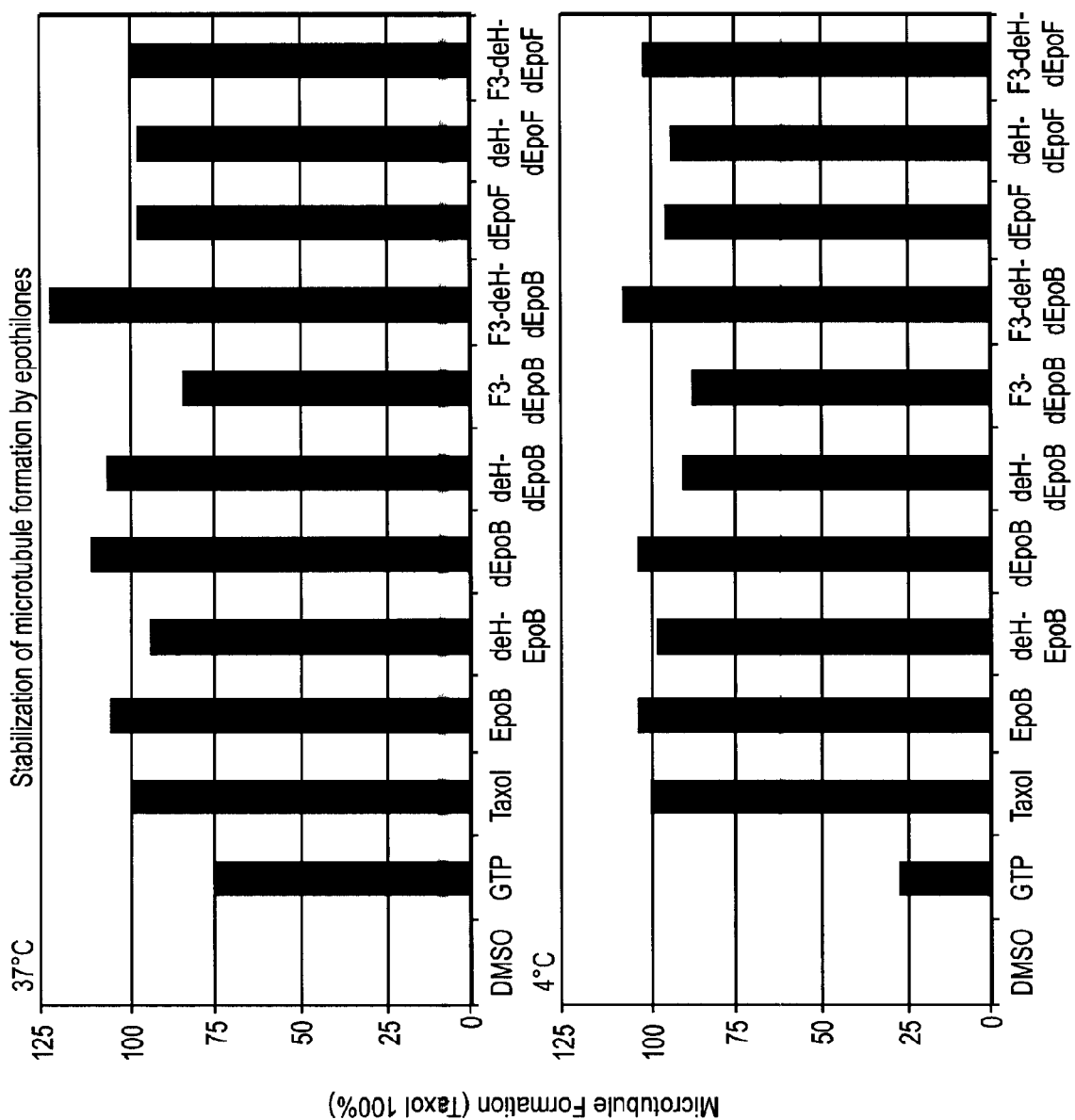
FIG. 93 shows stabilization of microtubule formation at 10 μM drug. Microtubules formed in the presence of 10 μM taxol was defined as 100%. Tubulin from bovine brain was a product of Sigma. The tubulin assembly assay was carried out according to the manufacturer's specifications. Tubulin (1 mg in 200 μl) was incubated with 790μ of buffer (0.1 M MES, 1 mM EGTA, 0.5 mM $MgCl_2$, 0.1 mM EDTA, and 2.5 M glyercol, pH 6.5) and with 10 μl of drug (final concentration 10 μM). For assembly, the incubation was carried out at 35° C. for 40 minutes, and for disassembly of the same samples, the incubation was carried out at 4° C. for 40 minutes. Aborbance at 350 nm was measured for the microtubule stabilization. Solvent blank (DMSO) was subtracted from the absorbance.

Curative Cancer Therapy of MX-1 Xenografts by Fludelone via Oral Administration. As shown in FIG. 90A, $F_3$-deH-dEpoB given orally at 30 mg/kg every two days for 7 times led to MX-1 tumor shrinkage and tumor disappearance in 2 out of 4 mice. Additional two doses (after skipping on dose) led to tumor disappearance in 4 out of 4 mice. By contrast, oral treatment of Taxol at the same dose and the same schedule of suppressed MX-1 tumor growth but did not lead to tumor shrinkage. Two days after the last dose of Taxol (D36), it induced tumor suppression of 66.9%. $F_3$-deH-dEpoB treatment induced moderate yet persistent decreases in body weight with maximal drop of 15% of the body weight (FIG. 90B). Taxol treatment induced little changes in body weight suggesting that oral administration of Taxol was not a suitable treatment apparently due to drug metabolic inactivation or poor bioavailability. In contrast to oral route of administration, our previous report (Chou, T.-C., O'Connor, O. A., Tong, W. P., Guan, Y., Zhang, X.-G., Stachel, S. J., Lee, C & Danishefsky, S. J. (2001) *Proc. Natl. Acad. Sci. USA* 98, 8113-8118; incorporated herein by reference), Taxol treatment of MX-1 tumor at 20 mg/kg via 6 hr i.v.-infusion could lead to tumor shrinkage and tumor disappearance.

Figure 84A:
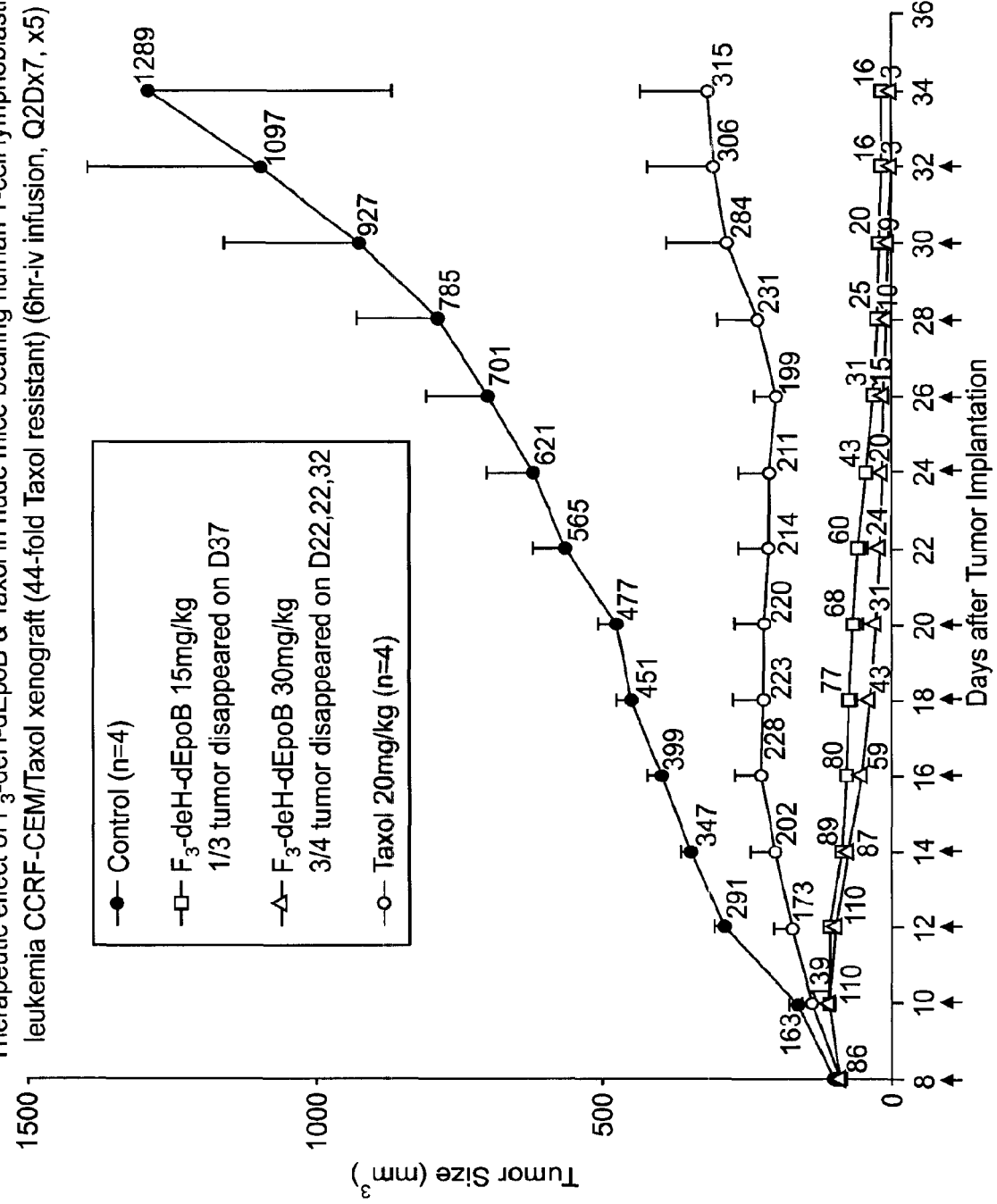
FIG. 84A shows the therapeutic effect as demonstrated by a reduction in tumor size.

Curative Therapeutic Effect of Fludelone against Taxol-Resistant CCRF-CEM/Taxol Xenografts. In our recent report (Chou, T.-C., Dong, H., Rivkin, A., Yoshimura, F., Gabarda, A. E., Cho, Y. S., Tong, W. P. & Danishefsky, S. J. (2003) *Angew Chem. Int. Ed. Engl.* 42, 4762-4767; incorporated herein by reference), we showed that $F_3$-deH-dEpoB at 20 mg/kg, Q2Dx7, 6 hr-i.v. infusion against Taxol-resistant human lung carcinoma A549/Taxol (44-fold resistance to paclitaxel in vitro) yielded complete tumor growth suppression but failed to achieve tumor disappearance. We now use another paclitaxel-resistant xenograft, CCRF-CEM/Taxol (44-fold resistance to paclitaxel in vitro). As shown in FIG. 84, Fludelone at 30 mg/kg Q2Dx7, 6 hr-i.v. infusion led to tumor disappearance in 2 out of 4 mice. Additional Q2Dx5 (after skipping one dose) lead to tumor disappearance in 3 out of 4 mice, with the final tumor suppression of 99.8% (FIG. 84A). At the reduced dose of 15 mg/kg, tumor disappearance occurred in only 1 out of 4 mice on the $5^{th}$ day after the two cycle treatment. The final tumor suppression on D34 was 98.8%. The parallel experiment with Taxol at 20 mg/kg yielded tumor growth suppression but with little or no tumor shrinkage. The final tumor suppression on D34 was 75.6%.

Figure 84B:
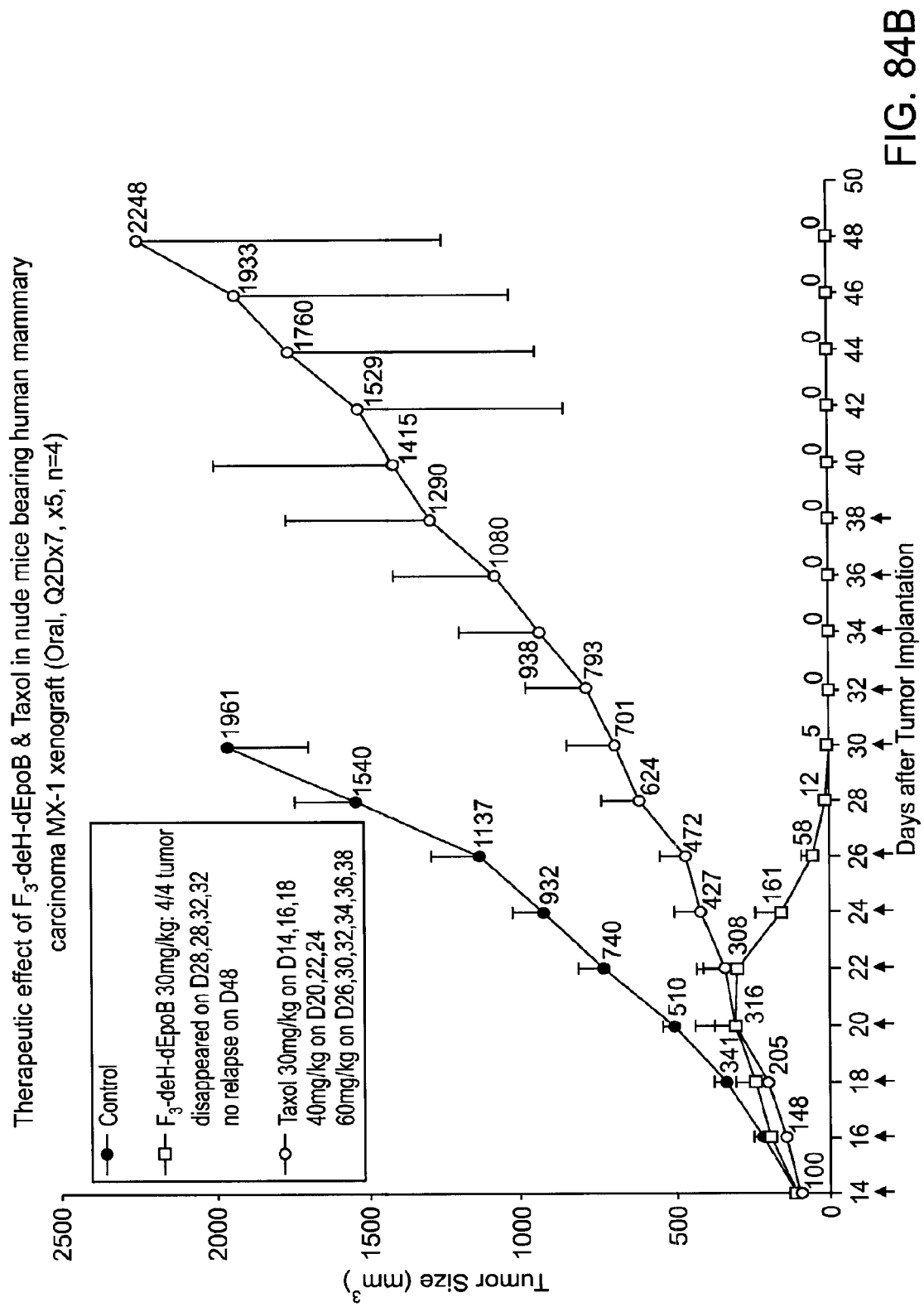
FIG. 84B shows changes in body weight during and after treatment.
Figure 85A:
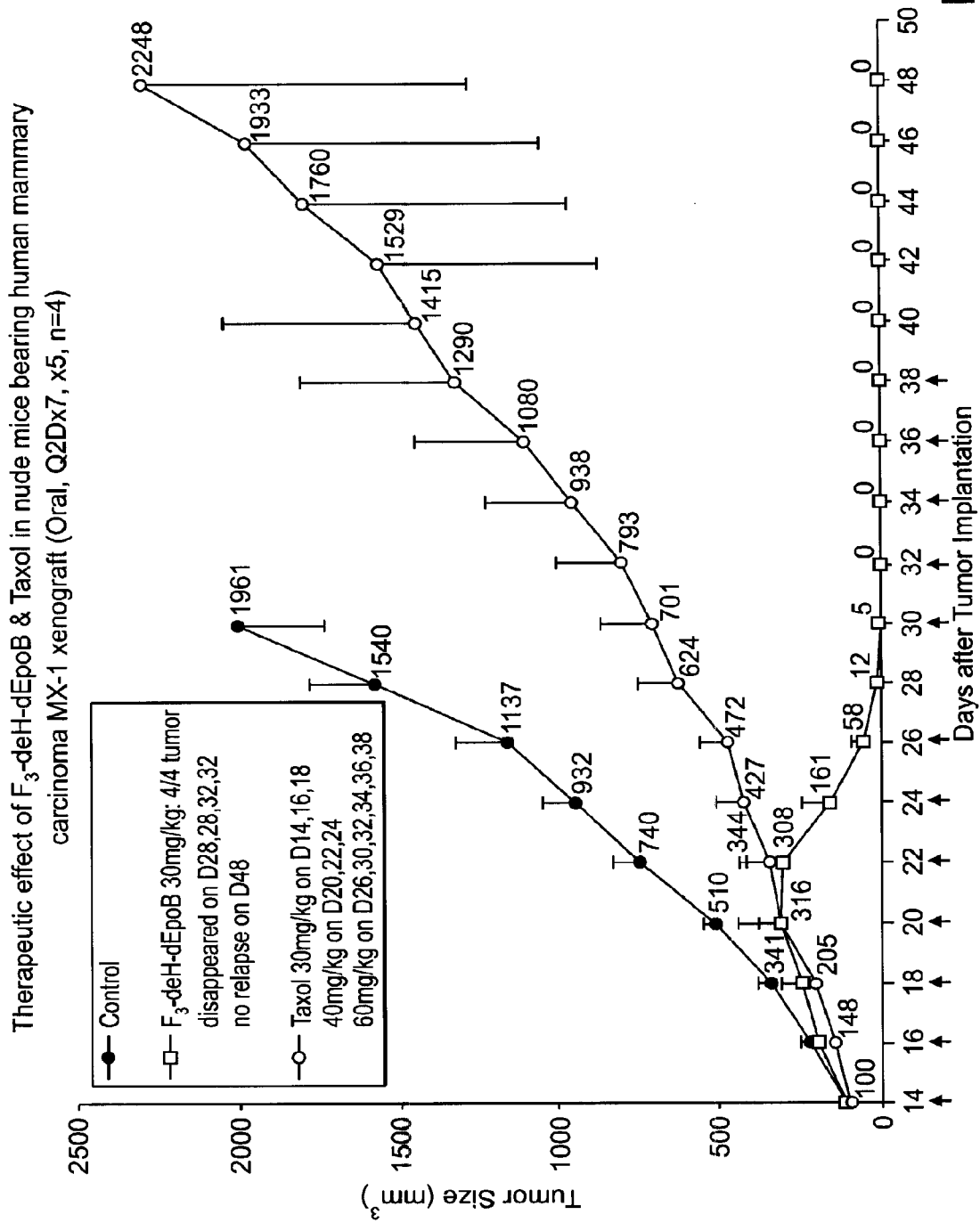
FIG. 85A shows the therapeutic effect as demonstrated by a reduction in tumor size.
Figure 85B:
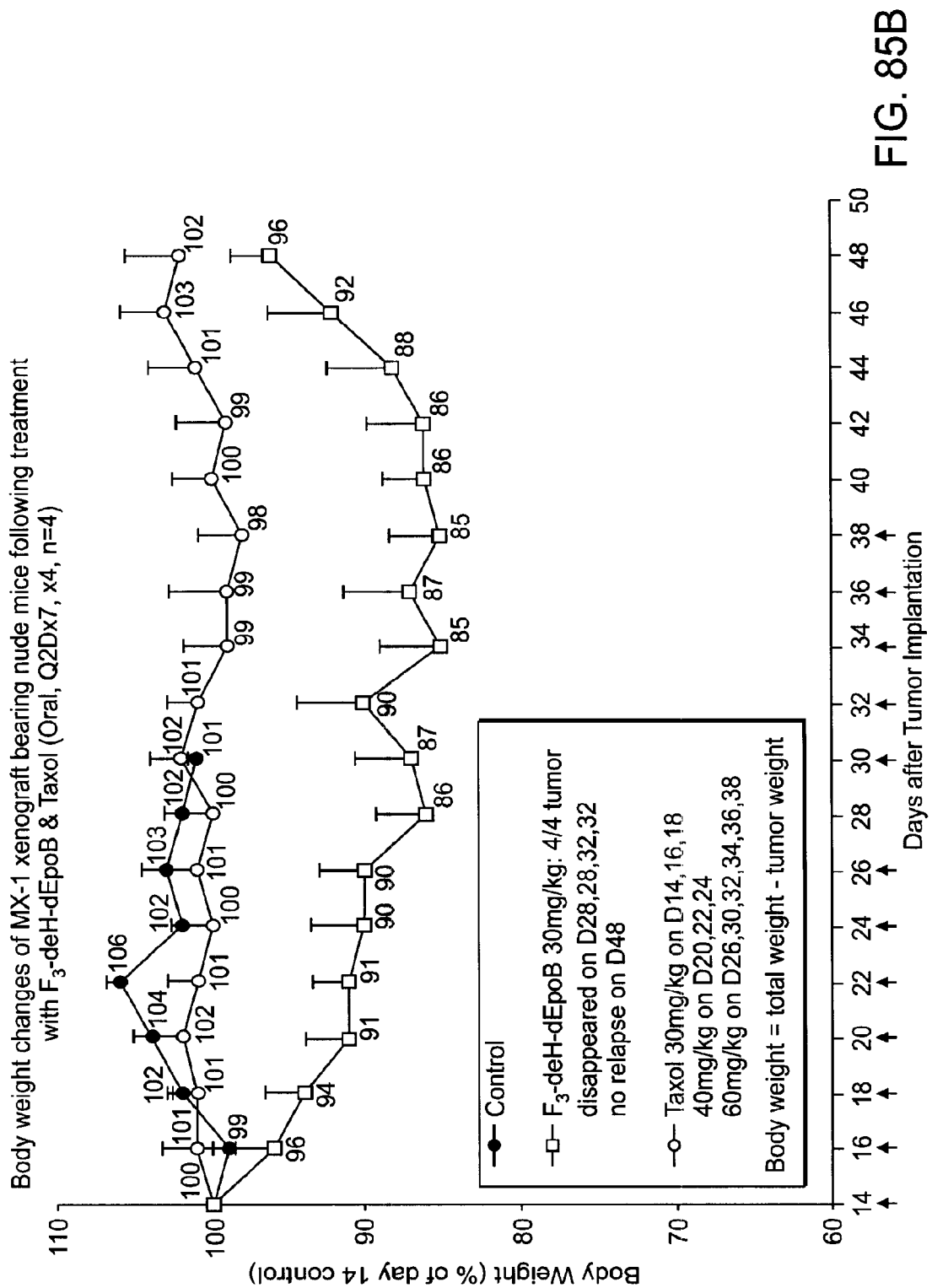
FIG. 85B shows changes in body weight.

Both $F_3$-deH-dEpoB (at 15 mg/kg and 30 mg/kg) and Taxol (20 mg/kg) persistently reduced the body weight during the first cycle of 7 treatments via 6 hr-i.v. infusion every other day. Skipping one treatment on D22 led to immediate gaining of body weight in all mice. The second cycle of treatment of Q2Dx5 again persistently reduced the body weight but without lethality to all mice tested (FIG. 84B).

Figure 86A:
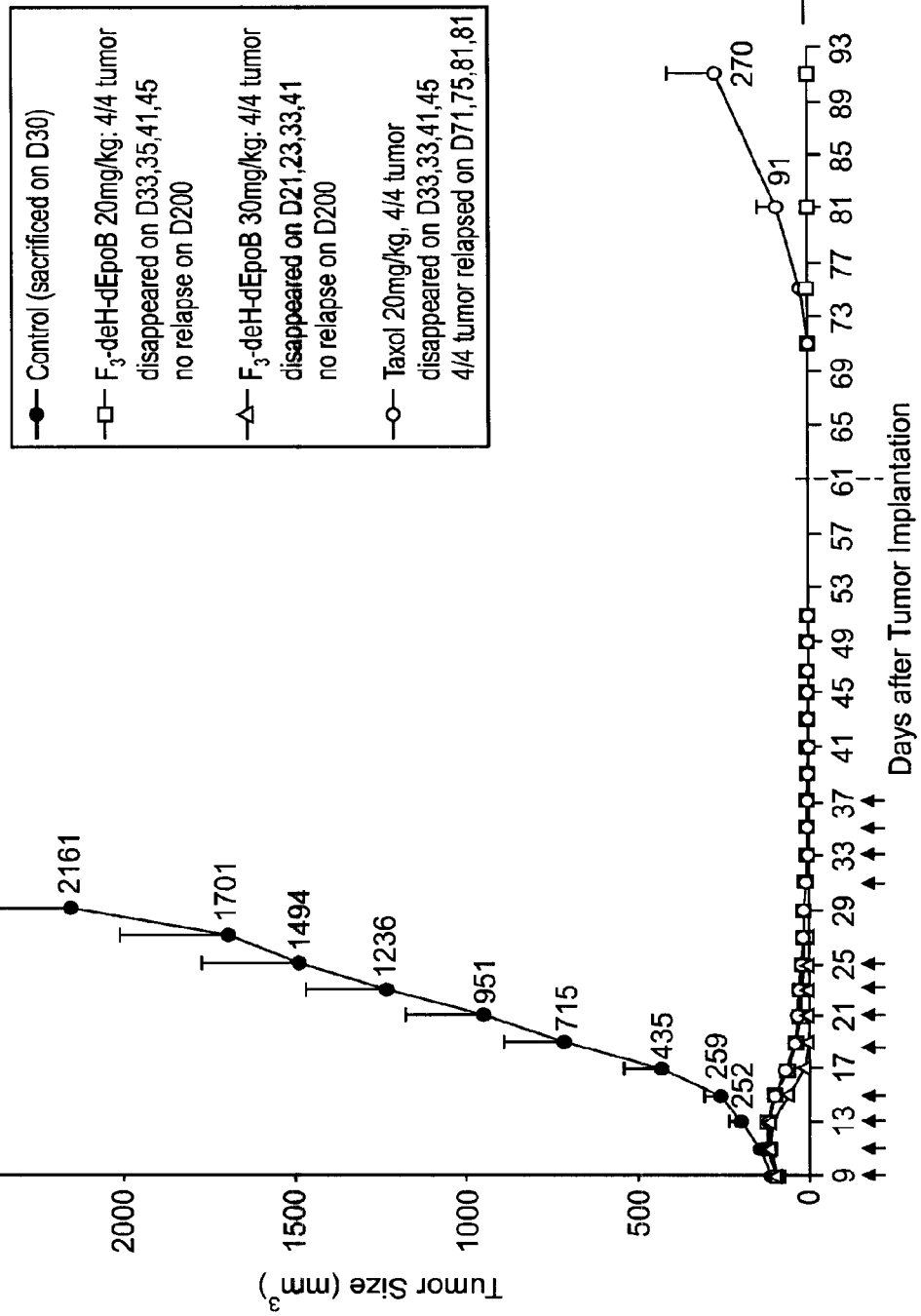
FIG. 86A shows the therapeutic effect as demonstrated by a reduction in tumor size.

Curative Therapy against Human Colon Carcinoma HCT-116 Xenografts by Fludelone. As shown in FIG. 86A, $F_3$-deH-dEpoB at 20 mg/kg and 30 mg/kg or Taxol at 20 mg/kg, Q2Dx4, 6 hr-i.v. infusion for 3 cycles all led to tumor disappearance in 4 out of 4 mice. The treatment started on D9 after tumor implantation. There was a one-dose-skip on D17 between the $1^{st}$ and $2^{nd}$ cycles and there was a two-dose-skip on D27 and D29 between the $2^{nd}$ and $3^{rd}$ cycles. D9-D37 was the 3-cycle therapy period and D37-D200 was the follow-up period. The experiment lasted 200 days which represent more than a quarter of the average life-span of the mice.

For $F_3$-deH-dEpoB at 30 mg/kg, tumor disappeared on D21, 23, 33 and 41 and at 20 mg/kg, tumor disappeared on D31, 35, 41, and 45. For both $F_3$-deH-dEpoB doses, there was no tumor relapse in 4 out of 4 mice on D200 when experiment was terminated. For Taxol at 20 mg/kg, tumor disappeared on D33, 33, 41 and 45 which were similar to the observation with $F_3$-deH-dEpoB at 20 mg/kg. However, in the Taxol treated group, tumor relapse occurred on D71, 75, 81 and 81.

Figure 86B:
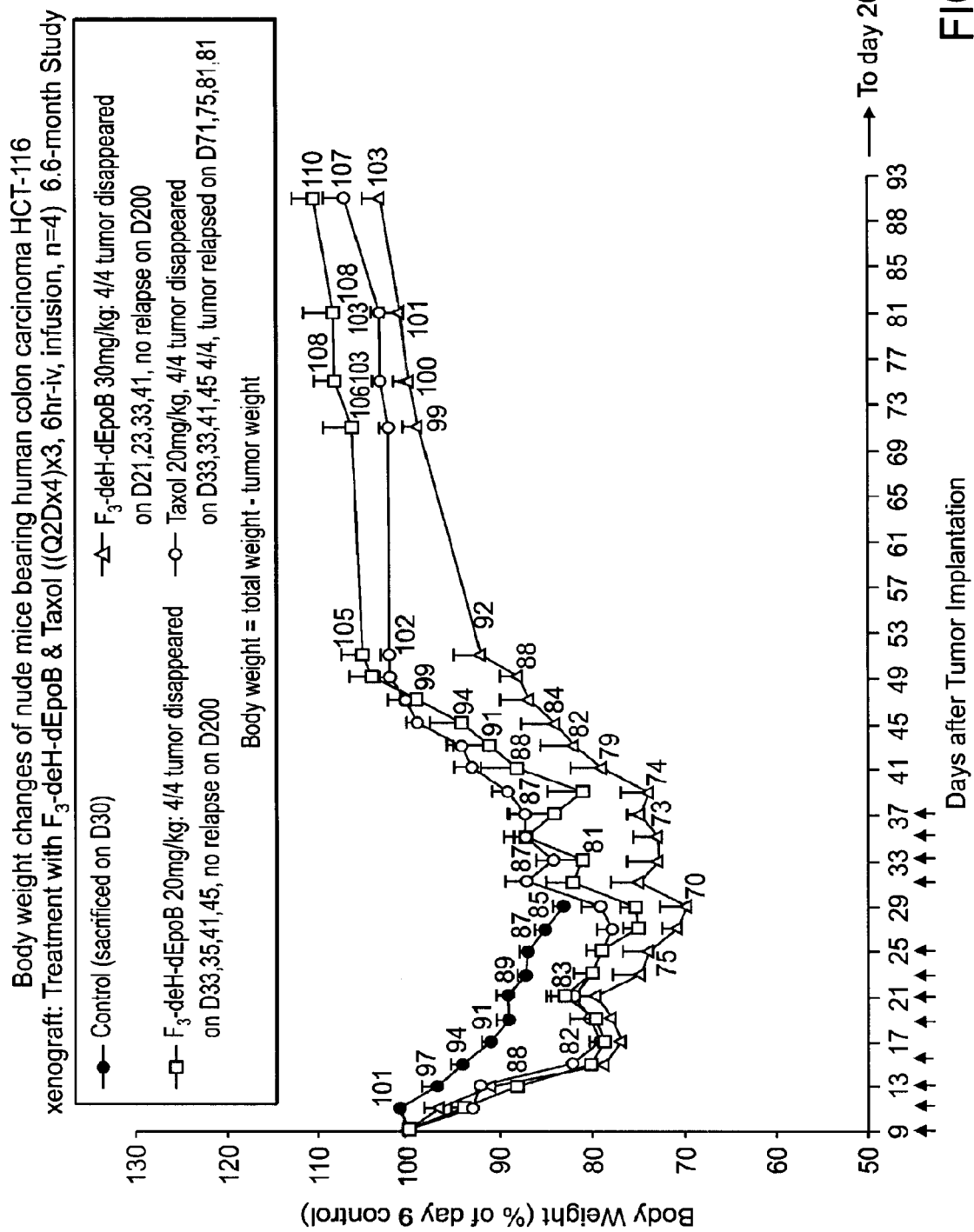
FIG. 86B shows changes in body weight.
Figure 87A:
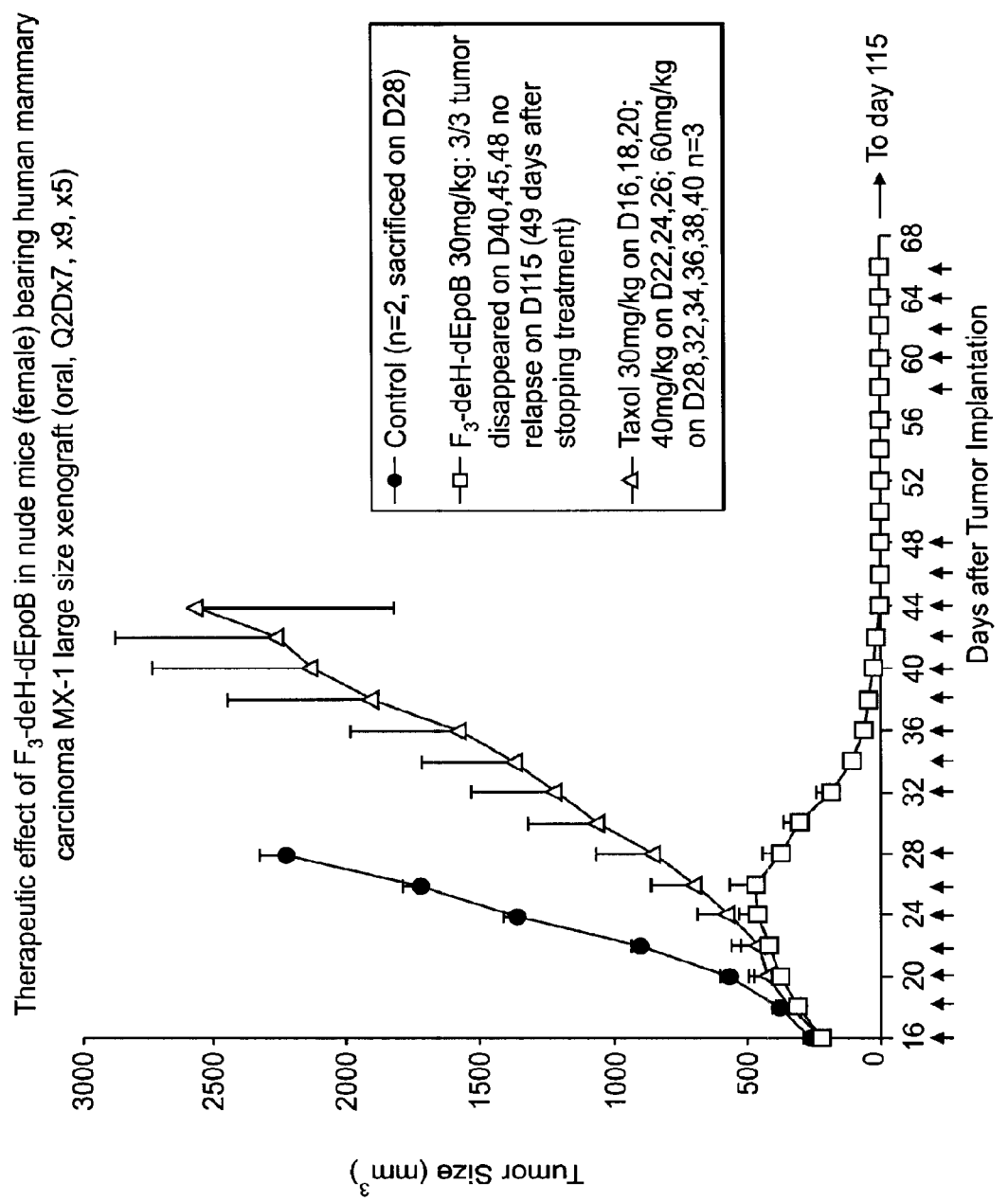
FIG. 87A shows the therapeutic effect as demonstrated by a reduction in tumor size.
Figure 87B:
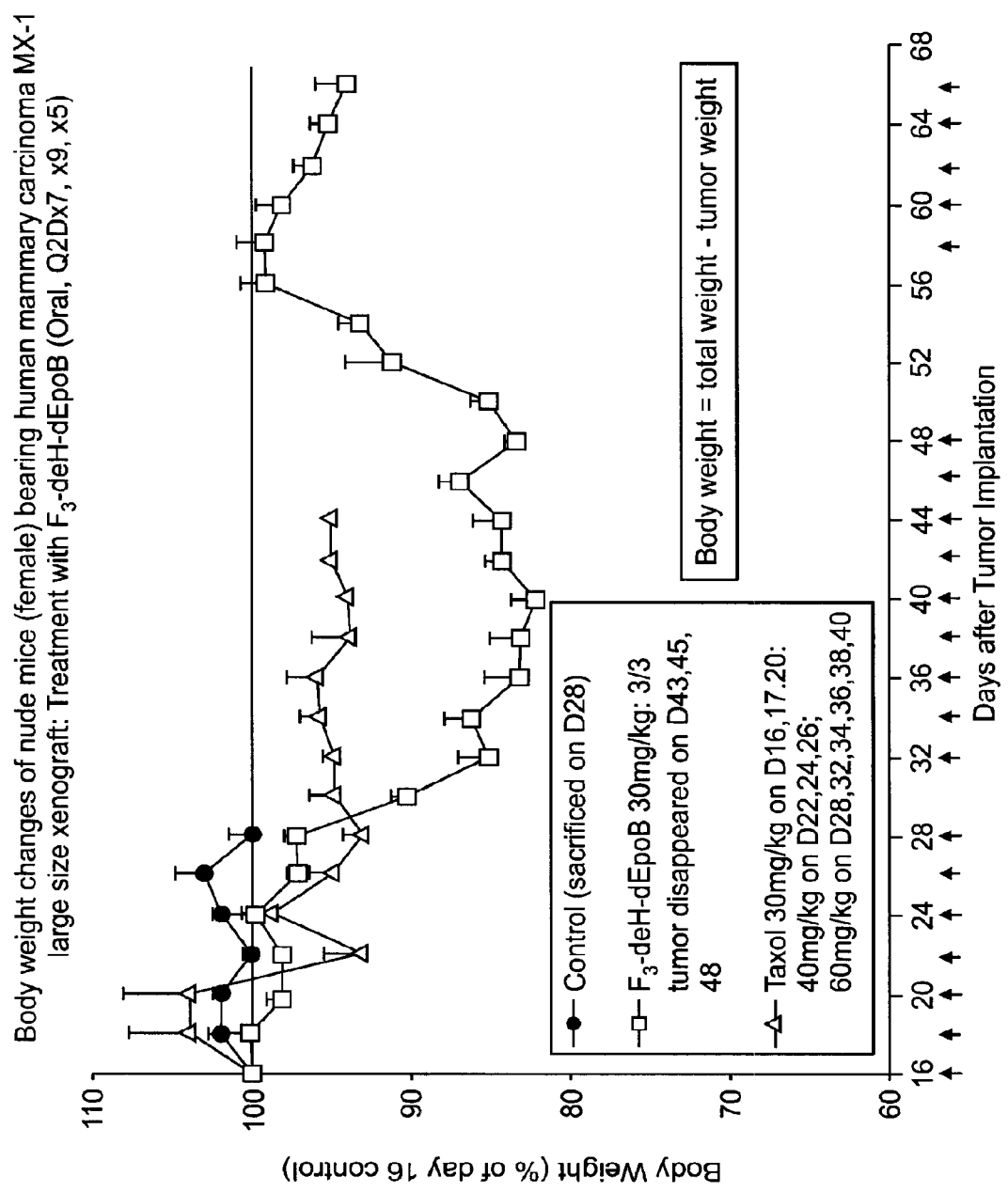
FIG. 87B shows changes in body weight.
Figure 88A:
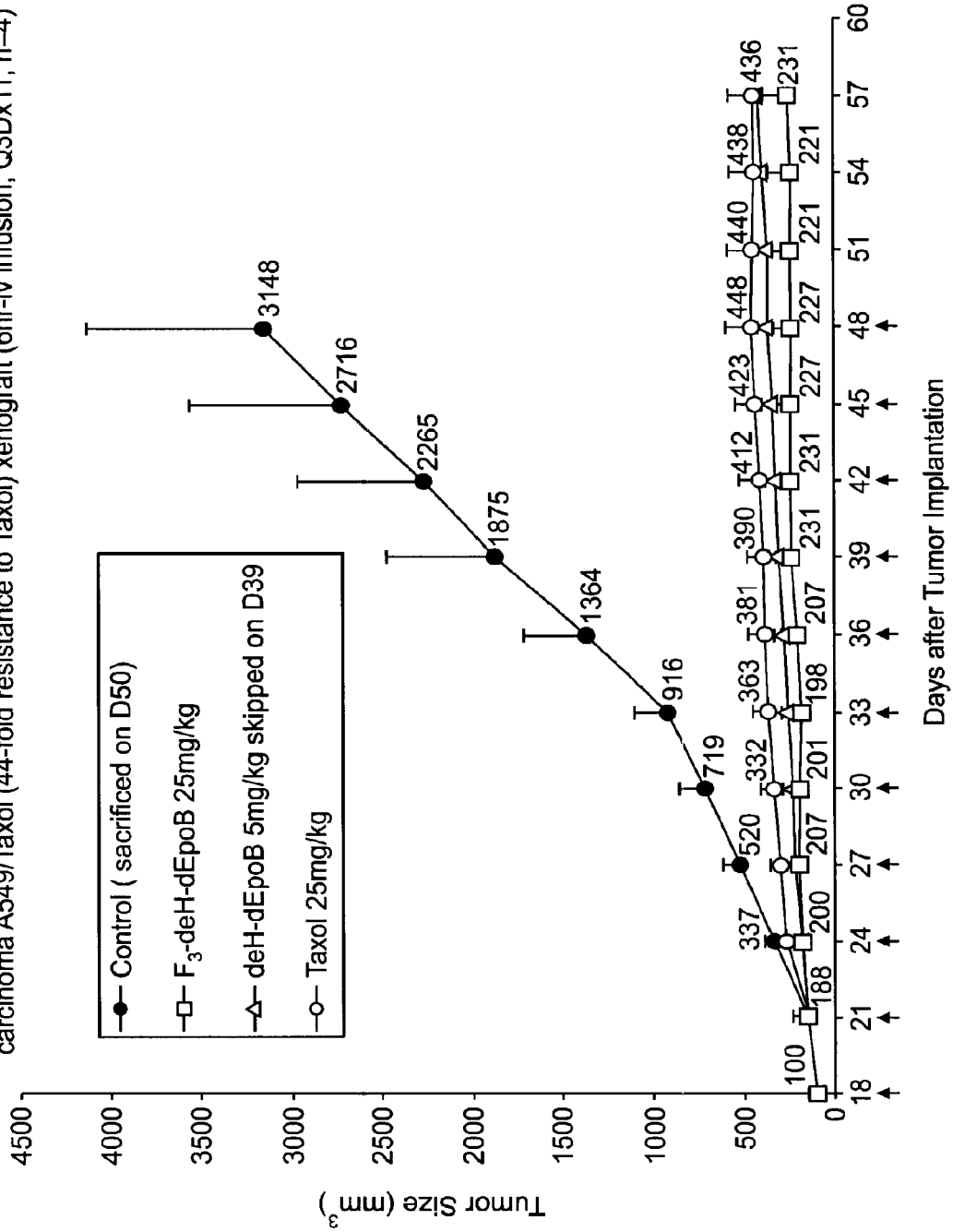
FIG. 88A shows the therapeutic effect as demonstrated by a reduction in tumor size.
Figure 88B:
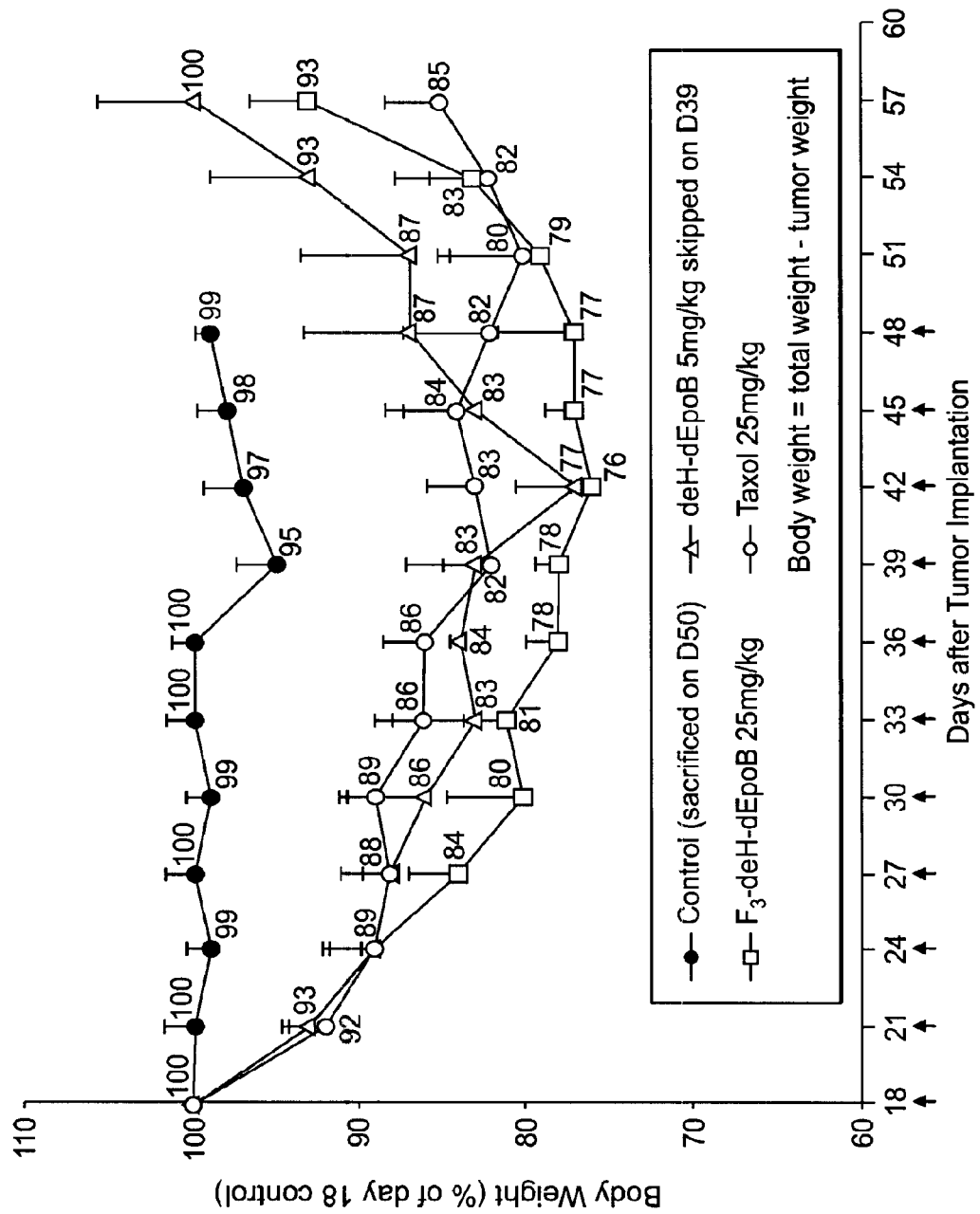
FIG. 88B shows changes in body weight.
Figure 89A:
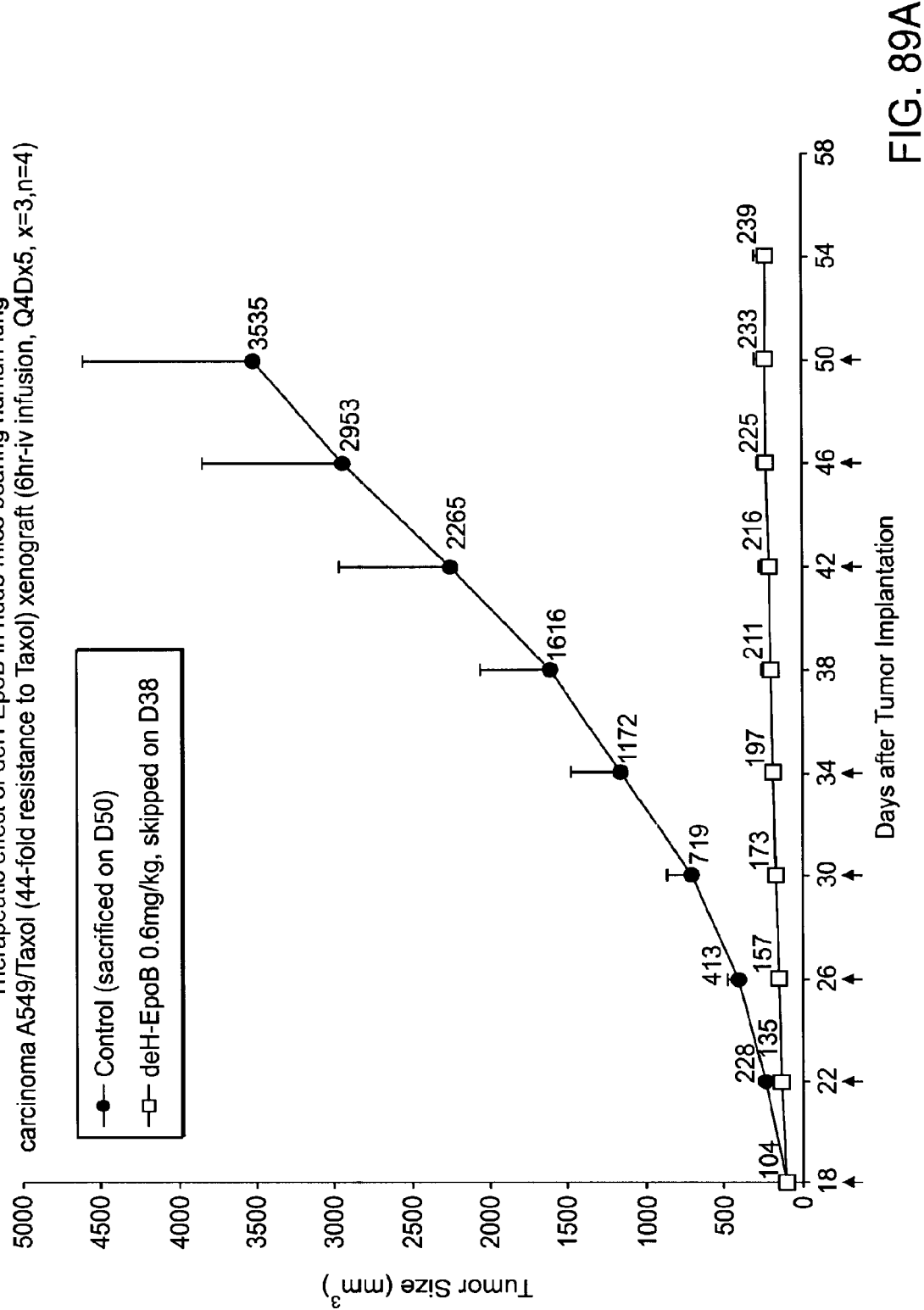
FIG. 89A shows the therapeutic effect as demonstrated by a reduction in tumor size.
Figure 89B:
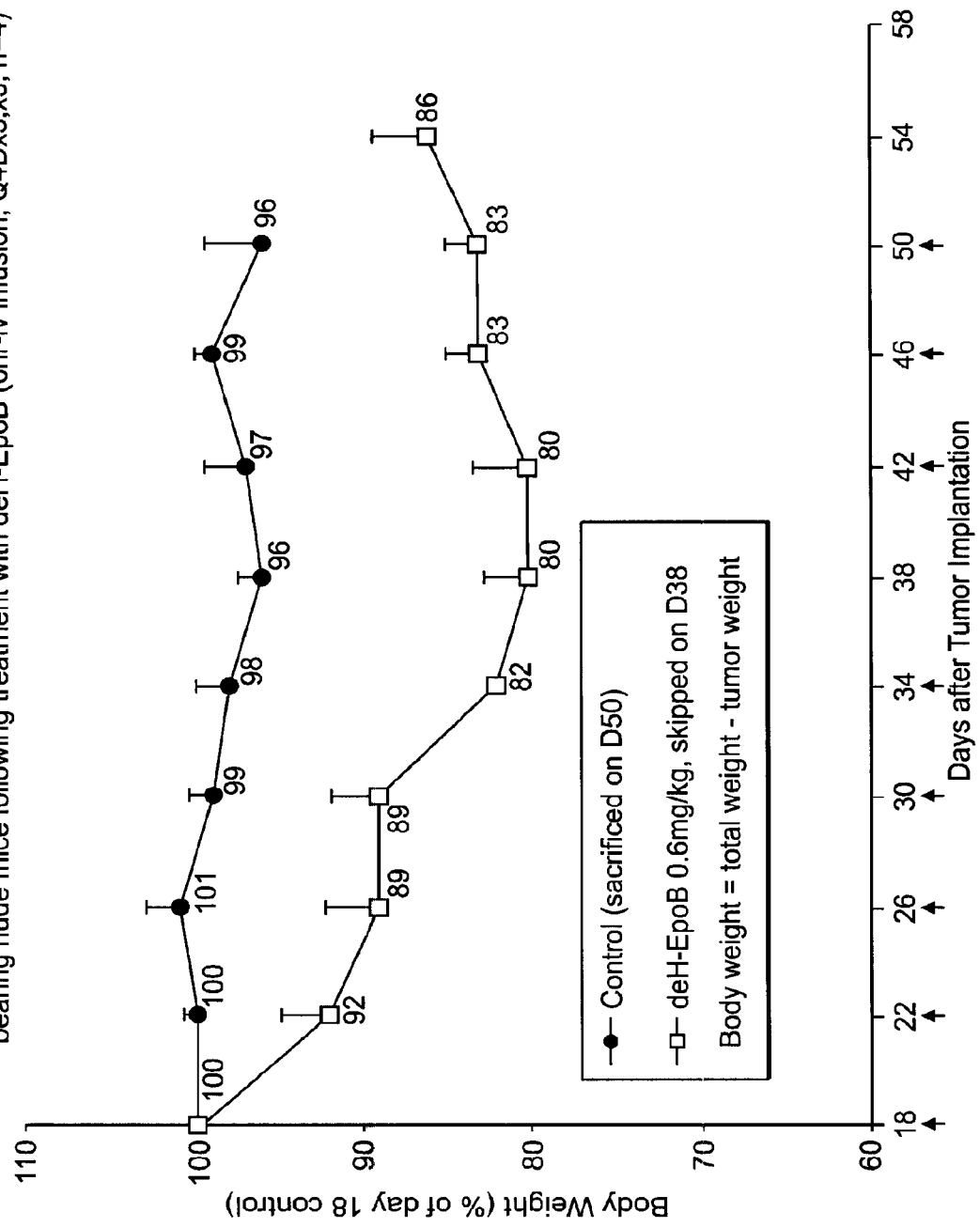
FIG. 89 shows the treatment of nude mice bearing human lung carcinoma A549/Taxol which is 44-fold resistant to Taxol using 9,10-dehyro-dEpoB. (6 hour iv infusion, Q4Dx5, x3).

The schedule of the treatment including the rest period is dictated by the body weight decreases and the physical conditions of the mice. For the $F_3$-deH-dEpoB treatment at 30 mg/kg dose, the maximal body weight loss was 30% but without lethality which occurred at the end of the $2^{nd}$ cycle of treatment (i.e., D29) (FIG. 86B). The body weight decreases and recovery for Taxol 20 mg/kg and $F_3$-deH-dEpoB 20 mg/kg were similar in both pattern and magnitude.

Example 15

Determination of the Mechanism of Action of Fluedelone ($F_3$-deH-dEpoB) and how it Differs from that of EpoD; Therapeutic Implications of these Differences Drug Sensitivity in Human Multiple Myeloma (MM) and Non-Hodgkins Lymphoma (NHL) Tumor Cell Lines MM accounts for 1% of all cancers and 10% of hematological malignancies, with 15,500 new cases diagnosed and >15,000 deaths in 2002. Treatment of MM with conventional chemotherapy is not curative, with a median survival of about 3 years (Barlogie B, Shaughnessy J, Tricot G, Jacobson J, Zangari M, Anaissie E, Walker R, Crowley J. "Treatment of multiple myeloma" *Blood* 2004; 103: 20-32; incorporated herein by reference). Although high-dose chemotherapy with hematopoietic stem cell support increases the rate of complete remission and event-free survival, almost every patient relapses, mandating the crucial need for salvage therapy options. Paclitaxel has been used to treat multiple myeloma and non-Hodgkin's lymphoma (Miller H J, Leong T, Khandekar J D, Greipp P R, Gertz M A, Kyle R A. "Paclitaxel as the initial treatment of multiple myeloma: an Eastern Cooperative Oncology Group Study (E1A93)" *Am. J. Clin. Oncol.* 1998; 21:553-556; Jazirehi A R, Bonavida B "Resveratrol modifies the expression of apoptotic regulatory proteins and sensitizes non-Hodgkin's lymphoma and multiple myeloma cell lines to paclitaxel-induced apoptosis" *Mol. Cancer Ther.* 2004; 3:71-84; each of which is incorporated herein by reference). However, the application was limited due to its high toxicity and multi-drug resistance. We have evaluated Fludelone and dEpoB against a panel of human MM and NHL lines that have been used in a number of recent studies in NOD/SCID xenograft models for evaluation of novel therapies, including 10-propargyl-10-deazaminopterin (PDX) (Wang E, O'Connor O, She Y, Zelenetz A, Sirotnak F M, Moore M A S "Activity of a novel anti-folate (PDX, 10-propargyl-10-deazaminopterin) against human lymphoma is superior to methotrexate and correlates with tumor RFC-1 gene expression" *Leukemia & Lymphoma* 2003, 44:1027-1035), anti-telomerase (Wang E S, Wu K, Chin A C, Gryaznov S, Moore M A S "Telomerase inhibition with an oligonucleotide telomerase template antagonist: in vitro and in vivo studies in multiple myeloma and lymphoma" *Blood* 2004; 103:258-66; incorporated herein by reference) and anti-VEGFR Mab (Wang E, Teruya-Feldstein j, Wu Y, Hicklin D J, Moore M A S "Targeting autocrine and paracrine VEGF receptor pathways regresses human lymphoma xenographs in vivo" *Blood*, in press; incorporated herein by reference). Both Fludelone and dEpoB can inhibit myleoma and lymphoma cell proliferation significantly. Myeloma cell lines are very sensitive to Fludelone and dEpoB with extremely low IC50s, while two NHL lines were inhibited at doses of Fudalone that were 5-10 fold higher than were effective in MM (Table 15-1).

TABLE 15-1

Cell growth inhibition and IC50 of Fludelone and dEpoB against a panel of normal human tumors and normal human cell populations as determined by the XTT tetrazonium assay.

| Tumor cell line | Histology | IC50 (nM) dEpoB | IC50 (nM) Fludelone |
|---|---|---|---|
| RPMI8226 | Myeloma | 36.67 ± 2.0 | 7.6 ± 1.2 |
| CAG | Myeloma | 61.34 ± 4.2 | 12.04 ± 1.8 |
| OPM-2 | Myeloma | 38.89 ± 3.3 | 8.2 ± 2.2 |
| H929 | Myeloma | 42.75 ± 4.5 | 9.2 ± 1.9 |
| MOLP-5 | Myeloma | 68.56 ± 5.5 | 14.4 ± 2.6 |
| RL | Lymphoma | 90 ± 11 | 80 ± 11 |
| SKI-DLBCL | Lymphoma | 72 ± 9.8 | 60 ± 4.2 |
| HS-27A | Marrow stroma | 100 ± 10 | 102 ± 8 |
| HS-5 | Marrow stroma | 100 ± 8 | 96 ± 7 |
| MRC-5 | Embryonic lung fibroblasts (human) | 8.2 ± 4.3 | 7.4 ± 2.7 |
| HT-29 | Colon Ca | 7.2 ± 2.2 | 4 ± 1.7 |
| HCT-116 | Colon Ca | 7.5 ± 3.1 | 3.6 ± 1.3 |
| MDA MB435 | Breast Ca | 7.8 ± 4.2 | 5.8 ± 2.8 |
| IGROV | Ovarian Ca | 15 ± 3.8 | 2 ± 1.2 |
| SKOV3 | Ovarian Ca | 13 ± 4.7 | 1.6 ± 0.5 |
| Ovcar-3 | Ovarian Ca | 14 ± 3.6 | 1.1 ± 0.4 |
| Ovcar-4 | Ovarian Ca | 16 ± 2.5 | 1.8 ± 0.7 |

Figure 96:
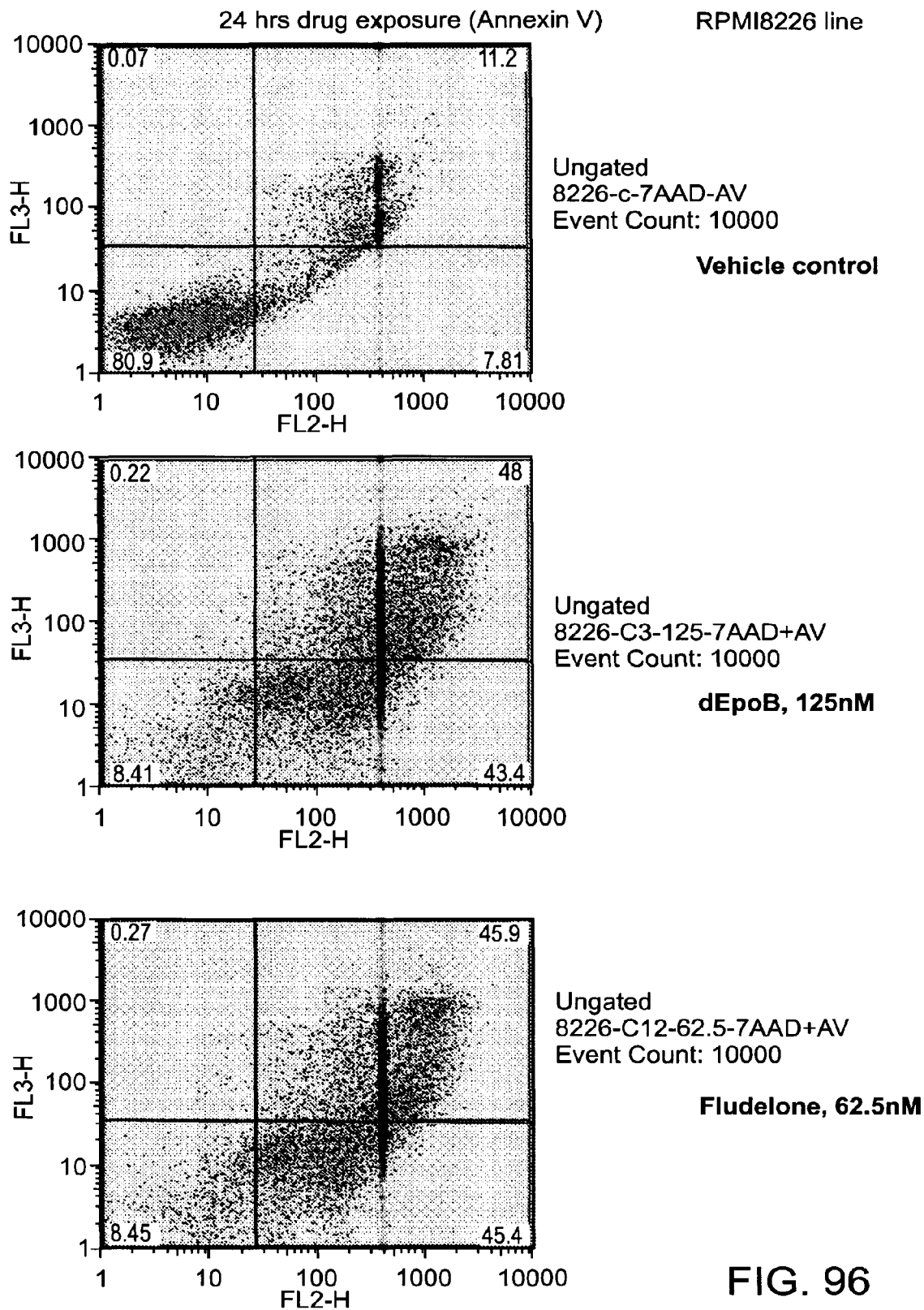
FIG. 96 shows Annexin V staining on the RPMI8226 myeloma cell line. In early apoptotic cells, the membrance phospholipids phosphatidylserine (PS) is translocated from the inner to the outer leaflet of the plasma membrane, thereby exposing PS to the external cellular environment. Annexin V is a 35-36 kD $Ca^{+2}$ dependent phospholipid-binding protein that has a high affinity for PS, and binds to cells with exposed PS. In conjunction with a vital dye such as 7-amino-actinomycin (7-AAD) staining dead cells, this assay allows the identification of early apoptotic cells. The data showed that the majority of cell either enter apoptosis or are dead after 24 hours treatment with dEpoB or Fludelone.

Normal bone marrow stromal cells (HS-27A and HS-5 lines) showed relative resistance to these compounds, indicating that Fludelone and dEpoB have a safe therapeutic window in MM. (Table 15-1). Fludelone has ~5 fold greater potency than dEpoB on MM cell lines while both drugs had a comparable toxicity to normal marrow stromal cells. Fetal human lung fibroblasts (MRC-5) were sensitive to dEpoB and Flu but a clear therapeutic window was evident with Flu even with these very sensitive normal cells. Fludelone and dEpoB cause myleoma and lymphoma cells to arrest at G2M phase (FIG. 95) and induced tumor cell apoptosis (FIGS. 96 and 97). We evaluated the duration of drug exposure in vitro necessary to cause apoptosis in the myeloma cells. Pulse exposure for 1, 2, 4, 8, and 24 hrs was followed by a washout of the drug and continued incubation for up to 48 hrs. Exposure of cells to either Fludelone or dEpoB for 24 hrs resulted in all cells being dead by 48 hrs. (FIG. 98). With dEpoB, incubation for 4-8 hrs. slowed cell expansion whereas the same duration of exposure to Fludelone decreased the number of cells from input by ~50%. A one hour exposure to dEpoB reduced but did not prevent tumor cell expansion over 48 hrs whereas with Flu, tumor numbers decreased by 50% (FIG. 98). Fludelone and dEpoB shared with paclitaxel the capacity to enhance microtubule bundle formation in tumor cells without appreciably changing the mass of microtubules in the cell shortly after exposure (FIG. 99). At a later time (~24 hrs) microtubules are disrupted and cell apoptosis occurs. In a comparison of Fludelone and dEpoB on primary CD138 MM cells obtained from patent marrow we showed that Fludalone but not dEpoB induced tumor apoptosis within 24 hrs.

Drug Sensitivity in Human Solid Tumor Cell Lines

Figure 100:
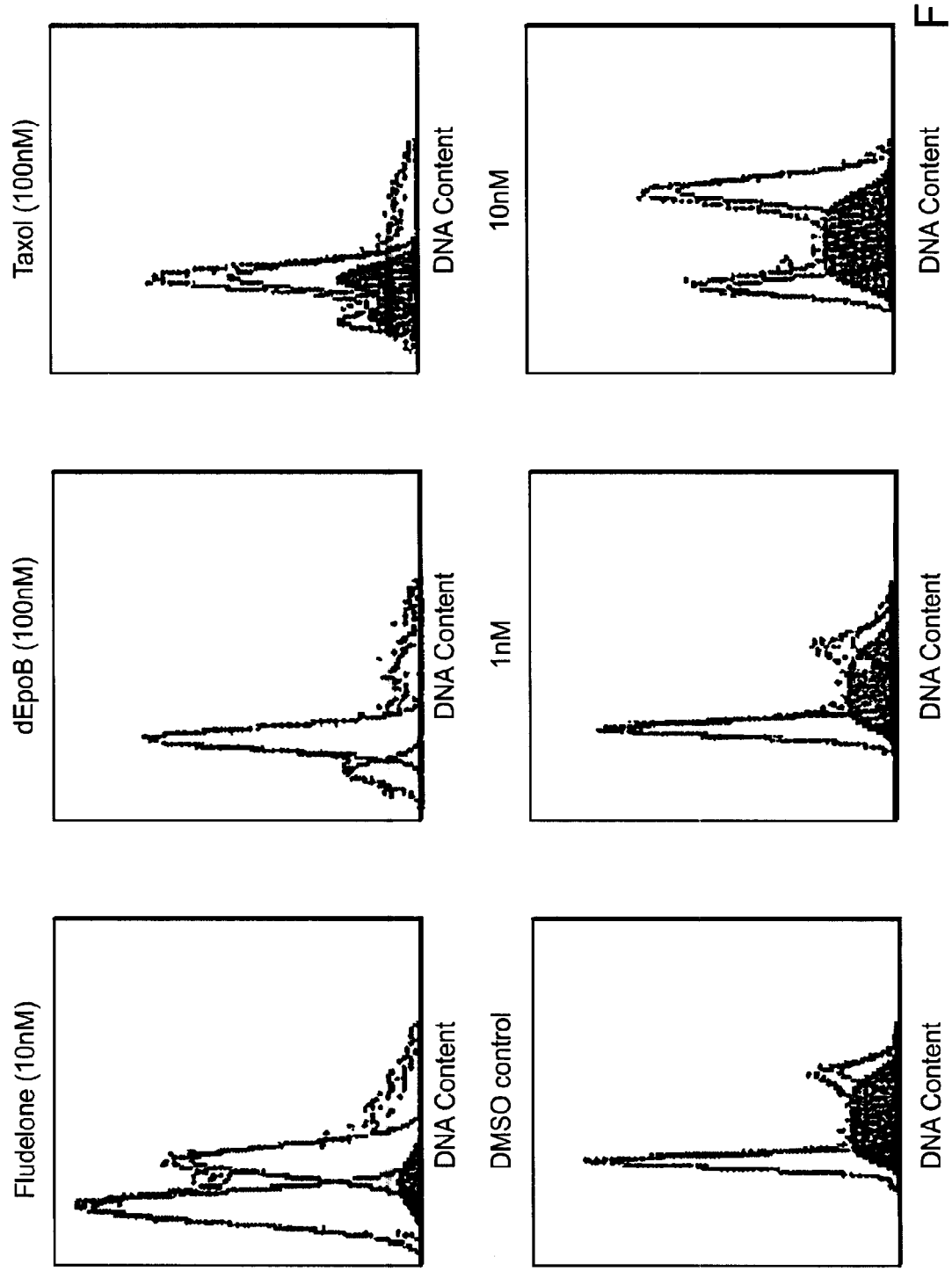
FIG. 100 is the cell cycle analysis determined by Propidium iodide DNA staining. Solid lines describe the values for G1 and G2, gray shaded area depict the cells in S phase, dotted line delineates the overall curve giving the number of doublets especially evident with Taxol (upper left image). Upper row demonstrates the G2M phase arrest after 24 hours of incubation with Fludelone (10 nM), dEpoB (100 nM), and Taxol (100 nM) of the ovarian cancer cell line IGROV. The lower row demonstrate the increase cell cycle arrest of HT-29 with increased concentrations of Fludelone. The 100 nM incubation with Fludelone resulted in massive apoptosis after 24 hours hampering cell cycle analysis in several cell lines including IGROV and HT-29.
Figure 101:
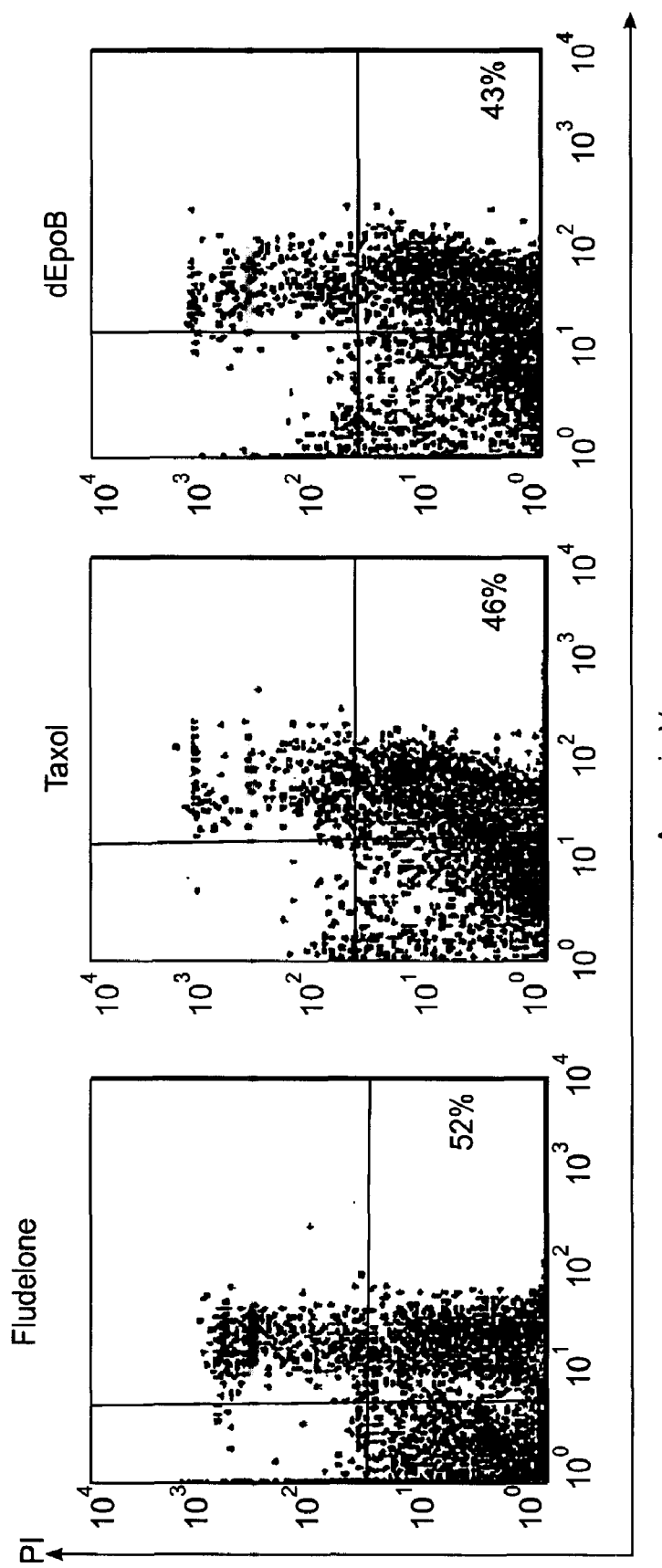
FIG. 101 shows Annexin V staining of the Ovcar3 ovarian cancer cell line after 24 hour incubation with 100 nM of Fludelone, Taxol, or dEpoB. Percentages given in the lower left quadrant is the percentage of Annexin V$^+$/Pl$^-$ negative cells, which resemble cells in the early apoptotic stage.
Figure 102:
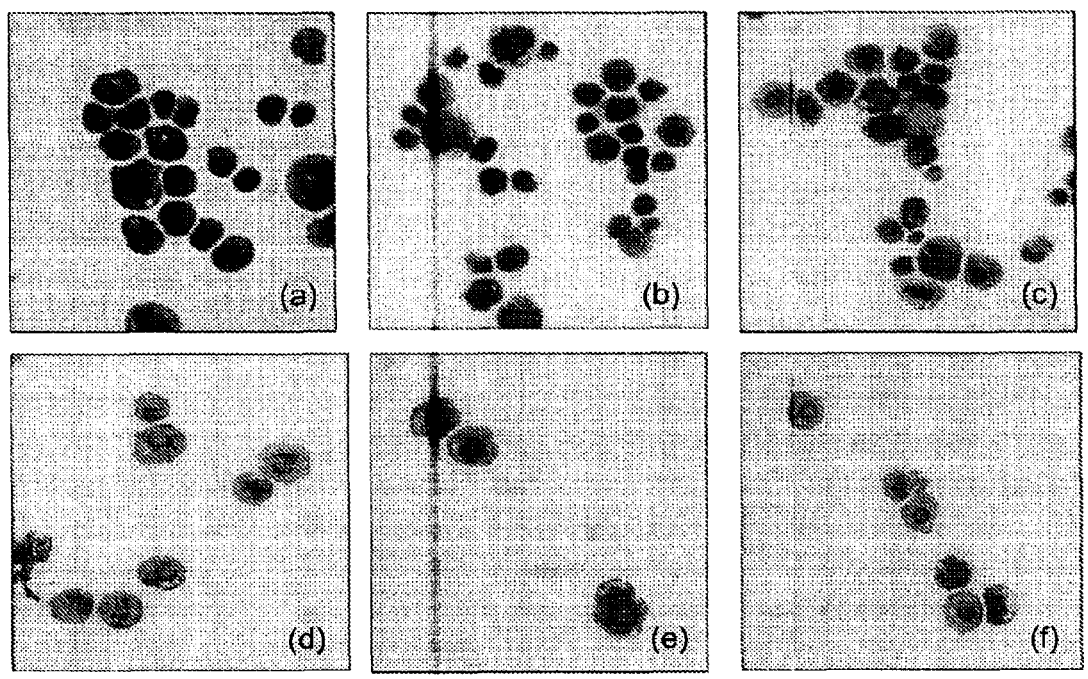
FIG. 102 is a cytospin of HT-29 colon cancer cells after 24 hours of treatment stained with HEMA 3 (200× magnification). (a) control cells treated with the dissolvent (DMSO). (b)-(d) Increased concentrations of Fludelone 1, 10, and 100 nM are shown. (e) HT-29 cells after the application of 100 nM dEpoB and (f) after 100 nM of Taxol. All three drugs produce the same phenotype after 24 hours apparent in a ring-like structure of the nucleus resulting in apoptosis.
Figure 103:
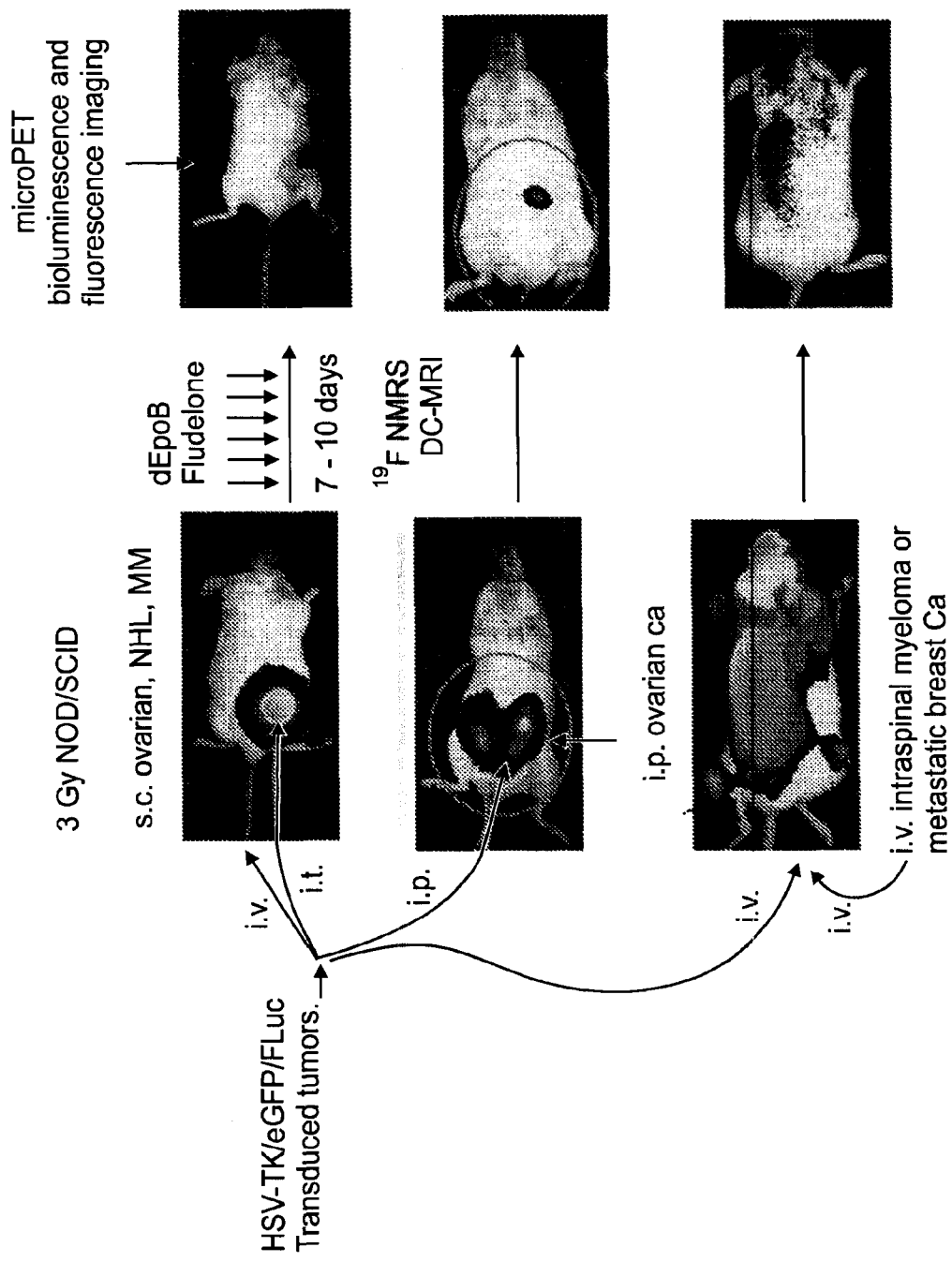
FIG. 103 shows the experimental design of a system for evaluating the action of Fludelone and dEpoB in disseminated and metastatic human tumor xenograft models.
Figure 104:
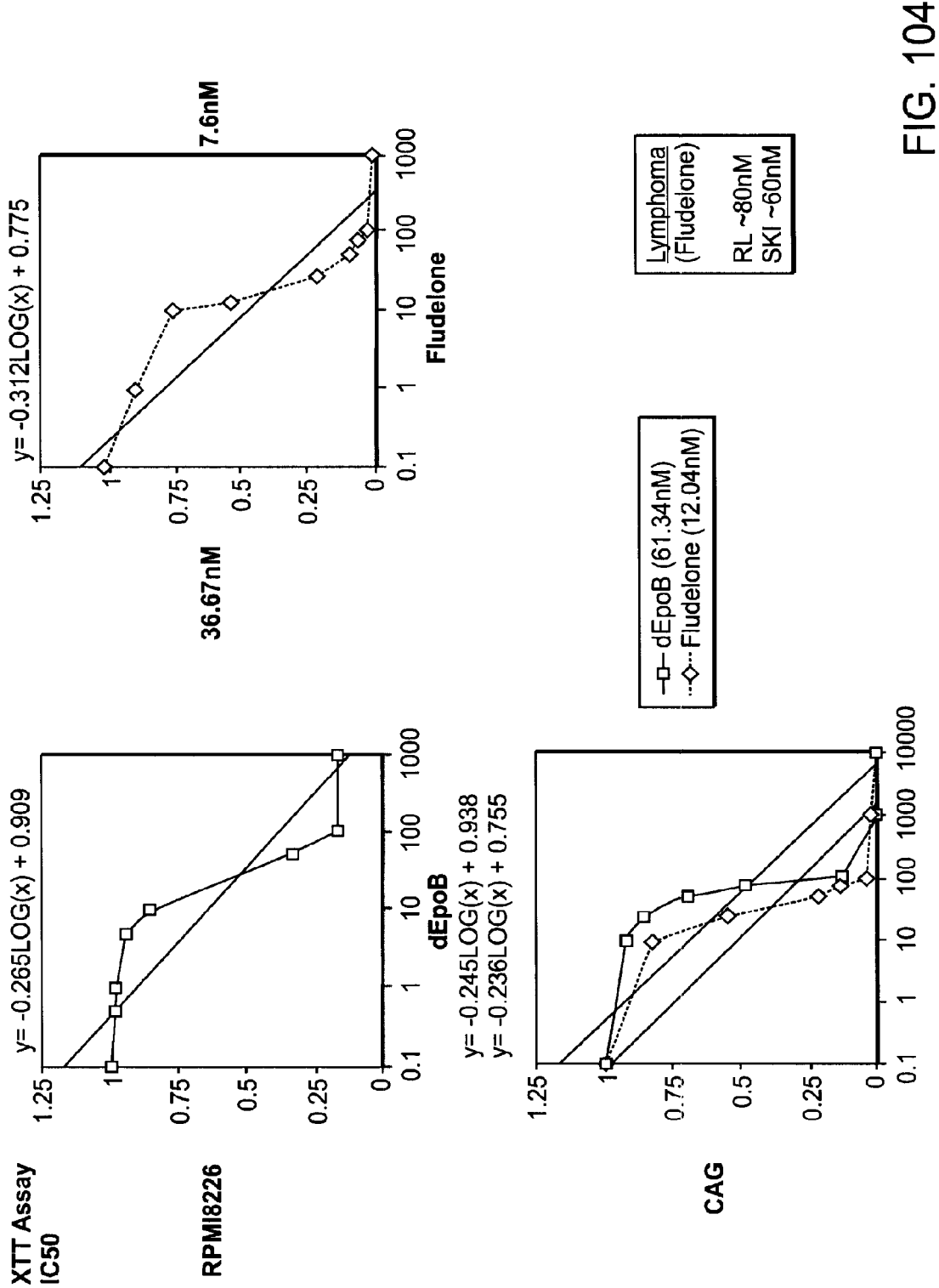
FIG. 104 shows cell proliferation and IC50 (the concentration for 50% cell inhibition) assays. Cell proliferation was determined using the sodium 3'-[1-(phenylamino-carbonyl)-3,4-tetrazolium]-bis(4-methoxy-6-nitro) benzene sulfonic acid hydrate (XTT), which measured the conversion of a tetrazolium compound into formazan by a mitochondrial dehydrogenase enzyme in live cells. The amount of formazan is proportional to the number of living cells present in the assay mixture. Each data point was the average of four independent determinations. The IC50 of Fludelone is about 7.6~36.67 nM and dEpoB 36.67~61.34 nM for myeloma cell lines (RPMI8226, CAG). The IC50 of Fludelone is about 60~80 nM for lymphoma lines (SKIDLBCL and RL).
Figure 105:
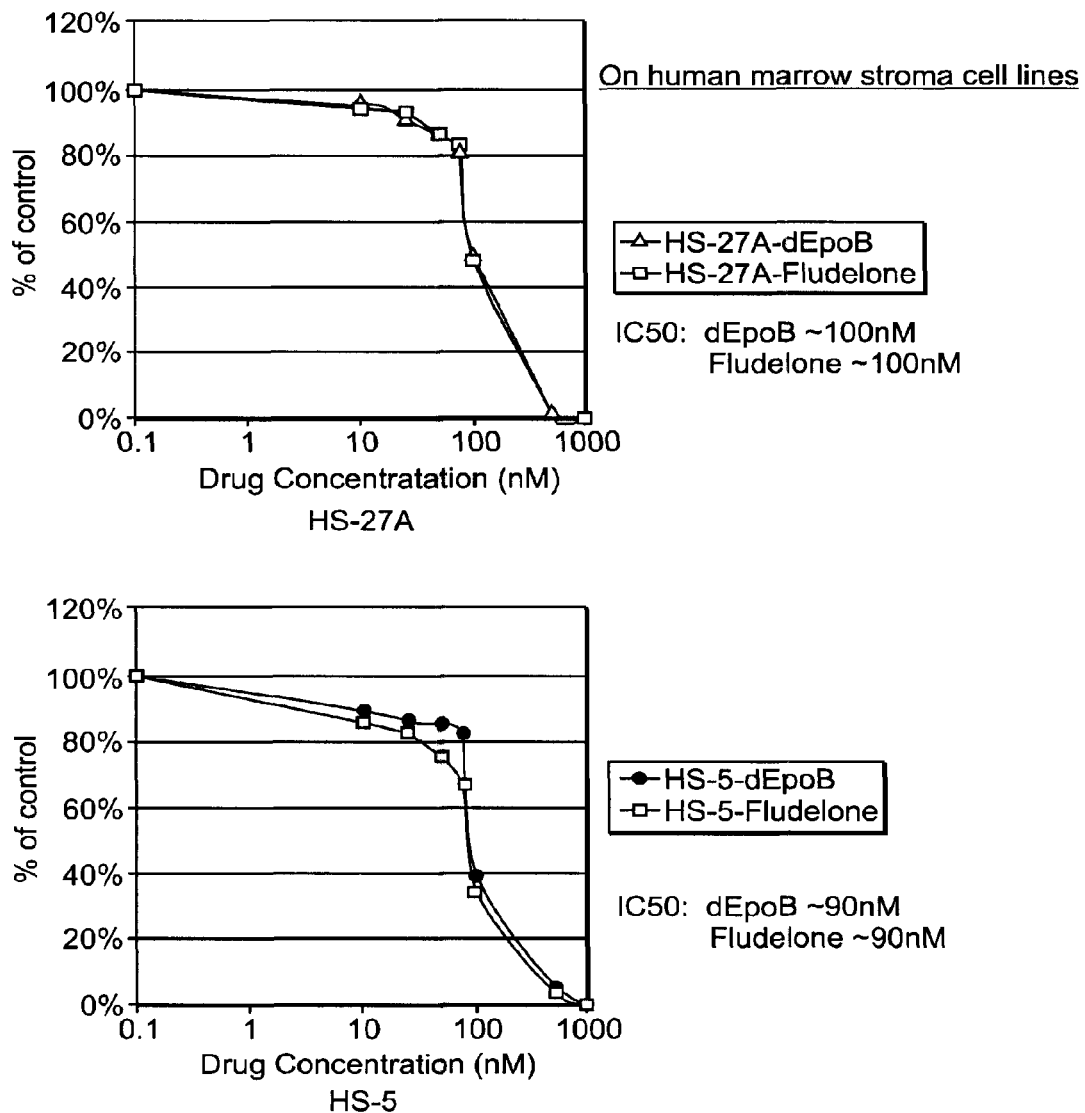
FIG. 105 shows cell proliferation and IC50 assays on normal stromal cells. The same method was used as described in FIG. 104. Human marrow stromal cell lines, HS-27A and HS-5 immortalized by E6/E7 genes, have normal marrow stromal function, which support stem cell self-renewal, and proliferation. The IC50 of Fludelone and dEpoB is about 90-100 nM for these stromal lines with a comparable population doubling time with tumor lines.
Figure 106:
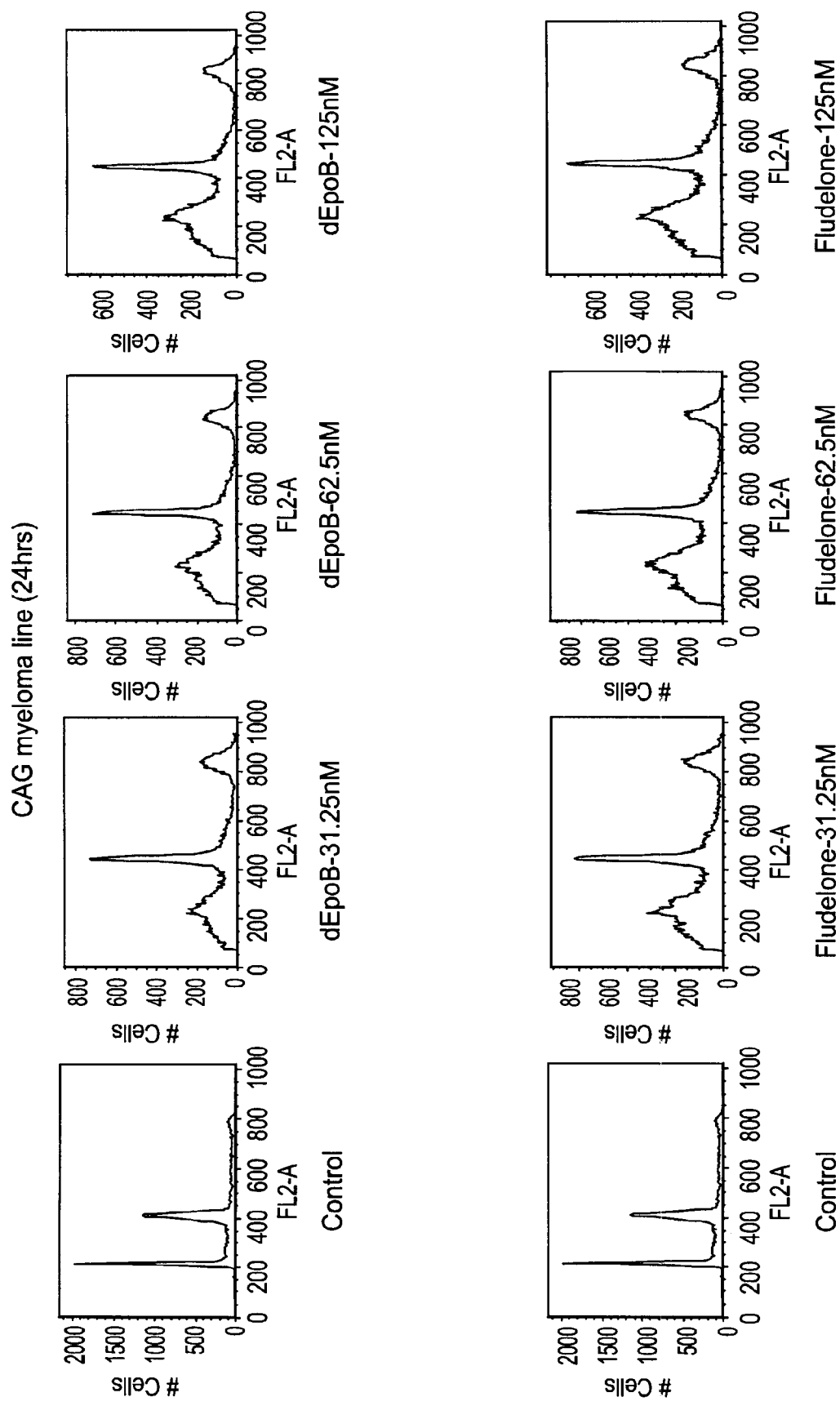
FIG. 106 shows the titration of Fludelone and dEpoB concentrations on cell cycle arrest. CAG myeloma cell lines were used. At the concentration of 31.25 nM, both drugs can absolutely blocked cell cycle at G2M phase (data below 31.25 nM is not shown).
Figure 107:
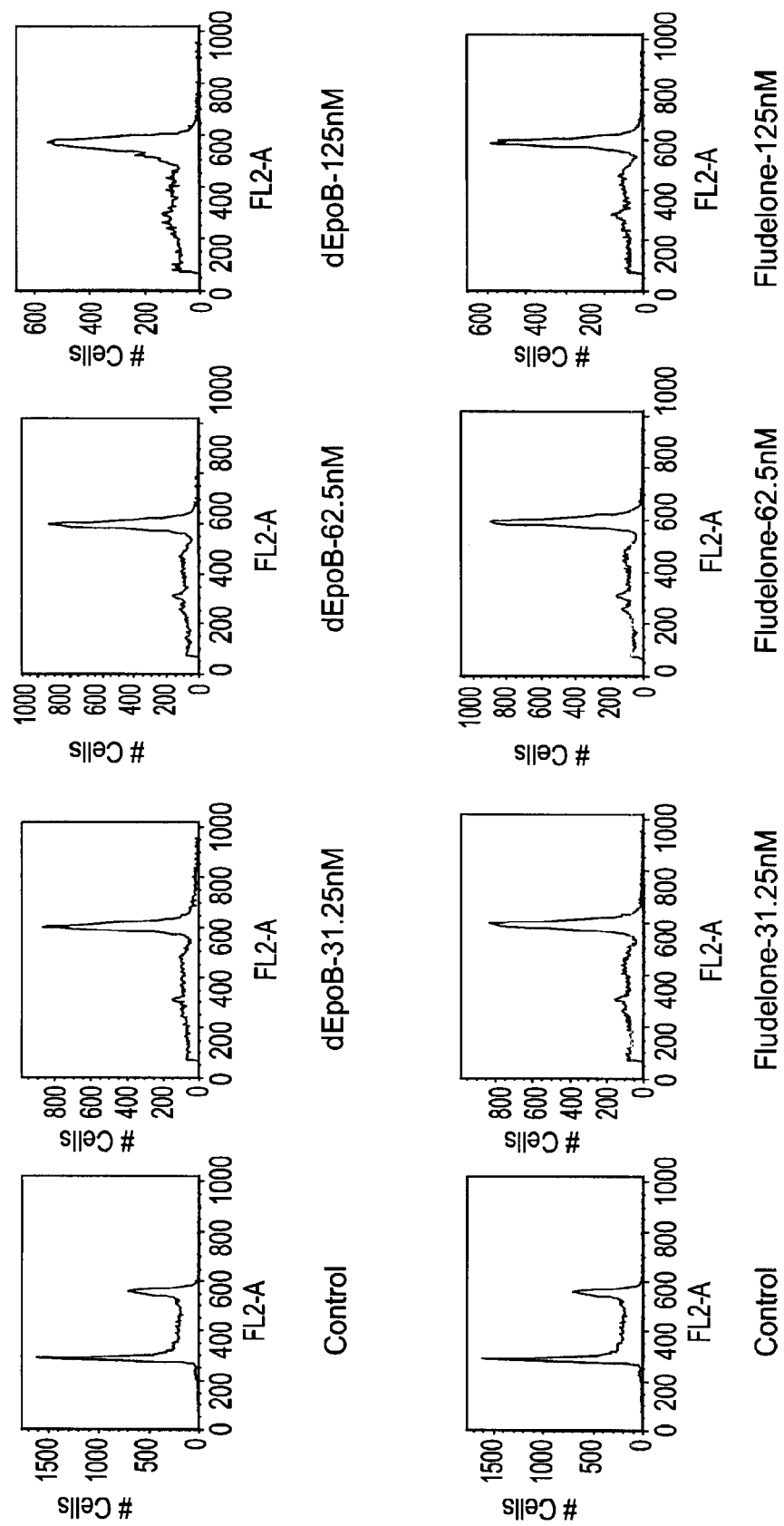
FIG. 107 shows the Titration of Fludelone and dEpoB concentration on cell cycle arrest. RPMI8226 myeloma cell lines were used. At the concentration of 31.25 nM, both drugs can absolutely blocked cell cycle at G2M phase (data below 31.25 nM is not shown).
Figure 108:
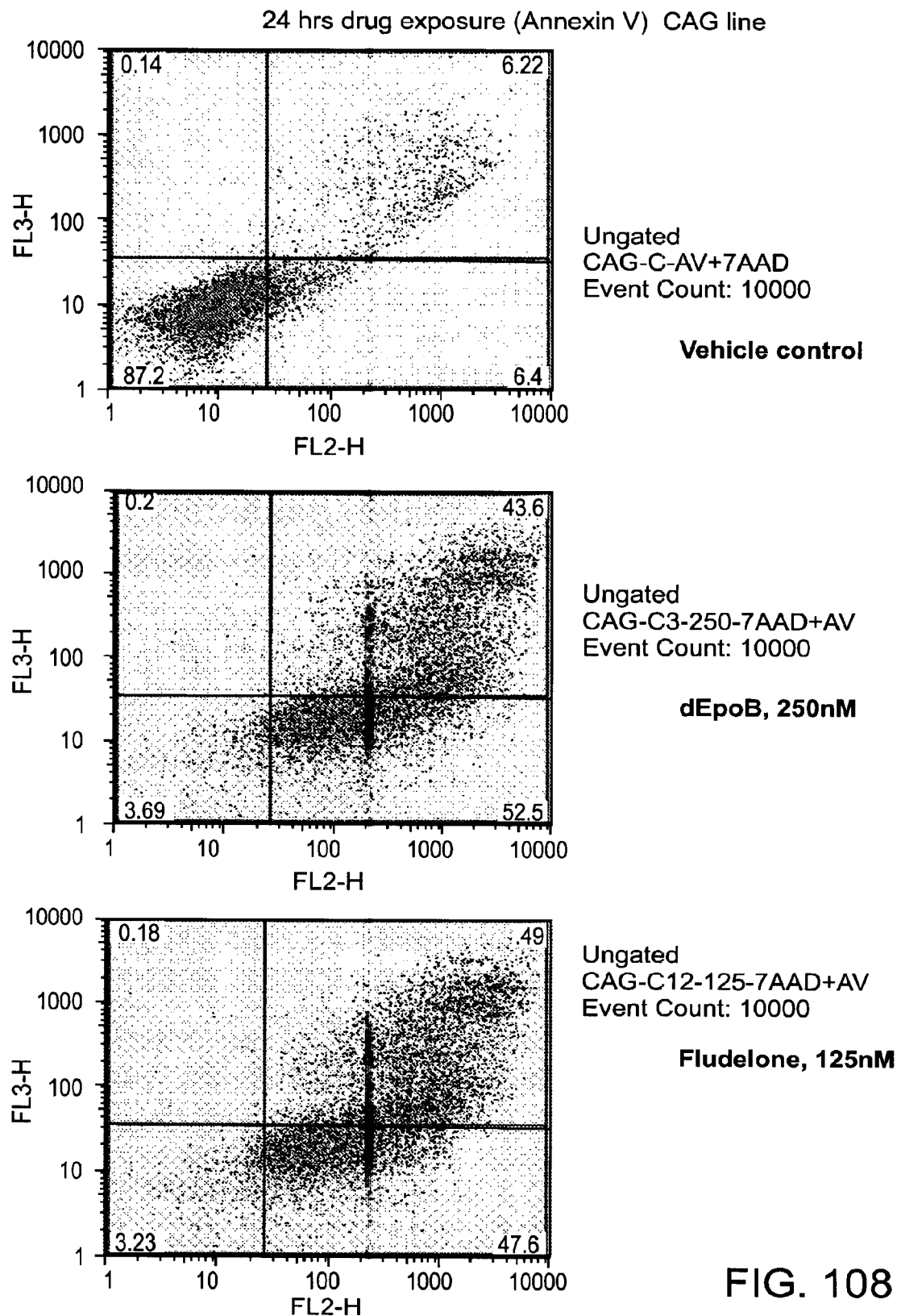
FIG. 108 shows Annexin V staining on the CAG myeloma cell lines. In early apoptotic cells, the membrane phospholipids phosphatidylserine (PS) is translocated from the inner to the outer leaflet of the plasma membrane, thereby exposing PS to the external cellular environment. Annexin V is a 35-36 kD Ca$^{2+}$ dependent phospholipids-binding protein that has a high affinity for PS, and binds to cells with exposed PS. In conjunction with a vital dye such as 7-amino-actinomycin (7-AAD) staining dead cells, this assay allows to identify early apoptotic cells. The data showed that the majority of cells either enter apoptosis or are dead after 24 hours treatment with Fludelone or dEpoB. Note that X-axis is Annexin staining and Y-axis is 7-AAD staining.
Figure 109:
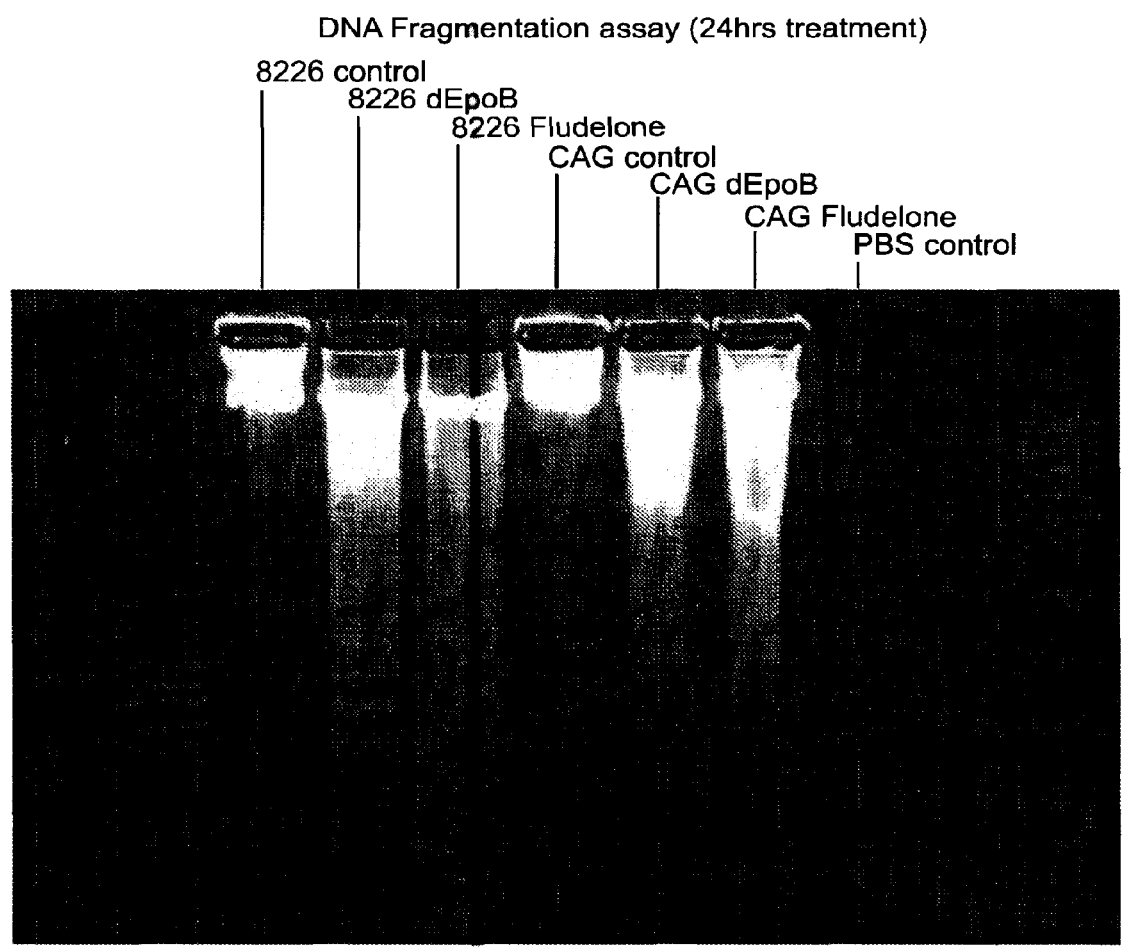
FIG. 109 is a DNA fragmentation assay. A major biochemical hallmark of apoptosis nucleosome excision from chromatin. Nucleosome excision is caused by endonuclease-mediated digestion of the exposed DNA linker regions between nucleosome in chromatin. Since the 180-200 base pairs of DNA around a histone core are conformationally protected from digestion, this endonuclease-mediated nucleosome excision is observable as a DNA ladder in agarose gels. The data showed that typical DNA ladders were detected after treatment of RPMI8226 and CAG myeloma cells with Fludelone or dEpoB for 24 hrs. The data implicated that cell apoptosis is induced by epothilones through the caspase pathway.
Figure 110:
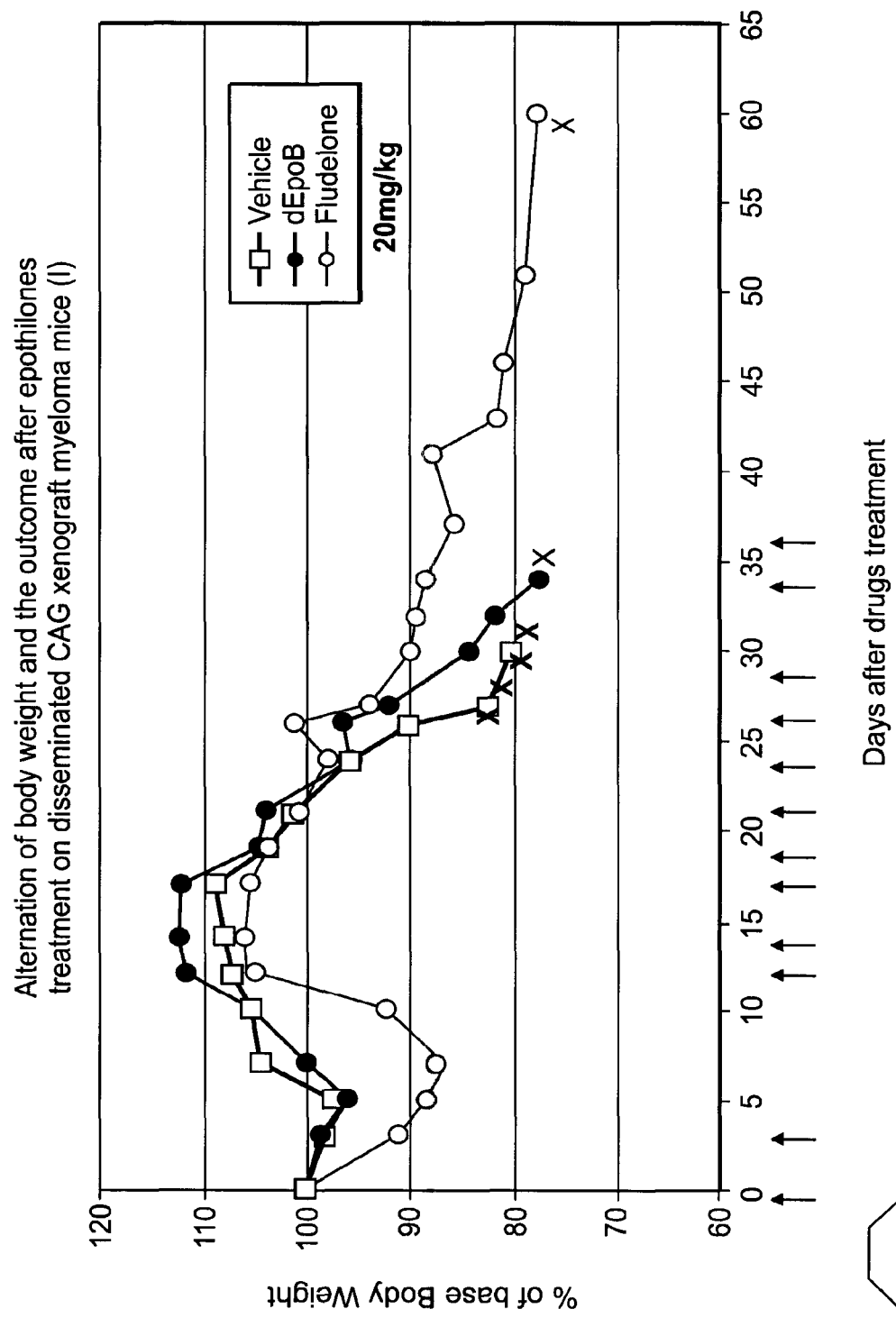
FIG. 110 shows the alternation of body weight and the outcome after epothilone (20 mg/kg) treatment of disseminated CAG xenograft myeloma mice. The data show that the control mice died in about 30 days and significant body weight loss was observed after 20 days of treatment. There is no significant difference in life span between mice treated with dEpoB and controls; however, mice treated with Fludelone showed a significant extension of survival days than either control and dEpoB groups. The number of mice used in each group was four, and mice were irradiated 300 Rad prior to injection of CAG cells.
Figure 111:
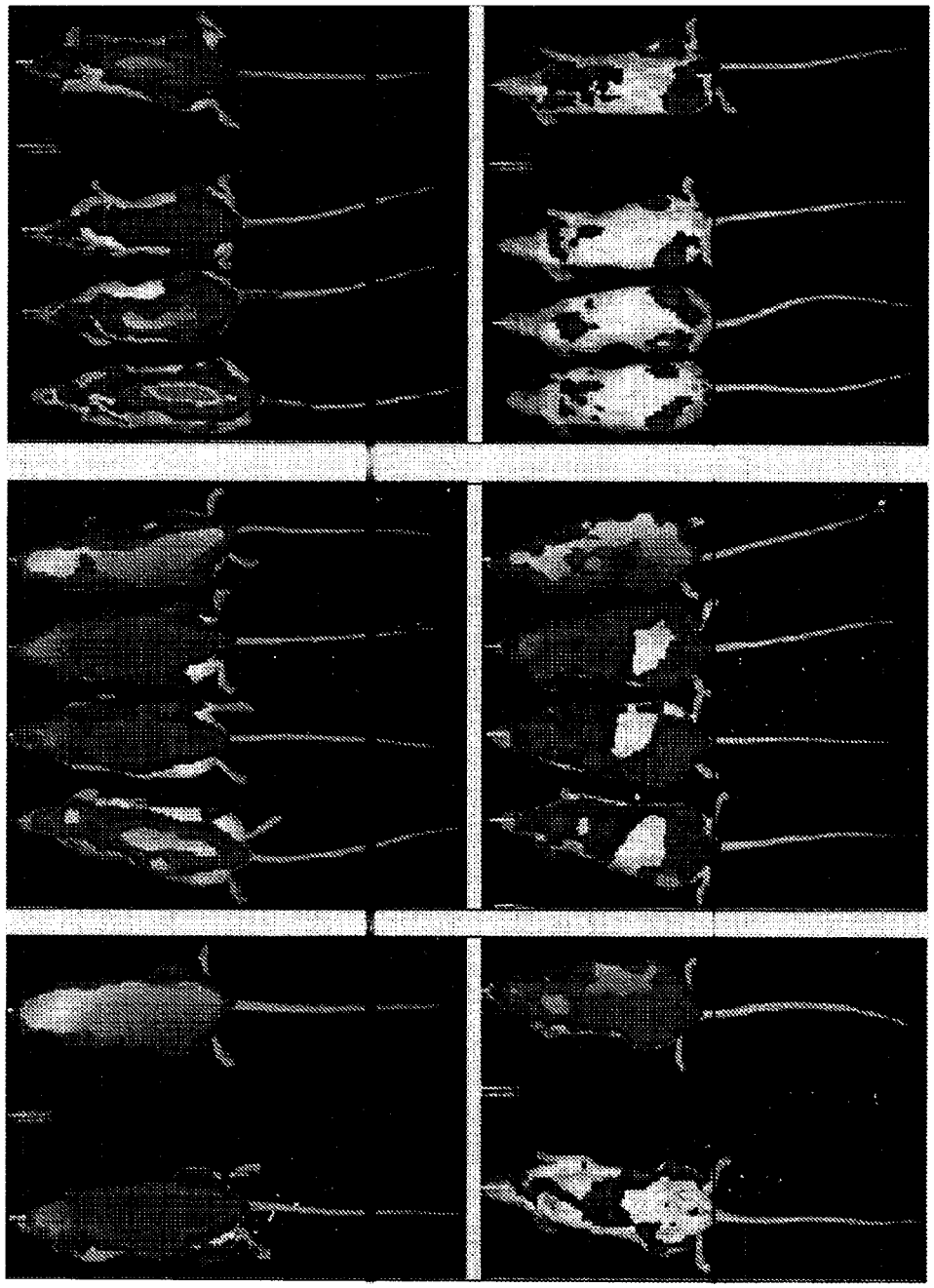
FIG. 111 shows the treatment of disseminated CAG xenograft myeloma mice at week 4. 10×10$^6$ CAG myeloma cells engineered with Luc-eGFP-TK fusion gene were injected intravenously into the mouse-tail vein, and the treatment was started when decent myeloma cells implantation was detected by bioluminescence imaging on day 7. The figure showed the bioluminescence images on mice treated with either control, or dEpoB, or Fludelone, respectively.
Figure 112:
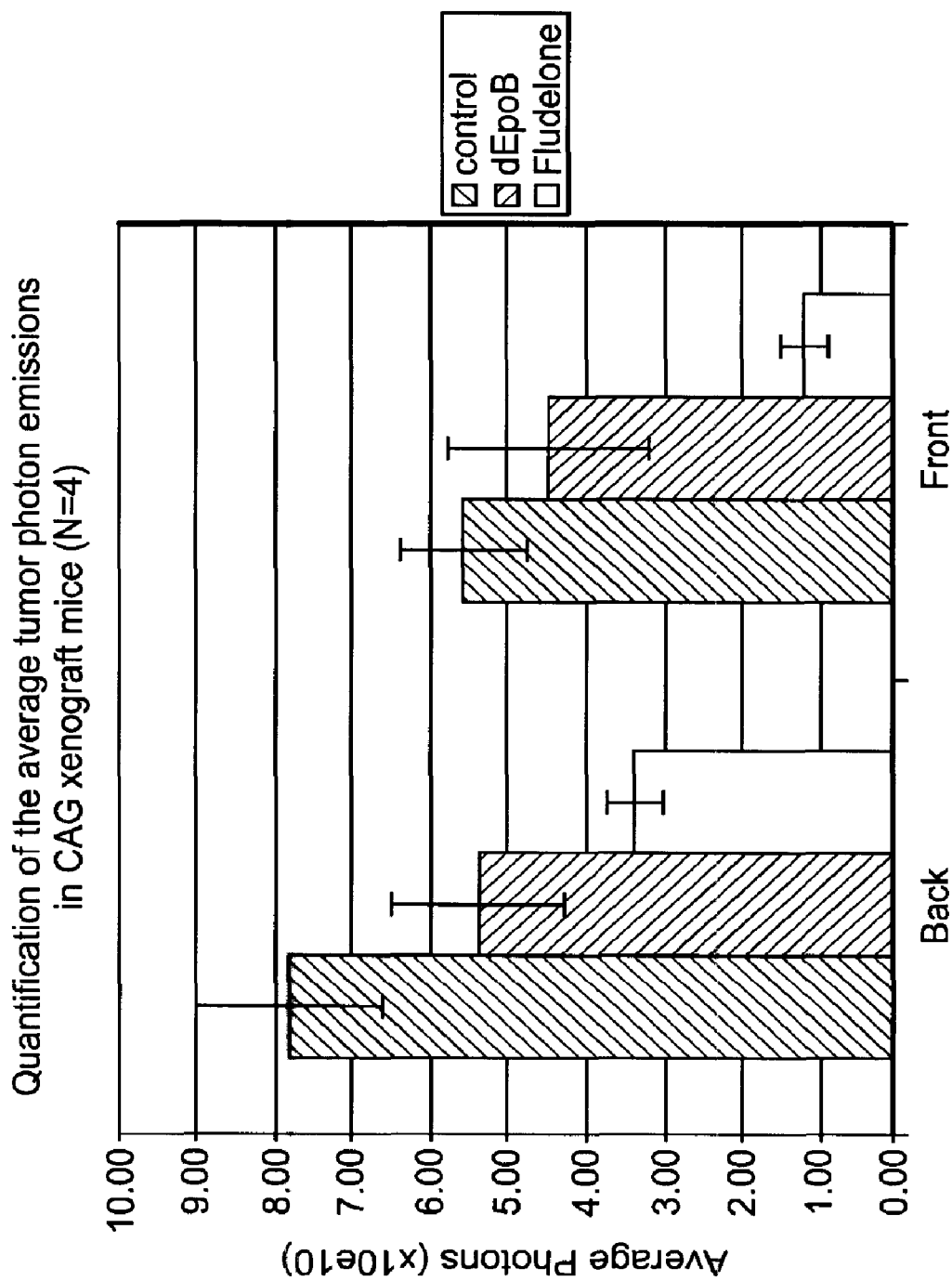
FIG. 112 shows quantification of the average tumor photon emissions in CAG xenograft mice (N=4). The figure show that mice treated with Fludelone had significant decreased tumor photon emissions than mice treated with either vehicle or dEpoB alone. Tumor photon emission correlates positively with tumor burden.
Figure 113:
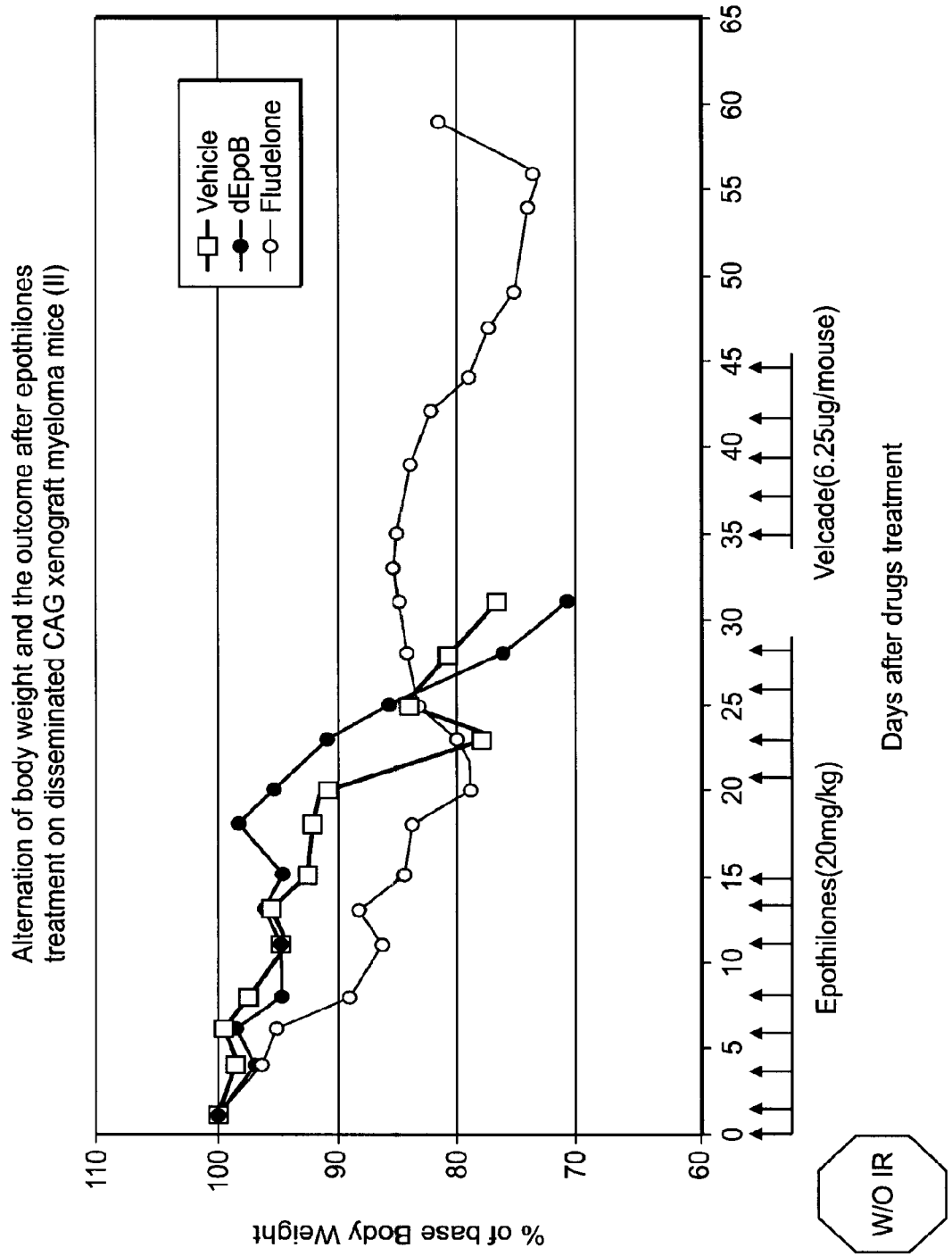
FIG. 113 shows alternations in body weight and the outcome after epothilone (20 mg/kg) treatment of disseminated CAG xenograft myeloma mice. The figure show a similar feature as FIG. 110 in the first 30 days; however, the only survival group of Fludelone-treated mice received additional 5 dosages of Velcade (6.25 ug/mouse, I.V) boost.
Figure 114:
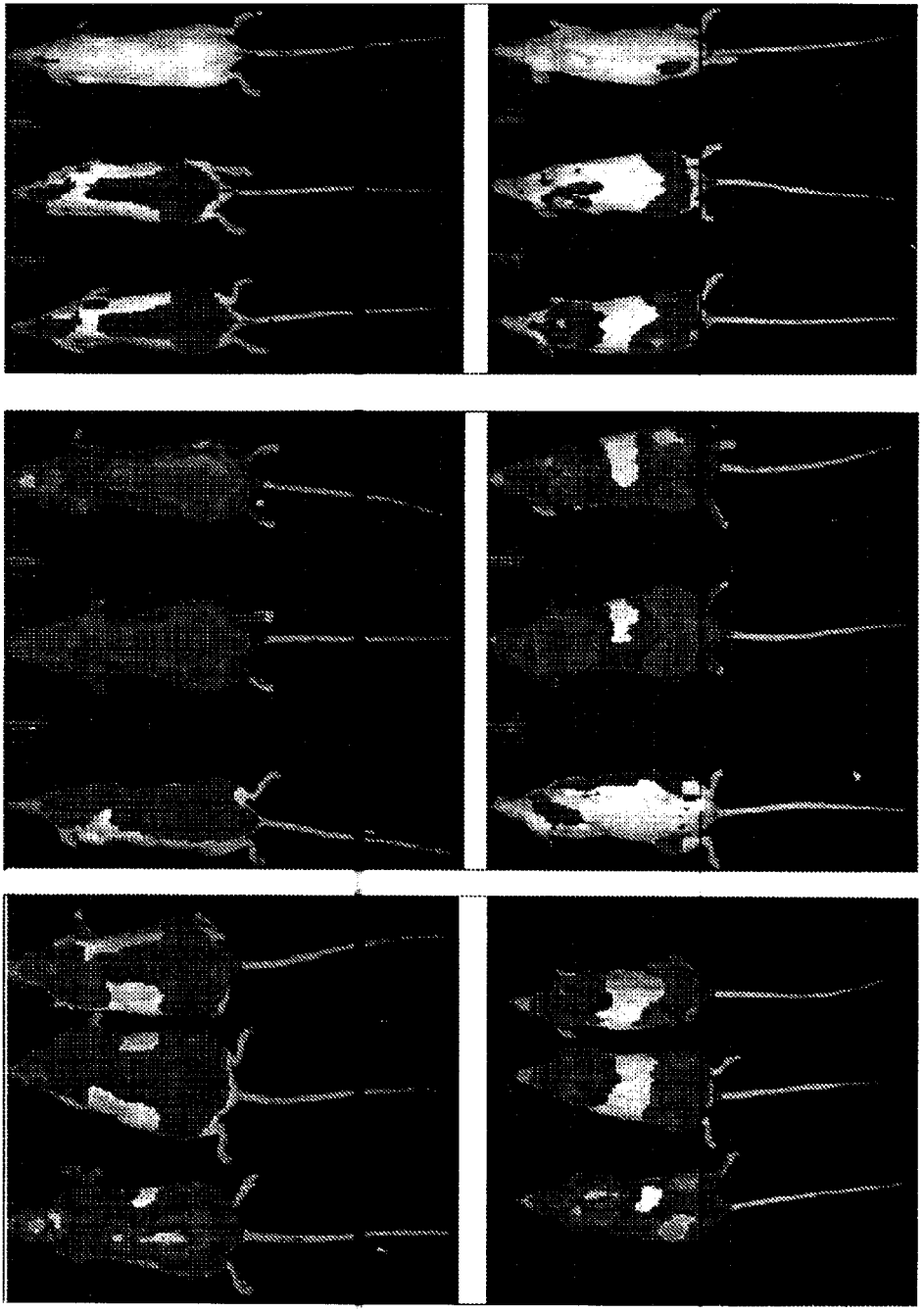
FIG. 114 shows the treatment of disseminated CAG xenograft myeloma mice at day 18. The figure shows the significant difference of images among groups, which reflects its tumor burden in the group.
Figure 115:
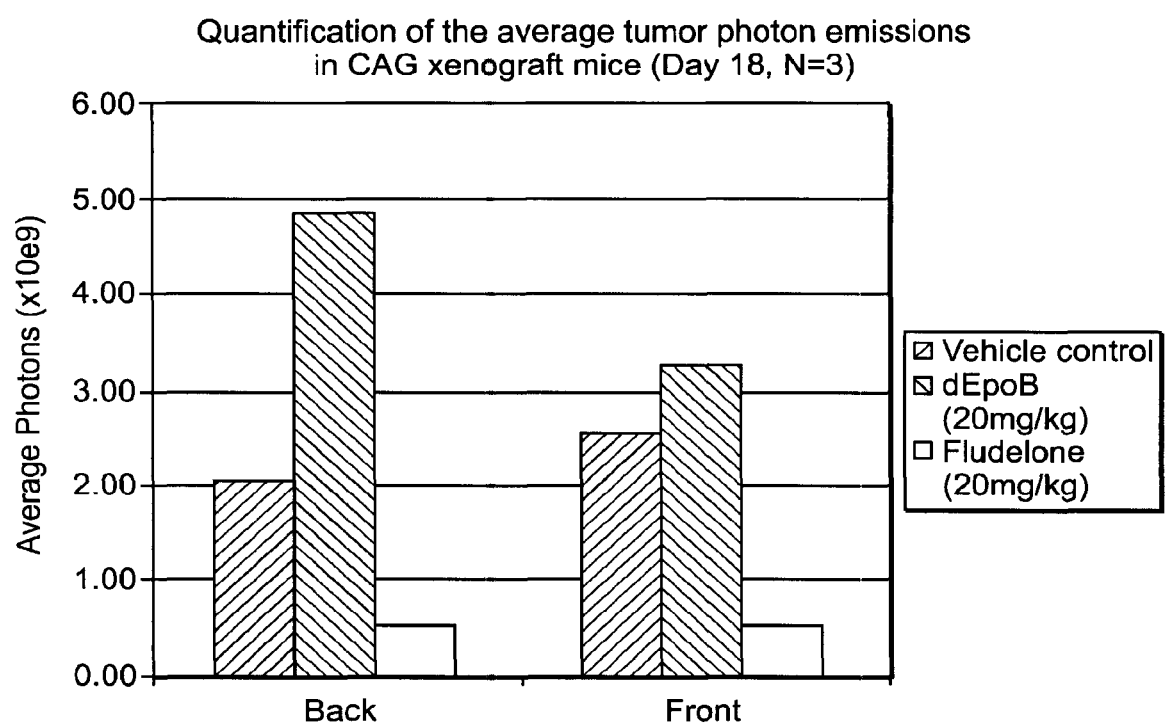
FIG. 115 shows the quantification of the average tumor photon emissions in the treatment of disseminated CAG xenograft myeloma mice at day 18. The figure shows the significant difference of images among groups, which reflects its tumor burden in the group.
Figure 116:
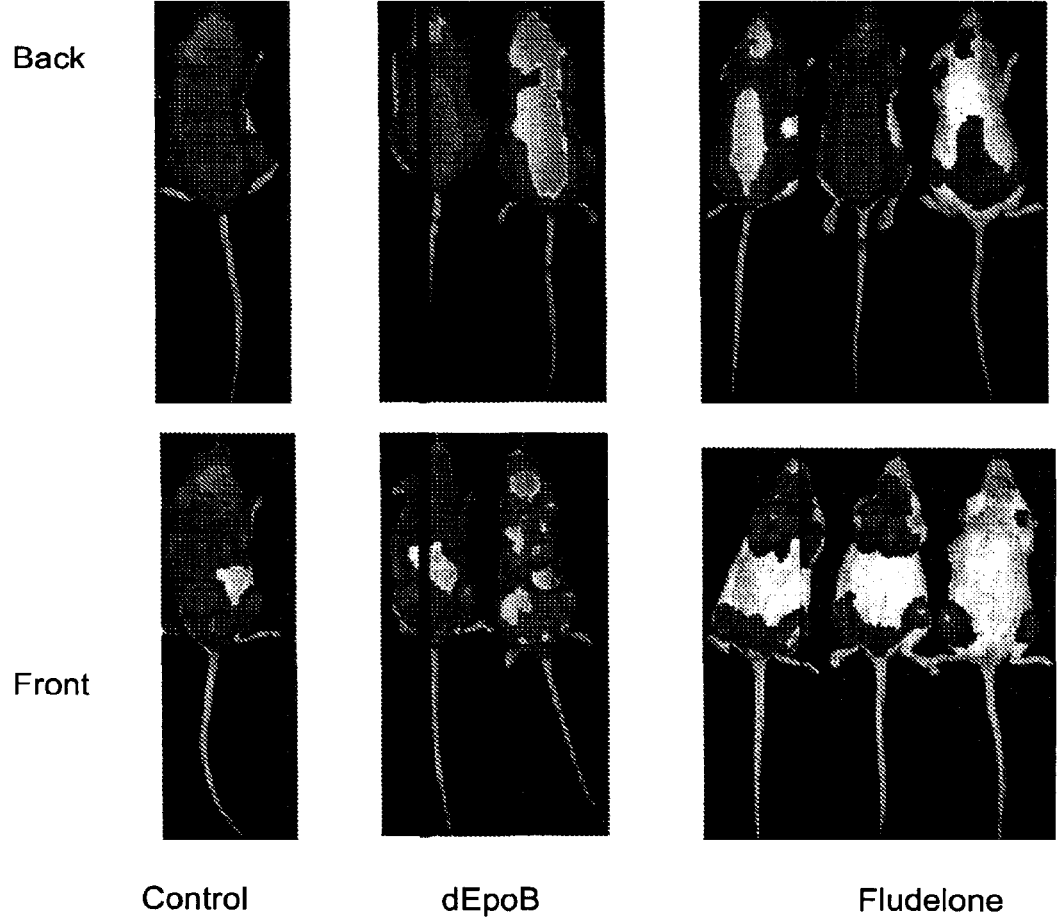
FIG. 116 shows the treatment of disseminated CAG xenograft myeloma mice at day 40. The figure shows the images difference, which reflects tumor burden in three groups of mice.
Figure 117:
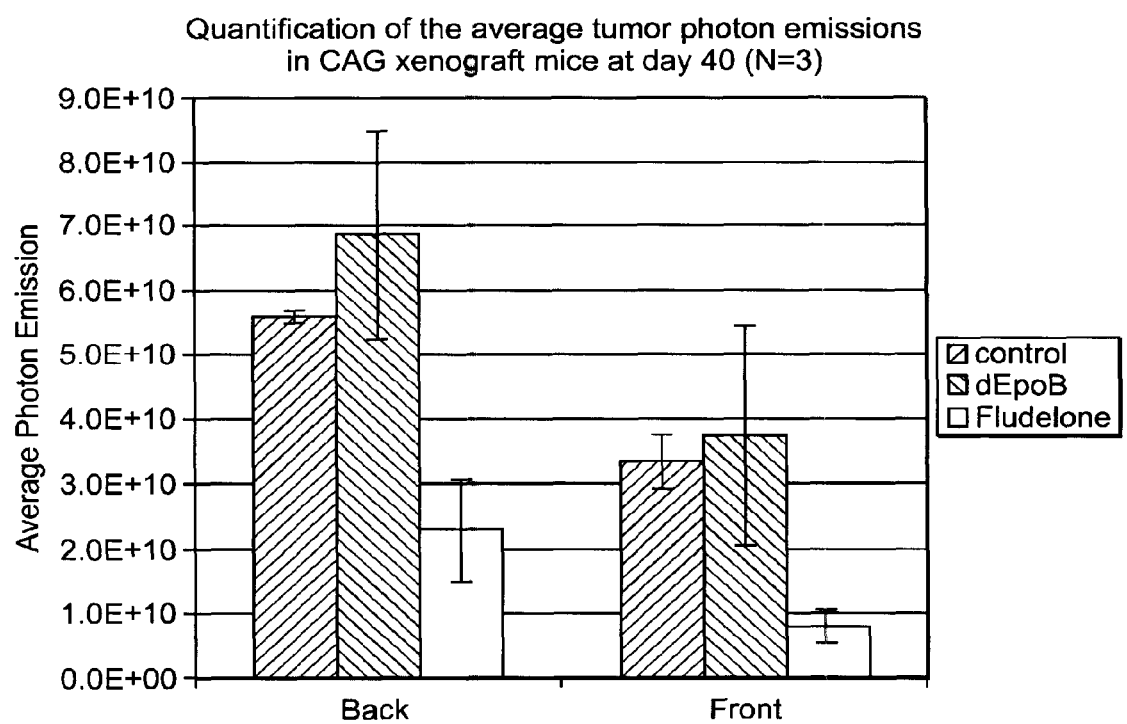
FIG. 117 shows the quantification of the average tumor photon emissions in the reatment of disseminated CAG xenograft myeloma mice at day 40. The figure shows the images difference, which reflects tumor burden in three groups of mice.
Figure 118:
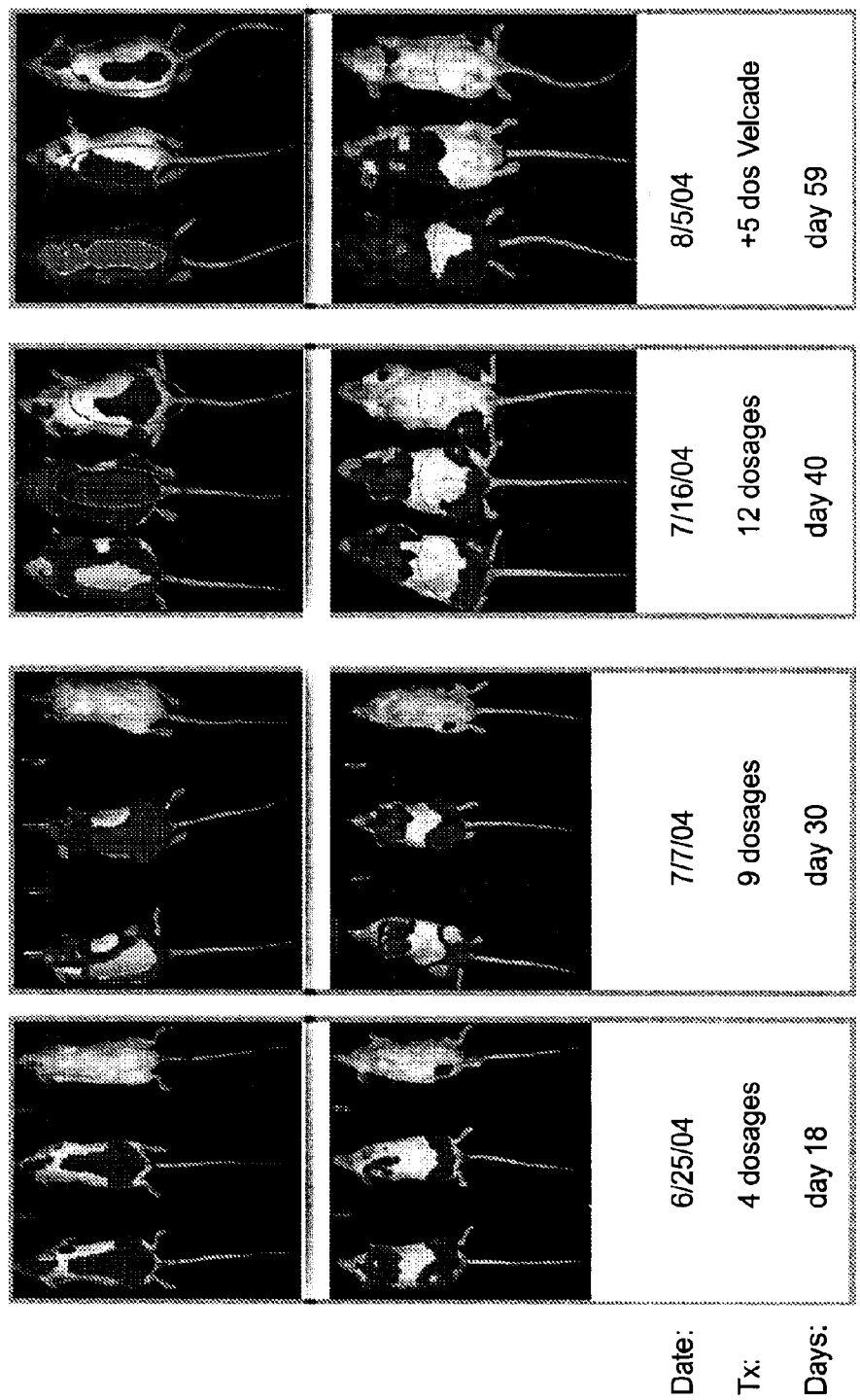
FIG. 118 shows CAG xenograft myeloma mice treated with Fludelone in combination with Velcade. Mice treated with Fludelone from day 0 to 28 (20 mg/kg, Q2d) and Velcade from day 35 to 45 (6.25 ug/mouse, I.V, 3/w). The treatment started on day 10 and the images are taken after 12 dosages of Fludelone and 5 dosages of Velcade at day 59. In comparison with the images on day 40, two of three mice had significantly decreased tumor burden in both femurs and invertebrate column.

The IC50s of Fludelone and dEpoB were determined on a panel of human solid tumor lines (colon, breast and ovarian) (Table 15-1). In every instance the Fludelone IC50 was lower than that of dEpoB. Ovarian cancer lines were particularly sensitive to Fludelone and 4/5 of the ovarian lines had a mean IC50 of 1.6 nM compared to a mean IC50 of 16.5 nM with dEpoB. Both drugs caused tumor cells to arrest in G2M phase (FIG. 100) and rapidly induced apoptosis (FIGS. 101 and 102).

Global Gene Expression of the RPMI-8226 Myeloma Cell Line at 6 and 18 Hrs after Treatment with dEpoB or Fludelone at ×10 of their Respective IC50s Global gene expression (Affymetric chip—AU133 2.0) comparison of differential gene expression in the RPMI-8226 human multiple myeloma cell line was undertaken at 6 or 18 hrs after treatment with dEpoB or Fludelone (at ×10 IC50 dose). In the comparison of Fludelone-treated RPMI-08226 with control untreated cells, at 6 hrs 5 genes were upregulated (Table 15-2) and at 18 hrs 48 genes were upregulated (Table 15-3). JUN was upregulated at both times (+3.25, +2.64). At 6 hrs 3 genes were downregulated (Table 15-2) and at 18 hrs 16 genes were downregulated (Table 15-3). HNRPD (heterogeneous nuclear ribonucleoprotein D-like) was downregulated at both times (−2.46, −3.25). In the comparison of dEpoB-treated RPMI-08226 with control untreated cells at 6 hrs 21 genes were upregulated (Table 15-2) and at 18 hrs. 26 genes were upregulated (Table 15-3). JUN (+5.66, +3.73) and Tubulin α3 (+2.64, +2.30) were upregulated at both times. At 6 hrs., three genes were downregulated (Table 15-2), and at 18 hrs., sixteen genes were downregulated (Table 15-3). HNRPD was downregulated both times (−4.92, −2.00). We then compared gene expression altered by Fludelone versus dEpoB (Table 15-2 and 15-3).

TABLE 15-2

Global gene expression (Affymetrix chip - AU133 2.0) comparison of differential gene expression in RPMI-8226 (human multiple myeloma cell line). Comparison of control with cells treated with Fludelone or dEpoB (at 10 IC50 dose) for 6 hrs.

| Fludelone 6 hr | Fold change | Desoxyepothilone B 6 hrs | Fold Change |
|---|---|---|---|
| JUN | +3.25 | IFI27 (Interferon-α inducible protein) | +18.38 |
| SKIL (SKI-Like-) | +2.83 | JUN | +5.66 |
| BASP1. (Brain abundant membrane attached signaling.) | +2.83 | G1P3*(Interferon-α inducible protein) | +5.28 |
| APP (Amyloid β precursor protein) | +2.14 | IFITM1* (Interferon-induced transmembrane protein1) | +4.92 |
| HMGCS1 (3-OH-3-methylglutaryl-Co-enzyme synthase) | +200 | APP (Amyloid β precursor protein) | +2.83 |
| | | CCL5 (Rantes chemokine) | +2.64 |
| | | TUBA3 (Tubulin α3) | +2.64 |
| | | INSIG1 (Insulin induced gene) | +2.46 |
| | | TRIM22 (Tripartite motif-containing 22) | +2.30 |
| | | HLA-DPA1* (Histocompatibility class II DPα1) | +2.30 |
| | | IFIT1* (Interferon-induced protein with tetratricopeptide repeats) | +2.30 |
| | | HMGCS1 (3-OH-3-methylglutaryl Coenzyme A) | +2.30 |
| | | MARCKS (Meristoylated alanine-rich PKC substrate) | +2.14 |
| | | ABCG1 (ABC transporter activity) | |
| | | MX1* (Myxovirus resistance, Interferon-inducible p78) | +2.14 |
| | | OAS1* (2',5'-oligoadenylate synthetase) | +2.00 |
| | | PLSCR1 (Phospholipid scramblase) | +2.00 |
| | | STS (Steroid sulfatase) | +2.00 |
| | | DUSP4 (Dual specificity phosphatase) | +2.00 |
| | | AP1S1 (Adaptor-related protein complex-1) | +2.00 |
| | | ARHE (Ras homology family E) | +2.00 |
| | | | +2.00 |
| HNRPD Heterogeneous nuclear ribonucleoprotein D). | −2.46 | HNRPD (Heterogeneous nuclear ribonuclear protein D) | −4.92 |
| | | HMOX1 (Heme oxygenase 1) | −2.30 |
| SUV39 H2. (Suppressor of variegation homolog). | −2.00 | HASA1A (heat shock 70 kDa protein) | −2.14 |
| HIST1. (Histone 1) | −2.00 | MAT2A (Methionine adenosyltransferase IIα) | −2.00 |

Underlined: - genes up- or down-regulated in both Fludelone or dEpoB-treated cells at 6 hrs.
*Interferon-inducible genes.

TABLE 15-3

Global gene expression (Affymetrix chip - AU133 2.0) comparison of differential gene expression in RPMI-8226 (human multiple myeloma cell line). Comparison of control with cells treated with Fludelone or dEpoB (at ×10 IC50 dose) for 18 hrs.

| Fludelone 18 hr | Fold change | Desoxyepothilone B 18 hrs | Fold Change |
|---|---|---|---|
| PRKDC (double-stranded break repair) | +21.11 | REPS1 (RALBP1 associated Eps domain) | +9.85 |
| Fibrillin 2 | +12.3 | PKD1 (Polycystic kidney disease 1) | +5.6 |
| REPS1 (RALP1 associated Eps domain) | +9.85 | JUN | +3.73 |
| PKD1 (Polycystic kidney disease 1) | +7.46 | SEMA3D (Ig sema domain) | +3.73 |
| TRIO (Triple functn domain guanyl NEF) | +4.29 | PRKCBP1 (Protein kinase C binding) | +3.03 |
| FLJ20241 (NFkB activating protein) | +3.73 | PCNX (Pecanex homology) | +3.03 |
| CCL3 (Chemokine MIP-1α) | +3.48 | GTF2H2 (General transcription factor IIH) | +2.83 |
| PCNX (Pecanex homolog) | +3.48 | KIAA1025 protein | +2.83 |
| KIAA1025 protein | +3.25 | TRIO (Triple functn domain guanyl NEF) | +2.83 |
| TRA2A (transformer 2α, mRNA splicing) | +3.03 | CCL3 (Chemokine MIP-1α) | +2.64 |
| GTF2H2 (General transcription factor IIH) | +3.03 | VEZATIN (transmembrane protein) | +2.46 |
| SLC13A1 (Sodium ion transporter) | +3.03 | TRA2A (transformer 2α, mRNA splicing) | +2.46 |
| PHC3 (Polyhomeotic like) | +2.83 | APRIN (Androgen induced proliferin inhi) | +2.46 |
| SEMA3D (Ig sema domain) | +2.83 | KIAA0191 protein | +2.46 |
| JUN | +2.64 | TUBA3 (Tubulin α3) | +2.30 |
| PRKCBP1 (Protein kinase C binding) | +2.64 | TMEM1 (transmembrane protein 1) | +2.30 |
| GA17 (Dendritic cell protein. | +2.64 | PHC3 (Polyhomeotic like) | +2.30 |
| SEC24D (SEC24 related gene family D) | +2.64 | SMA3 (hydrolase activity) | +2.30 |
| SMA3 (hydrolase activity) | +2.46 | AKAP9 (PRKA kinase anchor protein) | +2.14 |
| ETS2 (v-ets oncogene homologue) | +2.46 | INADL (PDZ, signaling cascade) | +2.14 |
| DNAJB1 (Hsp40 homolog subfamily B) | +2.30 | EIFA1 (Translation initiation factor 4A-1) | +2.14 |
| CCT8 (Chaperonin containing TCP1) | +2.30 | GAPCENA (rab6 GTPase activating) | +2.14 |
| EIFA1 (Translation initiation factor 4A-1) | +2.30 | MGC10526 (Sugar phosphotransferase) | +2.00 |
| TCS2 (Tuberous sclerosis 2) | +2.30 | ATP8B1 (ATPase Class 1) | +2.00 |
| CD72 (cell adhesion) | +2.30 | RPL23 (Ribosomal protein L23) | +2.00 |
| HSPA1A (Heat shock protein 70 kDa 1A) | +2.14 | RC3 (rabconnectin 3) | +2.00 |
| ZFY (Zinc finger protein-Y-linked) | +2.14 | | |
| AIP1 (Atropin-1 interacting protein) | +2.14 | | |
| RPL23 (Ribosomal protein L23) | +2.14 | | |
| TMEM1 (transmembrane protein-1) | +2.14 | | |
| KIAA0191 protein | +2.14 | | |
| HSPA1B (Heat shock protein 70 kDa 1B) | +2.00 | | |
| VEZATIN (transmembrane protein) | +2.00 | | |
| SERPINH1 (cysteine protease inhibitor) | +2.00 | | |
| MADH1 (mothers against decapentaplegic) | +2.00 | | |
| BAX (Bcl-2 associated protein) | +2.00 | | |
| APRIN (Androgen induced proliferin inhi) | +2.00 | | |
| APBB2 (amyloid β precursor protein-binding) | +2.00 | | |
| AKAP9 (PRKA kinase anchor protein) | +2.00 | | |
| APG16L (APG16 autophagy 16-like) | +2.00 | | |
| CENPC1 (Centromere protein C1) | +2.00 | | |
| ZF (HCF-binding transcription factor) | −6.50 | ZF (HCF-binding transcription factor) | −6.06 |
| CLorf29 (Chromsome 1 open reading frame) | −6.06 | Cyclin E2 | −3.03 |
| FLJ20130 (hypothetical protein) | −5.66 | MARS (Methionine-tRNA synthetase) | −2.83 |
| F11 (Coagulation factor X1) | −4.00 | POU4F1 (Pou domain transcription factor) | −2.46 |
| G1P3 (Interferon α inducible protein) | −3.73 | | −2.14 |
| HNRPD (heterogeneous nuclear ribonucleoprotein D-like) | −3.25 | NRTN (Neuturin) | |
| | | PABPN1 Poly(A) binding protein, nuclear) | −2.00 |
| Cyclin E2 | −2.64 | HNRPD (heterogeneous nuclear ribonucleoprotein D-like) | −2.00 |
| FLJ20045 (hypothetical protein) | −2.46 | | |
| CEB1 (Cyclin E binding, ubiquitin ligase) | −2.30 | | |
| FBXO5 (F box only protein 5) | −2.30 | | |
| NRTN (Neurturin) | −2.3 | | |
| DUSP6 (Dual specificity phosphatase) | −2.14 | | |
| POU4F1 (Pou domain transcription factor) | −2.14 | | |
| MARS (Methionine-tRNA synthetase) | −2.00 | | |
| HDAC9 (histone deacetylase 9) | −2.00 | | |
| CENPC1 (centromere protein C 1) | −2.00 | | |

Underlined: - genes up- or down-regulated in both Fludalone or dEpob treated cells at 18 hrs.
*Interferon-inducible genes.

At 6 hrs., five genes were upregulated by Fludelone, 21 by dEpoB, and three genes were upregulated by both while three genes were downregulated by Fludelone, four by dEpoB, and no genes by both. At 18 hrs., 48 genes were upregulated by Fludelone, 26 by dEpoB and 18 genes were upregulated by both while 16 genes were downregulated by Fludelone, 7 by dEpoB and 6 genes were downregulated by both. The proposal is designated to test the hypothesis that the increased anitumor efficacy of Fludelone over dEpoB and earlier epithelones was due to some additional tumor targeting mechanism in addition to microtubule stabilization. We therefore determined what genes were differentially up or downregulated by Flu when compared to dEpoB-treated MM cells (Table 15-4).

TABLE 15-4

Global gene expression (Affymetrix chip - AU133 2.0) comparison of differential gene expression in RPMI-8226 (human multiple myeloma cell line) treated with dEpoB or Fludelone (at ×10 IC50 dose) for 6 or 18 hrs. Genes shown were those changed selectively by Fudelone.

| 6 hr Gene difference | Fold Change | 18 hr gene difference | Fold Change |
|---|---|---|---|
| BCL3 | +3.25 | HMT-1 (Methyltransferase-like-1) | +11.3 |
| Heme oxygenase | +2.30 | | |
| IFI 27* (Interferon (IFN) α-inducible) | −7.46 | IFI 27* (Interferon (IFN) α-inducible) | −5.28 |
| GIP3* (IFNα-inducible). | −6.06 | GIP3* (IFNα-inducible). | −5.28 |
| T RIM34 (Tripartite motif-containing) | −5.66 | IFITM1* (IFN-induced transmembrane) | −3.25 |
| IFTM1* (IFN-induced transmembrane) | −4.00 | MX1* (Myxovirus resistance, IFN inducible). | −2.30 |
| HLA-II DPα* | −3.73 | | |
| AIM2* (Absent in melanoma) | −2.64 | DUSP4 (Dual specificity phosphatase) | −2.14 |
| PTPL (Tyrosine phosphatase-like) | −2.46 | PPAP2C (Phosphatidic acid phosphatase) | −2.14 |
| TRIM22 (Tripartite motif-containing) | −2.46 | PLSCR1* (Phospholipid scramblase) | −2.00 |
| CA4 (Carbonic anhydrase) | −2.14 | IFIT1* (IFN-induced protein tetra-tricopeptide repeats.) | −2.00 |
| MX1* (Myxovirus resistance, IFN inducible). | −2.00 | OAS2* (2'-5'-oligoadenylate synthetase-2) | −2.00 |
| | | TRIM22 (Tripartite motif containing-22) | −2.00 |
| | | CEB1 (Cyclin-E binding protein) | −2.00 |

Underlined: - genes downregulated in both Fudalone or dEpob-treated cells at both 6 and 18 hrs.
*Interferon-inducible genes.

At 6 hrs., two genes were upregulated, and at 18 hrs., one gene was upregulated. At 6 hrs., ten genes were downregulated, and at 18 hrs., eleven genes were downregulated and 4 genes were downregulated at both times (IFI27, −7.46, −5.28), GIP3 (−6.06, −5.28), IFTM1 (−4.00, −3.25), MX-1 (−2.00, −2.30). These are all are Interferon-inducible genes. Gene expression profiles of ovarian 1A9 and 1A9PTX22 ovarian xenografts have been reported to show diminished expression of IFN response genes (GIP3, IFI27, IFITM1, IFII6, ISG15) 24 hrs after treatment with paclitexal (Bani R M, Nicoletti M I, Alkharouf N W et al. "Gene expression correlating with response to paclitaxel in ovarian carcinoma xenografts" Mol. Cancer Thera. 2004; 3:111-121; incorporated herein by reference). Three of these genes (G1P3, IFI27, IFITM1) were strongly overexpressed at 6 hrs after dEpoB treatment of the RPMI-8226 cells but not with Fludelone, and these were also the genes whose expression most strongly distinguished the Fludelone and dEpoB gene profiles. Overexpression of IFN-responsive genes (e.g., IFR9) has recently been associated with resistance to paclitaxel in tumor cell lines and findings support the possible involvement of mediators of IFN signaling other than IFN itself, in responsiveness to paclitaxel (Luker K E, Pica C M, Schreiber R D, Piwnica-Worms D. "Overexpression of IRF9 confers resistance to antimicrotubule agents in breast cancer cells" Cancer Res. 2001; 61:6540-7; incorporated herein by reference). This novel IFN-independent role of IRF9 in the development of resistance to antimicrotubule agents was reported in approximately one half of breast and uterine cancers (Luker K E, Pica C M, Schreiber R D, Piwnica-Worms D. "Overexpression of IRF9 confers resistance to antimicrotubule agents in breast cancer cells" Cancer Res. 2001; 61:6540-7; incorporated herein by reference). Microarray analysis of tumor lines that were eEpoA or Taxol-resistant showed that the majority of genes which were highly expressed in EpoA-resistant tumors but not in Taxol-resistant tumors encoded interferon-inducible genes (Atadja A P, Yan-Neale T, Towbin H, Buxton F, Cohen D. "Gene expression profiling of epothilone A-resistant cells" Novartis Found Symp. 2002; 243:119-32; incorporated herein by reference). Remarkably, we found that 8/21 (38%) of all genes upregulated following dEpoB treatment of RPMI-8226 were IFN-inducible and none of these were changed by Flu treatment (Table 15-2 through 15-4). The following IFN-inducible genes were shown to be upregulated in 8226 MM cells following 6 hrs or 18 hrs of dEpoB treatment and not changed with Fludelone treatment. In order of degree of upregulation following dEpoB they were 1.) Interferon (IFN) α-inducible IFI 27 (+18.83 increase). This belongs to a family of small interferon-α-inducible genes of unknown function that are upregulated in inflammatory skin disease, epithelial cancers and wound repair (Suomela S, Cao L, Bowcock A and Saarialho-Kere U. "Interferon alpha-inducible protein 27 (IFI27) is upregulated in Psoriatic skin and certain epithelial cancers" J Invest. Dermatol. 2004; 122:717-721; incorporated herein by reference). 2. IFNα-inducible protein (clone IFI-6-16) GIP3 (Bani R M, Nicoletti M I, Alkharouf N W et al. "Gene expression correlating with response to paclitaxel in ovarian carcinoma xenografts" Mol. Cancer. Thera. 2004; 3:111-121; incorporated herein by reference) (+5.28 increase). 3.) IFN-induced transmembrane protein-1, IFTM1 (Bani et al.) (+4.92 increase). 4.) Myxovirus resistance, IFN inducible, MX1 (+2 increase at 6 hrs and +2.3 at 18 hrs). The MX1 genes confer selective innate resistance to influenza virus (Staeheli, Ad. Viral Res. 38:147, 1990; incorporated herein by reference). They may also serve basic cellular functions possibly as GTP-binding proteins (Amheiter H and Meier E. "Mx proteins: antiviral proteins by chance or necessity?" New Biol. 1990; 90 851; incorporated herein by reference). 5.) Phospholipid scramblase 1 gene PLSCR1. Transcriptional control of the gene is entirely regulated by a single IFN-stimulated response element located at the first exon (Zhou Q, Zhao J, Al-Zoghaibi F, Zhou A et al. "Transcriptional control of the human plasma membrane phospholipid scramplase 1 gene is mediated by interferon-alpha" Blood 2000; 95:2593-2599; incorporated herein by reference). PLSCR1 was implicated in remodeling of plasma membrane phospholipids and mobilization of phosphatidlyserine to the cell surface. It may contribute to the rapid transbilayer movement of plasma membrane phospholipids that is observed in injured or apoptotic cells that are exposed to elevated intracellular $Ca^{++}$. Studies show it can also translocate to nucleus and may act as a transcription factor (Ben-Efraim I, Zhou Q, Wiedmer T et al. "Phospholipid Scramblase 1 is imported into the nucleus by a receptor-mediated pathway and interacts with DNA" Biochem. 2004; 43:35181; incorporated herein by reference). 6.) Interferon-induced protein with tetracopeptide repeats, IFITI (+2.3 increase). It has been associated with systemic lupus erythematosus and protein-protein studies show that it may activate Rho proteins by interaction with Rho/Rac gunanine nucleotide exchange factors (Ye S, Pand H, Gu Y Y et al. "Protein interaction for an interferon-inducible syste-3526mic lupus associated gene, IFIT1" Rheumatology 2003; 42:1155-63; incorporated herein by reference). 7.) 2'-5'-oligoadenylate synthetase-2, OAS2 (+2 increase). This family (OAS1, OAS2, OAS3, OAS4) of interferon-induced genes are implicated in stress responses and are important for the anti-viral activity of interferon (Chebath, *Nature* 330:587, 1987; Meurs et al *J. Virol.* 66:5804, 1992; each of which is incorporated herein by reference). OAS2 catalyzes the synthesis of adenosine oligomers (2-5A). These then activate RNase L, an endoribonuclease latent in most mammalian cells, that in turn can inactivate viral (picornoviruses e.g. mengovirus) and cellular RNA (Anderson J B, Strabdbygard D J, Hartmann R, Justesen J. *Eur. J. Biochem.* 2004; 271:628-36; incorporated herein by reference). 8.) Histocompatibility class II DPα1, HLA-DPA1 (+2 increased). MHC-Class II are known mediators of the biological functions of IFN (Tissot C and Mechti J B C, "Molecular cloning of a new Interferon-induced factor that represses human immunodeficiency virus Type 1 long terminal repeat expression" *J. Biol. Chem.* 1995; 270:14891-14898; incorporated herein by reference).

SUMMARY

The CAG myeloma cell line displays many features of clinical multiple myeloma with both phenotype (CD38+CD138+CD45−) and in vivo engraftment. A xenograft NOD-SCID myeloma mouse model was established by intravenously injection of 10-15 million of CAG cells engineered with fusion HSV-TK-eGFP-Luciferase gene. Therefore whole animal imaging by luciferase bioluminescence can be applied to evaluate tumor burden and drug efficacy in real-time, non-invasively reporting in living mice. The myeloma mouse exhibits bone marrow infiltration and pathological osteolytic bone lesion after 7 to 20 days tumor injection. After implantation of tumor cells, the mice were randomized and divided into vehicle control, dEpoB and Fludelone treatment groups. The dose of both dEpoB and Fludelone was 20 mg/kg, and the drugs were administered by intraperitoneal route. The average number of dose was 10 for dEpoB and 12 for Fludelone during the first 30 days of treatment. In addition, five doses of Velcade (6.25 ug/mouse, i.v) were administered in 3 out of 7 mice initially treated with Fludelone between 35 to 45 days. The results showed that myeloma mice treated with Fludelone had significantly decreased tumor burden evaluated by bioluminescence imaging versus mice treated with dEpoB and controls. All control mice died within 30 days after initiation of treatment, however, Fludelone treated mice had at least doubled the survival time than controls. There was no difference in survival between control and dEpoB treated mice. In combination with the proteasome inhibitor, Velcade, the tumors localized in vertebrate column and femurs can be greatly reduced, indicating that this combination can attack myeloma cells even under marrow microenvironment protection.

Previous data has shown that myeloma cells treated with epothilones exhibited typical apoptosis characteristics. It is not clear whether caspase is involved in this process. Firstly, we investigated the activation of caspase 3, an effector caspase in the caspase pathway, in myeloma cells, by Western blot. With either dEpoB or Fludelone treatment, the myeloma cells showed increased 17 kd cleaved caspase 3, which correlates with its activity. Immunohistochemical staining of CAG myeloma cells using antibody specific to cleaved caspase-3 was used to show cytoplasmic and perinuclear localization features in apoptotic cells. These data confirmed that caspase was activated in epothilone treated cells. Secondly, we attempted to assay the activity of caspase 8 and 9, initiator caspase in the caspase pathway, by fluorometric method. Again both caspase 8 and 9 activities were found to be increased in myeloma cells. Note that increased caspase 9 activity was more prominent than caspase 8. The signals triggering the activation of caspase 8 or 9 are actively under investigation.

Drug cytotoxicity to hematopoietic stem cells is always a major concern. Human CD34+ stem cells were isolated from umbilical cord blood and incubated with either dEpoB or Fludelone alone for 24 hours. After washing out the drugs, apoptosis assays and 2 weeks progenitor assays were performed to evaluate the influence of epothilone to stem cells. Our data shows that there is no significant toxicity of dEpoB or Fludelone on non-cycling stem cells.

Example 16

(E)-9,10-Dehydroepothilones: A New Class of Microtubule Stabilizing Antitumor Agents with Highly Promising Characteristics in Murine Xenograft Models The synthesis of 26-$F_3$-[16]dEpoB (2) containing the usual 16-membered ring can be accomplished via a highly convergent strategy, related to that employed in the synthesis of 27-$F_3$-[17]ddEpoB (19). This strategy envisioned the formation of a E-9,10-olefin via a ring-closing metathesis reaction shown below (For an early instance of macrocyclization in a complex setting via a RCM see: Sinha, S. C.; Sun, J. *Angew. Chem. Int. Ed.* 2002, 41, 1381; incorporated herein by reference). We anticipated that chemoselective reduction of the E-9,10-olefin of 28 and 29 would furnish dEpoB (1) and the desired 26-$F_3$-dEpoB (2). The RCM precursor would be prepared by the union of the two fragments (21 or 24) and 123 through an esterification reaction. Coupling partner 123 would be constructed by deletion of the methylene spacer group (found in our earlier routes cf. compound 18) between the secondary methyl group at C8. As noted above, the in vitro level findings with the 17-membered epothilones containing the skipped diene arrangement (see 18), underscored the need for a corresponding investigation of the biological consequences of such a diene in the familiar 16-membered lactone setting. Given the presence of the cis 12,13-olefin in a dEpoB context, such a skipped diene would necessarily contain a 9,10-double bond.

Retrosynthesis of the 9,10-dehydroepothilones and 26-$F_3$-dEpoB

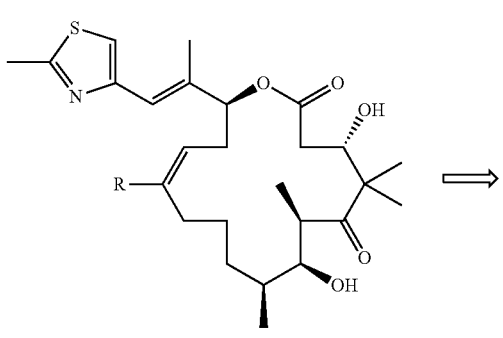

R = Me, dEpoB (1)
R = $CF_3$, 26-$F_3$-dEpoB (2)

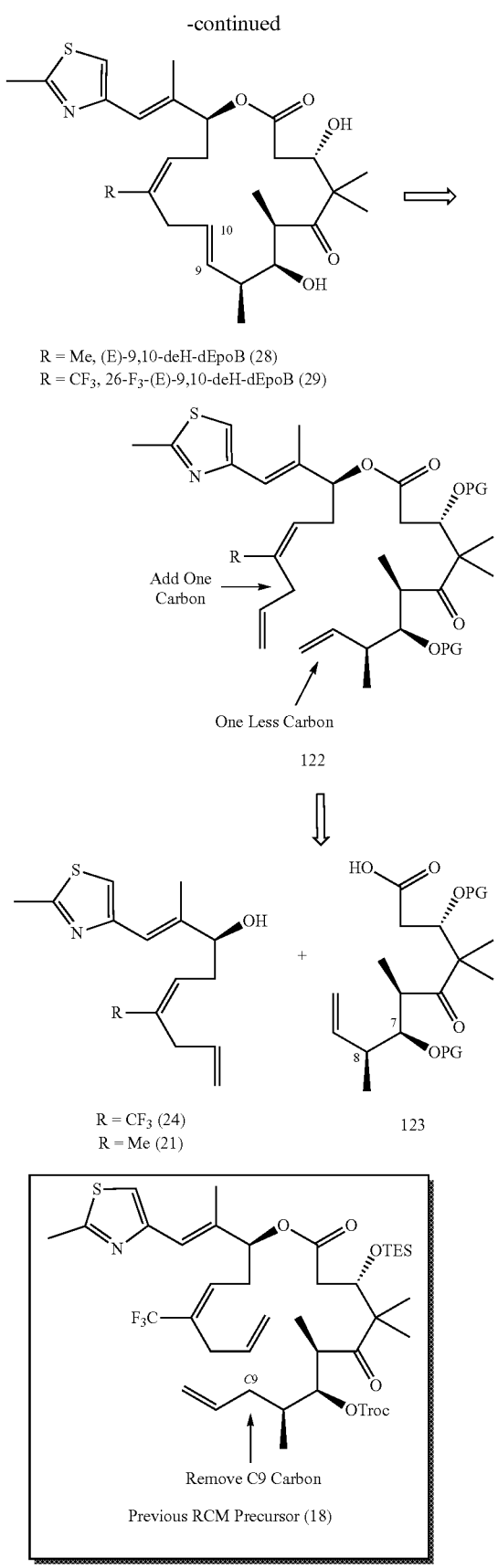

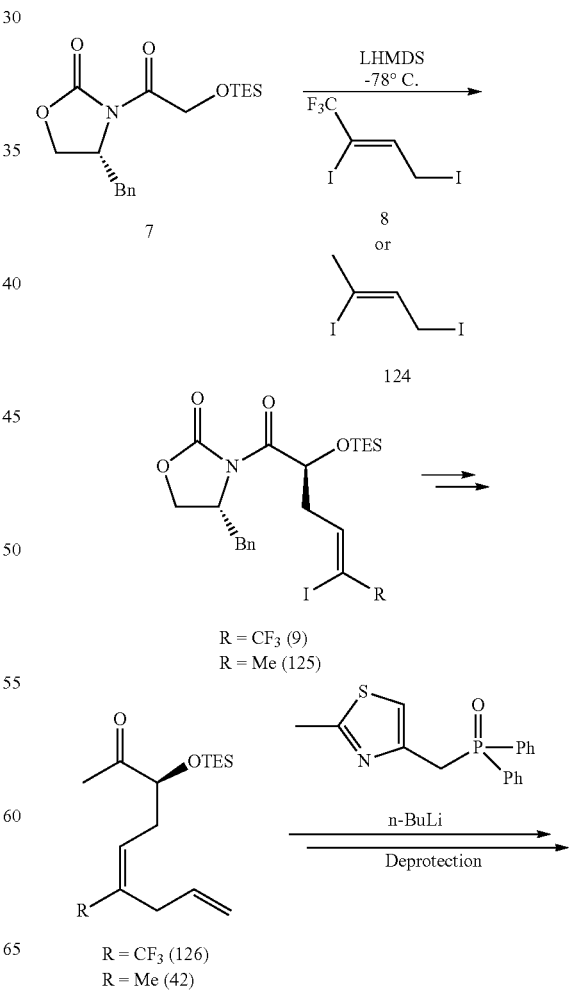

Alkylation of the oxazolidinone 7 (Lee, C. B.; Wu, Z.; Zhang, F.; Chappell, M. D.; Stachel, S. J.; Chou, T.-C., Guan, Y.; Danishefsky, S. J., *J. Am. Chem. Soc.* 2001, 123, 5249; incorporated herein by reference) with the readily synthesized trifluoro and methyl allyl iodides (8 and 124, respectively) allowed for the C15 stereo center to be set in the appropriate absolute configuration[t] with high diastereomeric access, (see products 9 or 125). The latter were converted to their corresponding Weinreb amides (Nahm, S.; Weinreb, S. M.; *Tetrahedron Lett.* 1981, 22, 3815; Levin, J. I.; Turos, E.; Weinreb, S. M. *Synth. Commun.* 1982, 12, 989; each of which is incorporated herein by reference) and thence to 126 and 42 en route to 24 and 21 by nucleophilic methylation (MeMgBr) and appropriate Horner Wittig olefinations (Lythgoe, B.; Nambudiry, M. E. N.; Ruston, S.; Tideswell, J.; Wright, P. W.; *Tetrahedron Lett.* 1975, 40, 3863; Lythgoe, B. *Chem. Soc. Rev.* 1981, 449; Toh, H. T.; Okamura, W. H. *J. Org. Chem.* 1983, 48, 1414; Baggiolini, E. G.; Iacobelli, J. A.; Hennessy, B. M.; Batcho, A. D.; Sereno, J. F.; Uskokovic, M. R. *J. Org. Chem.* 1986, 51, 3098; each of which is incorporated herein by reference). While the use of such oxazolidinones as chiral auxiliaries had been pioneered by Evans and associates (Evans, D. A.; Morrissey, M. M.; Dorow, R. L. *J. Am. Chem. Soc.* 1985, 107, 4346; Paterson, I.; Bower, S.; McLeod, M. D. *Tetrahedron Lett.* 1995, 36, 175; each of which is incorporated herein by reference), its application to the synthesis of optically defined glycolates by alkylation (rather than by hydroxylation) had not been developed.

Synthesis of Fragments 21 and 24

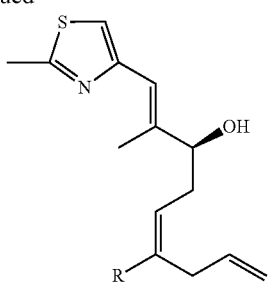

R = CF₃ (24)
R = Me (21)

The synthesis of the polypropionate fragment 25 was enabled by two critical aldol reactions, which established the relative configuration of the C3, C6, and C7 stereocenters. The first aldol reaction involved reaction of the Z-enolate of the ethyl ketone 30 with Roche aldehyde 31 (Cohen, N; Eichel, W. F.; Lopresti, R. J.; Neukom, C.; Saucy, G. *J. Org. Chem.* 1976, 41, 3505; Nagaoka, H.; Kishi, Y.; *Tetrahedron* 1981, 37, 3873; Roush, W. R.; Palkowitz, A. D.; Ando, K. *J. Am. Chem. Soc.* 1990, 112, 6348; each of which is incorporated herein by reference) to provide the desired 32 with high diastereoselectivity. Recourse to 31, allowed by this synthesis, is a significant advantage over the use of earlier aldehydes which required resolution for the attainment of enantiomerically pure starting materials.

Protection of the C7-alcohol followed by hydrolysis of the acetal provided the desired aldehyde 34 and set the stage for the second aldol reaction. Reaction of 34 with Duthaler's DAG (diacetone glucose) Ti-enolate (Duthaler, R. O.; Herold, P.; Lottenbach, W.; Oretle, K.; Reidiker, M. *Angew. Chem. Int. Ed. Engl.* 1989, 28, 495; incorporated herein by reference) afforded the desired hydroxy tert butyl ester 35 with very high (>95%) diastereoselectivity. The latter was then converted to the desired acid 25 in straightforward steps.

Synthesis of Acid 25

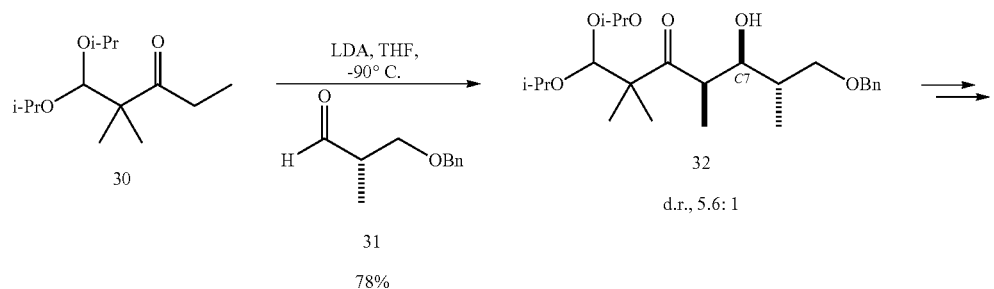

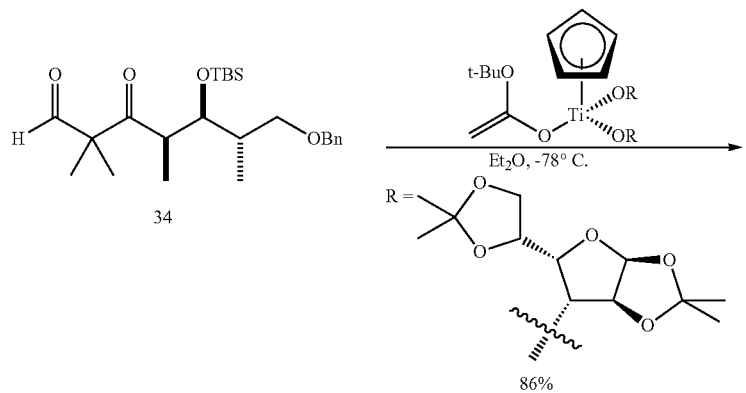

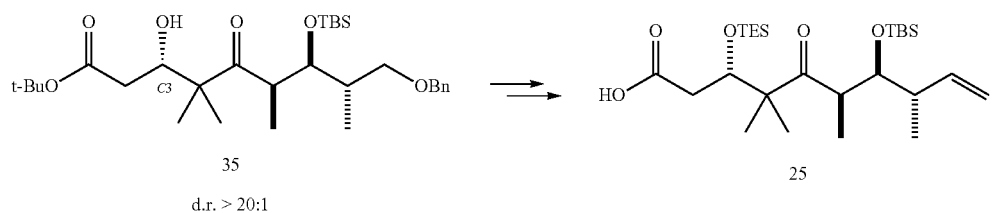

The allylic alcohols 24, 21, and the $C_1$-$C_9$ acid fragment 25 were united through an EDCI esterification protocol, thus providing the RCM precursors 26 and 27, respectively. Ring-closing metathesis reactions of 26 and 27 were carried out using an RCM catalyst (Scholl, M.; Trnka, T. M.; Morgan, J. P.; Grubbs, R. H. *Tetrahedron Lett.* 1999, 40, 2247; Grubbs, R. H.; Miller, S. J.; Fu, G. C. *Acc. Chem. Res.* 1995, 28, 446; Trnka, T. M.; Grubbs, R. H. *Acc. Chem. Res.* 2001, 34, 18; *Alkene Metathesis in Organic Chemistry Ed.*: Fürstner, A.; Springer, Berlin, 1998; Fürstner, A. *Angew. Chem. Int. Ed. Engl.* 2000, 39, 3012; Schrock, R. R. Top. *Organomet. Chem.* 1998, 1, 1; each of which is incorporated herein by reference) in toluene. These reactions did indeed provide the trans isomers 39a and 40a. However, the major products were 39b and 40b which had arisen from the obvious alternate RCM pathway. These unwanted RCM isomers predominated over the desired 39a and 40a by ratios of ca. 3:1. Finally, deprotection of the silyl ethers of 39a and 40a with HF-pyridine led to the desired E-9,10-dehydro-epothilones 28 (White, J. D.; Carter, R. G.; Sundermann, K. F.; Wartmann, M. *J. Am. Chem. Soc.* 2001, 123, 5407; White, J. D.; Carter, R. G.; Sundermann, K. F.; Wartmann, M. *J. Am. Chem. Soc.* (Addition/Correction) 2003, 125, 3190; each of which is incorporated herein by reference. With compound 28 of rigorously proven structure in hand, we were surprised to find that its spectral properties were not congruent with those previously reported for a compound presumed to be the same entity. The actual structure of the compound previously assigned as 28 has now been re-evaluated. In retrospect, it is clear that 28 had not been previously prepared and, in fact the whole family of (E)-9,10-dehydroepothilones reported here is a new genus.) and 29. As planned, the latter were converted to dEpoB (1) and 26-trifluoro-dEpoB (2) via diimide reduction of the E-9,10-olefin (Corey, E. J.; Mock, W. L.; Pasto, D. J. *Tetrahedron Lett.* 1961, 347; Pasto, D. J.; Taylor, R. T. *Org. React.* 1991, 40, 91; each of which is incorporated herein by reference).

By corresponding methodology, we synthesized the 9,10-dehydro-dEpoF (57) see below. The selective di-imide reductions of the E-9,10-olefins validated the structures of the various synthetic intermediates described above, thereby prompting re-evaluation of previous assignments in the literature.

Synthesis of 9,10-Dehydroepothilones

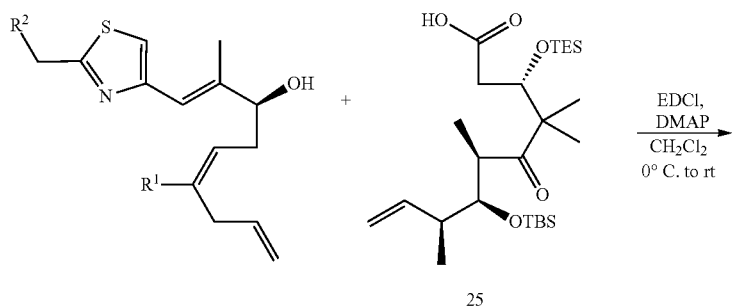

21 ($R^1$ = $CF_3$, $R^2$ = H), 24 ($R^1$ = Me, $R^2$ = H),
53 ($R^1$ = Me, $R^2$ = OTBS)

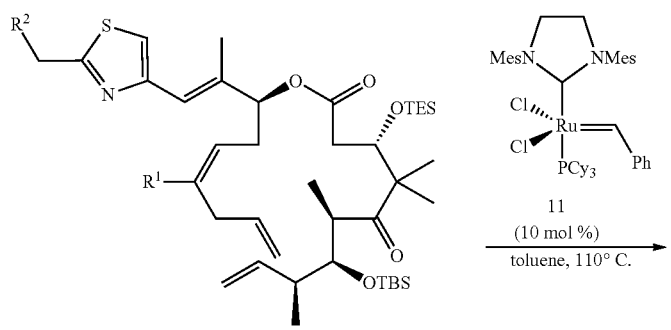

26 ($R^1$ = Me, $R^2$ = H, 79%)
27 ($R^1$ = $CF_3$, $R^2$ = H, 70%)
54 ($R^1$ = Me, $R^2$ = OTBS, 92% from ester)

-continued

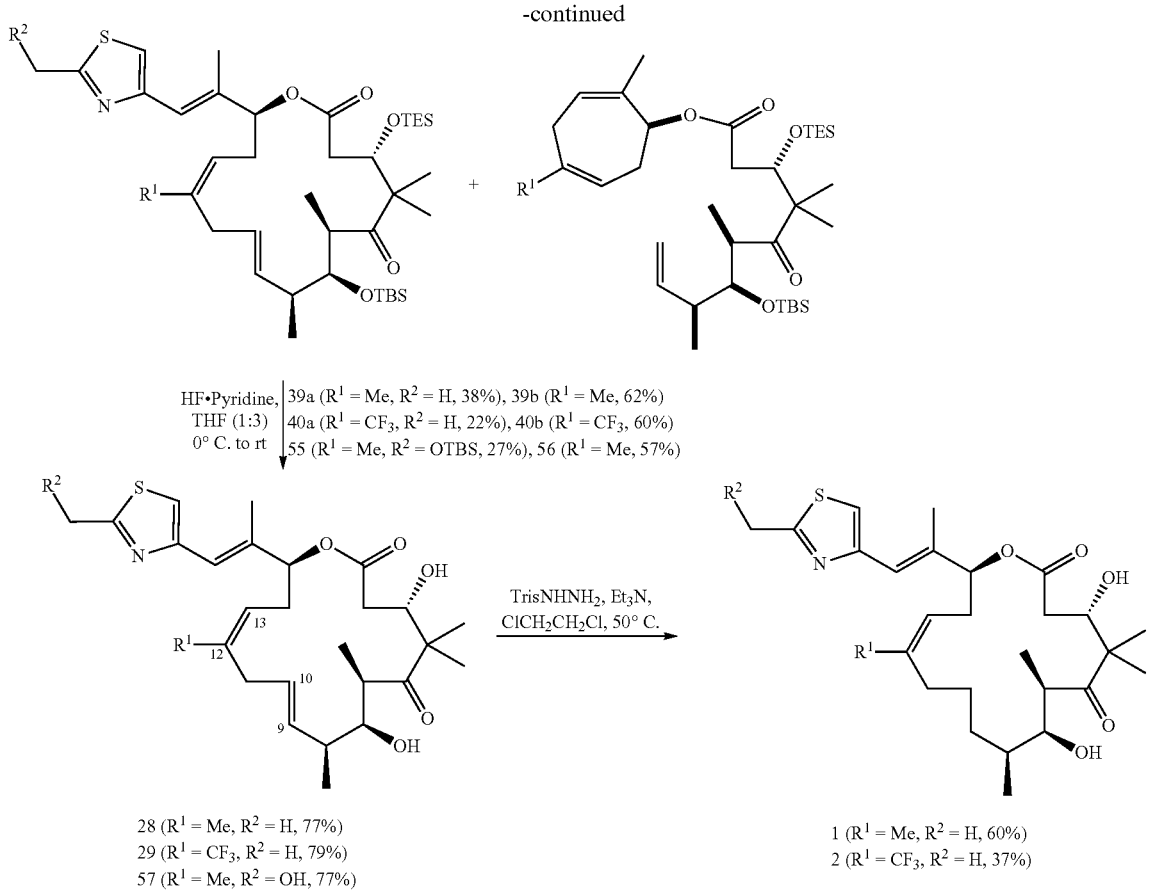

Examination of synthetic analogs (28, 29, and 57), in cell culture settings (see Supplemental Edition), revealed them to exert stronger inhibitory effects on various sensitive and MDR tumor cell lines than are exhibited by our current clinical candidate, dEpoB (1). The impressive cell growth inhibition exhibited by epothilones 28, 29, and 57 across a range of various drug-resistant tumors, prompted determination of the blood plasma stability of these new (E)-9,10 congeners. We recall that (E)-10,11-dehydro-dEpoB (Epo490) exhibits very poor plasma stability. Indeed, it was this plasma instability which had blocked further development of Epo490 (6). By contrast, on exposure of 28, 29, and 57 to murine plasma, we observed a much slower drug degradation as compared to dEpoB (1) (by a factor of ca. 7). This stability constitutes a substantial advance, from a drug availability perspective, relative to dEpoB (1), not to speak of epo 490 (6). Based on the preliminary cell culture and pharmacokinetic data of the (E)-9,10-dehydro derivatives 28 and 29, it would be appropriate to advance them for in vivo investigations. Such studies are, of course, rather more intensive of drug availability than in vitro measurements (Rivkin, A.; Yoshimura, F.; Gabarda, A. E.; Chou, T.-C.; Dong, H.; Tong, W. P.; Danishefsky, S. J. *J. Am. Chem. Soc.* 2003, 125, 2899; Chou, T.-C.; Dong, H.; Rivkin, A.; Yoshimura, F.; Gabarda, A. E.; Cho, Y. S.; Tong, W. P.; Danishefsky, S. J., *Angew. Chem., Int. Ed.* 2003, 42, 4761-4767; Yoshimura, F.; Rivkin, A.; Gabarda, A. E.; Chou, T. C.; Dong, H.; Sukenick, G.; Danishefsky, S. J., *Angew. Chem., Int. Ed.* 2003, 42, 2518-2521; each of which is incorporated herein by reference. For recent examples of alternative potent epothilone analogs, see: K. H. Altmann, G. Bold, G. Caravatti, A. Flörsheimer, V. Guagnano, M. Wartmann, *Bioorg. Med. Chem. Lett.* 2000, 10, 2765; K. C. Nicolaou, R. Scarpelli, B. Bollbuck, B. Werschkun, M. M. A. Pereira, M. Wartmann, K.-H. Altmann, D. Zaharevitz, R. Gussio, P. Giannakakou, *Chem. Biol.,* 2000, 7, 593; each of which is incorporated herein by reference).

This requirement, and indeed the possible eventual need to prepare multigram quantities of 9,10-dehdyro derivatives for further development, prompted a significant reassessment of our total synthesis route. Of course, the single most serious problem was that the RCM reaction on 26, 27, and 54 which produced 39b, 40b, and 56 only as minor products. The major pathway involved an RCM reaction which was strictly confined to the O-alkyl sector of 26, 27, and 54, leading primarily to the undesired 39b and 40b. Accordingly, it was decided to attempt to defer introduction of the thiazole (by olefination) subsequent to the RCM (vide infra).

With eventual processiblity in multigram scales as our goal, the syntheses of the alkyl and acyl fragments entering into the RCM reaction were re-structured. Compound 86 was readily synthesized as shown. It was used to alkylate oxazolidinone 7 in high diastereomeric excess. Following deprotection of the OTES group, and nucleophilic methylation, compound 90 was in hand. This α-hydroxyketone would serve as the acyl group acceptor in formation of the central ester to prepare the all critical RCM. An obvious concern was the possible vulnerability of such a hydroxyketone as an acyl acceptor to partial racemization or diversion to regioisomeric α-ketols.

Processible Synthesis Fragment 90

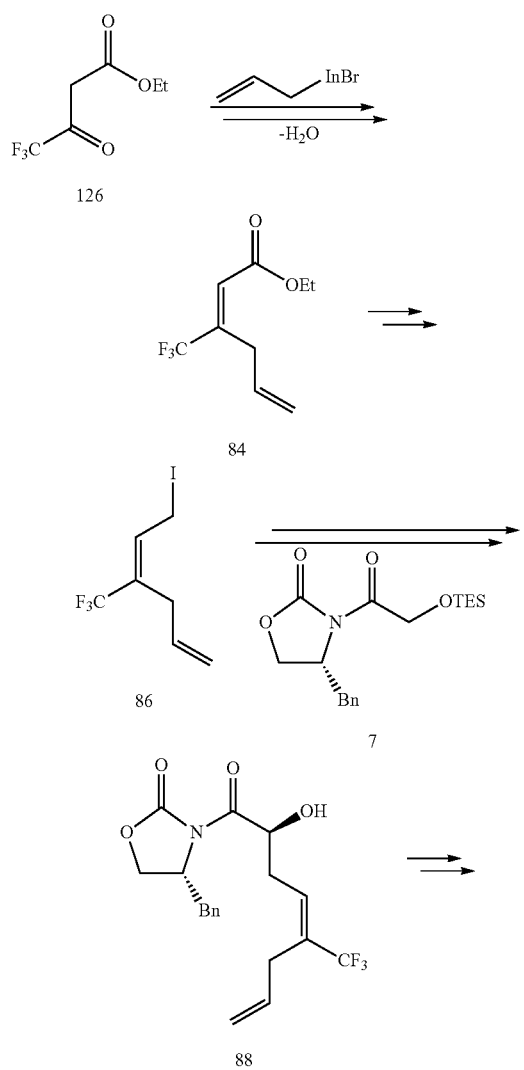

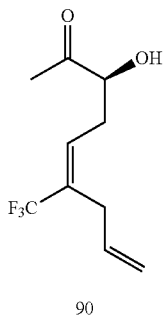

A serious problem in our earlier synthesis of the acid fragment 25 was the very expensive and technically demanding Duthaler chemistry (Duthaler, R. O.; Herold, P.; Lottenbach, W.; Oretle, K.; Reidiker, M. *Angew. Chem. Int. Ed. Engl.* 1989, 28, 495; incorporated herein by reference) to generate the desired S stereochemistry at the C3. To circumvent this problem, the aldol reaction was carried out without any chiral auxiliary to provide a 1:1 mixture of the corresponding β-hydroxy ketone. Reagent controlled asymmetric reduction of the derived keto function (see compound 69), using Noyori conditions (Noyori, R.; Ohkuma, T.; Kitamura, M.; Takaya, H.; Sayo, N.; Kumobayashi, H.; Akutagawa, S. *J. Am. Chem. Soc.* 1987, 109, 5856; incorporated herein by reference) generated the desired S stereochemistry at the C3 in high diastereomeric excess. The now available β-hydroxy ester 70 was transformed to acid 25 in several steps following earlier protocols (Chou, T. C.; O'Connor, O. A.; Tong, W. P.; Guan, Y.; Zhang, Z.-G.; Stachel, S. J.; Lee, C.; Danishefsky, S. J. *Proc. Natl. Acad. Sci. U.S.A.* 2001, 98, 8113; incorporated herein by reference).

Processible Synthesis of Acid 25

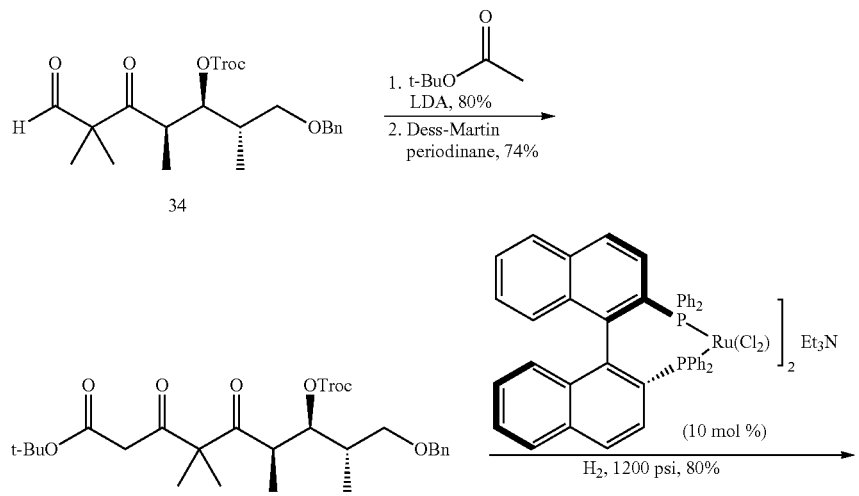

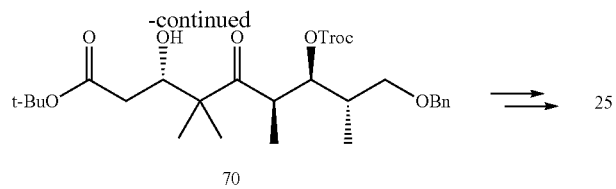

Remarkably, esterification of the resultant hydroxyketones 43 and 44 with the C$_1$-C$_9$ acid fragment 25 provided the corresponding RCM cyclization precursors 45 and 46 without noticeable racemization at C15, or loss of integrity of the initial α-ketol linkage. The ring-closing metathesis reaction of 45 and 46 was carried out using an RCM catalyst (Scholl, M.; Trnka, T. M.; Morgan, J. P.; Grubbs, R. H. *Tetrahedron Lett.* 1999, 40, 2247; Grubbs, R. H.; Miller, S. J.; Fu, G. C. *Acc. Chem. Res.* 1995, 28, 446; Trnka, T. M.; Grubbs, R. H. *Acc. Chem. Res.* 2001, 34, 18; *Alkene Metathesis in Organic Chemistry* Ed.: Fürstner, A.; Springer, Berlin, 1998; Fürstner, A. *Angew. Chem. Int. Ed. Engl.* 2000, 39, 3012; Schrock, R. R. *Top. Organomet. Chem.* 1998, 1, 1; each of which is incorporated herein by reference) in toluene. This reaction, now uncomplicated by alternate metathesis pathways, provided exclusively the trans isomers 47 and 48 in high yields. Installation of the thiazole moiety via a Wittig reaction proceeded with high E/Z selectivity and yield, to provide 28 and 29 following deprotection of the two silyl ethers (Hindupur, R. M.; Panicker, B.; Valluri, M.; Avery, M. A. *Tetrahedron Lett.* 2000, 2, 7341; incorporated herein by reference. Attempts to apply Avery's protocol for the installation of the thiazole gave the desired product in low yield and with poor E/Z selectivity). This route now meets the standards of amenability toward large scale synthesis.

We considered whether the incorporation of C9-C10 olefin in epothilone B (51, EpoB) would alter its biological profile in the same direction as was the case with its 12,13 desoxy counterparts. Toward this end, we studied the epoxidation of 28 with 2,2'-dimethydroxirane (DMDO). The reaction indeed proceeded with high chemoselectively at the more substituted C12-C13 olefin. There was obtained an 87% yield of a 1:2.6 ratio of the (E)-9,10-dehydroepothilone B (49) and its diastereomer bearing the α-12,13-oxirane (structure not shown). In vitro studies with 49 (whose configurations at C12 and C13 was established by its reduction to afford Epo B) revealed it to be roughly 2-4 fold more potent than the parent EpoB (51) in various cell lines. While compound 49 proved to be the most potent epothilone we encountered in our program, its narrow therapeutic index in xenografts, as well as its difficult accessibility (vide supra) served to discourage further its pre-clinical development. Interestingly, the unnatural α-oxirane was virtually devoid of activity.

Processible Synthesis of
(E)-9,10-Dehydroepothilones

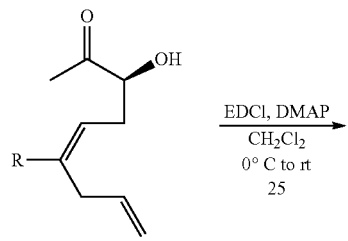

43, R = Me, 83%
44, R = CF$_3$, 76%

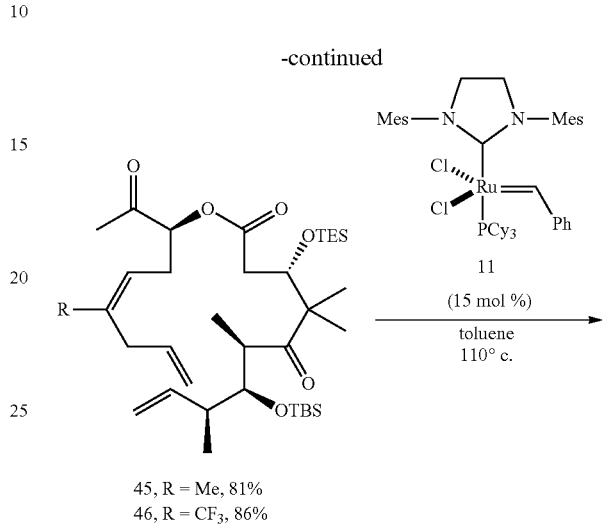

45, R = Me, 81%
46, R = CF$_3$, 86%

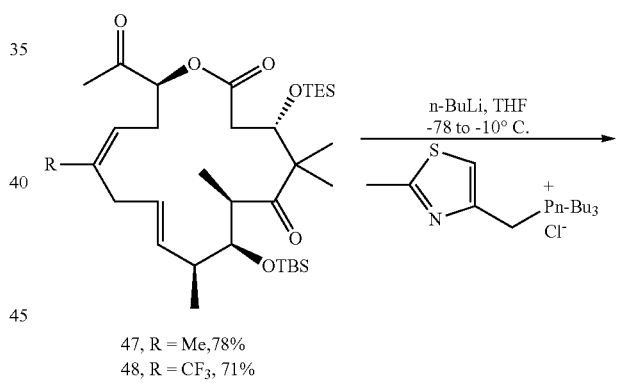

47, R = Me, 78%
48, R = CF$_3$, 71%

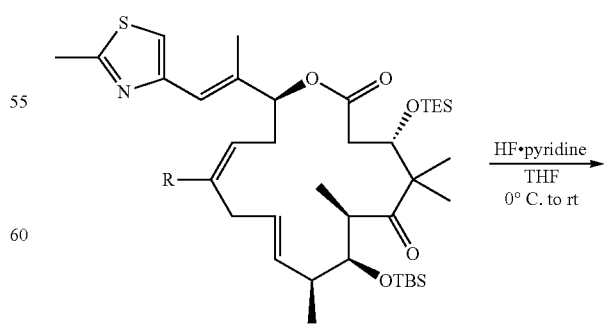

39a, R = Me, 76%
40a, R = CF$_3$, 70%

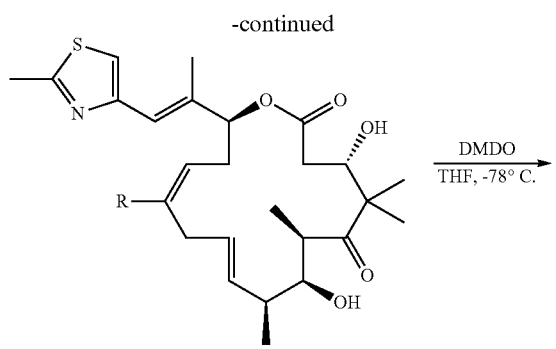

28, R = Me, 97%
29, R = CF₃, 98%

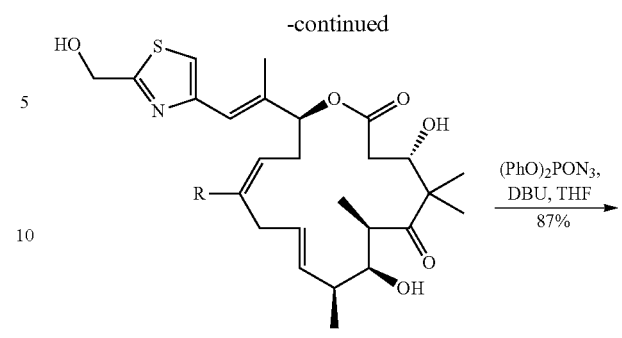

Two Steps:
R = Me, 54%, 57
R = CF₃, 71%, 59

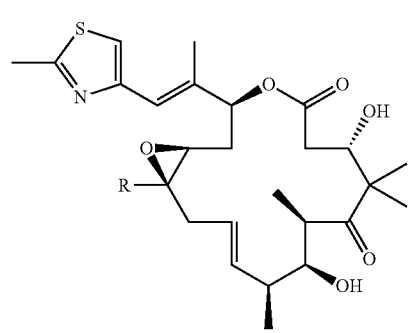

49, R = Me, 24%
+α isomer, 63% (major)

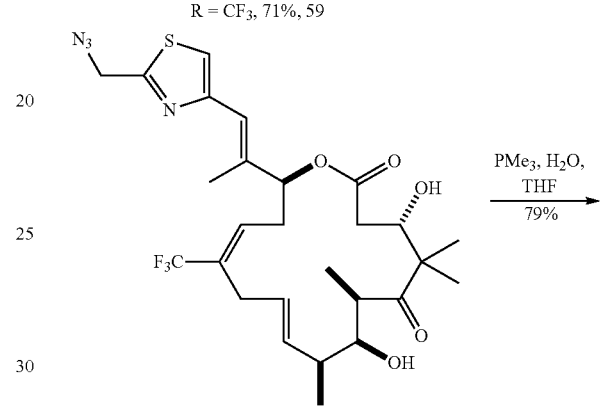

94

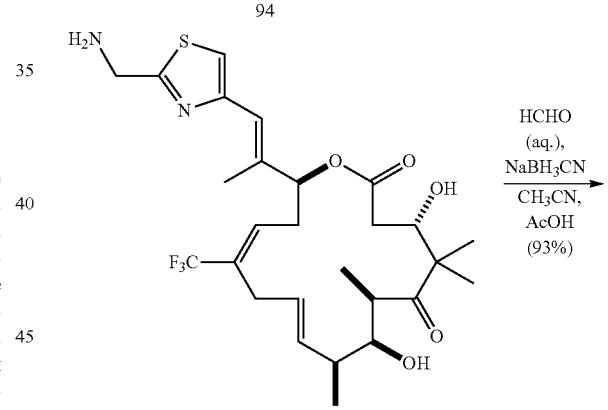

96

Another advantage of the restructured (second generation) synthesis, described above is that a variety of heterocycles can be installed via ketone intermediates 39a and 40a. This point is well highlighted by the synthesis of 9,10-dehydro-dEpoF. Wittig reaction of the ketone with the appropriate phosphonium ylides afforded the desired 9,10-dehydro-dEpoF compounds 57 and 59 in high yield and with high E/Z selectivity. Furthermore, we were able to efficiently convert the 21-hydroxy 59 to derivatives of the type 96 and 97, containing amino functionality at C21 in several steps as shown below.

Diversification of C-21 of
(E)-9,10-Dehydroepothilones

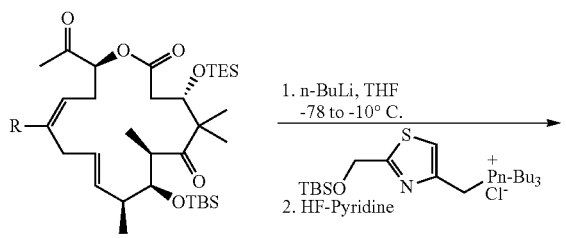

R = Me, 47
R = CF₃, 48

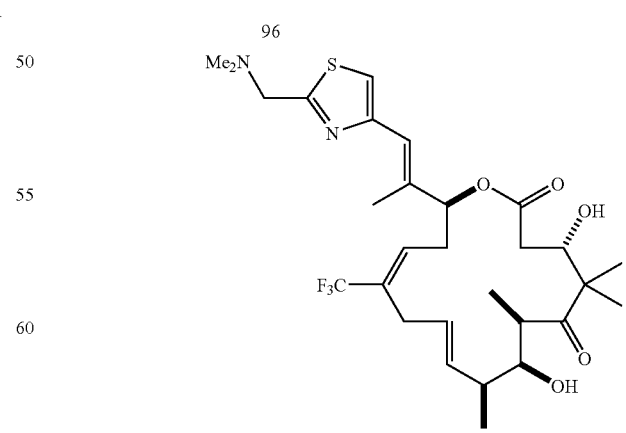

97

The fully synthetic epothilone analogs have been evaluated against a variety of cell types to determine their antitumor potential.

The most salient features of our findings, are as follow: One can expect a loss of ca. an order of magnitude in replacement of the C12-C13 β-epoxide by a E-12,13 double bond (compare EpoB and dEpoB in the sensitive CCRF-CEM cell line). Another expectation, is that inclusion of an E-9,10 double bond, in addition to the Z12,13-olefin leads to a significant increase in cytotoxicity across several cell lines.

Still another instructive trend was seen in comparing 12-trifluoro-E-9,10-dehydro-dEpoB (29) (Fludelone), with the corresponding E-9,10-dehydro compound 28. Inclusion of the three fluorine atoms at C26, attenuates cytotoxicity by up to a factor of 4, relative to (1). This attenuation effect of the 12-trifluoromethyl function is also seen in compounds lacking the 9,10-unsaturation (compare dEpoB (1) and 12-trifluoro-dEpoB (2)).

Given these data, and given the accessibility of these 9,10-dehydro compounds (including 12-trifluoro congeners) through chemical synthesis, we were in a position to initiate in vivo experiments on our most promising compounds. We describe here some particularly striking and promising results with compound 29 (Fludelone), which has emerged as a most exciting possibility for advancement to clinical evaluation. In vivo experiments were carried out using human tumor xenografts in immunodeficient nude mice. For all their imperfections, such models in oncology are widely used in evaluating (Fiebig, H. H.; Berger, D. P.; Preclinical Phase II trials. In: Boven, E. and Winograd, B., Editors, *The Nude Mouse in Oncology Research*, CRC Press, Boca Raton (1995), 318; incorporated herein by reference) the potential of anti-tumor lead compounds en route to clinical development.

Remarkably, treatment of MX-1 xenografts with 30 mg/kg dosages of Fludelone, resulted in complete tumor disappearance and the absence of any relapse for over two months after suspension of treatment (See FIG. 83A). Most importantly, these therapeutic successes can be achieved either by 6 hr-i.v. infusion or by oral administration (See FIGS. 83B and 87A). On the other hand, treatment of the MX-1 xenografts by oral administration of taxol did not affect the tumor (See FIGS. 83B and 87A). It goes without saying that if translatable to the human clinical setting, achievement of oral activity could be of significant advantage.

Taxol-resistant tumor xenografts (FIG. 84A) as well as human colon carcinoma (HCT-116, FIG. 86A) can also be cured with Fludelone by i.v. infusion. The experiments using human mammary carcinoma (MX-1) and human colon carcinoma (HCT-116) xenografts in nude mice lasted 6.0 and 6.6 months, respectively. There was no tumor relapse in either experiment during 4.3 and 5.3 months, respectively, following the cessation of treatment. For the HCT-116 experiment, taxol and Fludelone were compared at 20 mg/kg and both achieved tumor disappearance. The taxol treated group, relapsed 1.1 months after treatment was discontinued, whereas Fludelone-treated animals were tumor free for over 5.3 months.

These results have involved a particularly long and thorough therapeutic study using xenografts and report remarkably long periods of complete remission with parenteral or oral administration of a single antitumor agent.

Experimentals

General Pharmacology Methods:

Tumor and Cell Lines. The CCRF-CEM human lymphoblastic leukemia cells and their vinblastine resistant subline (CCRF-CEM/VBL$_{100}$, 720-fold resistance) were obtained from Dr. William Beck of the University of Illinois, Chicago, and CCRF-CEM/Taxol (44-fold resistance in vitro) were produced by exposing CCRF-CEM cells to increasing sublethal concentration (IC$_{50}$-IC$_{90}$) of paclitaxel during the six months. Human mammary carcinoma (MX-1), human lung carcinoma cells (A549) and human colon carcinoma (HCT-116) cells were obtained from American Type Culture Collection (ATCC, Rockville, Md.).

Animals. Athymic nude mice bearing the nu/nu gene were obtained from NCI, Frederick, Md. and used for all human tumor xenografts. Except otherwise indicated for the female nude mice, male nude mice 6 weeks or older weighing 20-22 g or more were used. Drugs were administered via the tail vein for 6 hours by iv infusion using a homemade infusion mini-catheter and restrainer. A programmable Harvard PHD2000 syringe pump with multitrack was used for the iv infusion. A typical 6 hr infusion volume for each drug in Cremophor/ethanol (1:1) was 100 µl in 2.0 ml of saline. For oral administration, both Fludelone and Taxol were dissolved in ethanol and diluted 5-fold with Tween-80. The Taxol solution should be used within 5 min to avoid precipitation. Tumor volume was assessed using a caliper to measure the length×width×height (or width). For tumor-bearing nude mice, the body weight during the course of experiment refers to the total weight minus the weight of the tumor. All animal studies were conducted in accordance with the guidelines for the National Institute of Health Guide for the Care and Use of Animals and the protocol approved by the Memorial Sloan-Kettering Cancer Center's Institutional Animal Care and Use Committee.

Cytotoxicity Assays. In preparation for in vitro cytotoxicity assays, cells were cultured at an initial density 2-5×10$^4$ cells per milliliter. They were maintained in a 5% CO$_2$-humidified atmosphere at 37° C. in RPMI medium 1640 (GIBCO/BRL) containing penicillin (100 units/mL), streptomycin (100 µg/mL, GIBCO/BRL), and 5% heat-inactivated FBS. For solid tumor cells growing in a monolayer (such as HCT-116 and A549), cytotoxicity of the drug was determined in 96-well microtiter plates by using the sulforhodamine B method (Skehan, P.; Storeng, R.; Scudiero, D.; Monks, A.; McMahon, J.; Vistica, D.; Warren, J. T.; Bokesch, H.; Kenney, S.; Boyd, M. R. *J. Natl. Cancer Inst.* 1990, 82, 1107; incorporated herein by reference). For cells grown in suspension (such as CCRF-CEM and its sublines), cytotoxicity was measured, in duplicate, by using the 2,3-bis-(2-methoxy-4-nitro-5-sulfophenyl)-5-carboxanilide)-2H-terazodium hydroxide (XTT) microculture method (Scudiero, D. A.; Shoemaker, R. H.; Paull, K. D.; Monks, A.; Tierney, S.; Nofziger, T. H.; Currens, M. J.; Seniff, D.; Boyd, M. R. *Cancer Res.* 1988, 48, 4827; incorporated herein by reference) in 96-well microtiter plates. For both methods, the absorbance of each well was measured with a microplate reader (Power Wave XS, Bio-Tek, Winooski, Vt.). Dose-effect relationship data from 6 to 7 concentrations of each drug, in duplicate, were analyzed with the median-effect plot by using a computer program (Chou, T.-C. & Talalay, P. T. *Adv. Enzyme Reg.* 1984, 22, 27; Chou, T.-C. & Hayball, M. *CalcuSyn for Windows* (Biosoft, Cambridge, U.K.) (1997); each of which is incorporated herein by reference).

General Chemical Methods: Reagents obtained from commercial suppliers were used without further purification unless otherwise noted. The following solvents were obtained from a dry solvent system (passed through a prepacked column of alumina) and used without further drying: tetrahydrofuran, methylene chrolide, diethyl ether, benzene, and toluene. Triethylamine, N,N-diisopropylethylamine, diisopropylamine, pyridine, and 2,6-lutidine were distilled from calcium hydride. All air and water sensitive reactions were performed in flame-dried glassware under a positive pressure of prepurified nitrogen gas or argon gas. NMR ($^1$H and $^{13}$C) spectra were recorded on Bruker AMX-400 MHz or Bruker Advance DRX-500 MHz as noted individually, referenced to CDCl$_3$ (7.27 ppm for $^1$H and 77.1 ppm for $^{13}$C) Infrared spectra (IR) were obtained on a Perkin-Elmer FT-IR model 1600 spectrometer. Optical rotations were obtained on a JASCO model DIP-370 digital polarimeter. Low resolution (electrospray) mass spectra were recorded on PE SCIEX API 100. Analytical thin-layer chromatography was performed on E. Merck silica gel 60 F254 plates. Compounds which were not UV active were visualized by dipping the plates in ethanolic para-anisaldehyde solution, ethanolic phosphomolybdic acid, or ceric ammonium molybdate or and heating. Preparative thin layer chromatography was performed using the indicated solvent on Whatman® (LK6F Silica gel 60A) TLC plate. Silica gel chromatography was performed using the indicated on Davisil® (grade 1740, type 60A, 170-400 mesh) silica gel.

Chemical shifts are reported in δ values relative to chloroform (δ 7.24 for proton and δ 77.0 for carbon NMR).

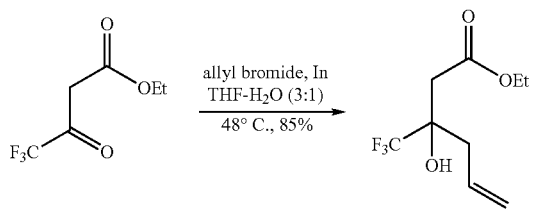

To a solution of ethyl 4,4,4-trifluoroacetoacetate (24.0 mL, 0.164 mol) in THF-water (3:1=V:V, 320 mL) at room temperature was added allyl bromide (20.0 mL, 1.4 equiv) followed by indium (powder, ~100 mesh, 25 g, 1.3 equiv) and the resulting mixture was stirred at 48° C. for 15 h. The reaction mixture was cooled to room temperature, quenched with 2 N aq. HCl (400 mL) and extracted with CH$_2$Cl$_2$ (400 mL, 2×200 mL). Combined organics were dried (MgSO$_4$), filtered, and concentrated in vacuo. Flash chromatography (hexanes→hexanes-ether 10:1→8:1→6:1→4:1) gave the alcohol as clear oil (31.64 g, 85% yield): IR (film) 3426 (br m), 2986 (m), 1713 (s), 1377 (m), 1345 (m), 1301 (m), 1232 (m), 1173 (s), 1095 (m), 1023 (m), 927 (m) cm$^{-1}$; $^1$H NMR (400 MHz, CDCl$_3$) δ 5.82 (m, 1H), 5.15 (m, 3H), 4.17 (m, 2H), 2.59 (m, 1H), 2.58 (d, J=3.4 Hz, 2H), 2.29 (dd, J=14.2, 8.6 Hz, 1H), 1.24 (t, J=7.2 Hz, 3H); $^{13}$C NMR (100 MHz, CDCl$_3$) δ 172.08, 130.89, 125.65 (q, J=280 Hz), 120.27, 73.79 (q, J=28 Hz), 61.55, 38.97, 35.65, 13.82; high resolution mass spectrum m/z 227.0895 [(M+H)$^+$; calcd for C$_9$H$_{14}$O$_3$F$_3$: 227.0895].

The alcohol is volatile. After the column chromatography, the alcohol was not completely concentrated. The yield was determined from overall weight and ratio between product and solvents obtained by integration of NMR.

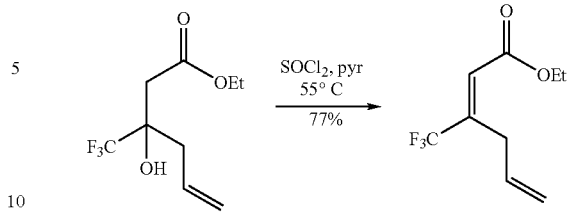

A mixture of alcohol (16.71 g, 0.07386 mol) and pyridine (15.0 mL, 2.5 equiv) was cooled to −10° C. and treated with thionyl chloride (11.3 mL, 2.1 equiv) slowly over 11 min (yellow precipitate). The resulting mixture was warmed to 55° C. (heating at 75° C. for 17 h gave complex mixture of chlorinated products) and stirred for 12 h. The reaction mixture was cooled to −5° C., quenched with water (200 mL) and extracted with CH$_2$Cl$_2$ (2×200 mL, 2×150 mL). Combined organics were washed with saturated NaHCO$_3$ (2×200 mL), and brine (200 mL), dried (MgSO$_4$), and concentrated in vacuo. Flash chromatography (pentane:ether 15:1) afforded the ester (11.90 g, 77% yield) as yellow oil: IR (film) 2986 (w), 1731 (s), 1308 (s), 1265 (w), 1227 (m), 1197 (s), 1133 (s), 1025 (m), 920 (w), 896 (w) cm$^{-1}$; $^1$H NMR (400 MHz, CDCl$_3$) δ 6.36 (s, 1H), 5.79 (ddt, J=16.9, 10.2, 6.6 Hz, 1H), 5.15 (dd, J=17.1, 1.5 Hz, 1H), 5.08 (dd, J=10.0, 1.4 Hz, 1H), 4.22 (q, J=7.1 Hz, 2H), 3.44 (d, J=6.5 Hz, 2H), 1.29 (t, J=7.1 Hz, 3H); $^{13}$C NMR (100 MHz, CDCl$_3$) δ 164.22, 143.37 (q, J=29 Hz), 132.71, 123.21 (q, J=274 Hz), 122.60 (q, J=6 Hz), 117.32, 60.85, 30.54, 13.85; high resolution mass spectrum m/z 209.0788 [(M+H)$^+$; calcd for C$_9$H$_{12}$O$_2$F$_3$: 209.0789].

The ester is volatile. After the column chromatography, the ester was not completely concentrated.

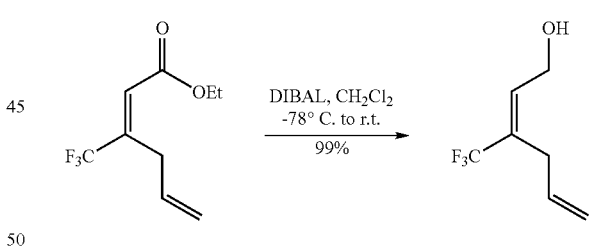

To a cooled (−75° C.) solution of the ester (7.12 g, 0.0342 mol) in CH$_2$Cl$_2$ (120 mL) was added a solution of DIBAL-H (75 mL, 2.2 equiv) in CH$_2$Cl$_2$ (1.0 M) over 35 min and the resulting mixture was warmed to room temperature over 3 h. The reaction mixture was cooled to 0° C., quenched with saturated NH$_4$Cl (12 mL) and stirred at room temperature for 20 min. The reaction mixture was diluted with ether (200 mL), dried (MgSO$_4$), and concentrated in vacuo. Flash chromatography (pentane:ether 3:1→1:1) provided the alcohol (5.68 g, 99%) as clear oil: IR (film) 3331 (br s), 2929 (m), 1642 (m), 1445 (m), 1417 (w), 1348 (s), 1316 (s), 1217 (s), 1175 (s), 1119 (s), 1045 (m), 985 (s), 921 (m), 831 (w) cm$^{-1}$; $^1$H NMR (400 MHz, CDCl$_3$) δ 6.33 (td, J=6.1, 1.6 Hz, 1H), 5.75 (ddt, J=17.2, 10.0, 6.2 Hz, 1H), 5.07 (m, 2H), 4.29 (ddd, J=6.3, 4.3, 2.1 Hz, 2H), 2.95 (d, J=6.2 Hz, 2H); $^{13}$C NMR (100 MHz, CDCl$_3$) δ 134.45 (q, J=6 Hz), 133.38, 127.97 (q, J=29 Hz), 123.76 (q, J=271 Hz), 116.25, 57.87, 29.79

Alcohol 56 is volatile. After the column chromatography, 56 was not completely concentrated.

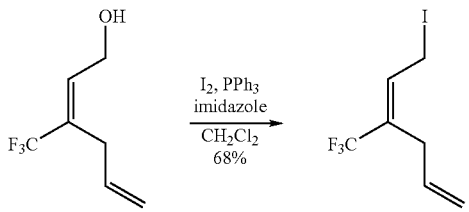

A cooled (0° C.) solution of alcohol (5.97 g, 0.0358 mol) in CH$_2$Cl$_2$ (50 mL) was treated with PPh$_3$ (11.17 g, 1.2 equiv), imidazole (3.55 g, 1.5 equiv) and I$_2$ (9.10 g, 1.1 equiv) (I$_2$ addition was the last) and the resulting (yellow cloudy) mixture was stirred at 0° C. for 10 min. The reaction mixture was quenched with saturated Na$_2$S$_2$O$_3$-saturated NaHCO$_3$ (1:1=V:V, 200 mL) and extracted with pentane (3×200 mL). Combined organice were washed with satureted Na$_2$S$_2$O$_3$-saturated NaHCO$_3$ (1:1=V:V, 200 mL), and brine (100 mL), dried (MgSO$_4$), and concentrated in vacuo. Flash chromatography (pentane) gave the iodide (6.69 g, 68%) as pale red oil (stored in −78° C. feezer): (IR Ifilm) 3083 (w), 2982 (w), 1636 (w), 1558 (w), 1456 (w), 1367 (w), 1317 (s), 1216 (m), 1181 (s), 1151 (s), 1120 (s), 989 (m), 921 (m), 896 (m) cm$^{-1}$; $^1$H NMR (400 MHz, CDCl$_3$) δ 6.45 (td, J=8.9, 1.5 Hz, 1H), 5.79 (ddt, J=16.8, 10.3, 6.2 Hz, 1H), 5.12 (m, 2H), 3.85 (ddd, J=8.9, 2.9, 1.4 Hz, 2H), 3.00 (dt, J=6.1, 1.4 Hz, 2H); $^{13}$C NMR (100 MHz, CDCl$_3$) δ 132.42, 131.64 (q, J=6 Hz), 129.63 (q, J=29 Hz), 123.64 (q, J=272 Hz), 117.00, 29.32, −4.27; low resolution mass spectrum m/z 298.7 [(M+Na)$^+$; calcd for C$_7$H$_8$F$_3$INa: 299.0].

The allyl iodide is volatile. After the column chromatography, the allyl iodide was not completely concentrated.

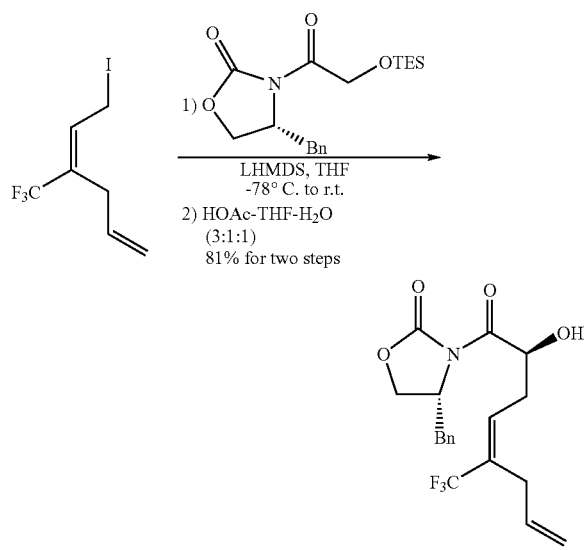

α-Hydroxyoxazolidinone. To a cooled (−78° C.) solution of TES protected 4-benzyl-3-hydroxyacetyl-oxazolidin-2-one (16.28 g, 1.92 equiv) in THF (160 mL) was added a solution of LHMDS (42.0 mL, 1.73 equiv) in THF (1.0 M) dropwise over 51 min and the resulting mixture was stirred at −78° C. for 35 min. The reaction mixture was treated with a solution of the allyl iodide (6.69 g, 24.2 mmol) in THF (10 mL) over 15 min and the resulting mixture was allowed to warm to room temperature slowly overnight. The reaction mixture was quenched with saturated NaHCO$_3$ (200 mL) and extracted with EtOAc (3×200 mL). Combined organics were washed with saturated NH$_4$Cl (150 mL), brine (150 mL), dried (MgSO$_4$), and concentrated in vacuo. Flash chromatography (hexanes-EtOAc 6:1->3:1) provided a mixture of alkylation products (13.6 g) which were used for the next reaction without further purification (diastereomers were not separable at this stage). A solution of the alkylation products in HOAc-water-THF (3:1:1=V:V:V, 200 mL) was stirred at room temperature for 4 h. The reaction mixture was concentrated in vacuo to remove HOAc, quenched with saturated NaHCO$_3$ (400 mL), and extracted with EtOAc (3×200 mL). Combined organics were dried (MgSO$_4$), and concentrated in vacuo. Flash chromatography (hexanes:EtOAc 3:1->2:1) provided the α-hydroxyoxazolidinone (7.55 g, 81% yield for two steps) as clear oil: [α]$_D^{20}$ (25° C.)-48.2° (c 1.08, CHCl$_3$); IR (film) 3486 (br s), 3030 (m), 2983 (s), 2925 (m), 1790 (s). 1682 (s), 1481 (m), 1393 (m), 1360 (m), 1217 (m), 1171 (m), 1113 (m), 992 (m), 919 (m), 847 (w) cm$^{-1}$; $^1$H NMR (400 MHz, CDCl$_3$) δ 7.32 (m, 3H), 7.17 (m, 2H), 6.33 (td, J=7.2, 1.5 Hz. 1H), 5.77 (ddt, J=16.6, 10.1, 6.2 Hz, 1H), 5.08 (m, 3H), 4.74 (ddt, J=4.8, 3.7, 4.4 Hz, 1H), 4.33 (dd, J=8.6, 8.6 Hz, 1H), 4.26 (dd, J=9.2, 3.4 Hz, 1H), 3.42 (br d, J=6.4 Hz, 1H), 3.24 (dd, J=13.5, 3.4 Hz, 1H), 2.99 (m, 2H), 2.79 (dd, J=13.5, 9.4 Hz, 1H), 2.70 (m, 1H), 2.50 (m, 1H); $^{13}$C NMR (125 MHz, CDCl$_3$) δ 173.93, 153.05, 134.43, 133.64, 129.98 (q, J=6 Hz), 129.82 (q, J=28 Hz), 129.29, 120.01, 127.58, 124.00 (q, J=272 Hz), 116.34, 69.60, 67.31, 54.95, 37.78, 32.29, 29.84; high resolution mass spectrum m/z 384.1421 [(M+H)$^+$; calcd for C$_{19}$H$_{21}$NO$_4$F$_3$: 384.1423].

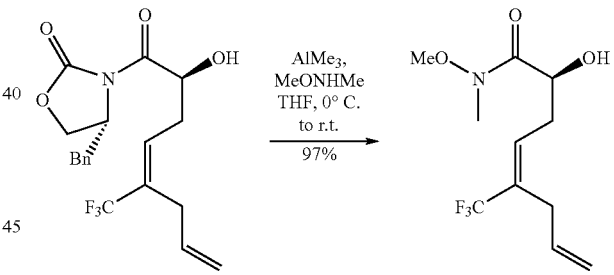

α-Hydroxyamide. A suspension of (MeO)NHMe.HCl (10.1 g, 5.25 equiv) in THF (100 mL) at 0° C. was treated with a solution of AlMe$_3$ (50 mL, 5.1 equiv) in toluene (2.0 M) dropwise and the resulting clear solution was stirred at room temperature for 34 min, then added slowly to a cooled (0° C.) solution of the α-hydroxyoxazolidinone (7.55 g, 19.7 mmol) in THF (70 mL) (cloudy→clear, pale yellow). The resulting mixture was warmed to room temperature and stirred for 12 h. The reaction mixture was cooled to 0° C., quenched by slow addition of 1N aq. tartaric acid (100 mL), stirred at room temperature for 25 min, and extracted with EtOAc (3×200 mL). Combined organics were dried (MgSO$_4$), and concentrated in vacuo. Flash chromatography (hexanes:EtOAc 2:1→1:1) gave the α-hydroxyamide (5.12 g, 97% yield) as clear oil: [α]$_D^{20}$ (24° C.) −57.2° (c 1.03, CHCl$_3$); IR (film) 3432 (br s), 3084 (w), 2980 (m), 2943 (m), 1652 (s), 1464 (m), 1373 (m), 1318 (m), 1214 (m), 1171 (m), 1112 (m), 991 (m), 919 (m), 818 (w) cm$^{-1}$; $^1$H NMR (400 MHz, CDCl$_3$) δ 6.32 (td, J=7.3, 1.5 Hz, 1H). 5.74 (ddt, J=16.9, 10.3, 6.1 Hz, 1H), 5.05 (m, 2H), 4.43 (dd, J=7.6, 3.5 Hz, 1H), 3.70 (s, 3H), 3.35 (br s, 1H), 3.24 (s, 3H), 2.94 (d, J=6.1 Hz, 2H), 2.59 (m, 1H), 2.36 (m, 1H); $^{13}$C NMR (100 MHz, CDCl$_3$) δ 173.43, 133.68, 130 59 (q, J=6 Hz), 129.25 (q, J=28 Hz), 124.05 (q, J=271 Hz), 116.17, 67.57, 61.44, 32.56, 32.38, 29.75; high resolution mass spectrum m/z 268.1161 [(M+H)$^+$; calcd for C$_{11}$H$_{17}$NO$_3$F$_3$: 268.1161].

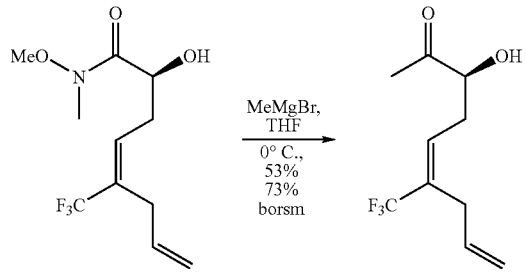

α-Hydroxyketone. To a cooled (0° C.) solution of α-hydroxyamide (4.87 g, 18.2 mmol) in THF (150 mL) was added a solution of MeMgBr (75 mL, 12 equiv) in ether (3.0 M). After 5 min, the reaction mixture was quenched with saturated NH$_4$Cl (250 mL), and extracted with EtOAc (5×200 mL). Combined organics were dried (MgSO$_4$), and concentrated in vacuo. Flash chromatography (hexanes:EtOAc 4:1→2:1→1:2) provided the α-hydroxyketone (2.16 g, 53% yield, 73% yield based on the recovered starting material) as clear oil and the starting material α-hydroxyamide (1.30 g, 27% yield): [α]$_D^{20}$ (23° C.) +58.5° (c 1.30, CHCl$_3$); IR (film) 3460 (br s), 3085 (w), 2984 (m), 2926 (m), 1716 (s), 1679 (m), 1641 (m), 1417 (m), 1361 (m), 1319 (s), 1247 (m), 1216 (s), 1172 (s), 1113 (s), 1020 (m), 994 (m), 968 (w), 919 (m) cm$^{-1}$; $^1$H NMR (500 MHz, CDCl$_3$) δ 6.21 (t, J=7.0 Hz, 1H), 5.75 (ddt, J=16.7, 10.4, 6.2 Hz, 1H), 5.07 (m, 2H), 4.26 (dt, J=7.1, 4.5 Hz, 1H), 3.51 (d, J=4.7 Hz, 1H), 2.96 (d, J=6.1 Hz, 2H), 2.66 (m, 1H), 2.42 (m, 1H), 2.19 (s, 3H); $^{13}$C NMR (100 MHz, CDCl$_3$) δ 208.53, 133.43, 129.80 (q, J=28 Hz), 129.76 (q, J=6 Hz), 123.85 (q, J=271 Hz), 116.32, 75.36, 31.22, 29.81, 25.11; high resolution mass spectrum m/z 223.0945 [(M+H)$^+$; calcd for C$_{10}$H$_{14}$NO$_2$F$_3$: 223.0946].

This reaction was not complete despite excess amount of MeMgBr.

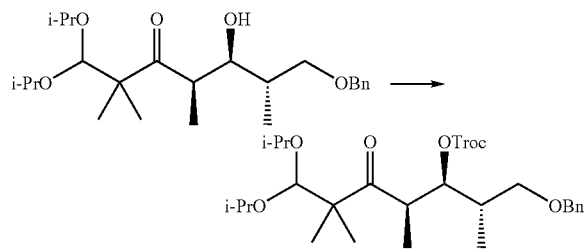

Carbonic acid 1-(2-benzyloxy-1-methylethyl)-5,5-diisopropoxy-2,4,4-trimethyl-3-oxopentyl ester 2,2,2-trichloroethyl ester To a solution of 7-Benzyloxy-5-hydroxy-1,1-diisopropoxy-2,2,4,6-tetramethyl-heptan-3-one (1.0 g, 2.4 mmol) and pyridine (0.8 mL, 7.3 mmol) in CH$_2$Cl$_2$ (10.0 mL) at 0° C. was added 2,2,2-trichloroethyl chloroformate (668.0 μL, 4.9 mmol) and the mixture was then allowed to warm to rt. After 1 h, the reaction mixture was quenched with brine and then extracted with CH$_2$Cl$_2$. The combined organic layers were dried over MgSO$_4$ and concentrated under reduced pressure. The crude product was purified by flash chromatography (gradient hexane to hexane/EtOAc 93:7) to give the desired product (1.285 g, 92%) as a clear oil: $^1$H NMR (400 MHz, CDCl$_3$) δ 1.03-1.09 (m, 12H), 1.15 (d, J=1.8 Hz, 3H), 1.17 (d, J=1.9 Hz, 3H), 1.19-1.21 (m, 6H), 1.97-2.11 (m, 1H), 3.2 (dd, J=6.2 and 9.0 Hz, 1H), 3.54 (dd, J=4.8 and 9.1 Hz, 1H), 3.57-3.60 (m, 1H), 3.82 (qd, J=3.6 and 5.9 Hz, 2H), 4.47 (s, 2H), 4.57 (s, 1H), 4.72 (d, J=11.9 Hz, 1H), 4.81 (d, J=11.9 Hz, 1H), 5.08 (t, J=6.0 Hz, 1H), 7.29-7.35 (m, 5H); $^{13}$C NMR (100 MHz, CDCl$_3$) δ 11.9, 15.0, 18.8, 21.4, 21.7, 22.3, 23.2, 23.4, 35.7, 42.5, 53.4, 53.9, 69.4, 70.9, 71.4, 73.3, 81.3, 94.7, 103.4, 127.5, 127.6, 128.2, 138.2, 154.0, 215.6; IR (film, NaCl, cm$^{-1}$) 2966, 1760, 1698, 1247; LRMS (ESI) calcd for C$_{27}$H$_{41}$O$_7$Cl$_3$Na [M+Na$^+$] 605.2, found 605.2; [α]$_D^{23}$=−20.4 (c=1.0, CHCl$_3$).

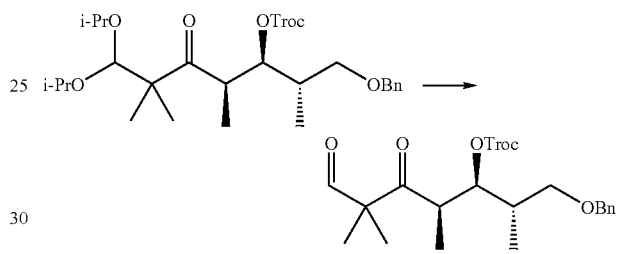

Carbonic acid 1-(2-benzyloxy-1-methylethyl)-2,4,4-trimethyl-3,5-dioxopentyl ester 2,2,2-trichloroethyl ester To solution of the starting material (1.28 g, 2.25 mmol) in 4:1 THF/H$_2$O (25 mL) was added p-TsOH (111.0 mg, 0.6 mmol). After heating at 70° C. for 5 h, the reaction mixture was poured into a cold (0° C.) sat. NaHCO$_3$ aq solution (12 mL) and then extracted with EtOAc. The combined organic layers were washed with brine, dried over MgSO$_4$ and concentrated under reduced pressure. The crude product was purified by flash chromatography (gradient hexane to hexane/EtOAc 84:16) to give product (793.2 mg, 76%) as a clear oil: $^1$H NMR (400 MHz, CDCl$_3$) δ 0.90 (d, J=5.8 Hz, 3H), 1.0 (d, J=6.9 Hz, 3H), 1.24 (s, 6H), 1.97-2.04 (m, 1H), 3.24 (dd, J=4.8 and 9.2 Hz, 1H), 3.34 (m, 1H), 3.42 (dd, J=5.8 and 9.2 Hz, 1H), 4.35 (d, J=11.9 Hz, 1H), 4.39 (d, J=11.9 Hz, 1H), 4.64 (d, J=11.9 Hz, 1H), 4.69 (d, J=11.9 Hz, 1H), 4.96 (t, J=6.0 Hz, 1H), 7.19-7.28 (m, 5H), 9.49 (s, 1H); $^{13}$C NMR (100 MHz, CDCl$_3$) −12.0, 14.8, 19.5, 19.6, 35.4, 43.3, 60.9, 71.1, 73.3, 80.37, 94.5, 127.7, 127.8, 128.3, 137.9, 154.1, 201.0, 210.1; IR (film, NaCl, cm$^{-1}$) 2973, 2880, 1758, 1701, 1453, 1380, 1248; LRMS (ESI) calcd for C$_{21}$H$_{27}$O$_6$Cl$_3$Na [M+Na$^+$] 503.0, found 503.0; [α]$_D^{23}$=−18.5 (c=0.8, CHCl$_3$).

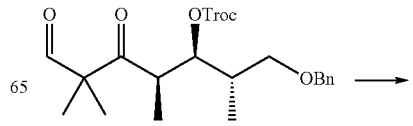

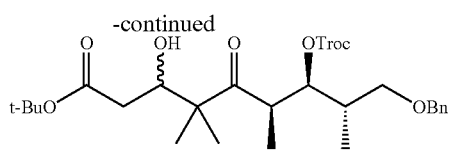

9-Benzyloxy-4,4,6,8-tetramethyl-3,5-dioxo-7-(2,2,2-trichloroethoxycarbonyloxy)-nonanoic acid tert-butyl ester To a solution of LDA (1.17 mmol, 0.3 M in Et$_2$O) at −78° C. was added t-butyl acetate (1.0 mmol, 135.0 μL). After 30 min, a solution of starting material (464.0 mg, 1 mmol) in Et$_2$O (2 mL) was slowly added over 15 min. After stirring for 1 h, the reaction was quenched with a sat. NH$_4$Cl aq solution and then extracted with EtOAc. The combined organic layers were washed with brine, dried over MgSO$_4$ and concentrated under reduced pressure. The crude product was purified by flash chromatography (gradient hexane to hexane/EtOAc 86:14) to give product (1:1 epimeric mixture, 461.4 mg, 80%) as a clear oil: $^1$H NMR (400 MHz, CDCl$_3$) δ 0.87 (d, J=5.3 Hz, 3H), 0.89 (d, J=5.5 Hz, 3H), 1.02-1.10 (m, 18H), 1.38 (s, 18H), 1.97-2.2 (m, 2H), 2.27-2.31 (m, 2H), 3.22-3.27 (m, 3H), 3.39-3.48 (m, 5H), 4.03-4.06 (m, 1H), 4.11-4.14 (m, 1H), 4.38-4.45 (m, 4H), 4.58-4.73 (m, 4H), 4.97 (t, J=5.8 Hz, 1H), 5.02 (t, J=5.8 Hz, 1H), 7.18-7.27 (m, 10H); $^{13}$C NMR (100 MHz, CDCl$_3$) δ 11.9, 12.7, 14.9, 15.2, 18.7, 19.3, 21.4, 21.6, 28.0, 35.6, 37.4, 41.7, 42.0, 51.8, 51.9, 71.3, 71.3, 72.5, 73.0, 73.3, 73.3, 80.6, 81.2, 81.3, 94.6, 127.5, 127.7, 127.8, 128.3, 138.0, 138.1, 154.0, 154.1, 172.3, 172.4, 216.0, 216.3; IR (film, NaCl, cm$^{-1}$) 3509, 2975, 1759, 1707, 1368, 1248, 1152; LRMS (ESI) calcd for C$_{27}$H$_{39}$O$_8$Cl$_3$Na [M+Na$^+$] 619.1, found 619.2.

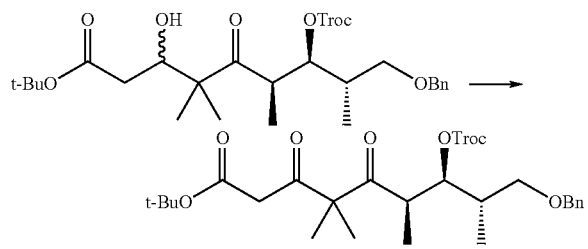

To a 0° C. solution of starting material (350.0 mg, 0.6 mmol) in CH$_2$Cl$_2$ (10 mL) was added Dess-Martin periodinane (398.0 mg, 0.9 mmol). The mixture was stirred at rt for 1 h and then poured into a well-stirred mixture of 1:1 sat. Na$_2$S$_2$O$_3$/sat. NaHCO$_3$. The layers were separated after 30 min. The aqueous layer was extracted three times with Et$_2$O. The combined organic extracts were washed with sat. NaHCO$_3$, brine, dried over MgSO$_4$ and concentrated under vacuum. The crude product was purified by flash chromatography (gradient hexane to hexane/EtOAc 91:9) to give product (258.4 mg, 74%) as a clear oil: $^1$H NMR (400 MHz, CDCl$_3$) δ 0.80 (d, J=6.9 Hz, 3H), 0.87 (d, J=6.9 Hz, 3H), 1.13 (s, 3H), 1.19 (s, 3H), 1.23 (s, 9H), 2.04-2.12 (m, 1H), 3.09-3.28 (m, 5H), 4.23 (s, 2H), 4.48 (d, J=11.9 Hz, 1H), 4.55 (d, J=11.9 Hz, 1H), 4.79 (dd, J=4.6 and 7.3 Hz, 1H), 7.04-7.13 (m, 5H); $^{13}$C NMR (100 MHz, CDCl$_3$) δ 11.7, 14.6, 20.7, 21.5, 27.9, 35.5, 42.2, 43.4, 63.3, 71.3, 73.3, 79.9, 81.5, 90.5, 94.5, 127.6, 127.7, 128.2, 138.0, 154.0, 166.2, 202.9, 210.0; IR (film, NaCl, cm$^{-1}$) 2977, 1758, 1697, 1368, 1248, 1154; LRMS (ESI) calcd for C$_{27}$H$_{37}$O$_8$Cl$_3$Na [M+Na$^+$] 617.1, found 617.1; [α]$^{23}_D$=−49.1 (c=0.9, CHCl$_3$).

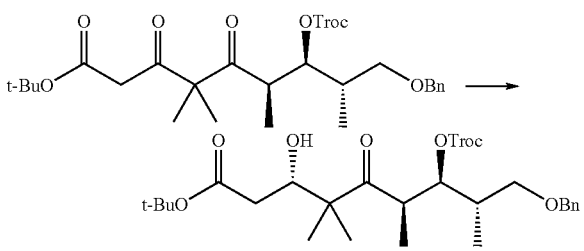

9-Benzyloxy-3-hydroxy-4,4,6,8-tetramethyl-5-oxo-7-(2,2,2-trichloroethoxycarbonyloxy)-nonanoic acid tert-butyl ester A bomb liner was charged with (R)-RuBINAP catalyst (16.8 mg, 10.0 μmol). HCl (555 μL, 0.2N in MeOH) was added and the mixture was then sonicated for 15 sec. Then a solution of starting material (59.4 mg, 0.1 mmol) in MeOH (555 μL) was added and the mixture transferred to a Parr apparatus. The vessel was purged with H$_2$ for 5 min and then pressurized to 1200 psi. After 17 h, the reaction was returned to atmospheric pressure and poured into a sat NaHCO$_3$ aq solution. The aqueous layer was extracted three times with EtOAc. The combined organic extracts were dried over MgSO$_4$ and concentrated under reduced pressure. The crude product was purified by flash chromatography (gradient hexane to hexane/EtOAc 88:12) to give product (47.6 mg, 80%) as a clear oil: $^1$H NMR (400 MHz, CDCl$_3$) δ 1.06 (d, J=6.9 Hz, 3H), 1.11 (d, J=6.8 Hz, 3H), 1.14 (s, 3H), 1.18 (s, 3H), 1.47 (s, 9H), 2.05-2.12 (m, 1H), 2.35-2.40 (m, 1H), 3.31-3.37 (m, 2H), 3.51-3.54 (m, 2H), 4.11-4.14 (m, 1H), 4.46 (s, 2H), 4.72 (d, J=11.9 Hz, 1H), 4.80 (d, J=11.9 Hz, 1H), 5.05 (dd, J=5.0 and 6.7 Hz, 1H), 7.27-7.35 (m, 5H); $^{13}$C NMR (100 MHz, CDCl$_3$) δ 12.0, 15.0, 19.3, 21.7, 28.0, 35.6, 37.5, 41.7, 51.8, 71.3, 73.0, 73.3, 80.6, 81.3, 94.7, 127.5, 127.7, 128.3, 138.2, 154.1, 172.4, 216; IR (film, NaCl, cm$^{-1}$) 3849, 2974, 2879, 1758, 1701, 1454, 1368, 1248, 1152, 926, 734; LRMS (ESI) calcd for C$_{27}$H$_{39}$O$_8$Cl$_3$Na [M+Na$^+$] 619.1, found 619.2; [α]$^{23}_D$=−13.0 (c=0.4, CHCl$_3$).

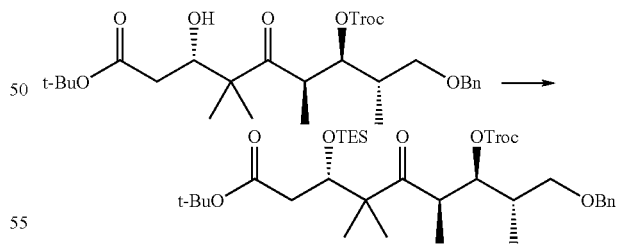

9-Benzyloxy-4,4,6,8-tetramethyl-5-oxo-7-(2,2,2-trichloroethoxycarbonyloxy)-3-(triethylsilanyloxy)-nonanoic acid tert-butyl ester To a solution of starting material (37.6 mg, 6.3 μmol) and imidazole (9.4 mg, 13.8 mmol) in DMF (0.4 mL) at 0° C. was added TESCl (11.6 μL, 69.3 mmol). After 3 h, the mixture was diluted with sat aq NaHCO$_3$. The aqueous layer was extracted three times with hexanes. The combined organic extracts were washed with brine, dried over MgSO₄ and concentrated under reduced pressure. The crude product was purified by flash chromatography (gradient hexane to hexane/EtOAc 93:7) to yield, in order of elution, product (22.9 mg, 51%), and recovered starting material (12.9 mg, 34%) as clear oils: ¹H NMR (400 MHz, CDCl₃) δ 0.66 (q, J=7.9 Hz, 6H), 0.96 (t, J=7.9 Hz, 9H), 1.01 (s, 3H), 1.05 (d, J=5.2 Hz, 3H), 1.07 (d, J=5.3 Hz, 3H), 1.35 (s, 3H). 1.44 (s, 9H), 2.05-2.11 (m, 2H), 2.50 (dd, J=3.5 and 17.2 Hz, 1H), 3.35 (dd, J=5.9 and 9.0 Hz, 1H), 3.49 (dd, J=4.0 and 9.0 Hz, 1H), 3.53 (dd, J=3.8 and 6.7 Hz, 1H), 4.18 (dd, J=3.5 and 6.5 Hz, 1H), 4.45 (s, 2H), 4.65 (d, J=11.9 Hz, 1H), 4.79 (d, J=11.9 Hz, 1H), 4.97 (dd, J=3.7 and 8.1 Hz, 1H), 7.29-7.52 (m, 5H); ¹³C NMR (125 MHz, CDCl₃) δ 5.3, 7.3, 10.9, 14.9, 21.3, 22.6, 28.4, 35.9, 41.1, 42.7, 53.7, 71.9, 73.7, 75.7, 80.1, 80.9, 95.1, 127.9, 128.0, 128.7, 138.6, 154.3, 171.7, 215.7; IR (film, NaCl, cm⁻¹) 2956, 2876, 1732, 1694, 1456, 1366, 1257, 1154, 1098, 988, 835, 774, 741; LRMS (ESI) calcd for $C_{33}H_{53}O_8SiCl_3Na$ [M+Na⁺] 733.2, found 733.3. $[\alpha]^{23}_D$=−16.1 (c=0.1, CHCl₃).

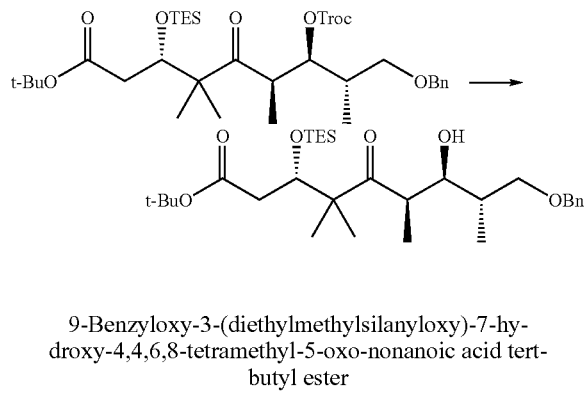

9-Benzyloxy-3-(diethylmethylsilanyloxy)-7-hydroxy-4,4,6,8-tetramethyl-5-oxo-nonanoic acid tert-butyl ester To a solution of starting material (22.9 mg, 3.2 μmol) in 1:1 THF/AcOH (1.4 mL) was added Zn (5.0 mg, 7.8 μmol, nanosize). The mixture was sonicated for 15 min. More Zn (5.0 mg, 7.8 μmol, nanosize) was added, followed by sonication for a further 15 min. The suspension was filtered through a celite pad, washing with EtOAc several times. The filtrates were washed with sat. NaHCO₃, brine, dried over MgSO₄ and concentrated under vacuum. The crude residue was passed through a short plug of silica gel eluting with hexane/EtOAc 4:1 to give 17.1 mg (99% yield) of product as colorless oil: ¹H NMR (400 MHz, CDCl₃) δ (m, 6H), 0.96 (t, J=7.9 Hz, 9H), 0.97 (d, J=6.8 Hz, 3H), 1.05 (d, J=6.8 Hz, 3H), 1.11 (s, 3H), 1.26 (s, 3H), 1.44 (s, 9H), 1.84-1.90 (m, 1H), 2.21 (dd, J=6.7 and 17.0 Hz, 1H), 2.36 (dd, J=6.7 and 17.0 Hz, 1H), 3.24-3.29 (m, 1H), 3.44-3.52 (m, 2H), 3.67 (dd, J=3.9 and 8.9 Hz, 1H), 4.36 (dd, J=3.5 and 6.5 Hz, 1H), 4.50 (d, J=12.0 Hz, 1H), 4.54 (d, J=12.0 Hz, 1H), 7.32-7.36 (m, 5H); ¹³C NMR (100 MHz, CDCl₃) δ 5.0, 6.9, 9.7, 13.9, 20.2, 21.8, 28.0, 36.3, 40.8, 41.5, 53.7, 72.5, 72.9, 73.2, 73.6, 80.7, 127.4, 127.5, 128.2, 138.6, 171.0, 221.4; IR (film, NaCl, cm⁻¹) 3502, 2959, 2875, 1731, 1683, 1456, 1366, 1154, 1098, 996, 739; LRMS (ESI) calcd for $C_{30}H_{52}O_6SiCl_3Na$ [M+Na⁺] 559.3, found 559.3; $[\alpha]^{23}_D$=−41.0 (c=0.4, CHCl₃).

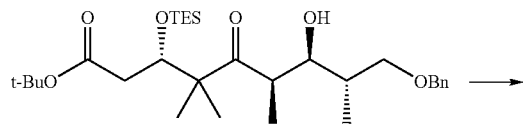

-continued

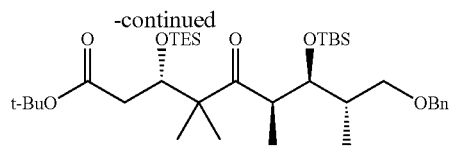

9-Benzyloxy-7-(tert-butyldimethylsilanyloxy)-3-(diethylmethylsilanyloxy)-4,4,6,8-tetramethyl-5-oxo-nonanoic acid tert-butyl ester To a solution of starting material (4.1 mg, 7.6 μmol) and 2,6-lutidine (10.0 μL, 43.5 mmol) in CH₂Cl₂ (0.2 mL) at −78° C. was added TBSOTf (10.0 μL, 85.8 mmol). After 2 h, more 2,6-lutidine (10.0 μL, 43.5 mmol) and TBSOTf (10.0 μL, 85.8 mmol) were added. After 6 h, the mixture was diluted with sat aq NaHCO₃. The aqueous layer was extracted three times with EtOAc. The combined organic extracts were washed with brine, dried over MgSO₄ and concentrated under reduced pressure. The crude product was purified by flash chromatography (gradient hexane to hexane/EtOAc 91:9) to give the product (5.4 mg, 82%) as a clear oil. Spectroscopic data agreed well with the reported values.

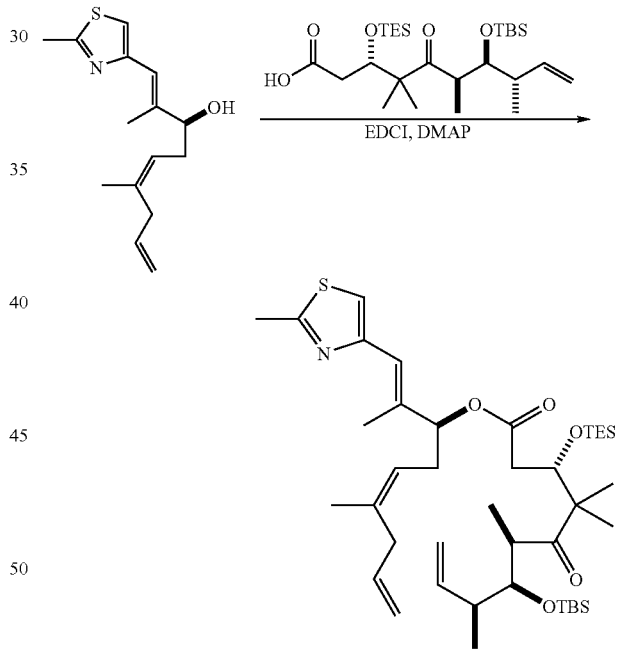

Acid and alcohol were azeotroped with dry benzene (5 mL×2) and dried under high vacuum prior to the reaction. To a solution of alcohol (639 mg, 2.63 mmol) in CH₂Cl₂ (13 mL) were added EDCI (576 mg, 3.09 mmol) and DMAP (366 mg, 3.09 mmol) at 0° C. To the mixture was added a solution of acid (1.11 g, as 1.88 mmol) in CH₂Cl₂ (5 mL+2 mL rinse) dropwise over 16 min at 0° C. After stirred at 0° C. for 1.5 h, the mixture was stirred at rt for 3.5 h. Following concentration of the reaction mixture, the residue was purified by flash column chromatography (SiO₂, hexane/EtOAc=30:1 to 20:1) gave ester (1.20 g, 1.61 mmol, 86% from t-butyl ester) as a colorless oil.

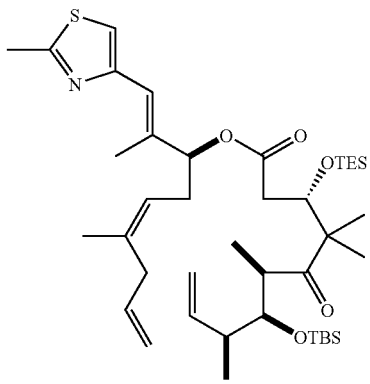

[α]$_D^{24}$ −25.1 (c 1.30, CHCl$_3$); IR (film) ν 2955, 2925, 2872, 1732, 1696, 1461, 1378, 1290, 1243, 1173, 1091, 985, 873, 773 cm$^{-1}$; $^1$H NMR (400 MHz, CDCl$_3$) δ 0.06 (3H, s), 0.06 (3H, s), 0.58-0.66 (6H, m), 0.92 (9H, s), 0.95 (9H, t, J=8.0 Hz), 1.02 (3H, d, J=6.5 Hz), 1.03 (3H, d, J=6.5 Hz), 1.07 (3H, s), 1.21 (3H, s), 1.67 (3H, s), 2.07 (3H, s), 2.05-2.12 (1H, m), 2.30 (1H, dd, J=16.9, 7.5 Hz), 2.39 (1H, dt, J=14.8, 6.7 Hz), 2.49 (1H, dd, J=17.0, 3.0 Hz), 2.50 (1H, dt, J=14.8, 6.7 Hz), 2.70 (3H, s), 2.74-2.30 (2H, m), 3.07 (1H, dd, J=7.0 Hz), 3.83 (1H, dd, J=7.1, 2.0 Hz), 4.35 (1H, dd, J=7.4, 2.8 Hz), 4.98-5.07 (4H, m), 5.16 (1H, brt, J=7.0 Hz), 5.23 (1H, t, J=6.9 Hz), 5.74 (1H, ddt, J=16.7, 10.2, 6.5 Hz), 5.91 (1H, ddd, J=17.8, 10.5, 7.8 Hz), 6.50 (1H, s), 6.95 (1H, s); $^{13}$C NMR (100 MHz, CDCl$_3$) δ −3.7, −3.3, 5.3 (3C), 7.2 (3C), 14.8, 15.2, 18.7, 18.9, 19.4, 20.3, 23.6, 23.7, 26.4 (3C), 31.7, 36.7, 40.1, 43.8, 46.4, 53.3, 74.2, 76.5, 79.6, 115.5, 115.6, 116.5, 120.5, 121.3, 135.8, 136.1, 137.4, 140.2, 152.9, 164.7, 171.5, 218.4; LRMS (EST) calcd for C$_{41}$H$_{71}$NO$_5$SSi$_2$Na [M+Na$^+$] 768.5, found 768.5; HRMS calcd. for C$_{41}$H$_{72}$NO$_5$SSi$_2$ [M+H$^+$] 746.4670, found 746.4680.

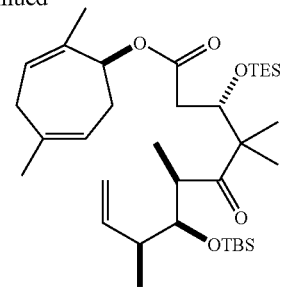

A solution of diene (26.9 mg, 36.1 μmol) in toluene (70 mL) was heated to reflux and treated with a solution of Grubbs' catalyst (3.1 mg, 3.61 μmol) in toluene (2 mL). The mixture was stirred for 25 min, cooled to 0° C., filtered through a pad of silica gel, which was rinsed with hexane/EtOAc=2/1. The combined filtrate was concentrated and purified by flash column chromatography (SiO$_2$, hexane/Et$_2$O=40:1 to 5:1) to give the desired product (9.9 mg, 13.8 μmol, 38%) and cycloheptadiene (14.4 mg, 22.3 μmol, 62%) both as a colorless oil.

[α]$_D^{25}$ −41.5 (c 0.715, CHCl$_3$); IR (film) ν 2955, 2884, 1737, 1690, 1467, 1378, 1249, 1179, 1102, 1014, 979, 879, 826, 773 cm$^{-1}$; $^1$H NMR (400 MHz, CDCl$_3$) δ 0.08 (3H, s), 0.12 (3H, s), 0.57 (6H, q, J=7.8 Hz), 0.89 (9H, t, J=8.0 Hz), 0.93 (9H, s), 1.04 (3H, s), 1.06 (3H, d, J=7.1 Hz), 1.12 (3H, s), 1.17 (3H, d, J=7.1 Hz), 1.68 (3H, s), 2.15 (3H, d, J=0.8 Hz), 2.14-2.27 (2H, m), 2.45 (1H, dd, J=14.0, 4.8 Hz), 2.50 (1H, dd, J=14.9, 3.2 Hz), 2.64-2.74 (2H, m), 2.72 (3H, s), 3.02 (1H, quintet, J=7.0 Hz), 3.10 (1H, dd, J=14.4, 7.3 Hz), 3.96 (1H, d, J=8.7 Hz), 4.43 (1H, dd, J=8.3, 2.9 Hz), 5.22 (1H, dd, J=9.8, 5.7 Hz), 5.33-5.42 (2H, m), 5.69 (1H, dd, J=15.8, 8.2 Hz), 6.57 (1H, s), 6.96 (1H, s); $^{13}$C NMR (100 MHz, CDCl$_3$) δ −3.3, −3.2, 5.6 (3C), 7.1 (3C), 15.0, 17.2, 18.8, 19.4, 21.4, 21.7, 23.8, 24.3, 26.5 (3C), 33.2, 35.6, 41.3, 41.8, 48.2, 54.0, 74.4, 77.4, 79.3, 116.4, 120.5, 121.0, 129.3, 132.1, 137.8, 138.0, 152.7, 164.8, 170.7, 216.8; LRMS (ESI) calcd for C$_{39}$H$_{68}$NO$_5$SSi$_2$ [M+H$^+$] 718.4, found 718.3; HRMS calcd. for C$_{39}$H$_{68}$NO$_5$SSi$_2$ [M+H$^+$] 718.4357, found 718.4355.

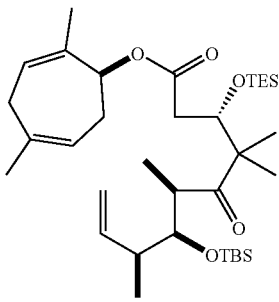

[α]$_D^{26}$ −38.5 (c 0.400, CHCl$_3$); IR (film) ν 2955, 2878, 1741, 1693, 1472, 1458, 1385, 1295, 1253, 1169, 1098, 988, 871, 837, 775 cm$^{-1}$; $^1$H NMR (400 MHz, CDCl$_3$) δ 0.07 (6H, s), 0.61-0.68 (6H, m), 0.93 (9H, s), 0.97 (9H, t, J=8.0 Hz), 1.03 (3H, d, J=7.0 Hz), 1.04 (3H, d, J=7.0 Hz), 1.10 (3H, s), 1.21 (3H, s), 1.65 (3H, s), 1.75 (3H, s), 2.06-2.14 (1H, m), 2.31 (1H, dd, J=17.2, 7.2 Hz), 2.34-2.51 (2H, m), 2.49 (1H, dd, J=17.1, 2.8 Hz), 2.65-2.81 (2H, m), 3.07 (1H, quintet, J=7.0 Hz), 3.84 (1H, dd, J=7.2, 2.1 Hz), 4.40 (1H, dd, J=7.2, 2.8 Hz), 4.98-5.09 (2H, m), 5.38-5.42 (1H, m), 5.65 (1H, t, J=5.9 Hz), 5.93 (1H, ddd, J=17.9, 10.1, 7.8 Hz); $^{13}$C NMR (100 MHz, CDCl$_3$) δ −3.6, −3.3, 5.4 (3C), 7.3 (3C), 15.3, 18.7, 19.0, 20.0, 22.1, 23.8, 25.8, 26.4 (3C), 31.3, 32.3, 40.0, 43.8, 46.3, 54.0, 72.5, 73.8, 76.5, 115.6, 119.8, 125.6, 136.5, 140.1, 140.6, 171.9, 218.5; LRMS (ESI) calcd for C$_{35}$H$_{64}$O$_5$Si$_2$Na [M+Na$^+$] 643.4, found 643.3; HRMS calcd. for C$_{35}$H$_{64}$O$_5$Si$_2$Na [M+Na$^+$] 643.4190, found 643.4219.

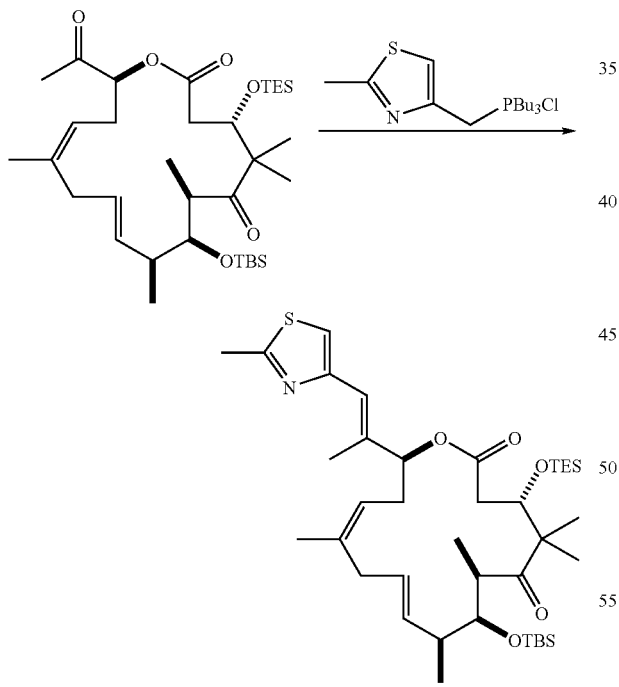

Via Wittig Reaction:
To a solution of Wittig reagent (19.1 mg, 54.7 μmol) in THF (0.4 mL) was added KHMDS (109 μL of a 0.5 M solution in toluene, 54.7 μmol) at 0° C. The mixture was stirred at 0° C. for 0.5 h and then cooled to −78° C. To the mixture was added dropwise a solution of ketone (5.7 mg, 9.12 μmol) in THF (0.3 mL), and the resulting mixture was allowed to warm to −20° C. over 1.5 h. The reaction was quenched with sat. aq. NH$_4$Cl (2 mL) and extracted with EtOAc (7 mL×3). The combined organic layers were dried over Na$_2$SO$_4$ and concentrated. The residue was purified by flash column chromatography (SiO$_2$, hexane/Et$_2$O=10:1) providing the 5.6 mg of inseparable olefin mixture (E/Z=9:1). The mixture was purified by preparative TLC (hexane/Et$_2$O=4:1) providing the pure desired isomer (5.0 mg, 6.96 μmol, 76%) as a colorless oil.

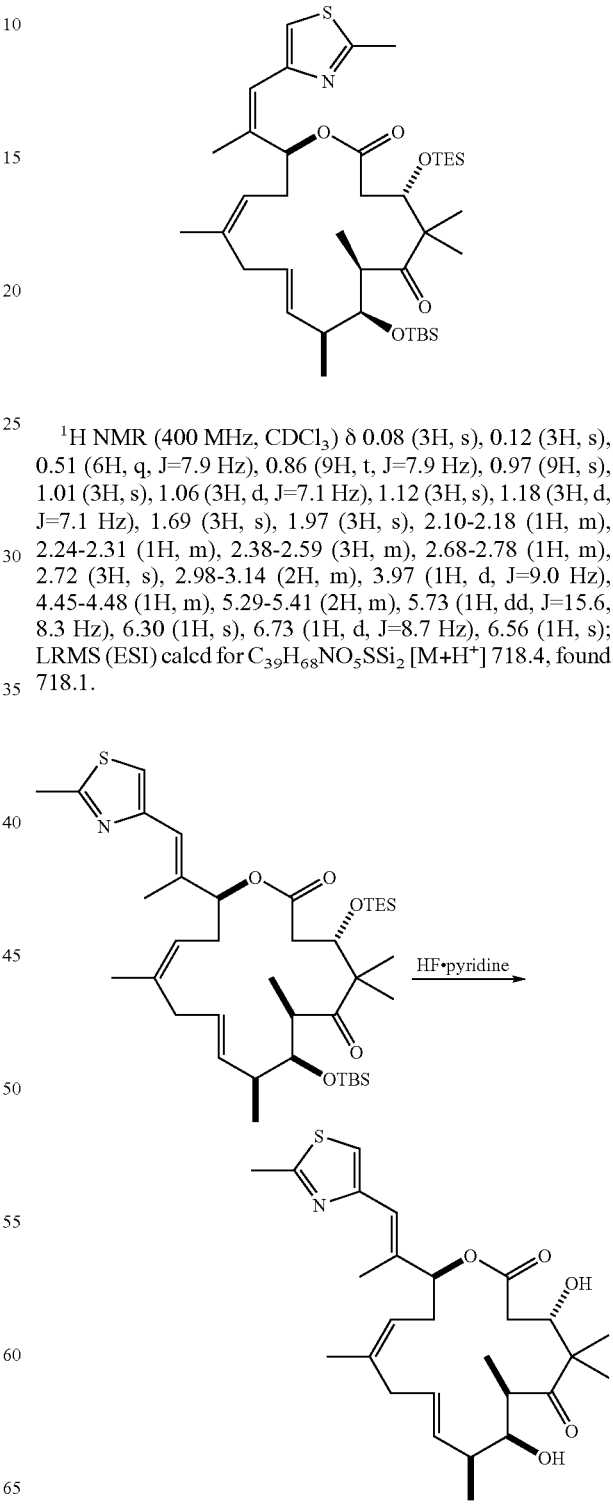

$^1$H NMR (400 MHz, CDCl$_3$) δ 0.08 (3H, s), 0.12 (3H, s), 0.51 (6H, q, J=7.9 Hz), 0.86 (9H, t, J=7.9 Hz), 0.97 (9H, s), 1.01 (3H, s), 1.06 (3H, d, J=7.1 Hz), 1.12 (3H, s), 1.18 (3H, d, J=7.1 Hz), 1.69 (3H, s), 1.97 (3H, s), 2.10-2.18 (1H, m), 2.24-2.31 (1H, m), 2.38-2.59 (3H, m), 2.68-2.78 (1H, m), 2.72 (3H, s), 2.98-3.14 (2H, m), 3.97 (1H, d, J=9.0 Hz), 4.45-4.48 (1H, m), 5.29-5.41 (2H, m), 5.73 (1H, dd, J=15.6, 8.3 Hz), 6.30 (1H, s), 6.73 (1H, d, J=8.7 Hz), 6.56 (1H, s); LRMS (ESI) calcd for C$_{39}$H$_{68}$NO$_5$SSi$_2$ [M+H$^+$] 718.4, found 718.1.

To a solution of silylether (298.8 mg, 0.416 mmol) in THF (6.5 mL) in a plastic tube was added HF.pyridine (3.2 mL) at 0° C., and the mixture was stirred at rt for 3 h. The reaction was quenched with dropwise addition of TMSOMe (30 mL) at 0° C. and the mixture was stirred at rt for 3 h. After concentration and drying under high vacuum, the residue was purified by flash column chromatography (SiO$_2$, hexane/EtOAc=1:1) to give alcohol (196.6 mg, 0.402 mmol, 97%) as a colorless solid.

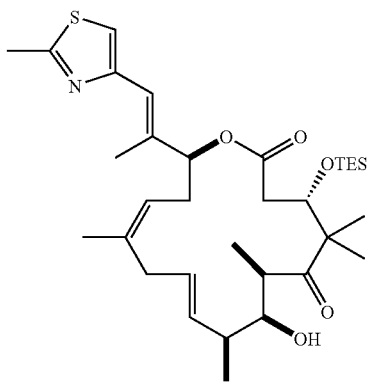

$[\alpha]_D^{25}$ −96.6 (c 0.235, CHCl$_3$); IR (film) ν 3502, 2970, 2927, 1733, 1685, 1506, 1456, 1375, 1251, 1152, 1040, 977 cm$^{-1}$; $^1$H NMR (400 MHz, CDCl$_3$) δ 1.06 (3H, s), 1.11 (3H, d, J=7.0 Hz), 1.22 (3H, d, J=6.8 Hz), 1.28 (3H, s), 1.72 (3H, s), 2.10 (3H, s), 2.31-2.40 (2H, m), 2.43 (1H, dd, J=16.0, 3.7 Hz), 2.49 (1H, dd, J=16.0, 9.2 Hz), 2.55-2.68 (2H, m), 2.71 (3H, s), 2.98 (1H, dd, J=14.4, 6.4 Hz), 3.16 (1H, quintet, J=6.2 Hz), 3.76 (1H, dd, J=5.9, 3.2 Hz), 4.30 (1H, dd, J=9.2, 3.7 Hz), 5.18 (1H, brt, J=7.3 Hz), 5.32 (1H, dd, J=8.4, 2.5 Hz), 5.63 (1H, dd, J=15.7, 6.4 Hz), 5.60 (1H, ddd, J=15.7, 6.9, 5.1 Hz), 6.60 (1H, s), 6.98 (1H, s); $^{13}$C NMR (100 MHz, CDCl$_3$) δ 15.1, 16.0, 17.7, 19.2, 19.5, 22.5, 23.6, 32.0, 35.0, 39.6, 40.3, 44.8, 53.3, 71.8, 75.6, 78.3, 116.1, 119.6, 120.5, 129.9, 131.3, 137.5, 138.2, 152.2, 165.0, 170.7, 218.8; LRMS (ESI) calcd for C$_{27}$H$_4$NO$_5$S [M+H$^+$] 490.3, found 490.2; HRMS calcd. for C$_{27}$H$_{40}$NO$_5$S [M+H$^+$] 490.2627, found 490.2602.

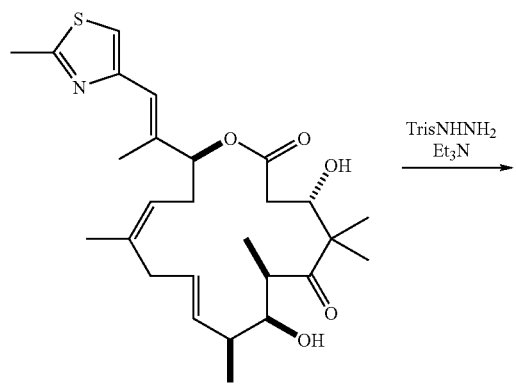

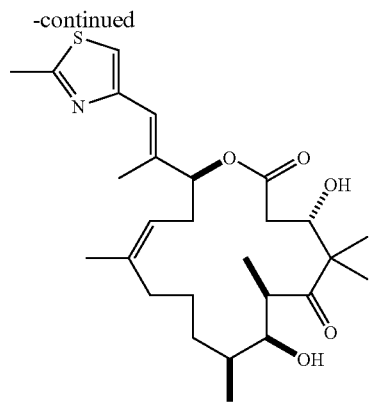

To a solution of olefin (1.2 mg, 2.5 μmol) and TrisNHNH$_2$ (29.3 mg, 98 μmol) in ClCH$_2$CH$_2$Cl (0.7 mL) at 50° C. was added Et$_3$N (13.7 μL, 98 μmol). The reaction was monitored by HPTLC (hexane/EtOAc/CH$_2$Cl$_2$=1/1/2). After stirring for 7 h, the mixture was cooled to rt, diluted with EtOAc and filtered through a pad of silica gel, which was rinsed with EtOAc. After concentrating, the residue was purified by preparative TLC (hexane/EtOAc/CH$_2$Cl$_2$=1/1/2) providing the reduced product (1.1 mg, 2.2 μmol, 91%) as a white solid. The spectral data of this compound was identical to those reported of dEpoB.

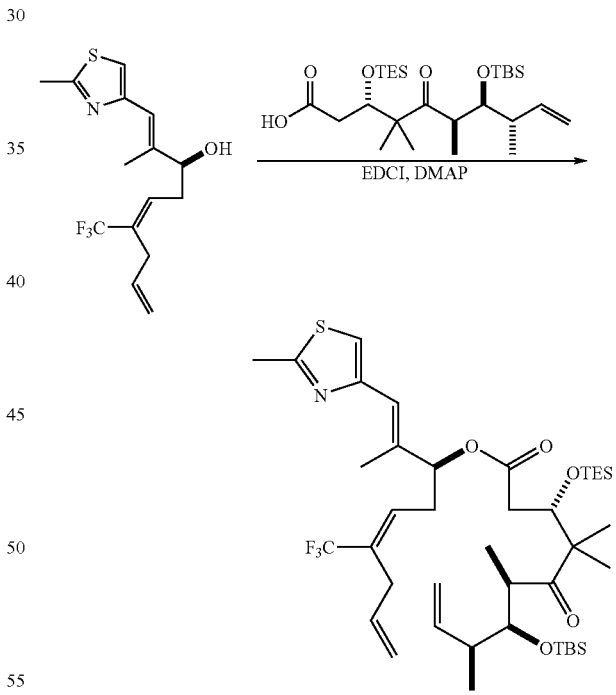

Acid and alcohol were azeotroped with dry benzene (5 mL×2) and dried under high vacuum prior to the reaction. To a solution of alcohol (10:1 mixture of isomers, 240 mg, 0.756 mmol) in CH$_2$Cl$_2$ (5 mL) were added EDCI (192.7 mg, 1.01 mmol) and DMAP (122.8 mg, 1.01 mmol) at 0° C. To the mixture was added a solution of acid (314.6 mg, 0.628 mmol) in CH$_2$Cl$_2$ (2 mL+1 mL rinse) dropwise over 15 min at 0° C. After stirring at 0° C. for 2 h, the mixture was stirred at rt for 2 h. After concentrating, the residue was carefully purified by flash column chromatography (SiO$_2$, hexane/EtOAc=20:1 to 15:1) to give ester (340.1 mg, 0.425 mmol, 68% based on acid) as a colorless oil.

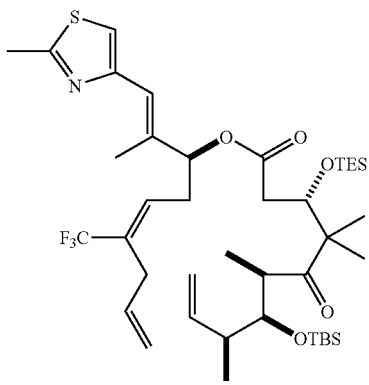

[α]$_D^{24}$ −27.5 (c 0.28, CHCl$_3$); IR (film) ν 2956, 2878, 1740, 1692, 1472, 1378, 1317, 1253, 1174, 1118, 988, 915, 872, 837, 775 cm$^{-1}$; $^1$H NMR (400 MHz, CDCl$_3$) δ 0.06 (6H, s), 0.57-0.65 (6H, m), 0.92 (9H, s), 0.94 (9H, t, J=7.9 Hz), 1.02 (3H, d, J=6.9 Hz), 1.03 (3H, d, J=6.8 Hz), 1.07 (3H, s), 1.22 (3H, s), 2.07-2.10 (1H, m), 2.09 (3H, s), 2.31 (1H, dd, J=16.9, 7.3 Hz), 2.51 (1H, dd, J=16.8, 3.0 Hz), 2.49-2.65 (2H, m), 2.71 (3H, s), 2.96-2.99 (2H, m), 3.06 (1H, quintet, J=7.1 Hz), 3.83 (1H, dd, J=7.3, 2.1 Hz), 4.35 (1H, dd, J=7.2, 3.0 Hz), 4.98-5.12 (4H, m), 5.30 (1H, t, J=6.7 Hz), 5.76 (1H, ddt, J=16.7, 10.2, 6.2 Hz), 5.92 (1H, ddd, J=17.8, 9.9, 7.8 Hz), 6.19 (1H, t, J=7.0 Hz), 6.51 (1H, s), 6.97 (1H, s); $^{13}$C NMR (100 MHz, CDCl$_3$) δ −3.7, −3.4, 5.2 (3C), 7.1 (3C), 14.7, 15.2, 18.6, 18.9, 19.3, 19.9, 23.8, 26.3 (3C), 30.1, 31.2, 40.0, 43.7, 46.3, 53.3, 73.9, 76.5, 77.9, 115.5, 116.5, 117.0, 121.5, 124.1 [q, $^1$J (C,F)=273.4 Hz], 129.6 [q, $^2$J (C,F)=28.5 Hz], 130.5 [q, $^3$J (C,F)=6.1 Hz], 133.6, 136.3, 140.1, 152.4, 164.8, 171.3, 218.3; LRMS (ESI) calcd for C$_{41}$H$_{68}$F$_3$NO$_5$SSi$_2$Na [M+Na$^+$] 822.4, found 822.4; HRMS calcd. for C$_{41}$H$_{69}$F$_3$NO$_5$SSi$_2$ [M+H$^+$] 800.4387, found 800.4374.

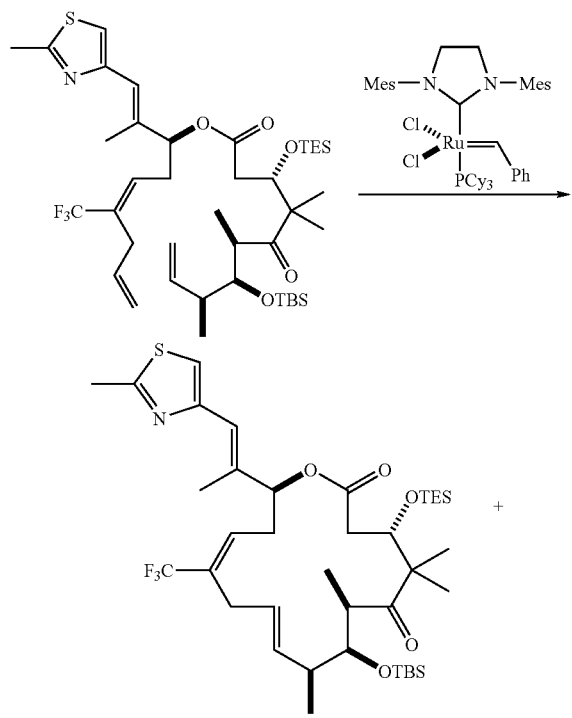

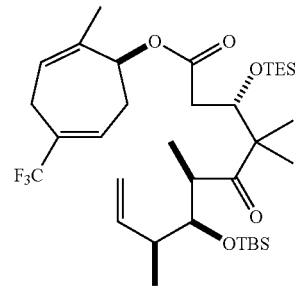

A solution of diene (57.6 mg, 72.0 μmol) in toluene (142 mL) was heated to reflux and treated with a solution of Grubbs' catalyst (6.1 mg, 7.20 μmol) in toluene (2 mL). The mixture was stirred for 28 min, cooled to 0° C., and filtered through a pad of silica gel, which was rinsed with hexane/EtOAc=2/1 (300 mL). The combine filtrate was concentrated and purified by flash column chromatography (SiO$_2$, hexane/Et$_2$O=40:1 to 15:2) to give the desired product (12.0 mg, 15.5 μmol, 22%) and cycloheptadiene (29.2 mg, 43.3 μmol, 60%) both as a colorless oils.

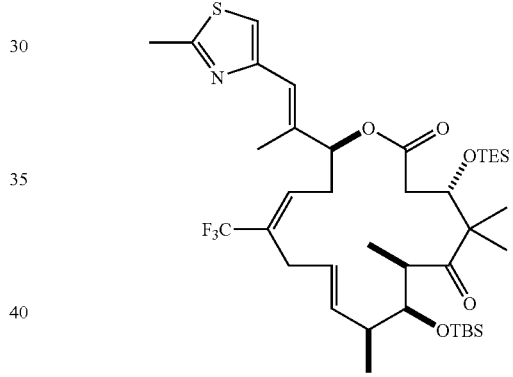

[α]$_D^{26}$ −17.1 (c 0.14, CHCl$_3$); IR (film) ν 2955, 2884, 1743, 1690, 1472, 1320, 1173, 1114, 1038, 1008, 873, 832, 773 cm$^{-1}$; $^1$H NMR (400 MHz, CDCl$_3$) δ 0.09 (3H, s), 0.12 (3H, s), 0.55 (6H, q, J=7.7 Hz), 0.88 (9H, t, J=8.0 Hz), 0.96 (9H, s), 1.01 (3H, s), 1.06 (3H, d, J=7.1 Hz), 1.12 (3H, s), 1.20 (3H, d, J=7.1 Hz), 2.07-2.17 (1H, m), 2.19 (3H, s), 2.38 (1H, dd, J=14.3, 3.5 Hz), 2.39-2.49 (1H, m), 2.50 (1H, dd, J=14.3, 7.3 Hz), 2.73 (3H, s), 2.77-2.91 (2H, m), 2.96-3.09 (2H, m), 3.98 (1H, dd, J=8.9 Hz), 4.54 (1H, dd, J=7.3, 3.4 Hz), 5.28-5.38 (1H, m), 5.63 (1H, dd, J=9.6, 2.3 Hz), 5.77 (1H, dd, J=15.9, 8.5 Hz), 6.21-6.28 (1H, m), 6.60 (1H, s), 6.99 (1H, s); $^{13}$C NMR (100 MHz, CDCl$_3$) δ −3.4, −3.3, 5.5 (3C), 7.0 (3C), 14.6, 17.1, 18.7, 19.4, 19.9, 21.3, 24.8, 26.4 (3C), 29.6, 32.8, 42.0, 42.1, 48.2, 54.1, 73.4, 76.9, 77.8, 117.0, 121.6, 124.3 [q, $^1$J (C,F)=273.5 Hz], 127.2, 130.6 [q, $^2$J (C,F)=28.2 Hz], 130.8 [q, $^3$J (C,F)=6.1 Hz], 133.2, 136.5, 152.3, 165.0, 170.1, 217.1; LRMS (ESI) calcd for C$_{39}$H$_{65}$F$_3$NO$_5$SSi$_2$ [M+H$^+$] 772.4, found 772.4; HRMS calcd. for C$_{39}$H$_{65}$F$_3$NO$_5$SSi$_2$ [M+H$^+$] 772.4074, found 772.4102.

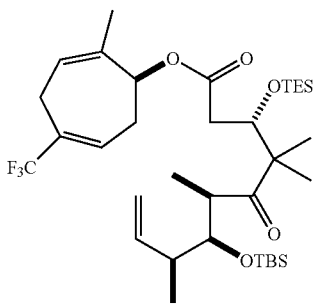

[α]$_D^{26}$ −35.6 (c 0.365, CHCl$_3$); IR (film) ν 2956, 2878, 1737, 1693, 1472, 1458, 1305, 1279, 1252, 1173, 1116, 988, 871, 775 cm$^{-1}$; $^1$H NMR (400 MHz, CDCl$_3$) δ 0.08 (6H, s), 0.64 (6H, q, J=7.8 Hz), 0.93 (9H, s), 0.96 (9H, t, J=7.8 Hz), 1.04 (6H, d, J=7.0 Hz), 1.10 (3H, s), 1.22 (3H, s), 1.70 (3H, s), 2.05-2.14 (1H, m), 2.32 (1H, dd, J=17.0, 7.1 Hz), 2.50 (1H, dd, J=17.0, 3.0 Hz), 2.51-2.63 (2H, m), 2.87 (1H, dd, J=18.4, 6.7 Hz), 2.90-3.02 (1H, m), 3.07 (1H, quintet, J=7.1 Hz), 3.85 (1H, dd, J=7.2, 2.0 Hz), 4.39 (1H, dd, J=7.1, 2.9 Hz), 4.98-5.08 (2H, m), 5.51 (1H, dd, J=8.1, 3.8 Hz), 5.67 (1H, t, J=5.9 Hz), 5.93 (1H, ddd, J=17.8, 10.5, 7.8 Hz), 6.29 (1H, t, J=5.5 Hz); $^{13}$C NMR (100 MHz, CDCl$_3$) δ −3.7, −3.4, 5.3 (3C), 7.1, (3C), 15.3, 18.7, 18.9, 19.6, 21.3, 23.9, 24.1, 26.3 (3C), 30.3, 40.0, 43.7, 46.3, 53.4, 70.9, 73.7, 76.5, 115.5, 123.4, 123.8 [q, $^1$J (C,F)=272.2 Hz], 129.1 [q, $^3$J (C,F)=6.1 Hz], 131.5 [q, $^2$J (C,F)=28.8 Hz], 138.1, 140.0, 171.7, 218.5; LRMS (ESI) calcd for C$_{35}$H$_{61}$F$_3$O$_5$Si$_2$Na [M+Na$^+$] 697.4, found 697.4; HRMS calcd. for C$_{35}$H$_{61}$F$_3$O$_5$Si$_2$Na [M+Na$^+$] 697.3907, found 697.3892.

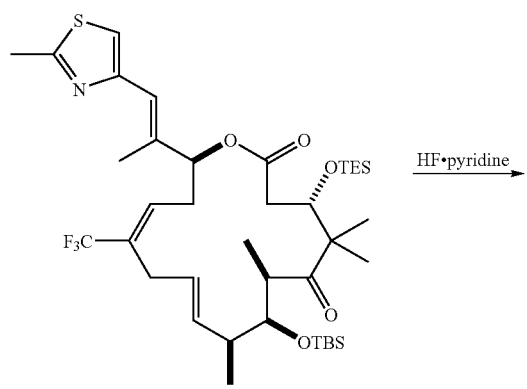

To a solution of silyl ether (1.78 g, 2.31 mmol) in THF (25 mL) in a plastic tube was added slowly HF.pyridine (12.5 mL) at 0° C., and the mixture was stirred at rt for 4 h. The reaction was quenched with dropwise addition of TMSOMe (80 mL) over 10 min at 0° C. The mixture was vigorously stirred at rt for 2.5 h. After concentrating and drying under high vacuum for 2 h, the residue was purified by flash column chromatography (SiO$_2$~50 g, hexane/EtOAc=1:1) to give diol (1.20 g, 2.21 mmol, 96%) as a colorless solid.

[α]$_D^{25}$ −54.6 (c 0.28, CHCl$_3$); IR (film) ν 3478, 2974, 2929, 1736, 1689, 1449, 1381, 1318, 1247, 1169, 1113, 1039, 983, 867, 736 cm$^{-1}$; $^{-1}$H NMR (400 MHz, CDCl$_3$) δ 1.05 (3H, s), 1.12 (3H, d, J=7.0 Hz), 1.23 (3H, d, J=6.8 Hz), 1.37 (3H, s), 2.04 (1H, brd, J=3.8 Hz, —OH), 2.12 (3H, s), 2.25-2.33 (1H, m), 2.38 (1H, dd, J=15.3, 3.0 Hz), 2.48 (1H, dd, J=15.4, 9.8 Hz), 2.54-2.61 (1H, m), 2.66-2.76 (1H, m), 2.71 (3H, s), 2.96 (1H, dd, J=16.5, 4.5 Hz), 3.02 (1H, dd, J=16.3, 6.5 Hz), 3.11 (1H, quintet, J=6.7 Hz), 3.19 (1H, brs, —OH), 3.74 (1H, brs), 4.35 (1H, brd, J=9.5 Hz), 5.42 (1H, dd, J=6.2, 4.1 Hz), 5.60 (1H, ddd, J=15.8, 5.6, 4.5 Hz), 5.66 (1H, dd, J=15.8, 5.8 Hz), 6.24 (1H, t, J=7.2 Hz), 6.64 (1H, s), 7.00 (1H, s); $^{13}$C NMR (100 MHz, CDCl$_3$) δ 15.1, 16.1, 17.7, 18.5, 19.3, 22.5, 28.8, 31.1, 39.6, 39.7, 45.0, 53.7, 71.4, 75.3, 76.8, 116.7, 120.2, 124.3 [q, $^1$J (C,F)=273.4 Hz], 127.9, 130.2 [q, $^3$J (C,F)=6.0 Hz], 130.6 [q, $^2$J (C,F)=28.4 Hz], 132.5, 136.7, 152.0, 165.4, 170.2, 218.4; LRMS (ESI) calcd for C$_{27}$H$_{37}$F$_3$NO$_5$S [M+H$^+$] 544.2, found 544.1; HRMS calcd. for C$_{27}$H$_{37}$F$_3$NO$_5$S [M+H$^+$] 544.2345, found 544.2346.

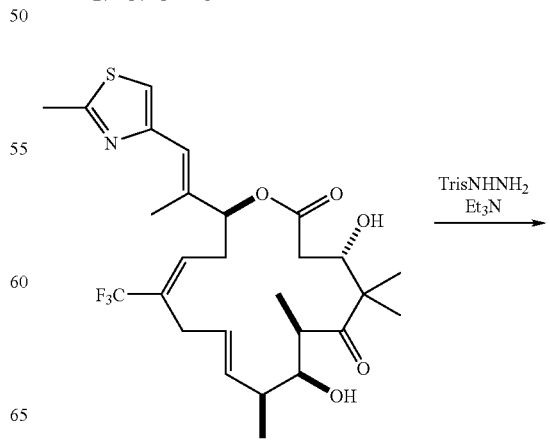

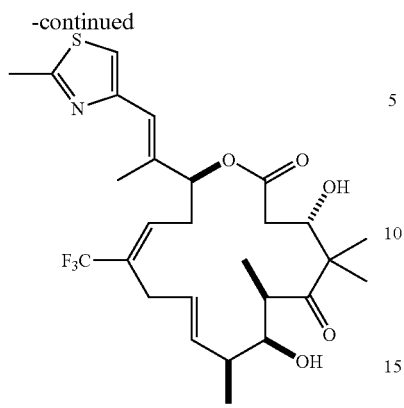

To a solution of diol (1.22 mg, 2.24 μmol) and TrisNHNH₂ (26.7 mg, 89.6 μmol) in ClCH₂CH₂Cl (1 mL) at 50° C. was added Et₃N (12.5 μL, 89.6 μmol). The reaction was monitored by HPTLC (hexane/EtOAc/CH₂Cl₂=1/1/2). After stirring for 6.5 h, further TrisNHNH₂ (26.7 mg, 89.6 μmol) and Et₃N (12.5 μL, 89.6 μmol) were added to the mixture. After stirring for 14 h, the mixture was cooled to rt, diluted with EtOAc and filtered through a pad of silica gel, which was rinsed with EtOAc. After concentrating, the residue was purified by preparative TLC (hexane/EtOAc/CH₂Cl₂=1/1/2) to give the reduced product (1.16 mg, 2.13 μmol, 94%) as a white solid.

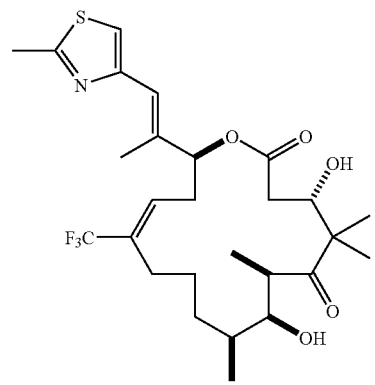

$[\alpha]_D^{24}$ −75.1 (c 0.35, CHCl₃); IR (film) ν 3483, 2968, 1337, 1685, 1466, 1381, 1322, 1247, 1168, 1113, 1010, 833, 736 cm⁻¹; ¹H NMR (400 MHz, CDCl₃) δ 1.03 (3H, d, J=7.0 Hz), 1.08 (3H, s), 1.19 (3H, d, J=6.8 Hz), 1.25-1.35 (2H, m), 1.37 (3H, s), 1.42-1.55 (2H, m), 1.65-1.82 (2H, m), 2.10 (3H, d, J=0.8 Hz), 2.21-2.47 (2H, m), 2.27 (1H, dd, J=14.2, 2.6 Hz), 2.48 (1H, dd, J=14.3, 10.8 Hz), 2.70 (3H, s), 2.70-2.28 (1H, m), 3.02 (1H, d, J=2.0 Hz, —OH), 3.19 (1H, qd, J=6.9, 2.2 Hz), 3.65 (1H, d, J=6.2 Hz, —OH), 3.69-3.72 (1H, m), 4.34 (1H, ddd, J=10.8, 6.2, 2.6 Hz), 5.28 (1H, dd, J=10.2, 2.2 Hz), 6.12 (1H, dd, J=10.2, 5.2 Hz), 6.61 (1H, s), 6.98 (1H, s); ¹³C NMR (100 MHz, CDCl₃) δ 13.0, 15.9, 16.0, 17.7, 19.1, 23.0, 25.6, 26.2, 31.3, 32.3, 37.4, 39.8, 41.6, 53.9, 72.3, 73.6, 77.7, 116.2, 119.9, 124.3 [q, ¹J (C,F)=274.4 Hz], 129.8 [q, ³J (C,F)=6.1 Hz], 132.6 [q, ²J (C,F)=27.8 Hz], 138.3, 151.7, 165.4, 170.2, 220.7; LRMS (ESI) calcd for C₂₇H₃₉F₃NO₅S [M+H⁺] 546.3, found 546.2; HRMS calcd. for C₂H₃₉F₃NO₅S [M+H⁺] 546.2501, found 546.2496.

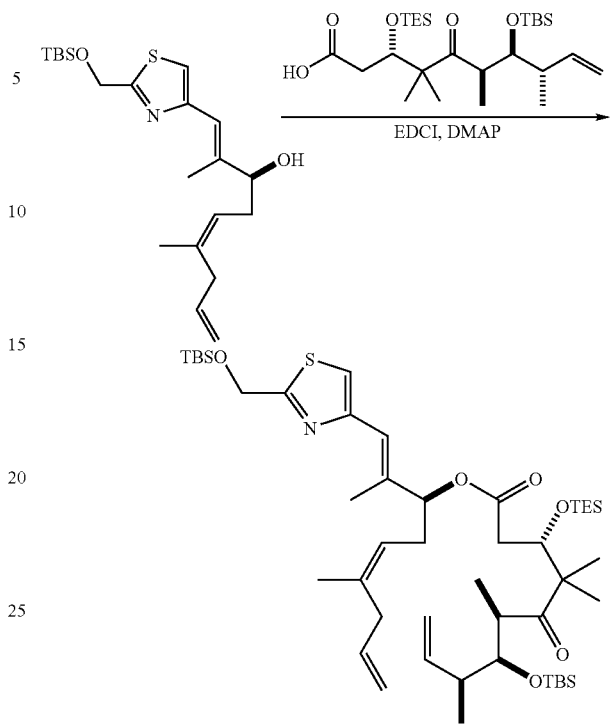

Acid and alcohol were azeotroped with dry benzene (3 mL×2) and dried under high vacuum prior to the reaction. To a solution of alcohol (68.0 mg, 0.173 mmol) in CH₂Cl₂ (1.3 mL) were added EDCI (37.8 mg, 0.197 mmol) and DMAP (24.1 mg, 0.197 mmol) at 0° C. To the mixture was added a solution of acid (72.6 mg, as 0.123 mmol) in CH₂Cl₂ (0.7 mL) dropwise over 5 min at 0° C. After stirring at 0° C. for 1 h, the mixture was stirred at rt for 2.5 h. After concentrating, the residue was purified by flash column chromatography (SiO₂, hexane/EtOAc=30:1) to give ester (99.5 mg, 0.114 mmol, 92% from t-butyl ester) as a colorless oil.

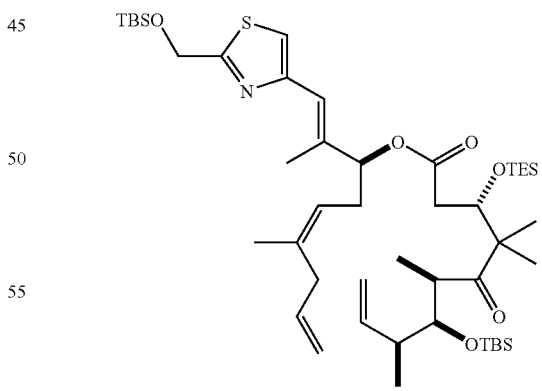

$[\alpha]_D^{25}$ −23.4 (c 0.56, CHCl₃); IR (film) ν 2955, 2931, 2880, 1735, 1696, 1506, 1472, 1386, 1362, 1294, 1254, 1174, 1104, 988, 878, 776, 742 cm⁻¹; ¹H NMR (400 MHz, CDCl₃) δ 0.06 (3H, s), 0.06 (3H, s), 0.14 (6H, s), 0.63 (6H, q, J=8.0 Hz), 0.92 (9H, s), 0.94 (9H, t, J=8.0 Hz), 0.97 (9H, s), 1.02 (3H, d, J=6.6 Hz), 1.05 (3H, d, J=6.5 Hz), 1.07 (3H, s), 1.21 (3H, s), 1.67 (3H, s), 2.06 (3H, d, J=0.8 Hz), 2.05-2.14 (1H, m), 2.30 (1H, dd, J=16.9, 7.5 Hz), 2.33-2.53 (2H, m), 2.50 (1H, dd, J=16.9, 2.7 Hz), 2.76-2.80 (2H, m), 3.07 (1H, quintet, J=7.0 Hz), 3.83 (1H, dd, J=7.0, 2.2 Hz), 4.35 (1H, dd, J=7.4, 2.8 Hz), 4.97 (2H, s), 4.97-5.07 (4H, m), 5.16 (1H, t, J=7.2 Hz), 5.24 (1H, t, J=6.9 Hz), 5.74 (1H, ddt, J=16.6, 10.0, 6.5 Hz), 5.91 (1H, ddd, J=17.6, 9.9, 7.7 Hz), 6.50 (1H, s), 7.06 (1H, s); $^{13}$C NMR (100 MHz, CDCl$_3$) δ −5.2 (2C), −3.7, −3.3, 5.3 (3C), 7.2 (3C), 14.7, 15.2, 18.5, 18.7, 18.9, 20.3, 23.6, 23.7, 26.0 (3C), 26.4 (3C), 31.7, 36.7, 40.1, 43.8, 46.4, 53.3, 63.4, 74.2, 76.5, 79.6, 115.5, 115.6, 116.6, 120.5, 121.3, 135.8, 136.1, 137.4, 140.1, 153.0, 171.5, 172.2, 218.4; LRMS (ESI) calcd for C$_{47}$H$_{86}$NO$_6$SSi$_3$ [M+H$^+$] 876.6, found 876.5; HRMS calcd. for C$_{47}$H$_{86}$NO$_6$SSi$_3$ [M+H$^+$] 876.5484, found 876.5482.

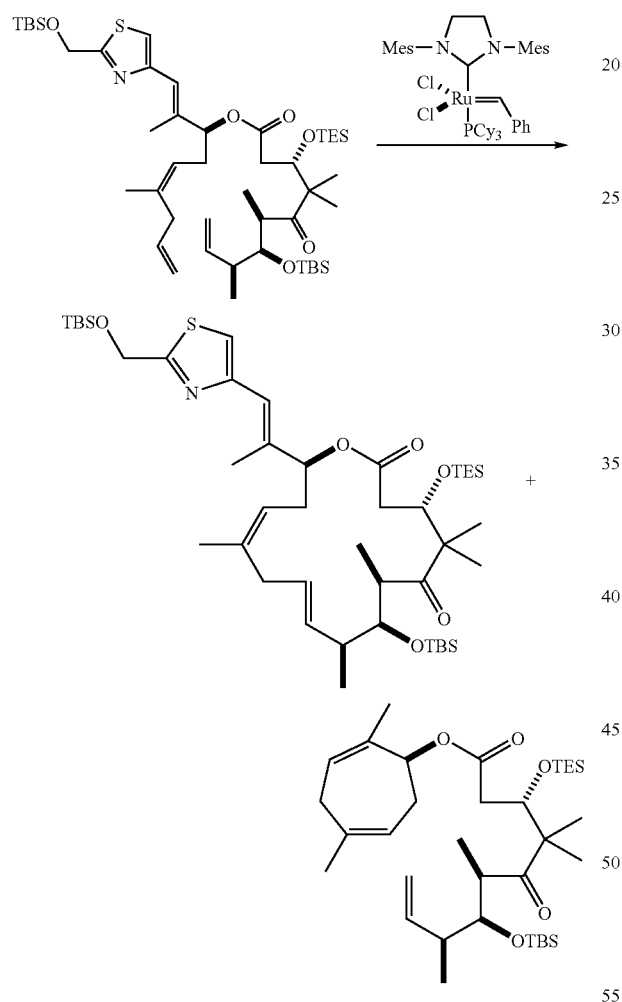

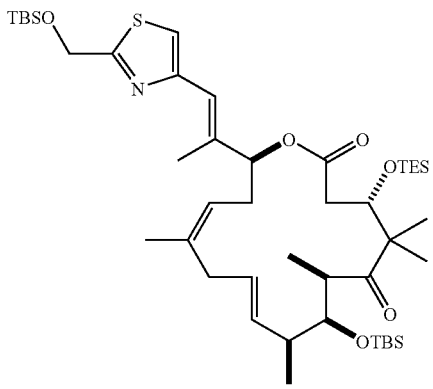

$[\alpha]_D^{24}$ −40.4 (c 0.26, CHCl$_3$); IR (film) ν 2955, 2930, 2879, 1740, 1694, 1472, 1387, 1362, 1253, 1200, 1107, 1007, 838, 776, 742 cm$^{-1}$; $^1$H NMR (400 MHz, CDCl$_3$) δ 0.08 (3H, s), 0.12 (3H, s), 0.15 (6H, s), 0.57 (6H, q, J=7.9 Hz), 0.88 (9H, t, J=8.0 Hz), 0.95 (9H, s), 0.97 (9H, s), 1.04 (3H, s), 1.06 (3H, d, J=7.1 Hz), 1.12 (3H, s), 1.17 (3H, d, J=7.0 Hz), 1.69 (3H, s), 2.06-2.30 (2H, m), 2.14 (3H, s), 2.45 (1H, dd, J=15.6, 3.6 Hz), 2.50 (1H, dd, J=14.9, 3.1 Hz), 2.63-2.75 (2H, m), 2.97-3.06 (1H, m), 3.10 (1H, dd, J=14.6, 7.7 Hz), 3.97 (1H, d, J=8.5 Hz), 4.44 (1H, dd, J=8.4, 2.9 Hz), 4.97 (2H, s), 5.22 (1H, dd, J=8.7, 5.2 Hz), 5.33-5.44 (2H, m), 5.70 (1H, dd, J=15.6, 8.1 Hz), 6.57 (1H, s), 7.07 (1H, s); $^{13}$C NMR (125 MHz, CDCl$_3$) δ −5.2, −3.3, −3.2, 5.6, 7.2, 7.3, 15.0, 17.2, 18.5, 18.8, 21.4, 23.9, 24.4, 26.0, 26.5, 33.3, 35.6, 41.4, 41.8, 48.2, 54.0, 63.5, 74.4, 78.1, 79.3, 116.6, 120.6, 121.0, 129.3, 132.1, 137.8, 137.9, 153.0, 170.7, 172.3, 216.8; LRMS (ESI) calcd for C$_{45}$H$_{82}$NO$_6$SSi$_3$ [M+H$^+$] 848.5, found 848.5; HRMS (ESI) calcd. for C$_{45}$H$_{82}$NO$_6$SSi$_3$ [M+H$^+$] 848.5171, found 848.5161.

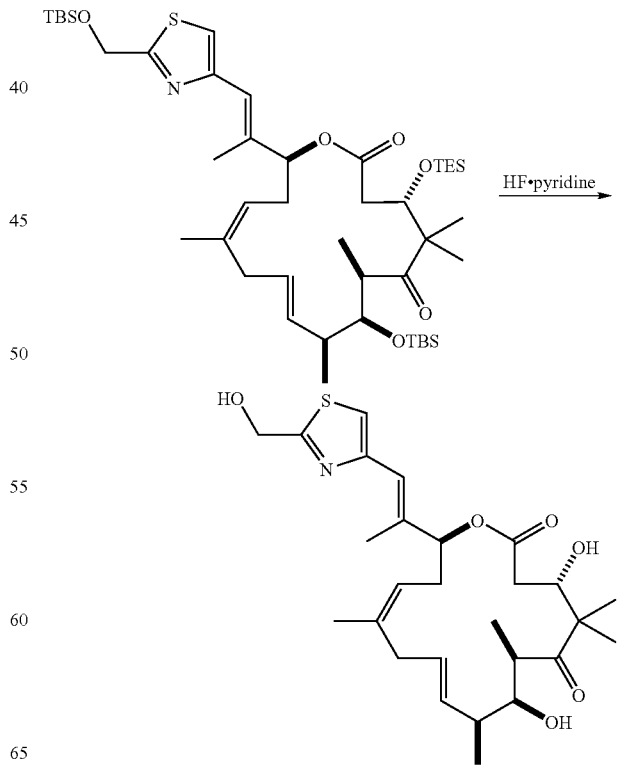

A solution of diene (69.7 mg, 79.5 µmol) in toluene (158 mL) was heated to reflux and treated with a solution of Grubbs' catalyst (6.7 mg, 7.95 mmol) in toluene (2 mL). The mixture was stirred for 11 min, cooled to 0° C., filtered through a pad of silica gel, which was rinsed with hexane/EtOAc=3/1 (280 mL). The combined filtrate was concentrated and purified by flash column chromatography (SiO$_2$, hexane/Et$_2$O=20:1 to 15:1) to give the desired product (18.4 mg, 21.7 µmol, 27%) and cycloheptadiene (28.3 mg, 45.5 mmol, 57%) both as a colorless oils.

To a solution of silylether (61.8 mg, 72.8 μmol) in THF (2 mL) in a plastic tube was added HF.pyridine (1 mL) at 0° C., and the mixture was stirred at rt for 3.2 h. The reaction was quenched with dropwise addition of TMSOMe (15 mL) at 0° C. The mixture was stirred at rt for 2 h. After concentrating and drying under high vacuum, the residue was purified by flash column chromatography (SiO$_2$, hexane/EtOAc=1:3) to give triol (32.4 mg, 64.1 μmol, 88%) as a white solid.

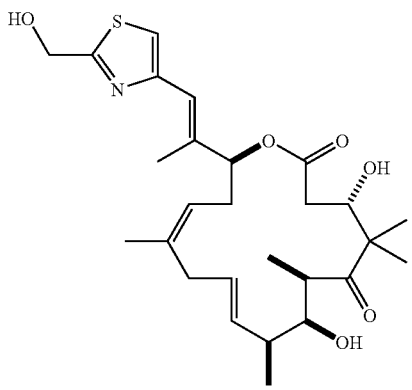

[α]$_D^{25}$ −108.4 (c 0.285, CHCl$_3$); IR (film) ν 3422, 2968, 2919, 2729, 1689, 1449, 1377, 1252, 1152, 1064, 978 cm$^{-1}$; $^1$H NMR (400 MHz, CDCl$_3$) δ 1.05 (3H, s), 1.12 (3H, d, J=6.9 Hz), 1.22 (3H, d, J=6.8 Hz), 1.32 (3H, s), 1.72 (3H, s), 2.08 (3H, s), 2.31-2.40 (3H, m), 2.43 (1H, dd, J=15.5, 3.5 Hz), 2.49 (1H, dd, J=15.5, 9.5 Hz), 2.55-2.67 (2H, m), 2.95 (1H, dd, J=14.6, 6.3 Hz), 3.13 (1H, quintet, J=6.6 Hz), 3.34 (1H, brs, —OH), 3.75 (1H, dd, J=6.6, 2.4 Hz), 4.06 (1H, brs, —OH), 4.33 (1H, dd, J=9.4, 3.0 Hz), 4.92 (2H, s), 5.18 (1H, t, J=6.9 Hz), 5.33 (1H, dd, J=8.0, 2.5 Hz), 5.52 (1H, dd, J=15.8, 6.4 Hz), 5.59 (1H, ddd, J=15.8, 6.6, 5.0 Hz), 6.63 (1H, s), 7.13 (1H, s); $^{13}$C NMR (100 MHz, CDCl$_3$) δ 15.3, 16.3, 17.8, 19.2, 22.8, 23.7, 31.9, 35.1, 39.7, 40.2, 45.0, 53.4, 61.8, 71.7, 75.8, 78.1, 116.7, 119.0, 120.5, 130.0, 131.2, 137.6, 138.9, 152.5, 170.0, 170.7, 218.7; LRMS (ESI) calcd for C$_{27}$H$_{39}$NO$_6$SNa [M+Na$^+$] 528.2, found 528.0; HRMS calcd. for C$_{27}$H$_{40}$NO$_6$S [M+H$^+$] 506.2576, found 506.2552.

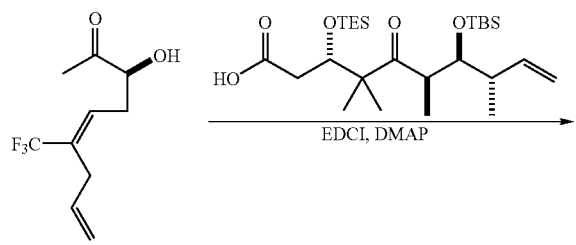

Crude acid (4.65 g, as 7.27 mmol) and alcohol (2.18 g, 9.84 mmol) were azeotroped with dry benzene and then dried under high vacuum for 20 min before reaction. To a solution of alcohol (2.18 g, 9.84 mmol) in CH$_2$Cl$_2$ (65 mL) were added EDCI (2.09 g, 10.9 mmol) and DMAP (1.33 g, 10.9 mmol) at 0° C. To the mixture was added a solution of crude acid (4.65 g, as 7.27 mmol) in CH$_2$Cl$_2$ (20 mL+5 mL rinse) dropwise over 20 min at 0° C. After stirring at 0° C. for 40 min, the mixture was stirred at rt for 4 h. After concentrating, the residue was purified by flash column chromatography (SiO$_2$~160 g, hexane/EtOAc=20:1) to give ester (4.85 g, 6.87 mmol, 94% from t-butyl ester) as a colorless oil.

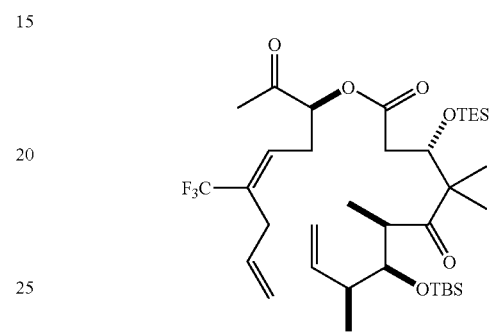

[α]$_D^{25}$ −22.7 (c 0.26, CHCl$_3$); IR (film) ν 2958, 2936, 2800, 1748, 1732, 1693, 1473, 1416, 1360, 1317, 1296, 1254, 1174, 1119, 989, 916, 872, 838, 776 cm$^{-1}$; $^1$H NMR (400 MHz, CDCl$_3$) δ 0.08 (3H, s), 0.08 (3H, s), 0.60 (6H, q, J=7.8 Hz), 0.93 (9H, s), 0.94 (9H, t, J=8.0 Hz), 1.04 (3H, d, J=7.0 Hz), 1.04 (3H, d, J=7.0 Hz), 1.11 (3H, s), 1.23 (3H, s), 2.05-2.14 (1H, m), 2.17 (3H, s), 2.40 (1H, dd, J=16.9, 7.0 Hz), 2.59 (1H, dd, J=17.0, 3.6 Hz), 2.56-2.64 (2H, m), 2.90-3.01 (2H, m), 3.06 (1H, quintet, J=7.0 Hz), 3.85 (1H, dd, J=7.3, 2.0 Hz), 4.38 (1H, d, J=7.0, 3.4 Hz), 4.97-5.14 (5H, m), 5.75 (1H, ddt, J=16.0, 9.9, 6.2 Hz), 5.92 (1H, ddd, J=17.8, 10.5, 7.8 Hz), 6.21 (1H, td, J=7.2, 1.5 Hz); $^{13}$C NMR (100 MHz, CDCl$_3$) δ −3.7, −3.4, 5.2 (3C), 7.1 (3C), 15.4, 18.7, 18.9, 19.5, 23.9, 26.3 (3C), 26.6, 28.5, 30.0, 39.8, 43.7, 46.3, 53.3, 73.6, 76.5, 77.1, 115.6, 117.8, 124.0 [q, $^1$J (C,F)=273.5 Hz], 129.2 [q, $^3$J (C,F)=6.1 Hz], 130.6 [q, $^2$J (C,F)=28.7 Hz], 133.4, 140.0, 171.8, 204.6, 218.4; LRMS (ESI) calcd for C$_{36}$H$_{63}$F$_3$O$_6$Si$_2$Na [M+Na$^+$] 727.4, found 727.3; HRMS calcd. for C$_{36}$H$_{64}$F$_3$O$_6$Si$_2$ [M+H$^+$] 705.4194, found 705.4193.

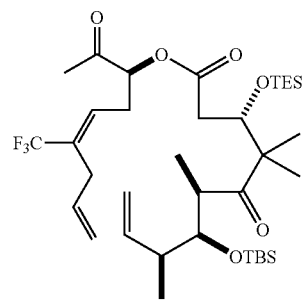

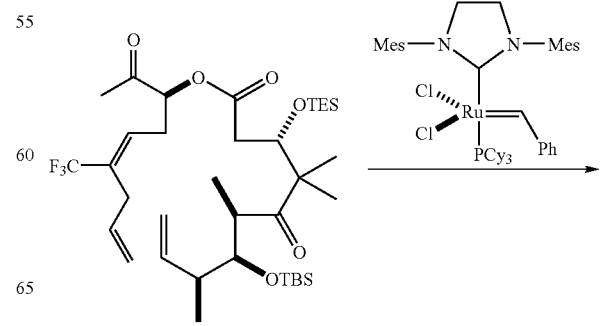

-continued

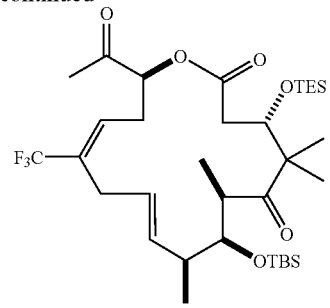

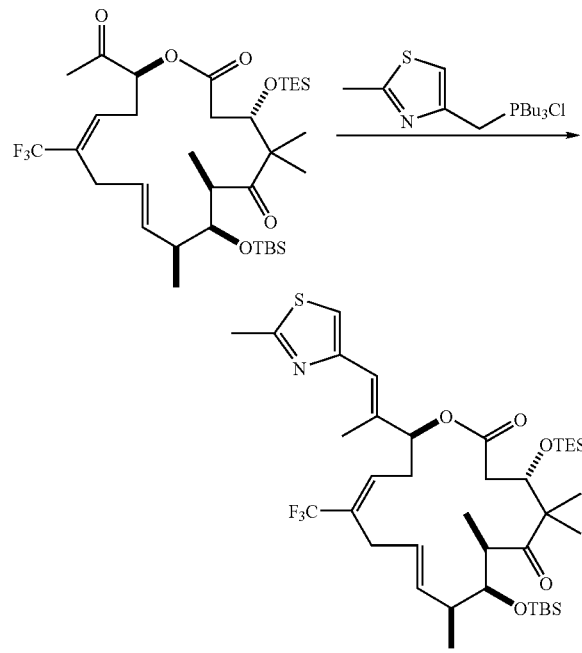

A solution of diene (510.0 mg, 0.723 mmol) in toluene (500 mL) was heated to reflux and treated with a solution of Grubbs' catalyst (92.1 mg, 0.109 mmol) in toluene (10 mL). The mixture was stirred for 17 min under reflux and immediately cooled to 0° C. and kept at 0° C. before filtration through a pad of silica gel. A second batch of diene (510.0 mg, 0.723 mmol) was processed identically and simultaneously. The combined reaction mixture were filtered through a pad of silica gel (100 g), which was rinsed with hexane/EtOAc=3/1 (1.4 L). The combine filtrate was concentrated and purified by flash column chromatography (SiO$_2$~65 g, hexane/Et$_2$O=10:1 to 5:1) to give macrolide (742.4 mg, 1.10 mmol, 76%) as a colorless amorphous oil.

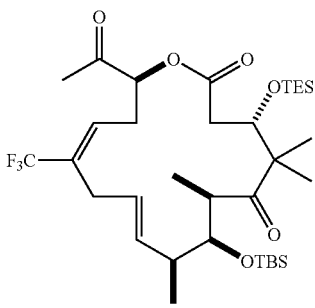

[α]$_D^{25}$ −7.5 (c 0.12, CHCl$_3$); IR (film) ν 2956, 2979, 1748, 1732, 1695, 1472, 1415, 1384, 1252, 1170, 1119, 1018, 986, 876, 835 cm$^{-1}$; $^1$H NMR (400 MHz, CDCl$_3$) δ 0.08 (3H, s), 0.10 (3H, s), 0.60 (6H, q, J=7.8 Hz), 0.93 (9H, s), 0.94 (9H, t, J=7.8 Hz), 1.03 (3H, d, J=7.1 Hz), 1.08 (3H, s), 1.13 (3H, d, J=7.0 Hz), 1.17 (3H, s), 2.26 (3H, s), 2.25-2.34 (1H, m), 2.64 (1H, dd, J=15.5, 5.0 Hz), 2.68-2.75 (2H, m), 2.76 (1H, dd, J=15.6, 6.4 Hz), 2.85 (1H, dd, J=15.6, 5.7 Hz), 2.97 (1H, dq, J=8.3, 6.9 Hz), 3.04 (1H, dd, J=15.6, 6.3 Hz), 3.92 (1H, dd, J=8.3, 1.2 Hz), 4.36 (1H, t, J=5.3 Hz), 5.30-5.39 (2H, m), 5.58 (1H, dd, J=15.5, 8.0 Hz), 6.13 (1H, brt, J=7.2 Hz); $^{13}$C NMR (100 MHz, CDCl$_3$) δ −3.6, −3.6, 5.4 (3C), 7.0 (3C), 17.5, 18.5, 19.0, 21.6, 23.5, 26.3 (3C), 26.5, 28.6, 29.1, 41.0, 42.3, 47.3, 54.1, 74.2, 76.8, 77.7, 124.0 [q, $^1$J (C,F)=273.7 Hz], 126.0, 128.7 [q, $^3$J (C,F)=5.9 Hz], 132.2 [q, $^2$J (C,F)=28.1 Hz], 133.8, 170.5, 204.1, 216.1; LRMS (ESI) calcd for C$_{34}$H$_{59}$F$_3$O$_6$Si$_2$Na [M+Na$^+$] 699.4, found 699.4; HRMS calcd. for C$_{34}$H$_{60}$F$_3$O$_6$Si$_2$ [M+H$^+$] 677.3881, found 677.3892.

Via Wittig Reaction:

Ketone was azeotroped with benzene (5 mL×2) and then dried under high vacuum for 0.5 h. To a solution of Wittig salt (907 mg, 2.59 mmol) in THF (19 mL) was added t-BuOK (2.4 L of a 1.0 M solution in THF, 2.43 mmol) dropwise over 5 min at 0° C. The mixture was stirred at 0° C. for 0.5 h and then cooled to −78° C. To the mixture was added dropwise a solution of ketone (1.10 g, 1.62 mmol) in THF (13 mL) over 10 min, and the resulting mixture was allowed to warm to −20° C. over 2 h. The reaction was quenched with sat. aqueous NH$_4$Cl (15 mL) and extracted with EtOAc (50 mL×3). The combined organic layers were washed with brine (20 mL), dried over Na$_2$SO$_4$ and concentrated. The residue was purified by flash column chromatography (SiO$_2$, hexane/Et$_2$O=20:1 to 10:1) to give the desired 16(E)-isomer (940 mg, 1.22 mmol, 75%) and the undesired 16(Z)-isomer (140.9 mg, 0.182 mmol, 11%) both as a colorless amorphous oil.

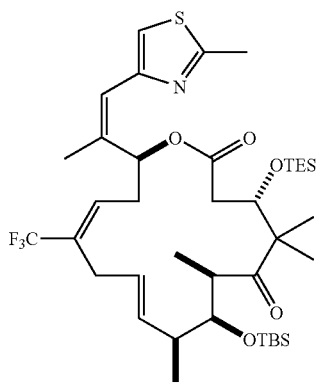

[α]$_D^{25}$ 62.7 (c 0.33, CHCl$_3$); IR (film) ν 2955, 2878, 1743, 1692, 1472, 1379, 1320, 1253, 1169, 1114, 1007, 956, 877, 835, 775 cm$^{-1}$; $^1$H NMR (400 MHz, CDCl$_3$) δ 0.09 (3H, s), 0.13 (3H, s), 0.49 (6H, q, J=7.8 Hz), 0.85 (9H, t, J=7.8 Hz), 0.97 (9H, s), 0.99 (3H, s), 1.06 (3H, d, J=7.1 Hz), 1.11 (3H, s), 1.20 (3H, d, J=7.1 Hz), 2.00 (3H, s), 2.03-2.13 (1H, m), 2.35 (1H, dd, J=14.3, 3.0 Hz), 2.46 (1H, dd, J=14.3, 7.8 Hz), 2.41-2.50 (1H, m), 2.73 (3H, s), 2.71-2.90 (2H, m) 2.98-3.12 (2H, m), 3.99 (1H, d, J=9.2 Hz), 4.56 (1H, dd, J=7.7, 2.8 Hz), 5.33 (1H, ddd, J=15.6, 8.9, 4.1 Hz), 5.82 (1H, dd, J=15.6, 8.4 Hz), 6.29 (1H, s), 6.33-6.40 (1H, m), 6.94 (1H, m), 7.09 (1H, brd, J=8.4 Hz); $^{13}$C NMR (100 MHz, CDCl$_3$) δ –3.2, –3.2, 5.5 (3C), 7.0 (3C), 17.2, 18.7, 19.3, 19.6, 20.0, 22.3, 24.9, 26.4 (3C), 29.7, 32.9, 41.9, 42.0, 48.6, 54.0, 72.2, 73.3, 77.0, 116.7, 120.7, 124.5 [q, $^1$J (C,F)=273.3 Hz], 127.9, 129.7 [q, $^2$J (C,F)=28.0 Hz], 131.9 [q, $^3$J (C,F)=6.1 Hz], 132.9, 136.6, 152.1, 165.4, 170.2, 217.4; LRMS (ESI) calcd for C$_{39}$H$_{65}$F$_3$NO$_5$SSi$_2$ [M+H$^+$] 772.4, found 772.4; HRMS calcd. for C$_{39}$H$_{65}$F$_3$NO$_5$SSi$_2$ [M+H$^+$] 772.4074, found 772.4044.

A solution of deH-dEpoB (12.2 mg, 24.9 mop in CH$_2$Cl$_2$ (1.25 mL) was cooled to –78° C. and treated with a cooled solution of DMDO (–78° C., 0.06 M in acetone, 914 μL, 54.8 μmol). The mixture was allowed to warm to –50° C. and stirred at –50° C. for 2.7 h. The excess DMDO was quenched at –50° C. by the addition of dimethylsulfide (117 μL) and the mixture was stirred at this temperature for 0.5 h. The solvent was removed in vacuo. Purification by preparative thin layer chromatography (hexane/EtOAc=1/2) gave β-epoxide (3.0 mg, 5.93 μmol, 24%) and α-epoxide (7.9 mg, 15.6 μmol, 63%) both as a colorless solids.

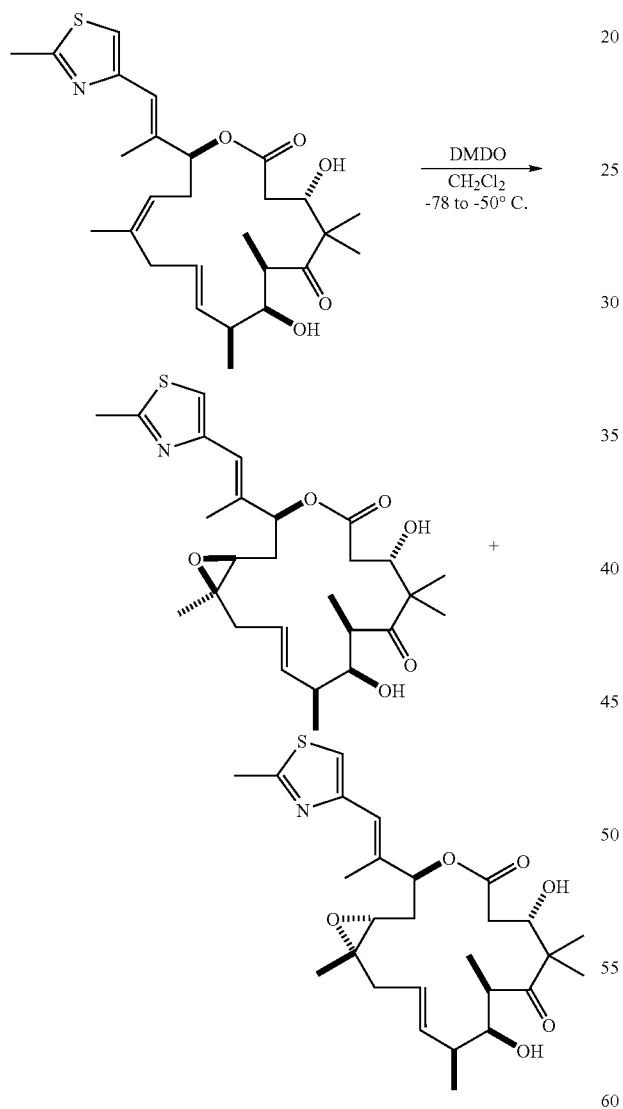

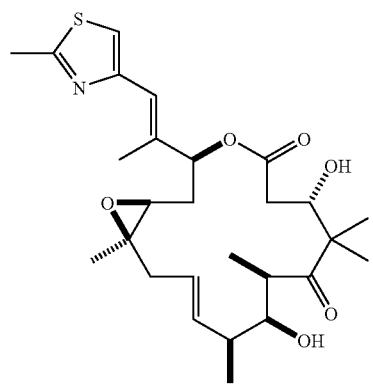

$[α]_D^{25}$ –78.5 (c 0.33, CHCl$_3$); IR (film) ν 3454, 2974, 2928, 1734, 1689, 1450, 1379, 1250, 1152, 1061, 978, 735 cm$^{-1}$; $^1$H NMR (400 MHz, CDCl$_3$) δ 1.03 (3H, s), 1.11 (3H, d, J=7.0 Hz), 1.14 (3H, d, J=6.9 Hz), 1.34 (3H, s), 1.36 (3H, s), 2.00 (1H, ddd, J=15.1, 7.3, 4.0 Hz), 2.14 (1H, dt, J=15.1, 5.2 Hz), 2.14 (3H, s), 2.21 (1H, dd, J=14.6, 8.0 Hz), 2.33 (1H, dd, J=14.7, 4.8 Hz), 2.47 (1H, dd, J=13.8, 3.3 Hz), 2.59 (1H, dd, J=13.8, 9.4 Hz), 2.73 (3H, s), 2.77 (1H, brs, OH), 2.93 (1H, dd, J=7.3, 4.8 Hz), 3.34 (1H, qd, J=6.9, 3.8 Hz), 3.75-3.82 (1H, m), 4.12-4.24 (2H, m, including OH), 5.54 (1H, ddd, J=15.7, 7.4, 5.0 Hz), 5.54-5.60 (1H, m), 5.64 (1H, dd, J=15.7, 5.6 Hz), 6.94 (1H, s), 7.01 (1H, s); $^1$H NMR (500 MHz, CD$_2$Cl$_2$) δ 0.91 (3H, s), 1.01 (3H, d, J=6.9 Hz), 1.03 (3H, d, J=6.9 Hz), 1.22 (3H, s), 1.27 (3H, s), 1.96-2.02 (1H, m), 2.04 (3H, d, J=0.7 Hz), 2.16-2.23 (2H, m), 2.33 (1H, dd, J=14.2, 3.1 Hz), 2.30-2.35 (1H, m), 2.44 (1H, dd, J=14.4, 10.3 Hz), 2.69 (3H, s), 2.77 (1H, t, J=5.9 Hz), 3.24 (1H, qd, J=6.9, 4.5 Hz), 3.63 (1H, t, J=4.1 Hz), 4.18-4.26 (1H, m), 5.37 (1H, t, J=4.5 Hz), 5.48 (1H, dtd, J=15.7, 6.7, 0.5 Hz), 5.58 (1H, dd, J=15.7, 6.2 Hz), 6.58 (1H, s), 7.00 (1H, s); $^{13}$C NMR (100 MHz, CDCl$_3$) δ 14.4, 16.3 (2C), 19.3, 19.7, 21.6, 22.6, 31.8, 35.9, 38.7, 39.6, 44.1, 52.8, 60.8, 61.8, 74.0, 75.7, 75.9, 116.5, 119.6, 124.3, 135.8, 136.2, 152.1, 165.2, 170.8, 221.5; LRMS calcd for C$_{27}$H$_{40}$NO$_6$S [M+H$^+$] 506.3, found 506.3; HRMS (ESI) calcd. for C$_{27}$H$_{40}$NO$_6$S [M+H$^+$] 506.2576, found 506.2566.

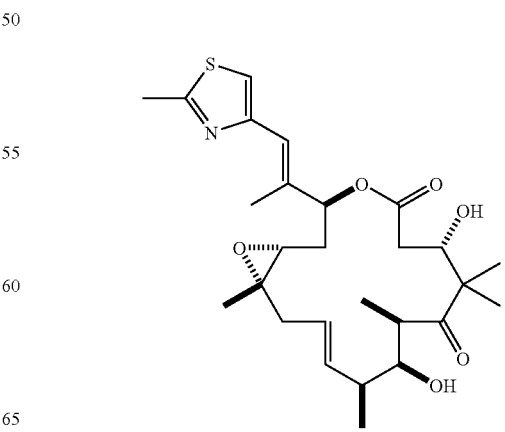

$[\alpha]_D^{25}$ −53.9 (c 0.700, CHCl$_3$); IR (film) ν 3460, 2976, 2928, 1735, 1688, 1506, 1451, 1378, 1252, 1186, 1151, 1087, 1042, 976, 879, 735 cm$^{-1}$; $^1$H NMR (400 MHz, CDCl$_3$) δ 1.00 (3H, s), 1.04 (3H, d, J=6.9 Hz), 1.12 (3H, d, J=7.0 Hz), 1.35 (3H, s), 1.35 (3H, s), 1.87 (1H, dt, J=15.0, 9.2 Hz), 2.03 (1H, dd, J=13.9, 9.2 Hz), 2.13 (3H, s), 2.13-2.19 (1H, m), 2.36 (1H, dd, J=13.9, 3.4 Hz), 2.39 (1H, dd, J=12.2, 2.1 Hz), 2.42-2.51 (1H, m), 2.49 (1H, dd, J=12.4, 10.9 Hz), 2.69 (1H, d, J=2.7 Hz), 2.72 (3H, s), 3.06 (1H, dd, J=9.7, 3.1 Hz), 3.54 (1H, qd, J=7.0, 1.8 Hz), 3.76-3.80 (1H, m), 4.07-4.14 (1H, m), 4.31 (1H, d, J=4.1 Hz), 5.52 (1H, dd, J=15.5, 8.7 Hz), 5.60 (1H, ddd, J=15.1, 9.4, 3.4 Hz), 5.71 (1H, d, J=8.4 Hz), 6.63 (1H, s), 6.99 (1H, s); $^{13}$C NMR (100 MHz, CDCl$_3$) δ 13.7, 15.3, 15.7, 18.5, 19.4, 21.2, 22.4, 32.5, 35.5, 39.1, 43.4, 43.8, 51.9, 61.3, 64.8, 73.5, 75.9, 76.4, 116.7, 120.1, 124.3, 137.5, 137.7, 152.3, 165.2, 171.0, 222.3; LRMS (ESI) calcd for C$_{27}$H$_{39}$NO$_6$SNa [M+Na$^+$] 528.2, found 528.2; HRMS calcd. for C$_{27}$H$_{40}$NO$_6$S [M+H$^+$] 506.2576, found 506.2583.

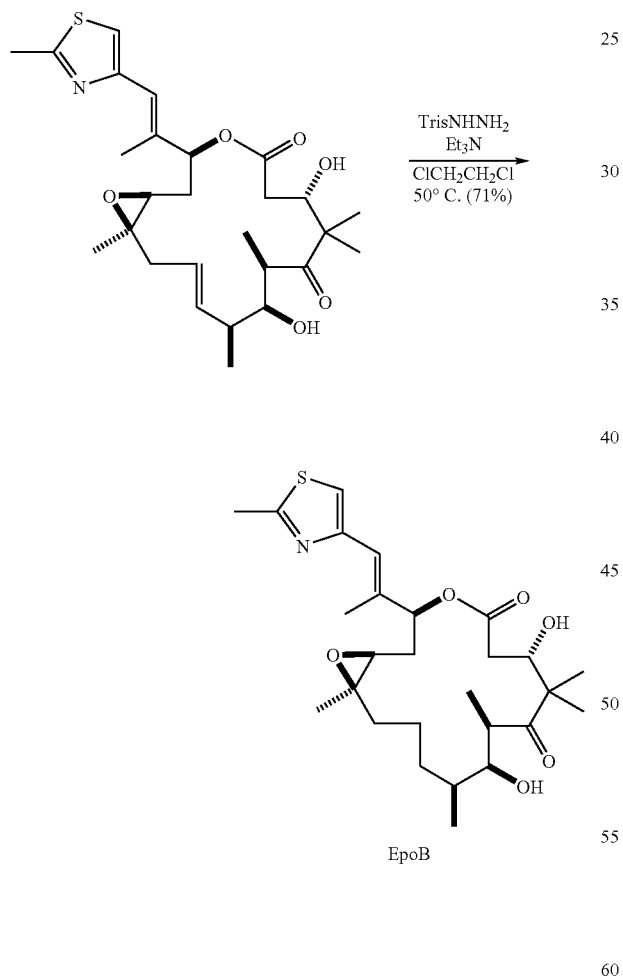

EpoB

To a solution of epoxide (0.7 mg, 1.38 μmol) and Tris-NHNH$_2$ (20.6 mg, 69 μmol) in ClCH$_2$CH$_2$Cl (0.4 mL) at 50° C. was added Et$_3$N (9.6 μL, 69 μmol). The reaction was monitored by HPTLC (hexane/EtOAc=1/2). After stirring for 6 h, the mixture was cooled to rt, diluted with EtOAc and filtered through a pad of silica gel, which was rinsed with EtOAc. After concentrating, the residue was purified by preparative TLC (hexane/EtOAc=1/2) to give reduced product (0.5 mg, 0.985 μmol, 71%) as a white solid.

The spectral data of this compound was identical to those reported for EpoB.

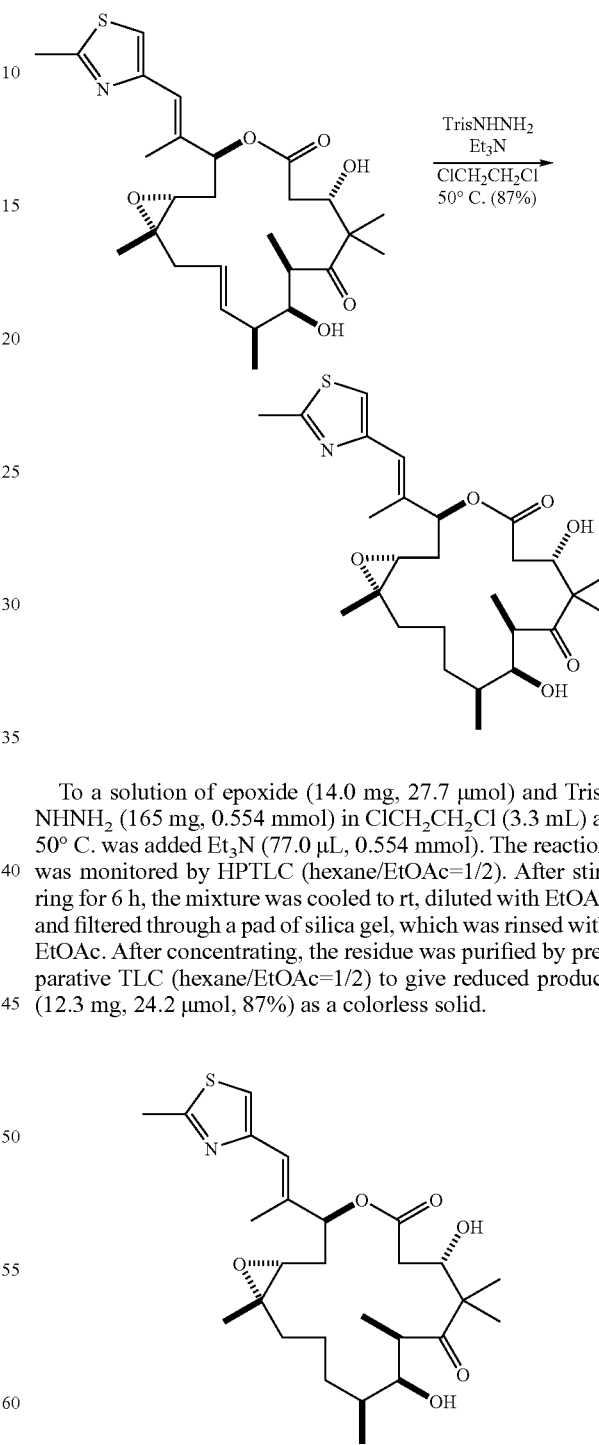

To a solution of epoxide (14.0 mg, 27.7 μmol) and Tris-NHNH$_2$ (165 mg, 0.554 mmol) in ClCH$_2$CH$_2$Cl (3.3 mL) at 50° C. was added Et$_3$N (77.0 μL, 0.554 mmol). The reaction was monitored by HPTLC (hexane/EtOAc=1/2). After stirring for 6 h, the mixture was cooled to rt, diluted with EtOAc and filtered through a pad of silica gel, which was rinsed with EtOAc. After concentrating, the residue was purified by preparative TLC (hexane/EtOAc=1/2) to give reduced product (12.3 mg, 24.2 μmol, 87%) as a colorless solid.

$[\alpha]_D^{24}$ −13.8 (c 0.61, CHCl$_3$); IR (film) ν 3475, 2971, 2875, 1735, 1689, 1456, 1382, 1253, 1181, 1151, 1056, 980, 884, 735 cm$^{-1}$; $^1$H NMR (400 MHz, CDCl$_3$) δ 0.95 (3H, d, J=7.1 Hz), 1.04 (3H, s), 1.11 (3H, d, J=7.0 Hz), 1.28 (3H, s), 1.37 (3H, s), 1.25-1.44 (2H, m), 1.45-1.59 (2H, m), 1.71-1.82 (3H, m), 1.86 (1H, dt, J=15.3, 9.5 Hz), 2.10 (1H, dd, J=15.3, 3.6 Hz), 2.13 (3H, s), 2.40 (1H, dd, J=12.5, 2.5 Hz), 2.49 (1H, dd, J=12.5, 11.0 Hz), 2.74 (3H, s), 2.80 (1H, brs, OH), 3.07 (1H, dd, J=10.3, 3.3 Hz), 3.34 (1H, qd, J=7.0, 0.5 Hz), 3.89 (1H, brs, OH), 4.03-4.09 (1H, m), 4.12-4.17 (1H, m), 5.69 (1H, d, J=9.1 Hz), 6.63 (1H, s), 7.00 (1H, s); $^{13}$C NMR (100 MHz, CDCl$_3$) δ 12.9, 15.4, 16.3, 18.8, 19.3, 21.6, 22.0, 23.0, 31.5, 32.1, 33.6, 38.6, 38.9, 42.6, 51.7, 62.6, 65.5, 71.2, 74.5, 76.3, 116.6, 119.9, 138.0, 152.2, 165.2, 170.6, 222.7; LRMS (ESI) calcd for C$_{27}$H$_{41}$NO$_6$SNa [M+Na$^+$] 530.3, found 530.2; HRMS calcd. for C$_{27}$H$_{42}$NO$_6$S [M+H$^+$] 508.2733, found 508.2754.

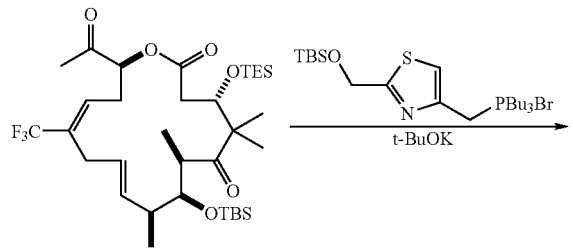

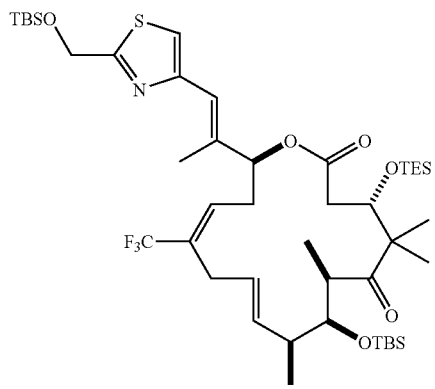

Ketone was azeotroped with benzene (5 mL×2) and then dried under high vacuum for 0.5 h. To a solution of Wittig salt (1.19 g, 2.27 mmol) in THF (18 mL) was added t-BuOK (2.2 L of a 1.0 M solution in THF, 2.20 mmol) dropwise over 5 min at 0° C. The mixture was stirred at 0° C. for 20 min and then cooled to −78° C. To the mixture was added dropwise a solution of ketone (1.06 g, 1.51 mmol) in THF (10 mL+2 mL rinse) over 10 min, and the resulting mixture was allowed to warm to −20° C. over 2 h. The reaction was quenched with sat. aqueous NH$_4$Cl (15 mL) and extracted with EtOAc (50 mL×3). The combined organic layers were washed with brine (20 mL), dried over Na$_2$SO$_4$ and concentrated. The residue was purified by flash column chromatography (SiO$_2$~65 g, hexane/Et$_2$O=30:1 to 20:1) to give the desired 16(E)-isomer (1.01 g, 1.11 mmol, 74%) and undesired 16(Z)-isomer (154.5 mg, 0.182 mmol, 11%) both as a colorless amorphous oil.

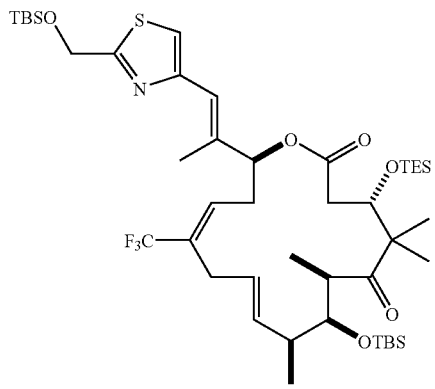

[α]$_D^{24}$ −19.0 (c 0.10, CHCl$_3$); IR (film) ν 2954, 2930, 2880, 1744, 1692, 1472, 1381, 1321, 1252, 1171, 1114, 1038, 1006, 837, 776 cm$^{-1}$; $^1$H NMR (400 MHz, CDCl$_3$) δ 0.09 (3H, s), 0.12 (3H, s), 0.15 (6H, s), 0.55 (6H, q, J=7.8 Hz), 0.87 (9H, t, J=8.0 Hz), 0.96 (9H, s), 0.97 (9H, s), 1.01 (3H, s), 1.06 (3H, d, J=7.1 Hz), 1.12 (3H, s), 1.20 (3H, d, J=7.1 Hz), 2.07-2.16 (1H, m), 2.18 (3H, d, J=1.0 Hz), 2.38 (1H, dd, J=14.4, 3.3 Hz), 2.34-2.46 (1H, m), 2.49 (1H, dd, J=14.4, 7.4 Hz), 2.78-2.90 (2H, m), 2.97-3.09 (2H, m), 3.98 (1H, d, J=8.9 Hz), 4.54 (1H, dd, J=7.3, 3.3 Hz), 4.97 (2H, s), 5.33 (1H, ddd, J=15.8, 8.6, 4.9 Hz), 5.63 (1H, dd, J=9.6, 2.4 Hz), 5.78 (1H, dd, J=15.8, 8.2 Hz), 6.22-6.27 (1H, m), 6.60 (1H, s), 7.09 (1H, s); $^{13}$C NMR (100 MHz, CDCl$_3$) δ −5.3 (2C), −3.4, −3.3, 5.5 (3C), 7.0 (3C), 14.6, 17.1, 18.4, 18.7, 19.8, 21.3, 24.8, 25.9 (3C), 26.4 (3C), 29.6, 32.9, 42.0, 42.1, 48.2, 54.1, 63.4, 73.4, 76.9, 77.8, 117.2, 121.7, 124.3 [q, $^1$J (C,F)=273.6 Hz], 127.2, 130.7 [q, $^2$J (C,F)=27.5 Hz], 130.8 [q, $^3$J (C,F)=6.2 Hz], 133.2, 136.4, 152.6, 170.1, 172.4, 217.1; LRMS (ESI) calcd. for C$_{45}$H$_{78}$F$_3$NO$_6$SSi$_3$Na [M+Na$^+$] 924.5, found 924.5; HRMS calcd. for C$_{45}$H$_{79}$F$_3$NO$_6$SSi$_3$ [M+H$^+$] 902.4888, found 902.4887.

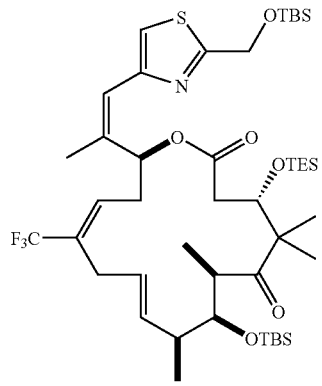

[α]$_D^{26}$ 65.7 (c 1.76, CHCl$_3$); IR (film) ν 2955, 2931, 2879, 1743, 1692, 1472, 1380, 1321, 1253, 1170, 1113, 1007, 836, 776 cm$^{-1}$; $^1$H NMR (400 MHz, CDCl$_3$) δ 0.07 (3H, s), 0.13 (3H, s), 0.16 (6H, s), 0.48 (6H, q, J=7.8 Hz), 0.84 (9H, t, J=7.9 Hz), 0.97 (18H, s), 0.98 (3H, s), 1.06 (3H, d, J=7.1 Hz), 1.11 (3H, s), 1.20 (3H, d, J=7.2 Hz), 2.00 (3H, s), 2.03-2.11 (1H, m), 2.33 (1H, dd, J=14.1, 2.8 Hz), 2.43 (1H, dd, J=14.0, 7.8 Hz), 2.40-2.48 (1H, m), 2.76-2.89 (2H, m), 2.97-3.10 (2H, m), 3.99 (1H, d, J=9.3 Hz), 4.57 (1H, dd, J=7.8, 2.6 Hz), 4.95 (1H, d, J=14.6 Hz), 5.00 (1H, d, J=14.6 Hz), 5.33 (1H, ddd, J=15.6, 9.1, 3.8 Hz), 5.82 (1H, dd, J=15.6, 8.3 Hz), 6.30 (1H, s), 6.32-6.38 (1H, m), 7.04 (1H, s), 7.11 (1H, dd, J=11.0, 2.3 Hz); $^{13}$C NMR (100 MHz, CDCl$_3$) δ −5.3 (2C), −3.2, −3.2, 5.5 (3C), 7.0 (3C), 17.2, 18.4, 18.8, 19.3, 19.8, 22.4, 25.1, 25.9 (3C), 26.5 (3C), 29.7, 33.0, 41.9, 42.1, 48.6, 54.0, 63.5, 72.1, 73.3, 76.9, 117.0, 120.8, 124.5 [q, $^1$J (C,F)=273.5 Hz], 127.9, 129.7 [q, $^2$J (C,F)=27.6 Hz], 131.9 [q, $^3$J (C,F)=6.1 Hz], 132.9, 136.4, 152.4, 170.1, 172.9, 217.5; LRMS (ESI) calcd for C$_{45}$H$_{78}$F$_3$NO$_6$SNa [M+Na$^+$] 924.5, found 924.5.

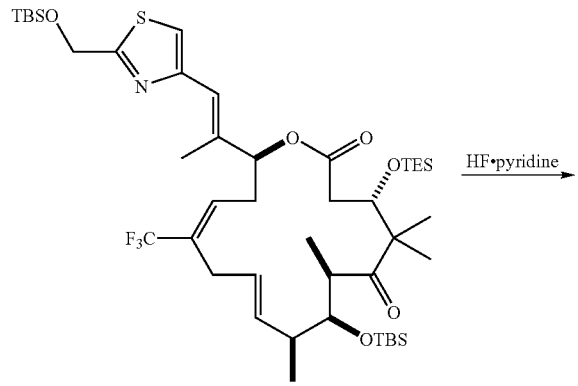

To a solution of silyl ether (1.04 g, 2.25 mmol) in THF (22 mL) in a plastic tube was added slowly HF.pyridine (11 mL) at 0° C., and the mixture was stirred at rt for 4.3 h. The reaction was quenched with dropwise addition of TMSOMe (75 mL) over 10 min at 0° C. The mixture was vigorously stirred at rt for 4.2 h. After concentrating and drying under high vacuum for 1 h, the residue was purified by flash column chromatography (SiO$_2$~25 g, hexane/EtOAc=3:4 to 1:2) to give triol (615.7 mg, 1.00 mmol, 96%) as a colorless powder.

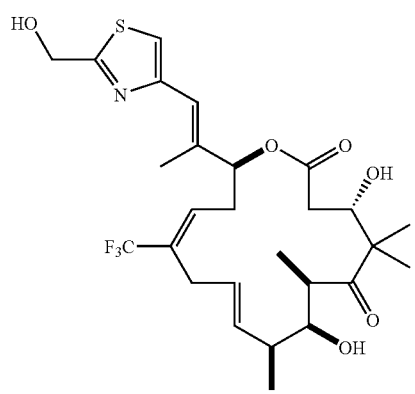

[α]$_D^{25}$ −57.7 (c 1.20, CHCl$_3$); IR (film) ν 3441, 2974, 2932, 1734, 1685, 1507, 1456, 1374, 1318, 1248, 1169, 1112, 1054, 982, 888, 737 cm$^{-1}$; $^1$H NMR (400 MHz, CDCl$_3$) δ 1.04 (3H, s), 1.12 (3H, d, J=6.9 Hz), 1.25 (3H, d, J=6.8 Hz), 1.36 (3H, s), 1.90 (1H, d, J=6.6 Hz, OH), 2.08 (3H, s), 2.23-2.32 (1H, m), 2.34 (1H, dd, J=15.7, 2.4 Hz), 2.49 (1H, dd, J=15.7, 10.1 Hz), 2.59-2.69 (2H, m), 2.95-3.01 (2H, m), 3.04 (1H, quintet, J=6.8 Hz), 3.72 (1H, td, J=7.0, 3.0 Hz), 3.78 (1H, d, J=5.7 Hz, OH), 4.38 (1H, ddd, J=10.1, 5.7, 2.4 Hz), 4.90 (2H, d, J=6.1 Hz), 5.10 (1H, t, J=6.1 Hz, OH), 5.44 (1H, t, J=4.7 Hz), 5.60 (1H, dd, J=15.9, 4.4 Hz), 5.66 (1H, dd, J=15.9, 5.0 Hz), 6.28 (1H, t, J=6.7 Hz), 6.73 (1H, s), 7.16 (1H, s); $^{13}$C NMR (100 MHz, CDCl$_3$) δ 16.0, 16.5, 17.4, 17.5, 22.9, 28.5, 30.3, 39.0, 39.6, 45.6, 54.0, 60.9, 70.6, 75.6, 75.7, 116.8, 119.2, 124.2 [q, $^1$J (C,F)=273.6 Hz], 127.9, 129.8 [q, $^2$J (C,F)=28.4 Hz], 130.3 [q, $^3$J (C,F)=5.9 Hz], 131.2, 137.0, 152.2, 169.8, 170.0, 218.3; LRMS (ESI) calcd for C$_{27}$H$_{37}$F$_3$NO$_6$SNa [M+H$^+$] 560.2, found 560.1; HRMS calcd. for C$_2$H$_{37}$F$_3$NO$_6$S [M+H$^+$] 560.2294, found 560.2299.

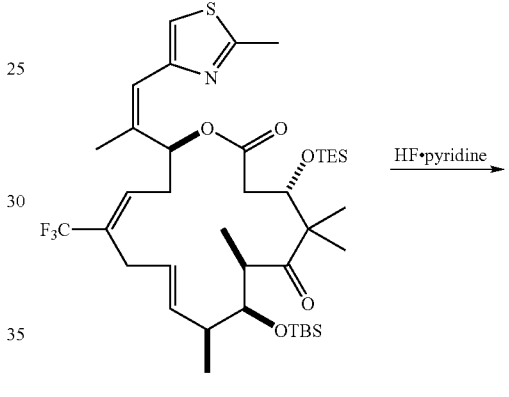

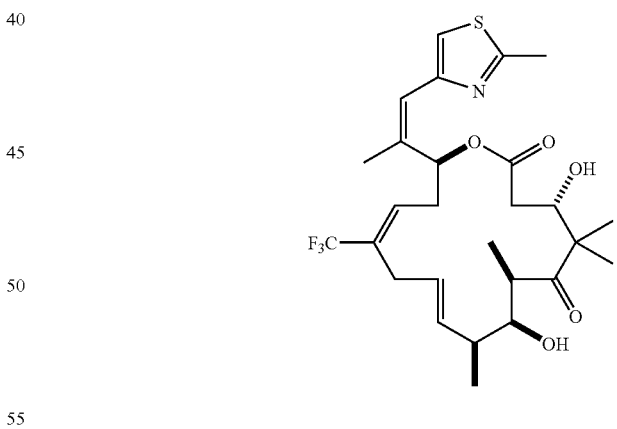

To a solution of silyl ether (42.8 mg, 55.4 μmol) in THF (1 mL) in a plastic tube was added slowly HF.pyridine (0.5 mL) at 0° C., and the mixture was stirred at rt for 4.3 h. The reaction was quenched with dropwise addition of TMSOMe (3.2 mL) over 10 min at 0° C. The mixture was vigorously stirred at rt for 1.5 h. After concentrating and drying under high vacuum for 1 h, the residue was purified by flash column chromatography (SiO$_2$, hexane/EtOAc=1:1) gave diol (23.6 mg, 43.4 μmol, 78%) as a colorless oil.

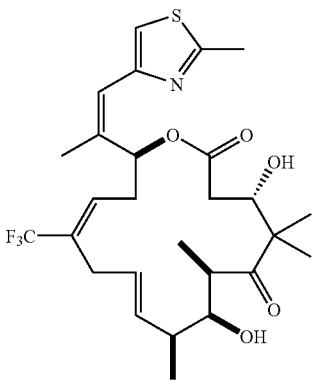

[α]$_D^{25}$ 31.6 (c 1.00, CHCl$_3$); IR (film) ν 2955, 2878, 1743, 1692, 1471, 1379, 1320, 1253, 1169, 1114, 1007, 877, 835, 741 cm$^{-1}$; $^1$H NMR (400 MHz, CDCl$_3$) δ 1.04 (3H, s), 1.11 (3H, d, J=6.9 Hz), 1.20 (3H, d, J=6.9 Hz), 1.30 (3H, s), 1.93 (3H, brs), 2.22 (1H, d, J=4.3 Hz, OH), 2.25-2.33 (1H, m), 2.38-2.41 (2H, m), 2.51-2.59 (2H, m), 2.70 (3H, s), 2.80-2.90 (1H, m), 2.94 (1H, dd, J=15.6, 4.7 Hz), 3.06 (1H, dd, J=15.6, 7.4 Hz), 3.19 (1H, quintet, J=6.6 Hz), 3.71-3.76 (1H, m), 4.26-4.32 (1H, m), 5.57 (1H, ddd, J=15.8, 7.2, 5.0 Hz), 5.67 (1H, dd, J=15.8, 6.8 Hz), 6.27 (1H, s), 6.33 (1H, dd, J=7.6, 6.3 Hz), 6.76 (1H, dd, J=8.3, 2.9 Hz), 6.94 (1H, s); $^{13}$C NMR (100 MHz, CDCl$_3$) δ 14.5, 17.9, 19.2, 19.5, 19.8, 22.2, 28.7, 32.4, 39.8 (2C), 44.7, 53.3, 71.9, 74.1, 75.1, 117.0, 120.4, 124.4 [q, $^1$J(C,F)=272.7 Hz], 128.4, 130.1 [q, $^2$J(C,F)=28.9 Hz], 131.5 [q, $^3$J(C,F)=5.9 Hz], 133.0, 136.9, 152.2, 165.5, 170.7, 218.5; LRMS (ESI) calcd for C$_{27}$H$_{36}$F$_3$NO$_5$SNa [M+Na$^+$] 566.2, found 566.3.

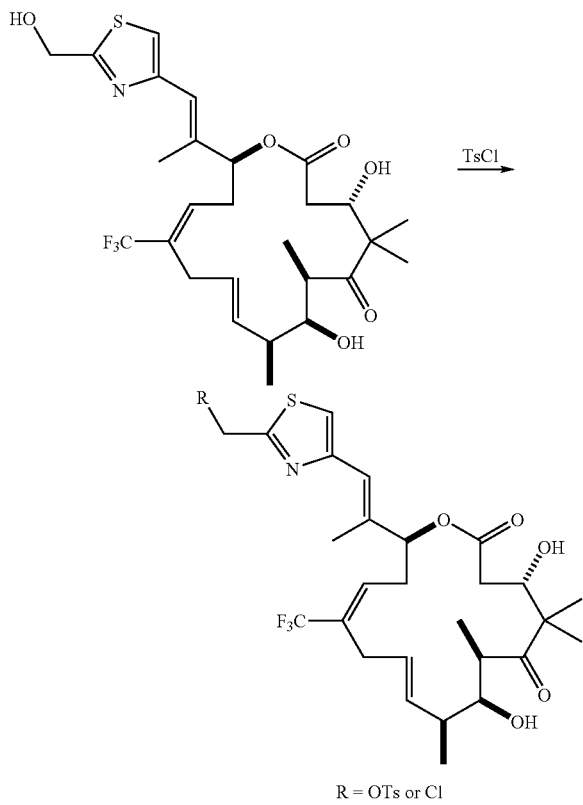

R = OTs or Cl

To a solution of alcohol (18.9 mg, 33.8 μmol) and Et$_3$N (18.8 μL, 0.135 mmol) in CH$_2$Cl$_2$ (1 mL) was added TsCl (12.9 mg, 67.5 μmol) followed by DMAP (2.1 mg, 16.9 μmol) at 0° C. After stirring at rt for 1.5 h, the mixture was filtered through a pad of silica gel (EtOAc rinse). After concentrated, the residue was purified by preparative TLC (hexane/EtOAc=1/1) to give tosylate (8.5 mg, 11.9 mmol, 35%) and chloride (4.3 mg, 7.44 μmol, 22%) both as a colorless powders.

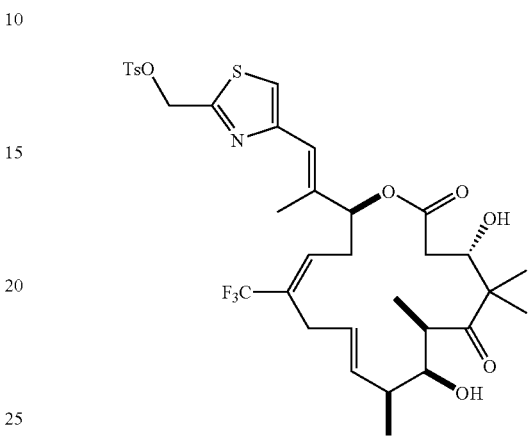

$^1$H NMR (400 MHz, CDCl$_3$) δ 1.06 (3H, s), 1.12 (3H, d, J=7.0 Hz), 1.23 (3H, d, J=6.7 Hz), 1.33 (3H, s), 1.99 (1H, d, J=5.5 Hz), 2.10 (3H, s), 2.25-2.34 (1H, m) 2.41 (1H, dd, J=15.5, 3.3 Hz), 2.47 (3H, s), 2.48 (1H, dd, J=15.7, 9.4 Hz), 2.51-2.63 (1H, m), 2.63 (1H, d, J=6.1 Hz, OH), 2.64-2.75 (1H, m), 2.91-3.05 (2H, m), 3.10 (1H, quintet, J=6.8 Hz), 3.70-3.75 (1H, m), 4.30 (1H, ddd, J=9.3, 6.1, 3.2 Hz), 5.32 (2H, s), 5.41 (1H, dd, J=5.8, 4.5 Hz), 5.57 (1H, ddd, J=15.8, 6.4, 4.6 Hz), 5.65 (1H, dd, J=15.8, 6.0 Hz), 6.21 (1H, t, J=7.1 Hz), 6.59 (1H, s), 7.18 (1H, s), 7.37 (2H, d, J=8.1 Hz), 7.84 (2H, d, J=8.3 Hz); LRMS (ESI) calcd for C$_{34}$H$_{42}$F$_3$NO$_8$S$_2$Na [M+Na$^+$] 736.2, found 736.3.

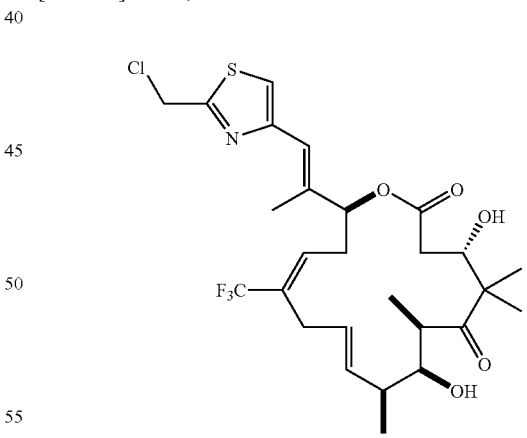

IR (film) ν 3494, 2975, 2935, 1734, 1689, 1319, 1248, 1170, 1113, 1040, 979, 738 cm$^{-1}$; $^1$H NMR (400 MHz, CDCl$_3$) δ 1.06 (3H, s), 1.12 (3H, d, J=6.9 Hz), 1.23 (3H, d, J=6.7 Hz), 1.34 (3H, s), 2.00 (1H, d, J=5.6 Hz, OH), 2.15 (3H, s), 2.25-2.35 (1H, m), 2.41 (1H, dd, J=15.5, 3.2 Hz), 2.49 (1H, dd, J=15.5, 9.4 Hz), 2.53-2.62 (1H, m), 2.69 (1H, d, J=6.1 Hz, OH), 2.66-2.76 (1H, m), 2.92-3.05 (2H, m), 3.11 (1H, quintet, J=6.4 Hz), 3.70-3.76 (1H, m), 4.32 (1H, ddd, J=9.2, 5.9, 3.1 Hz), 4.85 (2H, s), 5.43 (1H, dd, J=6.0, 4.4 Hz), 5.59 (1H, ddd, J=15.9, 6.4, 4.5 Hz), 5.66 (1H, dd, J=15.9, 6.1 Hz), 6.23 (1H, t, J=6.8 Hz), 6.63 (1H, s), 7.20 (1H, s); LRMS (ESI) calcd for C$_{27}$H$_{35}$ClF$_3$NO$_5$SNa [M+Na$^+$] 600.2, found 600.2.

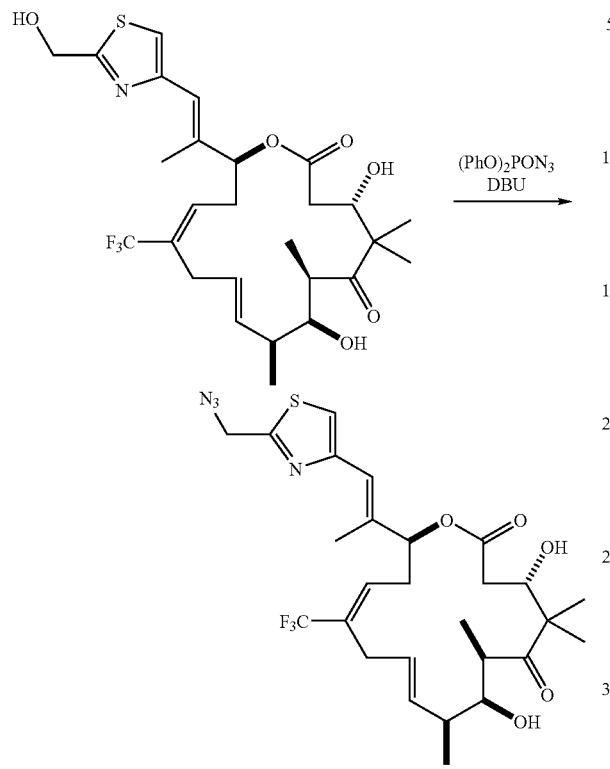

To a solution of triol (50.4 mg, 90.1 μmol) in THF (1 mL) was added (PhO)$_2$PON$_3$ (27.2 μL, 0.126 mmol) at 0° C. After 5 min, DBU (16.2 μL, 0.108 mmol) was added, and the mixture was stirred at 0° C. for 2 h then rt for 20.5 h. The mixture was diluted with EtOAc and quenched with water (2 mL), extracted with EtOAc (three times), and the combined organic layers were dried over Na$_2$SO$_4$. After concentrating, the residue was purified by flash column chromatography (SiO$_2$, hexane/EtOAc=3:2) to give azide (45.6 mg, 78.0 μmol, 87%) as a colorless powder.

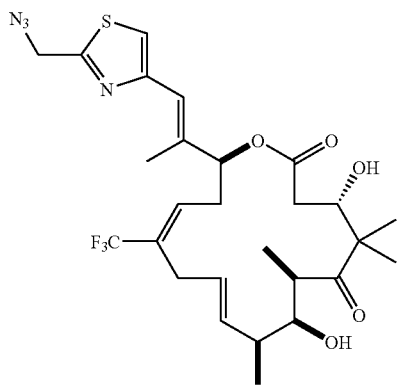

[α]$_D^{24}$ −60.3 (c 0.345, CHCl$_3$); IR (film) ν 3492, 2975, 2931, 2105, 1732, 1688, 1319, 1248, 1169, 1113, 982, 733 cm$^{-1}$; $^1$H NMR (400 MHz, CDCl$_3$) δ 1.05 (3H, s), 1.12 (3H, d, J=7.0 Hz), 1.23 (3H, d, J=6.8 Hz), 1.33 (3H, s), 2.01 (1H, d, J=5.5 Hz, OH), 2.17 (3H, s), 2.25-2.35 (1H, m), 2.41 (1H, dd, J=15.5, 3.2 Hz), 2.49 (1H, dd, J=15.5, 9.5 Hz), 2.54-2.60 (1H, m), 2.66 (1H, d, J=6.0 Hz), 2.65-2.76 (1H, m), 2.96 (1H, dd, J=16.0, 4.2 Hz), 3.03 (1H, dd, J=16.1, 6.7 Hz), 3.11 (1H, quintet, J=6.8 Hz), 3.71-3.76 (1H, m), 4.31 (1H, ddd, J=9.2, 5.9, 3.2 Hz), 4.65 (2H, s), 5.43 (1H, dd, J=6.0, 4.3 Hz), 5.58 (1H, ddd, J=15.8, 6.4, 4.6 Hz), 5.66 (1H, dd, J=15.8, 6.1 Hz), 6.23 (1H, t, J=7.3 Hz), 6.63 (1H, s), 7.18 (1H, s); $^{13}$C NMR (100 MHz, CDCl$_3$) δ 15.4, 15.9, 17.8, 18.6, 22.8, 28.7, 30.9, 39.5, 39.7, 45.1, 51.3, 53.5, 71.5, 75.4, 76.8, 118.2, 119.6, 122.7 [q, $^1$J (C,F)=273.6 Hz], 127.9, 130.0 [q, $^3$J (C,F)=6.1 Hz], 130.6 [q, $^2$J (C,F)=27.9 Hz], 132.3, 137.2, 153.1, 163.9, 170.0, 218.3; LRMS (EST) calcd for C$_{27}$H$_{35}$F$_3$N$_4$O$_5$SNa [M+Na$^+$] 607.2, found 607.2; HRMS calcd for C$_{27}$H$_{36}$F$_3$N$_4$O$_5$S [M+H$^+$] 585.2359 found 585.2344.

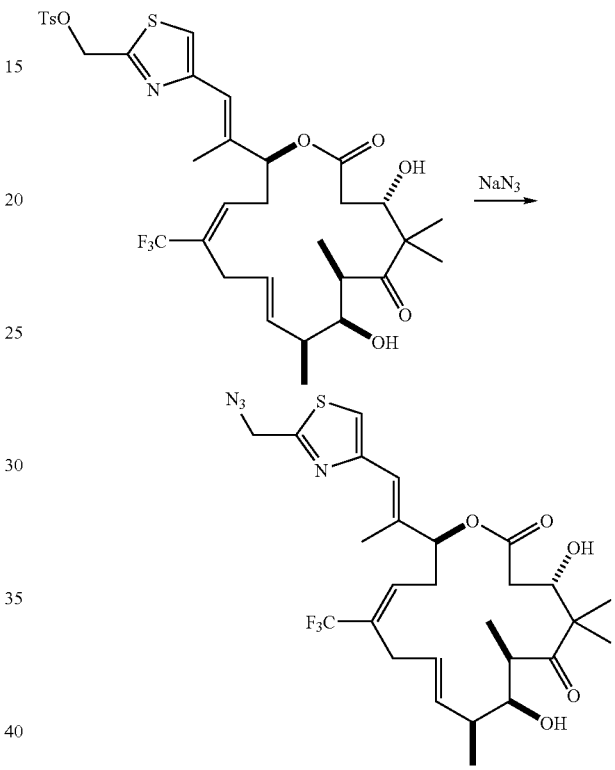

To a solution of tosylate (8.9 mg, 12.5 μmol) in DMF (0.4 mL) was added NaN$_3$ (12.2 mg, 0.188 mmol). After stirring at rt for 21 h, the mixture was quenched with sat. NH$_4$Cl(aq.) and extracted with EtOAc (three times). After concentrating, the residue was purified by preparative TLC (hexane/EtOAc=1:1) to give azide (6.9 mg, 11.8 μmol, 94%) as a colorless powder.

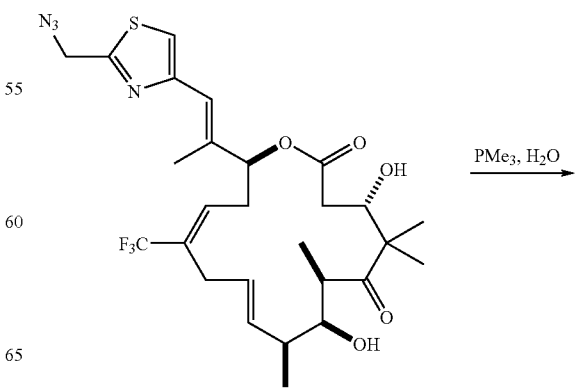

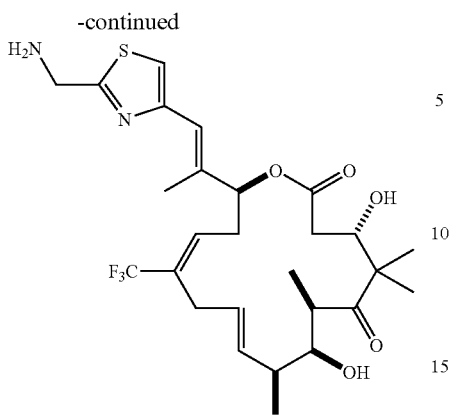

To a solution of azide (21.0 mg, 35.9 μmol) in THF (0.6 mL) was added PMe₃ (1.0 M in THF, 43.1 μL, 43.1 μmol). After 2 min, water (0.1 mL) was added and the mixture was stirred at rt for 3 h. Further PMe₃ (1.0 M in THF, 7.2 μL, 7.2 μmol) was added, and the mixture was stirred at rt for 1.5 h. 28% aqueous NH₄OH (54.5 μL) was added. After stirring at rt for 1 h, the mixture was directly purified by preparative TLC (CH₂Cl₂/MeOH=100:7.5) to give amine (15.9 mg, 28.5 μmol, 79%) as a colorless powder.

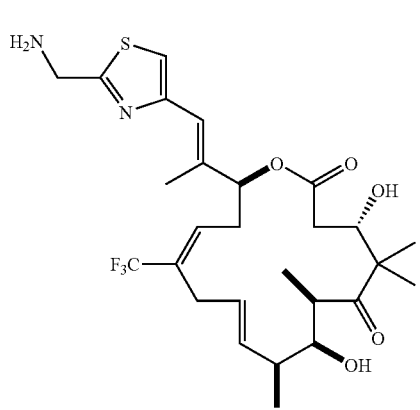

$[\alpha]_D^{26}$ −64.2 (c 0.815, CHCl₃); IR (film) ν 3504, 3363, 2975, 2931, 1733, 1688, 1450, 1383, 1318, 1248, 1169, 1113, 1054, 984, 736 cm⁻¹; ¹H NMR (400 MHz, CDCl₃) δ 1.05 (3H, s), 1.12 (3H, d, J=7.0 Hz), 1.23 (3H, d, J=6.8 Hz), 1.34 (3H, s), 2.12 (3H, d, J=0.7 Hz), 2.24-2.35 (1H, m), 2.39 (1H, dd, J=15.4, 3.0 Hz), 2.49 (1H, dd, J=15.4, 9.8 Hz), 2.54-2.63 (1H, m), 2.66-2.76 (1H, m), 2.97 (1H, dd, J=16.2, 4.2 Hz), 3.03 (1H, dd, J=16.3, 6.5 Hz), 3.10 (1H, quintet, J=6.8 Hz), 3.74 (1H, dd, J=6.7, 3.5 Hz), 4.18 (2H, s), 4.34 (1H, dd, J=9.8, 2.9 Hz), 5.43 (1H, dd, J=6.0, 4.3 Hz), 5.55-5.64 (1H, m), 5.67 (1H, dd, J=15.9, 5.8 Hz), 6.24 (1H, brt, J=7.3 Hz), 6.66 (1H, s), 7.10 (1H, s); ¹³C NMR (100 MHz, CDCl₃) δ 15.3, 16.1, 17.7, 18.2, 22.6, 28.7, 30.9, 39.4, 39.7, 43.9, 45.1, 53.8, 71.2, 75.3, 76.6, 116.8, 120.1, 124.2 [q, 1J (C,F)=273.5 Hz], 127.8, 130.2 [q, ³J (C,F)=6.1 Hz], 130.4 [q, ²J (C,F)=28.6 Hz], 132.2, 136.6, 152.3, 170.1, 172.7, 218.4; LRMS (ESI) calcd for C₂₇H₃₈F₃N₂O₅S [M+H⁺] 559.2, found 559.2; HRMS calcd for C₂₇H₃₈F₃N₂O₅S [M+H⁺] 559.2454 found 559.2440.

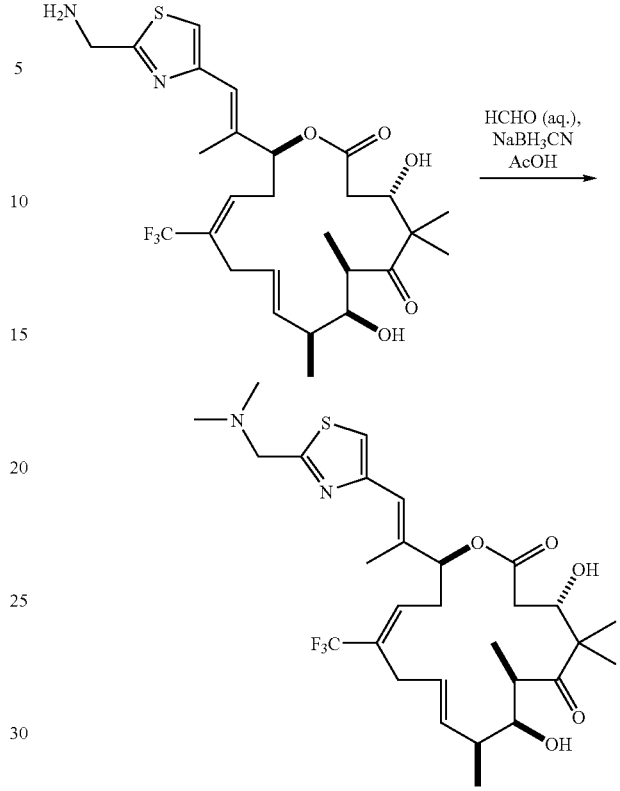

To a stirred solution of amine (15.9 mg, 28.5 mmol) in CH₃CN (0.78 mL) was added HCHO (37% aqueous solution, 31.4 μL, 0.143 mmol) followed by NaBH₃CN (1.0 M in THF, 85.5 μL, 85.5 mmol). The mixture was stirred at rt for 20 min. AcOH (1 drop) was added, and the mixture was stirred at rt for 40 min. The mixture was directly purified by preparative TLC (CH₂Cl₂/MeOH=100:8) to give dimethylamine (15.6 mg, 26.6 μmol, 93%) as a colorless powder.

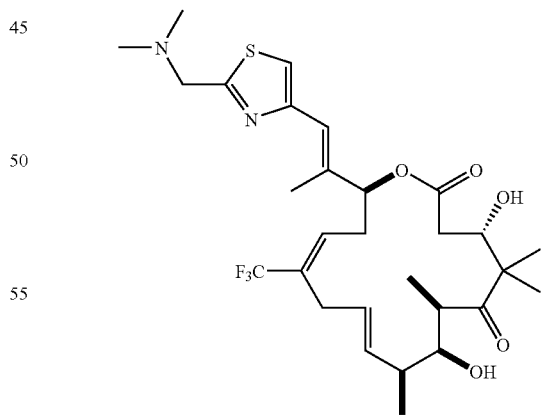

$[\alpha]_D^{24}$ −49.9 (c 0.74, CHCl₃); IR (film) ν 3424, 2974, 1729, 1689, 1468, 1318, 1247, 1169, 1112, 754 cm⁻¹; ¹H NMR (400 MHz, CDCl₃) δ 1.05 (3H, s), 1.12 (3H, d, J=6.9 Hz), 1.23 (3H, d, J=6.8 Hz), 1.33 (3H, s), 2.17 (3H, s), 2.24-2.35 (1H, m), 2.43 (1H, dd, J=157, 3.6 Hz), 2.49 (1H, dd, J=15.6, 9.1 Hz), 2.55-2.64 (2H, m, including OH), 2.68-2.77

(1H, m), 2.80 (3H, s), 2.81 (3H, s), 2.92-3.06 (2H, m), 3.10 (1H, quintet, J=6.8 Hz), 3.69-3.76 (1H, m), 4.25-4.34 (1H, m), 4.33 (2H, s), 5.42 (1H, t, J=5.5 Hz), 5.57 (1H, dt, J=15.8, 6.3 Hz), 5.66 (1H, dd, J=15.7, 6.4 Hz), 6.22 (1H, brt, J=7.2 Hz), 6.64 (1H, s), 7.30 (1H, s); $^{13}$C NMR (100 MHz, CDCl$_3$) δ 15.3, 15.8, 17.8, 18.8, 22.3, 28.8, 30.9, 39.6, 39.6, 45.2, 49.7, 49.7, 53.4, 61.5, 71.7, 75.4, 77.4, 119.2, 120.2, 124.2 [q, $^1$J (C,F)=273.5 Hz], 127.8, 129.9 [q, $^3$J (C,F)=6.2 Hz], 130.7 [q, $^2$J (C,F)=28.4 Hz], 132.4, 137.6, 154.2, 157.2, 170.0, 218.3; LRMS (ESI) calcd for $C_{29}H_{42}F_3N_2O_5S$ [M+H$^+$] 580.2, found 580.2.

Melting points; Both samples were not recrystallized, but purified by SiO$_2$.

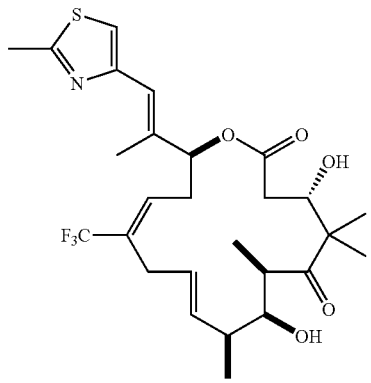

mp 90-94° C.

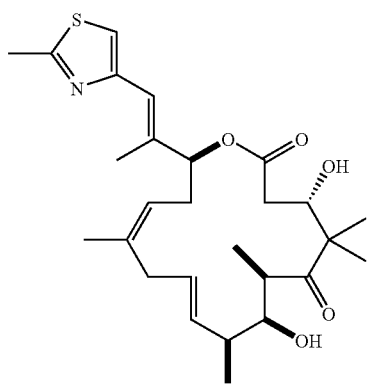

mp 78-81° C.

The invention claimed is:
1. A compound of the formula:

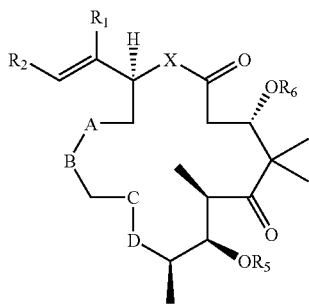

wherein $R_1$ is hydrogen or lower alkyl;
$R_2$ is a substituted or unsubstituted aryl, heteroaryl, arylalkyl, or heteroarylalkyl moiety;
$R_5$ and $R_6$ are each independently hydrogen or a protecting group;
X is O, S, C(R$_7$)$_2$, or NR$_7$, wherein each occurrence of R$_7$ is independently hydrogen or lower alkyl;
A-B represents CR$_A$=CR$_B$—, C(R$_A$)$_2$—C(R$_B$)$_2$—, or —C≡C—;
C-D represents —CR$_C$=CR$_D$—, —C(R$_C$)$_2$—C(R$_D$)$_2$—, or —C≡C—;
wherein each occurrence of R$_A$ is independently hydrogen; halogen; —OR$_{A'}$; —SR$_{A'}$; —N(R$_{A'}$)$_2$; —C(O)OR$_{A'}$; —C(O)R$_{A'}$; —CONHR$_{A'}$; —O(C=O)R$_{A'}$; —O(C=O)OR$_{A'}$; —NR$_{A'}$(C=O)R$_{A'}$; N$_3$; N$_2$R$_{A'}$; cyclic acetal; or cyclic or acyclic, linear or branched aliphatic, heteroaliphatic, aryl, or heteroaryl, optionally substituted with one or more of hydrogen; halogen; —OR$_{A'}$; —SR$_{A'}$; —N(R$_{A'}$)$_2$; —C(O)OR$_{A'}$; —C(O)R$_{A'}$; —CONHR$_{A'}$; —O(C=O)R$_{A'}$; —O(C=O)OR$_{A'}$; —NR$_{A'}$(C=O)R$_{A'}$; N$_3$; N$_2$R$_{A'}$; cyclic acetal; or cyclic or acyclic, linear or branched substituted or unsubstituted aliphatic, heteroaliphatic, aryl, or heteroaryl moiety;
R$_B$ is, independently for each occurrence, hydrogen; halogen; —OR$_{B'}$; —SR$_{B'}$; —N(R$_{B'}$)$_2$; —C(O)OR$_{B'}$; —C(O)R$_{B'}$; —CONHR$_{B'}$; —O(C=O)R$_{B'}$; —O(C=O)OR$_{B'}$; —NR$_{B'}$(C=O)R$_{B'}$; N$_3$; N$_2$R$_{B'}$; cyclic acetal; or cyclic or acyclic, linear or branched aliphatic, heteroaliphatic, aryl, or heteroaryl, optionally substituted with one or more of hydrogen; halogen; —OR$_{B'}$; —SR$_{B'}$; —N(R$_{B'}$)$_2$; —C(O)OR$_{B'}$; —C(O)R$_{B'}$; CONHR$_{B'}$; —O(C=O)R$_{B'}$; —O(C=O)OR$_{B'}$; —NR$_{B'}$(C=O)R$_{B'}$; N$_3$; N$_2$R$_{B'}$; cyclic acetal; or cyclic or acyclic, linear or branched substituted or unsubstituted aliphatic, heteroaliphatic, aryl, or heteroaryl moiety;
R$_C$ is, independently for each occurrence, hydrogen; halogen; —OR$_{C'}$; —SR$_{C'}$; —N(R$_{C'}$)$_2$; —C(O)OR$_{C'}$; —C(O)R$_{C'}$; —CONHR$_{C'}$; —O(C=O)R$_{C'}$; —O(C=O)OR$_{C'}$; —NR$_{C'}$(C=O)R$_{C'}$; N$_3$; N$_2$R$_{C'}$; cyclic acetal; or cyclic or acyclic, linear or branched aliphatic, heteroaliphatic, aryl, or heteroaryl, optionally substituted with one or more of hydrogen; halogen; —OR$_{C'}$; —SR$_{C'}$; —N(R$_{C'}$)$_2$; —C(O)OR$_{C'}$; —C(O)R$_{C'}$; —CONHR$_{C'}$; —O(C=O)R$_{C'}$; —O(C=O)OR$_{C'}$; —NR$_{C'}$(C=O)R$_{C'}$; N$_3$; N$_2$R$_{C'}$; cyclic acetal; or cyclic or acyclic, linear or branched substituted or unsubstituted aliphatic, heteroaliphatic, aryl, or heteroaryl moiety;
R$_D$ is, independently for each occurrence, hydrogen; halogen; —OR$_{D'}$; —SR$_{D'}$; —N(R$_{D'}$)$_2$; —C(O)OR$_{D'}$; —C(O)R$_{D'}$; —CONHR$_{D'}$; —O(C=O)R$_{D'}$; —O(C=O)OR$_{D'}$; —NR$_{D'}$(C=O)R$_{D'}$; N$_3$; N$_2$R$_{D'}$; cyclic acetal; or cyclic or acyclic, linear or branched aliphatic, heteroaliphatic, aryl, or heteroaryl, optionally substituted with one or more of hydrogen; halogen; —OR$_{D'}$; —SR$_{D'}$; —N(R$_{D'}$)$_2$; —C(O)OR$_{D'}$; —C(O)R$_{D'}$; —CONHR$_{D'}$; —O(C=O)R$_{D'}$; —O(C=O)OR$_{D'}$; —NR$_{D'}$(C=O)R$_{D'}$; N$_3$; N$_2$R$_{D'}$; cyclic acetal; or cyclic or acyclic, linear or branched substituted or unsubstituted aliphatic, heteroaliphatic, aryl, or heteroaryl moiety; or
wherein any two of R$_A$, R$_B$, R$_R$ or R$_D$ taken together may form a cyclic moiety and may be linked through an oxygen, sulfur, carbon or nitrogen atom, or any two adjacent groups R$_A$, R$_B$, R$_C$, or R$_D$, taken together, may form a 3-6-membered substituted or unsubstituted aliphatic, heteroaliphatic, aryl or heteroaryl ring;

wherein each occurrence of $R_{A'}$, $R_{B'}$, $R_{C'}$ and $R_{D'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, arylalkenyl, arylalkynyl, or heteroarylalkyl, heteroarylalkenyl, or heteroarylalkynyl moiety; and pharmaceutically acceptable derivatives thereof.

2. The compound of claim 1 of the formula:

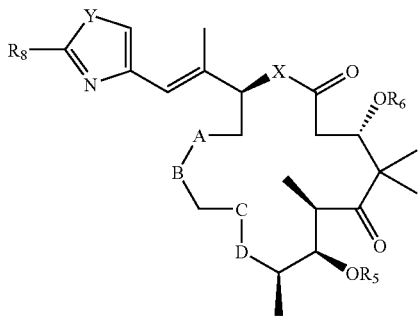

wherein
X is O, S, $C(R_7)_2$, or $NR_7$, wherein each occurrence of $R_7$ is independently hydrogen or lower alkyl;

Y is O or S;

$R_5$ and $R_6$ are each independently hydrogen or a protecting group;

$R_8$ is independently hydrogen, halogen, —$OR_9$, —$SR_9$, —$N(R_9)_2$, —$CZ_3$, —$CHZ_2$, —$CH_2Z$, where Z is F, Br, Cl, I, $OR_{B'}$, $NHR_{B'}$, $N(R_{B'})_2$, or $SR_{B'}$; —$(CV_2)_n$—$OR_9$, —$(CV_2)_nN(R_9)_2$, —$(CV_2)_nSR_9$, —(C=O)$R_9$, —O(C=O)$R_9$, —(C=O)$OR_9$, —O(C=O)$OR_9$; —NH(C=O)$R_9$, —NH(C=O)$OR_9$, —(C=O)$NHR_9$, or a cyclic or acyclic, linear or branched aliphatic, heteroaliphatic, aryl, heteroaryl, arylalkyl, or heteroarylalkyl moiety optionally substituted with one or more occurrences of halogen, —$OR_9$, —$SR_9$, —$N(R_9)_2$, —$(CV_2)_nOR_9$, —$(CV_2)_nN(R_9)_2$, —$(CV_2)_nSR_9$, —(C=O)$R_9$, —O(C=O)$R_9$, —(C=O)$OR_9$, —O(C=O)$OR_9$; —NH(C=O)$R_9$, —NH(C=O)$OR_9$, —(C=O)$NHR_9$, or a cyclic or acyclic, linear or branched, substituted or unsubstituted aliphatic, heteroaliphatic, aryl, heteroaryl, arylalkyl, or heteroarylalkyl moiety, wherein each occurrence of $R_9$ is independently hydrogen; a protecting group; a cyclic or acyclic, linear or branched, substituted or unsubstituted aliphatic, heteroaliphatic, aryl, or heteroaryl moiety; or is an epothilone, desoxyepothilone or analogues thereof; a polymer; carbohydrate; photoaffinity label; or radiolabel;

wherein each occurrence of V is independently hydrogen, halogen, hydroxyl, thio, amino, alkylamino, or protected hydroxyl, thio or amino; each occurrence of t is independently 0, 1 or 2;

and each occurrence of n is independently 0-10;

A-B represents $CR_A$=$CR_B$—, $C(R_A)_2$—$C(R_B)_2$—, or —C≡C—;

C-D represents —$CR_C$=$CR_D$—, —$C(R_C)_2$—$C(R_D)_2$—, or —C≡C—;

wherein each occurrence of $R_A$ is independently hydrogen; halogen; —$OR_{A'}$; —$SR_{A'}$; —$N(R_{A'})_2$; —C(O)$OR_{A'}$; —C(O)$R_{A'}$; —CONHR$_{A'}$; —O(C=O)$R_{A'}$; —O(C=O)$OR_{A'}$; —$NR_{A'}$(C=O)$R_{A'}$; $N_3$; $N_2R_{A'}$; cyclic acetal; or cyclic or acyclic, linear or branched aliphatic, heteroaliphatic, aryl, or heteroaryl, optionally substituted with one or more of hydrogen; halogen; —$OR_{A'}$; —$SR_{A'}$; —$N(R_{A'})_2$; —C(O)$OR_{A'}$; —C(O)$R_{A'}$; —CONHR$_{A'}$; —O(C=O)$R_{A'}$; —O(C=O)$OR_{A'}$; —$NR_{A'}$(C=O)$R_{A'}$; $N_3$; $N_2R_{A'}$; cyclic acetal; or cyclic or acyclic, linear or branched substituted or unsubstituted aliphatic, heteroaliphatic, aryl, or heteroaryl moiety;

$R_B$ is, independently for each occurrence, hydrogen; halogen; —$OR_{B'}$; —$SR_{B'}$; —$N(R_{B'})_2$; —C(O)$OR_{B'}$; —C(O)$R_{B'}$; —CONHR$_{B'}$; —O(C=O)$R_{B'}$; —O(C=O)$OR_{B'}$; —$NR_{B'}$(C=O)$R_{B'}$; $N_3$; $N_2R_{B'}$; cyclic acetal; or cyclic or acyclic, linear or branched aliphatic, heteroaliphatic, aryl, or heteroaryl, optionally substituted with one or more of hydrogen; halogen; —$OR_{B'}$; —$SR_{B'}$; —$N(R_{B'})_2$; —C(O)$OR_{B'}$; —C(O)$R_{B'}$; —CONHR$_{B'}$; —O(C=O)$R_{B'}$; —O(C=O)$OR_{B'}$; —$NR_{B'}$(C=O)$R_{B'}$; $N_3$; $N_2R_{B'}$; cyclic acetal; or cyclic or acyclic, linear or branched substituted or unsubstituted aliphatic, heteroaliphatic, aryl, or heteroaryl moiety;

$R_C$ is, independently for each occurrence, hydrogen; halogen; —$OR_{C'}$; —$SR_{C'}$; —$N(R_{C'})_2$; —C(O)$OR_{C'}$; —C(O)$R_{C'}$; —CONHR$_{C'}$; —O(C=O)$R_{C'}$; —O(C=O)$OR_{C'}$; —$NR_{C'}$(C=O)$R_{C'}$; $N_3$; $N_2R_{C'}$; cyclic acetal; or cyclic or acyclic, linear or branched aliphatic, heteroaliphatic, aryl, or heteroaryl, optionally substituted with one or more of hydrogen; halogen; —$OR_{C'}$; —$SR_{C'}$; —$N(R_{C'})_2$; —C(O)$OR_{C'}$; —C(O)$R_{C'}$; —CONHR$_{C'}$; —O(C=O)$R_{C'}$; —O(C=O)$OR_{C'}$; —$NR_{C'}$(C=O)$R_{C'}$; $N_3$; $N_2R_{C'}$; cyclic acetal; or cyclic or acyclic, linear or branched substituted or unsubstituted aliphatic, heteroaliphatic, aryl, or heteroaryl moiety;

$R_D$ is, independently for each occurrence, hydrogen; halogen; —$OR_{D'}$; —$SR_{D'}$; —$N(R_{D'})_2$; —C(O)$OR_{D'}$; —C(O)$R_{D'}$; —CONHR$_{D'}$; —O(C=O)$R_{D'}$; —O(C=O)$OR_{D'}$; —$NR_{D'}$(C=O)$R_{D'}$; $N_3$; $N_2R_{D'}$; cyclic acetal; or cyclic or acyclic, linear or branched aliphatic, heteroaliphatic, aryl, or heteroaryl, optionally substituted with one or more of hydrogen; halogen; —$OR_{D'}$; —$SR_{D'}$; —$N(R_{D'})_2$; —C(O)$OR_{D'}$; —C(O)$R_{D'}$; —CONHR$_{D'}$; —O(C=O)$R_{D'}$; —O(C=O)$OR_{D'}$; —$NR_{D'}$(C=O)$R_{D'}$; $N_3$; $N_2R_{D'}$; cyclic acetal; or cyclic or acyclic, linear or branched substituted or unsubstituted aliphatic, heteroaliphatic, aryl, or heteroaryl moiety; or wherein any two of $R_A$, $R_B$, $R_C$ or $R_D$ taken together may form a cyclic moiety and may be linked through an oxygen, sulfur, carbon or nitrogen atom, or any two adjacent groups $R_A$, $R_B$, $R_C$, or $R_D$, taken together, may form a 3-6-membered substituted or unsubstituted aliphatic, heteroaliphatic, aryl or heteroaryl ring;

wherein each occurrence of $R_{A'}$, $R_{B'}$, $R_{C'}$ and $R_{D'}$ is independently hydrogen; a protecting group; a linear or branched, substituted or unsubstituted, cyclic or acyclic, aliphatic, heteroaliphatic, aryl, heteroaryl, arylalkyl, arylalkenyl, arylalkynyl, arylalkenyl, arylalkynyl, or heteroarylalkyl, heteroarylalkenyl, or heteroarylalkynyl moiety; and pharmaceutically acceptable derivatives thereof.

3. The compound of claim 2, wherein A-B is —CH=C(R_B)—.

4. The compound of claim 2, wherein A-B is

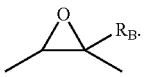

5. The compound of claim 2 wherein $R_B$ is methyl.
6. The compound of claim 2 wherein $R_B$ is —CF$_3$.
7. The compound of claim 2, wherein $R_8$ is methyl.
8. The compound of claim 2, wherein C-D is

wherein Z is O, S, NR$_Z$, or C(R$_Z$)$_2$, wherein R$_Z$ is hydrogen, halogen, lower acyl, or lower alkyl.

9. The compound of claim 8, wherein Z is NH or CH$_2$.
10. The compound of claim 8, wherein Z is O.
11. The compound of claim 2, 3, or 4, wherein C-D is

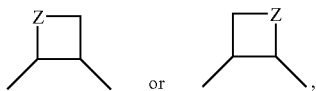

wherein Z is O, S, NR$_Z$, or C(R$_Z$)$_2$, wherein R$_Z$ is hydrogen, halogen, lower acyl, or lower alkyl.

12. The compound of claim 11, wherein Z is NH or CH$_2$.
13. The compound of claim 2, wherein Y is S.
14. The compound of claim 2, wherein Y is O.
15. The compound of claim 2, wherein C-D is —C(R$_C$)$_2$—C(R$_D$)$_2$—.
16. The compound of claim 15, wherein each occurrence of R$_C$ and R$_D$ is selected from the group consisting of hydrogen, lower alkyl, hydroxyl, halogen, or lower alkoxy.
17. A pharmaceutical composition comprising a compound of claim 1 and a pharmaceutically acceptable excipient.
18. The pharmaceutical composition of claim 17 further comprising Cremophor.
19. The pharmaceutical composition of claim 17 further comprising an additional cytotoxic agent.
20. A pharmaceutical composition comprising:
  a therapeutically effective amount of a compound of claim 1, or pharmaceutically acceptable salts thereof; and
  a pharmaceutically acceptable carrier or diluent,
  wherein the therapeutically effective amount of the compound is an amount sufficient to deliver about 0.001 to about 40 mg compound per kg body weight of a subject.

* * * * *